US012440484B2

(12) United States Patent
Lee et al.

(10) Patent No.: US 12,440,484 B2
(45) Date of Patent: Oct. 14, 2025

(54) 1,3,4-OXADIAZOLE HOMOPHTHALIMIDE DERIVATIVE COMPOUNDS AS HISTONE DEACETYLASE 6 INHIBITOR, AND THE PHARMACEUTICAL COMPOSITION COMPRISING THE SAME

(71) Applicant: Chong Kun Dang Pharmaceutical Corp., Seoul (KR)

(72) Inventors: Chang Sik Lee, Gyeonggi-do (KR); Jung Taek Oh, Gyeonggi-do (KR); Hokeun Yun, Gyeonggi-do (KR); Hyeseung Song, Gyeonggi-do (KR); Hyunjin Michael Kim, Gyeonggi-do (KR)

(73) Assignee: Chong Kun Dang Pharmaceutical Corporation (KR)

( * ) Notice: Subject to any disclaimer, the term of this patent is extended or adjusted under 35 U.S.C. 154(b) by 989 days.

(21) Appl. No.: 17/615,363

(22) PCT Filed: May 29, 2020

(86) PCT No.: PCT/IB2020/055110

§ 371 (c)(1),
(2) Date: Nov. 30, 2021

(87) PCT Pub. No.: WO2020/240493

PCT Pub. Date: Dec. 3, 2020

(65) Prior Publication Data

US 2023/0079386 A1 Mar. 16, 2023

(30) Foreign Application Priority Data

May 31, 2019 (KR) ........................ 10-2019-0064666

(51) Int. Cl.

*A61K 31/4439* (2006.01)
*A61K 31/4245* (2006.01)
*A61K 31/437* (2006.01)
*A61K 31/4725* (2006.01)
*A61K 31/496* (2006.01)
*A61K 31/506* (2006.01)
*A61K 31/517* (2006.01)
*A61K 31/5377* (2006.01)

(52) U.S. Cl.

CPC ...... *A61K 31/4439* (2013.01); *A61K 31/4245* (2013.01); *A61K 31/437* (2013.01); *A61K 31/4725* (2013.01); *A61K 31/496* (2013.01); *A61K 31/506* (2013.01); *A61K 31/517* (2013.01); *A61K 31/5377* (2013.01)

(58) Field of Classification Search

CPC ............ A61K 31/4439; A61K 31/4245; A61K 31/437; A61K 31/4725; A61K 31/496; A61K 31/506; A61K 31/517; A61K 31/5377

See application file for complete search history.

(56) References Cited

U.S. PATENT DOCUMENTS

| | | | |
|---|---|---|---|
| 4,871,753 | A | 10/1989 | Rorh |
| 6,075,039 | A | 6/2000 | Gallagher et al. |
| 8,901,156 | B2 | 12/2014 | Baloglu et al. |
| 8,981,084 | B2 | 3/2015 | Baloglu et al. |
| 9,670,193 | B2 | 6/2017 | Hebach et al. |
| 10,464,911 | B2 | 11/2019 | Lee et al. |
| 10,494,355 | B2 | 12/2019 | Kim et al. |
| 10,538,498 | B2 | 1/2020 | Lee et al. |
| 10,584,117 | B2 | 3/2020 | Lee et al. |
| 10,717,716 | B2 | 7/2020 | Lee et al. |
| 11,958,844 | B2 | 4/2024 | Lee et al. |
| 2005/0288282 | A1 | 12/2005 | Delorme et al. |
| 2006/0058298 | A1 | 3/2006 | Delorme et al. |
| 2007/0293530 | A1 | 12/2007 | Smil et al. |
| 2012/0027874 | A1 | 2/2012 | Charrier et al. |
| 2012/0289495 | A1 | 11/2012 | Baloglu et al. |

(Continued)

FOREIGN PATENT DOCUMENTS

| | | |
|---|---|---|
| CN | 101263121 | 9/2008 |
| CN | 102448461 | 5/2012 |

(Continued)

OTHER PUBLICATIONS

Schafer et al. Drug Discovery Today 2008, 13 (21/22), 913-916 (Year: 2008).*
Horig et al. Journal of Translational Medicine 2004, 2(44) (Year: 2004).*
Zhang et al. J Hematol Oncol, 2018 11, 111 (Year: 2018).*
Zhang et al. Circulation. 2014. 129(3). 346-358 (Year: 2014).*
Office Action in Canadian Appln. No. 3,139,026, mailed on Sep. 14, 2023, 5 pages.
Office Action in Chinese Appln. No. 202080039276.4, mailed on Nov. 24, 2024, 17 pages (with English translation).
Office Action in Chinese Appln. No. 202080039677, mailed on Nov. 25, 2023, 13 pages (with English translation).
Office Action in Indonesian Appln. No. P00202110627, mailed on May 22, 2023, 6 pages (with English translation).

(Continued)

*Primary Examiner* — Clinton A Brooks
*Assistant Examiner* — Jerica Katlynn Wilson
(74) *Attorney, Agent, or Firm* — Fish & Richardson P.C.

(57) ABSTRACT

The present invention relates to novel compounds having a histone deacetylase 6 (HDAC6) inhibitory activity, stereoisomers thereof or pharmaceutically acceptable salts thereof, a medicinal use thereof, and a method for preparing the same. The novel compounds according to the present invention, stereoisomers thereof or pharmaceutically acceptable salts thereof have the histone deacetylase 6 (HDAC6) inhibitory activity, and are effective in preventing or treating HDAC6-related diseases, comprising infectious diseases; neoplasm; endocrinopathy; nutritional and metabolic diseases; mental and behavioral disorders; neurological diseases; eye and ocular adnexal diseases; circulatory diseases; respiratory diseases; digestive diseases; skin and subcutaneous tissue diseases; musculoskeletal system and connective tissue diseases; and teratosis or deformities, or chromosomal aberration.

9 Claims, No Drawings

(56) References Cited

U.S. PATENT DOCUMENTS

| | | | |
|---|---|---|---|
| 2013/0059883 A1 | 3/2013 | Baloglu et al. |
| 2014/0005133 A1 | 1/2014 | Trivedi et al. |
| 2014/0005164 A1 | 1/2014 | Varrone et al. |
| 2014/0142105 A1 | 5/2014 | Hebach et al. |
| 2014/0329825 A1 | 11/2014 | Hebach et al. |
| 2015/0307497 A1 | 10/2015 | Sugimoto et al. |
| 2016/0244449 A1 | 8/2016 | Lu et al. |
| 2017/0015809 A1 | 1/2017 | Hawkins et al. |
| 2017/0145012 A1 | 5/2017 | Buckmelter et al. |
| 2018/0215743 A1 | 8/2018 | Lee et al. |
| 2018/0230113 A1 | 8/2018 | Lee et al. |
| 2018/0230114 A1 | 8/2018 | Lee et al. |
| 2018/0251437 A1 | 9/2018 | Lee et al. |
| 2018/0273495 A1 | 9/2018 | Kim et al. |
| 2019/0008836 A1 | 1/2019 | Kaieda et al. |
| 2021/0188831 A1 | 6/2021 | Lee et al. |
| 2021/0355089 A1 | 11/2021 | Chern et al. |
| 2023/0092890 A1 | 3/2023 | Lee et al. |

FOREIGN PATENT DOCUMENTS

| | | |
|---|---|---|
| CN | 102802623 | 11/2012 |
| CN | 103221047 | 7/2013 |
| CN | 103339111 | 10/2013 |
| CN | 104744446 | 7/2015 |
| CN | 103998446 | 11/2016 |
| CN | 107438607 | 12/2017 |
| CN | 108026056 | 5/2018 |
| CN | 108137518 | 6/2018 |
| CN | 108473495 | 8/2018 |
| CN | 108699048 | 10/2018 |
| CN | 114269739 | 4/2022 |
| EA | 201491060 | 9/2014 |
| EP | 0816356 | 1/1998 |
| EP | 3327019 | 5/2018 |
| EP | 3330259 | 6/2018 |
| JP | H10-059962 | 3/1998 |
| JP | 2005513123 | 5/2005 |
| JP | 2009542752 | 12/2009 |
| JP | 2011008205 | 1/2011 |
| JP | 2011502133 | 1/2011 |
| JP | 2012211149 | 11/2012 |
| JP | 2013517278 | 5/2013 |
| JP | 2013517281 | 5/2013 |
| JP | 2013533279 | 8/2013 |
| JP | 2014513071 | 5/2014 |
| JP | WO 2014077401 | 5/2014 |
| JP | 2014520794 | 8/2014 |
| JP | 2014524922 | 9/2014 |
| JP | 2014533721 | 12/2014 |
| JP | 2014533734 | 12/2014 |
| JP | 2018511573 | 4/2018 |
| JP | 2018521110 | 8/2018 |
| JP | 2019504821 | 2/2019 |
| JP | 2021532130 | 11/2021 |
| JP | 2022529695 | 6/2022 |
| JP | 2022537904 | 8/2022 |
| KR | 100265385 | 11/2000 |
| KR | 100903743 | 6/2009 |
| KR | 101262870 | 5/2013 |
| KR | 101320198 | 10/2013 |
| KR | 20130112911 | 10/2013 |
| KR | 20140097459 | 8/2014 |
| KR | 20147017436 | 8/2014 |
| KR | 101561860 | 10/2015 |
| KR | 20170013186 | 2/2017 |
| KR | 10-2022-0012243 | 2/2022 |
| RU | 2515611 | 8/2012 |
| WO | WO 2003028729 | 4/2003 |
| WO | WO 2007011626 | 1/2007 |
| WO | WO 2007032445 | 3/2007 |
| WO | WO 2007093827 | 8/2007 |
| WO | WO 2007107758 | 9/2007 |
| WO | WO 2009010479 | 1/2009 |
| WO | WO 2010109148 | 9/2010 |
| WO | WO 2010123933 | 10/2010 |
| WO | WO 2010126002 | 11/2010 |
| WO | WO 2011011186 | 1/2011 |
| WO | WO 2011088181 | 7/2011 |
| WO | WO 2011088192 | 7/2011 |
| WO | WO 2011091213 | 7/2011 |
| WO | WO 2011104680 | 9/2011 |
| WO | WO 2011133888 | 10/2011 |
| WO | WO 2012011592 | 1/2012 |
| WO | WO 2012013716 | 2/2012 |
| WO | WO 2012136492 | 10/2012 |
| WO | WO 2013008162 | 1/2013 |
| WO | WO 2013041407 | 3/2013 |
| WO | WO 2013052110 | 4/2013 |
| WO | WO 2013066833 | 5/2013 |
| WO | WO 2013066835 | 5/2013 |
| WO | WO 2013066838 | 5/2013 |
| WO | WO 2013066839 | 5/2013 |
| WO | WO 2013080120 | 6/2013 |
| WO | WO 2013134467 | 9/2013 |
| WO | WO 2015033301 | 3/2015 |
| WO | WO 2015087151 | 6/2015 |
| WO | WO 2016082930 | 6/2016 |
| WO | WO 2016134320 | 8/2016 |
| WO | WO 2017014170 | 1/2017 |
| WO | WO 2017014321 | 2/2017 |
| WO | WO 2017018803 | 2/2017 |
| WO | WO 2017018804 | 2/2017 |
| WO | WO 2017018805 | 2/2017 |
| WO | WO 2017023133 | 2/2017 |
| WO | WO 2017065473 | 4/2017 |
| WO | WO 2017222951 | 12/2017 |
| WO | WO 2017222952 | 12/2017 |
| WO | WO 2018213364 | 11/2018 |
| WO | WO 2020022794 | 1/2020 |
| WO | WO 2020212479 | 10/2020 |
| WO | WO 2021127643 | 6/2021 |

OTHER PUBLICATIONS

Office Action in Indonesian Appln. No. P00202111108, mailed on Jul. 6, 2023, 6 pages (with English translation).

Office Action in New Zealand Appln. No. 782015, mailed on Mar. 7, 2024, 3 pages.

Office Action in New Zealand Appln. No. 782551, mailed on Mar. 7, 2024, 3 pages.

Office Action in Vietnamese Appln. No. 1-2021-07143, mailed on Dec. 27, 2023, 4 pages (with English translation).

Office Action in Vietnamese Appln. No. 1-2021-07370, mailed on Dec. 27, 2023, 4 pages (with English translation).

Office Action for Korean Appln, No. 10-2020-0065508, dated Mar. 2, 2022, 15 pages (with Machine Translation).

ACS RN 904568-68-9, "Benz amide, 3,4,5-trimethoxy-N-[4-[5-(trifluoromethyl)-1,3,4-oxadiazol-2-yl]phenyl]" STN-Registry, Aug. 25, 2006, 1 page.

ACS RN 904653-05-0, "Benzamide, 3-methoxy-N-[4-[5-(trichloromethyl)-1,3,4-oxadiazol-2-yl]phenyl]", STN-Registry, dated Aug. 25, 2006, 1 page.

Office Action and Search Report for Chinese Application No. 201680044430.0, dated Aug. 21, 2020. 9 pages (with English translation).

Office Action and Search Report for Chinese Application No. 201680053218.0, dated Nov. 8, 2020, 14 pages (with English translation).

Office Action and Search Report for Chinese Application No. 201680058155.8, dated Jan. 6, 2021, 13 pages (with English translation).

Office Action and Search Report for Chinese Application No. 201680072029.8, dated Oct. 26, 2020, 12 pages (with English translation).

U.S. Appl. No. 17/263,333, filed Jan. 26, 2021, Chang Sik Lee.

Baijika, et al., "Synthesis and biological activities of 1, 3, 4-oxadiazole derivatives: A Review of Literature," Int. J. Adv. Res., [Published] Jan. 2018, vol. 6, No. 1, pp. 1114-1122.

Bolden et al., "Anticancer activities of histone deacetylase inhibitors", National Reviews, Drug Discovery, vol. 5, Sep. 2006, pp. 769-784.

(56) References Cited

OTHER PUBLICATIONS

Hassig et al., "Nuclear histone acetylases and deacetylases and transcriptional regulation: HATs off to HDACs," Current Opinion In Chemical Biology 1997, 1, pp. 300-308.
Hu et al., "HDAC6 α-tubulin deacetylase: A potential therapeutic target in neurodegenerative diseases," Journal of the Neurological Sciences, 304, 2011, pp. 1-8.
Matthias et al., "Mice Lacking Histone Deacetylase 6 Have Hyperacetylated Tubulin but Are Viable and Develop Normally," Molecular and Cellular Biology, Mar. 2008, vol. 28, pp. 1688-1701.
Methot et al., "Exploration of the internal cavity of histone deacetylase (HDAC) with selective HDAC1/HDAC2 inhibitors (SHI-1:2)," Bioorganic & Medicinal Chemistry Letters, 18, (2008), pp. 973-978.
Notice of Allowance in Korean Appln. No. 2018-0087455, dated Oct. 7, 2021, 4 pages (with English translation).
Office Action for TW108126316, dated Oct. 22, 2020 and English translation, 7 pages.
Office Action for TW109118219, dated Mar. 19, 2021 and English translation, 9 pages.
Office Action for TW109118221, dated Apr. 15, 2021 and English translation, 9 pages.
Office Action in Russian Appln. No. 2021104625, dated Jul. 23, 2021, 22 pages (with English translation).
PCT International Preliminary Report on Patentability in International Appln. No. PCT/KR2019/009228, dated Feb. 4, 2021, 6 pages.
PCT International Search Report and Written Opinion in International Application No. PCT/IB2020/055109, dated Sep. 4, 2020, 10 pages.
PCT International Search Report and Written Opinion in International Application No. PCT/IB2020/055110, dated Sep. 4, 2020, 12 pages.
PCT International Search Report and Written Opinion in International Application No. PCT/KR2019/009228, Nov. 11, 2019, 8 pages.
Piekarz et al., "Clinical Toxicities of Histone Deacetylase Inhibitors", Pharmaceuticals 2010, 3, pp. 2751-2767.
Santo et al., "Preclinical activity, pharmacodynamic, and pharmacokinetic properties of a selective HDAC6 inhibitor, ACY-1215, in combination with bortezomib in multiple myeloma," Blood, Mar. 15, 2012, vol. 119, No. 11, pp. 2579-2590.
Vishwakarma et al., "Tubastatin, a selective histone deacetylase 6 inhibitor shows anti-inflammatory and anti-rheumatic effects," International Immunopharmacology, 2013, 16, pp. 72-78.
Warrell et al., "Therapeutic Targeting of Transcription in Acute Promyelocytic Leukemia by Use of an Inhibitor of Histone Deacetylase," Journal of the National Cancer Institute, vol. 90, No. 21, Nov. 4, 1998, pp. 1621-1625.
Wiest et al., "Computational Exploration of Zinc Binding Groups for HDAC Inhibition," J. Org. Chem., May 17, 2013, 78, pp. 5051-5055.
Witt et al., "HDAC family: What are the cancer relevant targets?," Cancer Letters 277, 2009, 2, pp. 8-21.
Woster et al., "Discovery of a new class of histone deacetylase inhibitors with a novel zinc binding group," Med. Chem. Commun., 2015, online publication, 6 pages.
Yao et al., "HDAC6 Regulates Hsp90 Acetylation and Chaperone-Dependent Activation of Glucocorticoid Receptor," Molecular Cell, vol. 18, May 27, 2005, pp. 601-607.
Belikov, "Farmatsevticheskaya khimiya [Pharmaceutical Chemistry]", textbook, 4th ed., M.: "MEDpress-inform", Moscow, 2007, 622 p, pp. 27-29 (with English translation, 14 pages in total).
Gavrilov, "Pharmaceutical technology. The manufacturing of drugs," Textbook, M.: GEOTAR-Media, 2010, 624 p, p. 20 (with Machine translation, 6 pages in total).
Office Action in Malaysian Appln. No. PI2021006507, mailed on Sep. 25, 2024, 3 pages (with English translation).
Office Action in Mexican Appln. No. MX/a/2021/014315, mailed on Jul. 15, 2024, 9 pages (with English translation).
Office Action in New Zealand Appln. No. 782015, mailed on Sep. 24, 2024, 3 pages.
Dyson G., May P. "Chemistry of synthetic drugs", translated from English by Professor M.L. Belenky, Publishing House "MIR", Moscow, 1964, pp. 12-19 (with English translation, 21 pages in total).
Office Action in Mexican Appln. No. MX/a/2021/014372, mailed on Jul. 16, 2024, 8 pages (with English translation).
Popular Medical Encyclopedia, editor-in-chief V.I. Pokrovsky, 4th ed., St., "Book", 1997, p. 317 (drugs) (with Machine translation, 5 pages in total).
Cancer [online], "Cancer," Jun. 27, 2007, retrieved on Jul. 6, 2007, retrieved from URL <http://www.nlm.nih.gov/medlineplus/cancer.html>, 10 pages.
CAS No. 904635-69-4, "4-Morpholinecarboxamide, N-[4-[5-(trifluoromethyl)-1,3,4-oxadiazol-2-yl]phenyl]," STN Easy, dated Aug. 25, 2006, 1 page.
CAS No. 904652-71-7, "4-Morpholinecarboxamide, N-[4-[5-(dichloromethyl)-1,3,4-oxadiazol-2-yl]phenyl]," STN Easy, dated Aug. 25, 2006, 1 page.
CAS No. 904653-13-0, "4-Morpholinecarboxamide, N-[4-[5-(trichloromethyl)-1, 3,4-oxadiazol-2-yl]phenyl]," STN Easy, dated Aug. 25, 2006, 1 page.
Chemical Abstract compound RN No. 1355844-43-7, STN Express, dated Feb. 8, 2012, 1 page.
Chemical Abstract compound RN No. 1384673-31-7, STN Express, dated Jul. 27, 2012, 1 page.
Chemical Abstract compound RN No. 1436149-02-8, STN Express, dated Jun. 9, 2013, 1 page.
Chemical Abstract compound RN No. 1708354-35-1, STN Express, dated May 20, 2015, 1 page.
Chemical Abstract compound RN No. 1790675-44-3, STN Express, dated Jun. 29, 2015, 1 page.
Chemical Abstract compound RN No. 1798074-73-3, STN Express, dated Jul. 9, 2015, 1 page.
Chemical Abstract compound RN No. 904653-15-2, STN Express, dated Aug. 25. 2006, 1 page.
Chemical Abstract compound RN No. 904653-17-4, STN Express, Aug. 25, 2006, 1 page.
Chemical Abstract compound RN No. 904653-20-9, STN Express, dated Aug. 25, 2006, 2 pages.
Chemical Abstract compound RN No. 904653-21-0, STN Express, dated Aug. 25, 2006, 1 page.
Chemical Abstract compound RN No. 904653-22-1, STN Express, dated Aug. 25, 2006, 1 page.
Chen et al., "Computational exploration of zine binding groups for HDAC inhibition," J. Org. Chem., May 2013, 78(10):5051-5055.
Chen et al., "Discovery of 2-methylpyridine-based biaryl amides as y-secretase modulators for the treatment of Alzheimer's disease, "Bioorg. Med. Chem, 2013, 23(23):6447-6454.
Decision to Grant in Russian Appln. No. 2021104625, dated Dec. 3, 2021, 29 pages (with English Translation).
El-Din. et al., "Synthesis and in vitro antiproliferative activity of new 1,3,4-oxadiazole derivatives possessing sulfonamide moiety," Eur. J. Med. Chem, Jan. 2015, 90:45-52.
Extended European Search Report in European Appln. No. 16830836.9, dated Dec. 19, 2018, 7 pages.
Extended European Search Report in European Appln. No. 16830837.7, dated Dec. 17, 2018, 9 pages.
Extended European Search Report in European Appln. No. 16830838.5, dated Nov. 19, 2018, 7 pages.
Extended European Search Report in European Appln. No. 16833369.8, dated Apr. 1, 2019, 6 pages.
Golub et al., "Molecular Classification of Cancer: Class Discovery and Class Prediction by Gene Expression Monitoring," Science, Oct. 1991, 286:531-537.
International Preliminary Report on Patentability and Written Opinion for International Appln. No. PCT/KR2016/008214, dated Jan. 30, 2018, 8 pages.
International Preliminary Report on Patentability and Written Opinion for International Appln. No. PCT/KR2016/008216, dated Jan. 30, 2018, 9 pages.

(56) References Cited

OTHER PUBLICATIONS

International Preliminary Report on Patentability and Written Opinion for International Appln. No. PCT/KR2016/008218, dated Jan. 30, 2018, 8 pages.
International Preliminary Report on Patentability and Written Opinion for International Appln. No. PCT/KR2016/008622, dated Feb. 6, 2018, 8 pages.
International Preliminary Report on Patentability and Written Opinion for International Appln. No. PCT/KR2016/011355, dated Apr. 17, 2018, 6 pages.
International Search Report for International Appln. No. PCT/KR2016/008214, dated Nov. 24, 2016, 5 pages.
International Search Report for International Appln. No. PCT/KR2016/008216, dated Nov. 21, 2016, 12 pages (with English Translation).
International Search Report for International Appln. No. PCT/KR2016/008218, dated Nov. 21, 2016, 5 pages.
International Search Report for International Appln. No. PCT/KR2016/008622, dated Feb. 17. 2017, 5 pages.
International Search Report for International Appln. No. PCT/KR2016/011355, dated Jan. 26, 2017, 5 pages.
Lala et al., "Role of nitric oxide in tumor progression: Lessons from experimental tumors," Cancer Metastasis Rev., 1998, 17(1):91-106.
Manku, et al., "Synthesis and evaluation of lysine derived sulfamides as histone deacetylase inhibitors," Bioorg. Med. Chem. Lett., Feb. 2009, 19:1866-1870.
Murphy et al., "Regulation of the Dynamics of hsp90 Action on the Glucocorticoid Receptor by Acetylation/Deacetylation of the Chaperone," J. Biol. Chem., Oct. 2005, 280(40):33792-33799.
Office Action for Australian Appln. No. 2016299484, dated Aug. 28, 2018, 6 pages.
Office Action for Australian Appln. No. 2016299484, dated Dec. 18, 2018, 3 pages.
Office Action for Australian Appln. No. 2016299485, dated Sep. 13, 2018, 7 pages.
Office Action for Australian Appln. No. 2016299486, dated Jul. 21, 2018, 5 pages.
Office Action for Australian Appln. No. 2016303891, dated Nov. 16, 2018, 7 pages.
Office Action for Canadian Appln. No. 2987570, dated Oct. 18, 2018, 5 pages.
Office Action for Canadian Appln. No. 2993918, dated Dec. 4, 2018, 5 pages.
Office Action for Canadian Appln. No. 2993929, dated Dec. 4, 2018, 4 pages.
Office Action for Indian Appln. No. 201727037873, dated May 21, 2019, 7 pages.
Office Action for Indian Appln. No. 201817006324, dated Jun. 27, 2019, 6 pages.
Office Action for Japanese Appln. No. 2018-503804, dated Feb. 15, 2019, 4 pages (with English Translation).
Office Action for Japanese Appln. No. 2018-504096, dated Jan. 8, 2019, 5 pages (with English Translation).
Office Action for Japanese Appln. No. 2018-504720, dated Jan. 8, 2019, 19 pages (with English Translation).
Office Action for Japanese Appln. No. 2018-505725, dated Sep. 12, 2018, 3 pages.
Office Action for Japanese Appln. No. 2021-503874, dated Feb. 8, 2022, 7 pages (with English Translation).
Office Action for Korean Appln, No. 10-2016-0095332, dated May 9, 2017, 15 pages.
Office Action for Korean Appln, No. 10-2016-0095334, dated May 9, 2017, 17 pages.
Office Action for Korean Appln, No. 10-2016-0099508, dated May 9, 2017. 20 pages.
Office Action for Korean Appln, No. 10-2016-0131245, dated May 9, 2017, 7 pages.
Office Action for New Zealand Appln. No. 739211, dated Jun. 14, 2018, 3 pages.
Office Action for Russian Appln. No. 2018106877, dated Oct. 18, 2018, 16 pages (with English translation).
Office Action for Russian Appln. No. 2018106904, dated Sep. 20, 2018, 14 pages (with English translation).
Office Action for Russian Appln. No. 2018106914, dated Nov. 15, 2018, 14 pages (with English translation).
Office Action for Taiwanese Appln. No. 105132939, dated Nov. 2, 2017, 8 pages (with English translation).
Othman et al., "1,3,4-Oxadiazole, 1,3,4-thiadiazole and 1,2,4-triazole derivatives as potential antibacterial agents," Arab. J. Chem., 2014:1-16.
Pal et al., "Hydroxamic acid—A novel molecule for anticancer therapy," J. Adv. Pharm. Technol. Res., 2012, 3(2):92-99.
Rajak et al., "2,5-Disubstituted-1,3,4-oxadiazoles/thiadiazole as surface recognition moiety: Design and synthesis of novel hydroxamic acid based histone deacetylase inhibitors," Bioorg. Med. Chem. Lett., Aug. 2011, 21:5735-5738.
Rossi et al., "4-N-Hydroxy-4-[ 1-( sulfonyl )piperidin-4-yl ]-butyramides as HDAC inhibitors," Bioorg. Med. Chem. Lett., Sep. 2011, 21:6767-6769.
Extended European Search Report in European Appln. No. 20814548.2, dated Nov. 8, 2022, 5 pages.
Extended European Search Report in European Appln. No. 20815468.2, dated May 4, 2023, 13 pages.
Notice of Allowance in Australian Appln. No. 2020284167, dated May 1, 2023, 3 pages.
Notice of Allowance in Korean Appln. No. 2020-0065507, dated Nov. 10, 2022, 10 pages (with English translation).
Office Action for Australian Appln. No. 2020284167, dated Nov. 3, 2022, 3 pages.
Office Action for Australian Appln. No. 2020284606, dated Aug. 11, 2022, 8 pages.
Office Action for Canadian Appln. No. 3136223, dated Nov. 30, 2022, 4 pages.
Office Action for Canadian Appln. No. 3139026, dated Dec. 14, 2022, 6 pages.
Office Action for Indian Appln. No. 202137058528, dated Jul. 6, 2022, 5 pages.
Office Action for Indian Appln. No. 202137061193, dated Jul. 7, 2022, 6 pages.
Office Action for Japanese Appln. No. 2021-571486, dated Jan. 10, 2023, 12 pages (with English Translation).
Office Action for Japanese Appln. No. 2021-571498, dated Nov. 8, 2022, 12 pages (with English Translation).
Office Action for Malaysian Appln. No. PI2021006507, dated May 22, 2023, 4 pages.
Office Action for Russian Appln. No. 2021139516, dated Aug. 11, 2022, 20 pages (with English Translation).
Office Action for Russian Appln. No. 2021139540, dated Aug. 17, 2022, 32 pages (with English Translation).
Office Action in Chinese Appln. No. 201980049375.8, mailed on Sep. 20, 2023, 13 pages (with English translation).
Office Action in Malaysia Appln. No. PI2021000199, mailed on Dec. 1, 2023, 2 pages (with English translation).
Office Action in Mexico Appln. No. MX/a/2021/000737, mailed on Jun. 15, 2023, 8 pages (with English translation).
Office Action in New Zealand Appln. No. 771899, mailed on Aug. 22, 2023, 4 pages.
Office Action in Vietnam Appln. No. 51472w/SHTT-SC, mailed on Aug. 23, 2023, 4 pages (with English translation).
Silverman, "The Organic Chemistry of Drug Design and Drug Action," Second Edition, 2008, pp. 17-23.
Patani, G. A et al. Bioisosterism: A Rational Approach in Drug Design. Chemical reviews 1996, vol. 96, 8: 3147-3176. (Year: 1996).
U.S. Appl. No. 17/263,333 (U.S. Pat. No. 11,958,844), filed Jan. 26, 2021 (Apr. 16, 2024), Chang Sik Lee.
U.S. Appl. No. 17/614,967, filed Nov. 29, 2021, Chang Sik Lee.

* cited by examiner

1,3,4-OXADIAZOLE HOMOPHTHALIMIDE DERIVATIVE COMPOUNDS AS HISTONE DEACETYLASE 6 INHIBITOR, AND THE PHARMACEUTICAL COMPOSITION COMPRISING THE SAME

CROSS-REFERENCE TO RELATED APPLICATIONS

This application is a U.S. National Stage application, and claims priority of International Application No. PCT/IB2020/055110, filed May 29, 2020, which claims priority of Korean Application No. 10-2019-0064666, filed May 31, 2019. The contents of all of the prior applications are incorporated herein by reference in their entirety.

TECHNICAL FIELD

The present invention relates to 1,3,4-oxadiazole homophthalimide derivative compounds having a histone deacetylase 6 (HDAC6) inhibitory activity, stereoisomers thereof, pharmaceutically acceptable salts thereof, a use thereof in preparation of a medicament, a pharmaceutical composition comprising the same, a therapeutic method using the composition, and a method for preparing the same.

BACKGROUND

In cells, a post-translational modification such as acetylation serves as a very important regulatory module at the hub of biological processes, and is also strictly controlled by a number of enzymes. As a core protein constituting chromatin, histone functions as an axis, around which DNA winds, and thus helps a DNA condensation. Also, a balance between acetylation and deacetylation of histone plays a very important role in gene expression.

As an enzyme for removing an acetyl group from lysine residue of histone protein, which constitutes chromatin, histone deacetylase (HDAC) is known to be associated with gene silencing and induce a cell cycle arrest, angiogenic inhibition, immunoregulation, apoptosis, etc. (Hassig et al., Curr. Opin. Chem. Biol. 1997, 1, 300-308). Also, it is reported that the inhibition of HDAC enzyme functions induces cancer cells into committing apoptosis for themselves by lowering an activity of cancer cell survival-related factors and activating cancer cell death-related factors in the body (Warrell et al., J. Natl. Cancer Inst. 1998, 90, 1621-1625).

For humans, 18 HDACs are known and classified into four classes according to homology with yeast HDAC. In this case, eleven HDACs using zinc as a cofactor may be divided into three groups: Class I (HDAC1, 2, 3, 8), Class II (IIa: HDAC4, 5, 7, 9; IIb: HDAC6, 10) and Class IV (HDAC11). Further, seven HDACs of Class III (SIRT 1-7) use NAD+ as a cofactor instead of zinc (Bolden et al., Nat. Rev. Drug Discov. 2006, 5(9), 769-784).

Various HDAC inhibitors are now in a preclinical or clinical development stage, but only non-selective HDAC inhibitors have been known as an anti-cancer agent so far. Vorinostat (SAHA) and romidepsin (FK228) have obtained an approval as a therapeutic agent for cutaneous T-cell lymphoma, while panobinostat (LBH-589) has won an approval as a therapeutic agent for multiple myeloma. However, it is known that the non-selective HDAC inhibitors generally bring about side effects such as fatigue, nausea and the like at high doses (Piekarz et al., Pharmaceuticals 2010, 3, 2751-2767). It is reported that the side effects are caused by the inhibition of class I HDACs. Due to the side effects, etc., the non-selective HDAC inhibitors have been subject to restriction on drug development in other fields than an anticancer agent. (Witt et al., Cancer Letters 277 (2009) 8.21).

Meanwhile, it is reported that the selective inhibition of class II HDACs would not show toxicity, which have occurred in the inhibition of class I HDACs. In case of developing the selective HDAC inhibitors, it would be likely to solve side effects such as toxicity, etc., caused by the non-selective inhibition of HDACs. Accordingly, there is a chance that the selective HDAC inhibitors may be developed as an effective therapeutic agent for various diseases (Matthias et al., Mol. Cell. Biol. 2008, 28, 1688-1701).

HDAC6, one of the class IIb HDACs, is known to be mainly present in cytoplasma and contain a tubulin protein, thus being involved in the deacetylation of a number of non-histone substrates (HSP90, cortactin, etc.) (Yao et al., Mol. Cell 2005, 18, 601-607). HDAC6 has two catalytic domains, in which a zinc finger domain of C-terminal may bind to an ubiquitinated protein. HDAC6 is known to have a number of non-histone proteins as a substrate, and thus play an important role in various diseases such as cancer, inflammatory diseases, autoimmune diseases, neurological diseases, neurodegenerative disorders and the like (Santo et al., Blood 2012 119: 2579-2589; Vishwakarma et al., International Immunopharmacology 2013, 16, 72-78; Hu et al., J. Neurol. Sci. 2011, 304, 1-8).

A structural feature that various HDAC inhibitors have in common is comprised of a cap group, a linker and a zinc binding group (ZBG) as shown in a following structure of vorinostat. Many researchers have conducted a study on the inhibitory activity with regards to enzymes and selectivity through a structural modification of the cap group and the linker. Out of the groups, it is known that the zinc binding group plays a more important role in the enzyme inhibitory activity and selectivity (Wiest et al., J. Org. Chem. 2013 78: 5051-5065; Methot et al., Bioorg. Med. Chem. Lett. 2008, 18, 973-978).

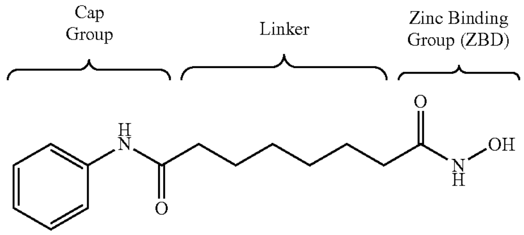 [SMILES: O=C(CCCCCCC(=O)Nc1ccccc1)NO]

Most of said zinc binding group is comprised of hydroxamic acid or benzamide, out of which hydroxamic acid derivatives show a strong HDAC inhibitory effect, but have a problem with low bioavailability and serious off-target activity. Benzamide contains aniline, and thus has a problem in that benzamide may produce toxic metabolites in vivo (Woster et al., Med. Chem. Commun. 2015, online publication).

Accordingly, unlike the non-selective inhibitors having side effects, there is a need to develop a selective HDAC6 inhibitor, which has a zinc binding group with improved bioavailability, while causing no side effects in order to treat cancer, inflammatory diseases, autoimmune diseases, neurological diseases, neurodegenerative disorders and the like.

PRIOR ART REFERENCE (Patent Document 1) International Patent Publication No. WO 2011/091213 (publicized on Jul. 28, 2011): ACY-1215

(Patent Document 2) International Patent Publication No. WO 2011/011186 (publicized on Jan. 27, 2011): Tubastatin (Patent Document 3) International Patent Publication No. WO 2013/052110 (publicized on Apr. 11, 2013): Sloan-K (Patent Document 4) International Patent Publication No. WO 2013/041407 (publicized on Mar. 28, 2013): Cellzome (Patent Document 5) International Patent Publication No. WO 2013/134467 (publicized on Sep. 12, 2013): Kozi (Patent Document 6) International Patent Publication No. WO 2013/008162 (publicized on Jan. 17, 2013): Novartis (Patent Document 7) International Patent Publication No. WO 2013/080120 (publicized on Jun. 6, 2013): Novartis (Patent Document 8) International Patent Publication No. WO 2013/066835 (publicized on May 10, 2013): Tempero (Patent Document 9) International Patent Publication No. WO 2013/066838 (publicized on May 10, 2013): Tempero (Patent Document 10) International Patent Publication No. WO 2013/066833 (publicized on May 10, 2013): Tempero (Patent Document 11) International Patent Publication No. WO 2013/066839 (publicized on May 10, 2013): Tempero

DETAILED DESCRIPTION OF THE INVENTION

Technical Problem

An objective of the present invention is to provide 1,3,4-oxadiazole homophthalimide derivative compounds having a selective HDAC6 inhibitory activity, stereoisomers thereof or pharmaceutically acceptable salts thereof.

Another objective of the present invention is to provide a method for preparing 1,3,4-oxadiazole homophthalimide derivative compounds, stereoisomers thereof or pharmaceutically acceptable salts thereof.

Still another objective of the present invention is to provide a pharmaceutical composition comprising 1,3,4-oxadiazole homophthalimide derivative compounds having a selective HDAC6 inhibitory activity, stereoisomers thereof or pharmaceutically acceptable salts thereof.

Still another objective of the present invention is to provide a pharmaceutical composition for preventing or treating HDAC6 activity-related diseases including cancer, inflammatory diseases, autoimmune diseases, neurological diseases or neurodegenerative disorders, comprising 1,3,4-oxadiazole homophthalimide derivative compounds, stereoisomers thereof or pharmaceutically acceptable salts thereof.

Still another objective of the present invention is to provide a method for preventing or treating HDAC6 activity-related diseases, comprising administering a therapeutically effective amount of a pharmaceutical composition comprising 1,3,4-oxadiazole homophthalimide derivative compounds, stereoisomers thereof or pharmaceutically acceptable salts thereof.

Still another objective of the present invention is to provide a method for selectively inhibiting HDAC6 by administering 1,3,4-oxadiazole homophthalimide derivative compounds, stereoisomers thereof or pharmaceutically acceptable salts thereof into mammals including humans.

Still another objective of the present invention is to provide a use of 1,3,4-oxadiazole homophthalimide derivative compounds, stereoisomers thereof or pharmaceutically acceptable salts thereof for preventing or treating HDAC6 activity-related diseases.

Still another objective of the present invention is to provide a use of 1,3,4-oxadiazole homophthalimide derivative compounds, stereoisomers thereof or pharmaceutically acceptable salts thereof in preparation of a medicament for preventing or treating HDAC6 activity-related diseases.

Technical Solution

The present inventors have found 1,3,4-oxadiazole homophthalimide derivative compounds having a histone deacetylase 6 (HDAC6) inhibitory activity and have used the same in preventing or treating HDAC6 activity-related diseases, thereby completing the present invention.

1,3,4-oxadiazole Homophthalimide Derivative Compounds

The present invention provides 1,3,4-oxadiazole homophthalimide derivative compounds represented by a following chemical formula I, stereoisomers thereof or pharmaceutically acceptable salts thereof:

[Chemical Formula I]

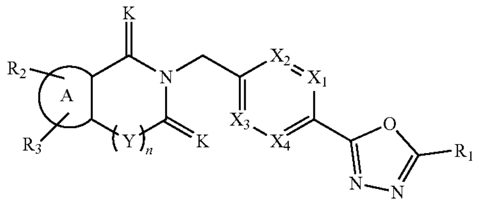

wherein, $X_1$ to $X_4$ are each independently $CR_0$ or N, in which each $R_0$ is independently hydrogen, halogen, straight or branched $-C_{1-7}$ alkyl, or straight or branched $-O-C_{1-7}$ alkyl when at least two of $X_1$ to $X_4$ are $CR_0$, $R_1$ is straight or branched $-C_{1-5}$ haloalkyl, $R_2$ and $R_3$ are each independently H, halogen,

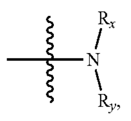

3- to 7-membered heterocycloalkyl containing one to three heteroatoms selected from group including N, O or S, 3- to 7-membered heterocycloalkenyl containing one to three heteroatoms selected from the group including N, O or S, 5- or 6-membered heteroaryl containing one to three heteroatoms selected from the group including N, O or S,

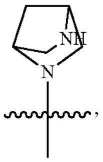,

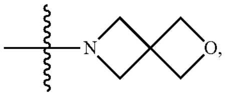 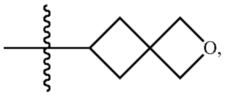 [SMILES: *C1CC2(COC2)C1]

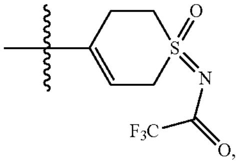 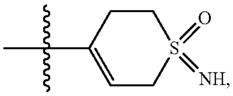

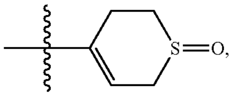

$C_{1-7}$ alkyl, 3- to 7-membered cycloalkyl, 3- to 7-membered cycloalkenyl, cyclopenta-1,3-diene, phenyl, indolyl,

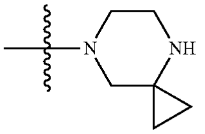 [SMILES: *N1CCNC2(CC2)C1] or 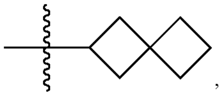,

{in which at least one hydrogen of said 3- to 7-membered heterocycloalkyl containing one to three heteroatoms selected from the group including N, O or S, 3- to 7-membered heterocycloalkenyl containing one to three heteroatoms selected from the group including N, O or S, 5- or 6-membered heteroaryl containing one to three heteroatoms selected from the group including N, O or S,

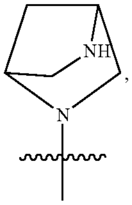, 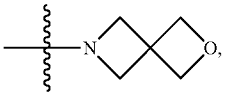

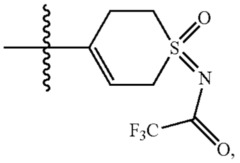

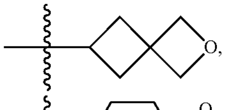

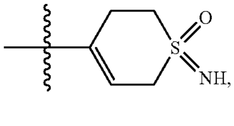 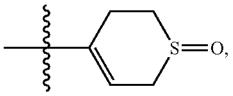

—$C_{1-7}$ alkyl, 3- to 7-membered cycloalkyl, 3- to 7-membered cycloalkenyl, cyclopenta-1,3-diene, phenyl, indolyl,

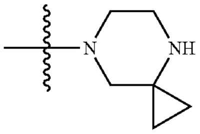 [SMILES: *N1CCNC2(CC2)C1] or 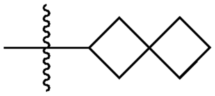

can be substituted with $R_4$, $R_4$ is halogen, —$C_{1-7}$ alkyl, —$C_{1-7}$ haloalkyl, —O—$C_{1-7}$ alkyl, —C(═O)—$C_{1-7}$ alkyl, —C(═O)—$C_{1-7}$ alkyl-OH, —C(═O)—O—$C_{1-7}$ alkyl, —S(═O)$_2$—$C_{1-7}$ alkyl, 3- to 7-membered cycloalkyl, 3- to 7-membered halocycloalkyl, 3- to 7-membered heterocycloalkyl containing one to three heteroatoms selected from the group including N, O or S, 5- or 6-membered heteroaryl containing one to three heteroatoms selected from the group including N, O or S,

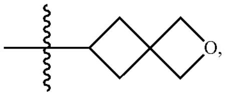

—$C_{1-7}$ alkyl-C(═O)—$R_5$, —$C_{1-7}$ alkyl-C(═O)—O—$R_6$, —$C_{1-7}$ alkyl-$R_7$, —$C_{1-7}$ alkyl-O—$R_8$, —$NR_9R_{10}$, —C(═O)—$NR_{11}R_{12}$ or —$C_{1-7}$ alkyl-$NR_{13}R_{14}$, in which $R_5$ is —$C_{1-7}$ alkyl, 3- to 7-membered heterocycloalkyl containing one to three heteroatoms selected from the group including N, O or S, 5- or 6-membered heteroaryl containing one to three heteroatoms selected from the group including N, O or S, 3- to 7-membered cycloalkyl, cyclopenta-1,3-diene or phenyl, $R_6$ is —$C_{1-7}$ alkyl, 3- to 7-membered heterocycloalkyl containing one to three heteroatoms selected from the group including N, O or S, 5- or 6-membered heteroaryl containing one to three heteroatoms selected from the group including N, O or S, 3- to 7-membered cycloalkyl, cyclopenta-1,3-diene or phenyl, $R_7$ is 3- to 7-membered heterocycloalkyl containing one to three heteroatoms selected from the group including N, O or S, 3- to 7-membered cycloalkyl, 5- or 6-membered heteroaryl containing one to three heteroatoms selected from the group including N, O or S, cyclopenta-1,3-diene or phenyl, $R_8$ is —$C_{1-7}$ alkyl, 3- to 7-membered heterocycloalkyl containing one to three heteroatoms selected from the group including N, O or S, 5- or 6-membered heteroaryl containing one to three heteroatoms selected from the group including N, O or S, 3- to 7-membered cycloalkyl, cyclopenta-1,3-diene or phenyl, $R_9$ and $R_{10}$ are each independently H or —$C_{1-7}$ alkyl, $R_{11}$ and $R_{12}$ are each independently H or —$C_{1-7}$ alkyl, and $R_{13}$ and $R_{14}$ are each independently H or —$C_{1-7}$ alkyl}, $R_x$ and $R_y$ are each independently —$C_{1-7}$ alkyl, —$C_{1-7}$ alkyl-$NR_{15}R_{16}$, H, —$C_{1-7}$ alkyl-O—$C_{1-7}$ alkyl, —C(═O)—$C_{1-7}$ alkyl, —C(═O)-heteroaryl [in this case, heteroaryl is 5- or 6-membered heteroaryl containing one to three heteroatoms selected from the group including N, O or S], —C(═O)-heterocycloalkyl [in this case, heterocycloalkyl is 3- to 7-membered heterocycloalkyl containing one to three heteroatoms selected from the group including N, O or S], —C(═O)-cycloalkyl [in this case, cycloalkyl is 3- to 7-membered cycloalkyl], —$C_{1-7}$ alkyl-O-heterocycloalkyl [in this case, heterocycloalkyl is 3- to 7-membered heterocycloalkyl containing one to three heteroatoms selected from the group including N, O or S] or —$C_{1-7}$ alkyl-cycloalkyl [in this case, cycloalkyl is 3- to 7-membered cycloalkyl], {in which at least one hydrogen of —$C_{1-7}$ alkyl, —$C_{1-7}$ alkyl-O—$C_{1-7}$ alkyl, —C(═O)—$C_{1-7}$ alkyl, —C(═O)-heteroaryl [in this case, heteroaryl is 5- or 6-membered heteroaryl containing one to three heteroatoms selected from the group including N, O or S], —C(═O)-heterocycloalkyl [in this case, heterocycloalkyl is 3- to 7-membered heterocycloalkyl containing one to three heteroatoms selected from the group including N, O or S], —C(═O)-cycloalkyl [in this case, cycloalkyl is 3- to 7-membered cycloalkyl], —$C_{1-7}$ alkyl-O-heterocycloalkyl [in this case, heterocycloalkyl is 3- to 7-membered heterocycloalkyl containing one to three heteroatoms selected from the group including N, O or S] or —$C_{1-7}$ alkyl-cycloalkyl [in this case, cycloalkyl is 3- to 7-membered cycloalkyl] can be substituted with —$C_{1-7}$ alkyl, halogen, —O—$C_{1-7}$ alkyl, 3- to 7-membered heterocycloalkyl containing one to three heteroatoms selected from the group including N, O or S, 5- or 6-membered heteroaryl containing one to three heteroatoms selected from the group including N, O or S, 3- to 7-membered cycloalkyl, —S(═O)$_2$—$C_{1-7}$ alkyl, —$CF_3$,

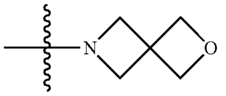 or 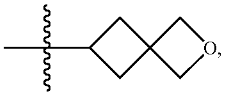 [SMILES: *C1CC2(COC2)C1]

and $R_{15}$ and $R_{16}$ are each independently H or —$C_{1-7}$ alkyl},

K is O or S,

Y is $CR_aR_b$, $NR_c$ or a single bond, $R_a$ and $R_b$ are each independently hydrogen, —$C_{1-7}$ alkyl, 3- to 7-membered cycloalkyl, —$C_{1-7}$ alkyl-O—$C_{1-7}$ alkyl, —$C_{1-7}$ alkyl-$NR_{17}R_{18}$, 3- to 7-membered heterocycloalkyl containing one to three heteroatoms selected from the group including N, O or S, —$C_{1-7}$ alkyl-C(═O)—$C_{1-7}$ alkyl or —$C_{1-7}$ alkyl-C(═O)—O—$C_{1-7}$ alkyl, or $R_a$ and $R_b$ are linked to each other to form 3- to 7-membered cycloalkyl, {in which at least one hydrogen of $C_{1-7}$ alkyl, 3- to 7-membered cycloalkyl, —$C_{1-7}$ alkyl-O—$C_{1-7}$ alkyl, —$C_{1-7}$ alkyl-$NR_{17}R_{18}$, 3- to 7-membered heterocycloalkyl containing one to three heteroatoms selected from the group including N, O or S, —$C_{1-7}$ alkyl-C(═O)—$C_{1-7}$ alkyl or —$C_{1-7}$ alkyl-C(═O)—O—$C_{1-7}$ alkyl can be substituted with —$C_{1-7}$ alkyl, halogen, —O—$C_{1-7}$ alkyl, 3- to 7-membered heterocycloalkyl containing one to three heteroatoms selected from the group including N, O or S, 5- or 6-membered heteroaryl containing one to three heteroatoms selected from the group including N, O or S, 3- to 7-membered cycloalkyl, —S(═O)$_2$—$C_{1-7}$ alkyl, —$CF_3$,

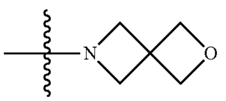 or 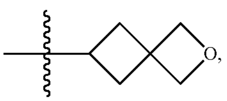

and $R_{17}$ and $R_{18}$ are each independently H or —$C_{1-7}$ alkyl}, $R_c$ is hydrogen, —$C_{1-7}$ alkyl, —$C_{1-7}$ alkyl-heterocycloalkyl (in this case, heterocycloalkyl is 3- to 7-membered heterocycloalkyl containing one to three heteroatoms selected from the group including N, O or S), —$C_{1-7}$ alkyl-phenyl, —$C_{1-7}$ alkyl-heteroaryl (in this case, heteroaryl is 5- or 6-membered heteroaryl containing one to three heteroatoms selected from the group including N, O or S), —$C_{1-7}$ alkyl-O—$C_{1-7}$ alkyl, —$C_{1-7}$ alkyl-$NR_{19}R_{20}$, —$C_{1-7}$ alkyl-cycloalkyl (in this case, cycloalkyl is 3- to 7-membered cycloalkyl), 3- to 7-membered heterocycloalkyl containing one to three heteroatoms selected from the group including N, O or S, 3- to 7-membered cycloalkyl, 5- or 6-membered heteroaryl containing one to three heteroatoms selected from the group including N, O or S, cyclopenta-1,3-diene, phenyl, —C(═O)-heterocycloalkyl (in this case, heterocycloalkyl is 3- to 7-membered heterocycloalkyl containing one to three heteroatoms selected from the group including N, O or S), —C(═O)-cycloalkyl (in this case, cycloalkyl is 3- to 7-membered cycloalkyl), —C(═O)-heteroaryl (in this case, heteroaryl is 5- or 6-membered heteroaryl containing one to three heteroatoms selected from the group including N, O or S), —C(═O)-phenyl, —C(═O)—$C_{1-7}$ alkyl, —C(═O)—$C_{1-7}$ alkyl-O—$C_{1-7}$ alkyl or —C(═O)—$C_{1-7}$ alkyl-$NR_{19}R_{20}$, (in which at least one hydrogen of —$C_{1-7}$ alkyl, —$C_{1-7}$ alkyl-heterocycloalkyl (Fin this case, heterocycloalkyl is 3- to 7-membered heterocycloalkyl containing one to three heteroatoms selected from the group including N, O or S), —$C_{1-7}$ alkyl-phenyl, —$C_{1-7}$ alkyl-heteroaryl (in this case, heteroaryl is 5- or 6-membered heteroaryl containing one to three heteroatoms selected from the group including N, O or S), —$C_{1-7}$ alkyl-O—$C_{1-7}$ alkyl, —$C_{1-7}$ alkyl-$NR_{19}R_{20}$, —$C_{1-7}$ alkyl-cycloalkyl (in this case, cycloalkyl is 3- to 7-membered cycloalkyl), 3- to 7-membered heterocycloalkyl containing one to three heteroatoms selected from the group including N, O or S, 3- to 7-membered cycloalkyl, 5- or 6-membered heteroaryl containing one to three heteroatoms selected from the group including N, O or S, cyclopenta-1,3-diene, phenyl, —C(═O)-heterocycloalkyl (in this case, heterocycloalkyl is 3- to 7-membered heterocycloalkyl containing one to three heteroatoms selected from the group including N, O or S), —C(═O)-cycloalkyl (in this case, cycloalkyl is 3- to 7-membered cycloalkyl), —C(═O)-heteroaryl (in this case, heteroaryl is 5- or 6-membered heteroaryl containing one to three heteroatoms selected from the group including N, O or S), —C(═O)-phenyl, —C(═O)—$C_{1-7}$ alkyl, —C(═O)—$C_{1-7}$ alkyl-O—$C_{1-7}$ alkyl or —C(═O)—$C_{1-7}$ alkyl-$NR_{19}R_{20}$ can be substituted with-$C_{1-7}$ alkyl, halogen, —O—$C_{1-7}$ alkyl, 3- to 7-membered heterocycloalkyl containing one to three heteroatoms selected from the group including N, O or S, —C(═O)—O—$C_{1-7}$ alkyl, 5- or 6-membered heteroaryl containing one to three heteroatoms selected from the group including N, O or S, heteroaryl-$C_{1-5}$ haloalkyl (in this case, heteroaryl is 5- or 6-membered heteroaryl containing one to three heteroatoms selected from the group including N, O or S), 3- to 7-membered cycloalkyl, —S(═O)$_2$—$C_{1-7}$ alkyl, —$CF_3$,

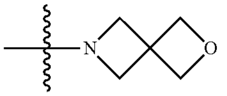 or 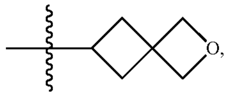

and $R_{19}$ and $R_{20}$ are each independently H or $-C_{1-7}$ alkyl),

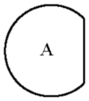

is phenylene or 5- or 6-membered heteroarylene containing one to three heteroatoms selected from the group including N, O or S, halogen is F, Cl, Br or I, and n is 0 or 1.

In the present specification, the terms used in the definition of a substituent of 1,3,4-oxadiazole homophthalimide derivative compounds of the present invention, stereoisomers thereof or pharmaceutically acceptable salts thereof are as follows.

In the present invention, the term "substitution" means that a hydrogen atom bonded to a carbon atom of a compound is replaced with another substituent, and a position to be substituted is not limited to a certain position, as long as the hydrogen atom is substituted, that is, a position where the substituent may be substituted. If there are two or more substitutions, the two or more substituents may be the same or different from each other.

In the present invention, the term "halogen" represents an element of a halogen group and includes, for example, fluoro (F), chloro (Cl), bromo (Br) or iodo (I).

In the present invention, the term "alkyl" refers to straight or branched saturated hydrocarbon having the specified number of carbon atoms unless otherwise specified.

In the present invention, the term "haloalkyl" means that at least one hydrogen atom bonded to straight or branched saturated hydrocarbon having the specified number of carbon atoms is substituted with halogen unless otherwise specified.

In the present invention, the term "heterocycloalkyl" means cyclic saturated hydrocarbon containing one to three heteroatoms selected from the group including N, O or S. Examples of heterocycloalkyl include, without limitation, azetidinyl, pyrrolidinyl, piperidinyl, piperazinyl, pyrrolidonyl, piperidonyl, morpholidinyl, imidazolidinyl, pyrazolidinyl, oxetanyl, tetrahydro-2H-pyranyl, morpholinyl, thiomorpholinyl, oxazolidinonyl, and thiazolidinonyl.

In the present invention, the term "heterocycloalkenyl" includes at least one double bond and means cyclic unsaturated hydrocarbon containing one to three heteroatoms selected from the group including N, O or S. Examples of heterocycloalkenyl include, without limitation, tetrahydropyridinyl, dihydrofuranyl, and 2,5-dihydro-1H-pyrrolyl.

In the present invention, the term "heteroaryl" means a heterocyclic aromatic group containing one to three heteroatoms selected from the group including N, O or S. Examples of heteroaryl include, without limitation, furanyl, pyrrolyl, thiophenyl, thiazolyl, isothiazolyl, imidazolyl, triazolyl, tetrazolyl, pyrazolyl, oxazolyl, isoxazolyl, pyridinyl, pyrazinyl, pyridazinyl, pyrimidinyl and triazinyl.

In the present invention, the term "cycloalkyl" means cyclic saturated hydrocarbon containing the specified number of carbon atoms. Examples of cycloalkyl include, without limitation, cyclopropyl, cyclobutyl, cyclopentyl, cyclohexyl and cycloheptyl.

In the present invention, the term "halocycloalkyl" means that at least one hydrogen atom bonded to cyclic saturated hydrocarbon containing the specified number of carbon atoms is substituted with halogen unless otherwise specified.

In the present invention, the term "cycloalkenyl" means cyclic unsaturated hydrocarbon which is comprised of the specified number of carbon atoms and includes at least one double bond. Examples of cycloalkenyl include, without limitation, cyclopropenyl, cyclobutenyl, cyclopentenyl, cyclohexenyl and cycloheptenyl.

In the present invention, the term "single bond" means that an atom is not present in a corresponding site. For example, if Y is a single bond in an X—Y—Z structure, X and Z are directly linked to form an X—Z structure.

In the present invention, out of said substituents,

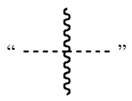

means a bonding point of an atom, which is linked to a rest of a molecule or a rest of a molecule fragment in a chemical structure.

In the present invention,

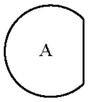

represents a structure fused by sharing two carbon atoms with another ring, and the two shared/fused carbon atoms mean two arranged in a row. For example,

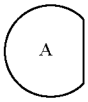

means phenylene or 5- or 6-membered heteroarylene containing one to three heteroatoms selected from the group including N, O or S. "5- or 6-membered heteroarylene" of said

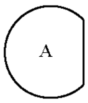

means furanylene, pyrrolylene, thiophenylene, thiazolylene, isothiazolylene, imidazolylene, triazolylene, tetrazolylene, pyrazolylene, oxazolylene, isoxazolylene, pyridinylene, pyrazinylene, pyridazinylene, pyrimidinylene, triazinylene and the like, which contain one to three heteroatoms selected from the group including N, O or S. In this case, said phenylene and said heteroarylene are fused by sharing two carbon atoms with another ring (a ring containing Y of the chemical formula I, having a structure represented by

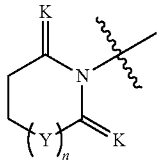

).

In this case, the two carbon atoms fused by sharing in phenylene or 5- or 6-membered heteroarylene are two arranged in a row out of carbon atoms constituting another ring (a ring containing Y of the chemical formula I). As an example, if

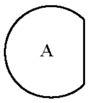

is phenylene, the chemical formula I may contain a structure of

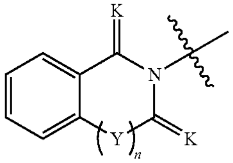

.

According to one embodiment aspect of the present invention, there is provided the compound represented by the above chemical formula I, wherein:

$X_1$ to $X_4$ are each independently $CR_0$ or N, in which $R_0$ is hydrogen, halogen or —O—$C_{1-7}$ alkyl, $R_1$ is —$C_{1-5}$ haloalkyl, $R_2$ and $R_3$ are each independently H, halogen,

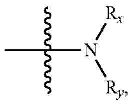

3- to 7-membered heterocycloalkyl containing one to three heteroatoms selected from group including N, O or S, 3- to 7-membered heterocycloalkenyl containing one to three heteroatoms selected from the group including N, O or S, 5- or 6-membered heteroaryl containing one to three heteroatoms selected from the group including N, O or S,

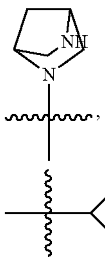, 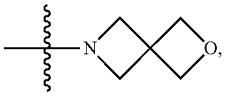

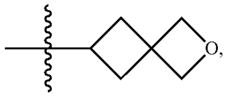 [SMILES: *C1CC2(COC2)C1]

-continued

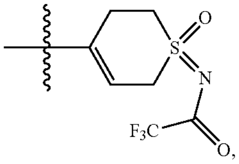 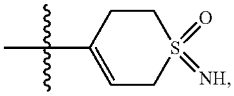

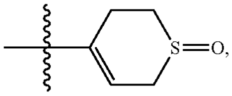

phenyl, indolyl,

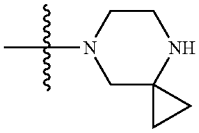

or —$C_{1-7}$ alkyl,

{in which at least one hydrogen of said 3- to 7-membered heterocycloalkyl containing one to three heteroatoms selected from the group including N, O or S, 3- to 7-membered heterocycloalkenyl containing one to three heteroatoms selected from the group including N, O or S, 5- or 6-membered heteroaryl containing one to three heteroatoms selected from the group including N, O or S,

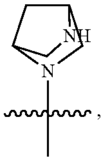, 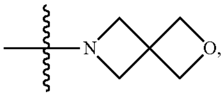

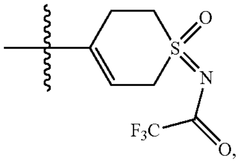

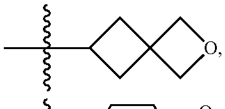

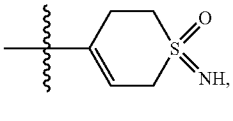 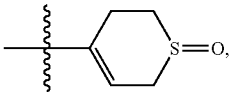

phenyl, indolyl,

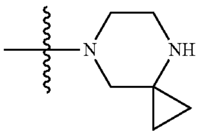

or —$C_{1-7}$ alkyl can be substituted with $R_4$, $R_4$ is halogen, —$C_{1-7}$ alkyl, —$C_{1-7}$ haloalkyl, —O—$C_{1-7}$ alkyl, —C(═O)—$C_{1-7}$ alkyl, —C(═O)—$C_{1-7}$ alkyl-OH, —C(═O)—O—$C_{1-7}$ alkyl, —S(═O)$_2$—$C_{1-7}$ alkyl, 3- to 7-membered cycloalkyl, 3- to 7-membered halocycloalkyl, 3- to 7-membered heterocycloalkyl containing one to three heteroatoms selected from the group including N, O or S, 5- or 6-membered heteroaryl containing one to three heteroatoms selected from the group including N, O or S,

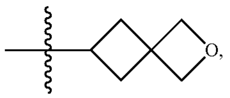

—$C_{1-7}$ alkyl-C(═O)—$R_5$, —$C_{1-7}$ alkyl-C(═O)—O—$R_6$, —$C_{1-7}$ alkyl-$R_7$, —$C_{1-7}$ alkyl-O—$R_8$, —$NR_9R_{10}$, —C(═O)—$NR_{11}R_{12}$ or —$C_{1-7}$ alkyl-$NR_{13}R_{14}$, in which $R_5$ is —$C_{1-7}$ alkyl or 3- to 7-membered heterocycloalkyl containing one to three heteroatoms selected from the group including N, O or S, $R_6$ is —$C_{1-7}$ alkyl, $R_7$ is 3- to 7-membered heterocycloalkyl containing one to three heteroatoms selected from the group including N, O or S or 3- to 7-membered cycloalkyl, $R_8$ is —$C_{1-7}$ alkyl, $R_9$ and $R_{10}$ are each independently H or —$C_{1-7}$ alkyl, $R_{11}$ and $R_{12}$ are each independently H or —$C_{1-7}$ alkyl, and $R_{13}$ and $R_{14}$ are each independently H or —$C_{1-7}$ alkyl}, $R_x$ and $R_y$ are each independently —$C_{1-7}$ alkyl, —$C_{1-7}$ alkyl-$NR_{15}R_{16}$, H, —$C_{1-7}$ alkyl-O—$C_{1-7}$ alkyl, —C(═O)—$C_{1-7}$ alkyl, —C(═O)-heteroaryl [in this case, heteroaryl is 5- or 6-membered heteroaryl containing one to three heteroatoms selected from the group including N, O or S], —C(═O)-heterocycloalkyl [in this case, heterocycloalkyl is 3- to 7-membered heterocycloalkyl containing one to three heteroatoms selected from the group including N, O or S] or —C(═O)-cycloalkyl [in this case, cycloalkyl is 3- to 7-membered cycloalkyl], {in which at least one hydrogen of —$C_{1-7}$ alkyl, —$C_{1-7}$ alkyl-O—$C_{1-7}$ alkyl, —C(═O)—$C_{1-7}$ alkyl, —C(═O)-heteroaryl [in this case, heteroaryl is 5- or 6-membered heteroaryl containing one to three heteroatoms selected from the group including N, O or S], —C(═O)-heterocycloalkyl [in this case, heterocycloalkyl is 3- to 7-membered heterocycloalkyl containing one to three heteroatoms selected from the group including N, O or S] or —C(═O)-cycloalkyl [in this case, cycloalkyl is 3- to 7-membered cycloalkyl] can be substituted with —$C_{1-7}$ alkyl, halogen, —O—$C_{1-7}$ alkyl, 3- to 7-membered heterocycloalkyl containing one to three heteroatoms selected from the group including N, O or S, 5- or 6-membered heteroaryl containing one to three heteroatoms selected from the group including N, O or S, 3- to 7-membered cycloalkyl, —S(═O)$_2$—$C_{1-7}$ alkyl, —$CF_3$,

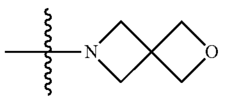

or

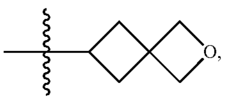 [SMILES: *C1CC2(COC2)C1]

and $R_{15}$ and $R_{16}$ are each independently H or —$C_{1-7}$ alkyl},

K is O or S,

Y is $CR_aR_b$, $NR_c$ or a single bond, $R_a$ and $R_b$ are each independently hydrogen, —$C_{1-7}$ alkyl, 3- to 7-membered cycloalkyl, —$C_{1-7}$ alkyl-O—$C_{1-7}$ alkyl, —$C_{1-7}$ alkyl-$NR_{17}R_{18}$, or $R_a$ and $R_b$ are linked to each other to form 3- to 7-membered cycloalkyl, {in which at least one hydrogen of —$C_{1-7}$ alkyl, 3- to 7-membered cycloalkyl, —$C_{1-7}$ alkyl-O—$C_{1-7}$ alkyl or —$C_{1-7}$ alkyl-$NR_{17}R_{18}$ can be substituted with —$C_{1-7}$ alkyl, halogen, —O—$C_{1-7}$ alkyl, 3- to 7-membered heterocycloalkyl containing one to three heteroatoms selected from the group including N, O or S, 5- or 6-membered heteroaryl containing one to three heteroatoms selected from the group including N, O or S, 3- to 7-membered cycloalkyl, —S(═O)$_2$—$C_{1-7}$ alkyl, —$CF_3$,

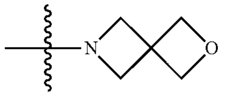

or

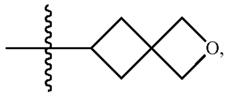

and $R_{17}$ and $R_{18}$ are each independently H or —$C_{1-7}$ alkyl}, $R_c$ is hydrogen, —$C_{1-7}$ alkyl, —$C_{1-7}$ alkyl-heterocycloalkyl (in this case, heterocycloalkyl is 3- to 7-membered heterocycloalkyl containing one to three heteroatoms selected from the group including N, O or S), —$C_{1-7}$ alkyl-phenyl, —$C_{1-7}$ alkyl-heteroaryl (in this case, heteroaryl is 5- or 6-membered heteroaryl containing one to three heteroatoms selected from the group including N, O or S), —$C_{1-7}$ alkyl-O—$C_{1-7}$ alkyl, —$C_{1-7}$ alkyl-$NR_{19}R_{20}$, —$C_{1-7}$ alkyl-cycloalkyl (in this case, cycloalkyl is 3- to 7-membered cycloalkyl), 3- to 7-membered heterocycloalkyl containing one to three heteroatoms selected from the group including N, O or S, 3- to 7-membered cycloalkyl, 5- or 6-membered heteroaryl containing one to three heteroatoms selected from the group including N, O or S, cyclopenta-1,3-diene, phenyl, —C(═O)-heterocycloalkyl (Ein this case, heterocycloalkyl is 3- to 7-membered heterocycloalkyl containing one to three heteroatoms selected from the group including N, O or S), —C(═O)-cycloalkyl (in this case, cycloalkyl is 3- to 7-membered cycloalkyl), —C(═O)-heteroaryl (in this case, heteroaryl is 5- or 6-membered heteroaryl containing one to three heteroatoms selected from the group including N, O or S), —C(═O)-phenyl, —C(═O)—$C_{1-7}$ alkyl, —C(═O)—$C_{1-7}$ alkyl-O—$C_{1-7}$ alkyl or —C(═O)—$C_{1-7}$ alkyl-$NR_{19}R_{20}$, (in which at least one hydrogen of —$C_{1-7}$ alkyl, —$C_{1-7}$ alkyl-heterocycloalkyl (Fin this case, heterocycloalkyl is 3- to 7-membered heterocycloalkyl containing one to three heteroatoms selected from the group including N, O or S), —$C_{1-7}$ alkyl-phenyl, —$C_{1-7}$ alkyl-heteroaryl (in this case, heteroaryl is 5- or 6-membered heteroaryl containing one to three heteroatoms selected from the group including N, O or S), —$C_{1-7}$ alkyl-O—$C_{1-7}$ alkyl, —$C_{1-7}$ alkyl-$NR_{19}R_{20}$, —$C_{1-7}$ alkyl-cycloalkyl (in this case, cycloalkyl is 3- to 7-membered cycloalkyl), 3- to 7-membered heterocycloalkyl containing one to three heteroatoms selected from the group including N, O or S, 3- to 7-membered cycloalkyl, 5- or 6-membered heteroaryl containing one to three heteroatoms selected from the group including N, O or S, cyclopenta-1,3-diene, phenyl, —C(═O)-heterocycloalkyl (in this case, heterocycloalkyl is 3- to 7-membered heterocycloalkyl containing one to three heteroatoms selected from the group including N, O or S), —C(═O)-cycloalkyl (in this case, cycloalkyl is 3- to 7-membered cycloalkyl), —C(═O)-heteroaryl (in this case, heteroaryl is 5- or 6-membered heteroaryl containing one to three heteroatoms selected from the group including N, O or S), —C(═O)-phenyl, —C(═O)—$C_{1-7}$ alkyl, —C(═O)—$C_{1-7}$ alkyl-O—$C_{1-7}$ alkyl or —C(═O)—$C_{1-7}$ alkyl-$NR_{19}R_{20}$ can be substituted with-$C_{1-7}$ alkyl, halogen, —O—$C_{1-7}$ alkyl, 3- to 7-membered heterocycloalkyl containing one to three heteroatoms selected from the group including N, O or S, —C(═O)—O—$C_{1-7}$ alkyl, 5- or 6-membered heteroaryl containing one to three heteroatoms selected from the group including N, O or S, heteroaryl-$C_{1-5}$ haloalkyl (in this case, heteroaryl is 5- or 6-membered heteroaryl containing one to three heteroatoms selected from the group including N, O or S), 3- to 7-membered cycloalkyl, —S(═O)$_2$—$C_{1-7}$ alkyl, —$CF_3$,

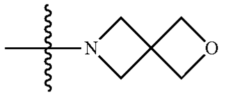

or

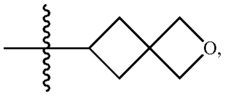

and $R_{19}$ and $R_{20}$ are each independently H or —$C_{1-7}$ alkyl),

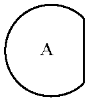

is phenylene or 5- or 6-membered heteroarylene containing one to three heteroatoms selected from the group including N, O or S, halogen is F, Cl, Br or I, and n is 0 or 1.

Also, according to a specific embodiment aspect of the present invention, there is provided the compound represented by the above chemical formula I, wherein:

$X_1$ to $X_4$ are each independently $CR_0$ or N, $R_0$ is hydrogen or halogen, $R_1$ is —$C_{1-5}$ haloalkyl, $R_2$ and $R_3$ are each independently H, halogen,

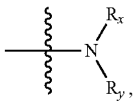

3- to 7-membered heterocycloalkyl containing one to three heteroatoms selected from group including N, O or S, 3- to 7-membered heterocycloalkenyl containing one to three heteroatoms selected from the group including N, O or S, 5- or 6-membered heteroaryl containing one to three heteroatoms selected from the group including N, O or S,

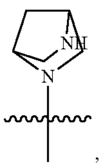

,

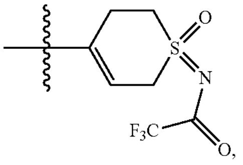

-continued

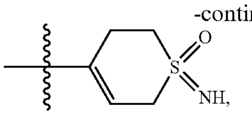

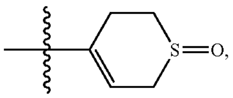

phenyl, indolyl,

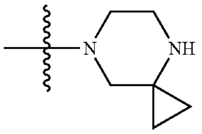

or

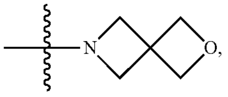

{in which at least one hydrogen of said 3- to 7-membered heterocycloalkyl containing one to three heteroatoms selected from the group including N, O or S, 3- to 7-membered heterocycloalkenyl containing one to three heteroatoms selected from the group including N, O or S, 5- or 6-membered heteroaryl containing one to three heteroatoms selected from the group including N, O or S,

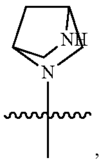

,

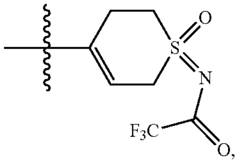

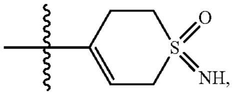

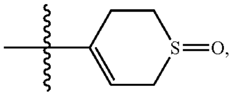

phenyl, indolyl,

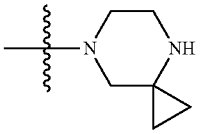

or

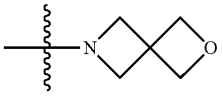

can be substituted with $R_4$, $R_4$ is halogen, —$C_{1-7}$ alkyl, —$C_{1-7}$ haloalkyl, —O—$C_{1-7}$ alkyl, —C(═O)—$C_{1-7}$ alkyl, —C(═O)—$C_{1-7}$ alkyl-OH, —C(═O)—O—$C_{1-7}$ alkyl, —S(═O)$_2$—$C_{1-7}$ alkyl, 3- to 7-membered cycloalkyl, 3- to 7-membered halocycloalkyl, 3- to 7-membered heterocycloalkyl containing one to three heteroatoms selected from the group including N, O or S, 5- or 6-membered heteroaryl containing one to three heteroatoms selected from the group including N, O or S,

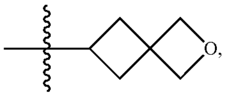

—$C_{1-7}$ alkyl-C(═O)—$R_5$, —$C_{1-7}$ alkyl-$R_7$, —$C_{1-7}$ alkyl-O—$R_8$, —$NR_9R_{10}$ or —C(═O)—$NR_{11}R_{12}$, in which $R_5$ is 3- to 7-membered heterocycloalkyl containing one to three heteroatoms selected from the group including N, O or S, $R_7$ is 3- to 7-membered heterocycloalkyl containing one to three heteroatoms selected from the group including N, O or S or 3- to 7-membered cycloalkyl, $R_8$ is $-C_{1-7}$ alkyl, $R_9$ and $R_{10}$ are each independently $-C_{1-7}$ alkyl, and $R_{11}$, and $R_{12}$ are each independently H or $-C_{1-7}$ alkyl}, $R_x$ and $R_y$ are each independently $-C_{1-7}$ alkyl or $-C_{1-7}$ alkyl-$NR_{15}R_{16}$, {in which $R_{15}$ and $R_{16}$ are each independently $-C_{1-7}$ alkyl}, K is O, Y is $CR_aR_b$, $NR_c$ or a single bond, $R_a$ and $R_b$ are each independently hydrogen or $-C_{1-7}$ alkyl, or $R_a$ and $R_b$ are linked to each other to form 3- to 7-membered cycloalkyl, $R_c$ is hydrogen, $-C_{1-7}$ alkyl, $-C_{1-7}$ alkyl-heterocycloalkyl [in this case, heterocycloalkyl is 3- to 7-membered heterocycloalkyl containing one to three heteroatoms selected from the group including N, O or S], $-C_{1-7}$ alkyl-phenyl, $-C_{1-7}$ alkyl-heteroaryl [in this case, heteroaryl is 5- or 6-membered heteroaryl containing one to three heteroatoms selected from the group including N, O or S], $-C_{1-7}$ alkyl-O$-C_{1-7}$ alkyl or $-C_{1-7}$ alkyl-$NR_{19}R_{20}$, {in which at least one hydrogen of $-C_{1-7}$ alkyl, $-C_{1-7}$ alkyl-heterocycloalkyl [in this case, heterocycloalkyl is 3- to 7-membered heterocycloalkyl containing one to three heteroatoms selected from the group including N, O or S], $-C_{1-7}$ alkyl-phenyl, $-C_{1-7}$ alkyl-heteroaryl [in this case, heteroaryl is 5- or 6-membered heteroaryl containing one to three heteroatoms selected from the group including N, O or S], $-C_{1-7}$ alkyl-O$-C_{1-7}$ alkyl or $-C_{1-7}$ alkyl-$NR_{19}R_{20}$ can be substituted with $-C_{1-7}$ alkyl, $-O-C_{1-7}$ alkyl, 3- to 7-membered heterocycloalkyl containing one to three heteroatoms selected from the group including N, O or S, heteroaryl-$C_{1-5}$ haloalkyl [in this case, heteroaryl is 5- or 6-membered heteroaryl containing one to three heteroatoms selected from the group including N, O or S] or $-C(=O)-O-C_{1-7}$ alkyl, and $R_{19}$ and $R_{20}$ are each independently $-C_{1-7}$ alkyl},

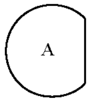

is phenylene, halogen is F or Br, and n is 0 or 1.

According to a more specific embodiment aspect of the present invention, there is provided the compound represented by the above chemical formula I, wherein:

$X_1$ to $X_4$ are each independently $CR_0$ or N, $R_0$ is hydrogen or F, $R_1$ is $CF_2H$, $R_2$ and $R_3$ are each independently H, F, Br,

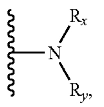

3- to 7-membered heterocycloalkyl containing one to three heteroatoms selected from group including N, O or S, 3- to 7-membered heterocycloalkenyl containing one to three heteroatoms selected from the group including N, O or S, 5- or 6-membered heteroaryl containing one to three heteroatoms selected from the group including N, O or S,

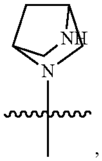,
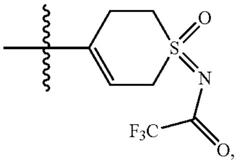
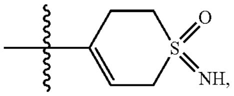
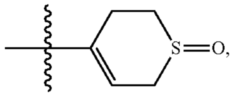

phenyl, indolyl,

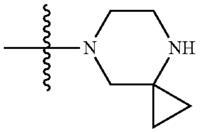 or 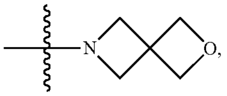

{in which at least one hydrogen of said 3- to 7-membered heterocycloalkyl containing one to three heteroatoms selected from the group including N, O or S, 3- to 7-membered heterocycloalkenyl containing one to three heteroatoms selected from the group including N, O or S, 5- or 6-membered heteroaryl containing one to three heteroatoms selected from the group including N, O or S,

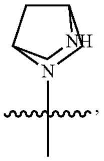,
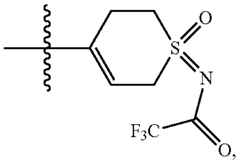
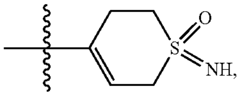
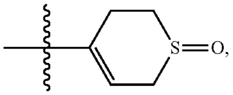

phenyl, indolyl,

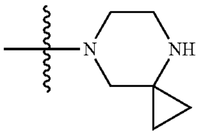 or 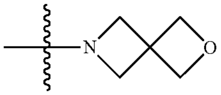

can be substituted with $R_4$, $R_4$ is F, $-C_{1-7}$ alkyl, $-C_{1-7}$ haloalkyl, $-O-C_{1-7}$ alkyl, $-C(=O)-C_{1-7}$ alkyl, $-C(=O)-C_{1-7}$ alkyl-OH, $-C(=O)-O-C_{1-7}$ alkyl, $-S(=O)_2-C_{1-7}$ alkyl, 3- to 7-membered cycloalkyl, 3- to 7-membered halocycloalkyl, 3- to 7-membered heterocycloalkyl containing one to three heteroatoms selected from the group including N, O or S, 5- or 6-membered heteroaryl containing one to three heteroatoms selected from the group including N, O or S,

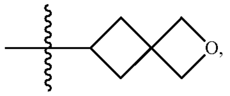

—$C_{1-7}$ alkyl-C(═O)—$R_5$, —$C_{1-7}$ alkyl-$R_7$, —$C_{1-7}$ alkyl-O—$R_8$, —$NR_9R_{10}$ or —C(═O)—$NR_{11}R_{12}$, in which $R_5$ is 3- to 7-membered heterocycloalkyl containing one to three heteroatoms selected from the group including N, O or S, $R_7$ is 3- to 7-membered heterocycloalkyl containing one to three heteroatoms selected from the group including N, O or S or 3- to 7-membered cycloalkyl, $R_8$ is —$C_{1-7}$ alkyl, $R_9$ and $R_{10}$ are each independently —$C_{1-7}$ alkyl, and $R_{11}$ and $R_{12}$ are each independently H or —$C_{1-7}$ alkyl}, $R_x$ and $R_y$ are each independently —$C_{1-7}$ alkyl or —$C_{1-7}$ alkyl-$NR_{15}R_{16}$, {in which $R_{15}$ and $R_{16}$ are each independently —$C_{1-7}$ alkyl}, K is O, Y is $CR_aR_b$, $NR_c$ or a single bond, $R_a$ and $R_b$ are each independently hydrogen or —$C_{1-7}$ alkyl, or $R_a$ and $R_b$ are linked to each other to form 3- to 7-membered cycloalkyl, $R_c$ is hydrogen, —$C_{1-7}$ alkyl, —$C_{1-7}$ alkyl-heterocycloalkyl [in this case, heterocycloalkyl is 3- to 7-membered heterocycloalkyl containing one to three heteroatoms selected from the group including N, O or S], —$C_{1-7}$ alkyl-phenyl, —$C_{1-7}$ alkyl-heteroaryl [in this case, heteroaryl is 5- or 6-membered heteroaryl containing one to three heteroatoms selected from the group including N, O or S], —$C_{1-7}$ alkyl-O—$C_{1-7}$ alkyl or —$C_{1-7}$ alkyl-$NR_{19}R_{20}$, {in which at least one hydrogen of —$C_{1-7}$ alkyl, —$C_{1-7}$ alkyl-heterocycloalkyl [in this case, heterocycloalkyl is 3- to 7-membered heterocycloalkyl containing one to three heteroatoms selected from the group including N, O or S], —$C_{1-7}$ alkyl-phenyl, —$C_{1-7}$ alkyl-heteroaryl [in this case, heteroaryl is 5- or 6-membered heteroaryl containing one to three heteroatoms selected from the group including N, O or S], —$C_{1-7}$ alkyl-O—$C_{1-7}$ alkyl or —$C_{1-7}$ alkyl-$NR_{19}R_{20}$ can be substituted with —$C_{1-7}$ alkyl, —O—$C_{1-7}$ alkyl, 3- to 7-membered heterocycloalkyl containing one to three heteroatoms selected from the group including N, O or S, heteroaryl-$C_{1-5}$ haloalkyl [in this case, heteroaryl is 5- or 6-membered heteroaryl containing one to three heteroatoms selected from the group including N, O or S] or —C(═O)—O—$C_{1-7}$ alkyl, and $R_{19}$ and $R_{20}$ are each independently —$C_{1-7}$ alkyl},

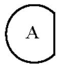

is phenylene, halogen is F or Br, and n is 0 or 1.

According to a specific embodiment aspect of the present invention, the compound represented by the above chemical formula I may be a compound represented by a following chemical formula I-1:

[Chemical Formula I-1]

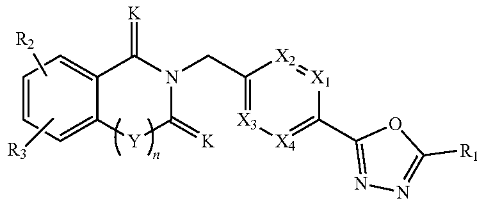

wherein $X_1$ to $X_4$, $R_1$ to $R_3$, Y, K and n are the same as defined in the chemical formula I.

The present invention provides 1,3,4-oxadiazole homophthalimide derivative compounds represented by a following chemical formula II, stereoisomers thereof or pharmaceutically acceptable salts thereof:

[Chemical Formula II]

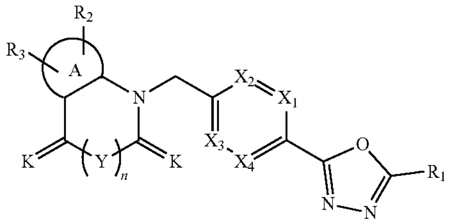

wherein,

A, $X_1$ to $X_4$, $R_1$ to $R_3$, Y, K and n are the same as defined in the chemical formula I.

According to a specific embodiment aspect of the present invention, there is provided the compound represented by the above chemical formula II, wherein:

$X_1$ to $X_4$ are each independently $CR_0$ or N, $R_0$ is hydrogen, $R_1$ is $CF_2H$, $R_2$ and $R_3$ are H, K is O, Y is $NR_c$, $R_c$ is —$C_{1-7}$ alkyl-phenyl, —$C_{1-7}$ alkyl-heteroaryl [in this case, heteroaryl is 5- or 6-membered heteroaryl containing one to three heteroatoms selected from the group including N, O or S] or —$C_{1-7}$ alkyl-O—$C_{1-7}$ alkyl, {in which at least one hydrogen of —$C_{1-7}$ alkyl-phenyl, —$C_{1-7}$ alkyl-heteroaryl [in this case, heteroaryl is 5- or 6-membered heteroaryl containing one to three heteroatoms selected from the group including N, O or S] or —$C_{1-7}$ alkyl-O—$C_{1-7}$ alkyl can be substituted with heteroaryl-$C_{1-5}$ haloalkyl [in this case, heteroaryl is 5- or 6-membered heteroaryl containing one to three heteroatoms selected from the group including N, O or S]},

is phenylene, halogen is F, and n is 1.

According to a specific embodiment aspect of the present invention, the compound represented by the above chemical formula II may be a compound represented by a following chemical formula II-1:

[Chemical Formula II-1]

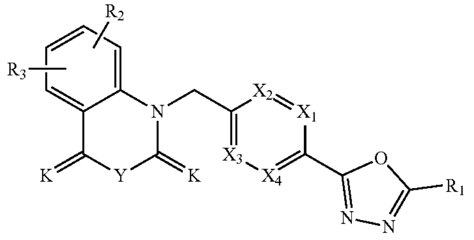

wherein, $X_1$ to $X_4$, $R_1$ to $R_3$, Y, K and n are the same as defined in the chemical formula I.

The present invention provides 1,3,4-oxadiazole homophthalimide derivative compounds described in a following table 1, stereoisomers thereof or pharmaceutically acceptable salts thereof.

TABLE 1

| Compound | Structure |
|---|---|
| 1 | 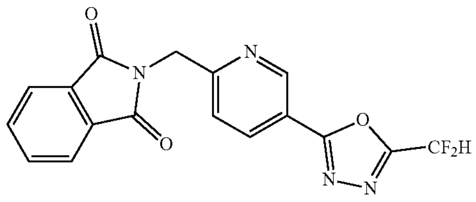 [SMILES: O=C1c2ccccc2C(=O)N1Cc1ccc(-c2nnc(C(F)F)o2)cn1] |
| 2 | 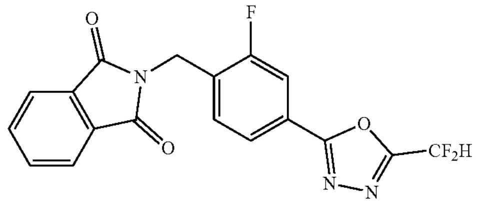 [SMILES: O=C1c2ccccc2C(=O)N1Cc1ccc(-c2nnc(C(F)F)o2)cc1F] |
| 3 | 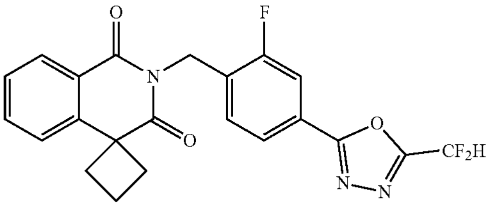 [SMILES: O=C1c2ccccc2C2(CCC2)C(=O)N1Cc1ccc(-c2nnc(C(F)F)o2)cc1F] |
| 4 | 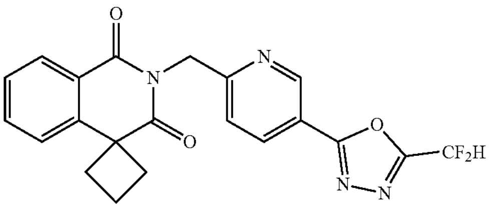 [SMILES: O=C1c2ccccc2C2(CCC2)C(=O)N1Cc1ccc(-c2nnc(C(F)F)o2)cn1] |
| 5 | 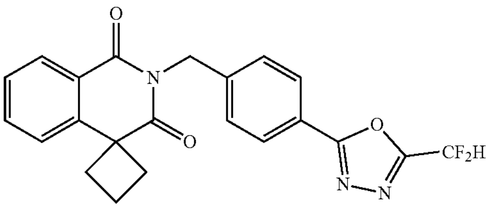 |

TABLE 1-continued
| Compound | Structure |
| --- | --- |
| 6 | 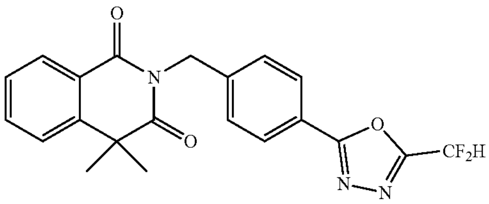 [SMILES: CC1(C)C(=O)N(Cc2ccc(-c3nnc(C(F)F)o3)cc2)C(=O)c2ccccc21] |
| 7 | 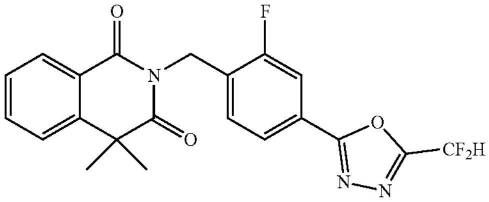 |
| 8 | 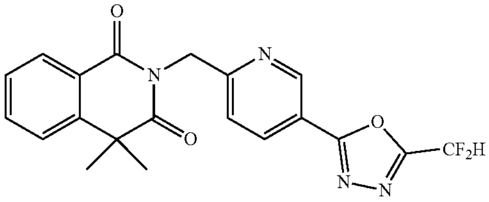 [SMILES: CC1(C)C(=O)N(Cc2ccc(-c3nnc(C(F)F)o3)cn2)C(=O)c2ccccc21] |
| 9 | 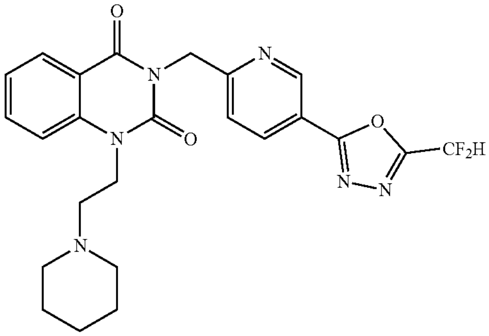 [SMILES: O=c1c2ccccc2n(CCN2CCCCC2)c(=O)n1Cc1ccc(-c2nnc(C(F)F)o2)cn1] |
| 10 | 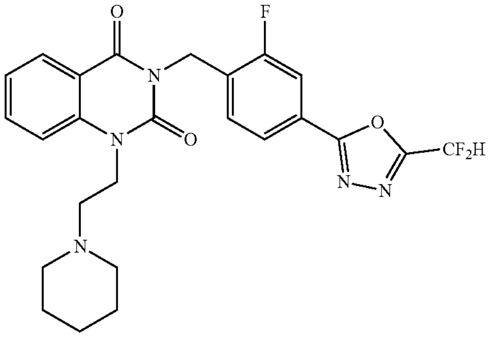 [SMILES: O=c1c2ccccc2n(CCN2CCCCC2)c(=O)n1Cc1ccc(-c2nnc(C(F)F)o2)cc1F] |

TABLE 1-continued
| Compound | Structure |
| --- | --- |
| 11 | 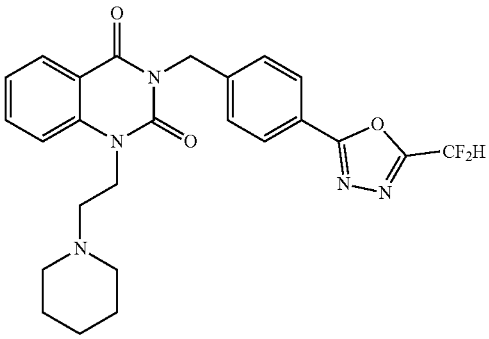 [SMILES: O=c1c2ccccc2n(CCN2CCCCC2)c(=O)n1Cc1ccc(-c2nnc(C(F)F)o2)cc1] |
| 12 | 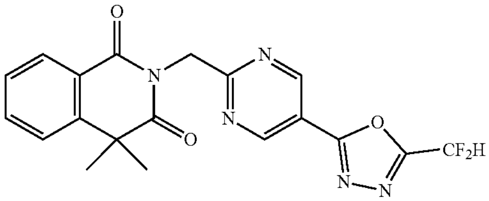 [SMILES: CC1(C)C(=O)N(Cc2ncc(-c3nnc(C(F)F)o3)cn2)C(=O)c2ccccc21] |
| 13 | 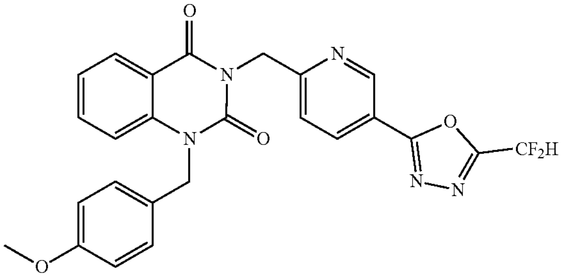 |
| 14 | 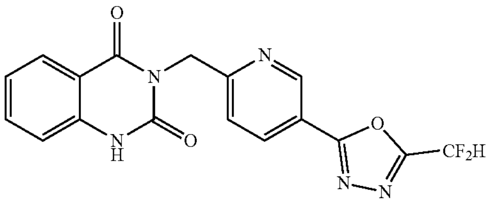 |
| 15 | 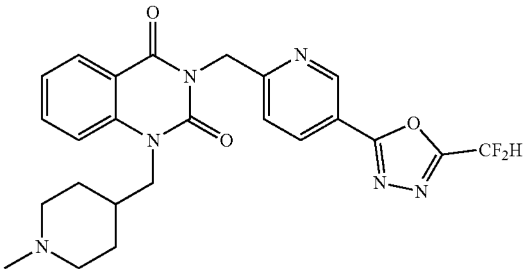 [SMILES: CN1CCC(Cn2c(=O)n(Cc3ccc(-c4nnc(C(F)F)o4)cn3)c(=O)c3ccccc32)CC1] |

TABLE 1-continued
| Compound | Structure |
| --- | --- |
| 16 | 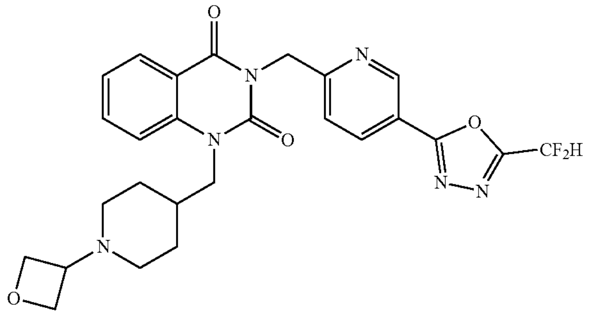 [SMILES: O=c1c2ccccc2n(CC2CCN(C3COC3)CC2)c(=O)n1Cc1ccc(-c2nnc(C(F)F)o2)cn1] |
| 17 | 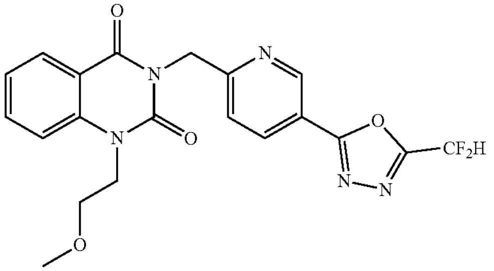 [SMILES: COCCn1c(=O)n(Cc2ccc(-c3nnc(C(F)F)o3)cn2)c(=O)c2ccccc21] |
| 18 | 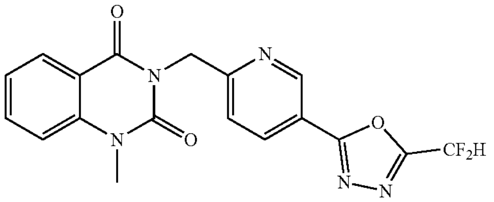 [SMILES: Cn1c(=O)n(Cc2ccc(-c3nnc(C(F)F)o3)cn2)c(=O)c2ccccc21] |
| 19 | 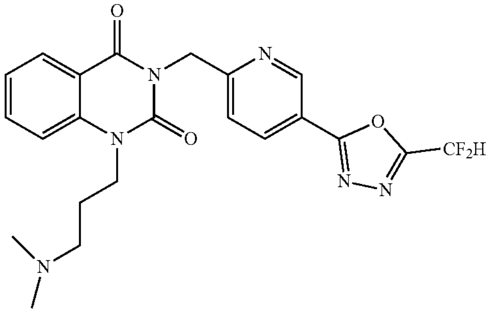 [SMILES: CN(C)CCCn1c(=O)n(Cc2ccc(-c3nnc(C(F)F)o3)cn2)c(=O)c2ccccc21] |
| 20 | 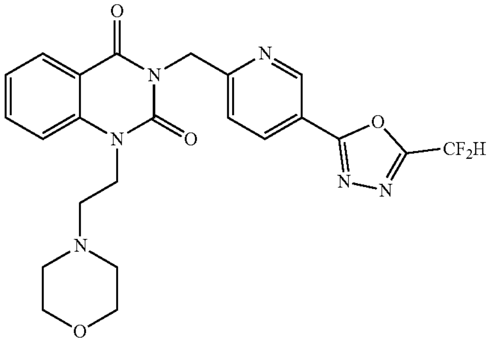 [SMILES: O=c1c2ccccc2n(CCN2CCOCC2)c(=O)n1Cc1ccc(-c2nnc(C(F)F)o2)cn1] |

TABLE 1-continued
| Compound | Structure |
| --- | --- |
| 21 | 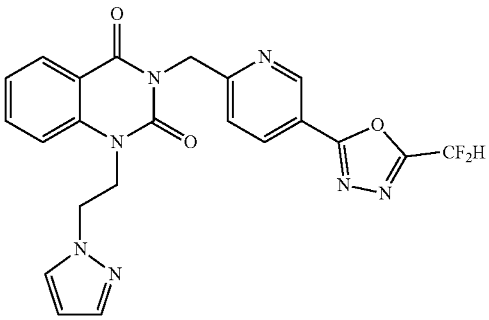 [SMILES: O=c1c2ccccc2n(CCn2cccn2)c(=O)n1Cc1ccc(-c2nnc(C(F)F)o2)cn1] |
| 22 | 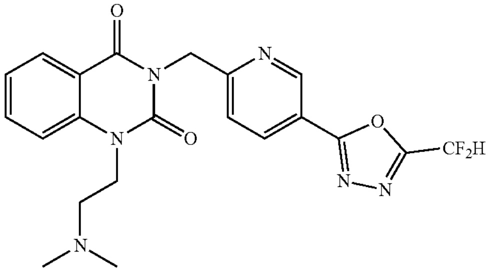 [SMILES: CN(C)CCn1c(=O)n(Cc2ccc(-c3nnc(C(F)F)o3)cn2)c(=O)c2ccccc21] |
| 23 | 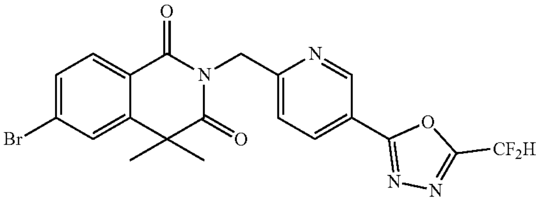 [SMILES: CC1(C)C(=O)N(Cc2ccc(-c3nnc(C(F)F)o3)cn2)C(=O)c2ccc(Br)cc21] |
| 24 | 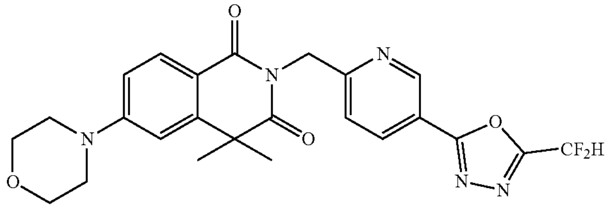 [SMILES: CC1(C)C(=O)N(Cc2ccc(-c3nnc(C(F)F)o3)cn2)C(=O)c2ccc(N3CCOCC3)cc21] |
| 25 | 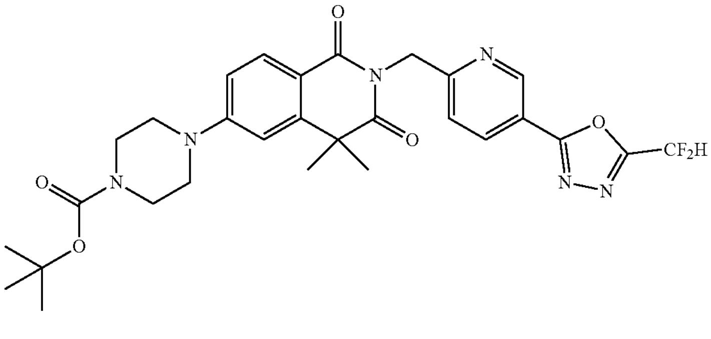 [SMILES: CC(C)(C)OC(=O)N1CCN(c2ccc3c(c2)C(C)(C)C(=O)N(Cc2ccc(-c4nnc(C(F)F)o4)cn2)C3=O)CC1] |
| 26 | 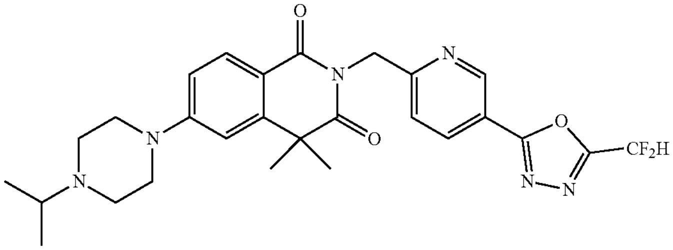 [SMILES: CC(C)N1CCN(c2ccc3c(c2)C(C)(C)C(=O)N(Cc2ccc(-c4nnc(C(F)F)o4)cn2)C3=O)CC1] |

TABLE 1-continued
| Compound | Structure |
|---|---|
| 27 | 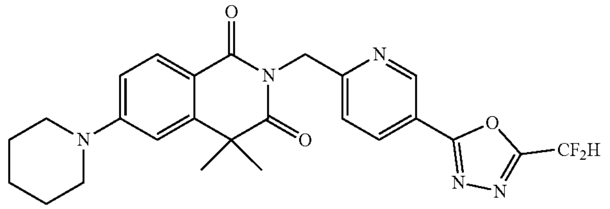 [SMILES: CC1(C)C(=O)N(Cc2ccc(-c3nnc(C(F)F)o3)cn2)C(=O)c2ccc(N3CCCCC3)cc21] |
| 28 | 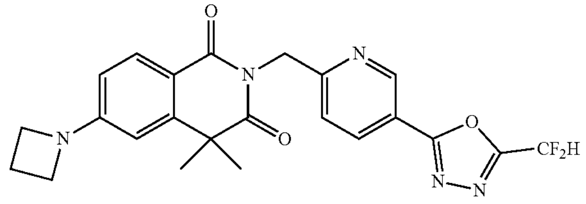 [SMILES: CC1(C)C(=O)N(Cc2ccc(-c3nnc(C(F)F)o3)cn2)C(=O)c2ccc(N3CCC3)cc21] |
| 29 | 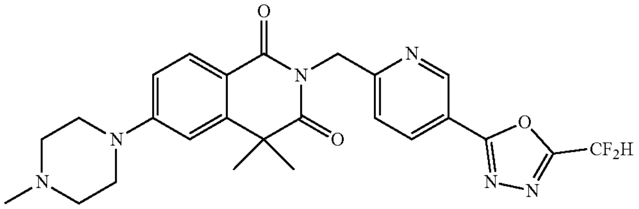 [SMILES: CN1CCN(c2ccc3c(c2)C(C)(C)C(=O)N(Cc2ccc(-c4nnc(C(F)F)o4)cn2)C3=O)CC1] |
| 30 | 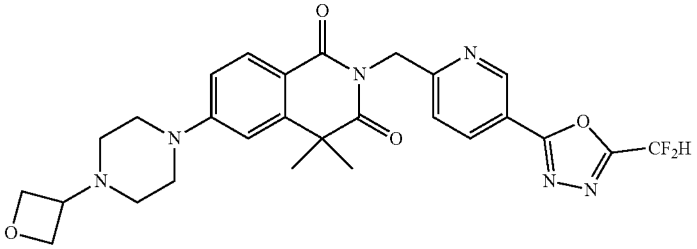 [SMILES: CC1(C)C(=O)N(Cc2ccc(-c3nnc(C(F)F)o3)cn2)C(=O)c2ccc(N3CCN(C4COC4)CC3)cc21] |
| 31 | 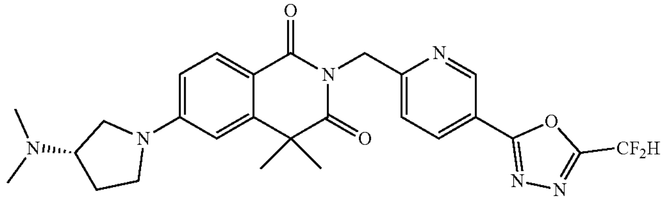 [SMILES: CN(C)[C@H]1CCN(c2ccc3c(c2)C(C)(C)C(=O)N(Cc2ccc(-c4nnc(C(F)F)o4)cn2)C3=O)C1] |
| 32 | 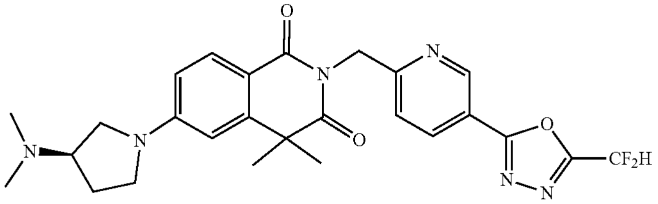 [SMILES: CN(C)[C@@H]1CCN(c2ccc3c(c2)C(C)(C)C(=O)N(Cc2ccc(-c4nnc(C(F)F)o4)cn2)C3=O)C1] |

TABLE 1-continued
| Compound | Structure |
| --- | --- |
| 33 | 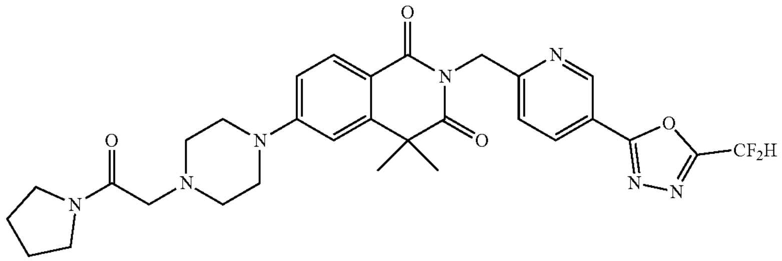 [SMILES: CC1(C)C(=O)N(Cc2ccc(-c3nnc(C(F)F)o3)cn2)C(=O)c2ccc(N3CCN(CC(=O)N4CCCC4)CC3)cc21] |
| 34 | 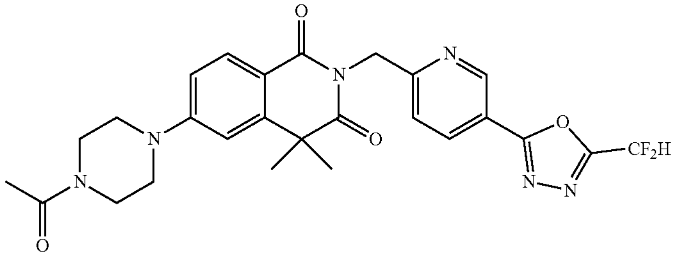 [SMILES: CC(=O)N1CCN(c2ccc3c(c2)C(C)(C)C(=O)N(Cc2ccc(-c4nnc(C(F)F)o4)cn2)C3=O)CC1] |
| 35 | 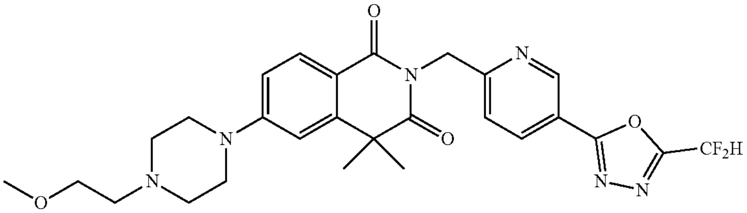 [SMILES: COCCN1CCN(c2ccc3c(c2)C(C)(C)C(=O)N(Cc2ccc(-c4nnc(C(F)F)o4)cn2)C3=O)CC1] |
| 36 | 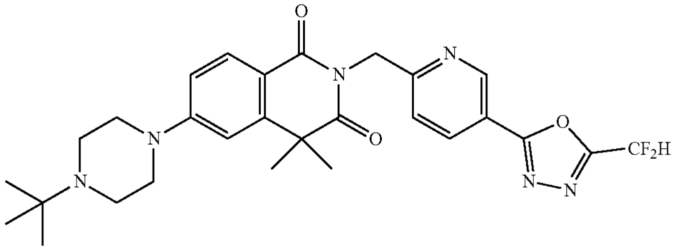 [SMILES: CC1(C)C(=O)N(Cc2ccc(-c3nnc(C(F)F)o3)cn2)C(=O)c2ccc(N3CCN(C(C)(C)C)CC3)cc21] |
| 37 | 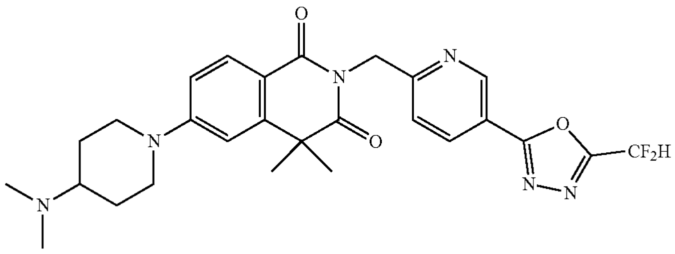 [SMILES: CN(C)C1CCN(c2ccc3c(c2)C(C)(C)C(=O)N(Cc2ccc(-c4nnc(C(F)F)o4)cn2)C3=O)CC1] |
| 38 | 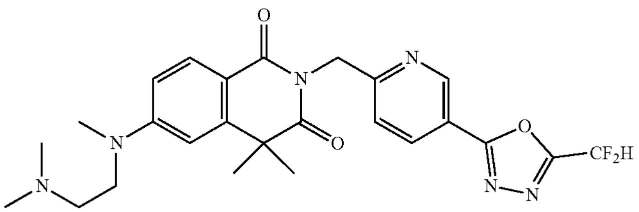 [SMILES: CN(C)CCN(C)c1ccc2c(c1)C(C)(C)C(=O)N(Cc1ccc(-c3nnc(C(F)F)o3)cn1)C2=O] |

TABLE 1-continued
| Compound | Structure |
|---|---|
| 39 | 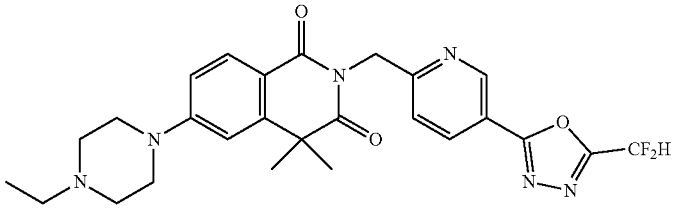 [SMILES: CCN1CCN(c2ccc3c(c2)C(C)(C)C(=O)N(Cc2ccc(-c4nnc(C(F)F)o4)cn2)C3=O)CC1] |
| 40 | 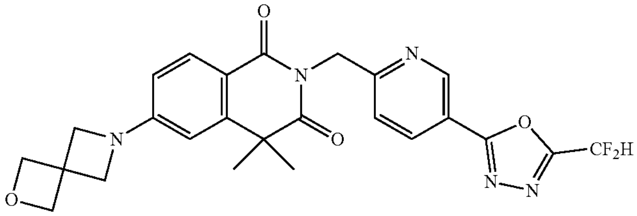 [SMILES: CC1(C)C(=O)N(Cc2ccc(-c3nnc(C(F)F)o3)cn2)C(=O)c2ccc(N3CC4(COC4)C3)cc21] |
| 41 | 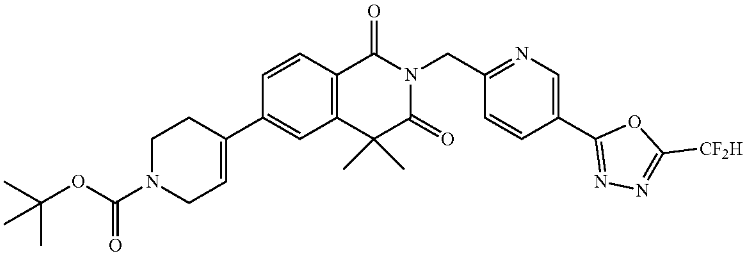 [SMILES: CC(C)(C)OC(=O)N1CC=C(c2ccc3c(c2)C(C)(C)C(=O)N(Cc2ccc(-c4nnc(C(F)F)o4)cn2)C3=O)CC1] |
| 42 | 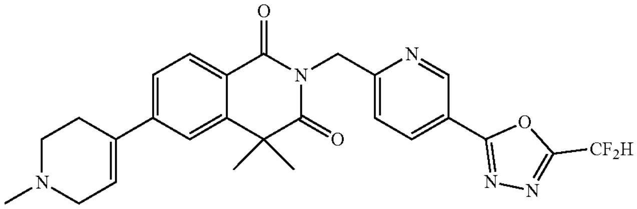 [SMILES: CN1CC=C(c2ccc3c(c2)C(C)(C)C(=O)N(Cc2ccc(-c4nnc(C(F)F)o4)cn2)C3=O)CC1] |
| 43 | 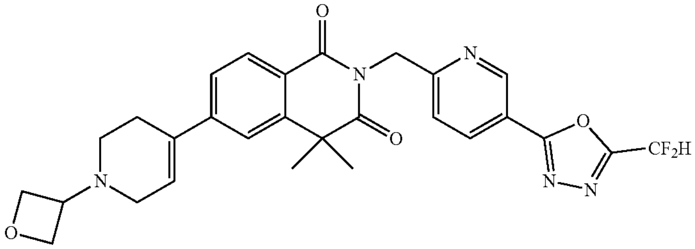 [SMILES: CC1(C)C(=O)N(Cc2ccc(-c3nnc(C(F)F)o3)cn2)C(=O)c2ccc(C3=CCN(C4COC4)CC3)cc21] |
| 44 | 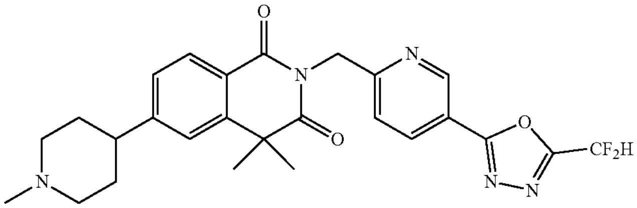 [SMILES: CN1CCC(c2ccc3c(c2)C(C)(C)C(=O)N(Cc2ccc(-c4nnc(C(F)F)o4)cn2)C3=O)CC1] |

TABLE 1-continued
| Compound | Structure |
|---|---|
| 45 | 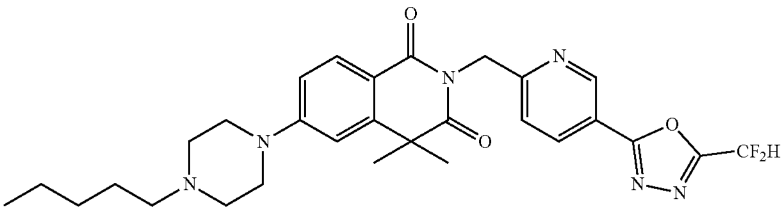 [SMILES: CCCCCN1CCN(c2ccc3c(c2)C(C)(C)C(=O)N(Cc2ccc(-c4nnc(C(F)F)o4)cn2)C3=O)CC1] |
| 46 | 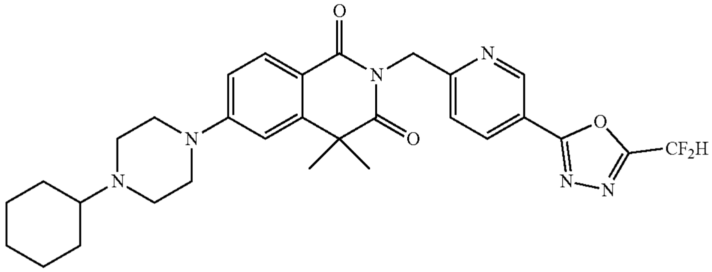 [SMILES: CC1(C)C(=O)N(Cc2ccc(-c3nnc(C(F)F)o3)cn2)C(=O)c2ccc(N3CCN(C4CCCCC4)CC3)cc21] |
| 47 | 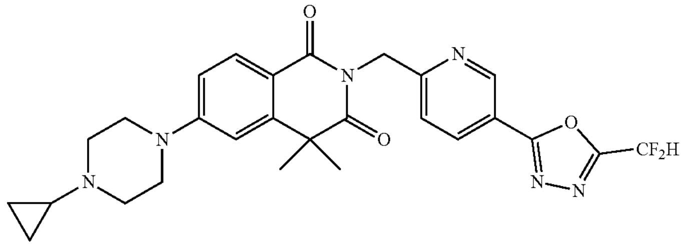 [SMILES: CC1(C)C(=O)N(Cc2ccc(-c3nnc(C(F)F)o3)cn2)C(=O)c2ccc(N3CCN(C4CC4)CC3)cc21] |
| 48 | 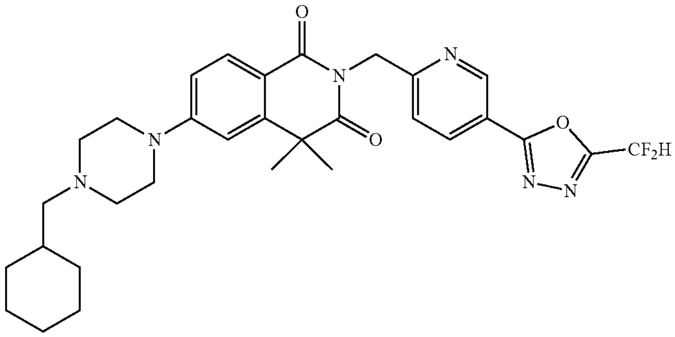 [SMILES: CC1(C)C(=O)N(Cc2ccc(-c3nnc(C(F)F)o3)cn2)C(=O)c2ccc(N3CCN(CC4CCCCC4)CC3)cc21] |
| 49 | 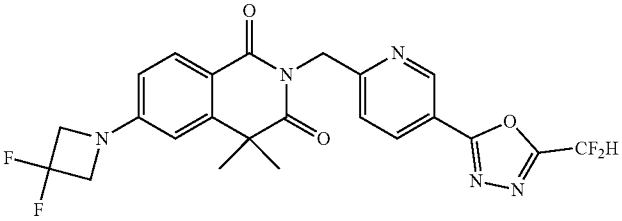 [SMILES: CC1(C)C(=O)N(Cc2ccc(-c3nnc(C(F)F)o3)cn2)C(=O)c2ccc(N3CC(F)(F)C3)cc21] |
| 50 | 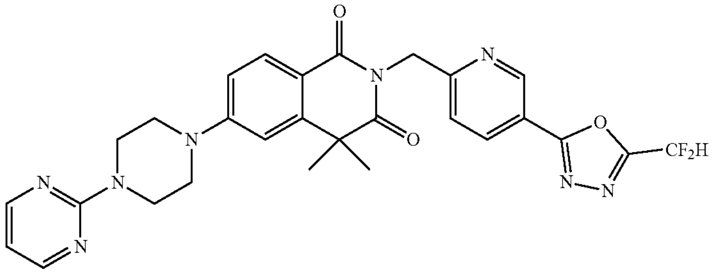 [SMILES: CC1(C)C(=O)N(Cc2ccc(-c3nnc(C(F)F)o3)cn2)C(=O)c2ccc(N3CCN(c4ncccn4)CC3)cc21] |

TABLE 1-continued
| Compound | Structure |
| --- | --- |
| 51 | 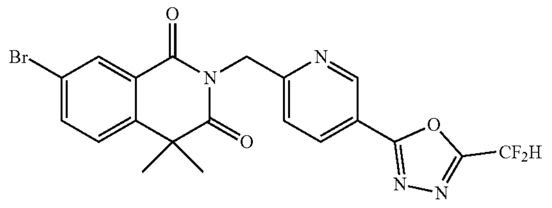 [SMILES: CC1(C)C(=O)N(Cc2ccc(-c3nnc(C(F)F)o3)cn2)C(=O)c2cc(Br)ccc21] |
| 52 | 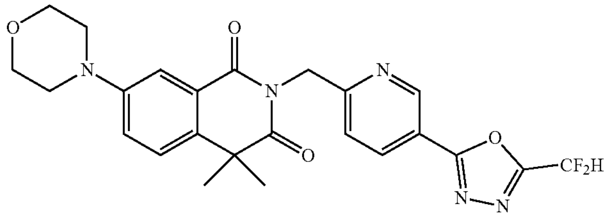 [SMILES: CC1(C)C(=O)N(Cc2ccc(-c3nnc(C(F)F)o3)cn2)C(=O)c2cc(N3CCOCC3)ccc21] |
| 53 | 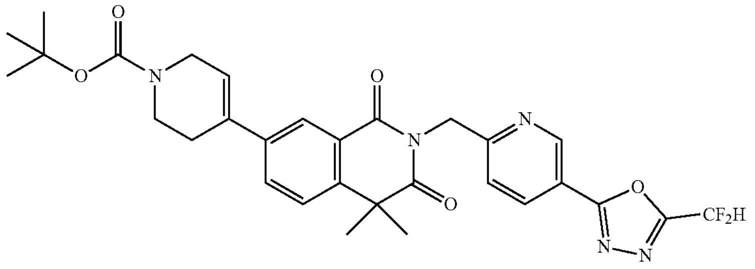 [SMILES: CC(C)(C)OC(=O)N1CC=C(c2ccc3c(c2)C(=O)N(Cc2ccc(-c4nnc(C(F)F)o4)cn2)C(=O)C3(C)C)CC1] |
| 54 | 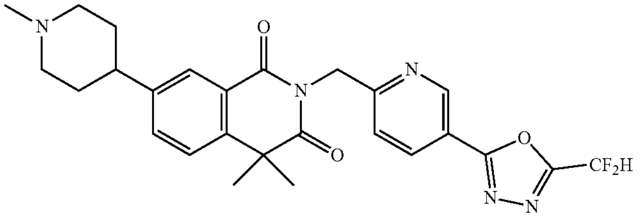 [SMILES: CN1CCC(c2ccc3c(c2)C(=O)N(Cc2ccc(-c4nnc(C(F)F)o4)cn2)C(=O)C3(C)C)CC1] |
| 55 | 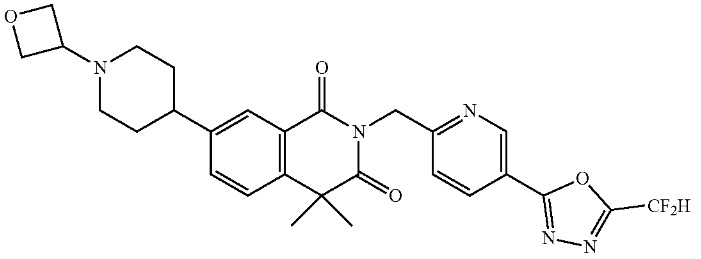 [SMILES: CC1(C)C(=O)N(Cc2ccc(-c3nnc(C(F)F)o3)cn2)C(=O)c2cc(C3CCN(C4COC4)CC3)ccc21] |
| 56 | 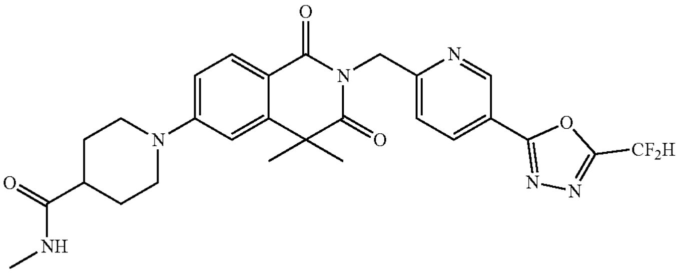 [SMILES: CNC(=O)C1CCN(c2ccc3c(c2)C(C)(C)C(=O)N(Cc2ccc(-c4nnc(C(F)F)o4)cn2)C3=O)CC1] |

TABLE 1-continued
| Compound | Structure |
| --- | --- |
| 57 | 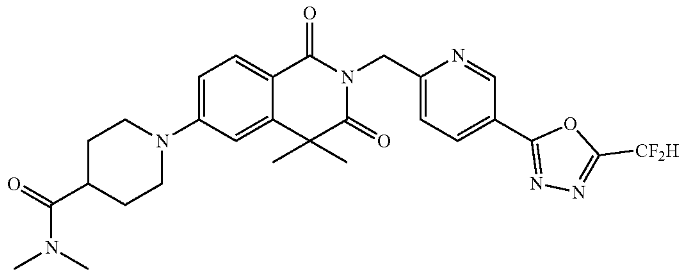 [SMILES: CN(C)C(=O)C1CCN(c2ccc3c(c2)C(C)(C)C(=O)N(Cc2ccc(-c4nnc(C(F)F)o4)cn2)C3=O)CC1] |
| 58 | 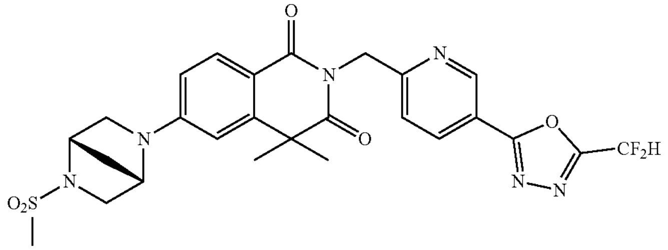 [SMILES: CC1(C)C(=O)N(Cc2ccc(-c3nnc(C(F)F)o3)cn2)C(=O)c2ccc(N3C[C@@H]4C[C@H]3CN4S(C)(=O)=O)cc21] |
| 59 | 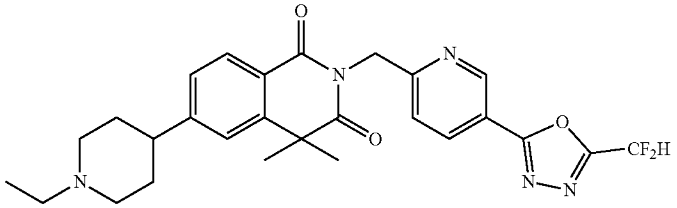 [SMILES: CCN1CCC(c2ccc3c(c2)C(C)(C)C(=O)N(Cc2ccc(-c4nnc(C(F)F)o4)cn2)C3=O)CC1] |
| 60 | 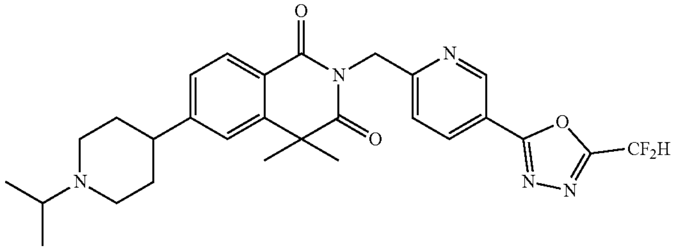 [SMILES: CC(C)N1CCC(c2ccc3c(c2)C(C)(C)C(=O)N(Cc2ccc(-c4nnc(C(F)F)o4)cn2)C3=O)CC1] |
| 61 | 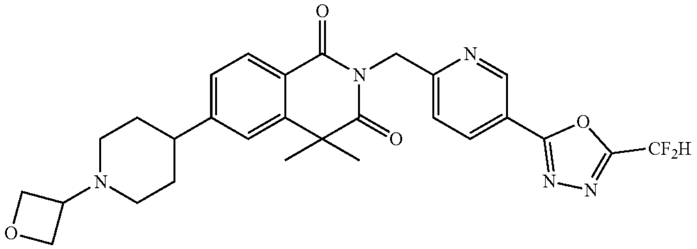 [SMILES: CC1(C)C(=O)N(Cc2ccc(-c3nnc(C(F)F)o3)cn2)C(=O)c2ccc(C3CCN(C4COC4)CC3)cc21] |
| 62 | 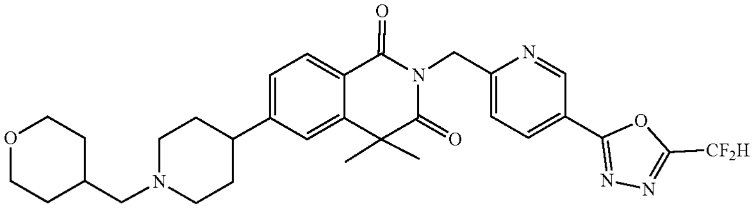 [SMILES: CC1(C)C(=O)N(Cc2ccc(-c3nnc(C(F)F)o3)cn2)C(=O)c2ccc(C3CCN(CC4CCOCC4)CC3)cc21] |

TABLE 1-continued
| Compound | Structure |
|---|---|
| 63 | 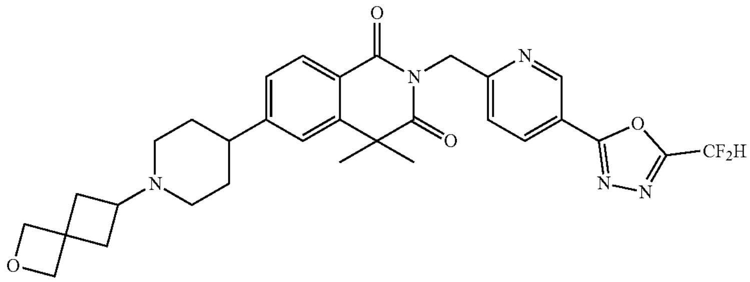 [SMILES: CC1(C)C(=O)N(Cc2ccc(-c3nnc(C(F)F)o3)cn2)C(=O)c2ccc(C3CCN(C4CC5(COC5)C4)CC3)cc21] |
| 64 | 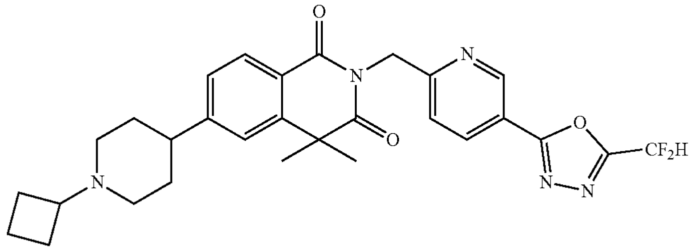 [SMILES: CC1(C)C(=O)N(Cc2ccc(-c3nnc(C(F)F)o3)cn2)C(=O)c2ccc(C3CCN(C4CCC4)CC3)cc21] |
| 65 | 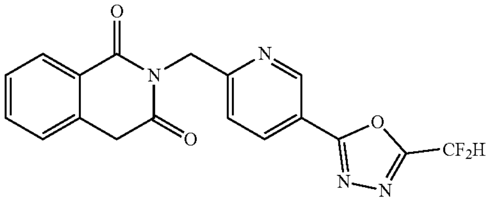 [SMILES: O=C1Cc2ccccc2C(=O)N1Cc1ccc(-c2nnc(C(F)F)o2)cn1] |
| 66 | 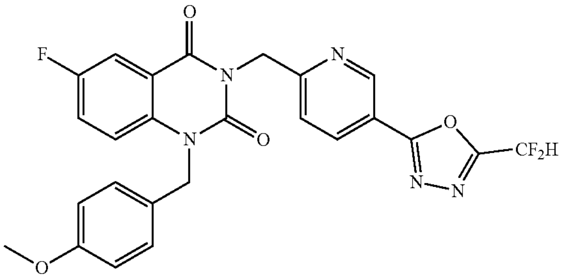 [SMILES: COc1ccc(Cn2c(=O)n(Cc3ccc(-c4nnc(C(F)F)o4)cn3)c(=O)c3cc(F)ccc32)cc1] |
| 67 | 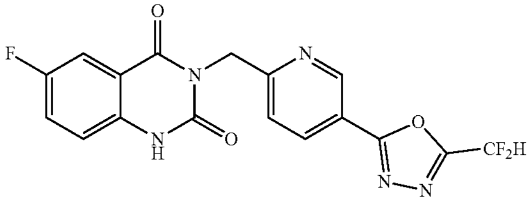 [SMILES: O=c1[nH]c2ccc(F)cc2c(=O)n1Cc1ccc(-c2nnc(C(F)F)o2)cn1] |
| 68 | 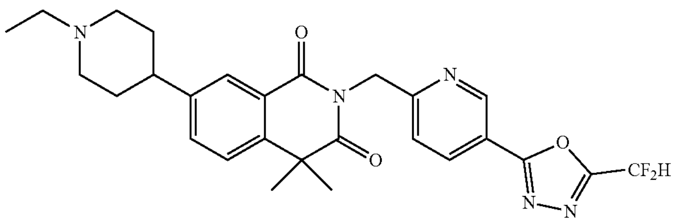 [SMILES: CCN1CCC(c2ccc3c(c2)C(=O)N(Cc2ccc(-c4nnc(C(F)F)o4)cn2)C(=O)C3(C)C)CC1] |

TABLE 1-continued
| Compound | Structure |
| --- | --- |
| 69 | 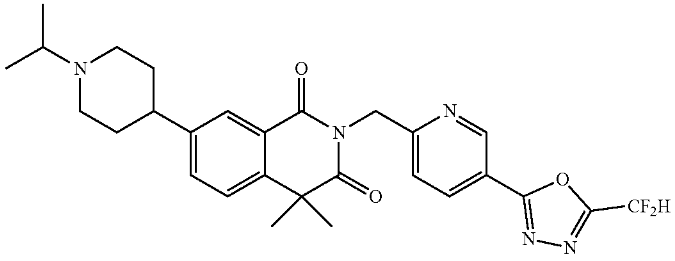 [SMILES: CC(C)N1CCC(c2ccc3c(c2)C(=O)N(Cc2ccc(-c4nnc(C(F)F)o4)cn2)C(=O)C3(C)C)CC1] |
| 70 | 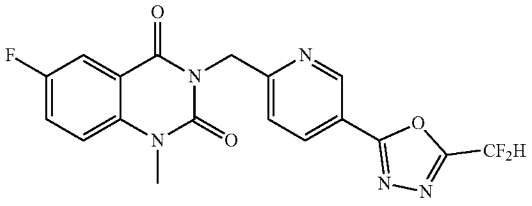 [SMILES: Cn1c(=O)n(Cc2ccc(-c3nnc(C(F)F)o3)cn2)c(=O)c2cc(F)ccc21] |
| 71 | 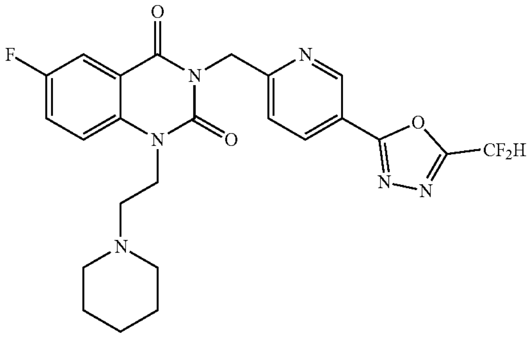 [SMILES: O=c1c2cc(F)ccc2n(CCN2CCCCC2)c(=O)n1Cc1ccc(-c2nnc(C(F)F)o2)cn1] |
| 72 | 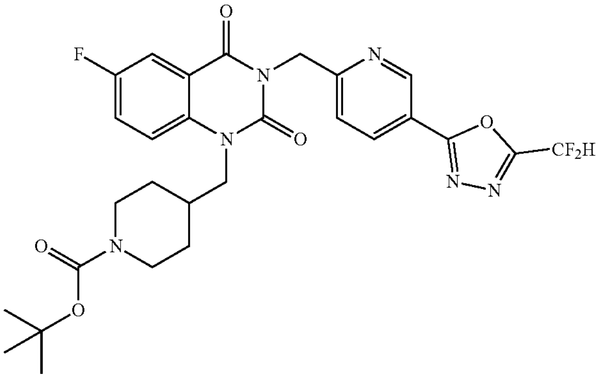 [SMILES: CC(C)(C)OC(=O)N1CCC(Cn2c(=O)n(Cc3ccc(-c4nnc(C(F)F)o4)cn3)c(=O)c3cc(F)ccc32)CC1] |
| 73 | 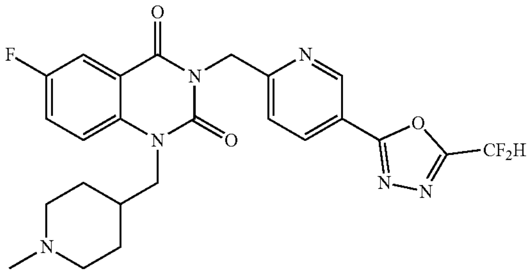 [SMILES: CN1CCC(Cn2c(=O)n(Cc3ccc(-c4nnc(C(F)F)o4)cn3)c(=O)c3cc(F)ccc32)CC1] |

TABLE 1-continued
| Compound | Structure |
|---|---|
| 74 | 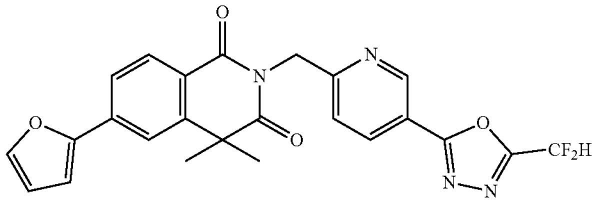 [SMILES: CC1(C)C(=O)N(Cc2ccc(-c3nnc(C(F)F)o3)cn2)C(=O)c2ccc(-c3ccco3)cc21] |
| 75 | 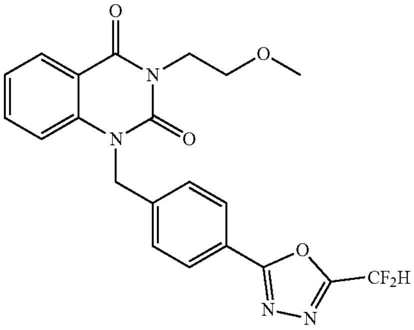 [SMILES: COCCn1c(=O)c2ccccc2n(Cc2ccc(-c3nnc(C(F)F)o3)cc2)c1=O] |
| 76 | 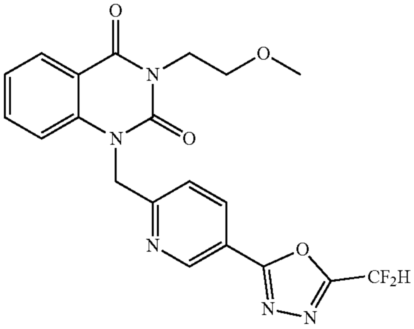 [SMILES: COCCn1c(=O)c2ccccc2n(Cc2ccc(-c3nnc(C(F)F)o3)cn2)c1=O] |
| 77 | 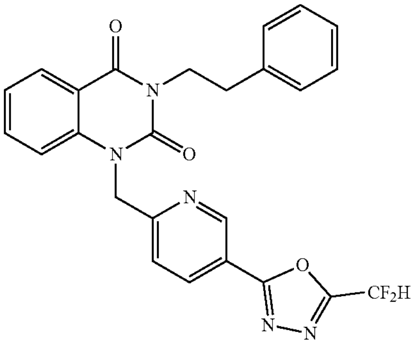 [SMILES: O=c1c2ccccc2n(Cc2ccc(-c3nnc(C(F)F)o3)cn2)c(=O)n1CCc1ccccc1] |
| 78 | 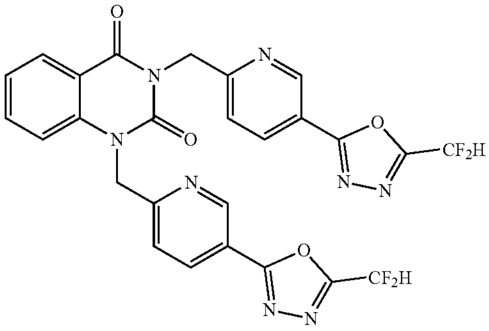 [SMILES: O=c1c2ccccc2n(Cc2ccc(-c3nnc(C(F)F)o3)cn2)c(=O)n1Cc1ccc(-c2nnc(C(F)F)o2)cn1] |

TABLE 1-continued
| Compound | Structure |
| --- | --- |
| 79 | 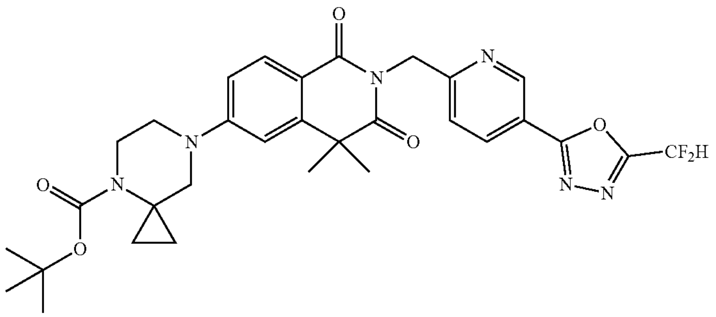 [SMILES: CC(C)(C)OC(=O)N1CCN(c2ccc3c(c2)C(C)(C)C(=O)N(Cc2ccc(-c4nnc(C(F)F)o4)cn2)C3=O)CC12CC2] |
| 80 | 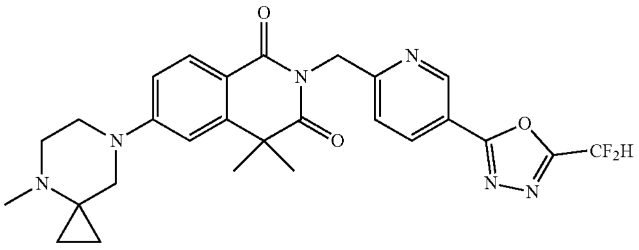 [SMILES: CN1CCN(c2ccc3c(c2)C(C)(C)C(=O)N(Cc2ccc(-c4nnc(C(F)F)o4)cn2)C3=O)CC12CC2] |
| 81 | 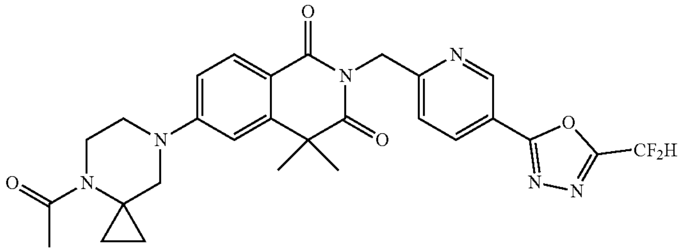 [SMILES: CC(=O)N1CCN(c2ccc3c(c2)C(C)(C)C(=O)N(Cc2ccc(-c4nnc(C(F)F)o4)cn2)C3=O)CC12CC2] |
| 82 | 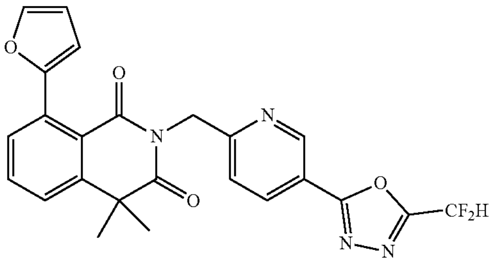 [SMILES: CC1(C)C(=O)N(Cc2ccc(-c3nnc(C(F)F)o3)cn2)C(=O)c2c(-c3ccco3)cccc21] |
| 83 | 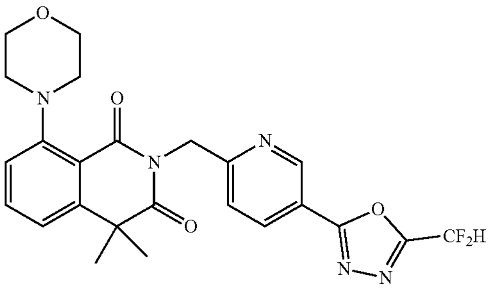 [SMILES: CC1(C)C(=O)N(Cc2ccc(-c3nnc(C(F)F)o3)cn2)C(=O)c2c(N3CCOCC3)cccc21] |

TABLE 1-continued
| Compound | Structure |
| --- | --- |
| 84 | 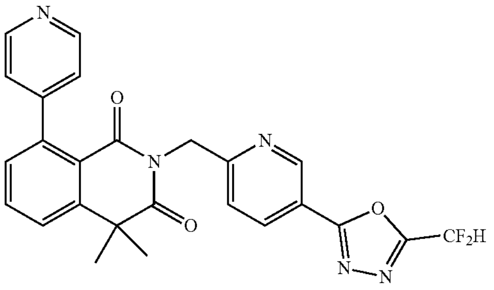 [SMILES: CC1(C)C(=O)N(Cc2ccc(-c3nnc(C(F)F)o3)cn2)C(=O)c2c(-c3ccncc3)cccc21] |
| 85 | 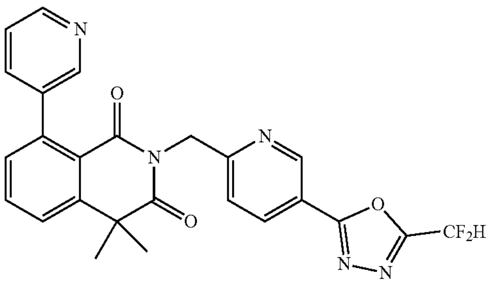 [SMILES: CC1(C)C(=O)N(Cc2ccc(-c3nnc(C(F)F)o3)cn2)C(=O)c2c(-c3cccnc3)cccc21] |
| 86 | 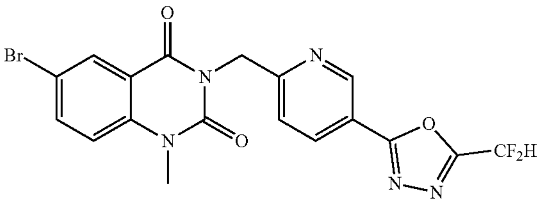 [SMILES: Cn1c(=O)n(Cc2ccc(-c3nnc(C(F)F)o3)cn2)c(=O)c2cc(Br)ccc21] |
| 87 | 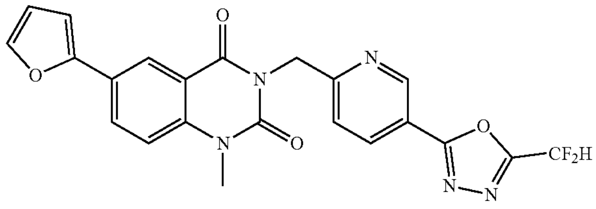 [SMILES: Cn1c(=O)n(Cc2ccc(-c3nnc(C(F)F)o3)cn2)c(=O)c2cc(-c3ccco3)ccc21] |
| 88 | 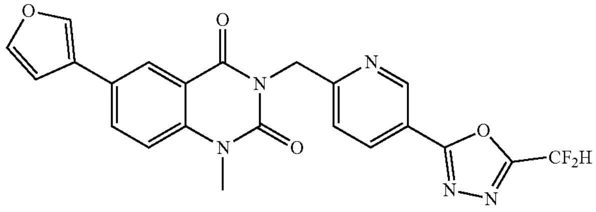 [SMILES: Cn1c(=O)n(Cc2ccc(-c3nnc(C(F)F)o3)cn2)c(=O)c2cc(-c3ccoc3)ccc21] |
| 89 | 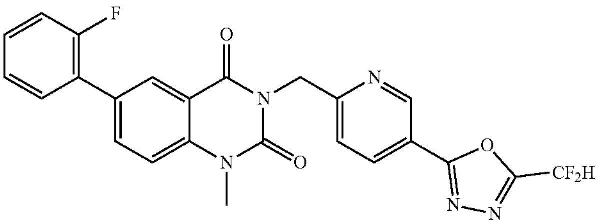 [SMILES: Cn1c(=O)n(Cc2ccc(-c3nnc(C(F)F)o3)cn2)c(=O)c2cc(-c3ccccc3F)ccc21] |

TABLE 1-continued
| Compound | Structure |
| --- | --- |
| 90 | 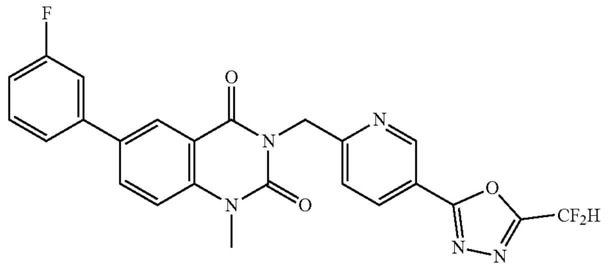 [SMILES: Cn1c(=O)n(Cc2ccc(-c3nnc(C(F)F)o3)cn2)c(=O)c2cc(-c3cccc(F)c3)ccc21] |
| 91 | 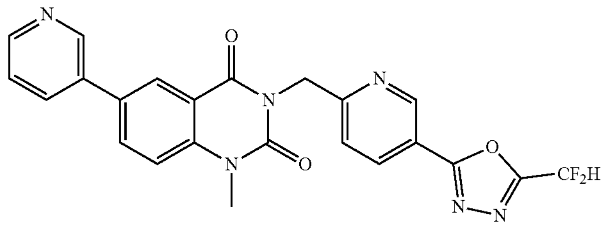 [SMILES: Cn1c(=O)n(Cc2ccc(-c3nnc(C(F)F)o3)cn2)c(=O)c2cc(-c3cccnc3)ccc21] |
| 92 | 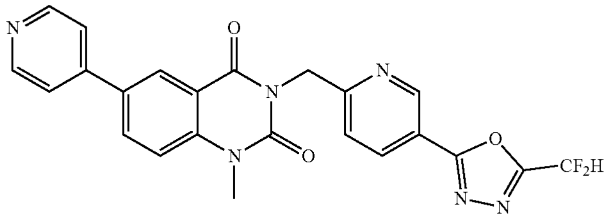 [SMILES: Cn1c(=O)n(Cc2ccc(-c3nnc(C(F)F)o3)cn2)c(=O)c2cc(-c3ccncc3)ccc21] |
| 93 | 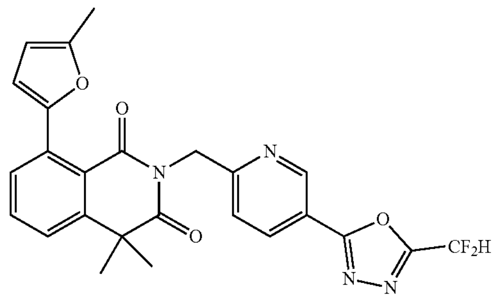 [SMILES: Cc1ccc(-c2cccc3c2C(=O)N(Cc2ccc(-c4nnc(C(F)F)o4)cn2)C(=O)C3(C)C)o1] |
| 94 | 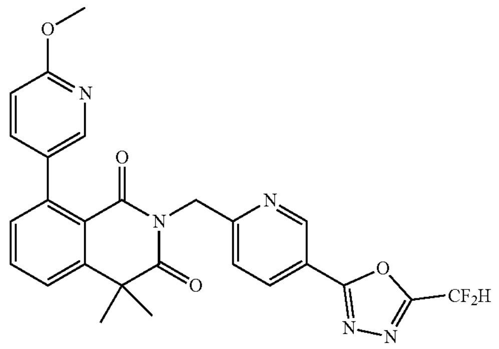 [SMILES: COc1ccc(-c2cccc3c2C(=O)N(Cc2ccc(-c4nnc(C(F)F)o4)cn2)C(=O)C3(C)C)cn1] |

TABLE 1-continued
| Compound | Structure |
| --- | --- |
| 95 | 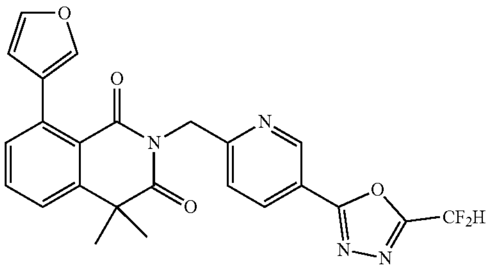 [SMILES: CC1(C)C(=O)N(Cc2ccc(-c3nnc(C(F)F)o3)cn2)C(=O)c2c(-c3ccoc3)cccc21] |
| 96 | 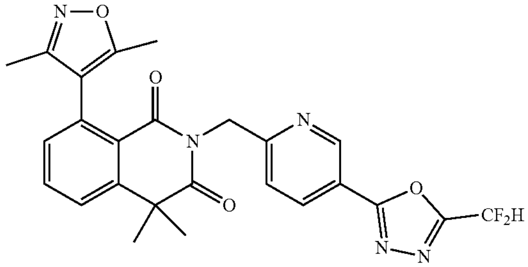 [SMILES: Cc1noc(C)c1-c1cccc2c1C(=O)N(Cc1ccc(-c3nnc(C(F)F)o3)cn1)C(=O)C2(C)C] |
| 97 | 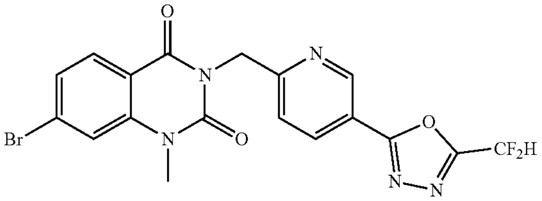 [SMILES: Cn1c(=O)n(Cc2ccc(-c3nnc(C(F)F)o3)cn2)c(=O)c2ccc(Br)cc21] |
| 98 | 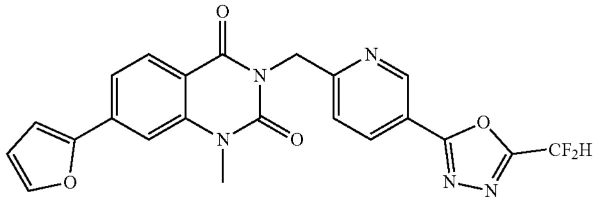 [SMILES: Cn1c(=O)n(Cc2ccc(-c3nnc(C(F)F)o3)cn2)c(=O)c2ccc(-c3ccco3)cc21] |
| 99 | 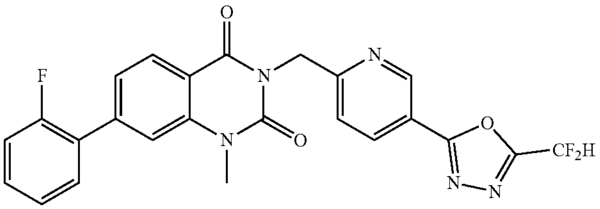 [SMILES: Cn1c(=O)n(Cc2ccc(-c3nnc(C(F)F)o3)cn2)c(=O)c2ccc(-c3ccccc3F)cc21] |
| 100 | 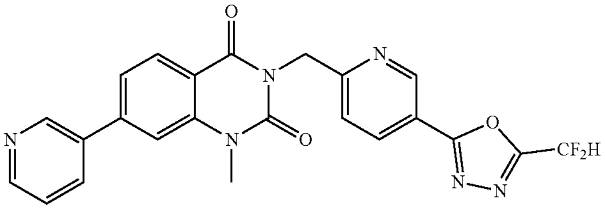 [SMILES: Cn1c(=O)n(Cc2ccc(-c3nnc(C(F)F)o3)cn2)c(=O)c2ccc(-c3cccnc3)cc21] |

TABLE 1-continued
| Compound | Structure |
| --- | --- |
| 101 | 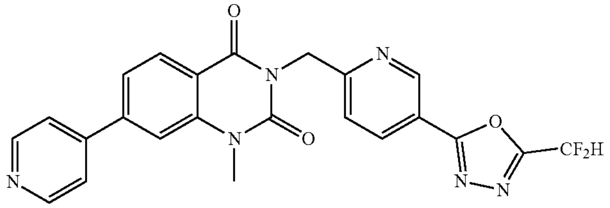 [SMILES: Cn1c(=O)n(Cc2ccc(-c3nnc(C(F)F)o3)cn2)c(=O)c2ccc(-c3ccncc3)cc21] |
| 102 | 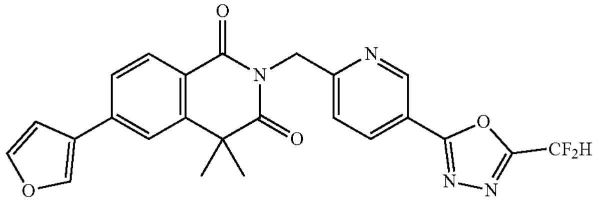 [SMILES: CC1(C)C(=O)N(Cc2ccc(-c3nnc(C(F)F)o3)cn2)C(=O)c2ccc(-c3ccoc3)cc21] |
| 103 | 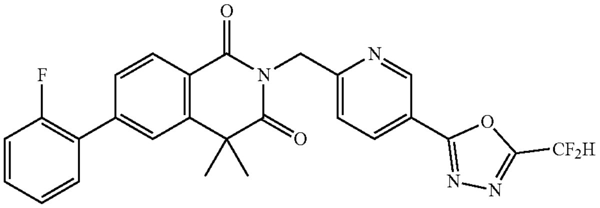 [SMILES: CC1(C)C(=O)N(Cc2ccc(-c3nnc(C(F)F)o3)cn2)C(=O)c2ccc(-c3ccccc3F)cc21] |
| 104 | 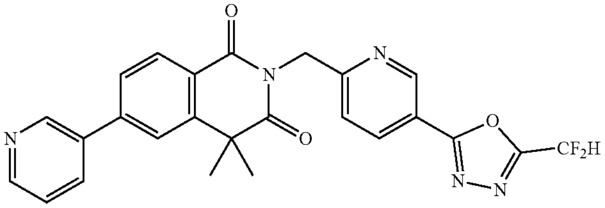 [SMILES: CC1(C)C(=O)N(Cc2ccc(-c3nnc(C(F)F)o3)cn2)C(=O)c2ccc(-c3cccnc3)cc21] |
| 105 | 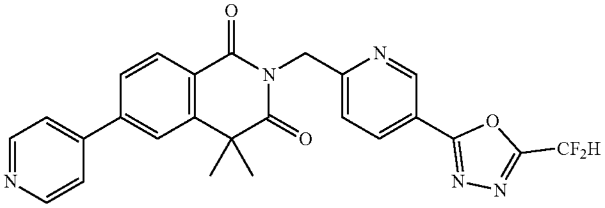 [SMILES: CC1(C)C(=O)N(Cc2ccc(-c3nnc(C(F)F)o3)cn2)C(=O)c2ccc(-c3ccncc3)cc21] |
| 106 | 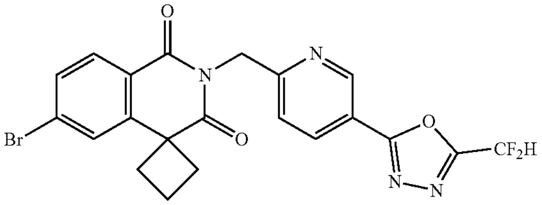 [SMILES: O=C1c2ccc(Br)cc2C2(CCC2)C(=O)N1Cc1ccc(-c2nnc(C(F)F)o2)cn1] |
| 107 | 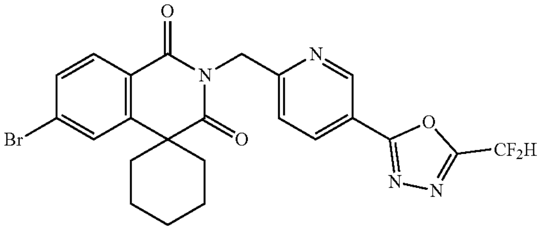 [SMILES: O=C1c2ccc(Br)cc2C2(CCCCC2)C(=O)N1Cc1ccc(-c2nnc(C(F)F)o2)cn1] |

TABLE 1-continued
| Compound | Structure |
| --- | --- |
| 108 | 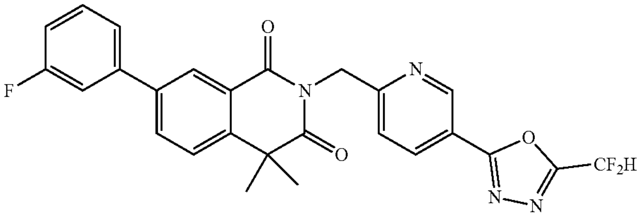 [SMILES: CC1(C)C(=O)N(Cc2ccc(-c3nnc(C(F)F)o3)cn2)C(=O)c2cc(-c3cccc(F)c3)ccc21] |
| 109 | 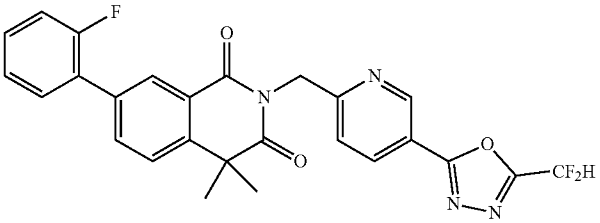 [SMILES: CC1(C)C(=O)N(Cc2ccc(-c3nnc(C(F)F)o3)cn2)C(=O)c2cc(-c3ccccc3F)ccc21] |
| 110 | 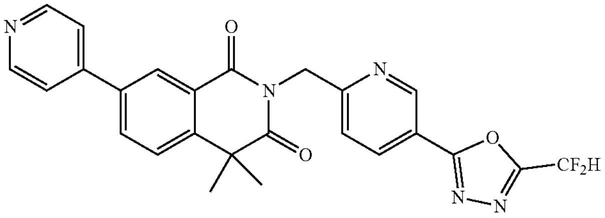 [SMILES: CC1(C)C(=O)N(Cc2ccc(-c3nnc(C(F)F)o3)cn2)C(=O)c2cc(-c3ccncc3)ccc21] |
| 111 | 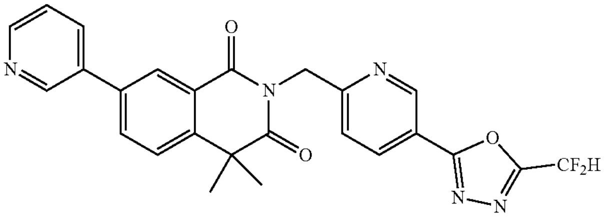 [SMILES: CC1(C)C(=O)N(Cc2ccc(-c3nnc(C(F)F)o3)cn2)C(=O)c2cc(-c3cccnc3)ccc21] |
| 112 | 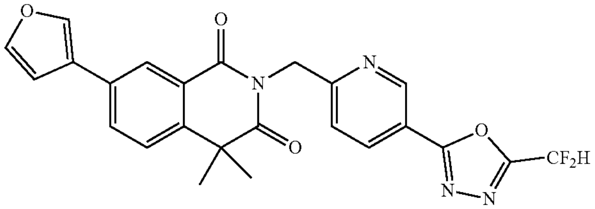 [SMILES: CC1(C)C(=O)N(Cc2ccc(-c3nnc(C(F)F)o3)cn2)C(=O)c2cc(-c3ccoc3)ccc21] |
| 113 | 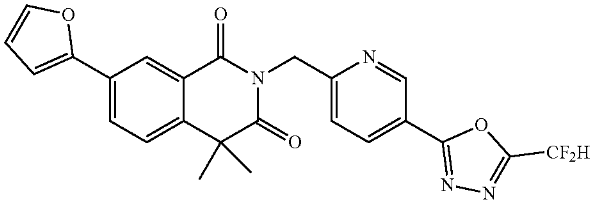 [SMILES: CC1(C)C(=O)N(Cc2ccc(-c3nnc(C(F)F)o3)cn2)C(=O)c2cc(-c3ccco3)ccc21] |
| 114 | 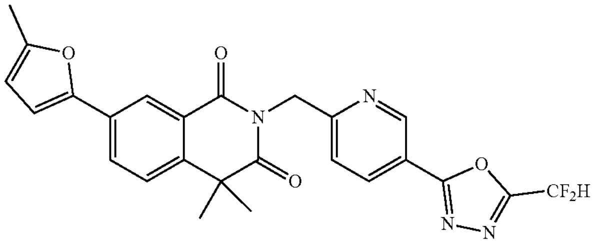 [SMILES: Cc1ccc(-c2ccc3c(c2)C(=O)N(Cc2ccc(-c4nnc(C(F)F)o4)cn2)C(=O)C3(C)C)o1] |

TABLE 1-continued
| Compound | Structure |
|---|---|
| 115 | 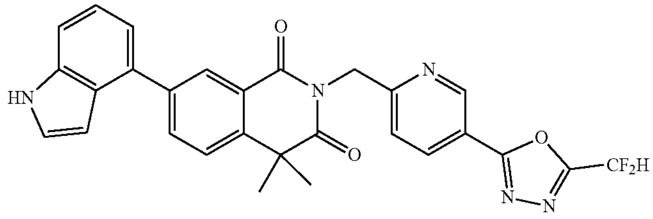 [SMILES: CC1(C)C(=O)N(Cc2ccc(-c3nnc(C(F)F)o3)cn2)C(=O)c2cc(-c3cccc4[nH]ccc34)ccc21] |
| 116 | 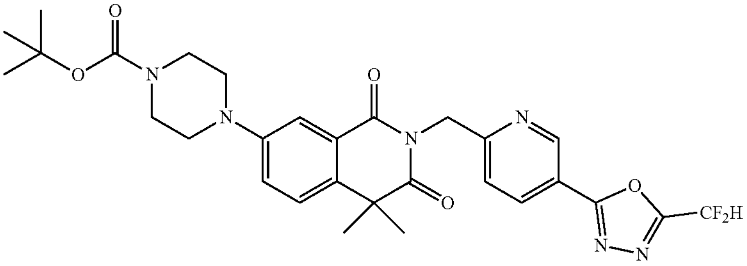 [SMILES: CC(C)(C)OC(=O)N1CCN(c2ccc3c(c2)C(=O)N(Cc2ccc(-c4nnc(C(F)F)o4)cn2)C(=O)C3(C)C)CC1] |
| 117 | 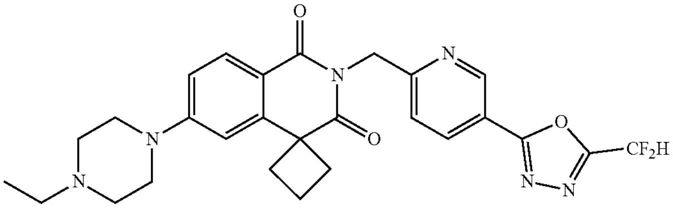 [SMILES: CCN1CCN(c2ccc3c(c2)C2(CCC2)C(=O)N(Cc2ccc(-c4nnc(C(F)F)o4)cn2)C3=O)CC1] |
| 118 | 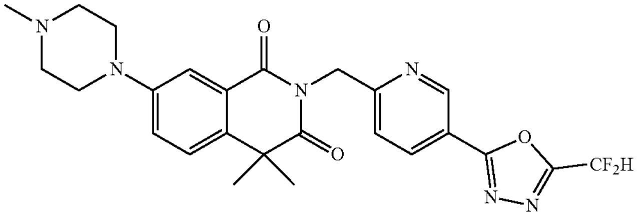 [SMILES: CN1CCN(c2ccc3c(c2)C(=O)N(Cc2ccc(-c4nnc(C(F)F)o4)cn2)C(=O)C3(C)C)CC1] |
| 119 | 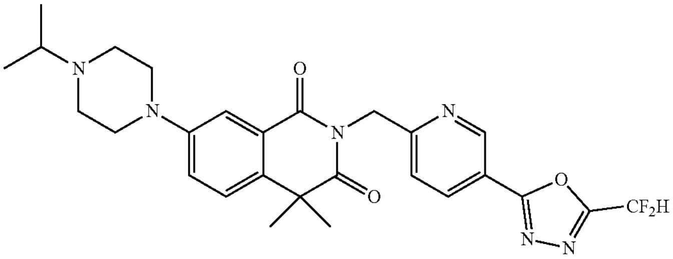 |
| 120 | 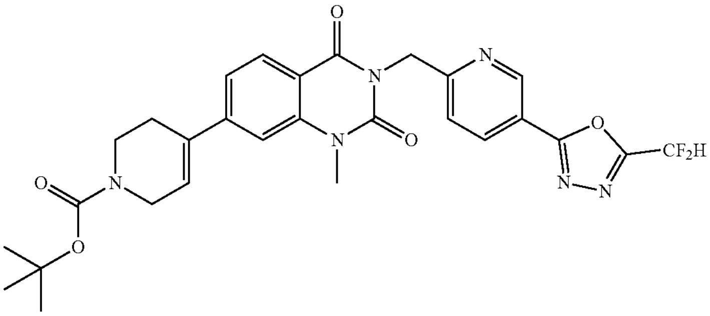 [SMILES: Cn1c(=O)n(Cc2ccc(-c3nnc(C(F)F)o3)cn2)c(=O)c2ccc(C3=CCN(C(=O)OC(C)(C)C)CC3)cc21] |

TABLE 1-continued
| Compound | Structure |
|---|---|
| 121 | 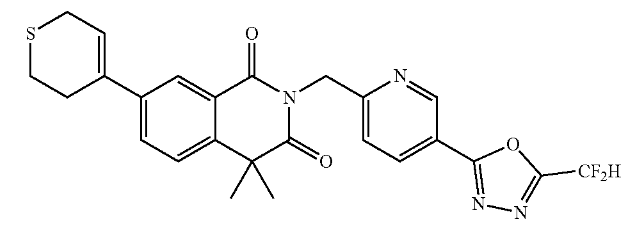 [SMILES: CC1(C)C(=O)N(Cc2ccc(-c3nnc(C(F)F)o3)cn2)C(=O)c2cc(C3=CCSCC3)ccc21] |
| 122 | 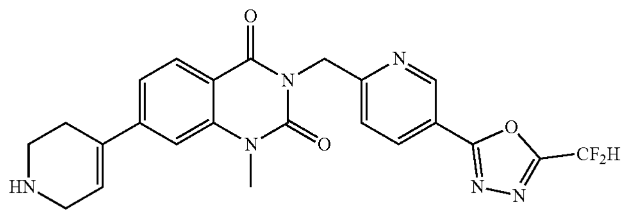 [SMILES: Cn1c(=O)n(Cc2ccc(-c3nnc(C(F)F)o3)cn2)c(=O)c2ccc(C3=CCNCC3)cc21] |
| 123 | 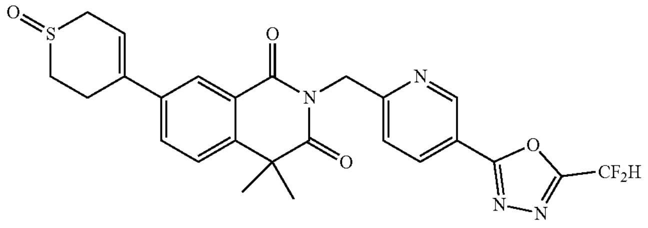 [SMILES: CC1(C)C(=O)N(Cc2ccc(-c3nnc(C(F)F)o3)cn2)C(=O)c2cc(C3=CCS(=O)CC3)ccc21] |
| 124 | 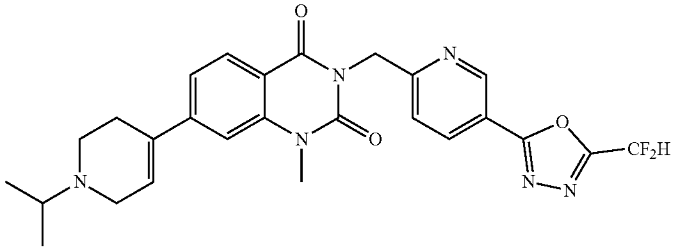 [SMILES: CC(C)N1CC=C(c2ccc3c(=O)n(Cc4ccc(-c5nnc(C(F)F)o5)cn4)c(=O)n(C)c3c2)CC1] |
| 125 | 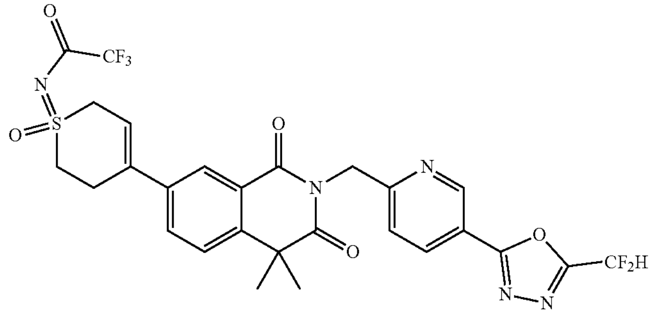 [SMILES: CC1(C)C(=O)N(Cc2ccc(-c3nnc(C(F)F)o3)cn2)C(=O)c2cc(C3=CCS(=O)(=NC(=O)C(F)(F)F)CC3)ccc21] |
| 126 | 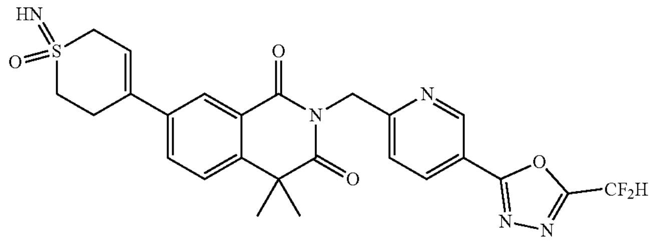 [SMILES: CC1(C)C(=O)N(Cc2ccc(-c3nnc(C(F)F)o3)cn2)C(=O)c2cc(C3=CCS(=N)(=O)CC3)ccc21] |

TABLE 1-continued
| Compound | Structure |
|---|---|
| 127 | 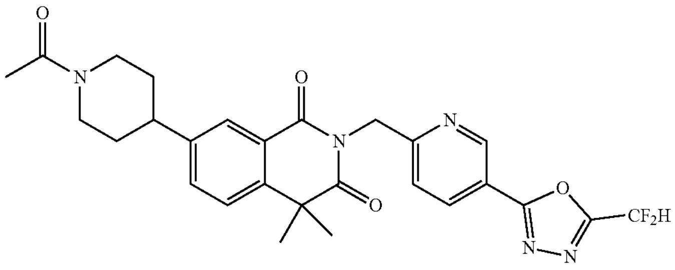 [SMILES: CC(=O)N1CCC(c2ccc3c(c2)C(=O)N(Cc2ccc(-c4nnc(C(F)F)o4)cn2)C(=O)C3(C)C)CC1] |
| 128 | 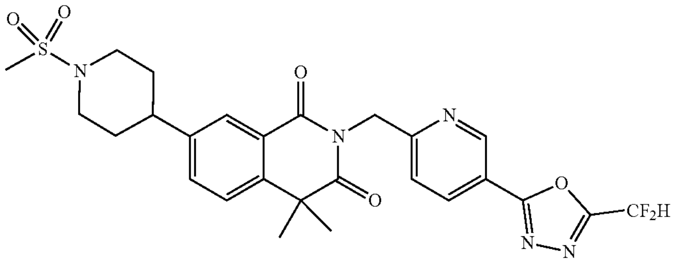 [SMILES: CC1(C)C(=O)N(Cc2ccc(-c3nnc(C(F)F)o3)cn2)C(=O)c2cc(C3CCN(S(C)(=O)=O)CC3)ccc21] |
| 129 | 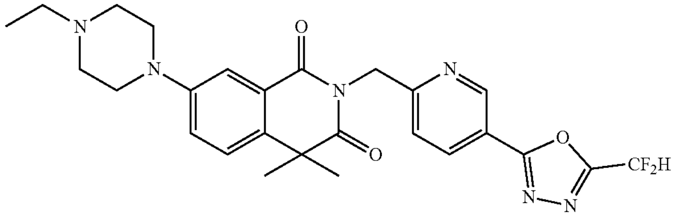 [SMILES: CCN1CCN(c2ccc3c(c2)C(=O)N(Cc2ccc(-c4nnc(C(F)F)o4)cn2)C(=O)C3(C)C)CC1] |
| 130 | 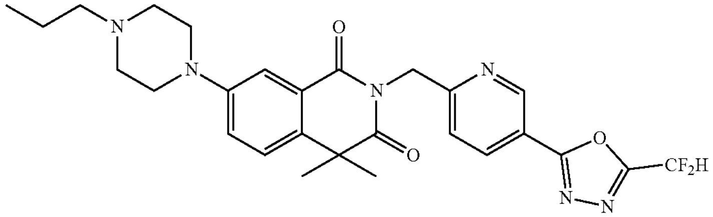 [SMILES: CCCN1CCN(c2ccc3c(c2)C(=O)N(Cc2ccc(-c4nnc(C(F)F)o4)cn2)C(=O)C3(C)C)CC1] |
| 131 | 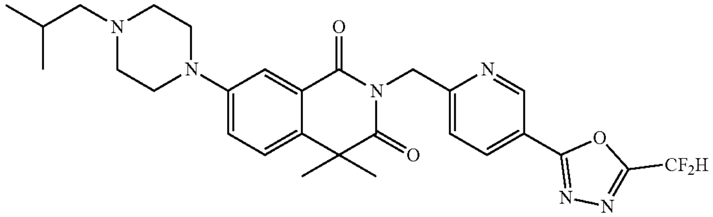 [SMILES: CC(C)CN1CCN(c2ccc3c(c2)C(=O)N(Cc2ccc(-c4nnc(C(F)F)o4)cn2)C(=O)C3(C)C)CC1] |
| 132 | 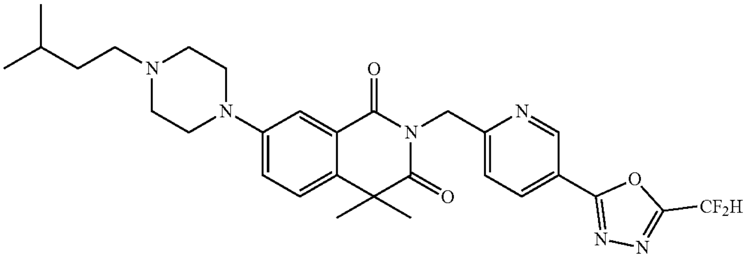 [SMILES: CC(C)CCN1CCN(c2ccc3c(c2)C(=O)N(Cc2ccc(-c4nnc(C(F)F)o4)cn2)C(=O)C3(C)C)CC1] |

TABLE 1-continued
| Compound | Structure |
|---|---|
| 133 | 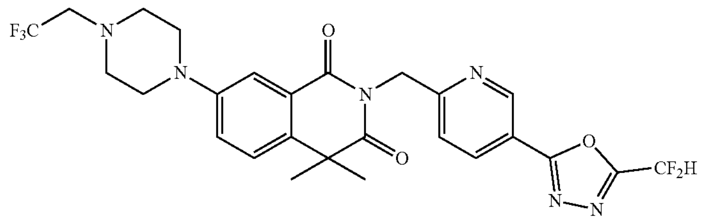 [SMILES: CC1(C)C(=O)N(Cc2ccc(-c3nnc(C(F)F)o3)cn2)C(=O)c2cc(N3CCN(CC(F)(F)F)CC3)ccc21] |
| 134 | 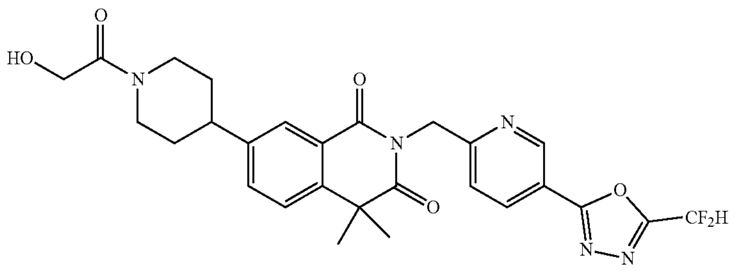 [SMILES: CC1(C)C(=O)N(Cc2ccc(-c3nnc(C(F)F)o3)cn2)C(=O)c2cc(C3CCN(C(=O)CO)CC3)ccc21] |
| 135 | 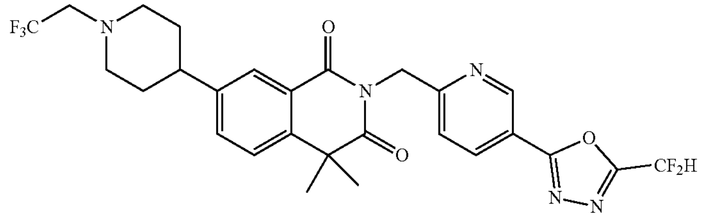 [SMILES: CC1(C)C(=O)N(Cc2ccc(-c3nnc(C(F)F)o3)cn2)C(=O)c2cc(C3CCN(CC(F)(F)F)CC3)ccc21] |
| 136 | 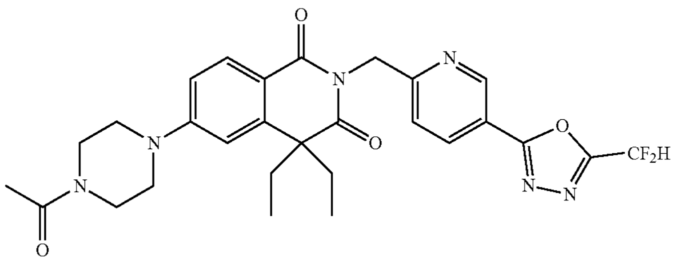 [SMILES: CCC1(CC)C(=O)N(Cc2ccc(-c3nnc(C(F)F)o3)cn2)C(=O)c2ccc(N3CCN(C(C)=O)CC3)cc21] |
| 137 | 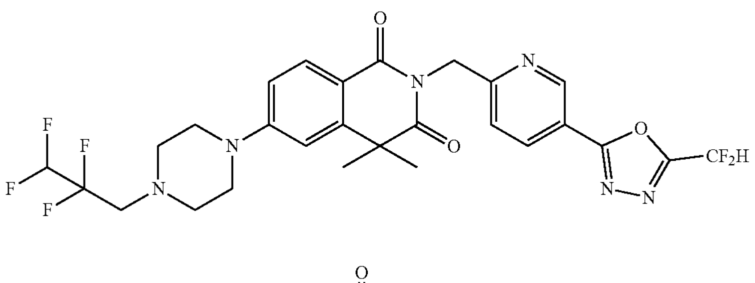 |
| 138 | 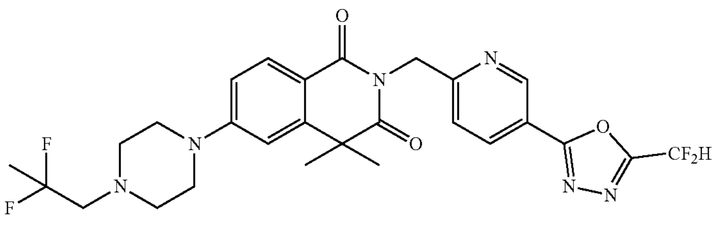 [SMILES: CC(F)(F)CN1CCN(c2ccc3c(c2)C(C)(C)C(=O)N(Cc2ccc(-c4nnc(C(F)F)o4)cn2)C3=O)CC1] |

TABLE 1-continued
| Compound | Structure |
| --- | --- |
| 139 | 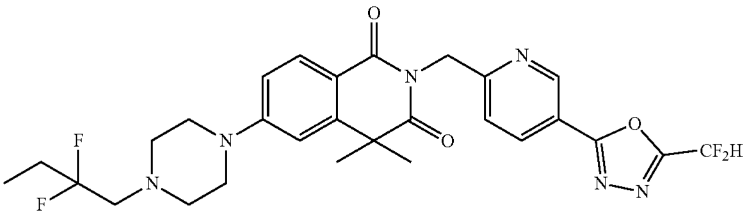 [SMILES: CCC(F)(F)CN1CCN(c2ccc3c(c2)C(C)(C)C(=O)N(Cc2ccc(-c4nnc(C(F)F)o4)cn2)C3=O)CC1] |
| 140 | 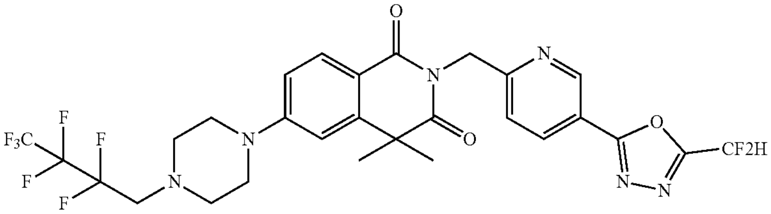 [SMILES: CC1(C)C(=O)N(Cc2ccc(-c3nnc(C(F)F)o3)cn2)C(=O)c2ccc(N3CCN(CC(F)(F)C(F)(F)C(F)(F)F)CC3)cc21] |
| 141 | 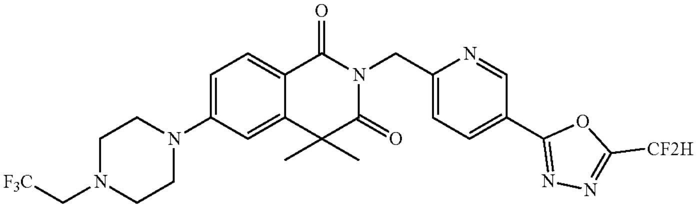 [SMILES: CC1(C)C(=O)N(Cc2ccc(-c3nnc(C(F)F)o3)cn2)C(=O)c2ccc(N3CCN(CC(F)(F)F)CC3)cc21] |
| 142 | 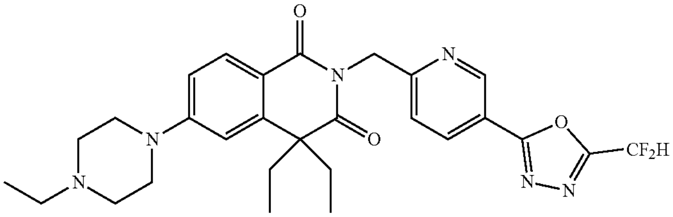 [SMILES: CCN1CCN(c2ccc3c(c2)C(CC)(CC)C(=O)N(Cc2ccc(-c4nnc(C(F)F)o4)cn2)C3=O)CC1] |
| 143 | 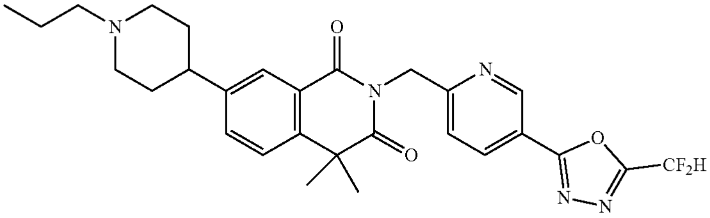 [SMILES: CCCN1CCC(c2ccc3c(c2)C(=O)N(Cc2ccc(-c4nnc(C(F)F)o4)cn2)C(=O)C3(C)C)CC1] |
| 144 | 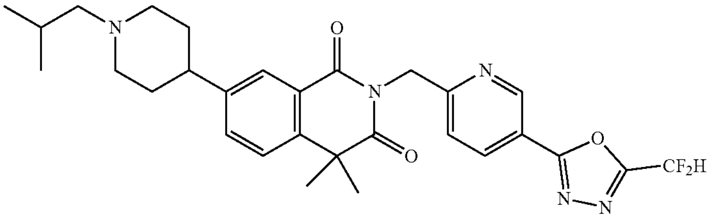 [SMILES: CC(C)CN1CCC(c2ccc3c(c2)C(=O)N(Cc2ccc(-c4nnc(C(F)F)o4)cn2)C(=O)C3(C)C)CC1] |
| 145 | 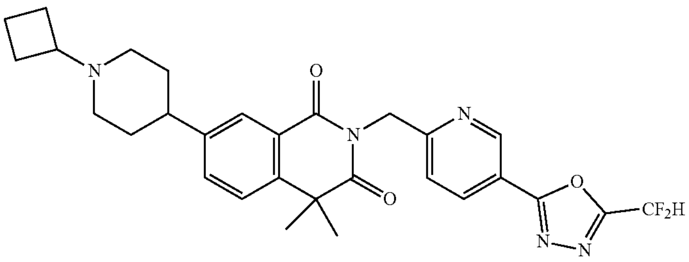 [SMILES: CC1(C)C(=O)N(Cc2ccc(-c3nnc(C(F)F)o3)cn2)C(=O)c2cc(C3CCN(C4CCC4)CC3)ccc21] |

TABLE 1-continued
| Compound | Structure |
|---|---|
| 146 | 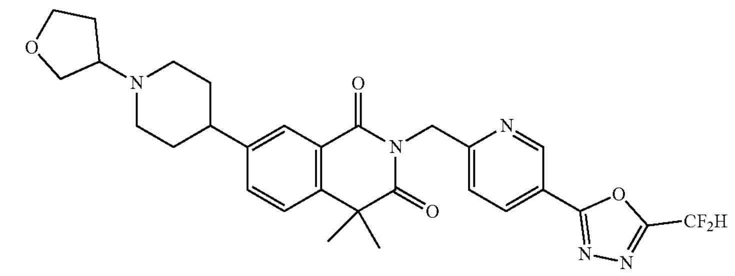 [SMILES: CC1(C)C(=O)N(Cc2ccc(-c3nnc(C(F)F)o3)cn2)C(=O)c2cc(C3CCN(C4CCOC4)CC3)ccc21] |
| 147 | 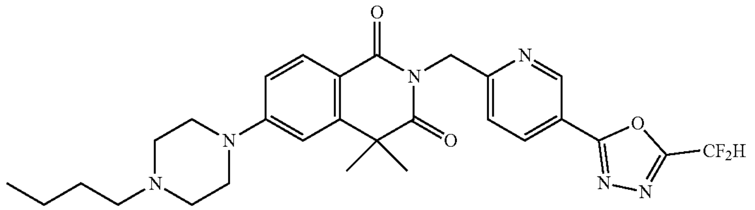 [SMILES: CCCCN1CCN(c2ccc3c(c2)C(C)(C)C(=O)N(Cc2ccc(-c4nnc(C(F)F)o4)cn2)C3=O)CC1] |
| 148 | 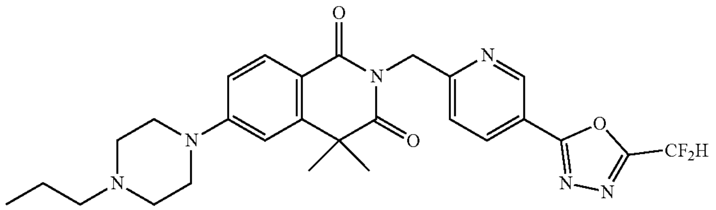 [SMILES: CCCN1CCN(c2ccc3c(c2)C(C)(C)C(=O)N(Cc2ccc(-c4nnc(C(F)F)o4)cn2)C3=O)CC1] |
| 149 | 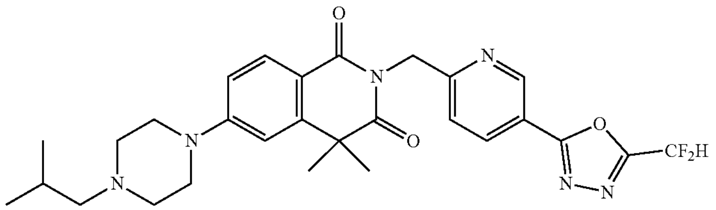 [SMILES: CC(C)CN1CCN(c2ccc3c(c2)C(C)(C)C(=O)N(Cc2ccc(-c4nnc(C(F)F)o4)cn2)C3=O)CC1] |
| 150 | 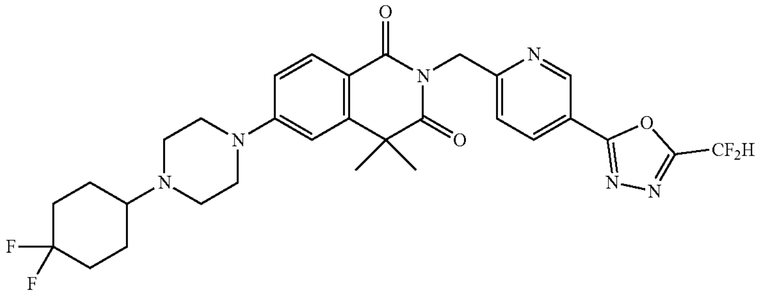 [SMILES: CC1(C)C(=O)N(Cc2ccc(-c3nnc(C(F)F)o3)cn2)C(=O)c2ccc(N3CCN(C4CCC(F)(F)CC4)CC3)cc21] |
| 151 | 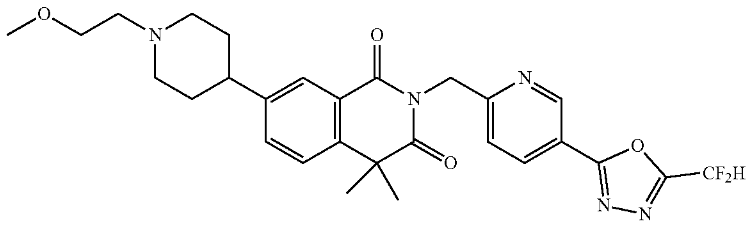 [SMILES: COCCN1CCC(c2ccc3c(c2)C(=O)N(Cc2ccc(-c4nnc(C(F)F)o4)cn2)C(=O)C3(C)C)CC1] |

TABLE 1-continued

| Compound | Structure |
| --- | --- |
| 152 | 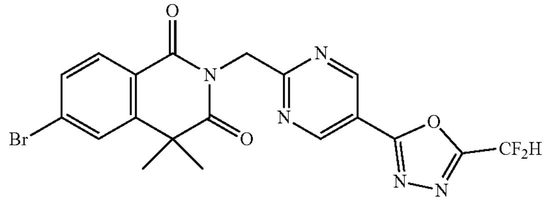 [SMILES: CC1(C)C(=O)N(Cc2ncc(-c3nnc(C(F)F)o3)cn2)C(=O)c2ccc(Br)cc21] |
| 153 | 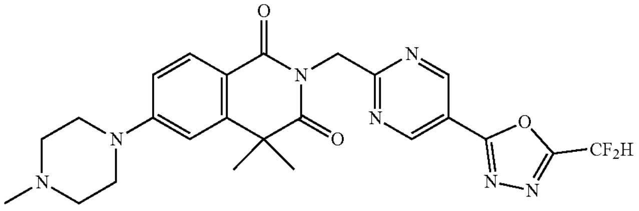 [SMILES: CN1CCN(c2ccc3c(c2)C(C)(C)C(=O)N(Cc2ncc(-c4nnc(C(F)F)o4)cn2)C3=O)CC1] |
| 154 | 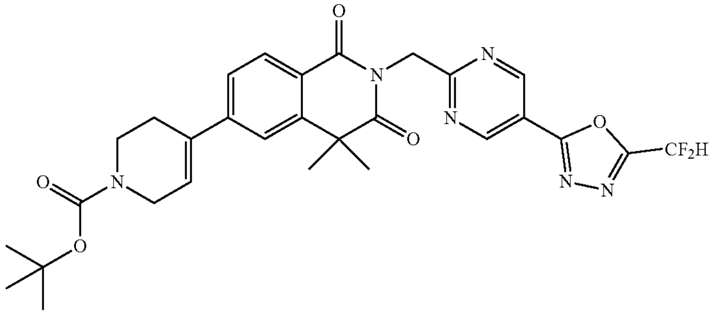 [SMILES: CC(C)(C)OC(=O)N1CC=C(c2ccc3c(c2)C(C)(C)C(=O)N(Cc2ncc(-c4nnc(C(F)F)o4)cn2)C3=O)CC1] |
| 155 | 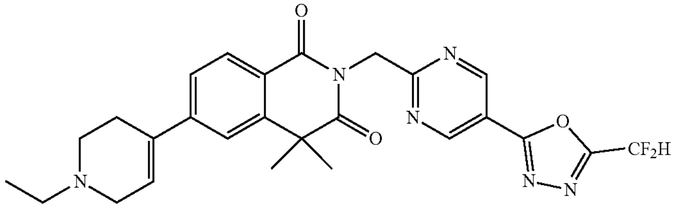 [SMILES: CCN1CC=C(c2ccc3c(c2)C(C)(C)C(=O)N(Cc2ncc(-c4nnc(C(F)F)o4)cn2)C3=O)CC1] |
| 156 | 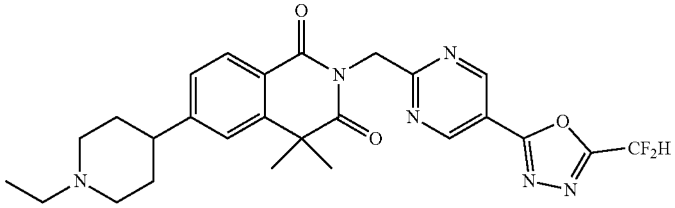 [SMILES: CCN1CCC(c2ccc3c(c2)C(C)(C)C(=O)N(Cc2ncc(-c4nnc(C(F)F)o4)cn2)C3=O)CC1] |

1,3,4-oxadiazole homophthalimide derivative compounds of the present invention may contain at least one asymmetric carbon, and thus may be present as a racemate, a racemic mixture, a single enantiomer (optical isomer), a mixture of diastereomers and respective diastereomers thereof. The stereoisomers may be separated by being split according to the related art, for example, column chromatography, HPLC or the like. Alternatively, respective stereoisomers of 1,3,4-oxadiazole homophthalimide derivative compounds of the present invention may be stereospecifically synthesized by using a generally known array of optically pure starting materials and/or reagents.

In the present invention, the term "pharmaceutically acceptable" means the one that is physiologically acceptable and does not conventionally cause an allergic reaction such as gastrointestinal disturbance and dizziness, or other reactions similar thereto, when being administered into a human, and the term "salt" means a salt prepared according to a conventional method as an acid addition salt formed by pharmaceutically acceptable free acid, and a method for preparing the pharmaceutically acceptable salt is generally known to those skilled in the art. The pharmaceutically acceptable salts include, for example, inorganic ion salts prepared from calcium, potassium, sodium, magnesium and the like; inorganic acid salts prepared from hydrochloric acid, nitric acid, phosphoric acid, bromic acid, iodic acid, hydroiodic acid, perchloric acid, sulfuric acid and the like; organic acid salts prepared from acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbric acid, carbonic acid, vanillic acid, etc.; sulfonic acid salts prepared from methanesulfonic acid, ethanesulfonic acid, benzenesulfonic acid, p-toluenesulfonic acid, naphthalenesulfonic acid and the like; amino acid salts prepared from glycine, arginine, lysine, etc.; amine salts prepared from trimethylamine, triethylamine, ammonia, pyridine, picoline, etc.; and the like, but types of salts meant in the present invention are not limited to the listed salts. In the present invention, preferable salts include hydrochloric acid, trifluoroacetic acid, citric acid, bromic acid, maleic acid, phosphoric acid, sulfuric acid and tartaric acid.

Method for Preparing 1,3,4-Oxadiazole Homophthalimide Derivative Compounds

The present invention provides a method for preparing 1,3,4-oxadiazole homophthalimide derivative compounds, stereoisomers thereof or pharmaceutically acceptable salts thereof.

In the present invention, a preferable method for preparing 1,3,4-oxadiazole homophthalimide derivative compounds, stereoisomers thereof or pharmaceutically acceptable salts thereof is the same as shown in the reaction formulas 1 to 14, and even a preparation method modified at a level apparent to those skilled in the art is also included therein.

[Reaction Formula 1]

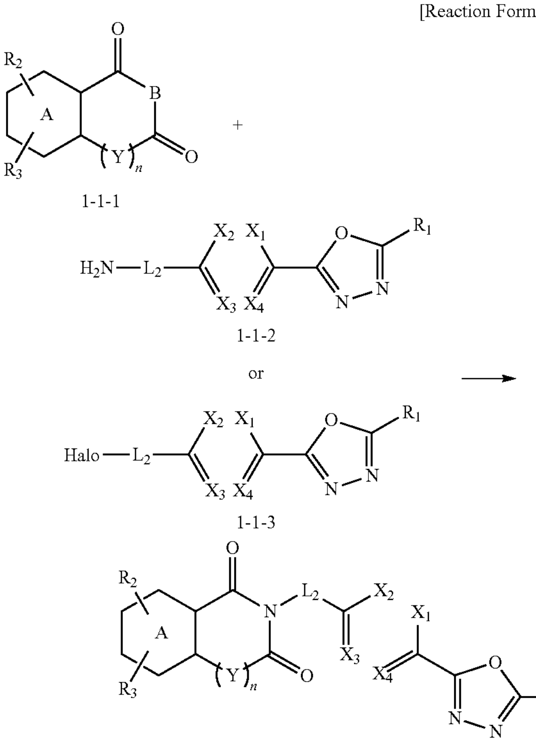

1-1-1

1-1-2 or 1-1-3

1-1-4

In the above reaction formula 1, A, $X_1$ to $X_4$, $R_1$ to $R_3$, Y and n are the same as described in the chemical formula I. Specifically, in the above reaction formula 1, A is phenyl, $X_1$ to $X_4$ are each independently CH, CF or N, $L_2$ is methylene ($CH_2$), B is N, $R_1$ is $CF_2H$, $R_2$ and $R_3$ are H, Y is methylene ($CH_2$) or C ($C_{1-7}$ alkyl)$_2$, Halo is halogen, and n is 0 or 1.

The above [Reaction Formula 1] shows a synthesis method of 1,3,4-oxadiazole compound having a heterocyclic ring structure, and a compound of the chemical formula 1-1-1 reacts with a compound of the chemical formula 1-1-2 or the chemical formula 1-1-3 so as to prepare a compound of the chemical formula 1-1-4 having a 1,3,4-oxadiazole structure.

In the present invention, the compounds prepared according to the above reaction formula include 1, 2, 12, 65 and the like.

[Reaction Formula 2]

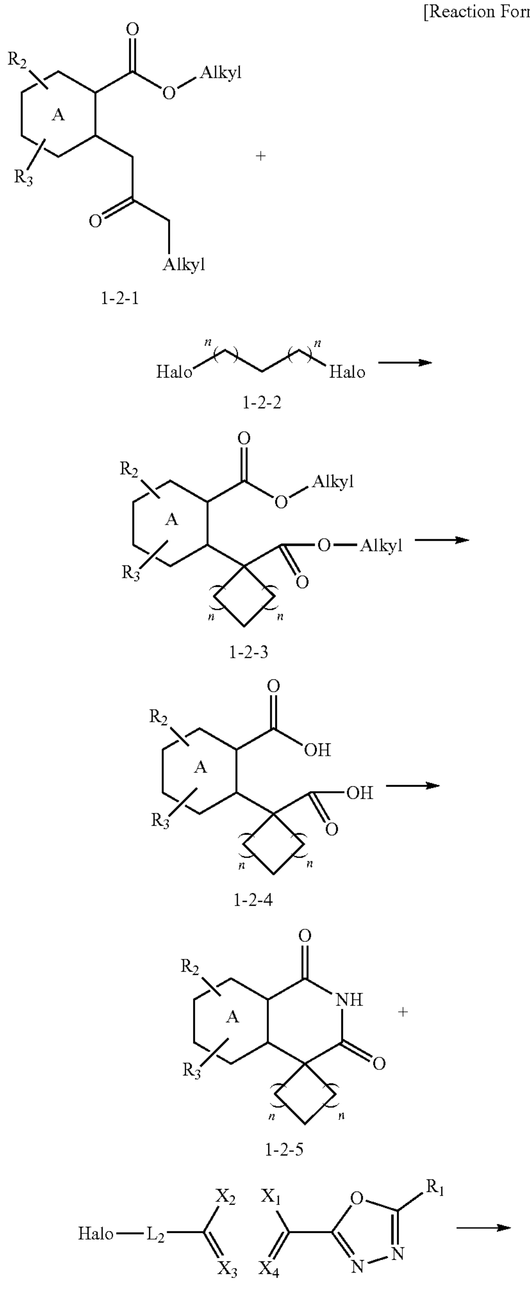

1-2-1

1-2-2

1-2-3

1-2-4

1-2-5

1-1-2

-continued

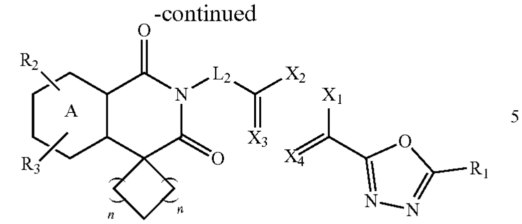

1-2-6

In the above reaction formula 2, A, $X_1$ to $X_4$ and $R_1$ to $R_3$ are the same as described in the chemical formula I. Specifically, in the above reaction formula 2, A is phenyl, $X_1$ to $X_4$ are each independently CH, CF or N, $L_2$ is methylene ($CH_2$), Riis $CF_2H$, $R_2$ and $R_3$ are H, Y is $CR_aR_b$ ($R_a$ and $R_b$ form cyclobutane), Halo is halogen, and Alkyl is $C_{1-7}$ alkyl.

The above [Reaction Formula 2] shows a synthesis method of 1,3,4-oxadiazole compound having a heterocyclic ring structure, and a compound of the chemical formula 1-2-1 is subjected to a substitution reaction with a compound of the chemical formula 1-2-2 so as to prepare a compound of the chemical formula 1-2-3, and then is subjected to a hydrolysis reaction so as to prepare a compound of the chemical formula 1-2-4. After that, the compound of the chemical formula 1-2-4 reacts with urea so as to prepare a compound of the chemical formula 1-2-5, and then is subjected to a substitution reaction with a compound of the chemical formula 1-1-2 so as to prepare a compound of the chemical formula 1-2-6.

In the present invention, the compounds prepared according to the above reaction formula include 3, 4, 5, 10 6, 10 7 and the like.

[Reaction Formula 3]

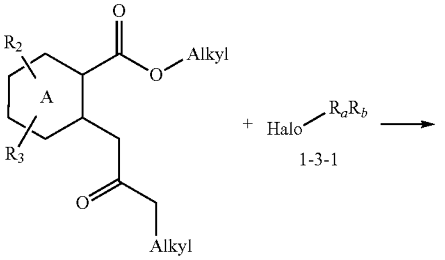

1-3-1

1-2-1

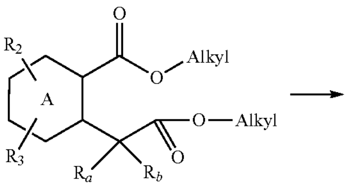

1-3-2

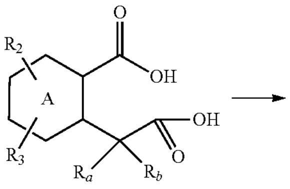

1-3-3

-continued

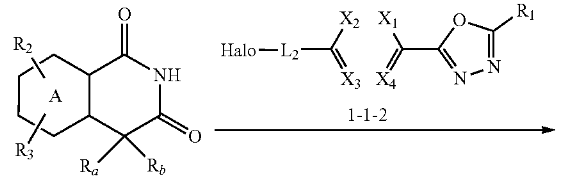

1-1-2

1-3-4

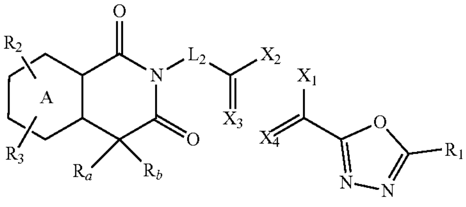

1-3-5

In the above reaction formula 3, A, $X_1$ to $X_4$, $R_1$ to $R_3$ and $R_a$ to $R_b$ are the same as described in the chemical formula I. Specifically, in the above reaction formula 3, A is phenyl, $X_1$ to $X_4$ are each independently CH, CF or N, $L_2$ is methylene ($CH_2$), Riis $CF_2H$, $R_2$ and $R_3$ are each independently H or halogen, $R_a$ and $R_b$ are $C_{1-7}$ alkyl, Halo is halogen, and Alkyl is $C_{1-7}$ alkyl.

The above [Reaction Formula 3] shows a synthesis method of 1,3,4-oxadiazole compound having a heterocyclic ring structure, and a compound of the chemical formula 1-2-1 is subjected to a substitution reaction with a compound of the chemical formula 1-3-1 so as to prepare a compound of the chemical formula 1-3-2, and then is subjected to a hydrolysis reaction so as to prepare a compound of the chemical formula 1-3-3. After that, the compound of the chemical formula 1-3-3 reacts with urea so as to prepare a compound of the chemical formula 1-3-4, and then is subjected to a substitution reaction with a compound of the chemical formula 1-1-2 so as to prepare a compound of the chemical formula 1-3-5.

In the present invention, the compounds prepared according to the above reaction formula include 6, 7, 8, 23, 51, 152 and the like.

[Reaction Formula 4]

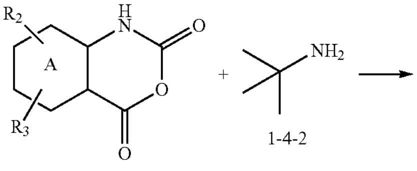

1-4-2

1-4-1

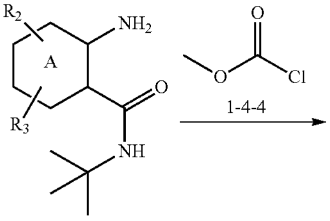

1-4-4

1-4-3

-continued

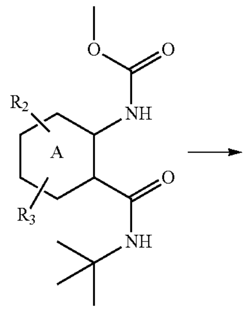

1-4-5

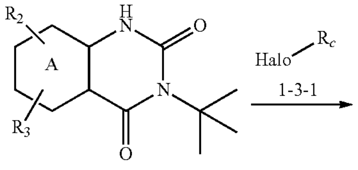

1-3-1

1-4-6

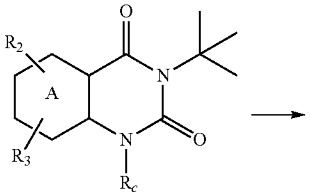

1-4-7

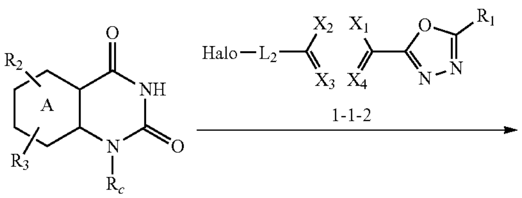

1-1-2

1-4-8

-continued

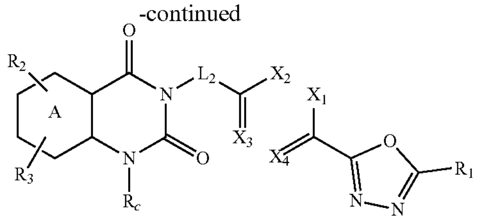

1-4-9

In the above reaction formula 4, A, $X_1$ to $X_4$, $R_1$ to $R_3$ and Re are the same as described in the chemical formula I. Specifically, in the above reaction formula 4, A is phenyl, $X_1$ to $X_4$ are each independently CH, CF or N, $L_2$ is methylene ($CH_2$), $R_1$ is $CF_2H$, $R_2$ and $R_3$ are each independently H or halogen, Re is $C_{1-7}$ alkyl-heterocycloalkyl, $C_{1-7}$ alkyl-phenyl or $C_{1-7}$ alkyl, Halo is halogen, and Alkyl is $C_{1-7}$ alkyl.

The above [Reaction Formula 4] shows a synthesis method of 1,3,4-oxadiazole compound having a heterocyclic ring structure, and a compound of the chemical formula 1-4-1 reacts with a compound of the chemical formula 1-4-2 so as to prepare a compound of the chemical formula 1-4-3, and then is subjected to a substitution reaction with a compound of the chemical formula 1-4-4 so as to prepare a compound of the chemical formula 1-4-5. After that, the compound of the chemical formula 1-4-5 reacts with potassium hydroxide so as to prepare a compound of the chemical formula 1-4-6, and then is subjected to a substitution reaction with a compound of the chemical formula 1-3-1 so as to prepare a compound of the chemical formula 1-4-7. The compound of the chemical formula 1-4-7 reacts with hydrochloric acid aqueous solution so as to prepare a compound of the chemical formula 1-4-8, and then is subjected to a substitution reaction with a compound of the chemical formula 1-1-2 so as to prepare a compound of the chemical formula 1-4-9.

In the present invention, the compounds prepared according to the above reaction formula include 9, 10, 11, 13, 66, 86, 97 and the like.

[Reaction Formula 5]

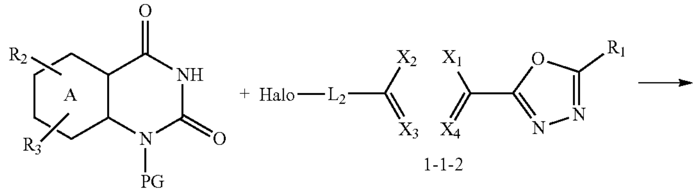

1-5-1

1-1-2

-continued

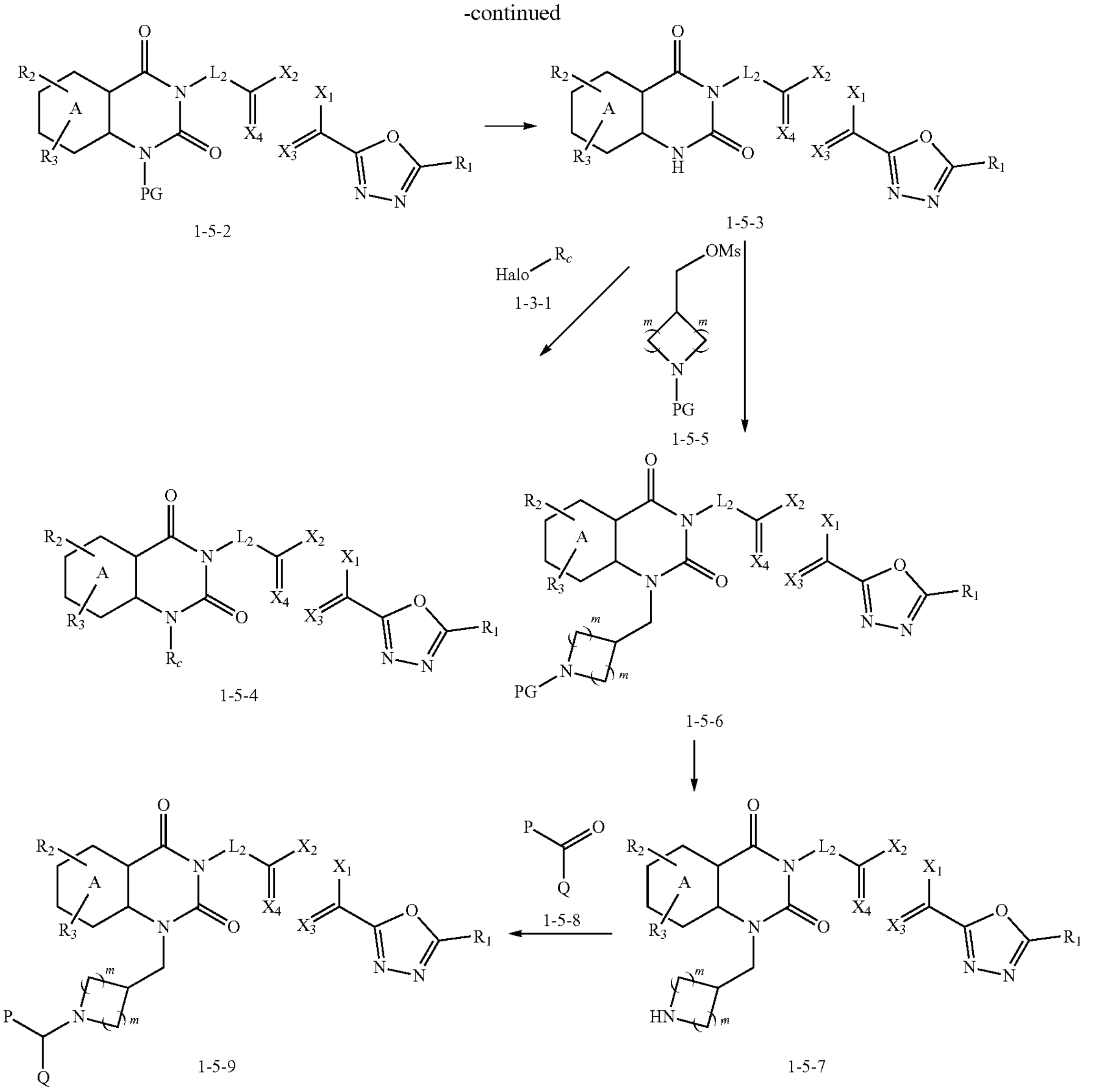

In the above reaction formula 5, A, $X_1$ to $X_4$, $R_1$ to $R_3$ and $R_c$ are the same as described in the chemical formula I. Specifically, in the above reaction formula 5, A is phenyl, $X_1$ to $X_4$ are each independently CH or N, $L_2$ is methylene ($CH_2$), $R_1$ is $CF_2H$, $R_2$ and $R_3$ are each independently H or halogen, RC is $C_{1-7}$ alkyl-heterocycloalkyl, $C_{1-7}$ alkyl-O—$C_{1-7}$ alkyl, $C_{1-7}$ alkyl, $C_{1-7}$ alkyl-N($C_{1-7}$ alkyl)$_2$ or $C_{1-7}$ alkyl-heteroaryl, Halo is halogen, Alkyl is $C_{1-7}$ alkyl, OMs is mesylate, PG is a protecting group, m is 2, and P and Q are hydrogen.

The above [Reaction Formula 5] shows a synthesis method of 1,3,4-oxadiazole compound having a heterocyclic ring structure, and a compound of the chemical formula 1-5-1, which is prepared in [Reaction Formula 4] and to which a protecting group is added, is subjected to a substitution reaction with a compound of the chemical formula 1-1-2 so as to prepare a compound of the chemical formula 1-5-2, and then the protecting group is removed therefrom so as to prepare compounds 14, 67 and the like of the chemical formula 1-5-3. After that, the compound of the chemical formula 1-5-3 is subjected to a substitution reaction with a compound of the chemical formula 1-3-1 so as to prepare a compound of the chemical formula 1-5-4.

Also, the compound of the chemical formula 1-5-3 is subjected to a substitution reaction with a compound of the chemical formula 1-5-5, to which a protecting group is added, so as to prepare a compound of the chemical formula 1-5-6, and then the protecting group is removed therefrom so as to prepare a compound of the chemical formula 1-5-7. After that, a reductive amination reaction is performed with a compound of the chemical formula 1-5-8 so as to prepare a compound of the chemical formula 1-5-9.

In the present invention, the compounds prepared according to the above reaction formula include 15, 16, 17, 18, 19, 20, 21, 22, 70, 71, 72, 73 and the like.

[Reaction Formula 6]

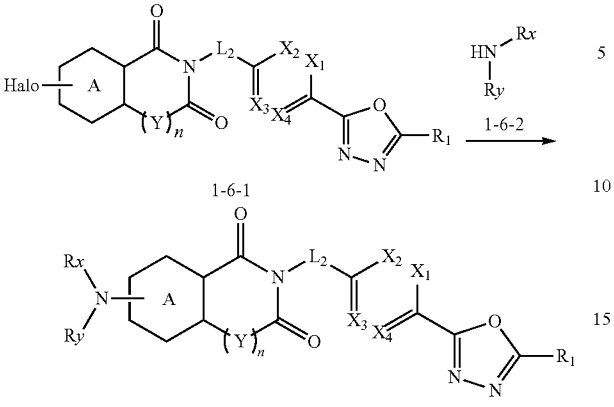

1-6-1

1-6-3

In the above reaction formula 6, A, $X_1$ to $X_4$, $R_1$ to $R_3$ and $R_x$ to $R_y$ are the same as described in the chemical formula I. Specifically, in the above reaction formula 6, A is phenyl, $X_1$ to $X_4$ are each independently CH or N, $L_2$ is methylene ($CH_2$), $R_1$ is $CF_2H$, $R_2$ and $R_3$ are each independently H or —$NR_xR_y$, $R_x$ and $R_y$ are linked together to form a ring along with a nitrogen atom bonded thereto {in this case, the formed ring may further contain one heteroatom of N or O, and at least one hydrogen of the formed ring to which $R_x$ and $R_y$ are linked together and bonded along with the nitrogen atom bonded thereto, may be substituted with $C_{1-7}$ alkyl, C(═O)—$C_{1-7}$ alkyl, 3- to 7-membered heterocycloalkyl containing one to three heteroatoms selected from the group including N, O or S, N($C_{1-7}$ alkyl)$_2$, $C_{1-7}$ alkyl-C(═O)-3- to 7-membered heterocycloalkyl [in this case, heterocycloalkyl contains one to three heteroatoms selected from the group including N, O or S], C(═O)—$C_{1-7}$ alkyl, $C_{1-7}$ alkyl-O—$C_{1-7}$ alkyl, C(═O)—O—$C_{1-7}$ alkyl, 3- to 7-membered cycloalkyl, $C_{1-7}$ alkyl-3- to 7-membered cycloalkyl, halogen, 5- or 6-membered heteroaryl [in this case, heteroaryl contains one to three heteroatoms selected from the group including N, O or S], C(═O)—NH—$C_{1-7}$ alkyl, C(═O)—N($C_{1-7}$ alkyl)$_2$ or S(═O)$_2$—$C_{1-7}$ alkyl}, Y is C($C_{1-7}$ alkyl)$_2$, n is 1, and Halo is halogen.

The above [Reaction Formula 6] shows a synthesis method of 1,3,4-oxadiazole compound having a heterocyclic ring structure, and a compound of the chemical formula 1-6-1 is subjected to C—N coupling (Buchwald reaction) with a compound of the chemical formula 1-6-2 so as to prepare a compound of the chemical formula 1-6-3.

In the present invention, the compounds prepared according to the above reaction formula include 24, 27, 28, 29, 31, 32, 33, 34, 35, 36, 37, 38, 39, 40, 41, 42, 43, 45, 46, 47, 48, 49, 50, 52, 56, 57, 58, 117, 153 and the like.

[Reaction Formula 7]

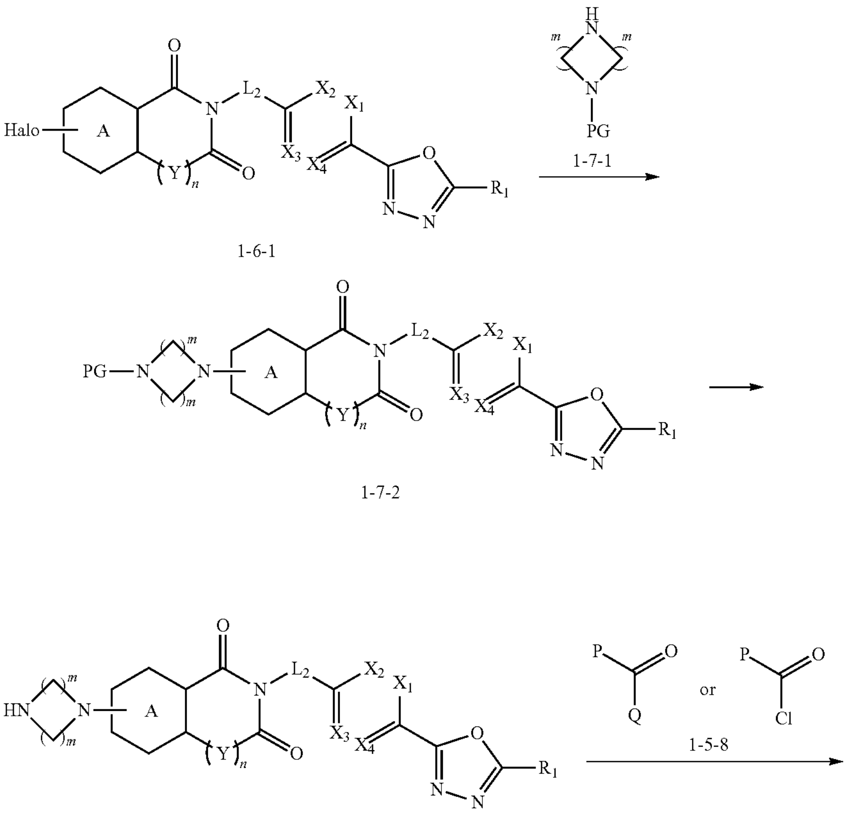

1-6-1

1-7-2

1-7-3

-continued

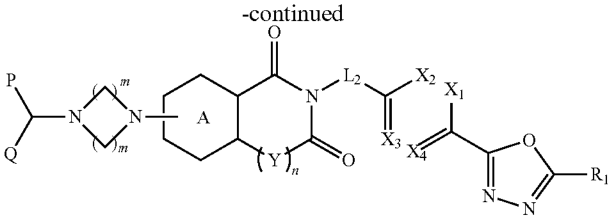

1-7-4

In the above reaction formula 7, A, $X_1$ to $X_4$, $R_1$ to $R_3$, Y and n are the same as described in the chemical formula I. Specifically, in the above reaction formula 7, A is phenyl, $X_1$ to $X_4$ are each independently CH or N, $L_2$ is methylene ($CH_2$), $R_1$ is $CF_2H$, $R_2$ and $R_3$ are each independently H or 3- to 7-membered heterocycloalkyl [in this case, heterocycloalkyl contains one to three heteroatoms selected from the group including N, O or S], Y is $C(C_{1-7}\ alkyl)_2$, n is 1, Halo is halogen, Alkyl is $C_{1-7}$ alkyl, PG is a protecting group, m is 2, P and Q are $C_{1-7}$ alkyl, or P and Q are linked together to form a ring along with a carbon atom bonded thereto, in which the formed ring may further contain one heteroatom of N or O.

The above [Reaction Formula 7] shows a synthesis method of 1,3,4-oxadiazole compound having a heterocyclic ring structure, and a compound of the chemical formula 1-6-1 is subjected to C—N coupling (Buchwald reaction) with a compound of the chemical formula 1-7-1 having a protecting group so as to prepare the compounds 25, 79 and the like of the chemical formula 1-7-2. After that, the protecting group is removed therefrom to prepare a compound of the chemical formula 1-7-3, and a reductive amination reaction and an acylation reaction are performed with a compound of the chemical formula 1-5-8 so as to prepare the compounds 26, 30, 80, 81, 136, 141, 142, 147, 148, 149, 150 and the like of the chemical formula 1-7-4.

[Reaction Formula 8]

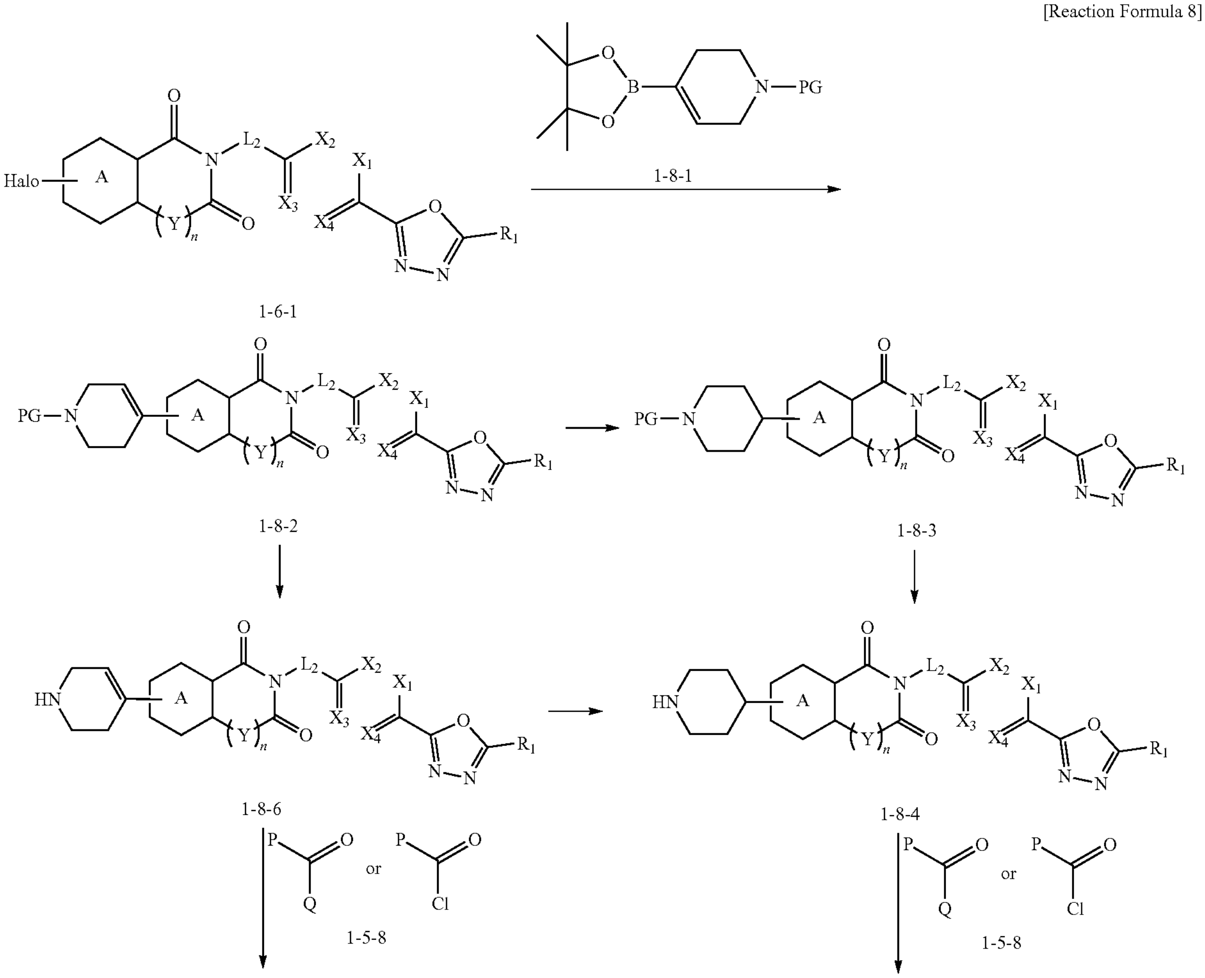

1-8-1

1-6-1

1-8-2

1-8-3

1-8-6 or 1-5-8

1-8-4 or 1-5-8

-continued

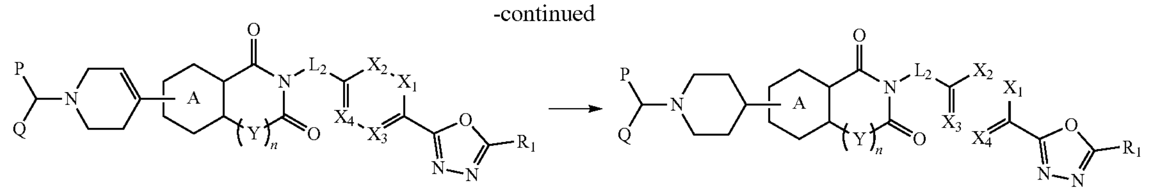

1-8-7 1-8-5

In the above reaction formula 8, A, $X_1$ to $X_4$, $R_1$ to $R_3$, Y and n are the same as described in the chemical formula I. Specifically, in the above reaction formula 8, A is phenyl, $X_1$ to $X_4$ are each independently CH or N, $L_2$ is methylene ($CH_2$), $R_1$ is $CF_2H$, $R_2$ and $R_3$ are each independently H or 3- to 7-membered heterocycloalkyl containing one to three heteroatoms selected from the group including N, O or S, Y is $C(C_{1-7}\ alkyl)_2$, n is 1, Halo is halogen, PG is a protecting group, P and Q are each independently H, $C_{1-7}$ alkyl or 3- to 7-membered heterocycloalkyl containing one to three heteroatoms selected from the group including N, O or S, or P and Q are linked together to form a ring along with a carbon atom bonded thereto, in which the formed ring may further contain one heteroatom of N or O.

The above [Reaction Formula 8] shows a synthesis method of 1,3,4-oxadiazole compound having a heterocyclic ring structure, and a compound of the chemical formula 1-6-1 is subjected to C—C coupling (Suzuki reaction) with a compound of the chemical formula 1-8-1 having a protecting group so as to prepare the compounds 41, 53, 120, 154 and the like of the chemical formula 1-8-2. A reduction reaction is performed to prepare a compound of the chemical formula 1-8-3, and then the protecting group is removed therefrom so as to prepare the compound 122 and the like of the chemical formula 1-8-4. After that, a compound of the chemical formula 1-5-8 is added into a compound of the chemical formula 1-8-4, and subjected to a reductive amination reaction so as to prepare a compound of the chemical formula 1-8-5.

Also, the protecting group is removed from the compound of the chemical formula 1-8-2 so as to prepare a compound of the chemical formula 1-8-6, and then subjected to a reductive amination reaction and an acylation reaction so as to prepare the compounds 42, 43, 124, 155 and the like of the chemical formula 1-8-7. After that, a reduction reaction is performed with the compound of the chemical formula 1-8-7 so as to prepare a compound of the chemical formula 1-8-5.

In the present invention, the compounds prepared according to the above reaction formula include 44, 54, 55, 59, 60, 61, 62, 63, 64, 68, 69, 127, 128, 134, 135, 143, 144, 145, 146, 151, 156 and the like.

[Reaction Formula 9]

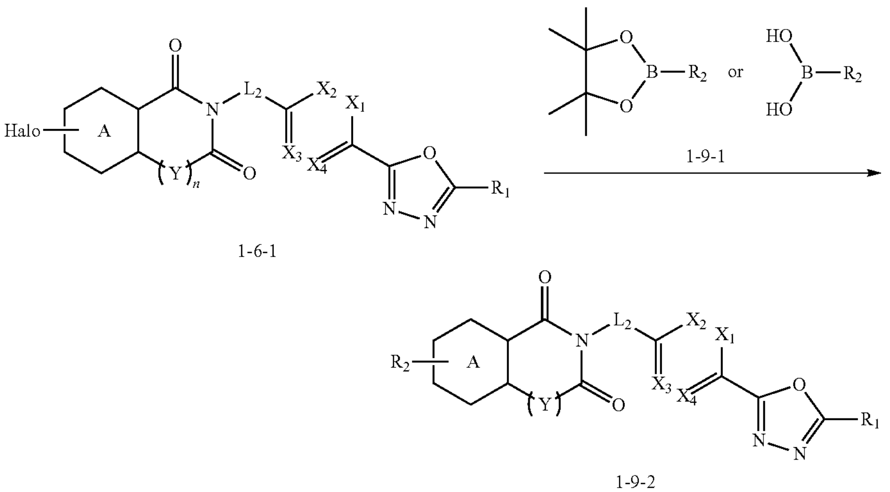

1-6-1

1-9-1

1-9-2

In the above reaction formula 9, A, $X_1$ to $X_4$, $R_1$, $R_2$, Y and n are the same as described in the chemical formula I. Specifically, in the above reaction formula 9, A is phenyl, $X_1$ to $X_4$ are each independently CH or N, $L_2$ is methylene ($CH_2$), $R_1$ is $CF_2H$, $R_2$ is 5- or 6-membered heteroaryl containing one to three heteroatoms selected from the group including N, O or S, or 3- to 7-membered heterocycloalkyl containing one to three heteroatoms selected from the group including N, O or S, Y is $C(C_{1-7}\ alkyl)_2$, Halo is halogen, and n is 1.

The above [Reaction Formula 9] shows a synthesis method of 1,3,4-oxadiazole compound having a heterocyclic ring structure, and a compound of the chemical formula 1-6-1 is subjected to C—C coupling (Suzuki reaction) with a compound of the chemical formula 1-9-1 so as to prepare a compound of the chemical formula 1-9-2.

In the present invention, the compounds prepared according to the above reaction formula include 74, 82, 83, 84, 85, 93, 94, 95, 96, 98, 99, 100, 101, 102, 103, 104, 105, 108, 109, 110, 111, 112, 113, 114, 115 and the like.

[Reaction Formula 10]

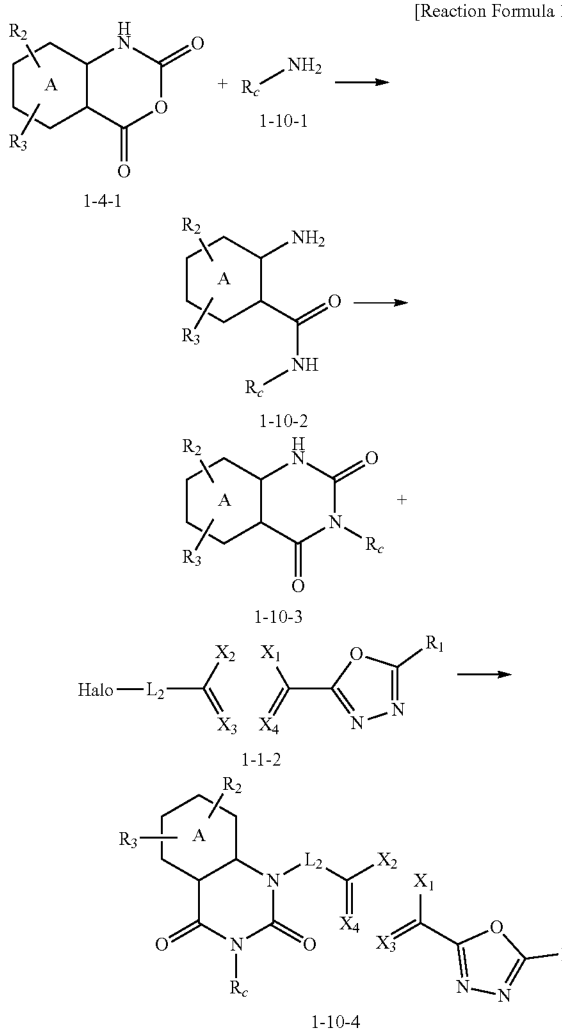

1-4-1 1-10-1 1-10-2 1-10-3 1-1-2 1-10-4

In the above reaction formula 10, A, $X_1$ to $X_4$, $R_1$ to $R_3$ and $R_c$ are the same as described in the chemical formula I. Specifically, in the above reaction formula 10, A is phenyl, $X_1$ to $X_4$ are each independently CH or N, $L_2$ is methylene ($CH_2$), $R_1$ is $CF_2H$, $R_2$ and $R_3$ are H, $R_c$ is $—C_{1-7}$ alkyl-O—$C_{1-7}$ alkyl, $—C_{1-7}$ alkyl-phenyl or $—C_{1-7}$ alkyl-5- or 6-membered heteroaryl containing one to three heteroatoms selected from the group including N, O or S, and Halo is halogen.

The above [Reaction Formula 10] shows a synthesis method of 1,3,4-oxadiazole compound having a heterocyclic ring structure, and a compound of the chemical formula 1-4-1 is subjected to a reaction with a compound of the chemical formula 1-10-1 so as to prepare a compound of the chemical formula 1-10-2, and then is subjected to a cyclization reaction so as to prepare a compound of the chemical formula 1-10-3. After that, a substitution reaction is performed with a compound of the chemical formula 1-1-2 so as to prepare the compounds 75, 77, 78 and the like of the chemical formula 1-10-4.

[Reaction Formula 11]

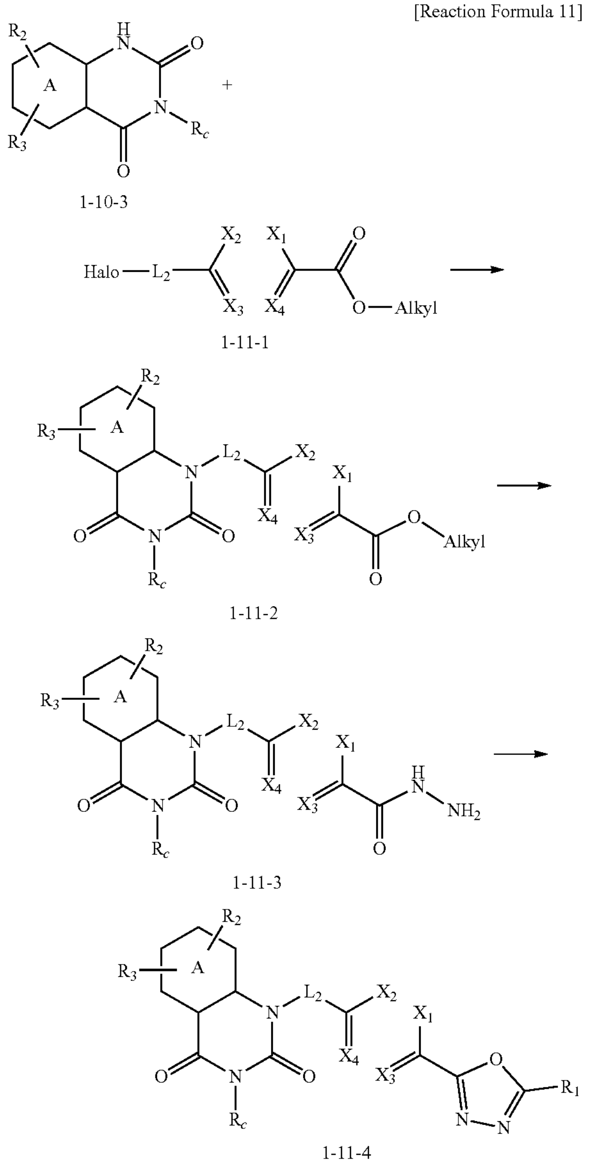

1-10-3 1-11-1 1-11-2 1-11-3 1-11-4

In the above reaction formula 11, A, $X_1$ to $X_4$, $R_1$ to $R_3$ and $R_c$ are the same as described in the chemical formula I. Specifically, in the above reaction formula 11, A is phenyl, $X_1$ to $X_4$ are each independently CH or N, $L_2$ is methylene ($CH_2$), $R_1$ is $CF_2H$, $R_2$ and $R_3$ are H, RC is $—C_{1-7}$ alkyl-O—$C_{1-7}$ alkyl, and Halo is halogen.

The above [Reaction Formula 11] shows a synthesis method of 1,3,4-oxadiazole compound having a heterocyclic ring structure, and a compound of the chemical formula 1-10-3 is subjected to a substitution reaction with a compound of the chemical formula 1-11-1 so as to prepare a compound of the chemical formula 1-11-2, then is subjected to a reaction with hydrazine to prepare a compound of the chemical formula 1-11-3, and then is subjected to a reaction with difluoroacetic anhydride so as to prepare the compound 76 and the like of the chemical formula 1-11-4.

[Reaction Formula 12]

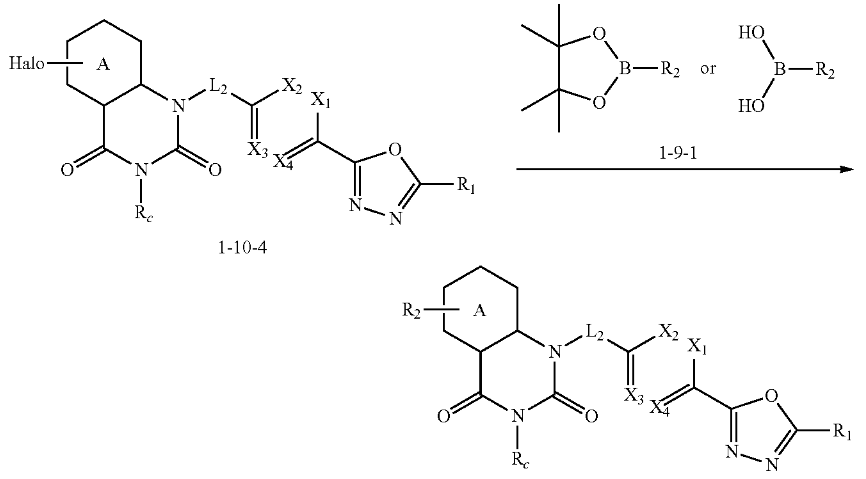

1-10-4

1-12-1

In the above reaction formula 12, A, $X_1$ to $X_4$, $R_1$, $R_2$ and $R_c$ are the same as described in the chemical formula I. Specifically, in the above reaction formula 12, A is phenyl, $X_1$ to $X_4$ are each independently CH or N, $L_2$ is methylene ($CH_2$), $R_1$ is $CF_2H$, $R_2$ is H, phenyl or 5- or 6-membered heteroaryl containing one to three heteroatoms selected from the group including N, O or S, RC is —$C_{1-7}$ alkyl, and Halo is halogen.

The above [Reaction Formula 12] shows a synthesis method of 1,3,4-oxadiazole compound having a heterocyclic ring structure, and a compound of the chemical formula 1-10-4 is subjected to C—C coupling (Suzuki reaction) with a compound of the chemical formula 1-9-1 so as to prepare a compound of the chemical formula 1-12-1.

In the present invention, the compounds prepared according to the above reaction formula include 87, 88, 89, 90, 91, 92 and the like.

[Reaction Formula 13]

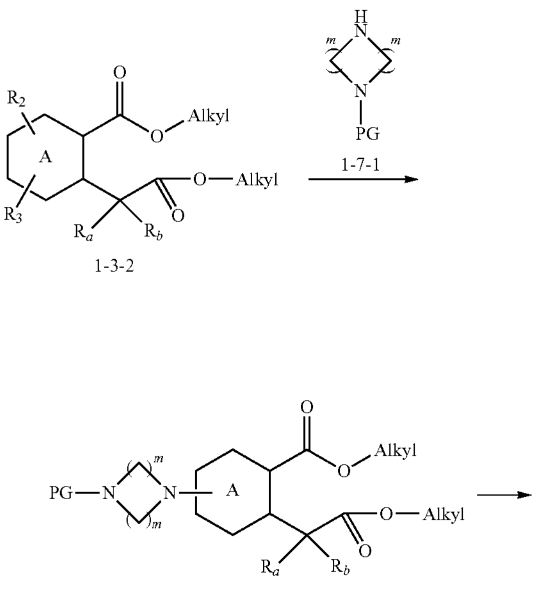

1-3-2

1-13-1

-continued

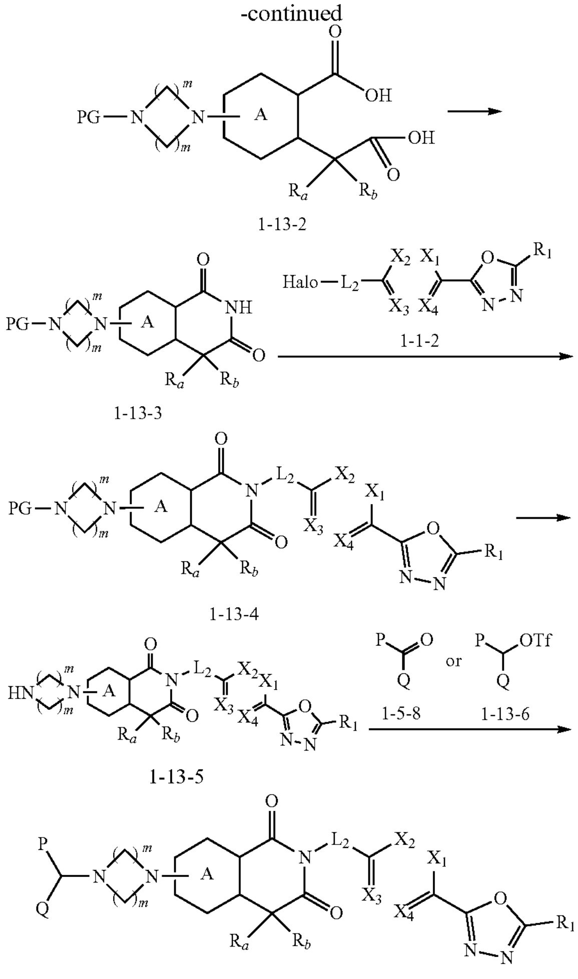

1-13-2

1-13-3

1-13-4

1-13-5

In the above reaction formula 13, A, $X_1$ to $X_4$, $R_1$, $R_a$ and $R_b$ are the same as described in the chemical formula I. Specifically, in the above reaction formula 13, A is phenyl, $X_1$ to $X_4$ are each independently CH or N, $L_2$ is methylene ($CH_2$), $R_1$ is $CF_2H$, $R_a$ and $R_b$ are —$C_{1-7}$ alkyl, Halo is halogen, Alkyl is $C_{1-7}$ alkyl, PG is a protecting group, m is 2, and P and Q are each independently hydrogen, $C_{1-7}$ alkyl or $C_{1-7}$ haloalkyl.

The above [Reaction Formula 13] shows a synthesis method of 1,3,4-oxadiazole compound having a heterocyclic ring structure, and a compound of the chemical formula 1-3-2 is subjected to C—N coupling (Buchwald reaction) with a compound of the chemical formula 1-7-1 having a protecting group so as to prepare a compound of the chemical formula 1-13-1, and then is subjected to a hydrolysis reaction so as to prepare a compound of the chemical formula 1-13-2. After that, the compound of the chemical formula 1-13-2 reacts with urea so as to prepare a compound of the chemical formula 1-13-3, and then is subjected to a substitution reaction with a compound of the chemical formula 1-1-2 so as to prepare the compound 116 and the like of the chemical formula 1-13-4. Also, the protecting group is removed from the compound of the chemical formula 1-13-4 so as to prepare a compound of the chemical formula 1-13-5, and then a reductive amination reaction and a substitution reaction are performed to prepare a compound of the chemical formula 1-13-7.

In the present invention, the compounds prepared according to the above reaction formula include 118, 119, 129, 130, 131, 132, 133, 137, 138, 139, 140 and the like.

[Reaction Formula 14]

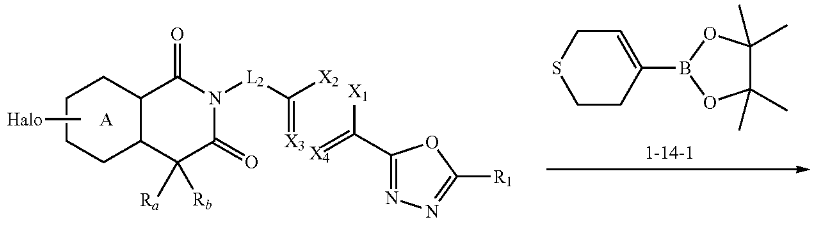

1-3-5

1-14-1

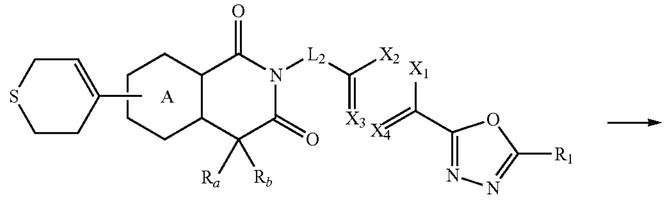

1-14-2

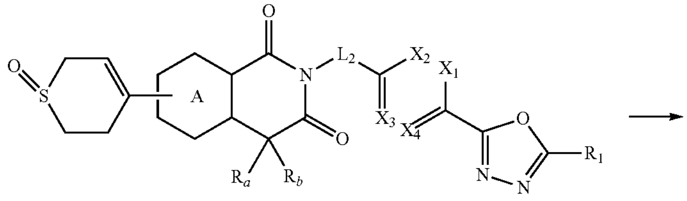

1-14-3

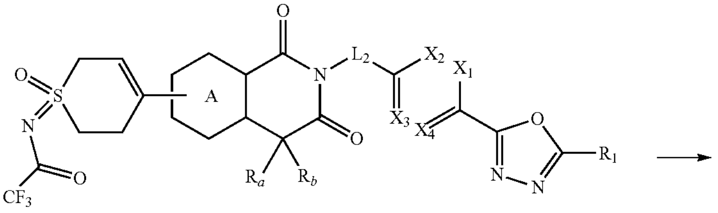

1-14-4

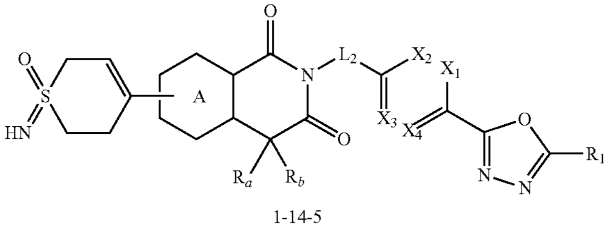

1-14-5

In the above reaction formula 14, A, $X_1$ to $X_4$, $R_1$, $R_a$ and $R_b$ are the same as described in the chemical formula I. Specifically, in the above reaction formula 14, A is phenyl, $X_1$ to $X_4$ are each independently CH or N, $L_2$ is methylene ($CH_2$), Riis $CF_2H$, $R_a$ and $R_b$ are —$C_{1-7}$ alkyl, and Halo is halogen.

The above [Reaction Formula 14] shows a synthesis method of 1,3,4-oxadiazole compound having a heterocyclic ring structure, and a compound of the chemical formula 1-3-5 is subjected to C—C coupling (Suzuki reaction) with a compound of the chemical formula 1-14-1 so as to prepare the compound 121 and the like of the chemical formula 1-14-2. After that, an oxidation reaction is performed with the compound of the chemical formula 1-14-2 so as to prepare the compound 123 and the like of the chemical formula 1-14-3, and then 2,2,2-trifluoroacetamide is used to prepare the compound 125 and the like of the chemical formula 1-14-3. After that, a trifluoroacetyl substitutent is removed therefrom to prepare the compound 126 and the like of the chemical formula 1-14-5.

Medicinal Use of 1,3,4-Oxadiazole Homophthalimide Derivative Compounds

The present invention provides a medicinal use of 1,3,4-oxadiazole homophthalimide derivative compounds, stereoisomers thereof or pharmaceutically acceptable salts thereof.

According to one embodiment aspect of the present invention, there is provided a pharmaceutical composition for preventing or treating histone deacetylase 6 activity-related diseases, comprising a compound represented by a following chemical formula I, stereoisomers thereof or pharmaceutically acceptable salts thereof as an effective component.

[Chemical Formula I]

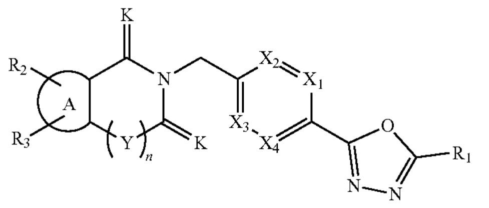

The above chemical formula I is the same as defined above.

According to one embodiment aspect of the present invention, there is provided a pharmaceutical composition for preventing or treating histone deacetylase 6 activity-related diseases, comprising a compound represented by a following chemical formula II, stereoisomers thereof or pharmaceutically acceptable salts thereof as an effective component.

[Chemical Formula II]

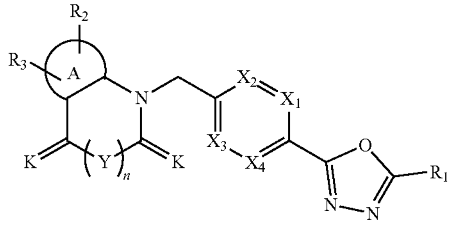

The above chemical formula II is the same as defined above.

The pharmaceutical composition of the present invention selectively inhibits histone deacetylase 6, thereby showing a remarkable effect on preventing or treating histone deacetylase 6 activity-related diseases.

In the present invention, the histone deacetylase 6 activity-related diseases include at least one selected from the group consisting of infectious diseases; neoplasm; endocrinopathy; nutritional and metabolic diseases; mental and behavioral disorders; neurological diseases; eye and ocular adnexal diseases; circulatory diseases; respiratory diseases; digestive diseases; skin and subcutaneous tissue diseases; musculoskeletal system and connective tissue diseases; and teratosis or deformities, and chromosomal aberration.

Said pharmaceutically acceptable salts are the same as described in the pharmaceutically acceptable salts of 1,3,4-oxadiazole homophthalimide derivative compounds of the present invention.

For administration, the pharmaceutical composition of the present invention may further comprise at least one type of a pharmaceutically acceptable carrier, in addition to 1,3,4-oxadiazole homophthalimide derivative compounds of the present invention, stereoisomers thereof or pharmaceutically acceptable salts thereof. As the pharmaceutically acceptable carrier, the followings may be used: saline solution, sterilized water, Ringer's solution, buffered saline, dextrose solution, maltodextrin solution, glycerol, ethanol and a mixture of at least one component thereof, and may be also used with the addition of other conventional additives such as antioxidants, buffer solutions, bacteriostatic agents, etc., if needed. Also, such pharmaceutical composition may be formulated into injectable dosage forms such as aqueous solutions, suspensions, emulsions, etc., pills, capsules, granules or tablets in such a way that diluents, dispersing agents, surfactants, binders and lubricants are additionally added thereto. Thus, the composition of the present invention may be patches, liquids and solutions, pills, capsules, granules, tablets, suppositories, etc. These preparations may be prepared according to a conventional method used for formulation in the art or a method disclosed in Remington's Pharmaceutical Science (latest edition), Mack Publishing Company, Easton Pa., and the composition may be formulated into various preparations according to each disease or component.

The composition of the present invention may be orally or parenterally administered (for example, applied intravenously, hypodermically, intraperitoneally or locally) according to an intended method, in which a dosage thereof varies in a range thereof depending on a patient's weight, age, gender, health condition and diet, an administration time, an administration method, an excretion rate, a severity of a disease and the like. A daily dosage of 1,3,4-oxadiazole homophthalimide derivative compounds of the present invention, stereoisomers thereof or pharmaceutically acceptable salts thereof may be about 1 to 1000 mg/kg, preferably 5 to 100 mg/kg, and may be administered at one time a day or several times a day by dividing the daily dosage of the compound.

In addition to 1,3,4-oxadiazole homophthalimide derivative compounds of the present invention, stereoisomers thereof or pharmaceutically acceptable salts thereof, Said pharmaceutical composition of the present invention may further comprise at least one effective component which shows a medicinal effect the same thereas or similar thereto.

The present invention provides a method for preventing or treating histone deacetylase 6 activity-related diseases, comprising administering a therapeutically effective amount of 1,3,4-oxadiazole homophthalimide derivative compounds of the present invention, stereoisomers thereof or pharmaceutically acceptable salts thereof.

In the present invention, the term "therapeutically effective amount" refers to an amount of 1,3,4-oxadiazole homophthalimide derivative compounds of the present invention, stereoisomers thereof or pharmaceutically acceptable salts thereof, which is effective in preventing or treating histone deacetylase 6 activity-related diseases.

In the present invention, the term "prevention" means a delay of occurrence of disease, disorder or condition. If the occurrence of disease, disorder or condition is delayed for an expected period of time, the prevention may be considered as complete.

In the present invention, the term "treatment" means the one that partially or completely reduces, ameliorates, alleviates, inhibits or delays the occurrence of a certain disease, disorder and/or condition, reduces a severity thereof, or reduces the occurrence of at least one symptom or feature thereof.

A method for preventing or treating histone deacetylase 6 activity-related diseases of the present invention includes not only dealing with the diseases themselves before expression of symptoms, but also inhibiting or avoiding the symptoms by administering 1,3,4-oxadiazole homophthalimide derivative compounds of the present invention. In managing the disease, a preventive or therapeutic dose of a certain active component may vary depending on a nature and severity of the disease or condition and a route of administering the active component. A dose and a frequency thereof may vary depending on an individual patient's age, weight and reactions. A suitable dose and usage may be easily selected by those skilled in the art, naturally considering such factors. Also, the method for preventing or treating histone deacetylase 6 activity-related diseases of the present invention may further include administering a therapeutically effective amount of an additional active agent, which is helpful in treating the diseases, along with 1,3,4-oxadiazole homophthalimide derivative compounds of the present invention, in which the additional active agent may show a synergy effect or an adjuvant effect together with 1,3,4-oxadiazole homophthalimide derivative compounds of the present invention.

The present invention also provides a use of 1,3,4-oxadiazole homophthalimide derivative compounds of the present invention, stereoisomers thereof or pharmaceutically acceptable salts thereof for preventing or treating histone deacetylase 6 activity-related diseases.

The present invention also provides a use of 1,3,4-oxadiazole homophthalimide derivative compounds of the present invention, stereoisomers thereof or pharmaceutically acceptable salts thereof in preparation of a medicament for treating histone deacetylase 6 activity-related diseases. To prepare a medicament, 1,3,4-oxadiazole homophthalimide derivative compounds of the present invention may be mixed with an acceptable adjuvant, diluent, carrier, etc., and may be prepared into a complex preparation together with other active agents, thus having a synergy action.

Also, the present invention provides a method for selectively inhibiting HDAC6 by administering 1,3,4-oxadiazole homophthalimide derivative compounds of the present invention, stereoisomers thereof or pharmaceutically acceptable salts thereof into mammals including humans.

In the present invention, the term "mammal including human" means mammals such as monkey, cow, horse, dog, cat, rabbit, rat, mouse, etc., and in particular includes humans.

In the present invention, the term "inhibition" means a decrease or hindrance in a given state, symptom, disorder or disease, or a significant decrease in biological activity or base activity of biological process.

Matters mentioned in the use, composition and therapeutic method of the present invention are equally applied, if not contradictory to each other.

Advantageous Effects

According to the present invention, 1,3,4-oxadiazole homophthalimide derivative compounds, stereoisomers thereof or pharmaceutically acceptable salts thereof can selectively inhibit HDAC6, and thus have a remarkably excellent effect of preventing or treating histone deacetylase 6 activity-related diseases.

BEST MODE FOR INVENTION

Hereinafter, the present invention will be described in more detail through the following examples and experimental examples. However, the following examples and the like are provided only for the purpose of illustrating the present invention, and thus the scope of the present invention is not limited thereto.

Synthesis of Compound 1, 2-((5-(5-(difluoromethyl)-1,3,4-oxadiazole-2-yl)pyridine-2-yl)methyl) isoindoline-1,3-dione

[Step 1] Synthesis of the Compound 1

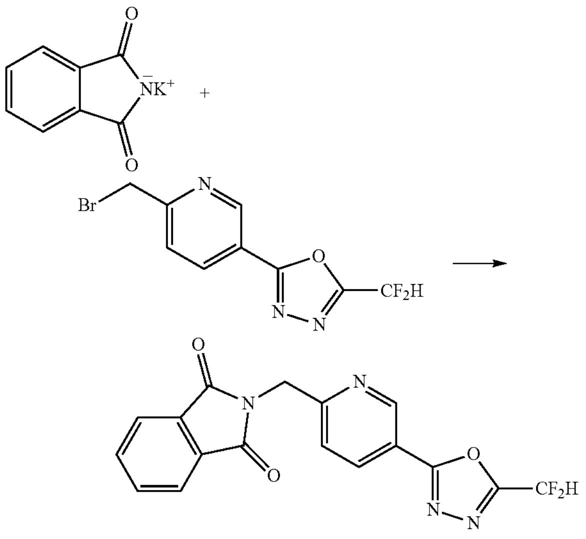

Potassium 1,3-dioxoisoindoline-2-ide (0.100 g, 0.540 mmol) and 2-(6-(bromomethyl)pyridine-3-yl)-5-(difluoromethyl)-1,3,4-oxadiazole (0.157 g, 0.540 mmol) were dissolved in N,N-dimethylformamide (5 mL) at 80° C., after which the resulting solution was stirred at the same temperature for 2 hours, and then a reaction was finished by lowering the temperature to room temperature. Solvent was removed from the reaction mixture under reduced pressure, after which ethyl acetate (20 mL) and hexane (10 mL) were inserted into the resulting concentrate and stirred to filter out a precipitated solid, then washed with hexane, and then dried to obtain a title compound (0.160 g, 83.2%) in a white solid form.

$^1H$ NMR (400 MHz, $CDCl_3$) δ 9.23 (d, J=2.2 Hz, 1H), 8.30 (dd, J=44.4, 12.6 Hz, 1H), 7.94~7.90 (m, 2H), 7.81~7.77 (m, 2H), 7.52~7.49 (m, 1H), 7.07 (s, 0.25H), 6.94 (s, 0.5H), 6.81 (s, 0.25H), 5.12 (s, 2H); LRMS (ES) m/z 357.2 ($M^+$+1).

Synthesis of Compound 2, 2-(4-(5-(difluoromethyl)-1,3,4-oxadiazole-2-yl)-2-fluorobenzyl)isoindoline-1,3-dione

[Step 1] Synthesis of the Compound 2

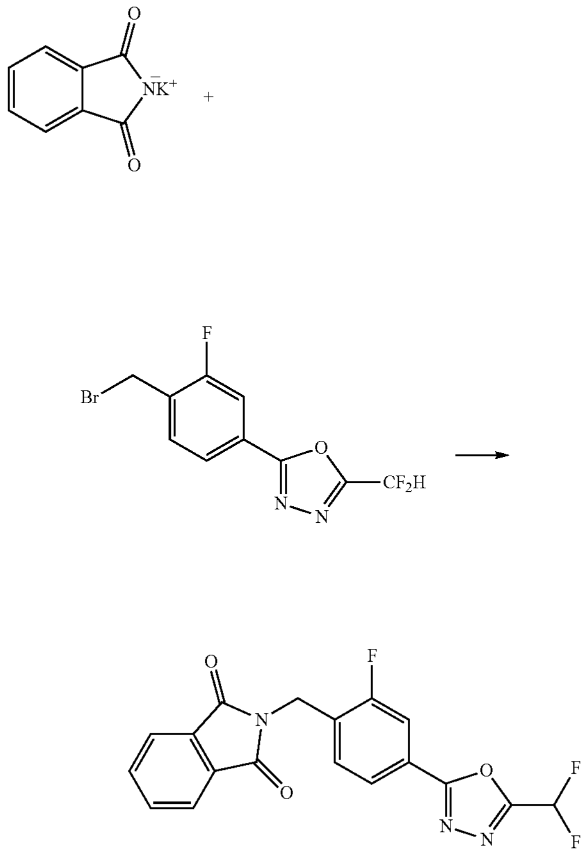

Potassium 1,3-dioxoisoindoline-2-ide (0.100 g, 0.540 mmol), 2-(4-(bromomethyl)-3-fluorophenyl)-5-(difluoromethyl)-1,3,4-oxadiazole (0.166 g, 0.540 mmol) and potassium carbonate (0.112 g, 0.810 mmol) were dissolved in N,N-dimethylformamide (10 mL) at 80° C., after which the resulting solution was stirred at the same temperature for 2 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.100 g, 49.6%) in a colorless oil form.

$^1$H NMR (400 MHz, $CDCl_3$) δ 7.91~7.75 (m, 6H), 5.12 (s, 2H), 7.53 (t, J=7.7 Hz, 1H), 7.05 (s, 0.25H), 6.92 (s, 0.5H), 6.79 (s, 0.25H), 5.01 (s, 2H).

Synthesis of Compound 3, 2'-(4-(5-(difluoromethyl)-1,3,4-oxadiazole-2-yl)-2-fluorobenzyl)-1'H-spiro[cyclobutane-1,4'-isoquinoline]-1',3'(2'H)-dione

[Step 1] Synthesis of methyl 2-(1-(methoxycarbonyl)cyclobutyl)benzoate

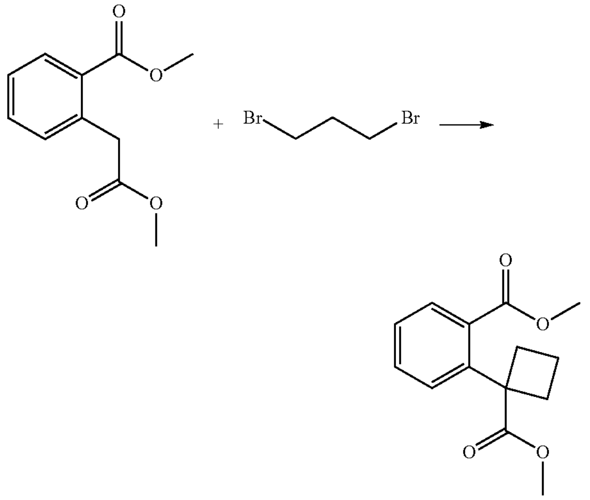

Methyl 2-(2-methoxy-2-oxoethyl)benzoate (3.000 g, 14.409 mmol) was dissolved in N,N-dimethylformamide (30 mL) at 0° C., after which sodium hydride (60.00%, 1.441 g, 36.021 mmol) was added into the resulting solution, and stirred at the same temperature for 30 minutes. 1,3-dibromopropane (2.909 g, 14.409 mmol) was added into the reaction mixture, and further stirred at room temperature for 8 hours. Water was poured into the resulting reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (2.220 g, 62.1%) in a colorless oil form.

[Step 2] Synthesis of 2-(1-carboxycyclobutyl)benzoic acid

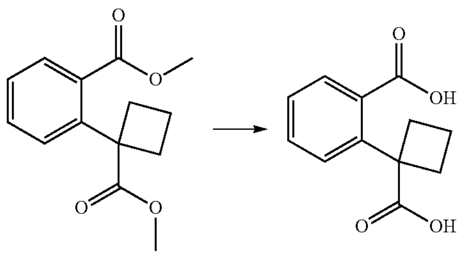 [SMILES: COC(=O)c1ccccc1C1(C(=O)OC)CCC1 ; O=C(O)c1ccccc1C1(C(=O)O)CCC1]

The methyl 2-(1-(methoxycarbonyl)cyclobutyl)benzoate (2.220 g, 8.942 mmol) prepared in the step 1 and sodium hydroxide (3.576 g, 89.415 mmol) were dissolved in methanol (25 mL)/water (25 mL) at room temperature, after which the resulting solution was stirred at the same temperature for 12 hours. Solvent was removed from the reaction mixture under reduced pressure, after which 1N-hydrochloric acid aqueous solution was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. An obtained product was used without an additional purification process (1.900 g, 96.5%, white solid).

[Step 3] Synthesis of 1'H-spiro[cyclobutane-1,4'-isoquinoline]-1',3'(2'H)-dione

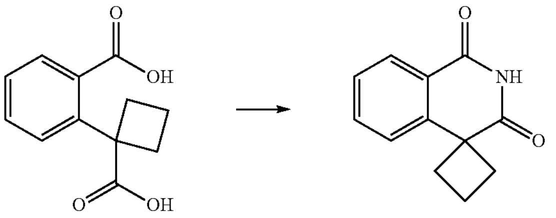 [SMILES: O=C(O)c1ccccc1C1(C(=O)O)CCC1 ; O=C1NC(=O)C2(CCC2)c2ccccc21]

The 2-(1-carboxycyclobutyl)benzoic acid (0.820 g, 3.724 mmol) prepared in the step 2 was mixed in dichlorobenzene (10 mL), then irradiated with microwave, then heated at 175° C. for 1 hour, and then a reaction was finished by lowering the temperature to room temperature. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. A precipitated solid was filtered, then washed with hexane, and then dried to obtain a title compound (0.660 g, 88.1%) in a white solid form.

[Step 4] Synthesis of the Compound 3

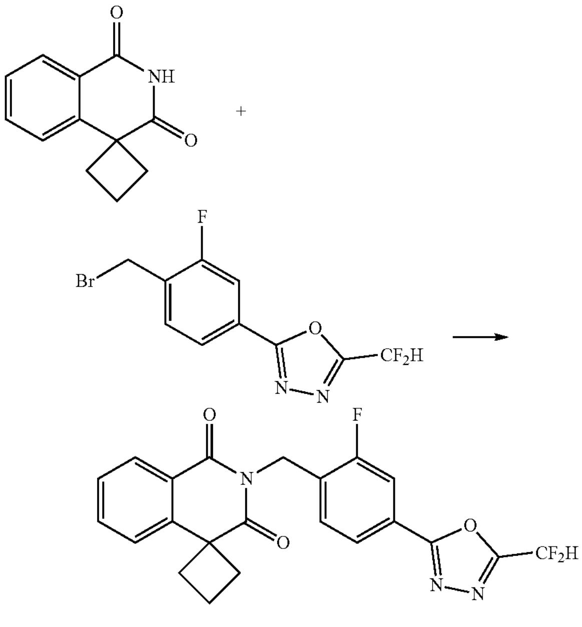

The 1'H-spiro[cyclobutane-1,4'-isoquinoline]-1',3'(2'H)-dione (0.150 g, 0.745 mmol) prepared in the step 3, 2-(4-(bromomethyl)-3-fluorophenyl)-5-(difluoromethyl)-1,3,4-oxadiazole (0.229 g, 0.745 mmol) and potassium carbonate (0.206 g, 1.491 mmol) were dissolved in N,N-dimethylformamide (5 mL) at 80° C., after which the resulting solution was stirred at the same temperature for 2 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.100 g, 31.4%) in a colorless oil form.

$^1H$ NMR (400 MHz, $CDCl_3$) δ 8.21~8.18 (m, 1H), 7.85~7.72 (m, 4H), 7.47~7.43 (m, 1H), 7.38 (t, J=7.9 Hz, 1H), 7.04 (s, 0.25H), 6.92 (s, 0.5H), 6.79 (s, 0.25H), 5.33 (s, 2H), 2.99~2.91 (m, 2H), 2.50~2.30 (m, 4H); LRMS (ES) m/z 428.4 ($M^+$+1).

Synthesis of Compound 4, 2'-((5-(5-(difluoromethyl)-1,3,4-oxadiazole-2-yl)pyridine-2-yl)methyl)-1'H-spiro[cyclobutane-1,4'-isoquinoline]-1',3'(2'H)-dione

[Step 1] Synthesis of the Compound 4

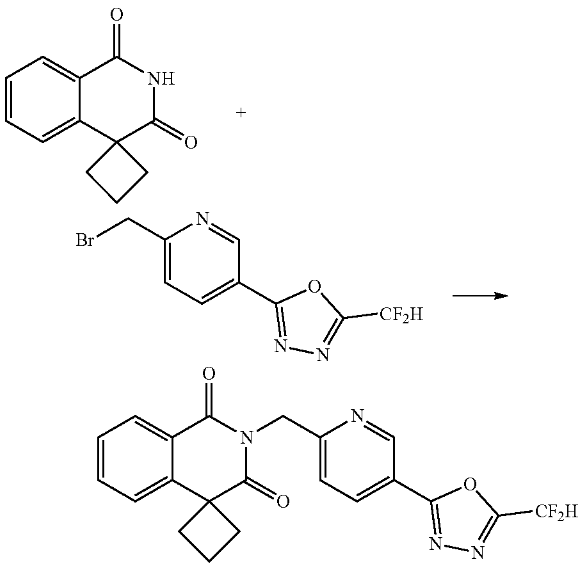

1'H-spiro[cyclobutane-1,4'-isoquinoline]-1',3'(2'H)-dione (0.150 g, 0.745 mmol), 2-(6-(bromomethyl)pyridine-3-yl)-5-(difluoromethyl)-1,3,4-oxadiazole (0.216 g, 0.745 mmol) and potassium carbonate (0.206 g, 1.491 mmol) were dissolved in N,N-dimethylformamide (5 mL) at 80° C., after which the resulting solution was stirred at the same temperature for 2 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.070 g, 22.9%) in a colorless oil form.

$^1H$ NMR (400 MHz, $CDCl_3$) δ 9.18 (dd, J=2.2, 0.9 Hz, 1H), 8.33 (dd, J=8.2, 2.2 Hz, 1H), 8.22~8.20 (m, 1H), 7.87~7.84 (m, 1H), 7.77~7.73 (m, 1H), 7.48~7.44 (m, 2H), 7.06 (s, 0.25H), 6.93 (s, 0.5H), 6.80 (s, 0.25H), 5.44 (s, 2H), 3.04~2.97 (m, 2H), 2.55~2.27 (m, 4H); LRMS (ES) m/z 411.3 ($M^+$+1).

Synthesis of Compound 5, 2'-(4-(5-(difluoromethyl)-1,3,4-oxadiazole-2-yl)benzyl)-1'H-spiro[cyclobutane-1,4'-isoquinoline]-1',3'(2'H)-dione

[Step 1] Synthesis of the Compound 5

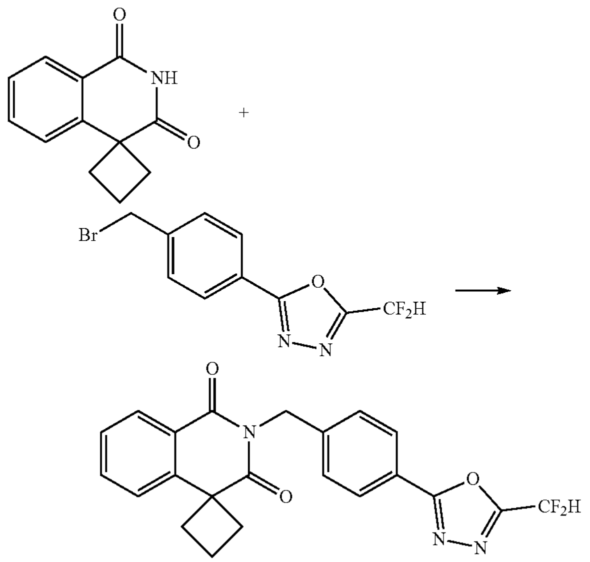

1'H-spiro[cyclobutane-1,4'-isoquinoline]-1',3'(2'H)-dione (0.150 g, 0.745 mmol), 2-(4-(bromomethyl)phenyl)-5-(difluoromethyl)-1,3,4-oxadiazole (0.215 g, 0.745 mmol) and potassium carbonate (0.206 g, 1.491 mmol) were dissolved in N,N-dimethylformamide (5 mL) at 80° C., after which the resulting solution was stirred at the same temperature for 2 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.100 g, 32.8%) in a colorless oil form.

$^1H$ NMR (400 MHz, $CDCl_3$) δ 8.19~8.17 (m, 1H), 8.02~8.00 (m, 2H), 7.81~7.79 (m, 1H), 7.73~7.68 (m, 1H), 7.60~7.57 (m, 2H), 7.45~7.41 (m, 1H), 7.03 (s, 0.25H), 6.90 (s, 0.5H), 6.77 (s, 0.25H), 5.24 (s, 2H), 2.94~2.87 (m, 2H), 2.47~2.25 (m, 4H); LRMS (ES) m/z 410.3 ($M^+$+1).

Synthesis of Compound 6, 2-(4-(5-(difluoromethyl)-1,3,4-oxadiazole-2-yl)benzyl)-4,4-dimethylisoquinoline-1,3(2H,4H)-dione

[Step 1] Synthesis of methyl 2-(1-methoxy-2-methyl-1-oxopropane-2-yl)benzoate

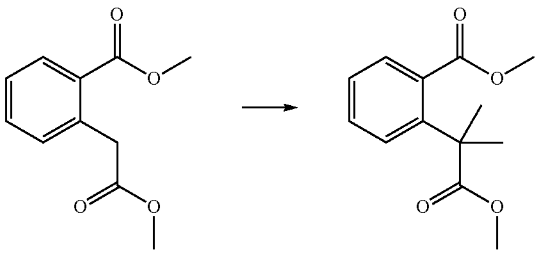 [SMILES: COC(=O)Cc1ccccc1C(=O)OC ; COC(=O)c1ccccc1C(C)(C)C(=O)OC]

Methyl 2-(2-methoxy-2-oxoethyl)benzoate (3.270 g, 15.705 mmol) was dissolved in N,N-dimethylformamide (30 mL) at 0° C., after which sodium hydride (60.00%, 1.884 g, 47.116 mmol) was added into the resulting solution, and stirred at the same temperature for 30 minutes. Iodomethane (2.933 mL, 47.116 mmol) was added into the reaction mixture, and further stirred at room temperature for 12 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 15%), and concentrated to obtain a title compound (3.000 g, 80.8%) in a colorless oil form.

[Step 2] Synthesis of 2-(2-carboxypropane-2-yl)benzoic acid

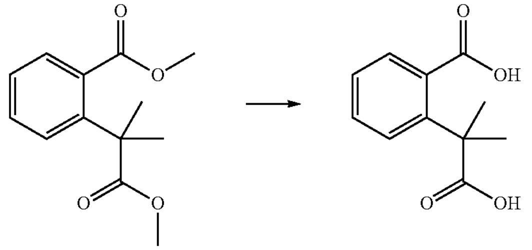 [SMILES: COC(=O)c1ccccc1C(C)(C)C(=O)OC ; CC(C)(C(=O)O)c1ccccc1C(=O)O]

The methyl 2-(1-methoxy-2-methyl-1-oxopropane-2-yl)benzoate (3.000 g, 12.697 mmol) prepared in the step 1 and lithium hydroxide (3.041 g, 126.973 mmol) were dissolved in methanol (15 mL)/water (15 mL) at room temperature, after which the resulting solution was stirred at the same temperature for 12 hours. 1N-hydrochloric acid aqueous solution was poured into the resulting reaction mixture, and an extraction was performed with dichloromethane. An organic layer was washed with saturated sodium chloride aqueous solution, then dehydrated with anhydrous sodium sulfate, then filtered, and then concentrated under reduced pressure. A precipitated solid was filtered, then washed with hexane, and then dried to obtain a title compound (2.500 g, 94.6%) in a white solid form.

[Step 3] Synthesis of 4,4-dimethylisoquinoline-1,3(2H,4H)-dione

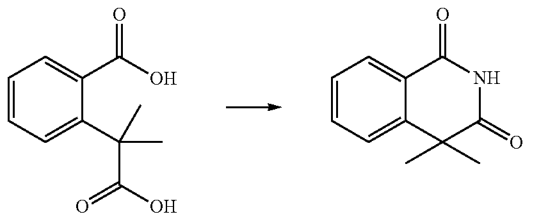

The 2-(2-carboxypropane-2-yl)benzoic acid (2.500 g, 12.007 mmol) prepared in the step 2 was mixed in 1,2-dichlorobenzene (10 mL), then irradiated with microwave, then heated at 175° C. for 1 hour, and then a reaction was finished by lowering the temperature to room temperature. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. A precipitated solid was filtered, then washed with hexane, and then dried to obtain a title compound (1.700 g, 74.8%) in a white solid form.

[Step 4] Synthesis of the Compound 6

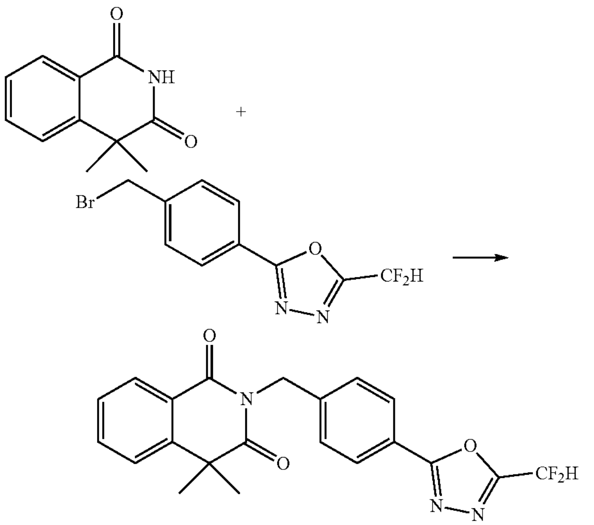

The 4,4-dimethylisoquinoline-1,3(2H,4H)-dione (0.100 g, 0.529 mmol) prepared in the step 3, 2-(4-(bromomethyl) phenyl)-5-(difluoromethyl)-1,3,4-oxadiazole (0.153 g, 0.529 mmol) and potassium carbonate (0.146 g, 1.057 mmol) were dissolved in N,N-dimethylformamide (10 mL), after which the resulting solution was stirred at 80° C. for 2 hours, and then further stirred at room temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.120 g, 57.1%) in a colorless oil form.

$^1H$ NMR (400 MHz, $CDCl_3$) δ 8.25~8.22 (m, 1H), 8.04~8.02 (m, 2H), 7.65~7.63 (m, 1H), 7.59~7.57 (m, 2H), 7.50~7.42 (m, 2H), 7.04 (s, 0.25H), 6.91 (s, 0.5H), 6.78 (s, 0.25H), 5.24 (s, 2H), 1.63 (s, 6H); LRMS (ES) m/z 398.3 ($M^+$+1).

Synthesis of Compound 7, 2-(4-(5-(difluoromethyl)-1,3,4-oxadiazole-2-yl)-2-fluorobenzyl)-4,4-dimethylisoquinoline-1,3(2H,4H)-dione

[Step 1] Synthesis of the Compound 7

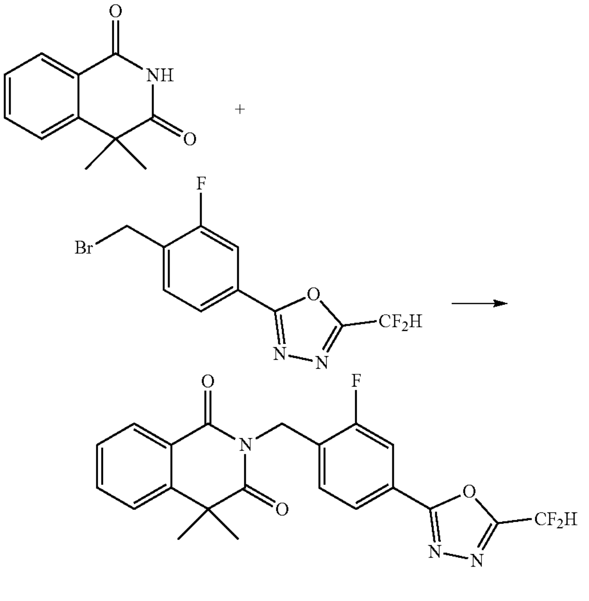

4,4-dimethylisoquinoline-1,3(2H,4H)-dione (0.200 g, 1.057 mmol), 2-(4-(bromomethyl)-3-fluorophenyl)-5-(difluoromethyl)-1,3,4-oxadiazole (0.325 g, 1.057 mmol) and potassium carbonate (0.292 g, 2.114 mmol) were dissolved in N,N-dimethylformamide (10 mL) at 80° C., after which the resulting solution was stirred at the same temperature for 3 hours, and then a reaction was finished by lowering the temperature to room temperature. Water was poured into the reaction mixture, and an extraction was performed with ethyl acetate. An organic layer was washed with saturated aqueous solution, then dehydrated with anhydrous sodium sulfate, then filtered, and then concentrated under reduced pressure. The resulting concentrate was purified via column chromatography ($SiO_2$, 12 g cartridge; /=0 to 30%), and concentrated to obtain a title compound (0.100 g, 22.8%) in a white solid form.

$^1H$ NMR (400 MHz, $CDCl_3$) δ 8.24 (dd, J=7.9, 1.4 Hz, 1H), 7.83~7.78 (m, 2H), 7.68~7.65 (m, 1H), 7.52~7.50 (m, 1H), 7.47~7.45 (m, 1H), 7.40~7.38 (m, 1H), 7.04 (s, 0.25H), 6.91 (s, 0.5H), 6.78 (s, 0.25H), 5.33 (s, 2H), 1.66 (s, 6H); LRMS (ES) m/z 416.4 ($M^+$+1).

Synthesis of Compound 8, 2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 8

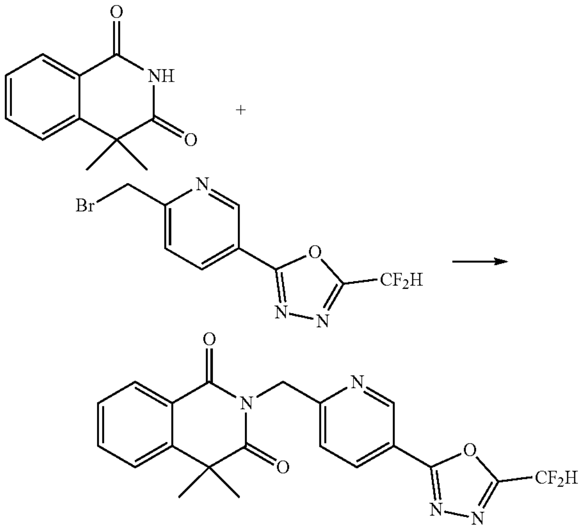

4,4-dimethylisoquinoline-1,3(2H,4H)-dione (0.200 g, 1.057 mmol), 2-(6-(bromomethyl)pyridine-3-yl)-5-(difluoromethyl)-1,3,4-oxadiazole (0.307 g, 1.057 mmol) and potassium carbonate (0.292 g, 2.114 mmol) were dissolved in N,N-dimethylformamide (10 mL) at 80° C., after which the resulting solution was stirred at the same temperature for 3 hours, and then a reaction was finished by lowering the temperature to room temperature. Water was poured into the reaction mixture, and an extraction was performed with ethyl acetate. An organic layer was washed with saturated aqueous solution, then dehydrated with anhydrous sodium sulfate, then filtered, and then concentrated under reduced pressure. The resulting concentrate was purified via column chromatography ($SiO_2$, 12 g cartridge; /=0 to 30%), and concentrated to obtain a title compound (0.180 g, 42.7%) in a white solid form.

$^1H$ NMR (400 MHz, $CDCl_3$) δ 9.17 (dd, J=2.2, 0.8 Hz, 1H), 8.33 (dd, J=8.2, 2.2 Hz, 1H), 8.24 (dd, J=7.9, 1.3 Hz, 1H), 7.68~7.65 (m, 1H), 7.53~7.51 (m, 1H), 7.47~7.43 (m, 2H), 7.05 (s, 0.25H), 6.93 (s, 0.5H), 6.80 (s, 0.25H), 5.42 (s, 2H), 1.69 (s, 6H); LRMS (ES) m/z 399.4 ($M^+$+1).

Synthesis of Compound 9, 3-((5-(5-(difluoromethyl)-1,3,4-oxadiazole-2-yl)pyridine-2-yl)methyl)-1-(2-(piperidine-1-yl)ethyl)quinazoline-2,4(1H,3H)-dione

[Step 1] Synthesis of 2-amino-N-(tert-butyl)benzamide

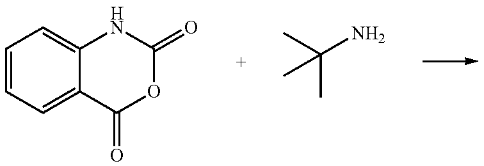

-continued

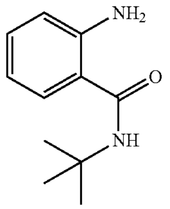

2H-benzo[d][1,3]oxazine-2,4(1H)-dione (15.300 g, 93.790 mmol), 2-methylpropane-2-amine (8.232 g, 112.548 mmol) and N,N-dimethylpyridine-4-amine (DMAP, 1.146 g, 9.379 mmol) were dissolved in N,N-dimethylformamide (100 mL) at room temperature, after which the resulting solution was stirred at the same temperature. Water (20 mL) was put into the reaction mixture and stirred, after which a precipitated solid was filtered, then washed with water, and then dried to obtain a title compound (9.500 g, 52.7%) in a light brown solid form.

[Step 2] Synthesis of methyl (2-(tert-butylcarbamoyl)phenyl)cabamate

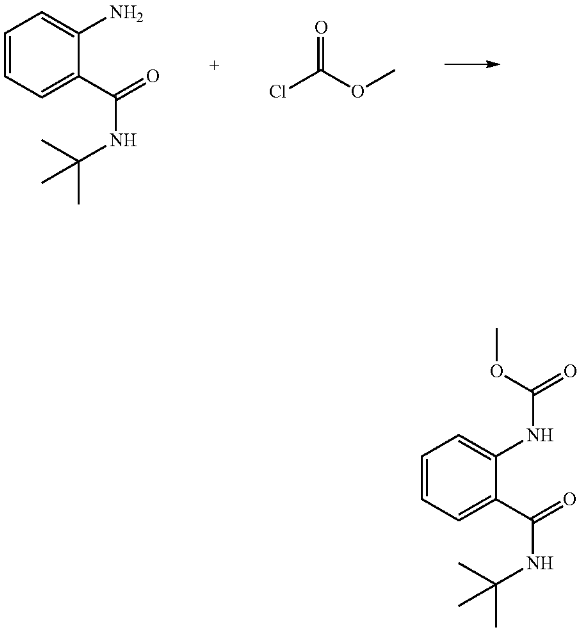

The 2-amino-N-(tert-butyl)benzamide (9.500 g, 49.412 mmol) prepared in the step 1, methyl carbonochloridate (7.003 g, 74.118 mmol) and sodium hydroxide (1.00 M solution, 98.825 mL, 98.825 mmol) were dissolved in 1,4-dioxane (50 mL) at room temperature, after which the resulting solution was stirred at the same temperature for 3 hours. 1M-hydrochloric acid aqueous solution (100 mL) was put into the reaction mixture and stirred, after which a precipitated solid was filtered, then washed with water, and then dried to obtain a title compound (8.700 g, 70.3%) in a white solid form.

[Step 3] Synthesis of 3-(tert-butyl)quinazoline-2,4(1H,3H)-dione

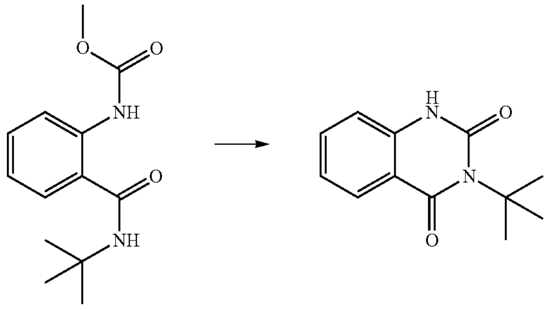 [SMILES: COC(=O)Nc1ccccc1C(=O)NC(C)(C)C ; CC(C)(C)n1c(=O)[nH]c2ccccc2c1=O]

The methyl (2-(tert-butylcarbamoyl)phenyl)cabamate (8.400 g, 33.560 mmol) prepared in the step 2 and potassium hydroxide (18.829 g, 335.597 mmol) were dissolved in ethanol (100 mL) at 80° C., after which the resulting solution was stirred at the same temperature for 12 hours, and then a reaction was finished by lowering the temperature to room temperature. 2M-hydrochloric acid aqueous solution (20 mL) was put into the reaction mixture and stirred, after which a precipitated solid was filtered, then washed with water, and then dried to obtain a title compound (6.000 g, 81.9%) in a beige solid form.

[Step 4] Synthesis of 3-(tert-butyl)-1-(2-(piperidine-1-yl)ethyl)quinazoline-2,4(1H,3H)-dione

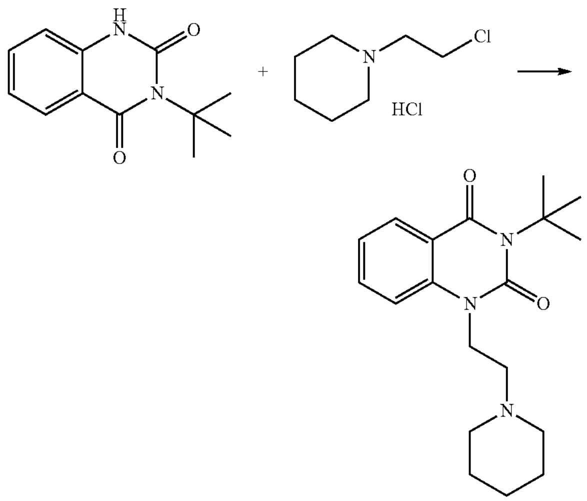

The 3-(tert-butyl)quinazoline-2,4(1H,3H)-dione (3.000 g, 13.745 mmol) prepared in the step 3 was dissolved in N,N-dimethylformamide (30 mL) at 0° C., after which sodium hydride (60.00%, 1.374 g, 34.363 mmol) was added into the resulting solution, and stirred at the same temperature for 30 minutes. 1-(2-chloroethyl)piperidine hydrochloride (3.037 g, 16.494 mmol) was added into the reaction mixture, and further stirred at room temperature for 12 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 50%), and concentrated to obtain a title compound (1.700 g, 37.5%) in a yellow solid form.

[Step 5] Synthesis of 1-(2-(piperidine-1-yl)ethyl)quinazoline-2,4(1H,3H)-dione hydrochloride

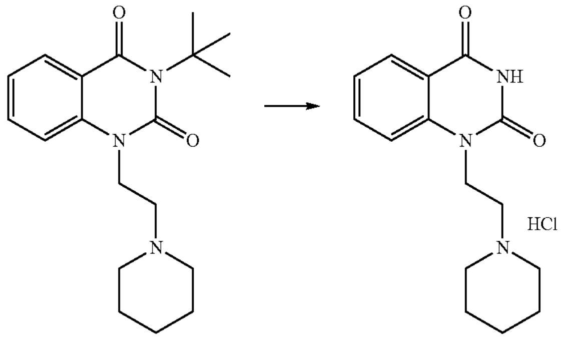 [SMILES: CC(C)(C)n1c(=O)c2ccccc2n(CCN2CCCCC2)c1=O ; O=c1[nH]c(=O)n(CCN2CCCCC2)c2ccccc12 ; Cl]

The 3-(tert-butyl)-1-(2-(piperidine-1-yl)ethyl)quinazoline-2,4(1H,3H)-dione (1.700 g, 5.160 mmol) prepared in the step 4 and hydrochloric acid (4.00 M solution in dioxane, 12.901 mL, 51.603 mmol) were mixed together at room temperature, after which the resulting mixture was heated under reflux for 12 hours, and cooled down to room temperature. After that, solvent was removed from the reaction mixture under reduced pressure, after which an obtained product was used without an additional purification process (1.500 g, 93.8%, white solid).

[Step 6] Synthesis of the Compound

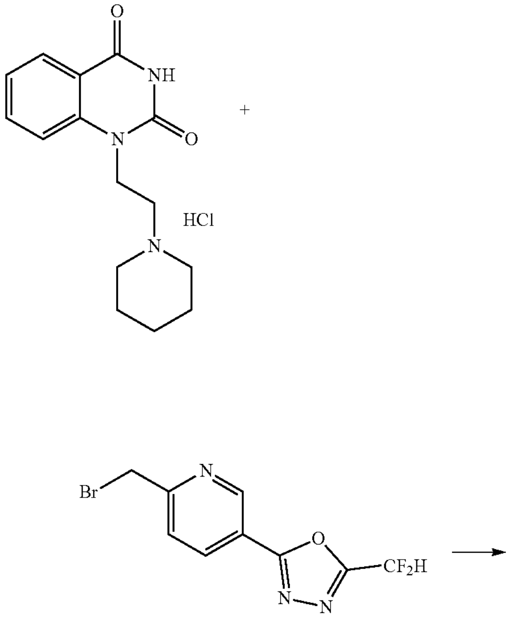

-continued

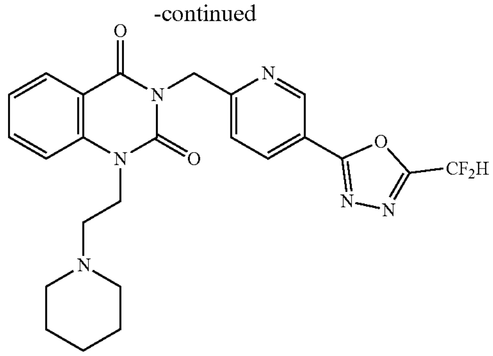

The 1-(2-(piperidine-1-yl)ethyl)quinazoline-2,4(1H,3H)-dione hydrochloride (0.180 g, 0.581 mmol) prepared in the step 5, 2-(6-(bromomethyl)pyridine-3-yl)-5-(difluoromethyl)-1,3,4-oxadiazole (0.219 g, 0.755 mmol) and potassium carbonate (0.161 g, 1.162 mmol) were dissolved in N,N-dimethylformamide (10 mL) at 80° C., after which the resulting solution was stirred at the same temperature for 30 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 80%), and concentrated to obtain a title compound (0.200 g, 71.3%) in a white solid form.

$^1H$ NMR (400 MHz, $CDCl_3$) δ 7.45~7.43 (m, 1H), 8.29 (dd, J=8.2, 2.2 Hz, 1H), 8.20 (dd, J=7.9, 1.6 Hz, 1H), 7.68~7.65 (m, 1H), 7.45~7.43 (m, 1H), 7.32~7.28 (m, 1H), 7.25~7.21 (m, 1H), 7.04 (s, 0.25H), 6.91 (s, 0.5H), 6.79 (s, 0.25H), 5.47 (s, 2H), 4.28~4.24 (m, 2H), 2.62~2.58 (m, 2H), 2.50~2.45 (m, 4H), 1.53~1.49 (m, 4H), 1.39~1.38 (m, 2H); LRMS (ES) m/z 483.6 ($M^+$+1).

Synthesis of Compound 10, 3-(4-(5-(difluoromethyl)-1,3,4-oxadiazole-2-yl)-2-fluorobenzyl)-1-(2-(piperidine-1-yl)ethyl)quinazoline-2,4(1H,3H)-dione

[Step 1] Synthesis of the Compound 10

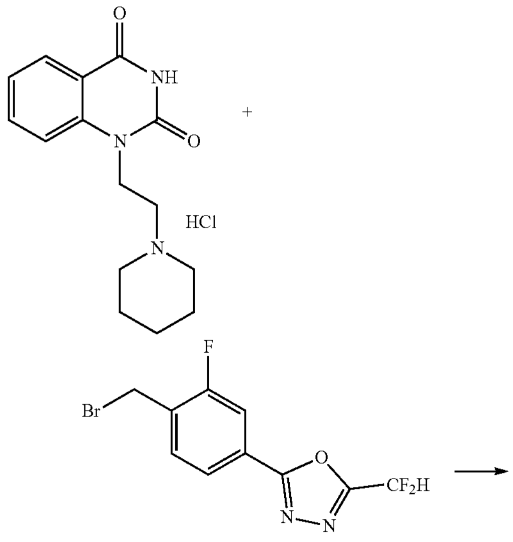

-continued

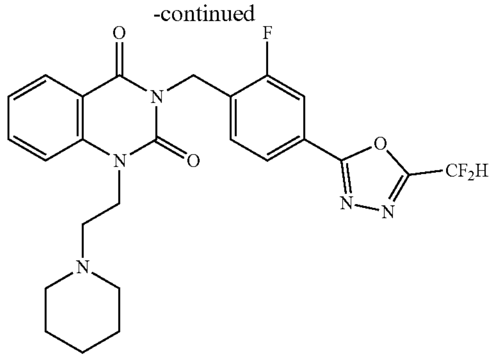

1-(2-(piperidine-1-yl)ethyl)quinazoline-2,4(1H,3H)-dione hydrochloride (0.200 g, 0.646 mmol), 2-(4-(bromomethyl)-3-fluorophenyl)-5-(difluoromethyl)-1,3,4-oxadiazole (0.258 g, 0.839 mmol) and potassium carbonate (0.178 g, 1.291 mmol) were dissolved in N,N-dimethylformamide (10 mL) at 80° C., after which the resulting solution was stirred at the same temperature for 30 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 80%), and concentrated to obtain a title compound (0.200 g, 62.0%) in a white solid form.

$^1H$ NMR (400 MHz, $CDCl_3$) δ 8.25 (dd, J=7.9, 1.5 Hz, 1H), 7.81~7.78 (m, 2H), 7.73~7.68 (m, 1H), 7.43~7.40 (m, 1H), 7.34~7.25 (m, 2H), 7.04 (s, 0.25H), 6.91 (s, 0.5H), 6.78 (s, 0.25H), 5.41 (s, 2H), 4.31~4.27 (m, 2H), 2.64~2.61 (m, 2H), 2.60~2.45 (m, 4H), 1.57~1.52 (m, 4H), 1.44~1.41 (m, 2H); LRMS (ES) m/z 458.0 ($M^+$+1).

Synthesis of Compound 11, 3-(4-(5-(difluoromethyl)-1,3,4-oxadiazole-2-yl)benzyl)-1-(2-(piperidine-1-yl)ethyl)quinazoline-2,4(1H,3H)-dione

[Step 1] Synthesis of the Compound 11

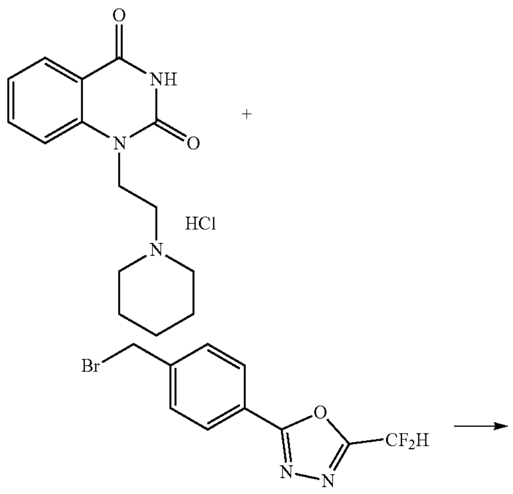

-continued

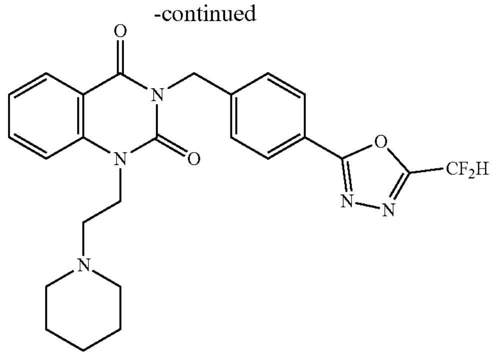

1-(2-(piperidine-1-yl)ethyl)quinazoline-2,4(1H,3H)-dione hydrochloride (0.190 g, 0.613 mmol), 2-(4-(bromomethyl)phenyl)-5-(difluoromethyl)-1,3,4-oxadiazole (0.230 g, 0.797 mmol) and potassium carbonate (0.170 g, 1.227 mmol) were dissolved in N,N-dimethylformamide (10 mL) at 80° C., after which the resulting solution was stirred at the same temperature for 30 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 80%), and concentrated to obtain a title compound (0.150 g, 50.8%) in a white solid form.

$^1H$ NMR (400 MHz, $CDCl_3$) δ 8.23 (dd, J=7.9, 1.5 Hz, 1H), 8.04~7.99 (m, 2H), 7.69~7.63 (m, 3H), 7.30~7.22 (m, 2H), 7.03 (s, 0.25H), 6.90 (s, 0.5H), 6.78 (s, 0.25H), 5.32 (s, 2H), 4.29~4.25 (m, 2H), 2.62~2.58 (m, 2H), 2.55~2.48 (m, 4H), 1.57~1.52 (m, 4H), 1.44~1.40 (m, 2H).

Synthesis of Compound 12, 2-((5-(5-(difluoromethyl)-1,3,4-oxadiazole-2-yl)pyrimidine-2-yl)methyl)-4,4-dimethylisoquinoline-1,3(2H,4H)-dione

[Step 1] Synthesis of the Compound 12

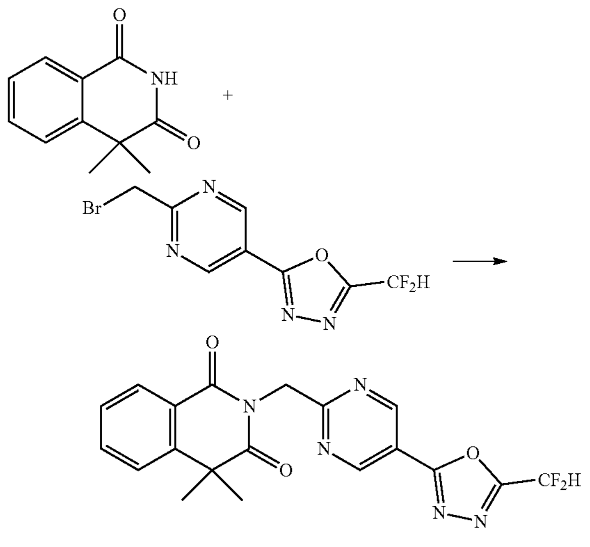

4,4-dimethylisoquinoline-1,3(2H,4H)-dione (0.200 g, 1.057 mmol), 2-(2-(bromomethyl)pyrimidine-5-yl)-5-(difluoromethyl)-1,3,4-oxadiazole (0.308 g, 1.057 mmol) and potassium carbonate (0.219 g, 1.586 mmol) were dissolved in N,N-dimethylformamide (5 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.150 g, 35.5%) in a colorless oil form.

$^1H$ NMR (400 MHz, $CDCl_3$) δ 9.30 (s, 2H), 8.24 (dd, J=7.9, 1.5 Hz, 1H), 7.71~7.67 (m, 1H), 7.55~7.53 (m, 1H), 7.48~7.44 (m, 1H), 7.08 (s, 0.25H), 6.95 (s, 0.5H), 6.82 (s, 0.25H), 5.55 (s, 2H), 1.72 (s, 6H); LRMS (ES) m/z 400.3 ($M^+$+1).

Synthesis of Compound 13, 3-((5-(5-(difluoromethyl)-1,3,4-oxadiazole-2-yl)pyridine-2-yl)methyl)-1-(4-methoxybenzyl)quinazoline-2,4(1H,3H)-dione

[Step 1] Synthesis of 3-(tert-butyl)-1-(4-methoxybenzyl)quinazoline-2,4(1H,3H)-dione

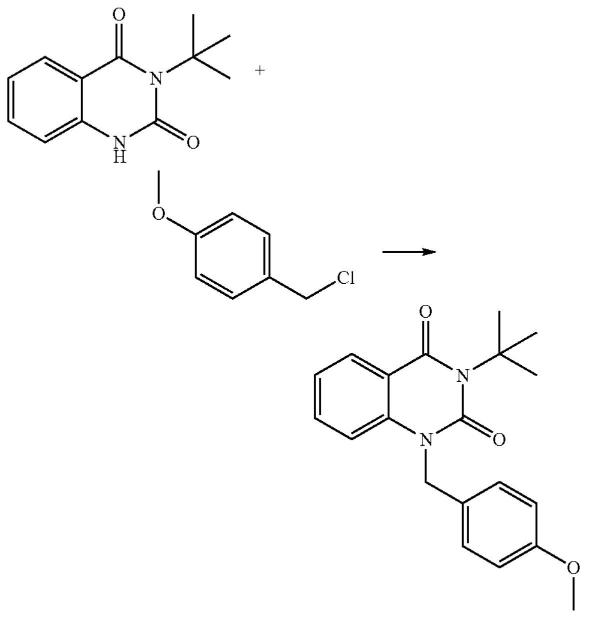

3-(tert-butyl)quinazoline-2,4(1H,3H)-dione (2.800 g, 12.829 mmol) was dissolved in N,N-dimethylformamide (30 mL) at 0° C., after which sodium hydride (60.00%, 1.026 g, 25.657 mmol) was added into the resulting solution, and stirred at the same temperature for 30 minutes. 1-(chloromethyl)-4-methoxybenzene (2.210 g, 14.112 mmol) was added into the reaction mixture, and further stirred at room temperature for 12 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 15%), and concentrated to obtain a title compound (3.400 g, 78.3%) in a yellow solid form.

[Step 2] Synthesis of 1-(4-methoxybenzyl)quinazoline-2,4(1H,3H)-dione

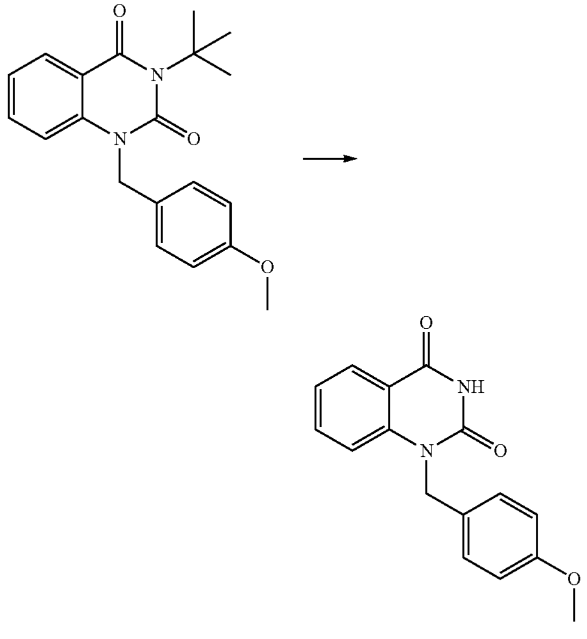

The 3-(tert-butyl)-1-(4-methoxybenzyl)quinazoline-2,4(1H,3H)-dione (3.400 g, 10.047 mmol) prepared in the step 1 and hydrochloric acid (6.00 M solution in $H_2O$, 10.047 mL, 60.282 mmol) were mixed together in 1,4-dioxane (15 mL) at room temperature, after which the resulting mixture was heated under reflux for 12 hours, and cooled down to room temperature. After that, a precipitated solid was filtered, then washed with hexane, and then dried to obtain a title compound (2.250 g, 79.3%) in a white solid form.

[Step 3] Synthesis of the Compound 13

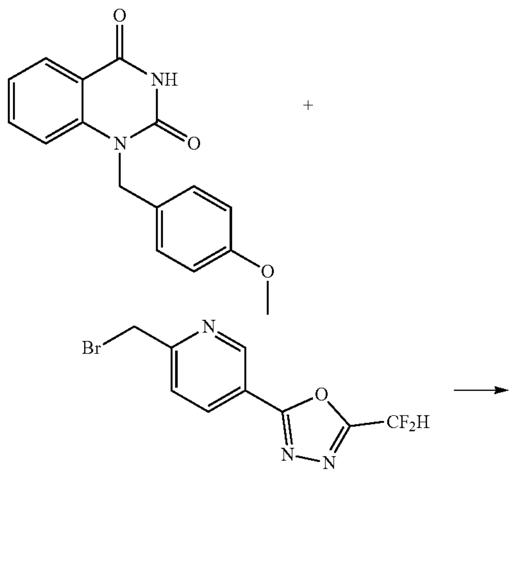

-continued

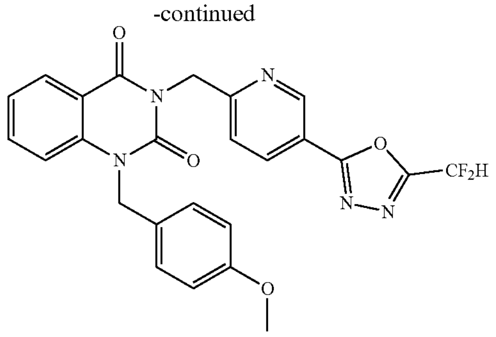

The 1-(4-methoxybenzyl)quinazoline-2,4(1H,3H)-dione (2.250 g, 7.970 mmol) prepared in the step 2, 2-(6-(bromomethyl)pyridine-3-yl)-5-(difluoromethyl)-1,3,4-oxadiazole (3.006 g, 10.361 mmol) and potassium carbonate (2.203 g, 15.940 mmol) were dissolved in N,N-dimethylformamide (30 mL) at 80° C., after which the resulting solution was stirred at the same temperature for 3 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 50%), and concentrated to obtain a title compound (3.200 g, 81.7%) in a white solid form.

$^1H$ NMR (400 MHz, $CDCl_3$) δ 9.24 (d, J=1.6 Hz, 1H), 8.37 (dd, J=8.2, 2.2 Hz, 1H), 8.27 (dd, J=7.9, 1.5 Hz, 1H), 7.63~7.59 (m, 1H), 7.53 (d, J=8.2 Hz, 1H), 7.26~7.22 (m, 4H), 7.07 (s, 0.25H), 6.94 (s, 0.5H), 6.89~6.87 (m, 2H), 6.81 (s, 0.25H), 5.60 (s, 2H), 5.36 (s, 2H), 3.79 (s, 3H).

Synthesis of Compound 14, 3-((5-(5-(difluoromethyl)-1,3,4-oxadiazole-2-yl)pyridine-2-yl)methyl)quinazoline-2,4(1H,3H)-dione

[Step 1] Synthesis of the Compound 14

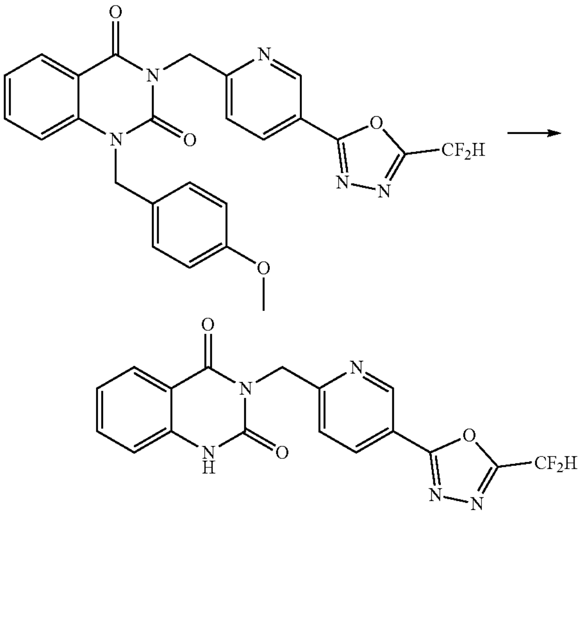

3-((5-(5-(difluoromethyl)-1,3,4-oxadiazole-2-yl)pyridine-2-yl)methyl)-1-(4-meth oxybenzyl)quinazoline-2,4(1H,3H)-dione (1.000 g, 2.035 mmol) and eerie ammonium nitrate (3.347 g, 6.104 mmol) were dissolved in acetonitrile (10 mL)/water (10 mL) at room temperature, after which the resulting solution was stirred at the same temperature for 3 hours. A precipitated solid was filtered, then washed with hexane, and then dried to obtain a title compound (0.680 g, 90.0%) in a yellow solid form.

$^1H$ NMR (400 MHz, $CDCl_3$) δ T11.59 (s, 1H), 9.09 (dd, J=2.2, 0.8 Hz, 1H), 8.37 (dd, J=8.3, 2.3 Hz, 1H), 7.95 (dd, J=8.2, 1.3 Hz, 1H), 7.73~7.69 (m, 1H), 7.67 (s, 0.25H), 7.61 (dd, J=8.3, 0.8 Hz, 1H), 7.54 (s, 0.5H), 7.41 (s, 0.25H), 7.26~7.22 (m, 2H), 5.32 (s, 2H).

Synthesis of Compound 15, 3-((5-(5-(difluoromethyl)-1,3,4-oxadiazole-2-yl)pyridine-2-yl)methyl)-1-((1-methylpiperidine-4-yl)methyl)quinazoline-2,4(1H,3H)-dione

[Step 1] Synthesis of tert-butyl 4-((3-((5-(5-(difluoromethyl)-1,3,4-oxadiazole-2-yl)pyridine-2-yl)methyl)-2,4-dioxo-3,4-dihydroquinazoline-1(2H)-yl)methyl)piperidine-1-carboxylate

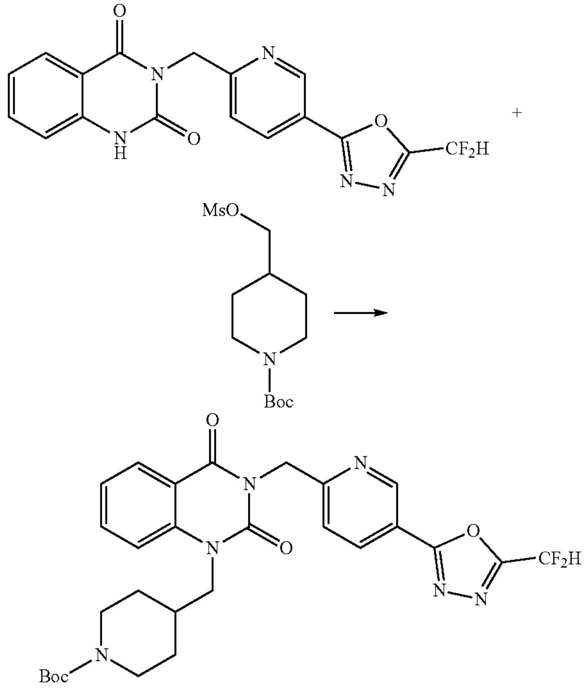

3-((5-(5-(difluoromethyl)-1,3,4-oxadiazole-2-yl)pyridine-2-yl)methyl)quinazoline-2,4(1H,3H)-dione (0.680 g, 1.831 mmol), tert-butyl 4-(((methylsulfonyl)oxy)methyl)piperidine-1-carboxylate (0.645 g, 2.198 mmol) and potassium carbonate (0.506 g, 3.663 mmol) were dissolved in N,N-dimethylformamide (15 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.500 g, 48.0%) in a white foam solid form.

[Step 2] Synthesis of 3-((5-(5-(difluoromethyl)-1,3,4-oxadiazole-2-yl)pyridine-2-yl)methyl)-1-(piperidine-4-ylmethyl)quinazoline-2,4(1H,3H)-dione

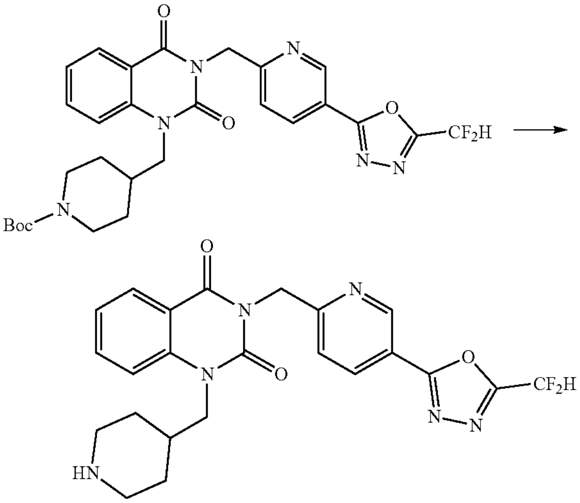

The tert-butyl 4-((3-((5-(5-(difluoromethyl)-1,3,4-oxadiazole-2-yl)pyridine-2-yl)methyl)-2,4-dioxo-3,4-dihydroquinazoline-1(2H)-yl)methyl)piperidine-1-carboxylate (0.500 g, 0.879 mmol) prepared in the step 1 and trifluoroacetic acid (0.337 mL, 4.397 mmol) were dissolved in dichloromethane (10 mL) at room temperature, after which the resulting solution was stirred at the same temperature for 3 hours. Solvent was removed from the reaction mixture under reduced pressure, after which saturated sodium hydrogen carbonate aqueous solution was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. An obtained product was used without an additional purification process (0.200 g, 48.5%, yellow oil).

[Step 3] Synthesis of the Compound 15

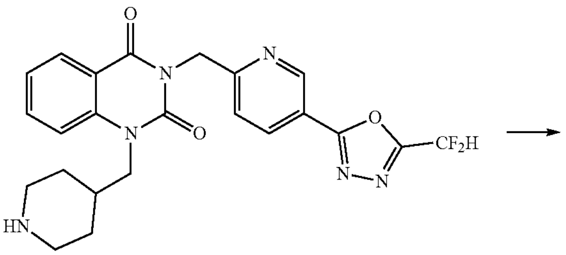

-continued

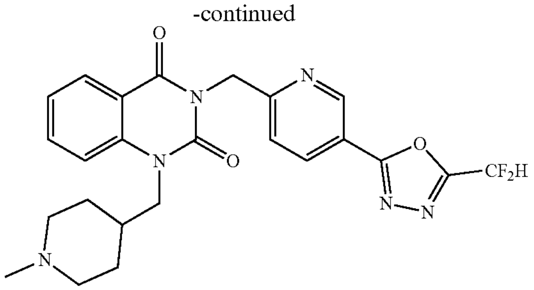

The 3-((5-(5-(difluoromethyl)-1,3,4-oxadiazole-2-yl)pyridine-2-yl)methyl)-1-(piperidine-4-ylmethyl)quinazoline-2,4(1H,3H)-dione (0.100 g, 0.213 mmol) prepared in the step 2, formaldehyde (0.013 g, 0.427 mmol) and sodium triacetoxyborohydride (0.090 g, 0.427 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.037 g, 35.9%) in a yellow oil form.

$^1$H NMR (400 MHz, $CDCl_3$) δ 9.17~9.16 (m, 1H), 8.34 (dd, J=8.2, 2.2 Hz, 1H), 8.27 (dd, J=7.9, 1.5 Hz, 1H), 7.74~7.72 (m, 1H), 7.51~7.48 (m, 1H), 7.32~7.28 (m, 1H), 7.06 (s, 0.25H), 6.93 (s, 0.5H), 6.80 (s, 0.25H), 5.51 (s, 2H), 4.13~4.11 (m, 2H), 3.29~3.15 (m, 3H), 2.48 (s, 3H), 2.29~2.26 (m, 2H), 1.81~1.70 (m, 4H); LRMS (ES) m/z 483.6 ($M^+$+1).

Synthesis of Compound 16, 3-((5-(5-(difluoromethyl)-1,3,4-oxadiazole-2-yl)pyridine-2-yl)methyl)-1-((1-(oxetan-3-yl)piperidine-4-yl)methyl)quinazoline-2,4(1H,3H)-dione

[Step 1] Synthesis of the Compound 16

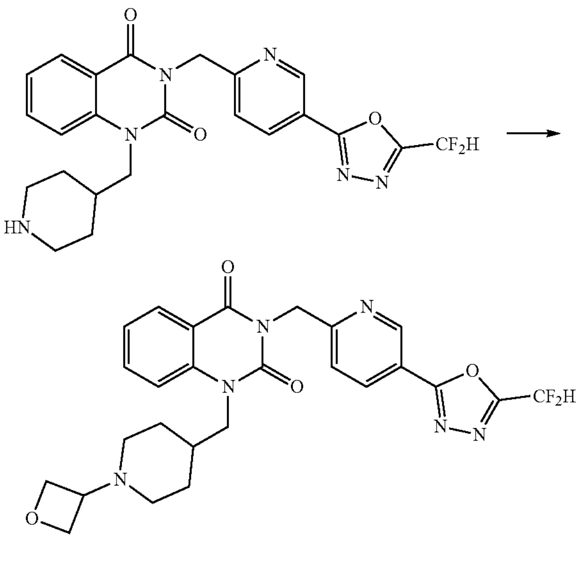

3-((5-(5-(difluoromethyl)-1,3,4-oxadiazole-2-yl)pyridine-2-yl)methyl)-1-(piperidine-4-ylmethyl)quinazoline-2,4(1H,3H)-dione (0.100 g, 0.213 mmol), oxetan-3-one (0.025 mL, 0.427 mmol) and sodium triacetoxyborohydride (0.090 g, 0.427 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.040 g, 35.7%) in a yellow oil form.

$^1$H NMR (400 MHz, $CDCl_3$) δ 9.19 (dd, J=2.2, 0.8 Hz, 1H), 8.35 (dd, J=8.2, 2.2 Hz, 1H), 8.29 (dd, J=7.9, 1.5 Hz, 1H), 7.73~7.70 (m, 1H), 7.51~7.48 (m, 1H), 7.33~7.26 (m, 2H), 7.06 (s, 0.25H), 6.93 (s, 0.5H), 6.80 (s, 0.25H), 5.53 (s, 2H), 4.67~4.60 (m, 4H), 4.16~4.11 (m, 1H), 3.45~3.40 (m, 1H), 2.85~2.75 (m, 2H), 2.02~1.74 (m, 4H), 1.60~1.50 (m, 2H); LRMS (ES) m/z 525.6 ($M^+$+1).

Synthesis of Compound 17, 3-((5-(5-(difluoromethyl)-1,3,4-oxadiazole-2-yl)pyridine-2-yl)methyl)-1-(2-methoxyeth yl)quinazoline-2,4(1H,3H)-dione

[Step 1] Synthesis of the Compound 17

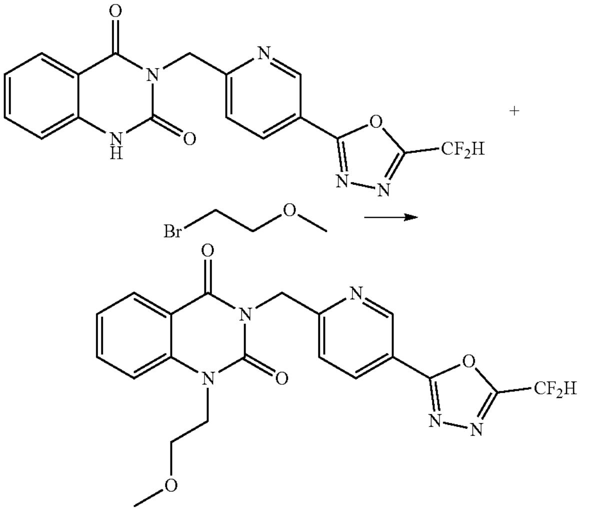

3-((5-(5-(difluoromethyl)-1,3,4-oxadiazole-2-yl)pyridine-2-yl)methyl)quinazoline-2,4(1H,3H)-dione (0.150 g, 0.404 mmol), 1-bromo-2-methoxyethane (0.112 g, 0.808 mmol) and potassium carbonate (0.112 g, 0.808 mmol) were dissolved in N,N-dimethylformamide (10 mL) at 80° C., after which the resulting solution was stirred at the same temperature for 3 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.080 g, 46.1%) in a brown oil form.

$^1$H NMR (400 MHz, $CDCl_3$) δ 9.21 (dd, J=2.2, 0.7 Hz, 1H), 8.34 (dd, J=8.2, 2.2 Hz, 1H), 8.25 (dd, J=7.9, 1.5 Hz, 1H), 7.72~7.68 (m, 1H), 7.49~7.43 (m, 2H), 7.30~7.26 (m, 1H), 7.06 (s, 0.25H), 6.93 (s, 0.5H), 6.80 (s, 0.25H), 5.52 (s, 2H), 4.37 (t, J=5.8 Hz, 2H), 3.74 (t, J=5.8 Hz, 2H), 3.36 (s, 2H); LRMS (ES) m/z 430.5 ($M^+$+1).

Synthesis of Compound 18, 3-((5-(5-(difluoromethyl)-1,3,4-oxadiazole-2-yl)pyridine-2-yl)methyl)-1-methylquinazoline-2,4(1H,3H)-dione

[Step 1] Synthesis of the Compound 18

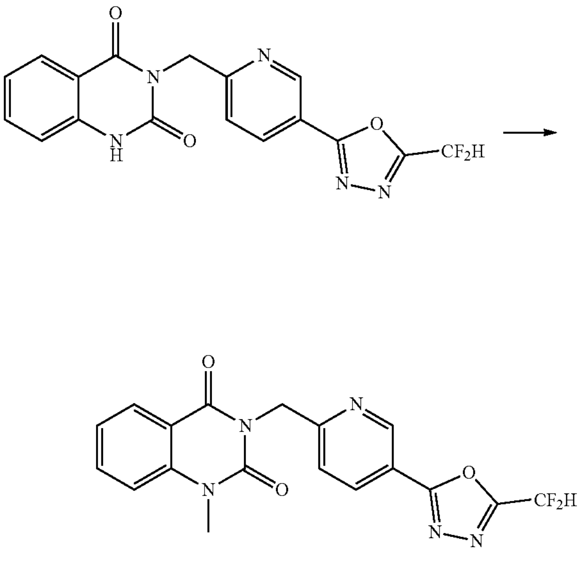

3-((5-(5-(difluoromethyl)-1,3,4-oxadiazole-2-yl)pyridine-2-yl)methyl)quinazoline-2,4(1H,3H)-dione (0.150 g, 0.404 mmol), iodomethane (0.050 mL, 0.808 mmol) and potassium carbonate (0.112 g, 0.808 mmol) were dissolved in N,N-dimethylformamide (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.080 g, 51.4%) in a colorless oil form.

$^1$H NMR (400 MHz, $CDCl_3$) δ 9.21~9.20 (m, 1H), 8.34 (dd, J=8.2, 2.2 Hz, 1H), 8.26~8.24 (m, 1H), 7.76~7.71 (m, 1H), 7.50 (d, J=8.2 Hz, 1H), 7.32~7.26 (m, 2H), 7.06 (s, 0.25H), 6.93 (s, 0.5H), 6.80 (s, 0.25H), 5.28 (s, 2H), 3.64 (s, 3H); LRMS (ES) m/z 386.5 ($M^+$+1).

Synthesis of Compound 19, 3-((5-(5-(difluoromethyl)-1,3,4-oxadiazole-2-yl)pyridine-2-yl)methyl)-1-(3-(dimethylamino)propyl)quinazoline-2,4(1H,3H)-dione

[Step 1] Synthesis of the Compound 19

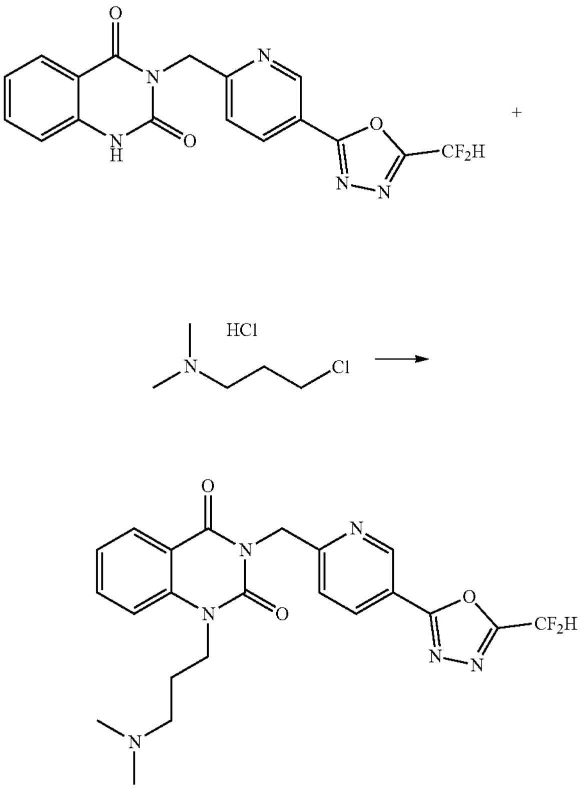

3-((5-(5-(difluoromethyl)-1,3,4-oxadiazole-2-yl)pyridine-2-yl)methyl)quinazoline-2,4(1H,3H)-dione (0.150 g, 0.404 mmol), 3-chloro-N,N-dimethylpropane-1-amine hydrochloride (0.096 g, 0.606 mmol) and potassium carbonate (0.195 g, 1.414 mmol) were dissolved in N,N-dimethylformamide (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.060 g, 32.5%) in a white foam solid form.

$^1$H NMR (400 MHz, $CDCl_3$) δ 9.22~9.21 (m, 1H), 8.35 (dd, J=8.2, 2.3 Hz, 1H), 8.28 (dd, J=7.9, 1.6 Hz, 1H), 7.75~7.71 (m, 1H), 7.50 (d, J=8.2 Hz, 1H), 7.41~7.36 (m, 2H), 7.32~7.30 (m, 1H), 7.06 (s, 0.25H), 6.93 (s, 0.5H), 6.80 (s, 0.25H), 5.53 (s, 2H), 4.24 (t, J=7.5 Hz, 2H), 2.48 (t, J=7.0 Hz, 2H), 2.31 (s, 6H), 2.01~1.93 (m, 2H); LRMS (ES) m/z 457.6 ($M^+$+1).

Synthesis of Compound 20, 3-((5-(5-(difluoromethyl)-1,3,4-oxadiazole-2-yl)pyridine-2-yl)methyl)-1-(2-morpholino ethyl)quinazoline-2,4(1H,3H)-dione

[Step 1] Synthesis of the Compound 20

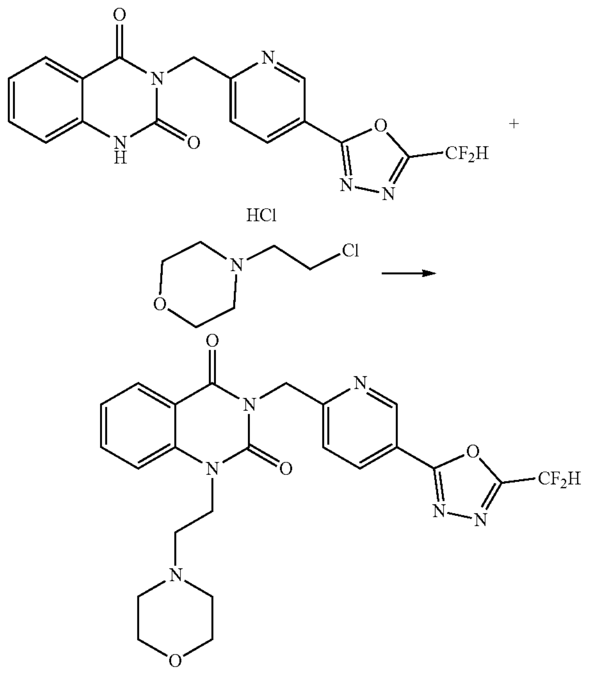

3-((5-(5-(difluoromethyl)-1,3,4-oxadiazole-2-yl)pyridine-2-yl)methyl)quinazoline-2,4(1H,3H)-dione (0.150 g, 0.404 mmol), 4-(2-chloroethyl)morpholine hydrochloride (0.113 g, 0.606 mmol) and potassium carbonate (0.195 g, 1.414 mmol) were dissolved in N,N-dimethylformamide (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.070 g, 35.8%) in a white foam solid form.

$^1$H NMR (400 MHz, $CDCl_3$) δ 9.22 (d, J=1.8 Hz, 1H), 8.35 (dd, J=8.2, 2.2 Hz, 1H), 8.28 (dd, J=7.8, 1.6 Hz, 1H), 7.75~7.71 (m, 1H), 7.51~7.48 (m, 1H), 7.33~7.28 (m, 2H), 7.06 (s, 1H), 6.93 (s, 1H), 6.80 (s, 1H), 5.52 (s, 2H), 4.33 (t, J=7.2 Hz, 2H), 4.33 (t, J=7.2 Hz, 2H), 3.68 (t, J=4.6 Hz, 4H), 2.71 (t, J=7.2 Hz, 2H), 2.58 (t, J=4.5 Hz, 4H); LRMS (ES) m/z 485.5 ($M^+$+1).

Synthesis of Compound 21, 1-(2-(1H-pyrazole-1-yl)ethyl)-3-((5-(5-(difluoromethyl)-1,3,4-oxadiazole-2-yl)pyridine-2-yl)methyl)quinazoline-2,4(1H,3H)-dione

[Step 1] Synthesis of the Compound 21

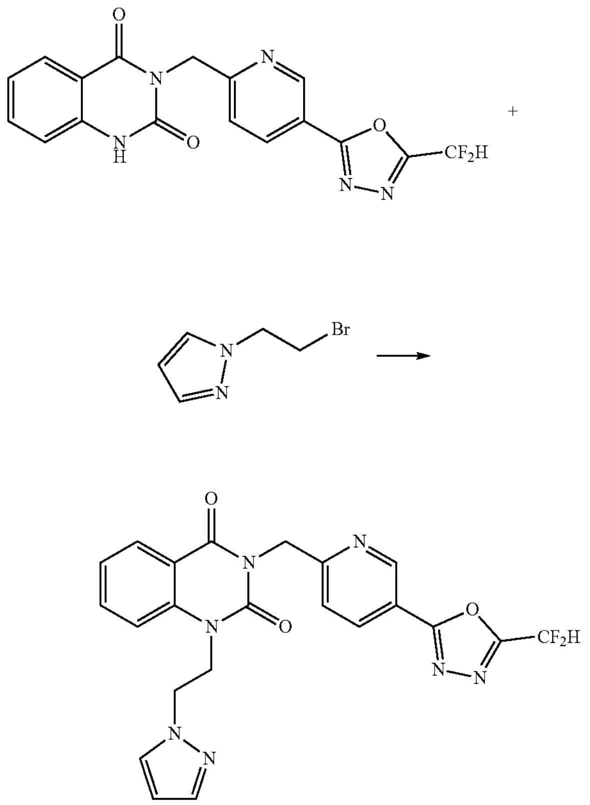

3-((5-(5-(difluoromethyl)-1,3,4-oxadiazole-2-yl)pyridine-2-yl)methyl)quinazoline-2,4(1H,3H)-dione (0.150 g, 0.404 mmol), 1-(2-bromoethyl)-1H-pyrazole (0.106 g, 0.606 mmol) and potassium carbonate (0.112 g, 0.808 mmol) were dissolved in N,N-dimethylformamide (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.030 g, 16.0%) in a colorless oil form.

$^1$H NMR (400 MHz, $CDCl_3$) δ 9.23~9.22 (m, 1H), 8.38 (dd, J=8.2, 2.3 Hz, 1H), 8.23 (dd, J=7.9, 1.4 Hz, 1H), 7.61~7.52 (m, 3H), 7.33 (dd, J=2.2, 0.6 Hz, 1H), 7.26~7.22 (m, 1H), 7.07 (s, 0.25H), 7.03 (d, J=8.5 Hz, 1H), 6.94 (s, 0.5H), 6.81 (s, 0.25H), 6.14~6.12 (m, 1H), 5.49 (s, 2H), 4.59~4.52 (m, 4H); LRMS (ES) m/z 466.5 ($M^+$+1).

Synthesis of Compound 22, 3-((5-(5-(difluoromethyl)-1,3,4-oxadiazole-2-yl)pyridine-2-yl)methyl)-1-(2-(dimethylamino)ethyl)quinazoline-2,4(1H,3H)-dione

[Step 1] Synthesis of the Compound 22

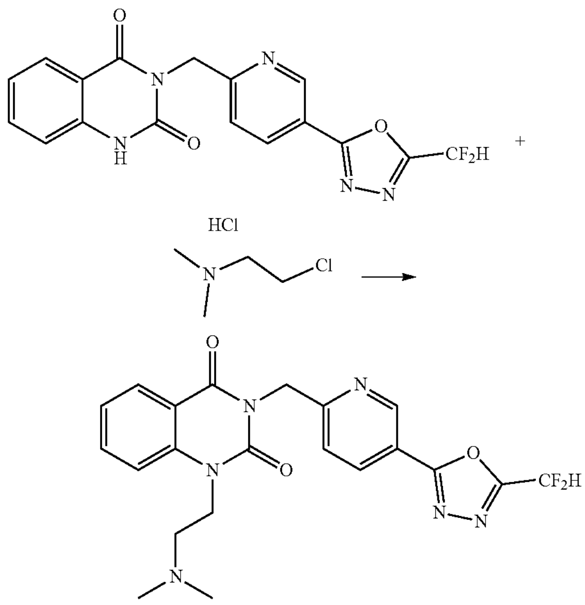

3-((5-(5-(difluoromethyl)-1,3,4-oxadiazole-2-yl)pyridine-2-yl)methyl)quinazoline-2,4(1H,3H)-dione (0.150 g, 0.404 mmol), 2-chloro-N,N-dimethylethane-1-amine hydrochloride (0.087 g, 0.606 mmol) and potassium carbonate (0.195 g, 1.414 mmol) were dissolved in N,N-dimethylformamide (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.040 g, 22.4%) in a white foam solid form.

$^1H$ NMR (400 MHz, $CDCl_3$) δ 9.21 (dd, J=2.2, 0.8 Hz, 1H), 8.35 (dd, J=8.2, 2.2 Hz, 1H), 8.28~8.25 (m, 1H), 7.80~7.73 (m, 1H), 7.50~7.48 (m, 1H), 7.33~7.29 (m, 2H), 7.06 (s, 0.25H), 6.93 (s, 0.5H), 6.80 (s, 0.5H), 5.52 (s, 2H), 4.31 (t, J=7.5 Hz, 2H), 2.66 (t, J=7.5 Hz, 2H), 2.36 (s, 6H); LRMS (ES) m/z 443.5 ($M^+$+1).

Synthesis of Compound 23, 6-bromo-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of methyl 4-bromo-2-(1-methoxy-2-methyl-1-oxopropane-2-yl)benzoate

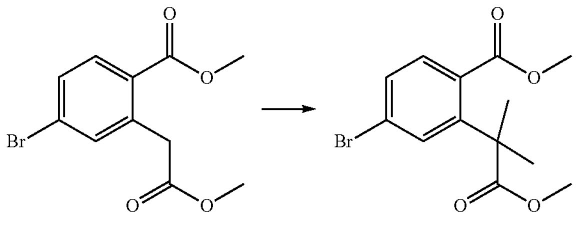 [SMILES: COC(=O)Cc1cc(Br)ccc1C(=O)OC ; COC(=O)c1ccc(Br)cc1C(C)(C)C(=O)OC]

Methyl 4-bromo-2-(2-methoxy-2-oxoethyl)benzoate (9.500 g, 33.088 mmol) was dissolved in N,N-dimethylformamide (50 mL) at 0° C., after which sodium hydride (60.00%, 3.970 g, 99.265 mmol) was added into the resulting solution and stirred for 30 minutes. Iodomethane (6.180 mL, 99.265 mmol) was slowly added into the reaction mixture, and further stirred at room temperature for 12 hours. 1N-hydrochloric acid aqueous solution (20 mL) was put into the reaction mixture and stirred, after which a precipitated solid was filtered, then washed with hexane, and then dried to obtain a title compound (7.290 g, 69.9%) in a white solid form.

[Step 2] Synthesis of 4-bromo-2-(2-carboxypropane-2-yl)benzoic acid

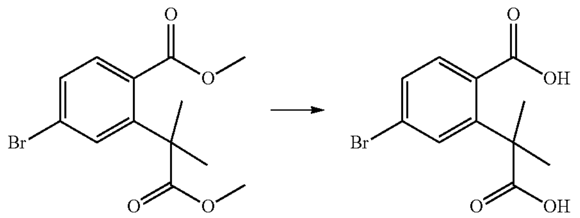 [SMILES: COC(=O)c1ccc(Br)cc1C(C)(C)C(=O)OC ; CC(C)(C(=O)O)c1cc(Br)ccc1C(=O)O]

The methyl 4-bromo-2-(1-methoxy-2-methyl-1-oxopropane-2-yl)benzoate (7.290 g, 23.131 mmol) prepared in the step 1 and potassium hydroxide (12.978 g, 231.311 mmol) were dissolved in methanol (30 mL)/water (60 mL) at 100° C., after which the resulting solution was stirred at the same temperature for 12 hours, and then a reaction was finished by lowering the temperature to room temperature. Solvent was removed from the reaction mixture under reduced pressure, after which 1N-hydrochloric acid aqueous solution was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. An obtained product was used without an additional purification process (6.000 g, 90.3%, white solid).

[Step 3] Synthesis of 6-bromo-4,4-dimethylisoquinoline-1,3(2H,4H)-dione

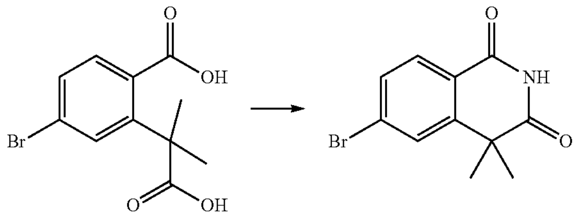 [SMILES: CC(C)(C(=O)O)c1cc(Br)ccc1C(=O)O ; CC1(C)C(=O)NC(=O)c2ccc(Br)cc21]

The 4-bromo-2-(2-carboxypropane-2-yl)benzoic acid (7.460 g, 25.983 mmol) prepared in the step 2 and urea (1.717 g, 28.581 mmol) were mixed in chlorobenzene (30 mL), then irradiated with microwave, then heated at 150° C. for 45 minutes, and then a reaction was finished by lowering the temperature to room temperature. A precipitated solid was filtered, then washed with hexane, and then dried to obtain a title compound (5.500 g, 79.0%) in a yellow solid form.

[Step 4] Synthesis of the Compound 23

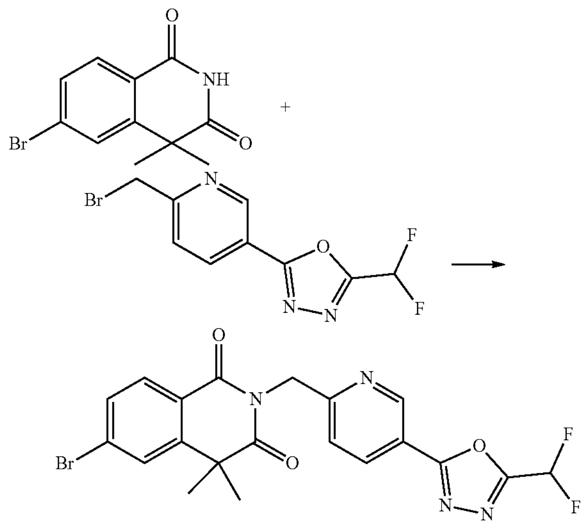

The 6-bromo-4,4-dimethylisoquinoline-1,3(2H,4H)-dione (1.400 g, 5.222 mmol) prepared in the step 3, 2-(6-(bromomethyl)pyridine-3-yl)-5-(difluoromethyl)-1,3,4-oxadiazole (2.272 g, 7.833 mmol) and potassium carbonate (1.443 g, 10.443 mmol) were dissolved in N,N-dimethylformamide (30 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 50%), and concentrated to obtain a title compound (2.200 g, 88.3%) in a yellow solid form.

$^1H$ NMR (400 MHz, $CDCl_3$) δ 9.18 (dd, J=2.2, 0.8 Hz, 1H), 8.36 (dd, J=8.2, 2.2 Hz, 1H), 8.13 (d, J=8.4 Hz, 1H), 7.68 (d, J=1.8 Hz, 1H), 7.62 (dd, J=8.4, 1.9 Hz, 1H), 7.47 (dd, J=8.2, 0.8 Hz, 1H), 7.06 (s, 0.25H), 6.93 (s, 0.5H), 6.80 (s, 0.25H), 5.42 (s, 2H), 1.70 (s, 6H).

Synthesis of Compound 24, 2-((5-(5-(difluoromethyl)-1,3,4-oxadiazole-2-yl)pyridine-2-yl)methyl)-4,4-dimethyl-6-morpholinoisoquinoline-1,3(2H,4H)-dione

[Step 1] Synthesis of the Compound 24

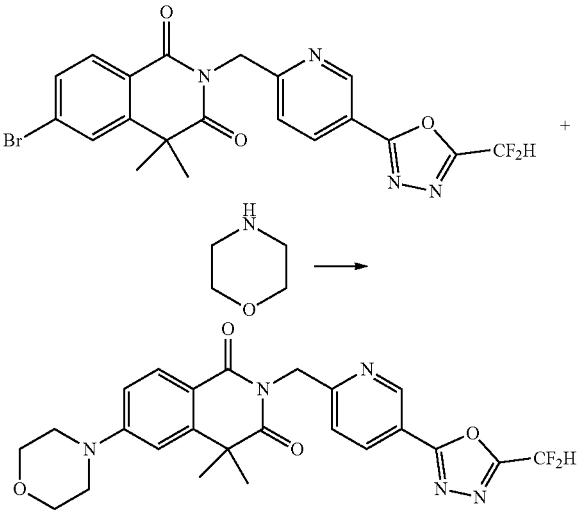

6-bromo-2-((5-(5-(difluoromethyl)-1,3,4-oxadiazole-2-yl)pyridine-2-yl)methyl)-4,4-dimethylisoquinoline-1,3(2H,4H)-dione (0.470 g, 0.985 mmol), morpholine (0.170 mL, 1.970 mmol), 4,5-bis(diphenylphosphino)-9,9-dimethylxanthene (Xantphos, 0.057 g, 0.098 mmol), tris(dibenzylideneacetone)dipalladium ($Pd_2(dba)_3$, 0.090 g, 0.098 mmol) and cesium carbonate (0.963 g, 2.954 mmol) were dissolved in toluene (5 mL) at 65° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 70%), and concentrated to obtain a title compound (0.220 g, 46.2%) in a yellow solid form.

$^1H$ NMR (400 MHz, DMSO-$d_6$) δ 9.07 (dd, J=2.2, 0.8 Hz, 1H), 8.37 (dd, J=8.3, 2.3 Hz, 1H), 7.92 (d, J=8.9 Hz, 1H), 7.68 (s, 1H), 7.56 (s, 1H), 7.53 (d, J=8.3 Hz, 1H), 7.43 (s, 1H), 7.10 (d, J=2.3 Hz, 1H), 7.06 (dd, J=8.9, 2.5 Hz, 1H), 5.26 (s, 2H), 3.76 (t, J=4.8 Hz, 4H), 3.38 (t, J=4.8 Hz, 4H), 1.61 (s, 6H).

Synthesis of Compound 25, tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)piperazine-1-carboxylate

[Step 1] Synthesis of the Compound 25

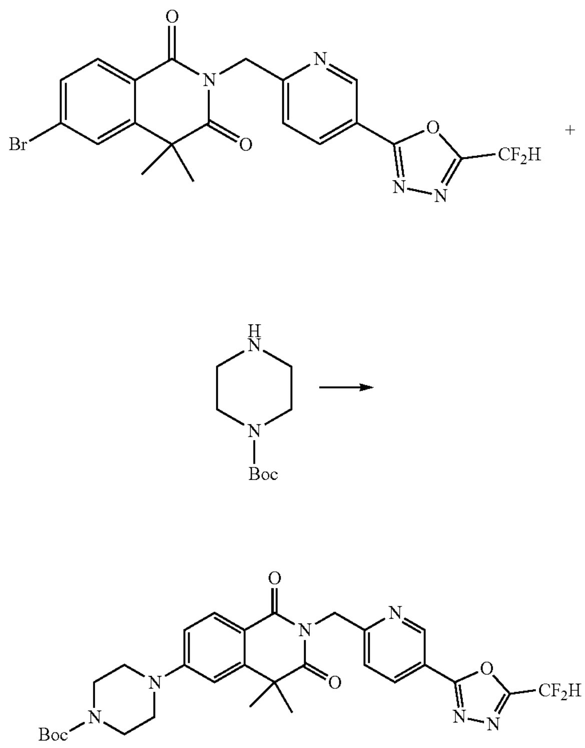

6-bromo-2-((5-(5-(difluoromethyl)-1,3,4-oxadiazole-2-yl)pyridine-2-yl)methyl)-4,4-dimethylisoquinoline-1,3(2H,4H)-dione (0.893 g, 1.871 mmol), tert-butyl piperazine-1-carboxylate (1.046 g, 5.613 mmol), 4,5-bis(diphenylphosphino)-9,9-dimethylxanthene (Xantphos, 0.108 g, 0.187 mmol), tris(dibenzylideneacetone)dipalladium ($Pd_2(dba)_3$, 0.171 g, 0.187 mmol) and cesium carbonate (1.829 g, 5.613 mmol) were dissolved in toluene (5 mL) at 65° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 70%), and concentrated to obtain a title compound (0.300 g, 27.5%) in a yellow solid form.

$^1H$ NMR (400 MHz, $CDCl_3$) δ 9.18 (dd, J=2.2, 0.8 Hz, 1H), 8.31 (dd, J=8.2, 2.2 Hz, 1H), 8.11 (d, J=8.9 Hz, 1H), 7.41 (dd, J=8.2, 0.8 Hz, 1H), 7.05 (s, 0.25H), 6.92 (s, 0.5H), 6.92~6.90 (m, 1H), 6.83 (d, J=2.4 Hz, 1H), 6.79 (s, 0.25H), 5.40 (s, 2H), 3.63 (t, J=5.2 Hz, 4H), 3.39 (t, J=5.2 Hz, 4H), 1.67 (s, 6H), 1.49 (s, 9H); LRMS (ES) m/z 583.6 ($M^+$+1).

Synthesis of Compound 26, 2-((5-(5-(difluoromethyl)-1,3,4-oxadiazole-2-yl)pyridine-2-yl)methyl)-6-(4-isopropylpiperazine-1-yl)-4,4-dimethylisoquinoline-1,3(2H,4H)-dione

[Step 1] Synthesis of the Compound 26

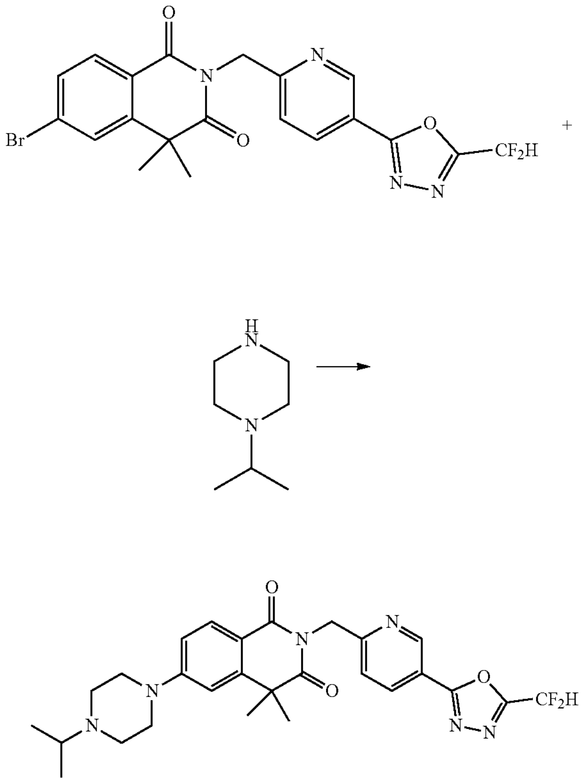

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), 1-isopropylpiperazine (0.060 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.087 g, 52.8%) in a colorless oil form.

$^1H$ NMR (400 MHz, $CDCl_3$) δ 9.20 (dd, J=2.2, 0.7 Hz, 1H), 8.32 (dd, J=8.2, 2.2 Hz, 1H), 8.10 (d, J=8.9 Hz, 1H), 7.42~7.39 (m, 1H), 7.06 (s, 0.25H), 6.94~6.91 (m, 1H), 6.92 (s, 0.5H), 6.84 (d, J=2.4 Hz, 0.25H), 6.80 (s, 1H), 5.40 (s, 2H), 3.43 (t, J=5.1 Hz, 4H), 2.78~2.69 (m, 5H), 1.68 (s, 6H), 1.12~1.10 (m, 6H).

Synthesis of Compound 27, 2-((5-(5-(difluoromethyl)-1,3,4-oxadiazole-2-yl)pyridine-2-yl)methyl)-4,4-dimethyl-6-(piperidine-1-yl)isoquinoline-1,3(2H, 4H)-dione

[Step 1] Synthesis of the Compound 27

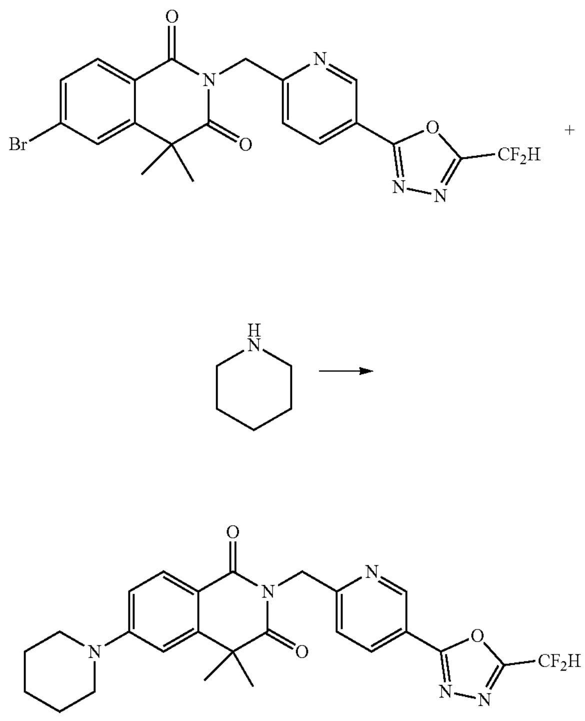

6-bromo-2-((5-(5-(difluoromethyl)-1,3,4-oxadiazole-2-yl)pyridine-2-yl)methyl)-4,4-dimethylisoquinoline-1,3(2H, 4H)-dione (0.150 g, 0.314 mmol), piperidine (0.040 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.080 g, 52.9%) in a yellow oil form.

$^1H$ NMR (400 MHz, $CDCl_3$) δ 9.21 (d, J=1.5 Hz, 1H), 8.32 (dd, J=8.2, 2.2 Hz, 1H), 8.08 (d, J=8.9 Hz, 1H), 7.41 (dd, J=8.2, 0.7 Hz, 1H), 7.06 (s, 0.25H), 6.93 (s, 0.5H), 6.93~6.90 (m, 1H), 6.83 (d, J=2.4 Hz, 1H), 6.80 (s, 0.25H), 5.41 (s, 2H), 3.42~3.40 (m, 4H), 1.71~1.68 (m, 12H); LRMS (ES) m/z 458.0 ($M^+$+1).

Synthesis of Compound 28, 6-(azetidine-1-yl)-2-((5-(5-(difluoromethyl)-1,3,4-oxadiazole-2-yl)pyridine-2-yl)methyl)-4,4-dimethylisoquinoline-1,3(2H, 4H)-dione

[Step 1] Synthesis of the Compound 28

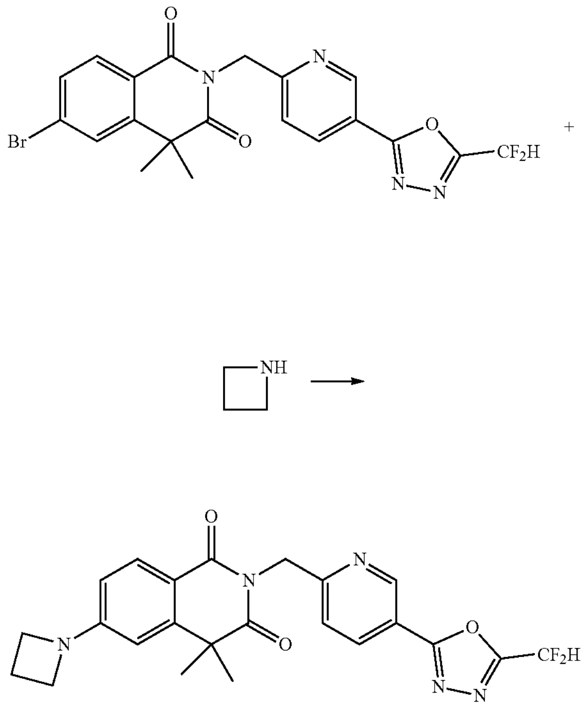

6-bromo-2-((5-(5-(difluoromethyl)-1,3,4-oxadiazole-2-yl)pyridine-2-yl)methyl)-4,4-dimethylisoquinoline-1,3(2H, 4H)-dione (0.150 g, 0.314 mmol), azetidine (0.027 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.050 g, 35.1%) in a yellow oil form.

$^1H$ NMR (400 MHz, $CDCl_3$) δ 9.21 (dd, J=2.2, 0.8 Hz, 1H), 8.32 (dd, J=9.2, 1.3 Hz, 1H), 8.07 (d, J=8.6 Hz, 1H), 7.41 (dd, J=8.2, 0.8 Hz, 1H), 7.06 (s, 0.25H), 6.93 (s, 0.5H), 6.80 (s, 0.25H), 6.42 (dd, J=8.7, 2.2 Hz, 1H), 6.29 (d, J=2.2 Hz, 1H), 5.41 (s, 2H), 4.07 (t, J=7.4 Hz, 4H), 2.50~2.46 (m, 2H), 1.70 (s, 6H).

Synthesis of Compound 29, 2-((5-(5-(difluoromethyl)-1,3,4-oxadiazole-2-yl)pyridine-2-yl)methyl)-4,4-dimethyl-6-(4-methylpiperazine-1-yl)isoquinoline-1,3(2H,4H)-dione

[Step 1] Synthesis of 2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione 2,2,2-trifluoroacetate

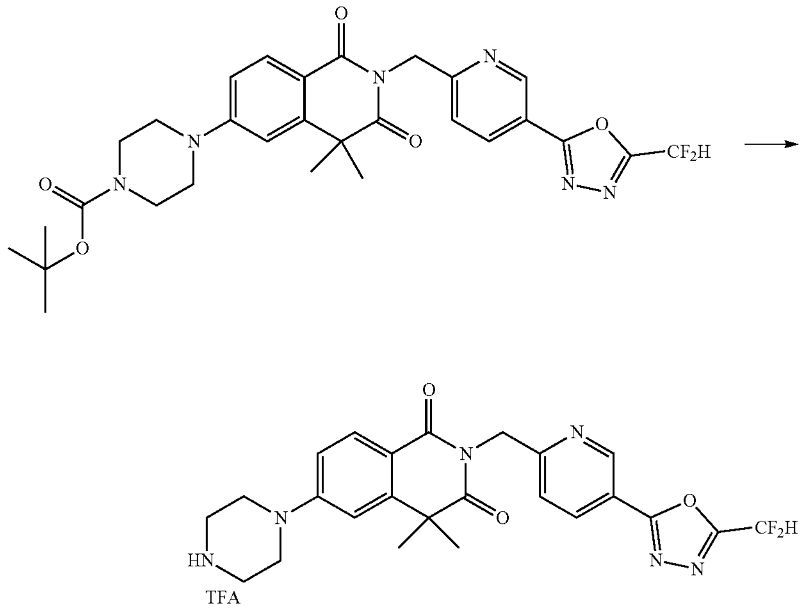

Tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)piperazine-1-carboxylate (0.300 g, 0.515 mmol) and trifluoroacetic acid (0.394 mL, 5.149 mmol) were dissolved in dichloromethane (10 mL) at room temperature, after which the resulting solution was stirred at the same temperature for 5 hours. Solvent was removed from the reaction mixture under reduced pressure, after which an obtained product was used without an additional purification process (0.300 g, 97.7%, yellow oil).

[Step 2] Synthesis of the Compound 29

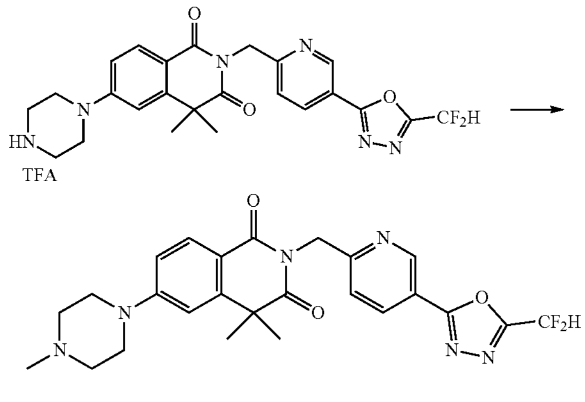

The 2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione 2,2,2-trifluoroacetate (0.178 g, 0.298 mmol) prepared in the step 1 and N,N-diisopropylethylamine (0.052 mL, 0.298 mmol) were dissolved in dichloromethane (10 mL), after which the resulting solution was stirred at room temperature for 30 minutes, and then formaldehyde (0.018 g, 0.597 mmol) and sodium triacetoxyborohydride (0.126 g, 0.597 mmol) were added thereinto and further stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/hexane=0 to 10%), and concentrated to obtain a title compound (0.090 g, 60.7%) in a colorless oil form.

$^1H$ NMR (400 MHz, $CDCl_3$) δ 9.18 (d, J=1.6 Hz, 1H), 8.31 (dd, J=8.2, 2.2 Hz, 1H), 8.09 (d, J=9.0 Hz, 1H), 7.40 (d, J=8.2 Hz, 1H), 7.05 (s, 0.25H), 6.93~6.90 (m, 1H), 6.92 (s, 0.5H), 6.83 (d, J=2.4 Hz, 1H), 6.80 (s, 0.25H), 5.39 (s, 2H), 3.43 (t, J=5.1 Hz, 4H), 2.63 (t, J=5.1 Hz, 4H), 2.38 (s, 3H), 1.66 (s, 6H); LRMS (ES) m/z 497.5 ($M^+$+1).

Synthesis of Compound 30, 2-((5-(5-(difluoromethyl)-1,3,4-oxadiazole-2-yl)pyridine-2-yl)methyl)-4,4-dimethyl-6-(4-(oxetan-3-yl)piperazine-1-yl)isoquinoline-1,3(2H,4H)-dione

[Step 1] Synthesis of the Compound 30

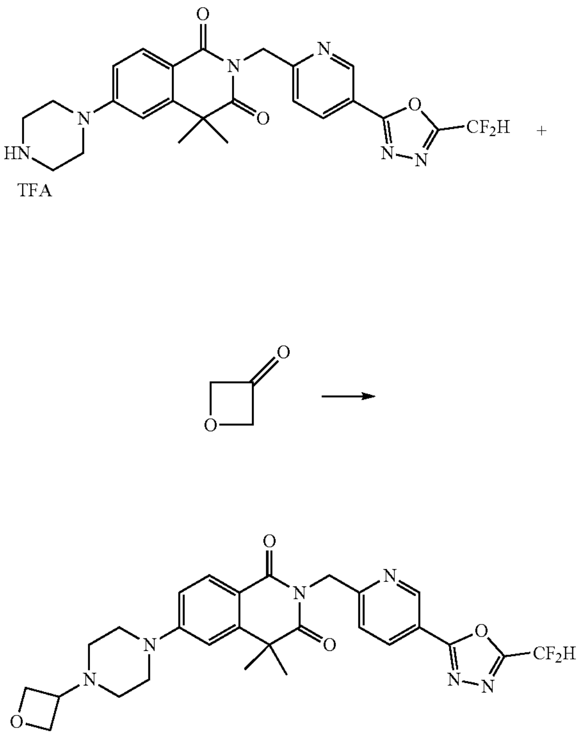

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione 2,2,2-trifluoroacetate (0.182 g, 0.305 mmol) and N,N-diisopropylethylamine (0.053 mL, 0.305 mmol) were dissolved in dichloromethane (10 mL), after which the resulting solution was stirred at room temperature for 30 minutes, and then oxetan-3-one (0.044 g, 0.610 mmol) and sodium triacetoxyborohydride (0.129 g, 0.610 mmol) were added thereinto and further stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/hexane=0 to 10%), and concentrated to obtain a title compound (0.100 g, 60.9%) in a colorless oil form.

$^1H$ NMR (400 MHz, $CDCl_3$) δ 9.19 (d, J=2.0 Hz, 1H), 8.32 (dd, J=8.2, 2.2 Hz, 1H), 8.10 (d, J=8.9 Hz, 1H), 7.41 (d, J=8.2 Hz, 1H), 7.06 (s, 0.25H), 6.94~6.91 (m, 1H), 6.92 (s, 0.5H), 6.84 (d, J=2.2 Hz, 1H), 6.80 (s, 0.25H), 5.40 (s, 2H), 4.74~4.65 (m, 4H), 3.59~3.56 (m, 1H), 3.45 (t, J=4.9 Hz, 4H), 2.53 (t, J=4.9 Hz, 4H), 1.67 (s, 6H); LRMS (ES) m/z 539.7 ($M^+$+1).

Synthesis of Compound 31, (S)-2-((5-(5-(difluoromethyl)-1,3,4-oxadiazole-2-yl)pyridine-2-yl)methyl)-6-(3-(dimethylamino)pyrrolidine-1-yl)-4,4-dimethylisoquinoline-1,3(2H,4H)-dione

[Step 1] Synthesis of the Compound 31

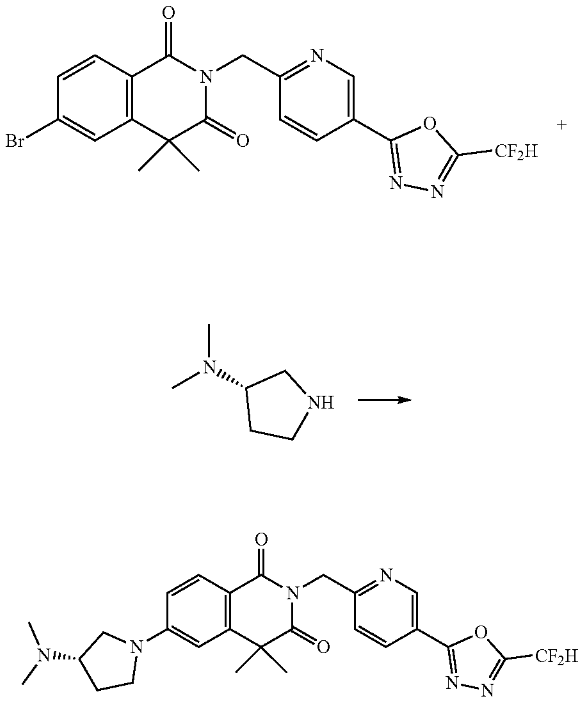

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), (S)—N,N-dimethylpyrrolidine-3-amine (0.054 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.079 g, 49.2%) in a colorless oil form.

$^1H$ NMR (400 MHz, $CDCl_3$) δ 9.20 (dd, J=2.2, 0.7 Hz, 1H), 8.31 (dd, J=8.2, 2.2 Hz, 1H), 8.08 (d, J=8.7 Hz, 1H), 7.41~7.38 (m, 1H), 7.06 (s, 0.25H), 6.93 (s, 0.5H), 6.80 (s, 0.25H), 6.59 (dd, J=8.9, 2.3 Hz, 1H), 5.40 (s, 2H), 3.63~3.57 (m, 2H), 3.45~3.43 (m, 1H), 3.27 (t, J=8.8 Hz, 2H), 2.95~2.85 (m, 1H), 2.35 (s, 6H), 2.31~2.27 (m, 1H), 2.05~1.99 (m, 1H), 1.68 (s, 6H); LRMS (ES) m/z 511.6 ($M^+$+1).

Synthesis of Compound 32, (R)-2-((5-(5-(difluoromethyl)-1,3,4-oxadiazole-2-yl)pyridine-2-yl) methyl)-6-(3-(dimethylamino)pyrrolidine-1-yl)-4,4-dimethylisoquinoline-1,3(2H,4H)-dione

[Step 1] Synthesis of the Compound 32

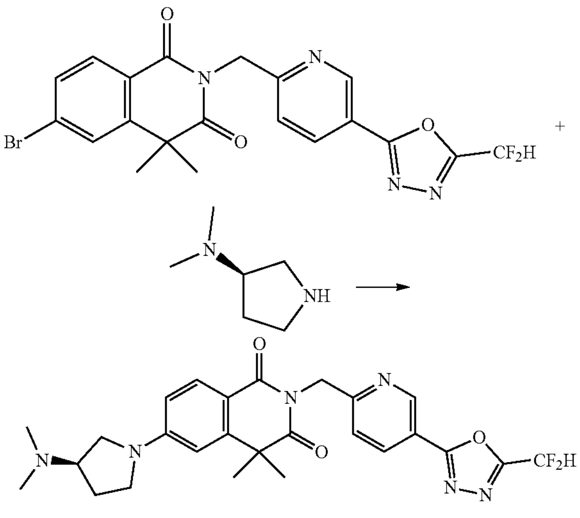

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), (R)—N,N-dimethylpyrrolidine-3-amine (0.054 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.050 g, 31.2%) in a colorless oil form.

$^1H$ NMR (400 MHz, $CDCl_3$) δ 9.20 (dd, J=2.2, 0.7 Hz, 1H), 8.31 (dd, J=8.2, 2.2 Hz, 1H), 8.08 (d, J=8.7 Hz, 1H), 7.41~7.38 (m, 1H), 7.06 (s, 0.25H), 6.93 (s, 0.5H), 6.80 (s, 0.25H), 6.59 (dd, J=8.9, 2.3 Hz, 1H), 5.40 (s, 2H), 3.63~3.57 (m, 2H), 3.45~3.43 (m, 1H), 3.27 (t, J=8.8 Hz, 2H), 2.95~2.85 (m, 1H), 2.35 (s, 6H), 2.31~2.27 (m, 1H), 2.05~1.99 (m, 1H), 1.68 (s, 6H); LRMS (ES) m/z 511.6 ($M^+$+1).

Synthesis of Compound 33, 2-((5-(5-(difluoromethyl)-1,3,4-oxadiazole-2-yl)pyridine-2-yl)methyl)-4,4-dimethyl-6-(4-(2-oxo-2-(pyrrolidine-1-yl)ethyl) piperazine-1-yl)isoquinoline-1,3(2H,4H)-dione

[Step 1] Synthesis of the Compound 33

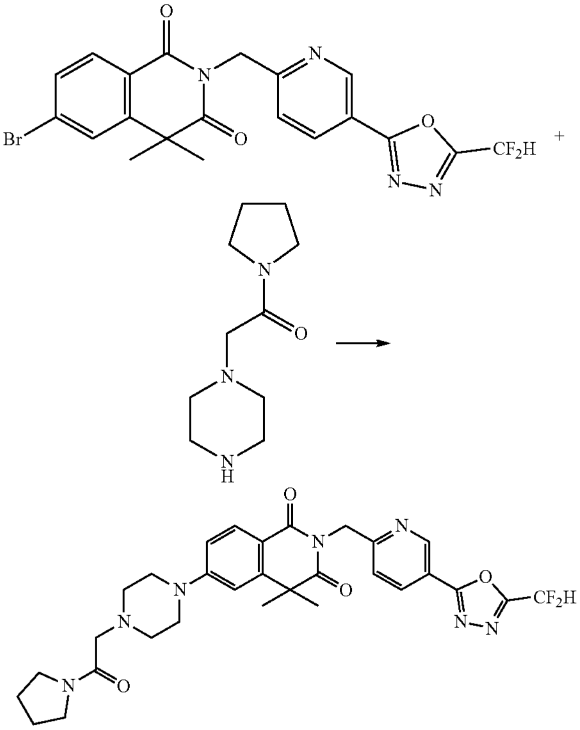

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), 2-(piperazine-1-yl)-1-(pyrrolidine-1-yl)ethane-1-one (0.093 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.100 g, 53.6%) in a yellow oil form.

$^1H$ NMR (400 MHz, $CDCl_3$) δ 9.18 (dd, J=2.2, 0.8 Hz, 1H), 8.30 (dd, J=8.2, 2.3 Hz, 1H), 8.08 (d, J=8.9 Hz, 1H), 7.40 (dd, J=8.3, 0.8 Hz, 1H), 7.06 (s, 0.25H), 6.92~6.90 (m, 1H), 6.92 (s, 0.5H), 6.82 (d, J=2.4 Hz, 1H), 6.80 (s, 0.25H), 5.40 (s, 1H), 3.51~3.42 (m, 8H), 3.20 (s, 2H), 2.75 (t, J=4.4 Hz, 4H), 1.98~1.85 (m, 4H), 1.67 (s, 6H); LRMS (ES) m/z 594.7 ($M^+$+1).

Synthesis of Compound 34, 6-(4-acetylpiperazine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 34

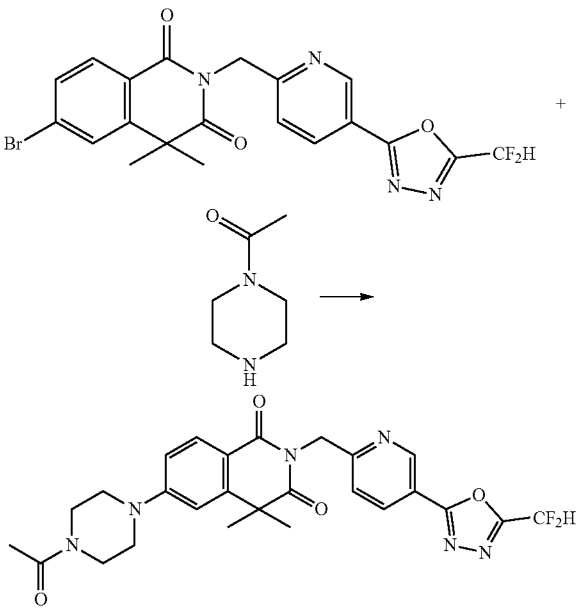

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), 1-(piperazine-1-yl)ethane-1-one (0.060 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.090 g, 54.6%) in a yellow oil form.

$^1H$ NMR (400 MHz, $CDCl_3$) δ 9.18 (dd, J=2.2, 0.7 Hz, 1H), 8.32 (dd, J=8.2, 2.2 Hz, 1H), 8.13 (d, J=8.8 Hz, 1H), 7.40~7.38 (m, 1H), 7.06 (s, 0.25H), 6.94~6.91 (m, 1H), 6.93 (s, 0.5H), 6.84 (d, J=2.4 Hz, 1H), 6.80 (s, 0.25H), 5.40 (s, 2H), 3.83~3.81 (m, 2H), 3.70~3.67 (m, 2H), 3.46~3.39 (m, 4H), 2.17 (s, 3H), 1.68 (s, 6H); LRMS (ES) m/z 525.6 ($M^++1$).

Synthesis of Compound 35, 2-((5-(5-(difluoromethyl)-1,3,4-oxadiazole-2-yl)pyridine-2-yl)methyl)-6-(4-(2-methoxy ethyl)piperazine-1-yl)-4,4-dimethylisoquinoline-1,3(2H,4H)-dione

[Step 1] Synthesis of the Compound 35

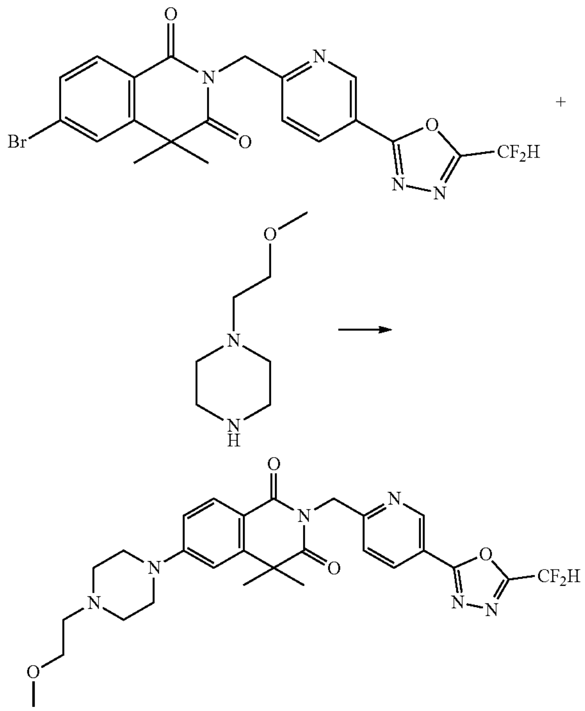

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), 1-(2-methoxyethyl)piperazine (0.068 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.100 g, 58.9%) in a colorless oil form.

$^1H$ NMR (400 MHz, $CDCl_3$) δ 9.19~9.19 (m, 1H), 8.31 (dd, J=8.3, 2.2 Hz, 1H), 8.09 (d, J=8.9 Hz, 1H), 7.40 (d, J=8.3 Hz, 1H), 7.06 (s, 1H), 6.93~6.90 (m, 1H), 6.93 (s, 1H), 6.80 (s, 1H), 5.40 (s, 2H), 3.58~3.56 (m, 2H), 3.47~3.42 (m, 3H), 3.39 (s, 3H), 2.70~2.65 (m, 6H), 1.67 (s, 6H); LRMS (ES) m/z 541.7 ($M^++1$).

Synthesis of Compound 36, 6-(4-(tert-butyl)piperazine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 36

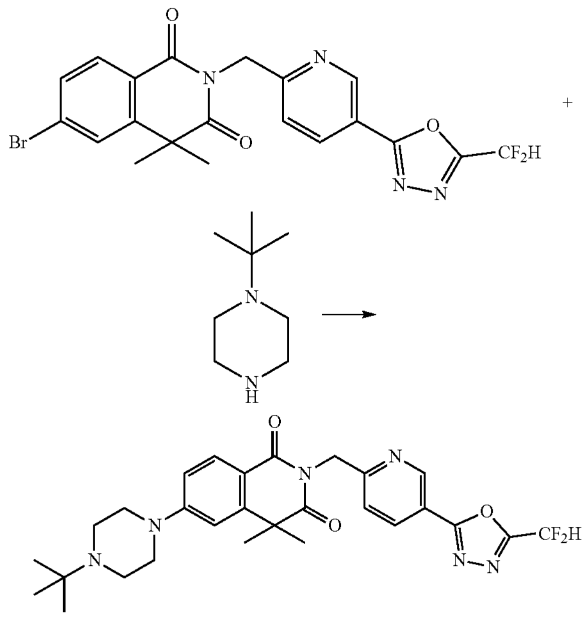

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), 1-(tert-butyl)piperazine (0.067 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.088 g, 52.0%) in a colorless oil form.

$^1$H NMR (400 MHz, $CDCl_3$) δ 9.21~9.19 (m, 1H), 8.32 (dd, J=8.2, 2.2 Hz, 1H), 8.10 (d, J=8.9 Hz, 1H), 7.41 (d, J=8.2 Hz, 1H), 7.06 (s, 0.25H), 6.94~6.91 (m, 1H), 6.92 (s, 0.5H), 6.84~6.83 (m, 1H), 6.80 (s, 0.25H), 5.41 (s, 2H), 3.42 (t, J=5.0 Hz, 4H), 2.77 (t, J=5.0 Hz, 4H), 1.68 (s, 6H), 1.14 (s, 9H); LRMS (ES) m/z 539.7 ($M^+$+1).

Synthesis of Compound 37, 2-((5-(5-(difluoromethyl)-1,3,4-oxadiazole-2-yl)pyridine-2-yl)methyl)-6-(4-(dimethylamino)piperidine-1-yl)-4,4-dimethylisoquinoline-1,3(2H,4H)-dione

[Step 1] Synthesis of the Compound 37

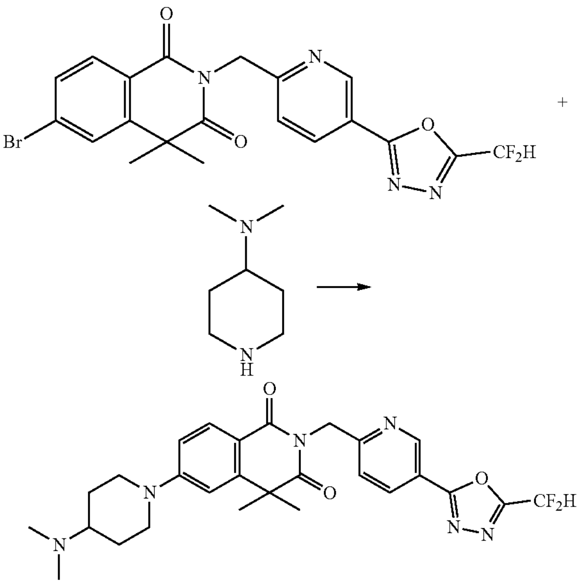

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), N,N-dimethylpiperidine-4-amine (0.060 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.080 g, 48.5%) in a yellow oil form.

$^1$H NMR (400 MHz, $CDCl_3$) δ 9.20~9.19 (m, 1H), 8.31 (dd, J=8.2, 2.2 Hz, 1H), 8.08 (d, J=8.9 Hz, 1H), 7.41 (d, J=8.3 Hz, 1H), 7.06 (s, 0.25H), 6.93~6.91 (m, 1H), 6.93 (s, 0.5H), 6.84 (d, J=2.4 Hz, 1H), 6.80 (s, 0.25H), 5.40 (s, 2H), 3.99~3.95 (m, 2H), 2.98~2.92 (m, 2H), 2.45~2.36 (m, 9H), 2.02~1.99 (m, 2H), 1.67 (s, 6H); LRMS (ES) m/z 525.6 ($M^+$+1).

Synthesis of Compound 38, 2-((5-(5-(difluoromethyl)-1,3,4-oxadiazole-2-yl)pyridine-2-yl)methyl)-6-((2-(dimethylamino)ethyl)(methyl)amino)-4,4-dimethylisoquinoline-1,3(2H,4H)-dione

[Step 1] Synthesis of the Compound 38

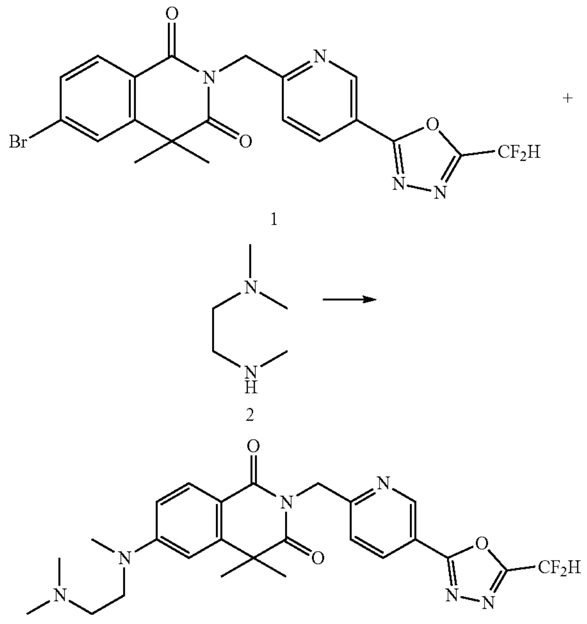

1

2

Prdt1

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), N1,N1,N2-trimethylethane-1,2-diamine (0.048 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.110 g, 70.2%) in a yellow oil form.

$^1$H NMR (400 MHz, $CDCl_3$) δ 9.19 (dd, J=2.2, 0.7 Hz, 1H), 8.31 (dd, J=8.3, 2.3 Hz, 1H), 8.07 (d, J=9.0 Hz, 1H), 7.40~7.38 (m, 1H), 7.06 (s, 1H), 6.93 (s, 1H), 6.80 (s, 1H), 6.72 (dd, J=9.0, 2.5 Hz, 1H), 6.63 (d, J=2.5 Hz, 1H), 5.40 (s, 2H), 3.58 (t, J=7.5 Hz, 2H), 3.10 (s, 3H), 2.53 (t, J=7.5 Hz, 2H), 2.33 (s, 6H), 1.67 (s, 6H); LRMS (ES) m/z 499.6 ($M^+$+1).

Synthesis of Compound 39, 2-((5-(5-(difluoromethyl)-1,3,4-oxadiazole-2-yl)pyridine-2-yl)methyl)-6-(4-ethylpiperazine-1-yl)-4,4-dimethylisoquinoline-1,3(2H,4H)-dione

[Step 1] Synthesis of the Compound 39

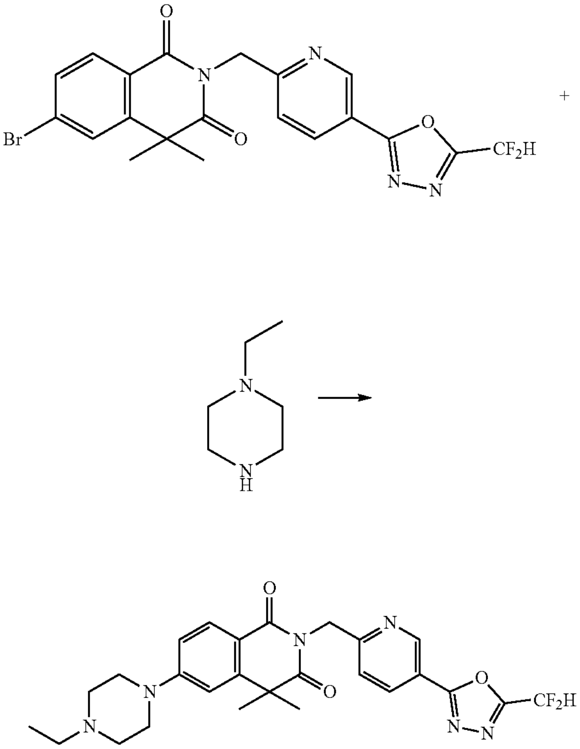

6-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), 1-ethylpiperazine (0.054 g, 0.471 mmol), 4,5-bis(diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.080 g, 49.9%) in a yellow oil form.

$^1$H NMR (400 MHz, $CDCl_3$) δ 9.19 (dd, J=2.2, 0.8 Hz, 1H), 8.31 (dd, J=8.2, 2.2 Hz, 1H), 8.09 (d, J=8.9 Hz, 1H), 7.41 (dd, J=8.7, 1.2 Hz, 1H), 7.06 (s, 0.25H), 6.94~6.91 (m, 1H), 6.93 (s, 0.5H), 6.84 (d, J=2.4 Hz, 1H), 6.80 (s, 0.25H), 5.40 (s, 2H), 3.43 (t, J=5.1 Hz, 4H), 2.63 (t, J=5.1 Hz, 4H), 2.51 (q, J=7.2 Hz, 2H), 1.67 (s, 6H), 1.15 (t, J=7.2 Hz, 3H); LRMS (ES) m/z 511.6 ($M^+$+1).

Synthesis of Compound 40, 2-((5-(5-(difluoromethyl)-1,3,4-oxadiazole-2-yl)pyridine-2-yl)methyl)-4,4-dimethyl-6-(2-oxa-6-azaspiro[3.3]heptane-6-yl) isoquinoline-1,3(2H,4H)-dione

[Step 1] Synthesis of the Compound 40

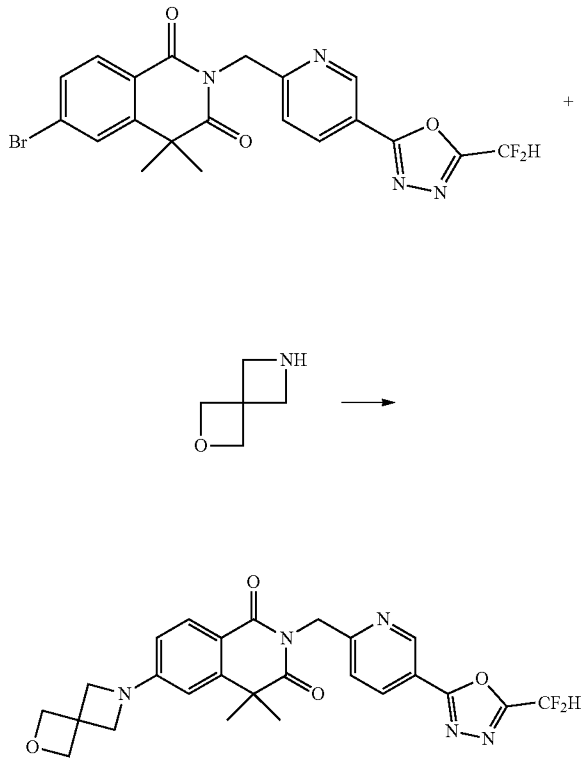

6-bromo-2-((5-(5-(difluoromethyl)-1,3,4-oxadiazole-2-yl)pyridine-2-yl)methyl)-4,4-dimethylisoquinoline-1,3(2H, 4H)-dione (0.150 g, 0.314 mmol), 2-oxa-6-azaspiro[3.3] heptane (0.031 g, 0.314 mmol), 4,5-bis (diphenylphosphino)-9,9-dimethylxanthene (Xantphos, 0.018 g, 0.031 mmol), tris(dibenzylideneacetone)dipalladium ($Pd_2(dba)_3$, 0.029 g, 0.031 mmol) and cesium carbonate (0.307 g, 0.943 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.049 g, 31.5%) in a white foam solid form.

$^1$H NMR (400 MHz, $CDCl_3$) δ 9.20 (dd, J=2.2, 0.8 Hz, 1H), 8.33 (dd, J=8.2, 2.2 Hz, 1H), 8.09 (d, J=8.6 Hz, 1H), 7.42 (dd, J=8.3, 0.8 Hz, 1H), 7.06 (s, 0.25H), 6.93 (s, 0.5H), 6.80 (s, 0.25H), 6.44 (dd, J=8.7, 2.3 Hz, 1H), 6.33 (d, J=2.2 Hz, 1H), 5.40 (s, 2H), 4.90 (s, 4H), 4.21 (s, 4H), 1.67 (s, 6H); LRMS (ES) m/z 496.6 ($M^+$+1).

Synthesis of Compound 41, tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)-3,6-dihydropyridine-1(2H)-carboxylate

[Step 1] Synthesis of the Compound 41

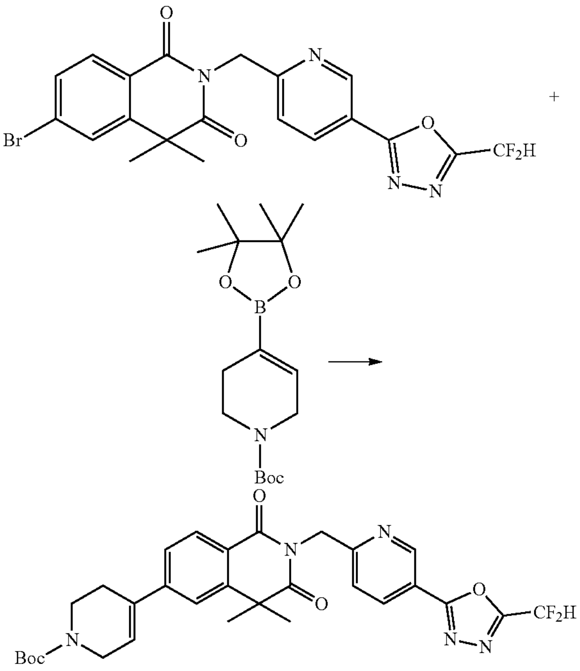

6-bromo-2-((5-(5-(difluoromethyl)-1,3,4-oxadiazole-2-yl)pyridine-2-yl)methyl)-4,4-dimethylisoquinoline-1,3(2H, 4H)-dione (0.700 g, 1.467 mmol), tert-butyl 4-(4,4,5,5-tetramethyl-1,3,2-dioxaborolane-2-yl)-3,6-dihydropyridine-1(2H)-carboxylat e (0.544 g, 1.760 mmol), [1,1'-bis (diphenylphosphino)ferrocene]dichloropalladium(II) (Pd (dppf)$Cl_2$, 0.107 g, 0.147 mmol) and sodium carbonate (0.311 g, 2.933 mmol) were dissolved in 1,2-dimethoxyethane (8 mL)/water (4 mL) at 90° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 70%), and concentrated to obtain a title compound (0.450 g, 52.9%) in a brown solid form.

$^1$H NMR (400 MHz, $CDCl_3$) δ 9.20~9.19 (m, 1H), 8.35 (dd, J=8.2, 2.2 Hz, 1H), 8.22 (d, J=8.0 Hz, 1H), 7.48~7.45 (m, 3H), 7.06 (s, 0.25H), 6.93 (s, 0.5H), 6.80 (s, 0.25H), 6.23 (br s, 1H), 5.44 (s, 2H), 4.16~4.13 (m, 2H), 3.70 (t, J=5.6 Hz, 2H), 2.59 (s, 2H), 1.71 (s, 6H), 1.52 (s, 9H); LRMS (ES) m/z 580.5 ($M^+$+1).

Synthesis of Compound 42, 2-((5-(5-(difluoromethyl)-1,3,4-oxadiazole-2-yl)pyridine-2-yl)methyl)-4,4-dimethyl-6-(1-methyl-1,2,3,6-tetrahydropyridine-4-yl)isoquinoline-1,3(2H,4H)-dione

[Step 1] Synthesis of 2-((5-(5-(difluoromethyl)-1,3,4-oxadiazole-2-yl)pyridine-2-yl)methyl)-4,4-dimethyl-6-(1,2,3,6-tetrahydropyridine-4-yl)isoquinoline-1,3(2H,4H)-dione 2,2,2-trifluoroacetate

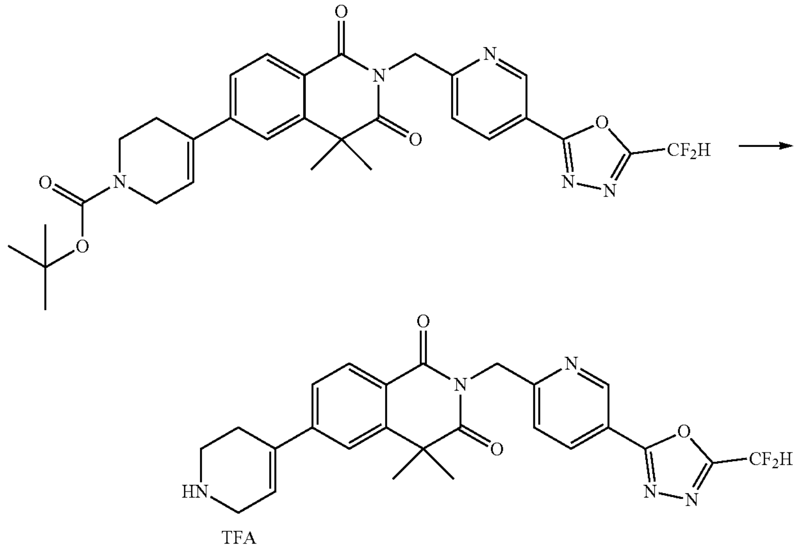

Tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)-3,6-dihydropyridine-1(2H)-carboxylate (0.450 g, 0.776 mmol) and trifluoroacetic acid (0.595 mL, 7.764 mmol) were dissolved in dichloromethane (10 mL) at room temperature, after which the resulting solution was stirred at the same temperature for 2 hours. Solvent was removed from the reaction mixture under reduced pressure, after which an obtained product was used without an additional purification process (0.460 g, 99.8%, brown oil).

[Step 2] Synthesis of the Compound 42

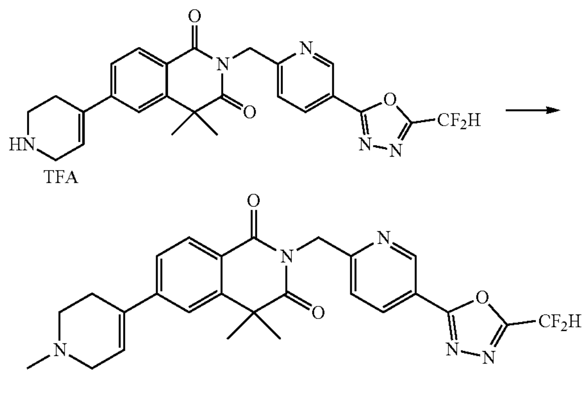

The 2-((5-(5-(difluoromethyl)-1,3,4-oxadiazole-2-yl)pyridine-2-yl)methyl)-4,4-dimethyl-6-(1,2,3,6-tetrahydropyridine-4-yl)isoquinoline-1,3(2H,4H)-dione 2,2,2-trifluoroacetate (0.200 g, 0.337 mmol) prepared in the step 1, formaldehyde (0.020 g, 0.674 mmol), N,N-diisopropylethylamine (0.059 mL, 0.337 mmol) and sodium triacetoxyborohydride (0.143 g, 0.674 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.080 g, 48.1%) in a colorless oil form.

$^1H$ NMR (400 MHz, $CDCl_3$) δ 9.17 (dd, J=2.2, 0.8 Hz, 1H), 8.33 (dd, J=8.2, 2.2 Hz, 1H), 8.19~8.17 (m, 1H), 7.48~7.42 (m, 3H), 7.06 (s, 0.25H), 6.93 (s, 0.5H), 6.80 (s, 0.25H), 6.24~6.22 (m, 1H), 5.41 (s, 2H), 3.27~3.25 (m, 2H), 2.81~2.79 (m, 2H), 2.69~2.67 (m, 2H), 2.48 (s, 3H), 1.70 (s, 6H); LRMS (ES) m/z 494.6 ($M^+$+1).

Synthesis of Compound 43, 2-((5-(5-(difluoromethyl)-1,3,4-oxadiazole-2-yl)pyridine-2-yl)methyl)-4,4-dimethyl-6-(1-(oxetan-3-yl)-1,2,3,6-tetrahydropyridine-4-yl)isoquinoline-1,3(2H,4H)-dione

[Step 1] Synthesis of the Compound 43

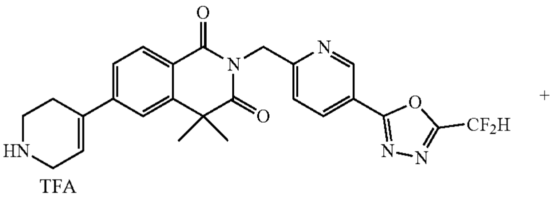

-continued

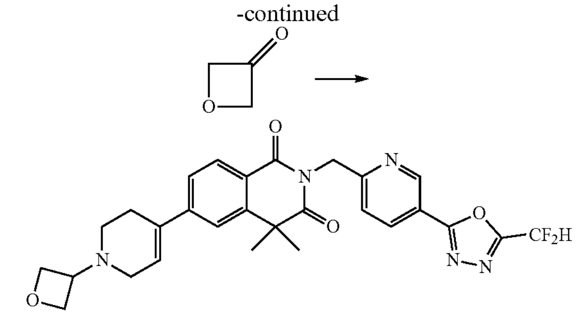

2-((5-(5-(difluoromethyl)-1,3,4-oxadiazole-2-yl)pyridine-2-yl)methyl)-4,4-dimethyl-6-(1,2,3,6-tetrahydropyridine-4-yl)isoquinoline-1,3(2H,4H)-dione 2,2,2-trifluoroacetate (0.200 g, 0.337 mmol), oxetan-3-one (0.049 g, 0.674 mmol), N,N-diisopropylethylamine (0.059 mL, 0.337 mmol) and sodium triacetoxyborohydride (0.143 g, 0.674 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.030 g, 16.6%) in a yellow oil form.

$^1H$ NMR (400 MHz, $CDCl_3$) δ 9.17 (dd, J=2.2, 0.8 Hz, 1H), 8.33 (dd, J=8.2, 2.2 Hz, 1H), 8.19~8.17 (m, 1H), 7.48~7.42 (m, 3H), 7.06 (s, 0.25H), 6.92 (s, 0.5H), 6.80 (s, 0.25H), 6.23 (t, J=3.5 Hz, 1H), 5.42 (s, 2H), 4.76~4.70 (m, 4H), 3.74~3.67 (m, 1H), 3.13~3.12 (m, 2H), 2.65 (s, 4H), 1.69 (s, 6H); LRMS (ES) m/z 536.6 ($M^+$+1).

Synthesis of Compound 44, 2-((5-(5-(difluoromethyl)-1,3,4-oxadiazole-2-yl)pyridine-2-yl)methyl)-4,4-dimethyl-6-(1-methylpiperidine-4-yl)isoquinoline-1,3(2H,4H)-dione

[Step 1] Synthesis of the Compound 44

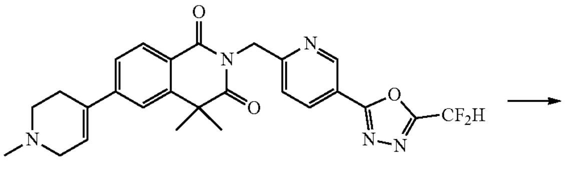

-continued

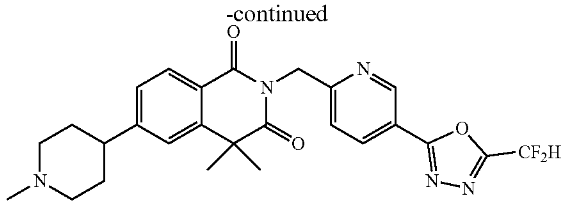

2-((5-(5-(difluoromethyl)-1,3,4-oxadiazole-2-yl)pyridine-2-yl)methyl)-4,4-dimethyl-6-(1-methyl-1,2,3,6-tetrahydropyridine-4-yl)isoquinoline-1,3(2H,4H)-dione (0.050 g, 0.101 mmol) was dissolved in methanol (5 mL) at room temperature, after which 10%-Pd/C (5 mg) was slowly added thereinto, and stirred for 12 hours in the presence of a hydrogen balloon attached thereto at the same temperature. The reaction mixture was filtered via a celite pad to remove a solid therefrom, after which solvent was removed from the resulting filtrate without the solid under reduced pressure. Then, the resulting concentrate was purified via column chromatography ($SiO_2$, 12 g cartridge; ethyl acetate/hexane=0 to 100%), and concentrated to obtain a title compound (0.018 g, 35.9%) in a colorless oil form.

$^1H$ NMR (400 MHz, $CDCl_3$) δ 9.18 (dd, J=1.8, 1.3 Hz, 1H), 8.34 (dd, J=8.2, 2.2 Hz, 1H), 8.19 (d, J=8.5 Hz, 1H), 7.44 (dd, J=8.2, 0.8 Hz, 1H), 7.38~7.33 (m, 2H), 7.06 (s, 0.25H), 6.93 (s, 0.5H), 6.80 (s, 0.25H), 5.43 (s, 2H), 3.18~3.15 (m, 2H), 2.70~2.65 (m, 1H), 2.28~2.22 (m, 2H), 2.05~1.90 (m, 4H), 1.69 (s, 6H); LRMS (ES) m/z 496.8 ($M^+$+1).

Synthesis of Compound 45, 2-((5-(5-(difluoromethyl)-1,3,4-oxadiazole-2-yl)pyridine-2-yl)methyl)-4,4-dimethyl-6-(4-pentylpiperazine-1-yl)isoquinoline-1,3(2H,4H)-dione

[Step 1] Synthesis of the Compound 45

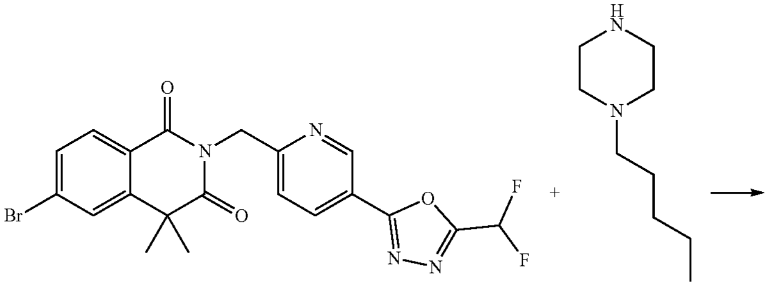

-continued

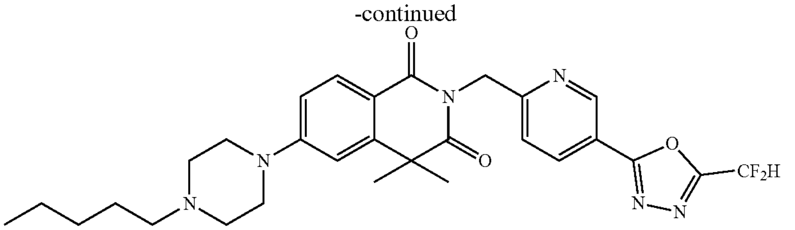

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), 1-pentylpiperazine (0.049 g, 0.314 mmol), 4,5-bis(diphenylphosphino)-9,9-dimethylxanthene (Xantphos, 0.012 g, 0.021 mmol), tris(dibenzylideneacetone)dipalladium ($Pd_2(dba)_3$, 0.019 g, 0.021 mmol) and cesium carbonate (0.205 g, 0.629 mmol) were dissolved in toluene (5 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.010 g, 8.6%) in a white solid form.

$^1H$ NMR (400 MHz, $CDCl_3$) δ 9.21 (dd, J=2.2, 0.8 Hz, 1H), 8.33 (dd, J=8.3, 2.3 Hz, 1H), 8.11 (d, J=8.9 Hz, 1H), 7.42 (dd, J=8.3, 0.8 Hz, 1H), 7.06 (s, 0.25H), 6.95~6.92 (m, 1H), 6.93 (s, 0.5H), 6.84 (d, J=2.4 Hz, 1H), 6.80 (s, 0.25H), 5.41 (s, 2H), 3.46 (t, J=4.8 Hz, 4H), 2.68~2.67 (m, 4H), 2.45~2.43 (m, 2H), 1.69 (s, 6H), 1.39~1.32 (m, 6H), 1.00~0.95 (m, 3H); LRMS (ES) m/z 553.6 ($M^+$+1).

Synthesis of Compound 46, 6-(4-cyclohexylpiperazine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 46

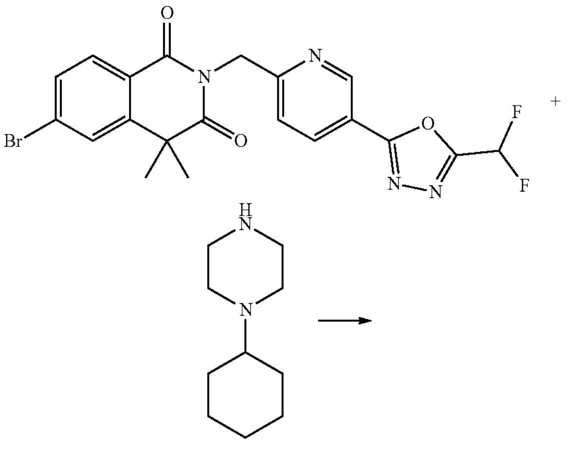

-continued

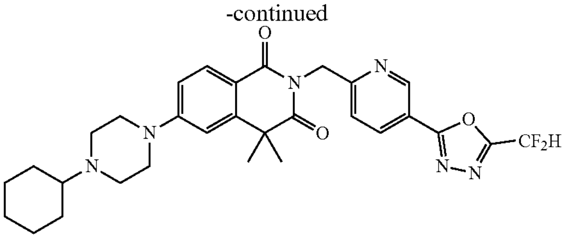

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), 1-cyclohexylpiperazine (0.053 g, 0.314 mmol), 4,5-bis(diphenylphosphino)-9,9-dimethylxanthene (Xantphos, 0.012 g, 0.021 mmol), tris(dibenzylideneacetone)dipalladium ($Pd_2(dba)_3$, 0.019 g, 0.021 mmol) and cesium carbonate (0.205 g, 0.629 mmol) were dissolved in toluene (5 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.020 g, 16.9%) in a white solid form.

$^1H$ NMR (400 MHz, $CDCl_3$) δ 9.20 (dd, J=2.2, 0.8 Hz, 1H), 8.32 (dd, J=8.2, 2.2 Hz, 1H), 8.10 (d, J=8.9 Hz, 1H), 7.41~7.38 (m, 1H), 7.06 (s, 0.25H), 6.94~6.91 (m, 1H), 6.93 (s, 0.5H), 6.84 (d, J=2.4 Hz, 1H), 6.80 (s, 0.25H), 5.41 (s, 2H), 3.41 (t, J=5.1 Hz, 4H), 2.75 (t, J=5.1 Hz, 4H), 2.60~2.55 (m, 2H), 2.45~2.35 (m, 1H), 2.05~1.82 (m, 2H), 1.68 (s, 6H), 1.29~1.24 (m, 2H); LRMS (ES) m/z 565.7 ($M^+$+1).

Synthesis of Compound 47, 6-(4-cyclopropylpiperazine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 47

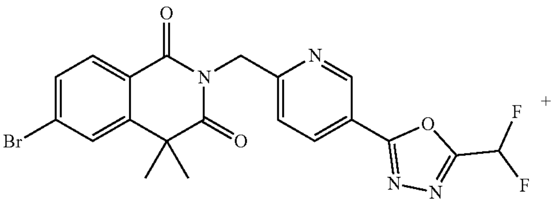

+

-continued

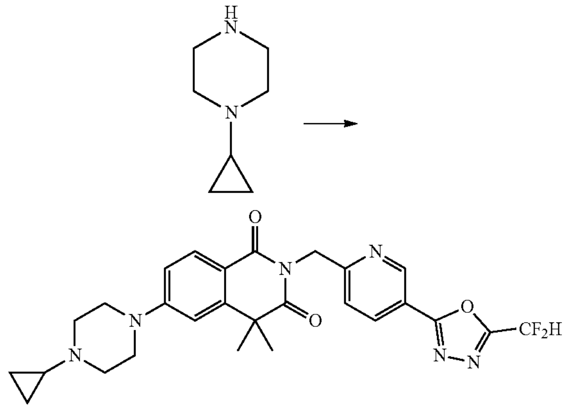

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), 1-cyclopropylpiperazine (0.040 g, 0.314 mmol), 4,5-bis(diphenylphosphino)-9,9-dimethylxanthene (Xantphos, 0.012 g, 0.021 mmol), tris(dibenzylideneacetone)dipalladium ($Pd_2(dba)_3$, 0.019 g, 0.021 mmol) and cesium carbonate (0.205 g, 0.629 mmol) were dissolved in toluene (5 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.020 g, 18.3%) in a white solid form.

$^1H$ NMR (400 MHz, $CDCl_3$) δ 9.20~9.19 (m, 1H), 8.32 (dd, J=8.2, 2.2 Hz, 1H), 8.10 (d, J=8.9 Hz, 1H), 7.41 (d, J=8.2 Hz, 1H), 7.06 (s, 0.25H), 6.94~6.91 (m, 1H), 6.93 (s, 0.5H), 6.84 (d, J=2.4 Hz, 1H), 6.80 (s, 0.25H), 5.41 (s, 2H), 3.38 (t, J=5.1 Hz, 4H), 2.80 (t, J=5.1 Hz, 4H), 1.71~1.67 (m, 7H), 0.53~0 0.49 (m, 4H); LRMS (ES) m/z 523.6 ($M^+$+1).

Synthesis of Compound 48, 6-(4-(cyclohexylmethyl)piperazine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 48

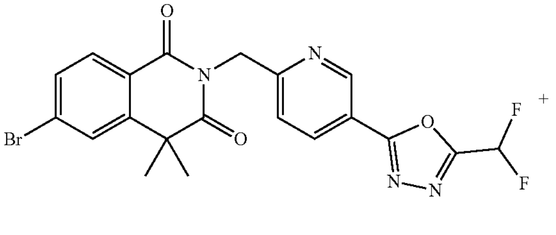

-continued

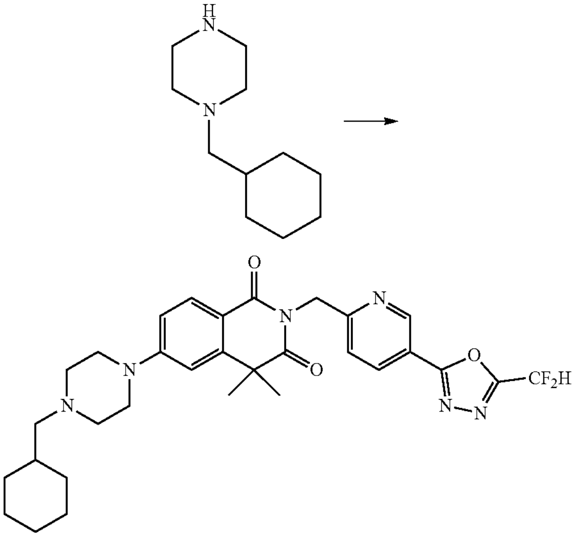

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), 1-(cyclohexylmethyl)piperazine (0.057 g, 0.314 mmol), 4,5-bis(diphenylphosphino)-9,9-dimethylxanthene (Xantphos, 0.012 g, 0.021 mmol), tris(dibenzylideneacetone)dipalladium ($Pd_2(dba)_3$, 0.019 g, 0.021 mmol) and cesium carbonate (0.205 g, 0.629 mmol) were dissolved in toluene (5 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.030 g, 24.7%) in a yellow solid form.

$^1H$ NMR (400 MHz, $CDCl_3$) δ 9.20 (dd, J=2.2, 0.7 Hz, 1H), 8.32 (dd, J=8.2, 2.2 Hz, 1H), 8.10 (d, J=8.9 Hz, 1H), 7.42~7.40 (m, 1H), 7.06 (s, 0.25H), 6.94~6.91 (m, 1H), 6.93 (s, 0.5H), 6.83 (d, J=2.4 Hz, 1H), 6.80 (s, 0.25H), 5.41 (s, 2H), 3.41 (t, J=5.1 Hz, 4H), 2.57 (t, J=5.1 Hz, 4H), 2.21 (d, J=7.2 Hz, 2H), 1.83~1.71 (m, 4H), 1.67~1.71 (m, 6H), 1.60~1.55 (m, 1H), 1.32~1.27 (m, 4H), 1.00~0.80 (m, 2H). LRMS (ES) m/z 579.6 ($M^+$+1).

Synthesis of Compound 49, 6-(3,3-difluoroazetidine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 49

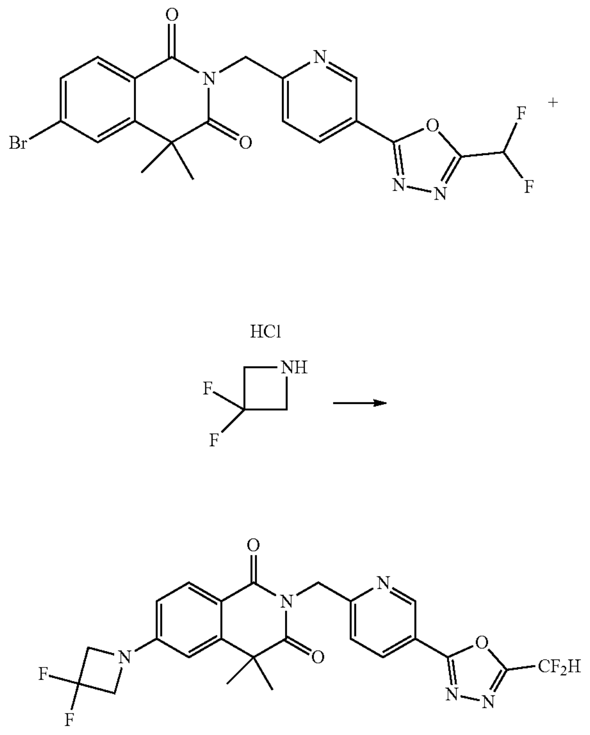

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), 3,3-difluoroazetidine hydrochloride (0.041 g, 0.314 mmol), 4,5-bis(diphenylphosphino)-9,9-dimethylxanthene (Xantphos, 0.012 g, 0.021 mmol), tris(dibenzylideneacetone)dipalladium ($Pd_2(dba)_3$, 0.019 g, 0.021 mmol) and cesium carbonate (0.205 g, 0.629 mmol) were dissolved in toluene (5 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.020 g, 19.5%) in a white solid form.

$^1$H NMR (400 MHz, $CDCl_3$) δ 9.20 (dd, J=5.5, 4.1 Hz, 1H), 8.34 (dd, J=8.2, 2.2 Hz, 1H), 8.15 (d, J=8.6 Hz, 1H), 7.43 (dd, J=8.2, 0.8 Hz, 1H), 7.06 (s, 0.25H), 6.93 (s, 0.5H), 6.80 (s, 0.25H), 6.52 (dd, J=8.6, 2.3 Hz, 1H), 6.41 (d, J=2.2 Hz, 1H), 5.41 (s, 2H), 4.39 (t, J=11.6 Hz, 4H), 1.68 (s, 6H); LRMS (ES) m/z 490.3 ($M^+$+1).

Synthesis of Compound 50, 2-((5-(5-(difluoromethyl)-1,3,4-oxadiazole-2-yl)pyridine-2-yl)methyl)-4,4-dimethyl-6-(4-(pyrimidine-2-yl)piperazine-1-yl) isoquinoline-1,3(2H,4H)-dione

[Step 1] Synthesis of the Compound 50

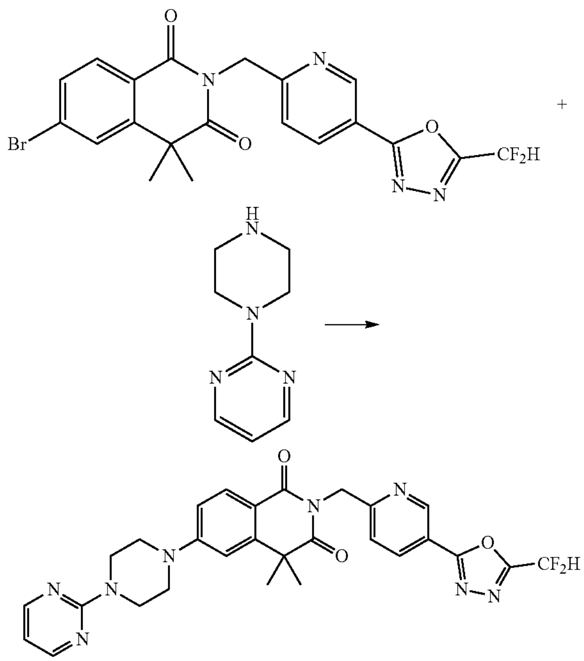

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), 2-(piperazine-1-yl)pyrimidine (0.052 g, 0.314 mmol), 4,5-bis(diphenylphosphino)-9,9-dimethylxanthene (Xantphos, 0.012 g, 0.021 mmol), tris(dibenzylideneacetone)dipalladium ($Pd_2(dba)_3$, 0.019 g, 0.021 mmol) and cesium carbonate (0.205 g, 0.629 mmol) were dissolved in toluene (5 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.020 g, 17.0%) in a colorless oil form.

$^1$H NMR (400 MHz, $CDCl_3$) δ 9.20 (dd, J=2.2, 0.8 Hz, 1H), 8.37 (d, J=4.8 Hz, 2H), 8.33 (dd, J=8.2, 2.2 Hz, 1H), 8.13 (d, J=8.9 Hz, 1H), 7.43~7.40 (m, 1H), 7.06 (s, 0.25H), 6.97 (dd, J=8.9, 2.5 Hz, 1H), 6.93 (s, 0.5H), 6.87 (d, J=2.4 Hz, 1H), 6.80 (s, 0.25H), 6.58 (t, J=4.8 Hz, 1H), 5.41 (s, 2H), 4.04 (t, J=5.3 Hz, 4H), 3.52 (t, J=5.3 Hz, 4H), 1.68 (s, 6H); LRMS (ES) m/z 561.5 ($M^+$+1).

Synthesis of Compound 51, 7-bromo-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of methyl 5-bromo-2-(1-methoxy-2-methyl-1-oxopropane-2-yl)benzoate

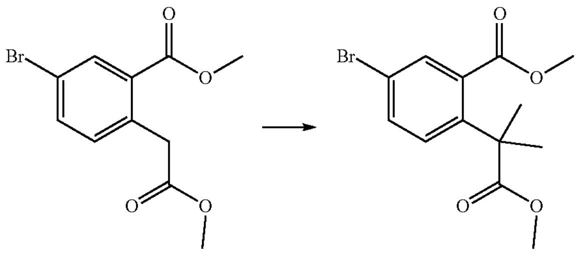 [SMILES: COC(=O)Cc1ccc(Br)cc1C(=O)OC ; COC(=O)c1cc(Br)ccc1C(C)(C)C(=O)OC]

Methyl 5-bromo-2-(2-methoxy-2-oxoethyl)benzoate (6.260 g, 21.803 mmol) was dissolved in N,N-dimethylformamide (50 mL) at 0° C., after which sodium hydride (60.00%, 2.616 g, 65.410 mmol) was added into the resulting solution, and stirred at the same temperature for 30 minutes. Iodomethane (4.072 mL, 65.410 mmol) was added into the reaction mixture, and further stirred at room temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 10%), and concentrated to obtain a title compound (5.300 g, 77.1%) in a colorless oil form.

[Step 2] Synthesis of 5-bromo-2-(2-carboxypropane-2-yl)benzoic acid

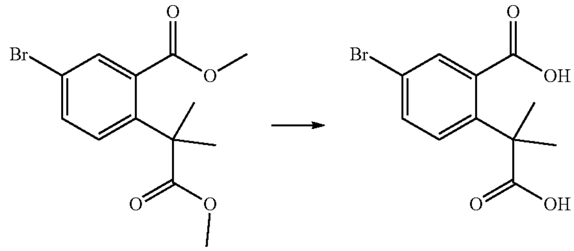 [SMILES: COC(=O)c1cc(Br)ccc1C(C)(C)C(=O)OC ; CC(C)(C(=O)O)c1ccc(Br)cc1C(=O)O]

The methyl 5-bromo-2-(1-methoxy-2-methyl-1-oxopropane-2-yl)benzoate (5.300 g, 16.817 mmol) prepared in the step 1 and potassium hydroxide (9.435 g, 168.169 mmol) were dissolved in methanol (30 mL)/water (60 mL) at 100° C., after which the resulting solution was stirred at the same temperature for 12 hours, and then a reaction was finished by lowering the temperature to room temperature. Solvent was removed from the reaction mixture under reduced pressure, after which 1N-hydrochloric acid aqueous solution was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. An obtained product was used without an additional purification process (4.800 g, 99.4%, white solid).

[Step 3] Synthesis of 7-bromo-4,4-dimethylisoquinoline-1,3(2H,4H)-dione

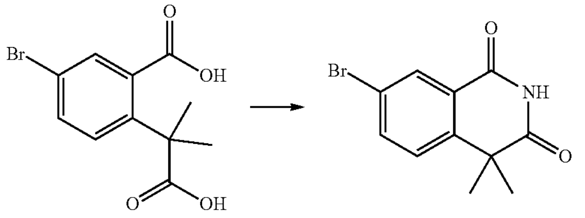 [SMILES: CC(C)(C(=O)O)c1ccc(Br)cc1C(=O)O ; CC1(C)C(=O)NC(=O)c2cc(Br)ccc21]

The 5-bromo-2-(2-carboxypropane-2-yl)benzoic acid (4.800 g, 16.718 mmol) prepared in the step 2 and urea (1.105 g, 18.390 mmol) were mixed in chlorobenzene (30 mL), then irradiated with microwave, then heated at 150° C. for 1 hour, and then a reaction was finished by lowering the temperature to room temperature. A precipitated solid was filtered, then washed with hexane, and then dried to obtain a title compound (4.480 g, 99.9%) in a white solid form.

[Step 4] Synthesis of the Compound 51

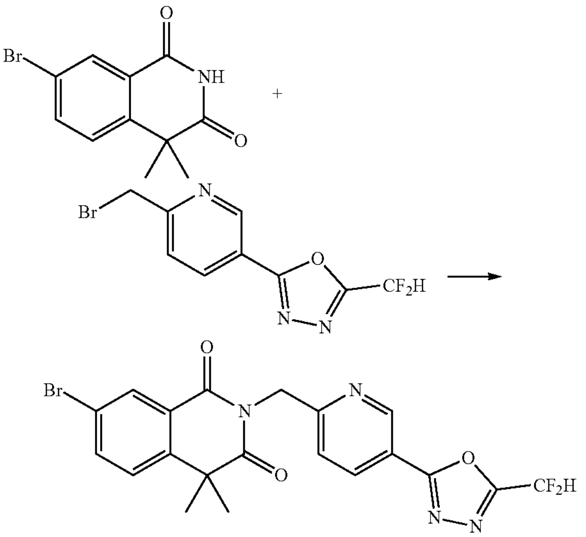

The 7-bromo-4,4-dimethylisoquinoline-1,3(2H,4H)-dione (4.480 g, 16.710 mmol) prepared in the step 3, 2-(6-(bromomethyl)pyridine-3-yl)-5-(difluoromethyl)-1,3,4-oxadiazole (7.270 g, 25.064 mmol) and potassium carbonate (4.619 g, 33.419 mmol) were dissolved in N,N-dimethylformamide (50 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/ hexane=0 to 50%), and concentrated to obtain a title compound (4.500 g, 56.4%) in a yellow solid form.

$^1$H NMR (400 MHz, DMSO-$d_6$) δ 9.06~9.05 (m, 1H), 8.37 (dd, J=8.3, 2.3 Hz, 1H), 8.16 (d, J=2.2 Hz, 1H), 7.95~7.93 (m, 1H), 7.75 (d, J=8.5 Hz, 1H), 7.68 (s, 0.25H), 7.63 (d, J=8.3 Hz, 1H), 7.55 (s, 0.5H), 7.42 (s, 0.25H), 5.30 (s, 2H), 1.61 (s, 6H).

Synthesis of Compound 52, 2-((5-(5-(difluoromethyl)-1,3,4-oxadiazole-2-yl)pyridine-2-yl)methyl)-4,4-dimethyl-7-morpholinoisoquinoline-1,3(2H,4H)-dione

[Step 1] Synthesis of the Compound 52

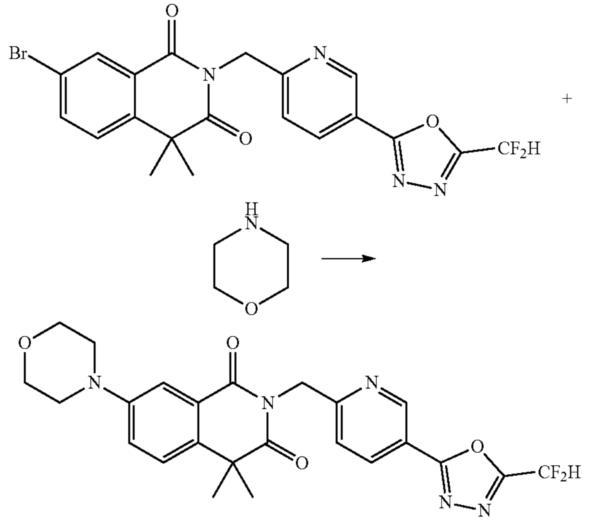

7-bromo-2-((5-(5-(difluoromethyl)-1,3,4-oxadiazole-2-yl)pyridine-2-yl)methyl)-4,4-dimethylisoquinoline-1,3(2H, 4H)-dione (0.100 g, 0.210 mmol), morpholine (0.027 mL, 0.314 mmol), 4,5-bis(diphenylphosphino)-9,9-dimethylxanthene (Xantphos, 0.012 g, 0.021 mmol), tris(dibenzylideneacetone)dipalladium ($Pd_2(dba)_3$, 0.019 g, 0.021 mmol) and cesium carbonate (0.205 g, 0.629 mmol) were dissolved in toluene (5 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.015 g, 14.8%) in a colorless oil form.

$^1$H NMR (400 MHz, $CDCl_3$) δ 9.21~9.20 (m, 1H), 8.34 (dd, J=8.2, 2.2 Hz, 1H), 7.72 (d, J=2.8 Hz, 1H), 7.43~7.40 (m, 2H), 7.26~7.25 (m, 1H), 7.06 (s, 0.25H), 6.93 (s, 0.5H), 6.80 (s, 0.25H), 5.41 (s, 2H), 3.89 (t, J=4.9 Hz, 4H), 3.26~3.23 (m, 4H), 1.67 (s, 6H); LRMS (ES) m/z 484.6 ($M^+$+1).

Synthesis of Compound 53, tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-7-yl)-3,6-dihydropyridine-1(2H)-carboxylate

[Step 1] Synthesis of the Compound 53

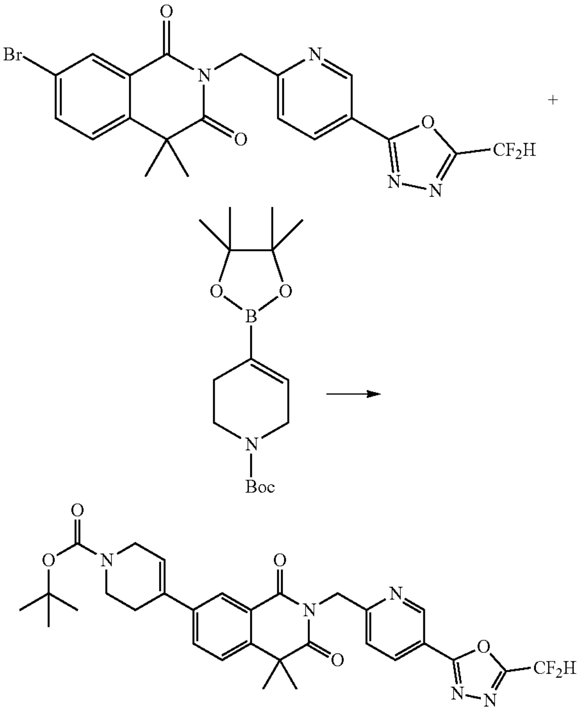

7-bromo-2-((5-(5-(difluoromethyl)-1,3,4-oxadiazole-2-yl)pyridine-2-yl)methyl)-4,4-dimethylisoquinoline-1,3(2H, 4H)-dione (1.000 g, 2.095 mmol), tert-butyl 4-(4,4,5,5-tetramethyl-1,3,2-dioxaborolane-2-yl)-3,6-dihydropyridine-1(2H)-carboxylat e (0.777 g, 2.514 mmol), [1,1'-bis(diphenylphosphino)ferrocene]dichloropalladium(II) (Pd(dppf)$Cl_2$, 0.153 g, 0.210 mmol) and sodium carbonate (0.444 g, 4.191 mmol) were dissolved in 1,2-dimethoxyethane (10 mL)/water (5 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 80%), and concentrated to obtain a title compound (0.490 g, 40.3%) in a yellow oil form.

$^1$H NMR (400 MHz, $CDCl_3$) δ 9.19 (d, J=2.0 Hz, 1H), 8.36 (dd, J=8.2, 2.2 Hz, 1H), 8.24 (s, 1H), 7.71 (dd, J=8.2, 2.0 Hz, 1H), 7.51~7.45 (m, 2H), 7.06 (s, 0.25H), 6.93 (s, 0.5H), 6.80 (s, 0.25H), 6.17 (s, 1H), 5.45 (s, 2H), 4.16~4.11 (m, 2H), 3.67 (t, J=5.6 Hz, 2H), 2.60~2.56 (m, 2H), 1.67 (s, 6H), 1.51 (s, 9H).

Synthesis of Compound 54, 2-((5-(5-(difluoromethyl)-1,3,4-oxadiazole-2-yl)pyridine-2-yl)methyl)-4,4-dimethyl-7-(1-methylpiperidine-4-yl)isoquinoline-1,3(2H,4H)-dione

[Step 1] Synthesis of tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-7-yl)piperidine-1-carboxylate

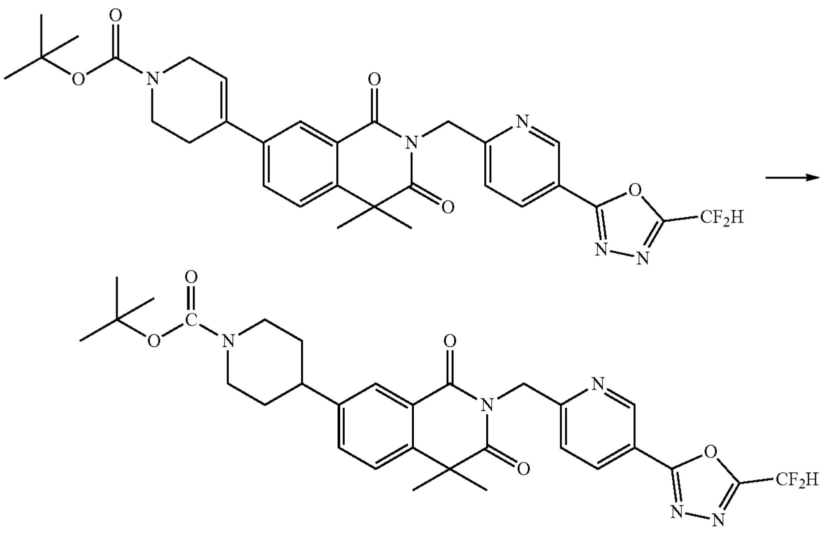

Tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-7-yl)-3,6-dihydropyridine-1(2H)-carboxylate (0.490 g, 0.845 mmol) was dissolved in methanol (10 mL) at room temperature, after which 10%-Pd/C (50 mg) was slowly added thereinto, and stirred for 12 hours in the presence of a hydrogen balloon attached thereto at the same temperature. An obtained product was used without an additional purification process (0.480 g, 97.6%, colorless oil).

[Step 2] Synthesis of 2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione 2,2,2-trifluoroacetate

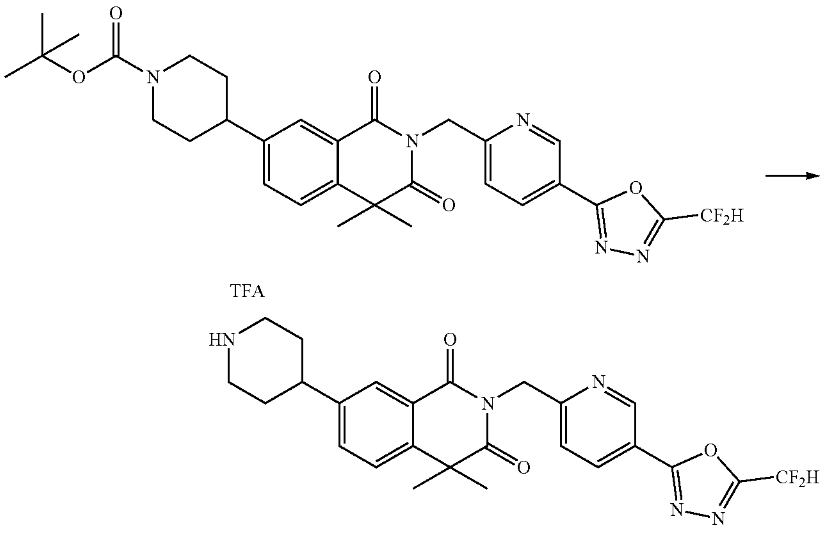

The tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-7-yl)piperidine-1-carboxylate (0.488 g, 0.839 mmol) prepared in the step 1 and trifluoroacetic acid (0.642 mL, 8.390 mmol) were dissolved in dichloromethane (10 mL) at room temperature, after which the resulting solution was stirred at the same temperature for 2 hours. Solvent was removed from the reaction mixture under reduced pressure, after which an obtained product was used without an additional purification process (0.490 g, 98.1%, yellow oil).

[Step 3] Synthesis of the Compound 54

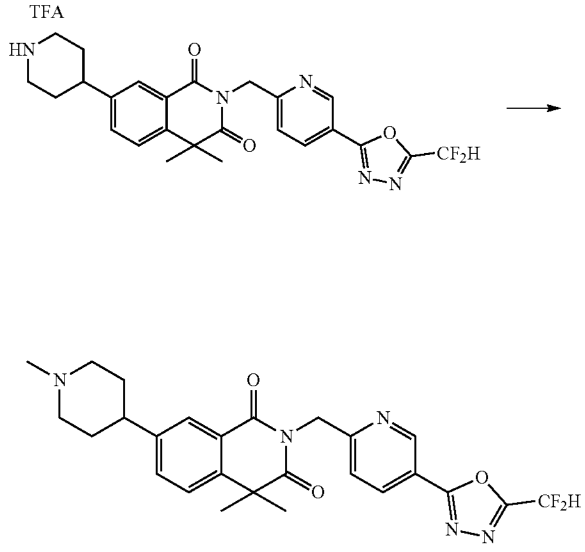

The 2-((5-(5-(difluoromethyl)-1,3,4-oxadiazole-2-yl) pyridine-2-yl)methyl)-4,4-dimethyl-7-(piperidine-4-yl)isoquinoline-1,3(2H,4H)-dione 2,2,2-trifluoroacetate (0.150 g, 0.252 mmol) prepared in the step 2, formaldehyde (0.015 g, 0.504 mmol), N,N-diisopropylethylamine (0.044 mL, 0.252 mmol) and sodium triacetoxyborohydride (0.107 g, 0.504 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.050 g, 40.1%) in a colorless oil form.

$^1$H NMR (400 MHz, $CDCl_3$) δ 9.14 (dd, J=2.2, 0.8 Hz, 1H), 8.32 (dd, J=8.2, 2.2 Hz, 1H), 8.06 (d, J=2.1 Hz, 1H), 7.58 (dd, J=8.2, 2.1 Hz, 1H), 7.45 (d, J=31.8 Hz, 1H), 7.44 (dd, J=8.0, 1.0 Hz, 1H), 7.06 (s, 0.25H), 6.93 (s, 0.5H), 6.80 (s, 0.25H), 5.40 (s, 2H), 3.62 (d, J=12.0 Hz, 2H), 2.88~2.81 (m, 6H), 2.27~2.25 (m, 2H), 2.06~2.03 (m, 2H), 1.67 (s, 6H); LRMS (ES) m/z 496.6 ($M^+$+1).

Synthesis of Compound 55, 2-((5-(5-(difluoromethyl)-1,3,4-oxadiazole-2-yl)pyridine-2-yl)methyl)-4,4-dimethyl-7-(1-(oxetan-3-yl)piperidine-4-yl)isoquinoline-1,3(2H,4H)-dione

[Step 1] Synthesis of the Compound 55

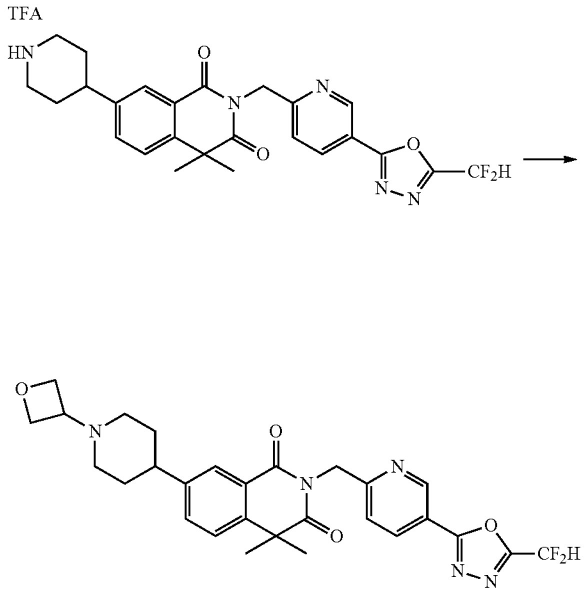

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione 2,2,2-trifluoroacetate (0.150 g, 0.252 mmol), oxetan-3-one (0.036 g, 0.504 mmol), N,N-diisopropylethylamine (0.044 mL, 0.252 mmol) and sodium triacetoxyborohydride (0.107 g, 0.504 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.030 g, 22.2%) in a colorless oil form.

$^1$H NMR (400 MHz, $CDCl_3$) δ 9.18 (dd, J=2.2, 0.8 Hz, 1H), 8.33 (dd, J=8.2, 2.3 Hz, 1H), 8.11 (d, J=2.0 Hz, 1H), 7.56 (dd, J=8.3, 2.0 Hz, 1H), 7.47~7.43 (m, 2H), 7.06 (s, 0.25H), 6.93 (s, 0.5H), 6.80 (s, 0.25H), 5.42 (s, 2H), 4.69~4.67 (m, 4H), 3.55~3.52 (m, 1H), 2.93~2.90 (m, 2H), 2.70~2.60 (m, 1H), 1.99~1.98 (m, 2H), 1.90~1.87 (m, 4H), 1.68 (s, 6H); LRMS (ES) m/z 538.6 ($M^+$+1).

Synthesis of Compound 56, 1-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)-N-methylpiperidine-4-carboxamide

[Step 1] Synthesis of the Compound 56

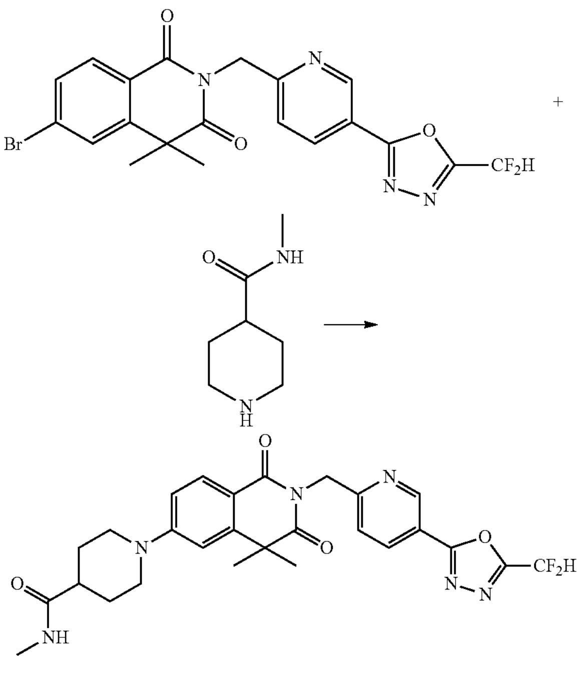

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), N-methylpiperidine-4-carboxamide (0.030 g, 0.210 mmol), tris(dibenzylideneacetone)dipalladium ($Pd_2(dba)_3$, 0.019 g, 0.021 mmol), 4,5-bis(diphenylphosphino)-9,9-dimethylxanthene (Xantphos, 0.012 g, 0.021 mmol) and cesium carbonate (0.205 g, 0.629 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.030 g, 26.6%) in a colorless oil form.

$^1H$ NMR (400 MHz, $CDCl_3$) δ 9.21~9.20 (m, 1H), 8.33 (dd, J=8.2, 2.2 Hz, 1H), 8.11~8.10 (m, 1H), 7.42~7.40 (m, 1H), 7.06 (s, 0.25H), 6.94~6.92 (m, 1H), 6.93 (s, 0.5H), 6.84 (d, J=2.4 Hz, 1H), 6.80 (s, 0.25H), 5.60~5.55 (m, 1H), 5.41 (s, 2H), 4.00~3.97 (m, 2H), 3.02~2.96 (m, 2H), 2.87~2.85 (m, 3H), 2.42~2.38 (m, 1H), 2.19~1.88 (m, 4H), 1.68 (s, 6H).

Synthesis of Compound 57, 1-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)-N,N-dimethylpiperidine-4-carboxamide

[Step 1] Synthesis of the Compound 57

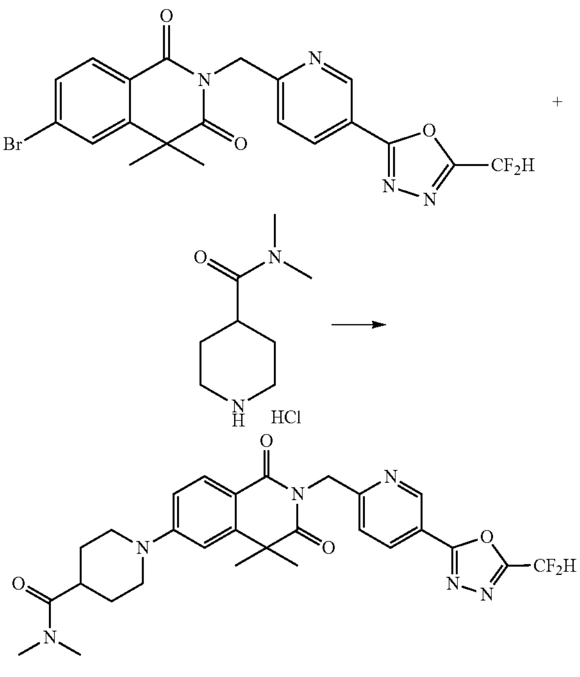

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), N,N-dimethylpiperidine-4-carboxamide hydrochloride (0.040 g, 0.210 mmol), tris(dibenzylideneacetone)dipalladium ($Pd_2(dba)_3$, 0.019 g, 0.021 mmol), 4,5-bis(diphenylphosphino)-9,9-dimethylxanthene (Xantphos, 0.012 g, 0.021 mmol) and cesium carbonate (0.205 g, 0.629 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.020 g, 17.3%) in a colorless oil form.

$^1H$ NMR (400 MHz, $CDCl_3$) δ 9.20 (dd, J=2.2, 0.6 Hz, 1H), 8.32 (dd, J=8.2, 2.2 Hz, 1H), 8.08 (d, J=8.9 Hz, 1H), 7.40 (dd, J=8.3, 0.5 Hz, 1H), 7.06 (s, 0.25H), 6.94~6.91 (m, 1H), 6.93 (s, 0.5H), 6.84 (d, J=2.4 Hz, 1H), 6.80 (s, 0.25H), 5.41 (s, 2H), 4.00~3.96 (m, 2H), 3.12 (s, 3H), 3.05~2.98 (m, 5H), 2.80~2.75 (m, 1H), 1.97~1.83 (m, 4H), 1.67 (s, 6H); LRMS (ES) m/z 553.6 ($M^+$+1).

Synthesis of Compound 58, 2-((5-(5-(difluoromethyl)-1,3,4-oxadiazole-2-yl)pyridine-2-yl)methyl)-4,4-dimethyl-6-((1S,4S)-5-(methylsulfonyl)-2,5-diazabicyclo[2.2.1]heptane-2-yl)isoquinoline-1,3(2H,4H)-dione

[Step 1] Synthesis of the Compound 58

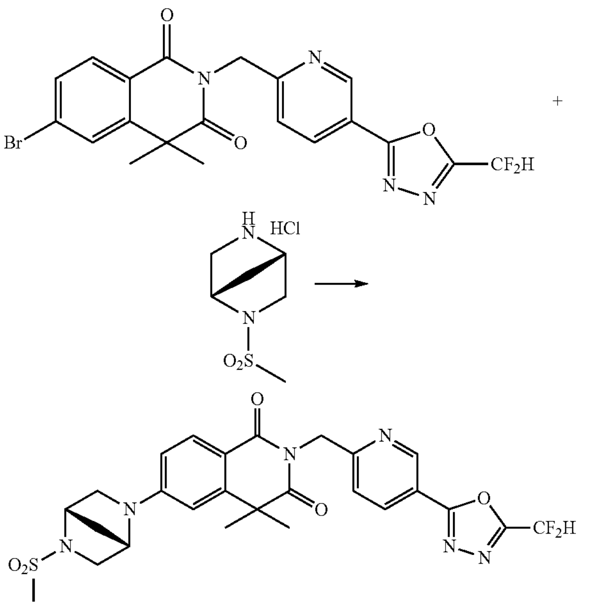

6-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), (1S,4S)-2-(methylsulfonyl)-2,5-diazabicyclo[2.2.1]heptane hydrochloride (0.045 g, 0.210 mmol), tris(dibenzylideneacetone)dipalladium ($Pd_2(dba)_3$, 0.019 g, 0.021 mmol), 4,5-bis(diphenylphosphino)-9,9-dimethylxanthene (Xantphos, 0.012 g, 0.021 mmol) and cesium carbonate (0.205 g, 0.629 mmol) were dissolved in toluene (10 mL) at 80° C., after which the resulting solution was stirred at the same temperature for 12 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.050 g, 41.7%) in a colorless oil form.

$^1H$ NMR (400 MHz, $CDCl_3$) δ 9.21~9.20 (m, 1H), 8.33 (dd, J=8.2, 2.3 Hz, 1H), 8.11 (d, J=8.8 Hz, 1H), 7.42 (d, J=8.3 Hz, 1H), 7.06 (s, 0.25H), 6.93 (s, 0.5H), 6.80 (s, 0.25H), 6.63 (dd, J=8.8, 2.4 Hz, 1H), 6.49 (d, J=2.3 Hz, 1H), 5.41 (s, 2H), 4.67 (s, 2H), 3.69~3.66 (m, 1H), 3.58~3.50 (m, 3H), 2.92 (s, 3H), 2.50~2.04 (m, 2H), 1.67 (s, 6H); LRMS (ES) m/z 573.6 ($M^+$+1).

Synthesis of Compound 59, 2-((5-(5-(difluoromethyl)-1,3,4-oxadiazole-2-yl)pyridine-2-yl)methyl)-6-(1-ethylpiperidine-4-yl)-4,4-dimethylisoquinoline-1,3(2H,4H)-dione

[Step 1] Synthesis of 2-((5-(5-(difluoromethyl)-1,3,4-oxadiazole-2-yl)pyridine-2-yl)methyl)-4,4-dimethyl-6-(piperidine-4-yl)isoquinoline-1,3(2H,4H)-dione 2,2,2-trifluoroacetate

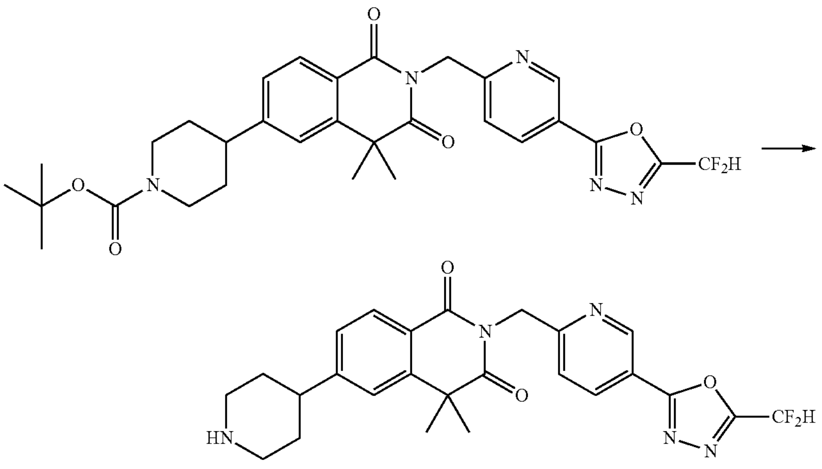

TFA

Tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)piperidine-1-carboxylate (1.340 g, 2.304 mmol) and trifluoroacetic acid (1.764 mL, 23.039 mmol) were dissolved in dichloromethane (10 mL) at room temperature, after which the resulting solution was stirred at the same temperature for 3 hours. Solvent was removed from the reaction mixture under reduced pressure, after which an obtained product was used without an additional purification process (1.300 g, 94.7%, brown oil).

[Step 2] Synthesis of the Compound 59

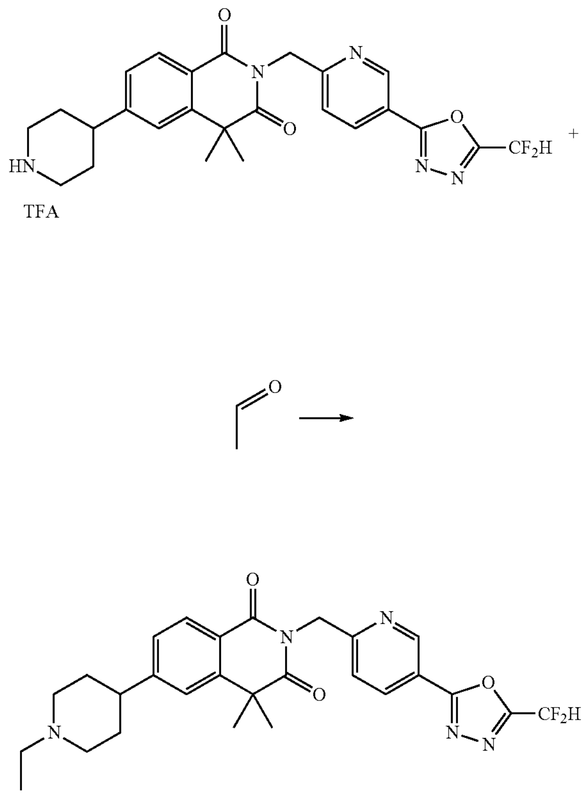

The 2-((5-(5-(difluoromethyl)-1,3,4-oxadiazole-2-yl) pyridine-2-yl)methyl)-4,4-dimethyl-6-(piperidine-4-yl)isoquinoline-1,3(2H,4H)-dione 2,2,2-trifluoroacetate (0.200 g, 0.336 mmol) prepared in the step 1 and N,N-diisopropylethylamine (0.058 mL, 0.336 mmol) were dissolved in dichloromethane (10 mL), after which the resulting solution was stirred at room temperature for 30 hours, and then acetaldehyde (0.030 g, 0.672 mmol) and sodium triacetoxyborohydride (0.142 g, 0.672 mmol) were added thereinto and further stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure.

The resulting concentrate was purified via column chromatography ($SiO_2$, 12 g cartridge; ethyl acetate/hexane=0 to 100%), and concentrated to obtain a title compound (0.080 g, 46.7%) in a colorless oil form.

$^1$H NMR (400 MHz, $CDCl_3$) δ 9.18~9.17 (m, 1H), 8.33 (dd, J=8.2, 2.2 Hz, 1H), 8.19 (d, J=8.1 Hz, 1H), 7.45~7.41 (m, 2H), 7.36~7.33 (m, 1H), 7.06 (s, 0.25H), 6.93 (s, 0.5H), 6.80 (s, 0.25H), 5.42 (s, 2H), 3.53~3.49 (m, 2H), 2.92~2.86 (m, 2H), 2.77~2.76 (m, 1H), 2.53~2.47 (m, 2H), 2.24~2.20 (m, 2H), 2.02~1.98 (m, 2H), 1.67 (s, 6H), 1.33~1.30 (m, 3H); LRMS (ES) m/z 510.6 ($M^+$+1).

Synthesis of Compound 60, 2-((5-(5-(difluoromethyl)-1,3,4-oxadiazole-2-yl)pyridine-2-yl)methyl)-6-(1-isopropylpiperidine-4-yl)-4,4-dimethylisoquinoline-1,3(2H,4H)-dione

[Step 1] Synthesis of the Compound 60

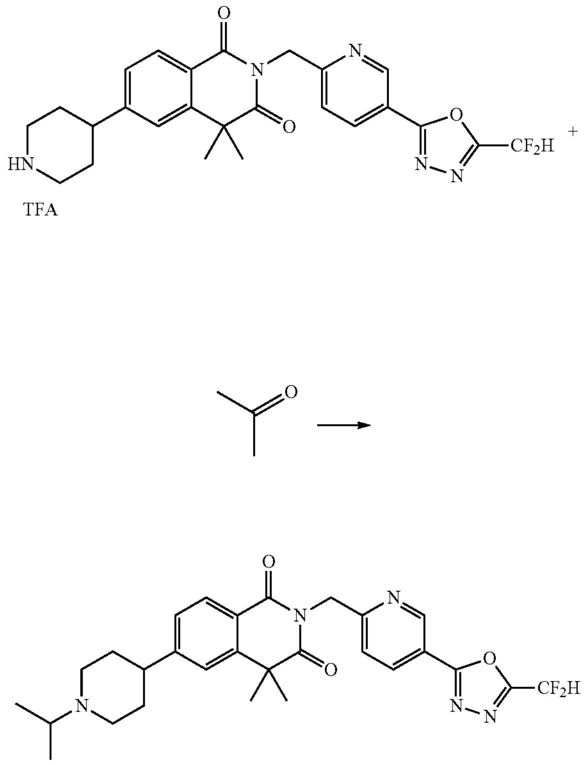

2-((5-(5-(difluoromethyl)-1,3,4-oxadiazole-2-yl)pyridine-2-yl)methyl)-4,4-dimethyl-6-(piperidine-4-yl)isoquinoline-1,3(2H,4H)-dione 2,2,2-trifluoroacetate (0.200 g, 0.336 mmol) and N,N-diisopropylethylamine (0.058 mL, 0.336 mmol) were dissolved in dichloromethane (10 mL), after which the resulting solution was stirred at room temperature for 30 hours, and then acetone (0.039 g, 0.672 mmol) and sodium triacetoxyborohydride (0.142 g, 0.672 mmol) were added thereinto and further stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.050 g, 28.4%) in a colorless oil form.

$^1$H NMR (400 MHz, $CDCl_3$) δ 9.19~9.18 (m, 1H), 8.34 (dd, J=8.2, 2.2 Hz, 1H), 8.21 (d, J=8.1 Hz, 1H), 7.45~7.43 (m, 2H), 7.35 (dd, J=8.1, 1.5 Hz, 1H), 7.06 (s, 1H), 6.93 (s, 1H), 6.80 (s, 1H), 5.42 (s, 2H), 3.69~3.50 (m, 3H), 2.87~2.82 (m, 3H), 2.53~2.49 (m, 2H), 2.09~2.06 (m, 2H), 1.67 (s, 6H), 1.42~1.38 (m, 6H); LRMS (ES) m/z 524.6 ($M^+$+1).

Synthesis of Compound 61, 2-((5-(5-(difluoromethyl)-1,3,4-oxadiazole-2-yl)pyridine-2-yl)methyl)-4,4-dimethyl-6-(1-(oxetan-3-yl)piperidine-4-yl)isoquinoline-1,3(2H,4H)-dione

[Step 1] Synthesis of the Compound 61

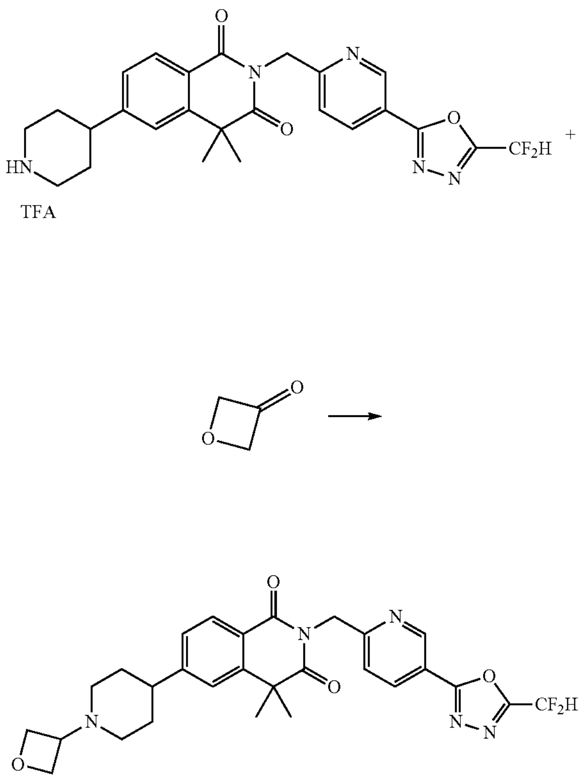

2-((5-(5-(difluoromethyl)-1,3,4-oxadiazole-2-yl)pyridine-2-yl)methyl)-4,4-dimethyl-6-(piperidine-4-yl)isoquinoline-1,3(2H,4H)-dione 2,2,2-trifluoroacetate (0.200 g, 0.336 mmol) and N,N-diisopropylethylamine (0.058 mL, 0.336 mmol) were dissolved in dichloromethane (10 mL), after which the resulting solution was stirred at room temperature for 30 hours, and then oxetan-3-one (0.048 g, 0.672 mmol) and sodium triacetoxyborohydride (0.142 g, 0.672 mmol) were added thereinto and further stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.100 g, 55.4%) in a colorless oil form.

$^1H$ NMR (400 MHz, $CDCl_3$) δ 9.19~9.18 (m, 1H), 8.34 (dd, J=8.2, 2.2 Hz, 1H), 8.20 (d, J=8.1 Hz, 1H), 7.45 (d, J=8.2 Hz, 1H), 7.38~7.33 (m, 2H), 7.06 (s, 0.25H), 6.93 (s, 0.5H), 6.80 (s, 0.25H), 5.43 (s, 2H), 4.73~4.67 (m, 4H), 3.58~3.54 (m, 1H), 2.96~2.93 (m, 2H), 1.70~1.60 (m, 1H), 2.09~2.00 (m, 2H), 1.93~1.88 (m, 4H), 1.67 (s, 6H); LRMS (ES) m/z 538.6 ($M^+$+1).

Synthesis of Compound 62, 2-((5-(5-(difluoromethyl)-1,3,4-oxadiazole-2-yl)pyridine-2-yl)methyl)-4,4-dimethyl-6-(1-((tetrahydro-2H-pyran-4-yl)methyl)piperidine-4-yl)isoquinoline-1,3(2H,4H)-dione

[Step 1] Synthesis of the Compound 62

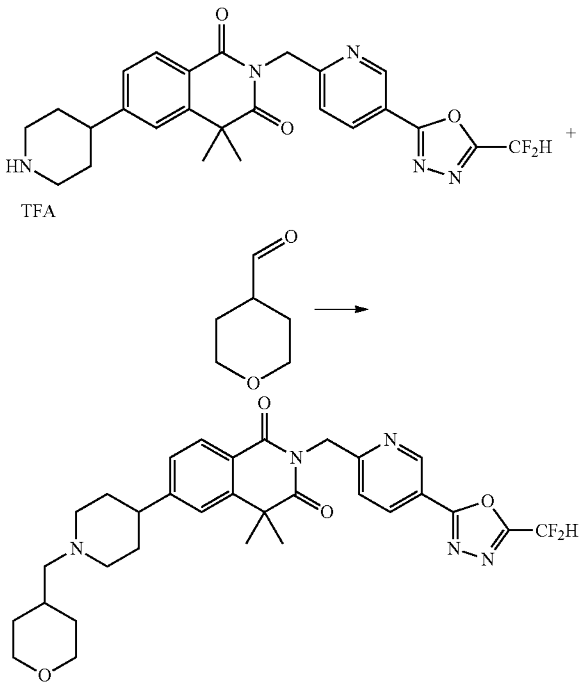

2-((5-(5-(difluoromethyl)-1,3,4-oxadiazole-2-yl)pyridine-2-yl)methyl)-4,4-dimethyl-6-(piperidine-4-yl)isoquinoline-1,3(2H,4H)-dione 2,2,2-trifluoroacetate (0.200 g, 0.336 mmol) and N,N-diisopropylethylamine (0.058 mL, 0.336 mmol) were dissolved in dichloromethane (10 mL), after which the resulting solution was stirred at room temperature for 30 hours, and then tetrahydro-2H-pyran-4-carbaldehyde (0.077 g, 0.672 mmol) and sodium triacetoxyborohydride (0.142 g, 0.672 mmol) were added thereinto and further stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.060 g, 30.8%) in a colorless oil form.

$^1H$ NMR (400 MHz, $CDCl_3$) δ 9.19~9.18 (m, 1H), 8.34 (dd, J=8.2, 2.2 Hz, 1H), 8.19 (d, J=8.1 Hz, 1H), 7.45 (d, J=8.2 Hz, 1H), 7.40 (d, J=1.3 Hz, 1H), 7.36 (dd, J=8.2, 1.6 Hz, 1H), 7.06 (s, 0.25H), 6.93 (s, 0.5H), 6.80 (s, 0.25H), 5.43 (s, 2H), 4.16~4.11 (m, 2H), 3.46~4.41 (m, 2H), 3.05~2.85 (m, 1H), 2.69~2.68 (m, 1H), 2.48~2.47 (m, 2H), 2.34~2.28 (m, 2H), 2.08~2.05 (m, 2H), 1.93~1.90 (m, 2H), 1.73~1.70 (m, 2H), 1.67 (s, 6H), 1.42~1.39 (m, 2H); LRMS (ES) m/z 580.6 ($M^+$+1).

Synthesis of Compound 63, 6-(1-(2-oxaspiro[3.3]heptane-6-yl)piperidine-4-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 63

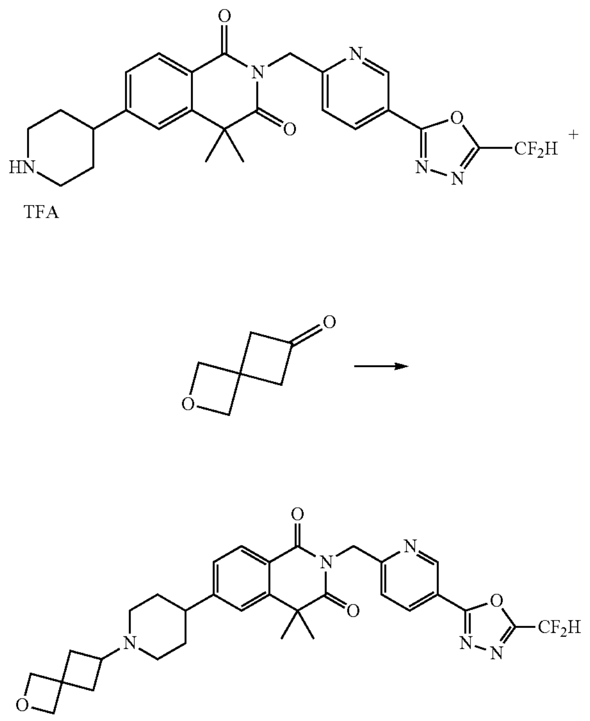

2-((5-(5-(difluoromethyl)-1,3,4-oxadiazole-2-yl)pyridine-2-yl)methyl)-4,4-dimethyl-6-(piperidine-4-yl)isoquinoline-1,3(2H,4H)-dione 2,2,2-trifluoroacetate (0.200 g, 0.336 mmol) and N,N-diisopropylethylamine (0.058 mL, 0.336 mmol) were dissolved in dichloromethane (10 mL), after which the resulting solution was stirred at room temperature for 30 hours, and then 2-oxaspiro[3.3]heptane-6-one (0.075 g, 0.672 mmol) and sodium triacetoxyborohydride (0.142 g, 0.672 mmol) were added thereinto and further stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.020 g, 10.3%) in a colorless oil form.

$^1H$ NMR (400 MHz, $CDCl_3$) δ 9.18 (dd, J=2.2, 0.8 Hz, 1H), 8.34 (dd, J=8.2, 2.3 Hz, 1H), 8.18 (d, J=8.1 Hz, 1H), 7.44 (dd, J=8.2, 0.8 Hz, 1H), 7.37 (d, J=1.4 Hz, 1H), 7.32 (dd, J=8.2, 1.4 Hz, 1H), 7.06 (s, 0.25H), 6.93 (s, 0.5H), 6.80 (s, 0.25H), 5.42 (s, 2H), 4.74~4.63 (m, 8H), 4.16~4.12 (m, 1H), 3.15~3.13 (m, 2H), 2.68~2.61 (m, 3H), 2.47~2.45 (m, 2H), 2.30~2.28 (m, 2H), 1.68 (s, 6H); LRMS (ES) m/z 578.6 ($M^+$+1).

Synthesis of Compound 64, 6-(1-cyclobutylpiperidine-4-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 64

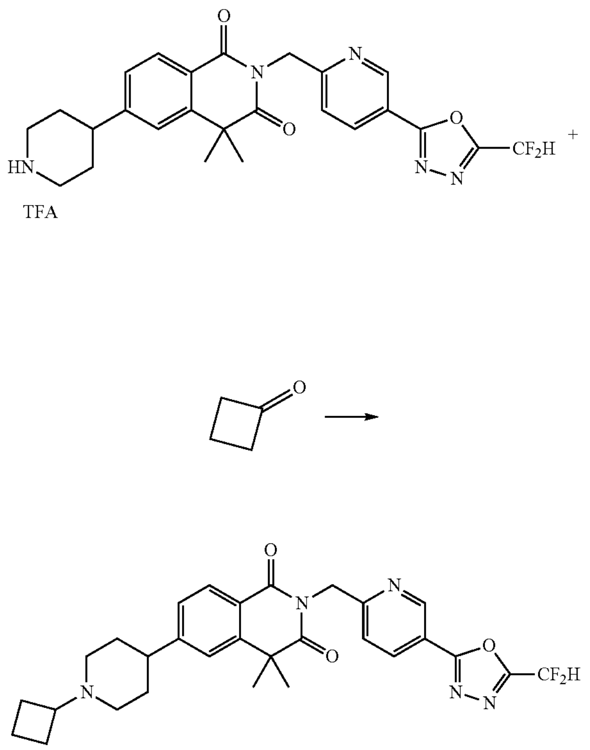

2-((5-(5-(difluoromethyl)-1,3,4-oxadiazole-2-yl)pyridine-2-yl)methyl)-4,4-dimethyl-6-(piperidine-4-yl)isoquinoline-1,3(2H,4H)-dione 2,2,2-trifluoroacetate (0.200 g, 0.336 mmol) and N,N-diisopropylethylamine (0.058 mL, 0.336 mmol) were dissolved in dichloromethane (10 mL), after which the resulting solution was stirred at room temperature for 30 hours, and then cyclobutanone (0.047 g, 0.672 mmol) and sodium triacetoxyborohydride (0.142 g, 0.672 mmol) were added thereinto and further stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.100 g, 55.6%) in a colorless oil form.

$^1H$ NMR (400 MHz, $CDCl_3$) δ 9.19~9.18 (m, 1H), 8.34 (dd, J=8.2, 2.2 Hz, 1H), 8.19 (d, J=8.1 Hz, 1H), 7.44 (d, J=8.3 Hz, 1H), 7.40 (d, J=1.4 Hz, 1H), 7.34 (dd, J=8.2, 1.6 Hz, 1H), 7.06 (s, 0.25H), 6.93 (s, 0.5H), 6.80 (s, 0.25H), 5.43 (s, 2H), 3.43~3.38 (m, 2H), 2.99~2.93 (m, 1H), 2.72~2.68 (m, 1H), 2.24~2.01 (m, 8H), 1.98~1.71 (m, 4H), 1.68 (s, 6H); LRMS (ES) m/z 536.6 ($M^+$+1).

Synthesis of Compound 65, 2-((5-(5-(difluoromethyl)-1,3,4-oxadiazole-2-yl)pyridine-2-yl)methyl) isoquinoline-1,3(2H,4H)-dione

[Step 1] Synthesis of 2-(6-(azidomethyl)pyridine-3-yl)-5-(difluoromethyl)-1,3,4-oxadiazole

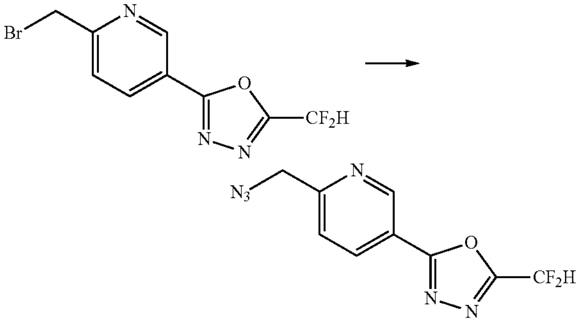

2-(6-(bromomethyl)pyridine-3-yl)-5-(difluoromethyl)-1,3,4-oxadiazole (3.000 g, 10.342 mmol) and sodium azide (1.009 g, 15.513 mmol) were dissolved in N,N-dimethylformamide (5 mL) at room temperature, after which the resulting solution was stirred at the same temperature for 12 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. An obtained product was used without an additional purification process (2.310 g, 88.6%, white solid).

[Step 2] Synthesis of (5-(5-(difluoromethyl)-1,3,4-oxadiazole-2-yl)pyridine-2-yl)methanamine

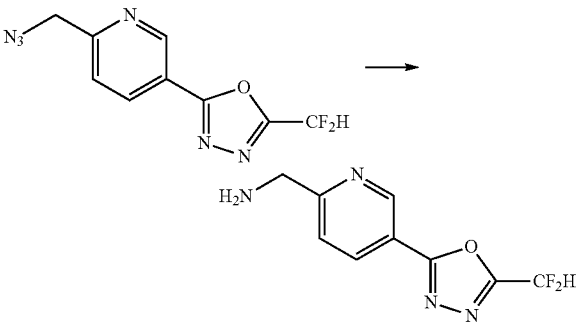

The 2-(6-(azidomethyl)pyridine-3-yl)-5-(difluoromethyl)-1,3,4-oxadiazole (1.500 g, 5.948 mmol) prepared in the step 1 was dissolved in methanol (20 mL) at room temperature, after which 10%-Pd/C (100 mg) was slowly added thereinto, and stirred for 12 hours in the presence of a hydrogen balloon attached thereto at the same temperature. The reaction mixture was filtered via a celite pad to remove a solid therefrom, after which solvent was removed from a resulting filtrate under reduced pressure, and then an obtained product was used without an additional purification process (1.300 g, 96.6%, brown solid).

[Step 3] Synthesis of the Compound 65

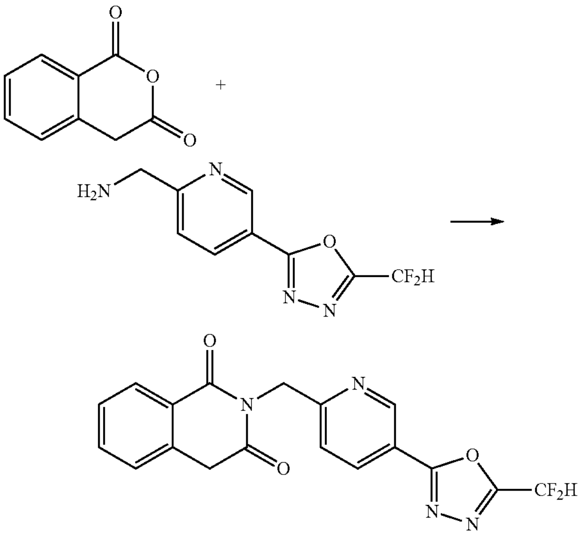

The (5-(5-(difluoromethyl)-1,3,4-oxadiazole-2-yl)pyridine-2-yl)methanamine (1.235 g, 5.458 mmol) prepared in the step 2 and isochromene-1,3-dione (0.590 g, 3.639 mmol) were dissolved in toluene (10 mL) at 100° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.150 g, 11.1%) in a colorless oil form.

$^1H$ NMR (400 MHz, $CDCl_3$) δ 9.22~9.21 (m, 1H), 8.36 (dd, J=8.2, 2.2 Hz, 1H), 8.25 (d, J=7.3 Hz, 1H), 7.67~7.63 (m, 1H), 7.52~7.50 (m, 1H), 7.38~7.36 (m, 1H), 7.06 (s, 0.25H), 6.93 (s, 0.5H), 6.80 (s, 0.25H), 5.45 (s, 2H), 4.20 (s, 2H); LRMS (ES) m/z 371.4 ($M^+$+1).

Synthesis of Compound 66, 3-((5-(5-(difluoromethyl)-1,3,4-oxadiazole-2-yl)pyridine-2-yl)methyl)-6-fluoro-1-(4-methoxybenzyl)quinazoline-2,4(1H,3H)-dione

[Step 1] Synthesis of 2-amino-N-(tert-butyl)-5-fluorobenzamide

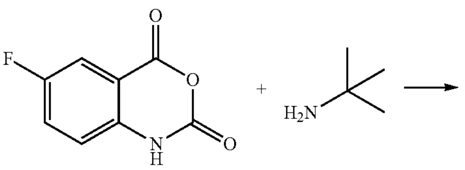

-continued

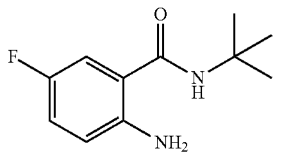

6-fluoro-2H-benzo[d][1,3]oxazine-2,4(1H)-dione (5.000 g, 27.606 mmol), 2-methylpropane-2-amine (2.423 g, 33.127 mmol) and N,N-dimethylpyridine-4-amine (DMAP, 0.337 g, 2.761 mmol) were dissolved in N,N-dimethylformamide (30 mL) at room temperature, after which the resulting solution was stirred at the same temperature for 12 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (2.700 g, 46.5%) in a yellow solid form.

[Step 2] Synthesis of methyl (2-(tert-butylcarbamoyl)-4-fluorophenyl)cabamate

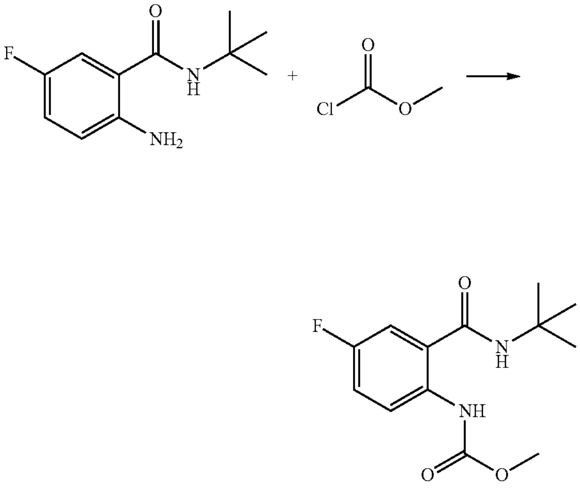

The 2-amino-N-(tert-butyl)-5-fluorobenzamide (2.700 g, 12.842 mmol) prepared in the step 1, methyl carbonochloridate (1.456 g, 15.410 mmol) and sodium hydroxide (1.00 M solution in $H_2O$, 25.684 mL, 25.684 mmol) were dissolved in 1,4-dioxane (20 mL) at room temperature, after which the resulting solution was stirred at the same temperature for 12 hours. 1N-hydrochloric acid aqueous solution (10 mL) was put into the reaction mixture and stirred, after which a precipitated solid was filtered, then washed with hexane, and then dried to obtain a title compound (2.570 g, 74.6%) in a white solid form.

[Step 3] Synthesis of 3-(tert-butyl)-6-fluoroquinazoline-2,4(1H,3H)-dione

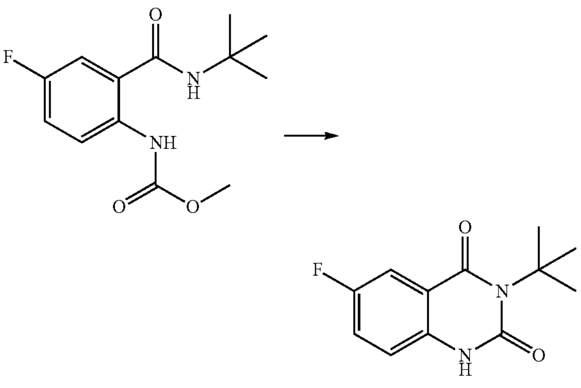

The methyl (2-(tert-butylcarbamoyl)-4-fluorophenyl)cabamate (2.570 g, 9.579 mmol) prepared in the step 2 and potassium hydroxide (5.374 g, 95.792 mmol) were dissolved in ethanol (50 mL) at 80° C., after which the resulting solution was stirred at the same temperature for 12 hours, and then a reaction was finished by lowering the temperature to room temperature. Water (10 mL) was put into the reaction mixture and stirred, after which a precipitated solid was filtered, then washed with hexane, and then dried to obtain a title compound (1.520 g, 67.2%) in a white solid form.

[Step 4] Synthesis of 3-(tert-butyl)-6-fluoro-1-(4-methoxybenzyl)quinazoline-2,4(1H,3H)-dione

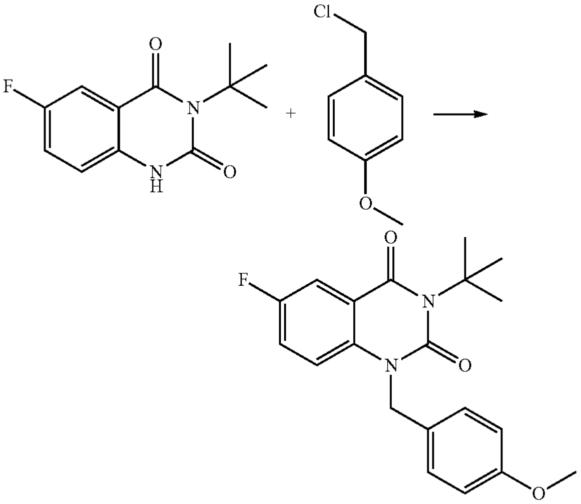

The 3-(tert-butyl)-6-fluoroquinazoline-2,4(1H,3H)-dione (1.520 g, 6.434 mmol) prepared in the step 3 was dissolved in N,N-dimethylformamide (20 mL) at 0° C., after which sodium hydride (60.00%, 0.386 g, 9.651 mmol) was added into the resulting solution, and stirred at the same temperature for 30 minutes. 1-(chloromethyl)-4-methoxybenzene (1.310 g, 8.364 mmol) was added into the reaction mixture, and further stirred at room temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (1.660 g, 72.4%) in a white solid form.

[Step 5] Synthesis of 6-fluoro-1-(4-methoxybenzyl) quinazoline-2,4(1H,3H)-dione

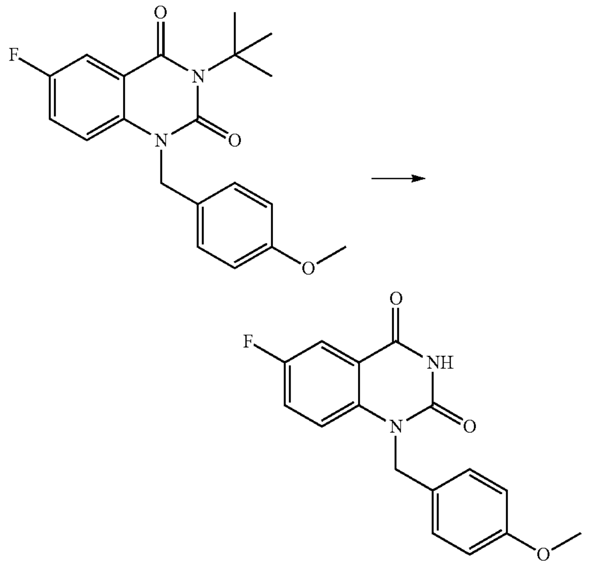

The 3-(tert-butyl)-6-fluoro-1-(4-methoxybenzyl)quinazoline-2,4(1H,3H)-dione (1.660 g, 4.658 mmol) prepared in the step 4 and hydrochloric acid (4.00 M solution in dioxane, 23.288 mL, 93.154 mmol) were mixed together at 10° C., after which the resulting reaction mixture was stirred at the same temperature for 12 hours, and then a reaction was finished by lowering the temperature to room temperature. Water (10 mL) was put into the reaction mixture and stirred, after which a precipitated solid was filtered, then washed with hexane, and then dried to obtain a title compound (1.250 g, 89.4%) in a white solid form.

[Step 6] Synthesis of the Compound 66

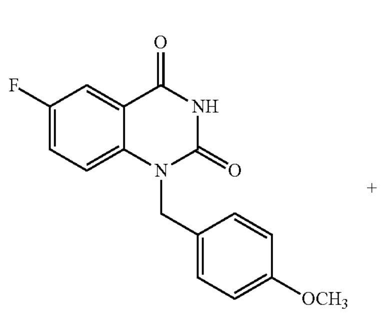

-continued

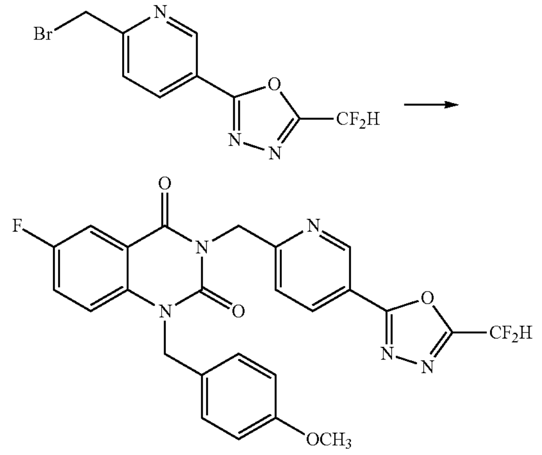

The 6-fluoro-1-(4-methoxybenzyl)quinazoline-2,4(1H,3H)-dione (1.250 g, 4.163 mmol) prepared in the step 5, 2-(6-(bromomethyl)pyridine-3-yl)-5-(difluoromethyl)-1,3,4-oxadiazole (1.570 g, 5.411 mmol) and potassium carbonate (1.151 g, 8.325 mmol) were dissolved in N,N-dimethylformamide (20 mL) at 90° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (1.600 g, 75.4%) in a white solid form.

$^1H$ NMR (400 MHz, $CDCl_3$) δ 9.25~9.24 (m, 1H), 8.39 (dd, J=8.2, 2.2 Hz, 1H), 7.94 (dd, J=8.1, 3.1 Hz, 1H), 7.54 (d, J=8.2 Hz, 1H), 7.34~7.30 (m, 1H), 7.23~7.19 (m, 3H), 7.07 (s, 0.25H), 6.94 (s, 0.5H), 6.90~6.88 (m, 2H), 6.81 (s, 0.25H), 5.60 (s, 2H), 5.35 (s, 2H), 3.80 (s, 3H); LRMS (ES) m/z 510.6 ($M^+$+1).

Synthesis of Compound 67, 3-((5-(5-(difluoromethyl)-1,3,4-oxadiazole-2-yl)pyridine-2-yl)methyl)-6-fluoroquinazoline-2,4(1H,3H)-dione

[Step 1] Synthesis of the Compound 67

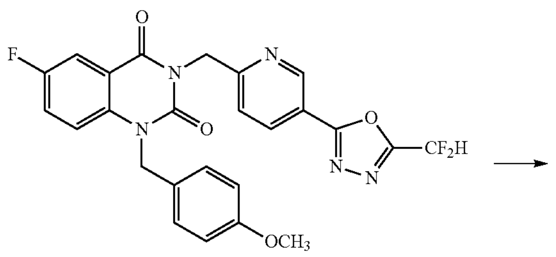

-continued

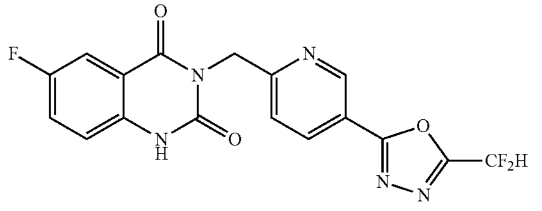

3-((5-(5-(difluoromethyl)-1,3,4-oxadiazole-2-yl)pyridine-2-yl)methyl)-6-fluoro-1-(4-methoxybenzyl)quinazoline-2,4(1H,3H)-dione (1.600 g, 3.141 mmol) and ceric ammonium nitrate (5.165 g, 9.422 mmol) were dissolved in acetonitrile (20 mL)/water (20 mL) at room temperature, after which the resulting solution was stirred at the same temperature for 12 hours. A precipitated solid was filtered, then washed with hexane, and then dried to obtain a title compound (0.900 g, 73.6%) in a yellow solid form.

$^1$H NMR (400 MHz, DMSO-$d_6$) δ 9.09~9.08 (m, 1H), 8.38 (dd, J=8.3, 2.3 Hz, 1H), 7.69 (s, 0.25H), 7.67~7.61 (m, 3H), 7.56 (s, 0.5H), 7.43 (s, 0.25H), 7.31~7.28 (m, 1H), 7.12~6.99 (m, 1H), 5.31 (s, 2H); LRMS (ES) m/z 390.5 ($M^+$+1).

Synthesis of Compound 68, 2-((5-(5-(difluoromethyl)-1,3,4-oxadiazole-2-yl)pyridine-2-yl)methyl)-7-(1-ethylpiperidine-4-yl)-4,4-dimethylisoquinoline-1,3(2H,4H)-dione

[Step 1] Synthesis of the Compound 68

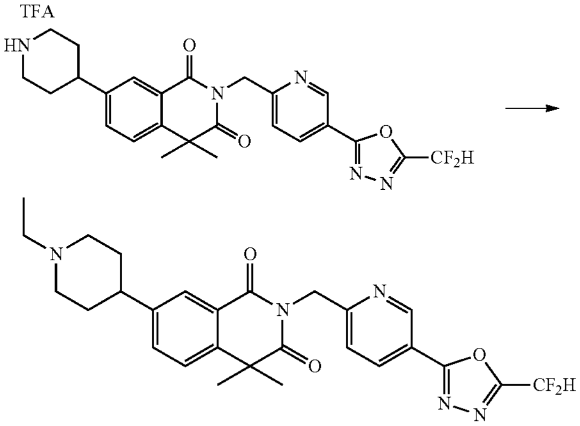

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione 2,2,2-trifluoroacetate (0.120 g, 0.202 mmol) and N,N-diisopropylethylamine (0.035 mL, 0.202 mmol) were dissolved in dichloromethane (10 mL) at room temperature, after which acetaldehyde (0.018 g, 0.403 mmol) and sodium triacetoxyborohydride (0.085 g, 0.403 mmol) were added into the resulting solution and stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; dichloromethane/methanol=0 to 10%), and concentrated to obtain a title compound (0.023 g, 22.4%) in a colorless oil form.

$^1$H NMR (400 MHz, $CDCl_3$) δ 9.17 (dd, J=2.2, 0.7 Hz, 1H), 8.33 (dd, J=8.2, 2.2 Hz, 1H), 8.09 (d, J=2.0 Hz, 1H), 7.60 (dd, J=8.2, 2.0 Hz, 1H), 7.50 (d, J=8.2 Hz, 1H), 7.45 (dd, J=8.2, 0.6 Hz, 1H), 7.06 (s, 0.25H), 6.93 (s, 0.5H), 6.80 (s, 0.25H), 5.42 (s, 2H), 3.52 (d, J=11.7 Hz, 1H), 2.94~2.88 (m, 2H), 2.82~2.75 (m, 1H), 2.59~2.53 (m, 2H), 2.21~2.18 (m, 2H), 2.02~2.00 (m, 2H), 1.68 (s, 6H), 1.34~1.30 (m, 3H); LRMS (ES) m/z 510.6 ($M^+$+1).

Synthesis of Compound 69, 2-((5-(5-(difluoromethyl)-1,3,4-oxadiazole-2-yl)pyridine-2-yl)methyl)-7-(1-isopropylpiperidine-4-yl)-4,4-dimethylisoquinoline-1,3(2H,4H)-dione

[Step 1] Synthesis of the Compound 69

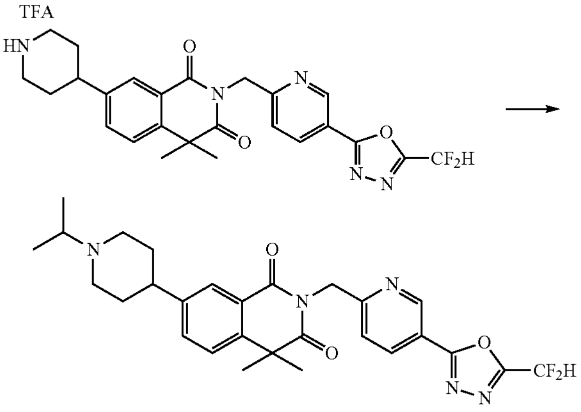

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione 2,2,2-trifluoroacetate (0.120 g, 0.202 mmol) and N,N-diisopropylethylamine (0.035 mL, 0.202 mmol) were dissolved in dichloromethane (10 mL) at room temperature, after which acetone (0.030 mL, 0.403 mmol) and sodium triacetoxyborohydride (0.085 g, 0.403 mmol) were added into the resulting solution and stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; dichloromethane/methanol=0 to 10%), and concentrated to obtain a title compound (0.040 g, 37.9%) in a colorless oil form.

$^1$H NMR (400 MHz, $CDCl_3$) δ 9.17~9.16 (m, 1H), 8.34~8.31 (m, 1H), 8.06 (s, 1H), 7.63~7.62 (m, 1H), 7.52~7.50 (m, 1H), 7.45~7.43 (m, 1H), 7.06 (s, 0.25H), 6.93 (s, 0.5H), 6.80 (s, 0.25H), 5.42 (s, 2H), 3.54~3.51 (m, 3H), 2.83~2.80 (m, 3H), 2.45~2.35 (m, 2H), 2.08~2.02 (m, 2H), 1.67 (s, 6H), 1.38~1.36 (m, 6H); LRMS (ES) m/z 524.6 ($M^+$+1).

Synthesis of Compound 70, 3-((5-(5-(difluoromethyl)-1,3,4-oxadiazole-2-yl)pyridine-2-yl)methyl)-6-fluoro-1-methylquinazoline-2,4(1H,3H)-dione

[Step 1] Synthesis of the Compound 70

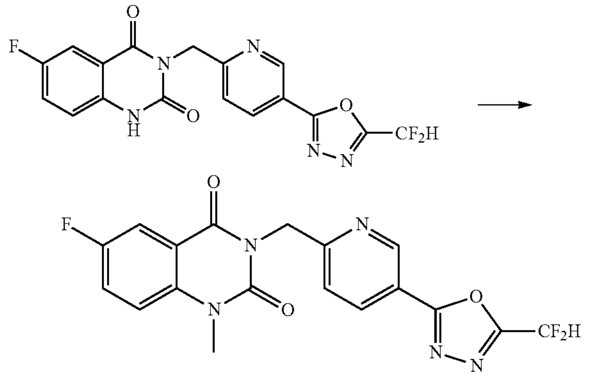

3-((5-(5-(difluoromethyl)-1,3,4-oxadiazole-2-yl)pyridine-2-yl)methyl)-6-fluoroquinazoline-2,4(1H,3H)-dione (0.100 g, 0.257 mmol), iodomethane (0.032 mL, 0.514 mmol) and potassium carbonate (0.071 g, 0.514 mmol) were dissolved in N,N-dimethylformamide (5 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.030 g, 29.0%) in a white foam solid form.

$^1H$ NMR (400 MHz, $CDCl_3$) δ 9.22~9.21 (m, 1H), 8.36 (dd, J=8.2, 2.2 Hz, 1H), 7.94 (dd, J=8.0, 3.0 Hz, 1H), 7.53~7.43 (m, 2H), 7.28~7.25 (m, 1H), 7.06 (s, 0.25H), 6.93 (s, 0.5H), 6.80 (s, 0.25H), 5.52 (s, 2H), 3.65 (s, 3H); LRMS (ES) m/z 404.4 ($M^+$+1).

Synthesis of Compound 71, 3-((5-(5-(difluoromethyl)-1,3,4-oxadiazole-2-yl)pyridine-2-yl)methyl)-6-fluoro-1-(2-(piperidine-1-yl)ethyl)quinazoline-2,4(1H,3H)-dione

[Step 1] Synthesis of the Compound 71

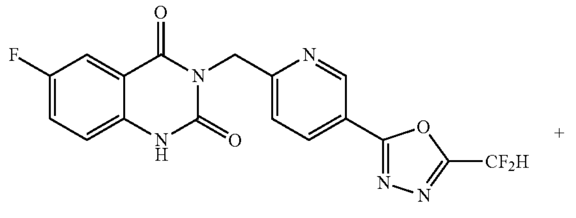

-continued

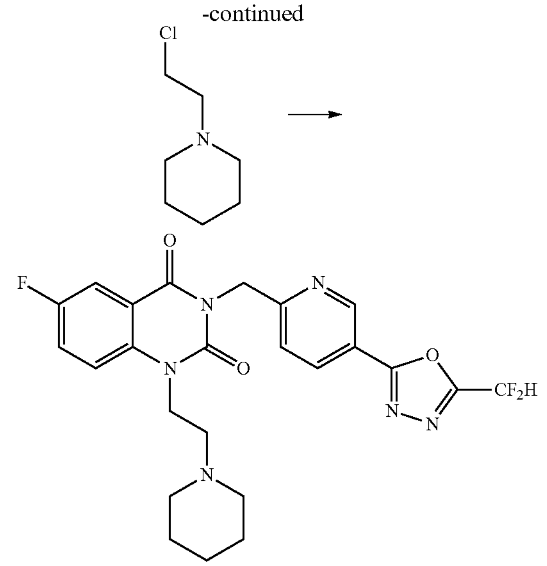

3-((5-(5-(difluoromethyl)-1,3,4-oxadiazole-2-yl)pyridine-2-yl)methyl)-6-fluoroquinazoline-2,4(1H,3H)-dione (0.100 g, 0.257 mmol), 1-(2-chloroethyl)piperidine (0.076 g, 0.514 mmol) and potassium carbonate (0.124 g, 0.899 mmol) were dissolved in N,N-dimethylformamide (5 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 50%), and concentrated to obtain a title compound (0.020 g, 15.6%) in a white foam solid form.

$^1H$ NMR (400 MHz, $CDCl_3$) δ 9.20 (dd, J=2.2, 0.8 Hz, 1H), 8.33 (dd, J=8.2, 2.2 Hz, 1H), 7.91 (dd, J=8.1, 3.0 Hz, 1H), 7.49~7.33 (m, 3H), 7.06 (s, 0.25H), 6.93 (s, 0.5H), 6.80 (s, 0.25H), 5.50 (s, 2H), 4.28 (t, J=7.4 Hz, 2H), 2.64 (t, J=6.3 Hz, 2H), 2.55~2.45 (m, 4H), 1.58~1.53 (m, 4H), 1.47~1.40 (m, 2H); LRMS (ES) m/z 501.5 ($M^+$+1).

Synthesis of Compound 72, Tert-butyl 4-((3-((5-(5-(difluoromethyl)-1,3,4-oxadiazole-2-yl)pyridine-2-yl)methyl)-6-fluoro-2,4-dioxo-3,4-dihydroquinazoline-1(2H)-yl)methyl)piperidine-1-carboxylate

[Step 1] Synthesis of the Compound 72

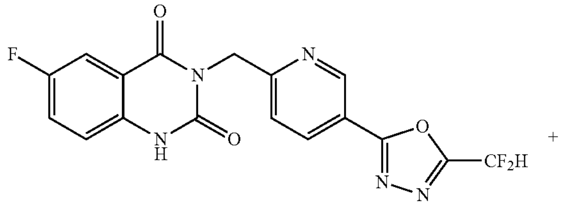

-continued

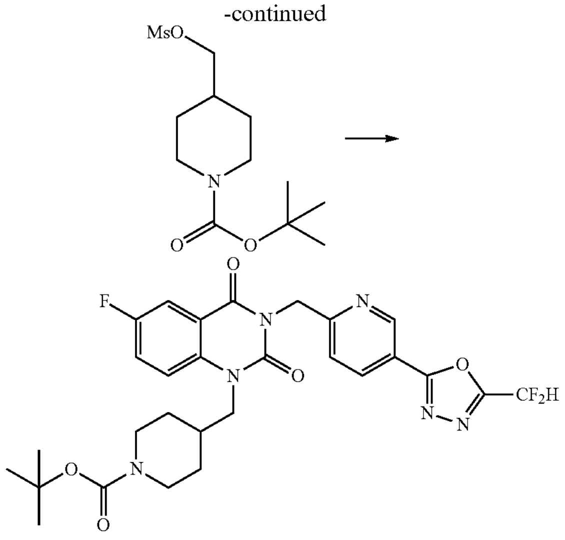

3-((5-(5-(difluoromethyl)-1,3,4-oxadiazole-2-yl)pyridine-2-yl)methyl)-6-fluoroquinazoline-2,4(1H,3H)-dione (0.283 g, 0.727 mmol), tert-butyl 4-(((methylsulfonyl)oxy)methyl)piperidine-1-carboxylate (0.427 g, 1.454 mmol) and potassium carbonate (0.201 g, 1.454 mmol) were dissolved in N,N-dimethylformamide (5 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.166 g, 38.9%) in a colorless oil form.

$^1H$ NMR (400 MHz, $CDCl_3$) δ 9.16~9.15 (m, 1H), 8.35 (dd, J=8.1, 2.1 Hz, 1H), 7.93 (dd, J=8.0, 3.1 Hz, 1H), 7.50~7.44 (m, 2H), 7.23~7.20 (m, 1H), 7.06 (s, 0.25H), 6.93 (s, 0.5H), 6.80 (s, 0.25H), 5.50 (s, 2H), 4.14~4.08 (m, 4H), 2.65~2.60 (m, 2H), 2.05~2.03 (m, 1H), 1.68~1.65 (m, 2H), 1.45 (s, 9H), 1.27~1.25 (m, 2H); LRMS (ES) m/z 587.5 ($M^+$+1).

Synthesis of Compound 73, 3-((5-(5-(difluoromethyl)-1,3,4-oxadiazole-2-yl)pyridine-2-yl)methyl)-6-fluoro-1-((1-methylpiperidine-4-yl)methyl)quinazoline-2,4(1H,3H)-dione

[Step 1] Synthesis of 3-((5-(5-(difluoromethyl)-1,3,4-oxadiazole-2-yl)pyridine-2-yl)methyl)-6-fluoro-1-(piperidine-4-ylmethyl)quinazoline-2,4(1H,3H)-dione 2,2,2-trifluoroacetate

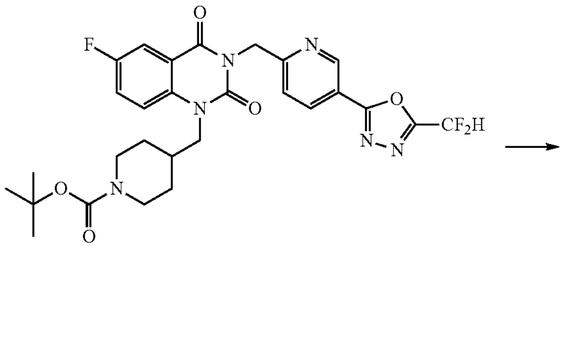

-continued

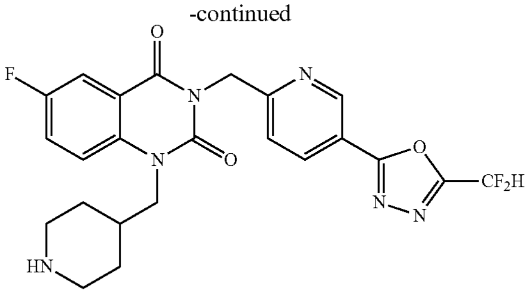

TFA

Tert-butyl 4-((3-((5-(5-(difluoromethyl)-1,3,4-oxadiazole-2-yl)pyridine-2-yl)methyl)-6-fluoro-2,4-dioxo-3,4-dihydroquinazoline-1(2H)-yl)methyl)piperidine-1-carboxylate (0.166 g, 0.283 mmol) and trifluoroacetic acid (0.217 mL, 2.830 mmol) were dissolved in dichloromethane (10 mL) at room temperature, after which the resulting solution was stirred at the same temperature for 3 hours. Solvent was removed from the reaction mixture under reduced pressure, after which an obtained product was used without an additional purification process (0.160 g, 94.2%, brown oil).

[Step 2] Synthesis of the Compound 73

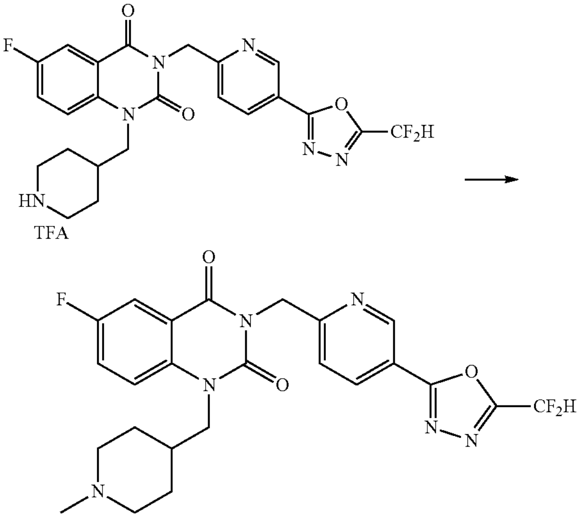

The 3-((5-(5-(difluoromethyl)-1,3,4-oxadiazole-2-yl)pyridine-2-yl)methyl)-6-fluoro-1-(piperidine-4-ylmethyl)quinazoline-2,4(1H,3H)-dione 2,2,2-trifluoroacetate (0.160 g, 0.266 mmol) prepared in the step 1, formaldehyde (0.016 g, 0.533 mmol), sodium triacetoxyborohydride (0.113 g, 0.533 mmol) and N,N-diisopropylethylamine (0.046 mL, 0.266 mmol) were dissolved in dichloromethane (10 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.080 g, 60.0%) in a white foam solid form.

$^1$H NMR (400 MHz, $CDCl_3$) δ 9.17~9.16 (m, 1H), 8.38 (dd, J=8.2, 2.1 Hz, 1H), 7.96 (dd, J=7.9, 3.0 Hz, 1H), 7.54 (d, J=8.2 Hz, 1H), 7.48~7.45 (m, 1H), 7.38~7.37 (m, 1H), 7.07 (s, 0.25H), 6.94 (s, 0.5H), 6.81 (s, 0.25H), 5.51 (s, 2H), 3.78~3.77 (m, 2H), 3.77~3.76 (m, 1H), 3.60~3.50 (m, 2H), 2.76 (s, 3H), 2.65~2.55 (m, 2H), 2.13~2.06 (m, 2H), 1.90~1.85 (m, 2H); LRMS (ES) m/z 501.5 ($M^+$+1).

Synthesis of Compound 74, 2-((5-(5-(difluoromethyl)-1,3,4-oxadiazole-2-yl)pyridine-2-yl)methyl)-6-(furan-2-yl)-4, 4-dimethylisoquinoline-1,3(2H, 4H)-dione

[Step 1] Synthesis of the Compound 74

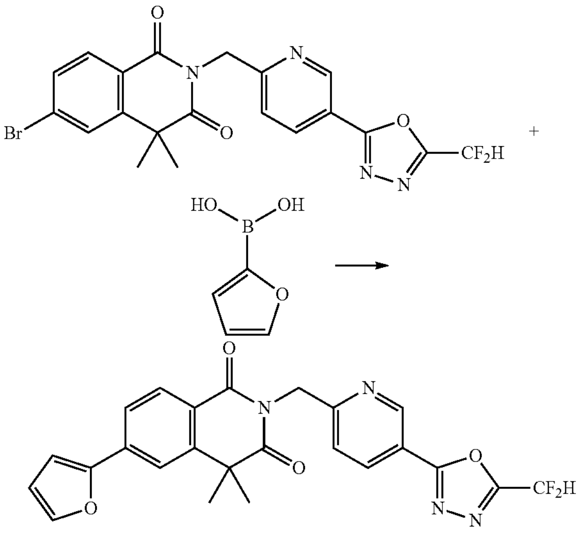

6-bromo-2-((5-(5-(difluoromethyl)-1,3,4-oxadiazole-2-yl)pyridine-2-yl)methyl)-4,4-dimethylisoquinoline-1,3(2H, 4H)-dione (0.150 g, 0.314 mmol), furan-2-ylboronic acid (0.053 g, 0.471 mmol), [1,1'-bis(diphenylphosphino)ferrocene]dichloropalladium(II) (Pd(dppf)$C_{12}$, 0.023 g, 0.031 mmol) and sodium carbonate (0.067 g, 0.629 mmol) were dissolved in 1,2-dimethoxyethane (6 mL)/water (3 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a desired title compound (0.003 g, 20.6%) in a colorless oil form.

$^1$H NMR (400 MHz, $CDCl_3$) δ 9.21 (dd, J=2.2, 0.8 Hz, 1H), 8.36 (dd, J=8.2, 2.2 Hz, 1H), 8.27 (dd, J=8.3, 0.3 Hz, 1H), 7.82 (d, J=1.5 Hz, 1H), 7.74 (dd, J=8.3, 1.6 Hz, 1H), 7.59 (dd, J=1.8, 0.7 Hz, 1H), 7.47 (dd, J=8.2, 0.8 Hz, 1H), 7.06 (s, 0.25H), 6.93 (s, 0.5H), 6.89 (dd, J=3.4, 0.7 Hz, 1H), 6.80 (s, 0.25H), 6.58~6.57 (m, 1H), 5.45 (s, 2H), 1.76 (s, 2H).

Synthesis of Compound 75, 1-(4-(5-(difluoromethyl)-1,3,4-oxadiazole-2-yl)benzyl)-3-(2-methoxyethyl)quinazoline-2,4(1H,3H)-dione

[Step 1] Synthesis of 2-amino-N-(2-methoxyethyl)benzamide

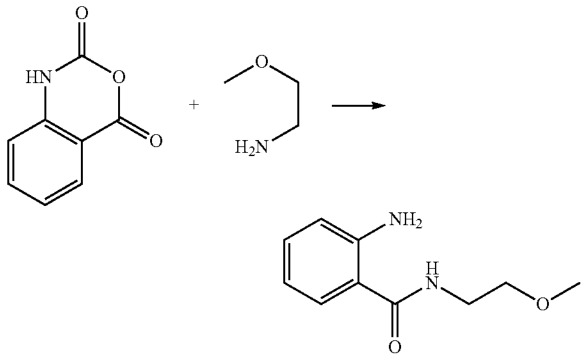

2H-benzo[d][1,3]oxazine-2,4(1H)-dione (10.000 g, 61.301 mmol), 2-methoxyethane-1-amine (4.604 g, 61.301 mmol) and triethylamine (8.544 mL, 61.301 mmol) were dissolved in ethanol (50 mL) at 80° C., after which the resulting solution was stirred at the same temperature for 12 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure.

The resulting concentrate was purified via column chromatography ($SiO_2$, 40 g cartridge; ethyl acetate/hexane=0 to 30%), and concentrated to obtain a title compound (9.800 g, 82.3%) in a colorless oil form.

[Step 2] Synthesis of 3-(2-methoxyethyl)quinazoline-2,4(1H,3H)-dione

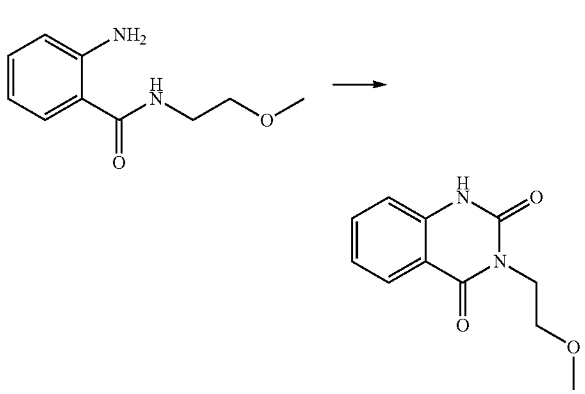

The 2-amino-N-(2-methoxyethyl)benzamide (1.500 g, 7.723 mmol) prepared in the step 1 and 1,1'-carbonyldiimidazole (CDI, 1.252 g, 7.723 mmol) were dissolved in tetrahydrofuran (20 mL) at room temperature, after which the resulting solution was stirred at the same temperature for 12 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure.

The resulting concentrate was purified via column chromatography ($SiO_2$, 12 g cartridge; ethyl acetate/hexane=0 to 30%), and concentrated to obtain a title compound (1.300 g, 76.4%) in a white solid form.

[Step 3] Synthesis of the Compound 75

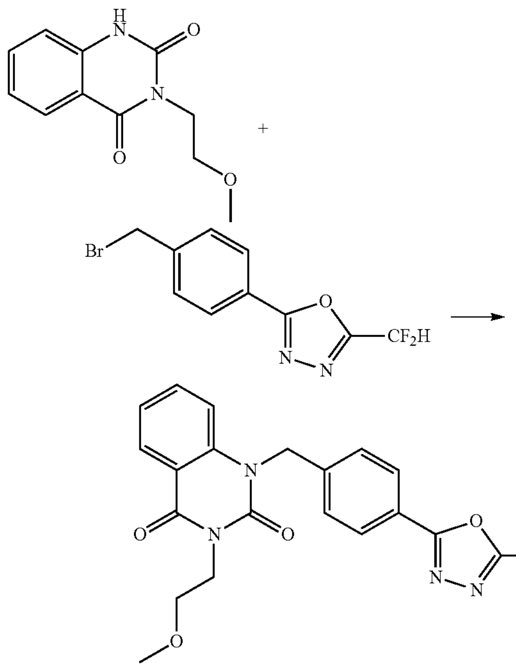

The 3-(2-methoxyethyl)quinazoline-2,4(1H,3H)-dione (0.100 g, 0.454 mmol) prepared in the step 2 was dissolved in N,N-dimethylformamide (10 mL) at 0° C., after which sodium hydride (60.00%, 0.027 g, 0.681 mmol) was added into the resulting solution, and stirred at the same temperature for 30 minutes. 2-(4-(bromomethyl)phenyl)-5-(difluoromethyl)-1,3,4-oxadiazole (0.131 g, 0.454 mmol) was added into the reaction mixture, and further stirred at room temperature for 2 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.050 g, 25.7%) in a colorless oil form.

$^1H$ NMR (400 MHz, $CDCl_3$) δ 8.29 (dd, J=7.9, 1.4 Hz, 1H), 8.1 (dd, J=6.7, 1.8 Hz, 2H), 7.59~7.55 (m, 1H), 7.47 (d, J=8.6 Hz, 2H), 7.29~7.25 (m, 1H), 7.06~7.04 (m, 1H), 7.06 (s, 0.25H), 6.92 (s, 0.5H), 6.79 (s, 0.25H), 5.48 (s, 2H), 4.45 (t, J=5.7 Hz, 2H), 3.77 (t, J=5.7 Hz, 2H), 3.42 (s, 3H); LRMS (ES) m/z 429.3 ($M^++1$).

Synthesis of Compound 76, 1-((5-(5-(difluoromethyl)-1,3,4-oxadiazole-2-yl)pyridine-2-yl)methyl)-3-(2-methoxyeth yl)quinazoline-2,4(1H,3H)-dione

[Step 1] Synthesis of methyl 6-((3-(2-methoxyethyl)-2,4-dioxo-3,4-dihydroquinazoline-1(2H)-yl) methyl)nicotinate

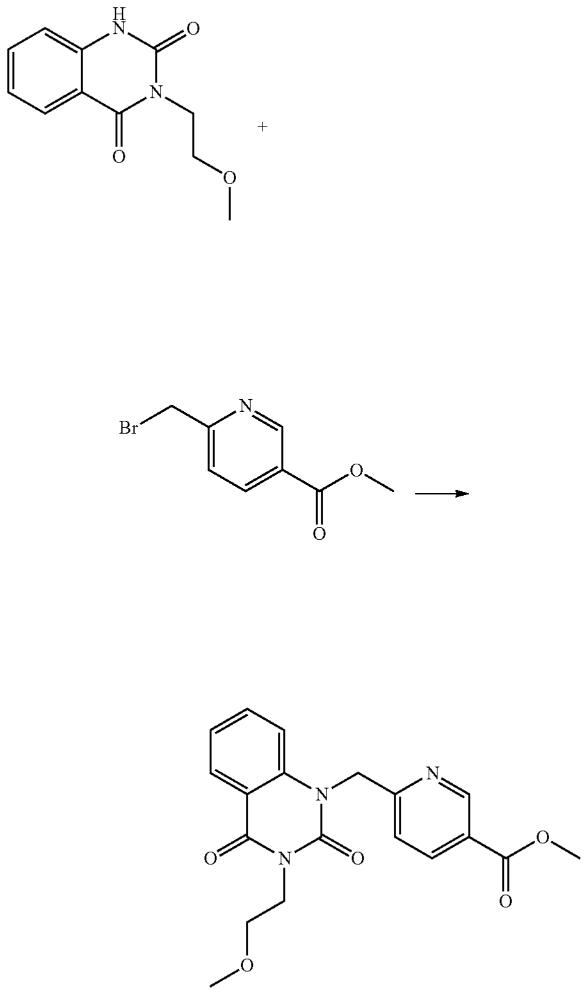

3-(2-methoxyethyl)quinazoline-2,4(1H,3H)-dione (0.300 g, 1.362 mmol) was dissolved in N,N-dimethylformamide (10 mL) at 0° C., after which sodium hydride (60.00%, 0.109 g, 2.724 mmol) was added into the resulting solution, and stirred at the same temperature for 30 minutes. Methyl 6-(bromomethyl)nicotinate (0.313 g, 1.362 mmol) was added into the reaction mixture, and further stirred at room temperature for 2 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.300 g, 59.6%) in a colorless oil form.

[Step 2] Synthesis of 6-((3-(2-methoxyethyl)-2,4-dioxo-3,4-dihydroquinazoline-1(2H)-yl)methyl)nicotinohydrazide

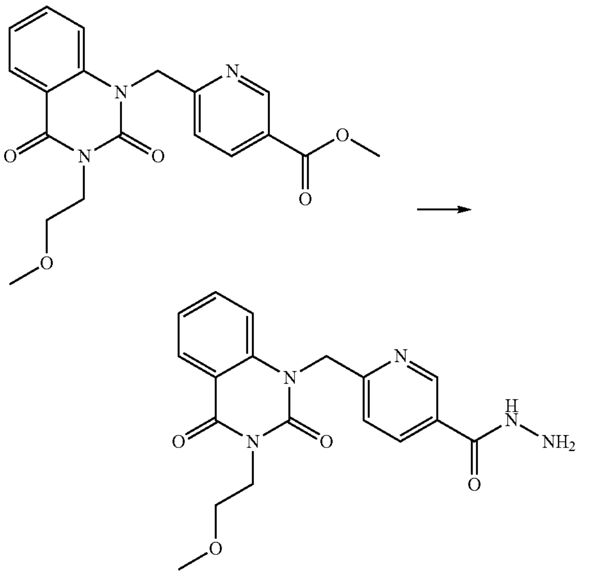

The methyl 6-((3-(2-methoxyethyl)-2,4-dioxo-3,4-dihydroquinazoline-1(2H)-yl)methyl)nicotinate (0.090 g, 0.244 mmol) prepared in the step 1 and hydrazine monohydrate (0.237 mL, 4.873 mmol) were dissolved in ethanol (20 mL) at 80° C., after which the resulting solution was stirred at the same temperature for 12 hours, and then a reaction was finished by lowering the temperature to room temperature. Solvent was removed from the reaction mixture under reduced pressure, after which an obtained product was used without an additional purification process (0.090 g, 100.0%, white solid).

[Step 3] Synthesis of the Compound 76

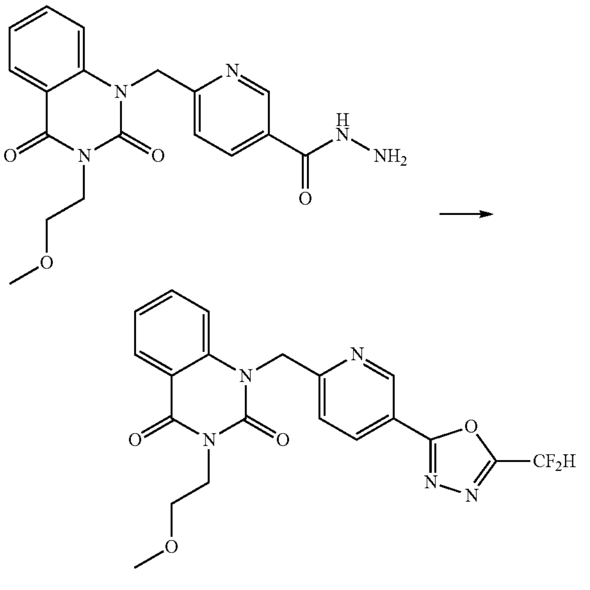

The 6-((3-(2-methoxyethyl)-2,4-dioxo-3,4-dihydroquinazoline-1(2H)-yl)methyl)nicotinohydrazide (0.090 g, 0.244 mmol) prepared in the step 2, 2,2-difluoroacetic anhydride (0.091 mL, 0.731 mmol) and imidazole (0.050 g, 0.731 mmol) were dissolved in dichloromethane (10 mL) at 45° C., after which the resulting solution was stirred at the same temperature for 12 hours, and then a reaction was finished by lowering the temperature to room temperature. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.030 g, 28.7%) in a colorless oil form.

$^1H$ NMR (400 MHz, $CDCl_3$) δ 9.32~9.30 (m, 1H), 8.36 (dd, J=8.2, 2.2 Hz, 1H), 8.26 (dd, J=7.9, 1.6 Hz, 1H), 7.62~7.58 (m, 1H), 7.49 (d, J=8.2 Hz, 1H), 7.28~7.20 (m, 2H), 7.07 (s, 0.25H), 6.94 (s, 0.5H), 6.81 (s, 0.25H), 5.58 (s, 2H), 4.43 (t, J=5.7 Hz, 2H), 3.76 (t, J=5.7 Hz, 2H), 3.40 (s, 3H); LRMS (ES) m/z 430.4 ($M^+$+1).

Synthesis of Compound 77, 1-((5-(5-(difluoromethyl)-1,3,4-oxadiazole-2-yl)pyridine-2-yl)methyl)-3-phenethylquinazoline-2,4(1H,3H)-dione

[Step 1] Synthesis of 2-amino-N-phenethylbenzamide

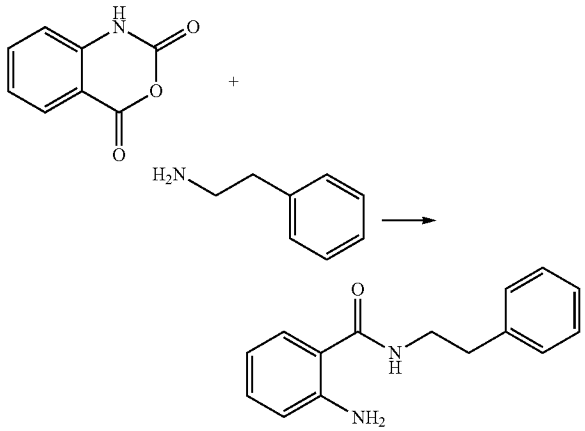

2H-benzo[d][1,3]oxazine-2,4(1H)-dione (3.000 g, 18.390 mmol), 2-phenylethane-1-amine (2.674 g, 22.068 mmol) and N,N-dimethylpyridine-4-amine (DMAP, 0.225 g, 1.839 mmol) were dissolved in N,N-dimethylformamide (30 mL) at room temperature, after which the resulting solution was stirred at the same temperature for 12 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 50%), and concentrated to obtain a title compound (4.000 g, 90.5%) in a brown oil form.

[Step 2] Synthesis of methyl (2-(phenethylcarbamoyl)phenyl)cabamate

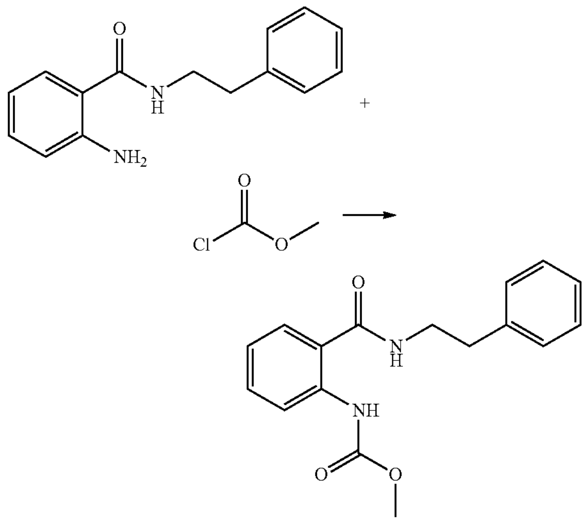

The 2-amino-N-phenethylbenzamide (4.000 g, 16.645 mmol) prepared in the step 1, methyl carbonochloridate (1.887 g, 19.974 mmol) and sodium hydroxide (1.00 M solution in $H_2O$, 33.290 mL, 33.290 mmol) were dissolved in 1,4-dioxane (30 mL) at room temperature, after which the resulting solution was stirred at the same temperature for 12 hours. 1N-hydrochloric acid aqueous solution was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (0.790 g, 15.9%) in a colorless oil form.

[Step 3] Synthesis of 3-phenethylquinazoline-2,4(1H,3H)-dione

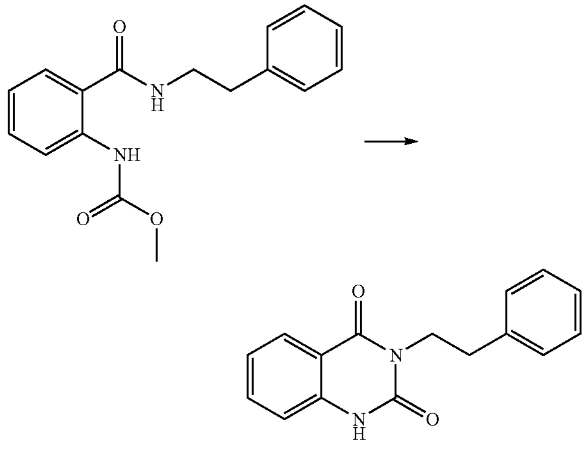

The methyl (2-(phenethylcarbamoyl)phenyl)cabamate (0.790 g, 2.648 mmol) prepared in the step 2 and potassium hydroxide (1.486 g, 26.480 mmol) were dissolved in ethanol (10 mL) at 80° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.500 g, 70.9%) in a white solid form.

[Step 4] Synthesis of the Compound 77

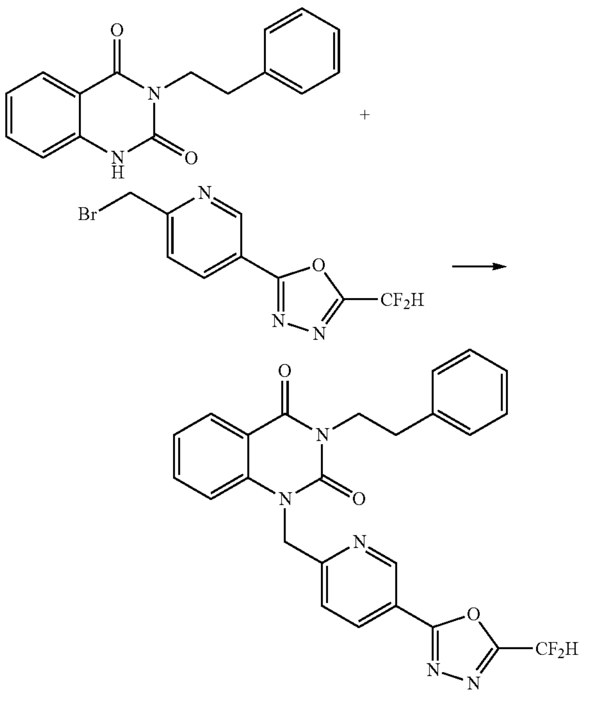

The 3-phenethylquinazoline-2,4(1H,3H)-dione (0.150 g, 0.563 mmol) prepared in the step 3 was dissolved in N,N-dimethylformamide (10 mL) at 0° C., after which sodium hydride (60.00%, 0.034 g, 0.845 mmol) was added into the resulting solution, and stirred at the same temperature for 30 minutes. 2-(6-(bromomethyl)pyridine-3-yl)-5-(difluoromethyl)-1,3,4-oxadiazole (0.196 g, 0.676 mmol) was added into the reaction mixture, and further stirred at room temperature for 2 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.130 g, 48.5%) in a white foam solid form.

$^1H$ NMR (400 MHz, $CDCl_3$) δ 9.32 (dd, J=2.2, 0.8 Hz, 1H), 8.35 (dd, J=5.9, 2.4 Hz, 1H), 8.29 (dd, J=7.9, 1.3 Hz,

1H), 7.62~7.58 (m, 1H), 7.37~7.26 (m, 8H), 7.08 (s, 0.25H), 6.95 (s, 0.5H), 6.82 (s, 0.25H), 5.56 (s, 2H), 4.44~4.40 (m, 2H), 3.10~3.06 (m, 2H); LRMS (ES) m/z 475.9 ($M^{+}$+1).

Synthesis of Compound 78, 1,3-bis((5-(5-(difluoromethyl)-1,3,4-oxadiazole-2-yl)pyridine-2-yl)methyl)quinazoline-2,4(1H,3H)-dione

[Step 1] Synthesis of the Compound 78

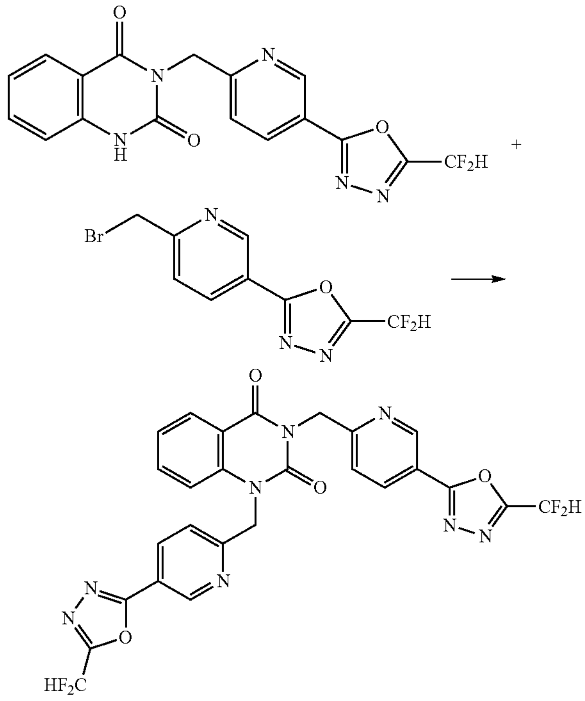

3-((5-(5-(difluoromethyl)-1,3,4-oxadiazole-2-yl)pyridine-2-yl)methyl)quinazoline-2,4(1H,3H)-dione (0.060 g, 0.162 mmol), 2-(6-(bromomethyl)pyridine-3-yl)-5-(difluoromethyl)-1,3,4-oxadiazole (0.052 g, 0.178 mmol) and potassium carbonate (0.045 g, 0.323 mmol) were dissolved in N,N-dimethylformamide (10 mL), after which the resulting solution was stirred at 50° C. for 18 hours, and then further stirred at room temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 80%), and concentrated to obtain a title compound (0.050 g, 53.3%) in a white solid form.

$^{1}$H NMR (400 MHz, $CDCl_3$) δ 9.31 (d, J=2.2 Hz, 1H), 9.23 (d, J=2.1 Hz, 1H), 8.39~8.36 (m, 2H), 8.28 (dd, J=8.0, 1.2 Hz, 1H), 7.63~7.61 (m, 1H), 7.56~7.51 (m, 2H), 7.31~7.28 (m, 2H), 7.07 (s, 0.5H), 6.95~6.94 (m, 1H), 6.82~6.81 (m, 0.5H), 5.61~5.60 (m, 4H), 2.18 (s, 6H).

Synthesis of Compound 79, tert-butyl 7-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)-4,7-diazaspiro[2.5]octane-4-carboxylate

[Step 1] Synthesis of the Compound 79

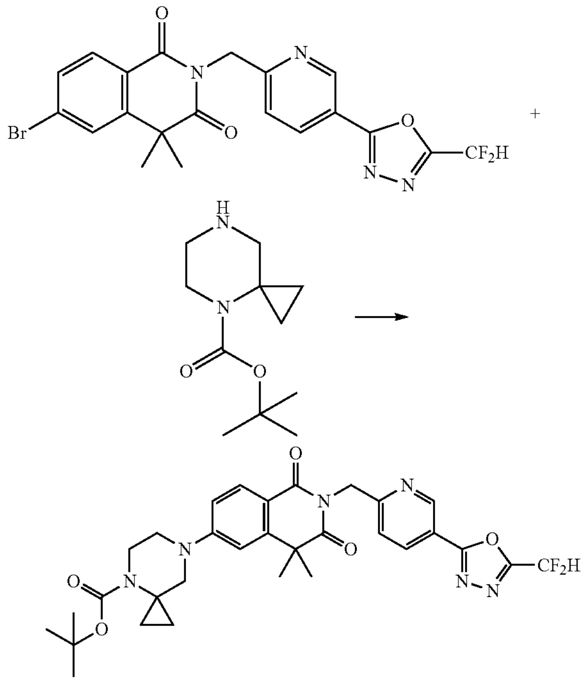

6-bromo-2-((5-(5-(difluoromethyl)-1,3,4-oxadiazole-2-yl)pyridine-2-yl)methyl)-4,4-dimethylisoquinoline-1,3(2H,4H)-dione (0.500 g, 1.048 mmol), tert-butyl 4,7-diazaspiro[2.5]octane-4-carboxylate (0.334 g, 1.571 mmol), tris(dibenzylideneacetone)dipalladium ($Pd_2(dba)_3$, 0.096 g, 0.105 mmol), 4,5-bis(diphenylphosphino)-9,9-dimethylxanthene (Xantphos, 0.061 g, 0.105 mmol) and cesium carbonate (1.024 g, 3.143 mmol) were dissolved in toluene (5 mL) at 80° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.230 g, 36.1%) in a colorless oil form.

$^{1}$H NMR (400 MHz, $CDCl_3$) δ 9.16 (d, J=1.8 Hz, 1H), 8.29 (dd, J=8.2, 2.2 Hz, 1H), 8.07 (d, J=8.9 Hz, 1H), 7.39 (d, J=8.3 Hz, 1H), 7.05 (s, 0.25H), 6.92 (s, 0.5H), 6.86 (dd, J=9.0, 2.3 Hz, 1H), 6.79 (s, 0.25H), 6.76 (d, J=2.3 Hz, 1H), 5.37 (s, 2H), 3.73 (t, J=5.2 Hz, 2H), 3.38 (t, J=5.2 Hz, 2H), 3.15 (s, 2H), 1.65 (s, 6H), 1.47 (s, 9H), 1.08~1.07 (m, 2H), 0.87~0.86 (m, 2H).

Synthesis of Compound 80, 2-((5-(5-(difluoromethyl)-1,3,4-oxadiazole-2-yl)pyridine-2-yl)methyl)-4,4-dimethyl-6-(4-methyl-4,7-diazaspiro[2.5]octane-7-yl)isoquinoline-1,3(2H,4H)-dione

[Step 1] Synthesis of 2-((5-(5-(difluoromethyl)-1,3,4-oxadiazole-2-yl)pyridine-2-yl)methyl)-4,4-dimethyl-6-(4,7-diazaspiro[2.5]octane-7-yl)isoquinoline-1,3(2H,4H)-dione 2,2,2-trifluoroacetate

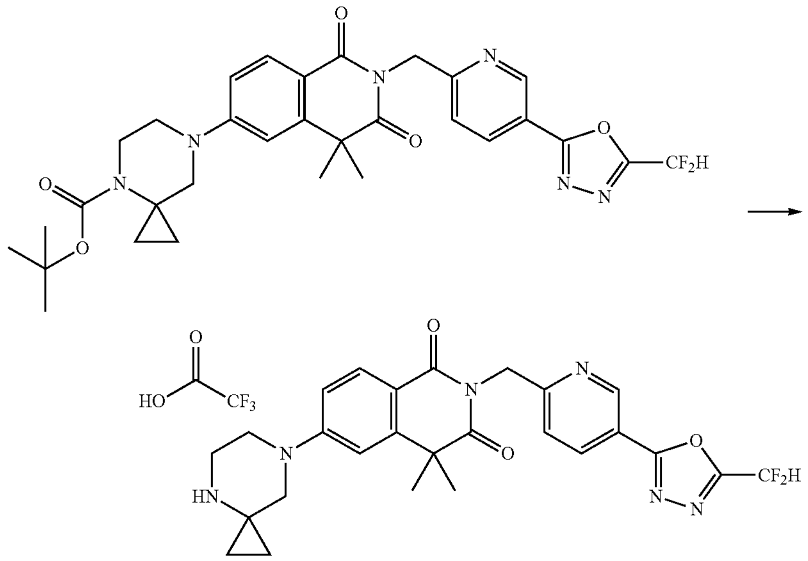

Tert-butyl 7-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-6-yl)-4,7-diazaspiro[2.5]octane-4-carboxylate (0.230 g, 0.378 mmol) and trifluoroacetic acid (0.289 mL, 3.779 mmol) were dissolved in dichloromethane (10 mL) at room temperature, after which the resulting solution was stirred at the same temperature for 18 hours. Solvent was removed from the reaction mixture under reduced pressure, after which an obtained product was used without an additional purification process (0.220 g, 93.5%, brown oil).

[Step 2] Synthesis of the Compound 80

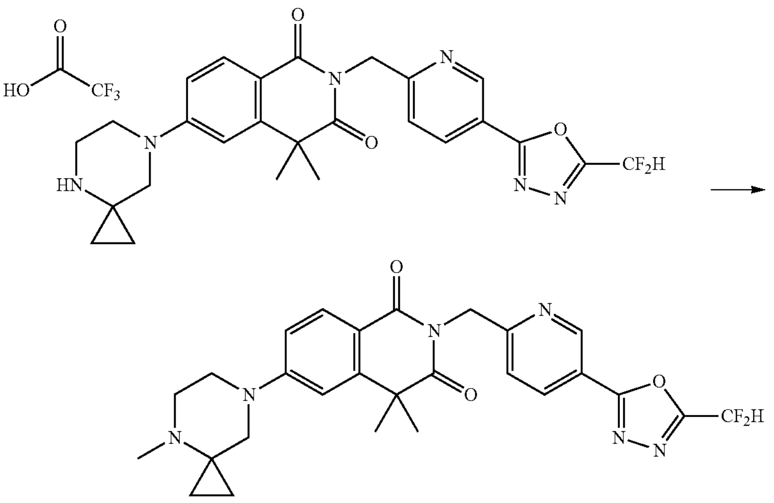

The 2-((5-(5-(difluoromethyl)-1,3,4-oxadiazole-2-yl) pyridine-2-yl)methyl)-4,4-dimethyl-6-(4,7-diazaspiro[2.5] octane-7-yl)isoquinoline-1,3(2H,4H)-dione 2,2,2-trifluoro-acetate (0.100 g, 0.161 mmol) prepared in the step 1, N,N-diisopropylethylamine (0.028 mL, 0.161 mmol), formaldehyde (0.010 g, 0.321 mmol) and sodium triacetoxyborohydride (0.068 g, 0.321 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.050 g, 59.6%) in a colorless oil form.

$^1$H NMR (400 MHz, $CDCl_3$) δ 9.19 (d, J=2.2 Hz, 1H), 8.31 (dd, J=8.2, 2.2 Hz, 1H), 8.09 (d, J=8.9 Hz, 1H), 7.41 (d, J=8.2 Hz, 1H), 7.05 (s, 0.25H), 6.96 (s, 0.5H), 6.88 (dd, J=9.2, 2.2 Hz, 1H), 6.80~6.78 (m, 1.25H), 5.41 (s, 2H), 3.47~3.39 (m, 2H), 3.17 (s, 2H), 3.15~3.12 (m, 2H), 2.45 (s, 3H), 1.69 (s, 6H), 0.87 (t, J=5.7 Hz, 2H), 0.61 (t, J=5.8 Hz, 2H).

Synthesis of Compound 81, 6-(4-acetyl-4,7-diazaspiro[2.5]octane-7-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 81

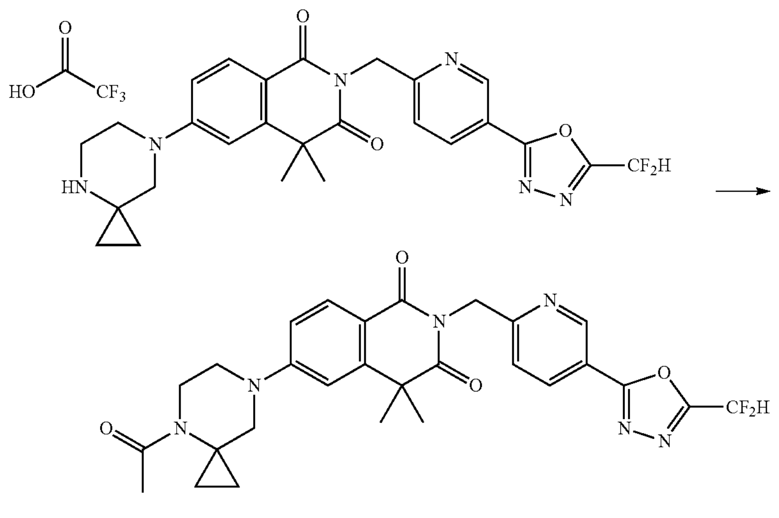

2-((5-(5-(difluoromethyl)-1,3,4-oxadiazole-2-yl)pyridine-2-yl)methyl)-4,4-dimethyl-6-(4,7-diazaspiro[2.5]octane-7-yl)isoquinoline-1,3(2H,4H)-dione 2,2,2-trifluoroacetate (0.100 g, 0.161 mmol), acetyl chloride (0.023 mL, 0.321 mmol), and N,N-diisopropylethylamine (0.084 mL, 0.482 mmol) were dissolved in dichloromethane (5 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 100%), and concentrated to obtain a title compound (0.060 g, 67.8%) in a colorless oil form.

$^1$H NMR (400 MHz, $CDCl_3$) δ 9.18~9.17 (m, 1H), 8.31 (dd, J=8.2, 2.2 Hz, 1H), 7.41 (d, J=8.1 Hz, 1H), 7.05 (s, 0.25H), 6.92 (s, 0.5H), 6.86 (dd, J=9.0, 2.4 Hz, 1H), 6.79 (s, 0.25H), 6.76 (d, J=2.4 Hz, 1H), 5.39 (s, 2H), 4.00~3.80 (m, 2H), 3.47~3.43 (m, 2H), 3.20 (s, 2H), 2.23 (s, 3H), 1.66 (s, 6H), 1.14~1.08 (m, 4H).

Synthesis of Compound 82, 2-((5-(5-(difluoromethyl)-1,3,4-oxadiazole-2-yl)pyridine-2-yl)methyl)-8-(furan-2-yl)-4, 4-dimethylisoquinoline-1,3(2H, 4H)-dione

[Step 1] Synthesis of 2-bromo-6-(carboxymethyl)benzoic acid

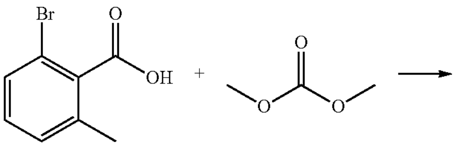

-continued

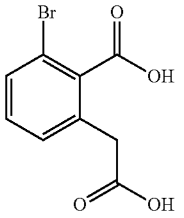

Diisopropylamine (27.691 mL, 186.003 mmol) was dissolved in tetrahydrofuran (300 mL) at −78° C., after which n-butyllithium (2.50 M solution, 74.401 mL, 186.003 mmol) was added into the resulting solution and stirred at the same temperature for 1 hour and then stirred at room temperature for 10 minutes. 2-bromo-6-methylbenzoic acid (10.000 g, 46.501 mmol) and dimethyl carbonate (7.830 mL, 93.002 mmol) were added into the reaction mixture at −78° C., and further stirred at room temperature for 18 hours. Water was poured into the reaction mixture, and an extraction was performed with ethyl acetate. 1N-hydrochloric acid aqueous solution was added into an aqueous solution layer, and an extraction was performed with ethyl acetate. An organic layer was washed with saturated sodium chloride aqueous solution, then dehydrated with anhydrous magnesium sulfate, then filtered, and then concentrated under reduced pressure. An obtained product was used without an additional purification process (7.700 g, 63.9%, yellow oil).

[Step 2] Synthesis of methyl 2-bromo-6-(2-methoxy-2-oxoethyl)benzoate

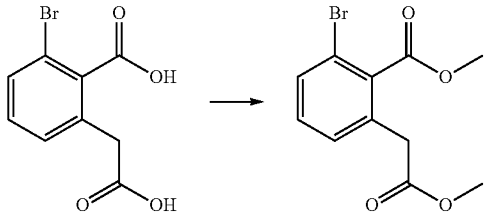 [SMILES: O=C(O)Cc1cccc(Br)c1C(=O)O ; COC(=O)Cc1cccc(Br)c1C(=O)OC]

The 2-bromo-6-(carboxymethyl)benzoic acid (7.700 g, 29.723 mmol) prepared in the step 1, dimethyl sulfate (11.247 g, 89.169 mmol) and potassium carbonate (12.324 g, 89.169 mmol) were dissolved in 1,4-dioxane (150 mL) at room temperature, after which the resulting solution was stirred at 80° C. for 18 hours, and then a reaction was finished by lowering the temperature to room temperature. Solvent was removed from the reaction mixture under reduced pressure, after which 1N-hydrochloric acid aqueous solution was poured into the resulting concentrate, and then an extraction was performed with ethyl acetate. An organic layer was washed with saturated sodium chloride aqueous solution, then dehydrated with anhydrous magnesium sulfate, then filtered, and then concentrated under reduced pressure. An obtained product was used without an additional purification process (8.500 g, 99.6%, yellow oil).

[Step 3] Synthesis of methyl 2-bromo-6-(1-methoxy-2-methyl-1-oxopropane-2-yl)benzoate

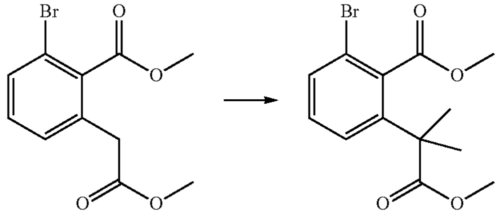 [SMILES: COC(=O)Cc1cccc(Br)c1C(=O)OC ; COC(=O)c1c(Br)cccc1C(C)(C)C(=O)OC]

The methyl 2-bromo-6-(2-methoxy-2-oxoethyl)benzoate (8.500 g, 29.605 mmol) prepared in the step 2 and sodium hydride (60.00%, 0.059 g, 1.480 mmol) were dissolved in N,N-dimethylformamide (200 mL) at ° C., after which iodomethane (2.212 mL, 35.526 mmol) was added into the resulting solution, and stirred at room temperature for 18 hours. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. The resulting concentrate was purified via column chromatography ($SiO_2$, 80 g cartridge; ethyl acetate/hexane=0 to 10%), and concentrated to obtain a title compound (3.600 g, 38.6%) in a white solid form.

[Step 4] Synthesis of 2-bromo-6-(2-carboxypropane-2-yl)benzoic acid

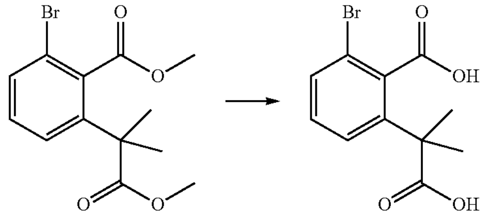 [SMILES: COC(=O)c1c(Br)cccc1C(C)(C)C(=O)OC ; CC(C)(C(=O)O)c1cccc(Br)c1C(=O)O]

The methyl 2-bromo-6-(1-methoxy-2-methyl-1-oxopropane-2-yl)benzoate (3.600 g, 11.423 mmol) prepared in the step 3 and potassium hydroxide (6.409 g, 114.228 mmol) were dissolved in methanol (15 mL)/water (30 mL) at room temperature, after which the resulting solution was heated under reflux for 18 hours, and then a reaction was finished by lowering the temperature to room temperature. Solvent was removed from the reaction mixture under reduced pressure, after which 1N-hydrochloric acid aqueous solution was put into the resulting concentrate and stirred to filter out a precipitated solid, then washed with water, and then dried to obtain a title compound (3.250 g, 90.3%) in a light yellow solid form.

[Step 5] Synthesis of 8-bromo-4,4-dimethylisoquinoline-1,3(2H,4H)-dione

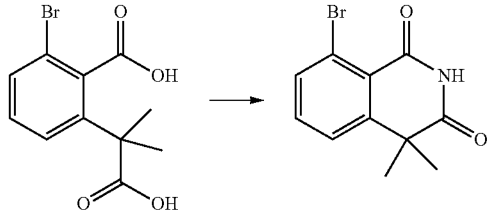 [SMILES: CC(C)(C(=O)O)c1cccc(Br)c1C(=O)O ; CC1(C)C(=O)NC(=O)c2c(Br)cccc21]

The 2-bromo-6-(2-carboxypropane-2-yl)benzoic acid (3.250 g, 11.320 mmol) prepared in the step 4 and urea (0.680 g, 11.320 mmol) were mixed in 1,2-dichlorobenzene (20 mL) at room temperature, after which the resulting mixture was irradiated with microwave, then heated at 150° C. for 45 minutes, and then a reaction was finished by lowering the temperature to room temperature. A precipitated solid was filtered, then washed with hexane, and then dried, after which the resulting filtrate was recrystallized with hexane at −10° C. and filtered to obtain a solid. Then, the solid was washed with hexane and dried to obtain a title compound (2.670 g, 88.0%) in a light yellow solid form.

[Step 6] Synthesis of 8-bromo-2-((5-(5-(difluoromethyl)-1,3,4-oxadiazole-2-yl)pyridine-2-yl)methyl)-4,4-dimethylisoquinoline-1,3(2H,4H)-dione

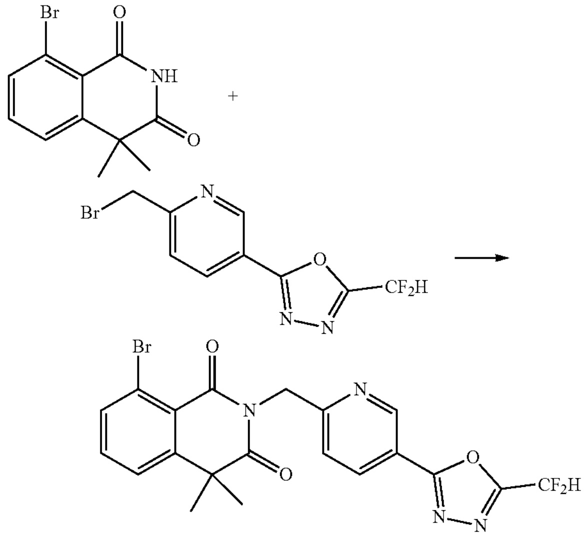

The 8-bromo-4,4-dimethylisoquinoline-1,3(2H,4H)-dione (2.000 g, 7.460 mmol) prepared in the step 5, 2-(6-(bromomethyl)pyridine-3-yl)-5-(difluoromethyl)-1,3,4-oxadiazole (2.380 g, 8.206 mmol), potassium carbonate (3.093 g, 22.379 mmol) and potassium iodide (0.124 g, 0.746 mmol) were dissolved in N,N-dimethylformamide (30 mL) at room temperature, after which the resulting solution was stirred at 80° C. for 18 hours, and then a reaction was finished by lowering the temperature to room temperature. Solvent was removed from the reaction mixture under reduced pressure, after which saturated sodium hydrogen carbonate aqueous solution was poured into the resulting concentrate, and then an extraction was performed with dichloromethane. An organic layer was washed with saturated sodium chloride aqueous solution, then dehydrated with anhydrous magnesium sulfate, then filtered, and then concentrated under reduced pressure. The resulting concentrate was purified via column chromatography ($SiO_2$, 12 g cartridge; ethyl acetate/hexane=10 to 40%), and concentrated to obtain a title compound (1.640 g, 46.1%) in a yellow solid form.

[Step 7] Synthesis of the Compound 82

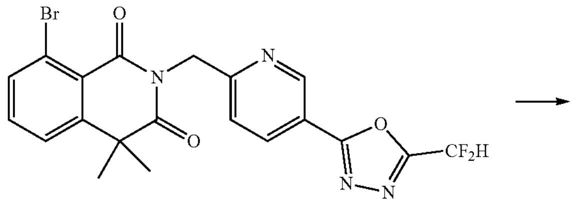

-continued

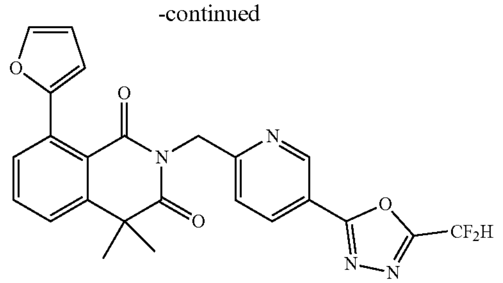

The 8-bromo-2-((5-(5-(difluoromethyl)-1,3,4-oxadiazole-2-yl)pyridine-2-yl)methyl)-4,4-dim ethylisoquinoline-1,3(2H,4H)-dione (0.200 g, 0.419 mmol) prepared in the step 6, furan-2-ylboronic acid (0.056 g, 0.503 mmol), [1,1'-bis(di-tert-butylphosphino)ferrocene]palladium(II) dichloride ($Pd(dtbpf)Cl_2$, 0.014 g, 0.021 mmol) and cesium carbonate (0.410 g, 1.257 mmol) were mixed in 1,4-dioxane (3 mL)/water (1 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=10 to 30%), and concentrated to obtain a title compound (0.046 g, 23.6%) in a light yellow solid form.

$^1H$ NMR (400 MHz, $CDCl_3$) δ 9.18 (d, J=1.6 Hz, 1H), 8.32 (dd, J=8.2, 2.0 Hz, 1H), 7.70-7.66 (m, 1H), 7.60 (dd, J=8.0, 1.2 Hz, 1H), 7.53-7.50 (m, 2H), 7.42 (d, J=8.2 Hz, 1H), 7.06-6.80 (m, 1H), 6.52 (d, J=1.2 Hz, 2H), 5.40 (s, 2H), 1.76 (s, 6H); LRMS (ES) m/z 465.2 ($M^+$+1).

Synthesis of Compound 83, 2-((5-(5-(difluoromethyl)-1,3,4-oxadiazole-2-yl)pyridine-2-yl)methyl)-4,4-dimethyl-8-morpholinoisoquinoline-1,3(2H,4H)-dione

[Step 1] Synthesis of the Compound 83

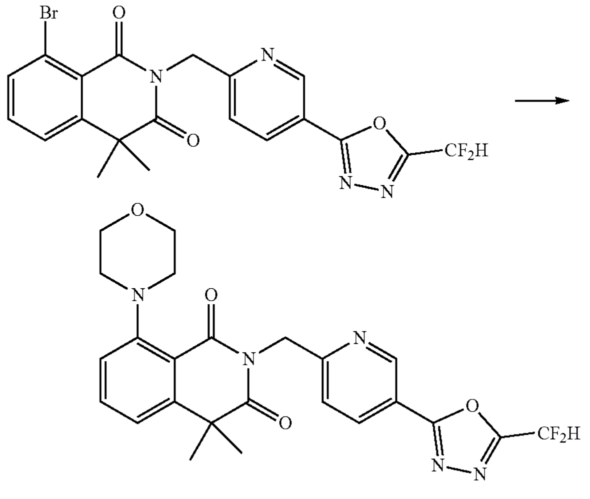

8-bromo-2-((5-(5-(difluoromethyl)-1,3,4-oxadiazole-2-yl)pyridine-2-yl)methyl)-4,4-dim ethylisoquinoline-1,3(2H,4H)-dione (0.068 g, 0.142 mmol) prepared in the step 6 of the compound 82, tris(dibenzylideneacetone)dipalladium ($Pd_2(dba)_3$, 0.013 g, 0.014 mmol), 4,5-bis(diphenylphosphino)-9,9-dimethylxanthene (Xantphos, 0.008 g, 0.014 mmol) and cesium carbonate (0.139 g, 0.427 mmol) were dissolved in 1,4-dioxane (2 mL) at room temperature, after which the resulting solution was stirred at 80° C. for 18 hours, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 40%), and concentrated to obtain a title compound (0.005 g, 7.3%) in a yellow solid form.

$^1$H NMR (400 MHz, $CDCl_3$) δ 9.17 (d, J=1.5 Hz, 1H), 8.35 (dd, J=8.2, 2.2 Hz, 1H), 7.60 (t, J=8.0 Hz, 1H), 7.50 (d, J=8.5 Hz, 1H), 7.23 (d, J=7.8 Hz, 1H), 7.13 (d, J=8.0 Hz, 1H), 7.07-6.81 (m, 1H), 5.44 (s, 2H), 3.97-3.95 (m, 4H), 3.24-3.23 (m, 4H), 1.71 (s, 6H); LRMS (ES) m/z 484.3 ($M^+$+1).

Synthesis of Compound 84, 2-((5-(5-(difluoromethyl)-1,3,4-oxadiazole-2-yl)pyridine-2-yl)methyl)-4,4-dimethyl-8-(pyridine-4-yl)isoquinoline-1,3(2H,4H)-dione

[Step 1] Synthesis of the Compound 84

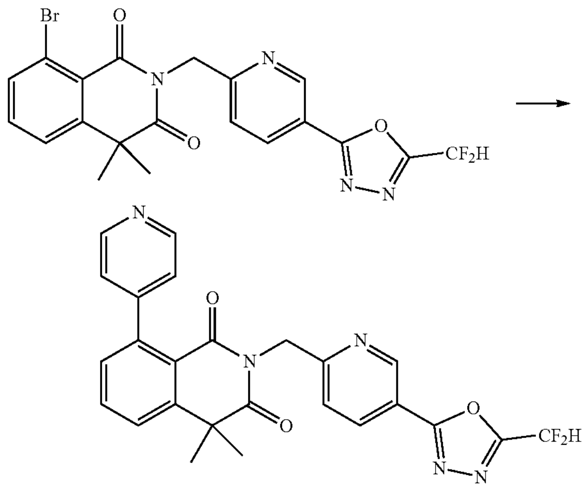

The 8-bromo-2-((5-(5-(difluoromethyl)-1,3,4-oxadiazole-2-yl)pyridine-2-yl)methyl)-4,4-dim ethylisoquinoline-1,3(2H,4H)-dione (0.150 g, 0.314 mmol) prepared in the step 6 of the compound 82, pyridine-4-ylboronic acid (0.046 g, 0.377 mmol), [1,1'-bis(di-tert-butylphosphino)ferrocene] palladium(II) dichloride ($Pd(dtbpf)Cl_2$, 0.010 g, 0.016 mmol) and cesium carbonate (0.307 g, 0.943 mmol) were mixed in 1,4-dioxane (3 mL)/water (1 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=10 to 60%), and concentrated to obtain a title compound (0.042 g, 28.1%) in a gray solid form.

$^1$H NMR (400 MHz, $CDCl_3$) δ 9.14 (d, J=1.5 Hz, 1H), 8.60-8.59 (m, 2H), 8.29 (dd, J=8.2, 2.2 Hz, 1H), 7.72-7.64 (m, 2H), 7.39 (d, J=8.7 Hz, 1H), 7.23-7.21 (m, 3H), 7.05-6.80 (m, 1H), 5.30 (s, 2H), 1.76 (s, 6H); LRMS (ES) m/z 476.3 ($M^+$+1).

Synthesis of Compound 85, 2-((5-(5-(difluoromethyl)-1,3,4-oxadiazole-2-yl)pyridine-2-yl)methyl)-4,4-dimethyl-8-(pyridine-3-yl)isoquinoline-1,3(2H,4H)-dione

[Step 1] Synthesis of the Compound 85

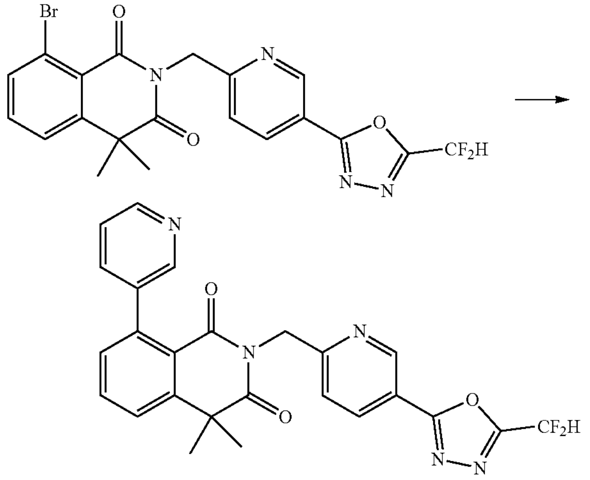

The 8-bromo-2-((5-(5-(difluoromethyl)-1,3,4-oxadiazole-2-yl)pyridine-2-yl)methyl)-4,4-dim ethylisoquinoline-1,3(2H,4H)-dione (0.150 g, 0.314 mmol) prepared in the step 6 of the compound 82, pyridine-3-ylboronic acid (0.046 g, 0.377 mmol), [1,1'-bis(di-tert-butylphosphino)ferrocene] palladium(II) dichloride ($Pd(dtbpf)Cl_2$, 0.010 g, 0.016 mmol) and cesium carbonate (0.307 g, 0.943 mmol) were mixed in 1,4-dioxane (3 mL)/water (1 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 12 g cartridge; ethyl acetate/hexane=10 to 60%), and concentrated to obtain a title compound (0.047 g, 31.5%) in a white solid form.

$^1$H NMR (400 MHz, $CDCl_3$) δ 9.16 (dd, J=2.1, 0.6 Hz, 1H), 8.59 (dd, J=4.9, 1.4 Hz, 1H), 8.53 (d, J=1.7 Hz, 1H), 8.31 (dd, J=8.2, 2.2 Hz, 1H), 7.74-7.65 (m, 3H), 7.40-7.33

(m, 3H), 7.30-7.27 (m, 1H), 7.06-6.80 (m, 1H), 5.31 (s, 2H), 1.78 (s, 6H); LRMS (ES) m/z 476.2 ($M^{+}$+1).

Synthesis of Compound 86, 6-bromo-3-((5-(5-(difluoromethyl)-1,3,4-oxadiazole-2-yl)pyridine-2-yl)methyl)-1-methylquinazoline-2,4(1H,3H)-dione

[Step 1] Synthesis of 2-amino-5-bromo-N-(tert-butyl)benzamide

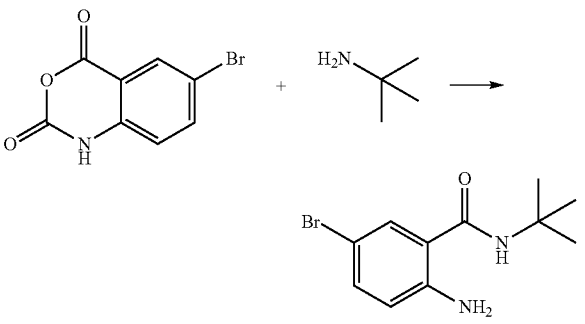

6-bromo-2H-benzo[d][1,3]oxazine-2,4(1H)-dione (8.000 g, 33.054 mmol), 2-methylpropane-2-amine (2.901 g, 39.665 mmol) and N,N-dimethylpyridine-4-amine (DMAP, 0.404 g, 3.305 mmol) were dissolved in N,N-dimethylformamide (30 mL) at room temperature, after which the resulting solution was stirred at the same temperature for 12 hours. Water (20 mL) was put into the reaction mixture and stirred, after which a precipitated solid was filtered, then washed with hexane, and then dried to obtain a title compound (5.500 g, 61.4%) in a white solid form.

[Step 2] Synthesis of methyl (4-bromo-2-(tert-butylcarbamoyl)phenyl)cabamate

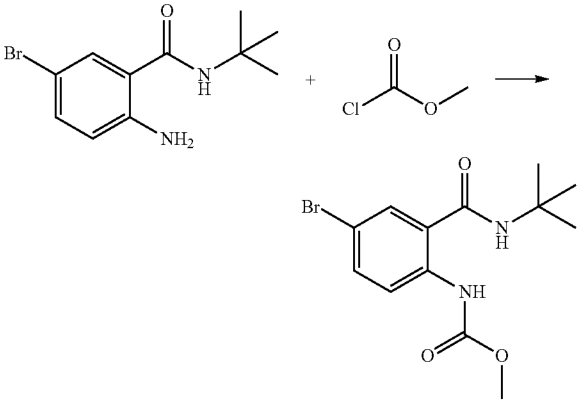

The 2-amino-5-bromo-N-(tert-butyl)benzamide (4.300 g, 15.858 mmol) prepared in the step 1, methyl carbonochloridate (1.498 g, 15.858 mmol) and N,N-diisopropylethylamine (4.143 mL, 23.787 mmol) were dissolved in dichloromethane (50 mL) at room temperature, after which the resulting solution was stirred at the same temperature for 12 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (2.280 g, 43.7%) in a yellow solid form.

[Step 3] Synthesis of 6-bromo-3-(tert-butyl)quinazoline-2,4(1H,3H)-dione

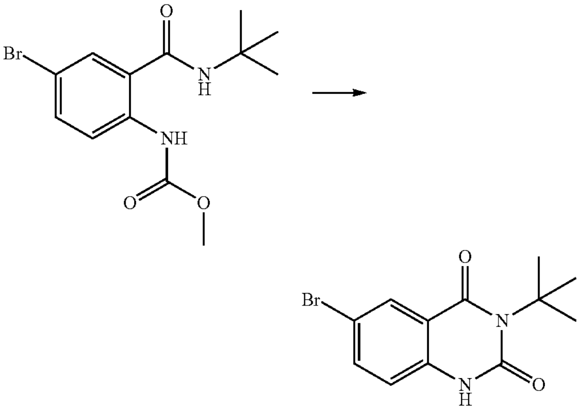

The methyl (4-bromo-2-(tert-butylcarbamoyl)phenyl)cabamate (2.280 g, 6.926 mmol) prepared in the step 2 and potassium hydroxide (3.886 g, 69.261 mmol) were dissolved in ethanol (20 mL) at 80° C., after which the resulting solution was stirred at the same temperature for 12 hours, and then a reaction was finished by lowering the temperature to room temperature. Hydrochloric acid (20 mL) was put into the reaction mixture and stirred, after which a precipitated solid was filtered, then washed with hexane, and then dried to obtain a title compound (1.830 g, 88.9%) in a white solid form.

[Step 4] Synthesis of 6-bromo-3-(tert-butyl)-1-methylquinazoline-2,4(1H,3H)-dione

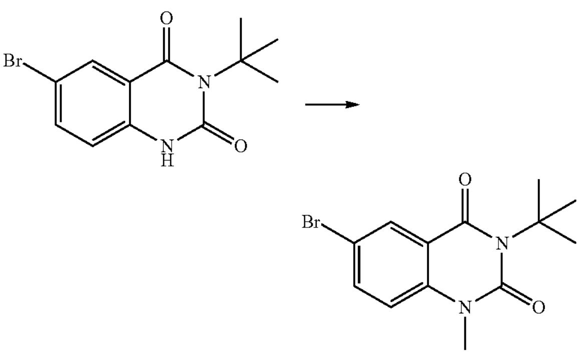

The 6-bromo-3-(tert-butyl)quinazoline-2,4(1H,3H)-dione (1.830 g, 6.159 mmol) prepared in the step 3 was dissolved in N,N-dimethylformamide (20 mL) at 0° C., after which sodium hydride (60.00%, 0.369 g, 9.238 mmol) was added into the resulting solution, and stirred at the same temperature for 30 minutes. Iodomethane (0.575 mL, 9.238 mmol) was added into the reaction mixture, and further stirred at room temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 50%), and concentrated to obtain a title compound (1.440 g, 75.1%) in a colorless oil form.

[Step 5] Synthesis of 6-bromo-1-methylquinazoline-2,4(1H,3H)-dione

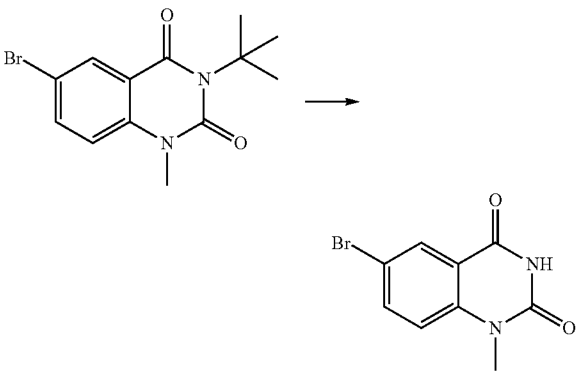

The 6-bromo-3-(tert-butyl)-1-methylquinazoline-2,4(1H, 3H)-dione (1.300 g, 4.178 mmol) prepared in the step 4 and hydrochloric acid (6.00 M solution in $H_2O$, 17.407 mL, 104.441 mmol) were dissolved in 1,4-dioxane (25 mL) at 100° C., after which the resulting solution was stirred at the same temperature for 18 hours, and then a reaction was finished by lowering the temperature to room temperature. A precipitated solid was filtered, then washed with hexane, and then dried to obtain a title compound (0.980 g, 92.0%) in a white solid form.

[Step 6] Synthesis of the Compound 86

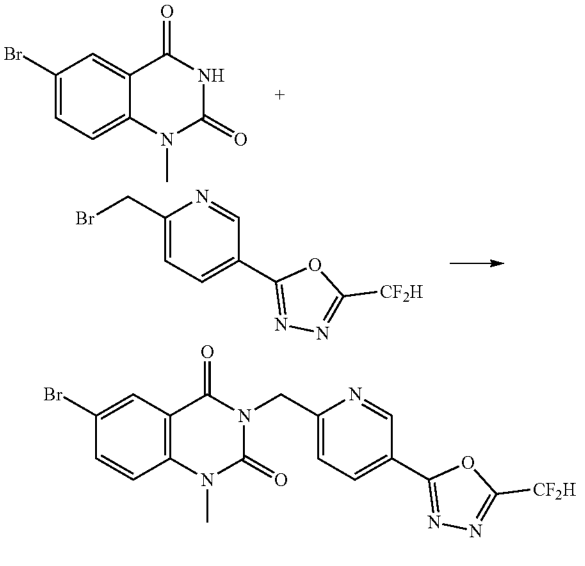

The 6-bromo-1-methylquinazoline-2,4(1H,3H)-dione (0.980 g, 3.842 mmol) prepared in the step 5, 2-(6-(bromomethyl)pyridine-3-yl)-5-(difluoromethyl)-1,3,4-oxadiazole (1.226 g, 4.226 mmol) and potassium carbonate (1.062 g, 7.684 mmol) were dissolved in N,N-dimethylformamide (20 mL) at 45° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 50%), and concentrated to obtain a title compound (1.600 g, 89.7%) in a white solid form.

LRMS (ES) m/z 465.4 ($M^+$+1).

Synthesis of Compound 87, 3-((5-(5-(difluoromethyl)-1,3,4-oxadiazole-2-yl)pyridine-2-yl)methyl)-6-(furan-2-yl)-1-methylquinazoline-2,4(1H,3H)-dione

[Step 1] Synthesis of the Compound 87

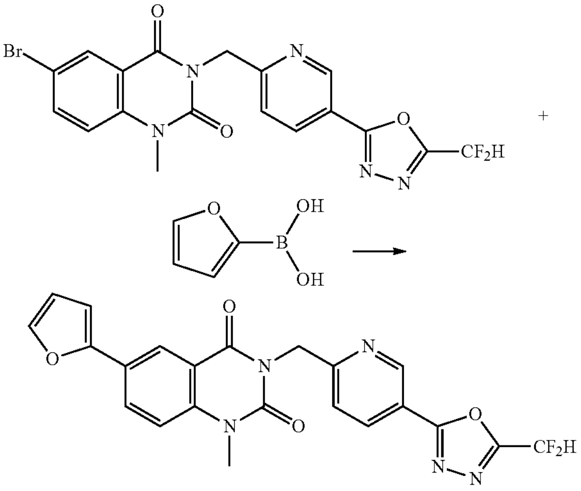

6-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol), furan-2-ylboronic acid (0.036 g, 0.323 mmol), [1,1'-bis(diphenylphosphino)ferrocene]dichloropalladium (II, 0.014 g, 0.022 mmol) and cesium carbonate (0.105 g, 0.323 mmol) were mixed in 1,4-dioxane (9 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.020 g, 20.6%) in a white solid form.

$^1H$ NMR (400 MHz, $CDCl_3$) δ 9.24 (d, J=1.6 Hz, 1H), 8.52 (d, J=2.1 Hz, 1H), 8.37 (dd, J=8.2, 2.2 Hz, 1H), 8.05 (dd, J=8.7, 2.2 Hz, 1H), 7.53~7.51 (m, 2H), 7.31 (d, J=8.8 Hz, 1H), 7.06 (s, 0.25H), 6.93 (s, 0.5H), 6.80 (s, 0.25H), 6.75 (dd, J=3.4, 0.7 Hz, 1H), 6.53 (dd, J=3.4, 1.8 Hz, 1H), 5.55 (s, 2H), 3.68 (s, 3H); LRMS (ES) m/z 452.2 ($M^+$+1).

Synthesis of Compound 88, 3-((5-(5-(difluoromethyl)-1,3,4-oxadiazole-2-yl)pyridine-2-yl)methyl)-6-(furan-3-yl)-1-methylquinazoline-2,4(1H,3H)-dione

[Step 1] Synthesis of the Compound 88

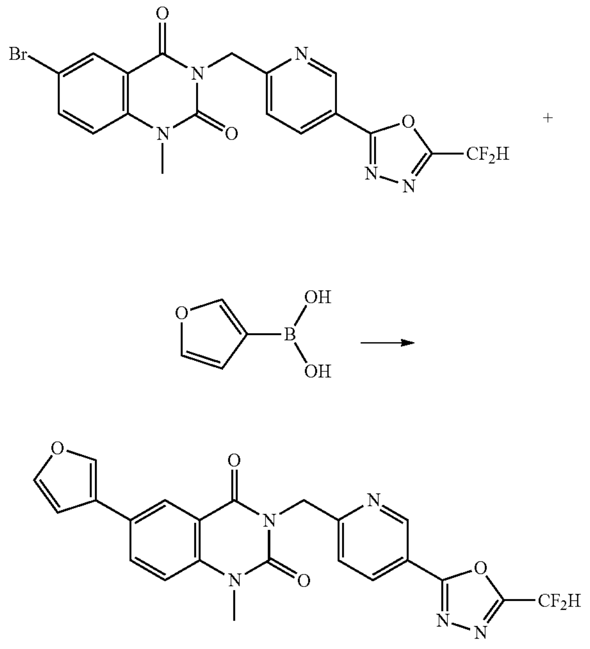

6-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol), furan-3-ylboronic acid (0.036 g, 0.323 mmol), [1,1'-bis(diphenylphosphino)ferrocene]dichloropalladium (II, 0.014 g, 0.022 mmol) and cesium carbonate (0.105 g, 0.323 mmol) were mixed in 1,4-dioxane (9 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.030 g, 30.9%) in a white solid form.

$^1H$ NMR (400 MHz, $CDCl_3$) δ 9.23~9.22 (m, 1H), 8.37~8.34 (m, 2H), 7.86~7.81 (m, 2H), 7.30~7.28 (m, 1H), 7.06 (s, 0.25H), 6.93 (s, 0.5H), 6.80 (s, 0.25H), 6.77 (dd, J=1.9, 0.9 Hz, 1H), 5.55 (s, 2H), 3.67 (s, 3H).

Synthesis of Compound 89, 3-((5-(5-(difluoromethyl)-1,3,4-oxadiazole-2-yl)pyridine-2-yl)methyl)-6-(2-fluorophenyl)-1-methylquinazoline-2,4(1H,3H)-dione

[Step 1] Synthesis of the Compound 89

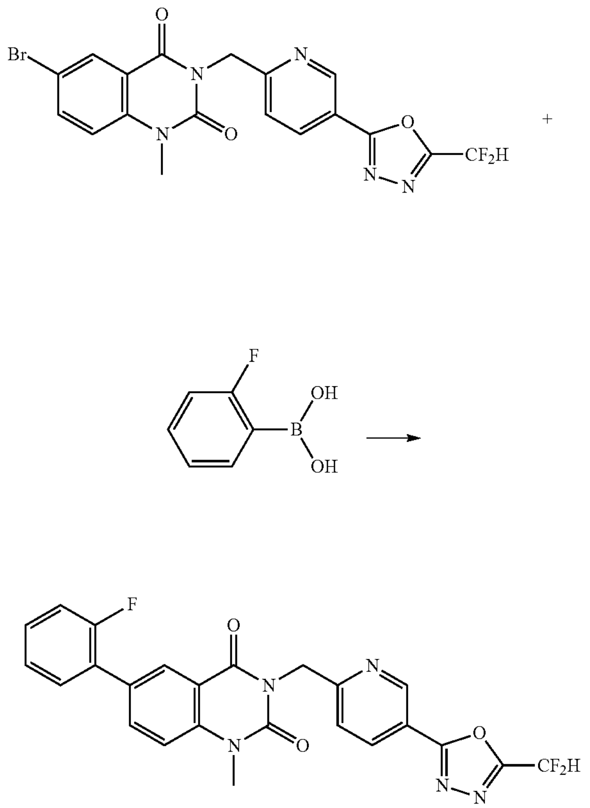

6-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol), (2-fluorophenyl)boronic acid (0.045 g, 0.323 mmol), [1,1'-bis(diphenylphosphino)ferrocene]dichloropalladium (II, 0.014 g, 0.022 mmol) and cesium carbonate (0.105 g, 0.323 mmol) were mixed in 1,4-dioxane (9 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.020 g, 19.4%) in a white solid form.

$^1H$ NMR (400 MHz, $CDCl_3$) δ 9.24 (d, J=1.8 Hz, 1H), 8.45 (d, J=1.8 Hz, 1H), 8.37 (dd, J=8.3, 2.2 Hz, 1H), 7.98 (dt, J=8.6, 2.0 Hz, 1H), 7.54~7.49 (m, 2H), 7.41~7.35 (m, 2H), 7.28~7.26 (m, 1H), 7.24~7.17 (m, 1H), 7.06 (s, 1H), 6.93 (s, 1H), 6.80 (s, 1H), 5.56 (s, 2H), 3.70 (s, 3H); LRMS (ES) m/z 480.2 ($M^+$+1).

Synthesis of Compound 90, 3-((5-(5-(difluoromethyl)-1,3,4-oxadiazole-2-yl)pyridine-2-yl)methyl)-6-(3-fluorophenyl)-1-methylquinazoline-2,4(1H,3H)-dione

[Step 1] Synthesis of the Compound 90

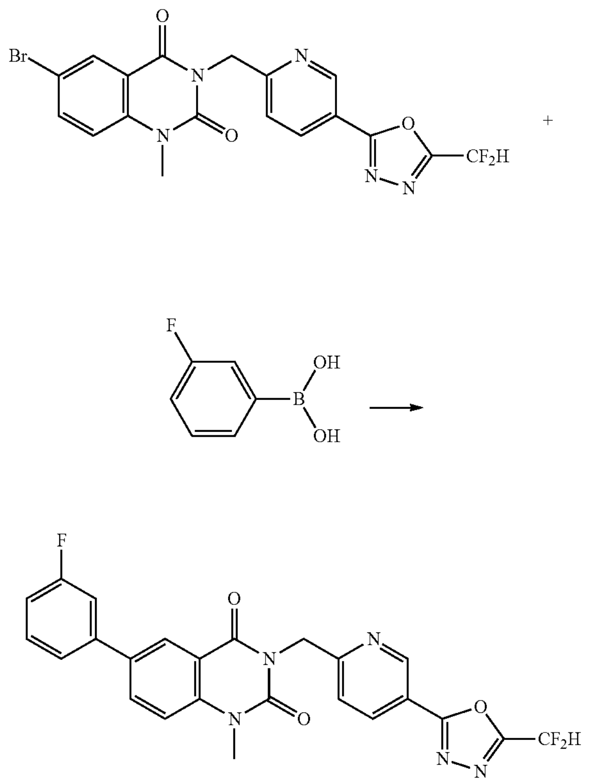

6-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol), (3-fluorophenyl)boronic acid (0.045 g, 0.323 mmol), [1,1'-bis(diphenylphosphino)ferrocene]dichloropalladium (II, 0.014 g, 0.022 mmol) and cesium carbonate (0.105 g, 0.323 mmol) were mixed in 1,4-dioxane (9 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.030 g, 29.0%) in a white solid form.

$^1H$ NMR (400 MHz, $CDCl_3$) δ 9.24 (dd, J=2.2, 0.8 Hz, 1H), 8.50 (d, J=2.2 Hz, 1H), 8.37 (dd, J=8.2, 2.2 Hz, 1H), 7.97 (dd, J=8.7, 2.3 Hz, 1H), 7.54 (dd, J=8.2, 0.7 Hz, 1H), 7.46~7.44 (m, 1H), 7.38~7.33 (m, 1H), 7.12~7.07 (m, 1H), 7.06 (s, 0.25H), 6.93 (s, 0.5H), 6.80 (s, 0.25H), 5.57 (s, 2H), 3.70 (s, 3H).

Synthesis of Compound 91, 3-((5-(5-(difluoromethyl)-1,3,4-oxadiazole-2-yl)pyridine-2-yl)methyl)-1-methyl-6-(pyridine-3-yl)quinazoline-2,4(1H,3H)-dione

[Step 1] Synthesis of the Compound 91

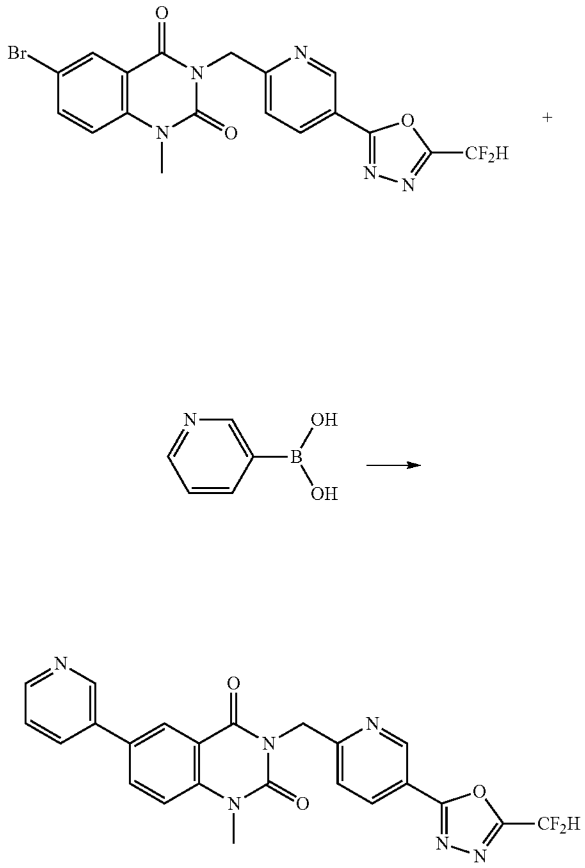

6-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol), pyridine-3-ylboronic acid (0.040 g, 0.323 mmol), [1,1'-bis(diphenylphosphino)ferrocene]dichloropalladium (II, 0.014 g, 0.022 mmol) and cesium carbonate (0.105 g, 0.323 mmol) were mixed in 1,4-dioxane (9 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.025 g, 25.1%) in a white solid form.

$^1H$ NMR (400 MHz, $CDCl_3$) δ 9.24 (d, J=2.2 Hz, 1H), 8.93 (d, J=2.4 Hz, 1H), 8.66 (dd, J=4.6, 1.3 Hz, 1H), 8.51 (d, J=2.2 Hz, 1H), 8.38 (dd, J=8.4, 2.4 Hz, 1H), 7.55 (d, J=8.2 Hz, 1H), 7.46~7.40 (m, 2H), 7.06 (s, 0.25H), 6.93 (s, 0.5H), 6.80 (s, 0.25H), 5.57 (s, 2H), 3.71 (s, 3H); LRMS (ES) m/z 463.2 ($M^+$+1).

Synthesis of Compound 92, 3-((5-(5-(difluoromethyl)-1,3,4-oxadiazole-2-yl)pyridine-2-yl)methyl)-1-methyl-6-(pyridine-4-yl)quinazoline-2,4(1H,3H)-dione

[Step 1] Synthesis of the Compound 92

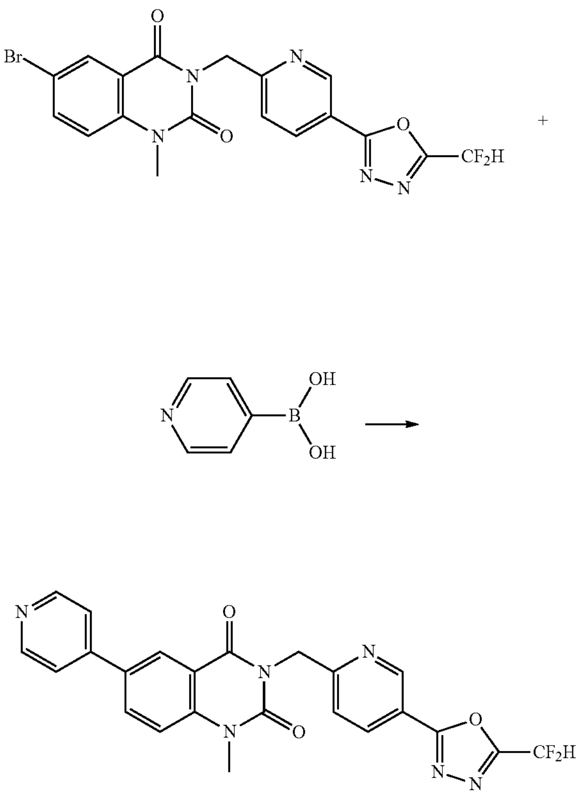

6-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol), pyridine-4-ylboronic acid (0.040 g, 0.323 mmol), [1,1'-bis(diphenylphosphino)ferrocene]dichloropalladium (II, 0.014 g, 0.022 mmol) and cesium carbonate (0.105 g, 0.323 mmol) were mixed in 1,4-dioxane (9 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.030 g, 30.1%) in a white solid form.

$^1$H NMR (400 MHz, $CDCl_3$) δ 9.23 (d, J=1.6 Hz, 1H), 8.72~8.71 (m, 2H), 8.58 (d, J=2.2 Hz, 1H), 8.37 (dd, J=8.2, 2.2 Hz, 1H), 8.04 (dd, J=8.7, 2.3 Hz, 1H), 7.59~7.53 (m, 3H), 7.42 (d, J=8.7 Hz, 1H), 7.06 (s, 1H), 6.93 (s, 1H), 6.80 (s, 1H), 5.56 (s, 2H), 3.71 (s, 2H).

Synthesis of Compound 93, 2-((5-(5-(difluoromethyl)-1,3,4-oxadiazole-2-yl)pyridine-2-yl)methyl)-4,4-dimethyl-8-(5-methylfuran-2-yl)isoquinoline-1,3(2H,4H)-dione

[Step 1] Synthesis of the Compound 93

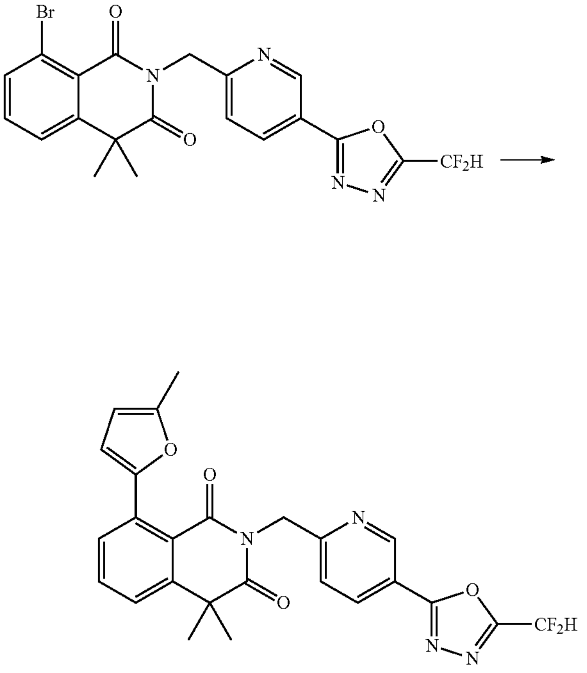

The 8-bromo-2-((5-(5-(difluoromethyl)-1,3,4-oxadiazole-2-yl)pyridine-2-yl)methyl)-4,4-dim ethylisoquinoline-1,3(2H,4H)-dione (0.150 g, 0.314 mmol) prepared in the step 6 of the compound 82, 4,4,5,5-tetramethyl-2-(5-methylfuran-2-yl)-1,3,2-dioxaborolane (0.078 g, 0.377 mmol), [1,1'-bis(di-tert-butylphosphino)ferrocene]palladium(II) dichloride (Pd(dtbpf)$Cl_2$, 0.010 g, 0.016 mmol) and cesium carbonate (0.307 g, 0.943 mmol) were mixed in 1,4-dioxane (3 mL)/water (1 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 12 g cartridge; ethyl acetate/hexane=0 to 30%), and concentrated to obtain a title compound (0.020 g, 13.3%) in a yellow oil form.

$^1$H NMR (400 MHz, $CDCl_3$) δ 9.19 (dd, J=2.1, 0.7 Hz, 1H), 8.32 (dd, J=8.2, 2.2 Hz, 1H), 7.67-7.63 (m, 1H), 7.56-7.51 (m, 2H), 7.43 (d, J=8.2 Hz, 1H), 7.06-6.80 (m, 1H), 6.44 (d, J=3.1 Hz, 1H), 6.09 (dd, J=2.1, 1.0 Hz, 1H), 5.40 (s, 2H), 2.31 (s, 3H), 1.74 (s, 6H); LRMS (ES) m/z 479.2 ($M^+$+1).

Synthesis of Compound 94, 2-((5-(5-(difluoromethyl)-1,3,4-oxadiazole-2-yl)pyridine-2-yl)methyl)-8-(6-methoxypyridine-3-yl)-4,4-dimethylisoquinoline-1,3(2H,4H)-dione

[Step 1] Synthesis of the Compound 94

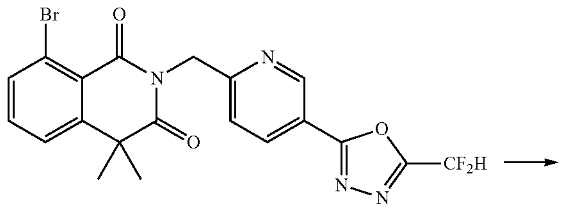

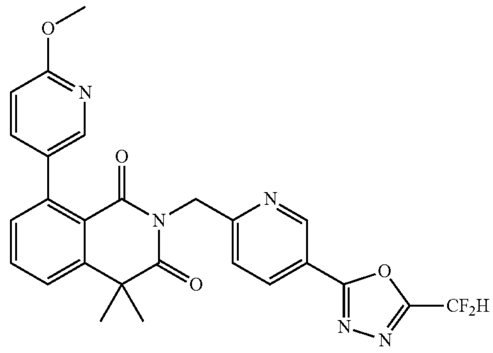

The 8-bromo-2-((5-(5-(difluoromethyl)-1,3,4-oxadiazole-2-yl)pyridine-2-yl)methyl)-4,4-dim ethylisoquinoline-1,3(2H,4H)-dione (0.150 g, 0.314 mmol) prepared in the step 6 of the compound 82, (6-methoxypyridine-3-yl)boronic acid (0.058 g, 0.377 mmol), [1,1'-bis(di-tert-butylphosphino)ferrocene]palladium(II) dichloride (Pd(dtbpf)$Cl_2$, 0.010 g, 0.016 mmol) and cesium carbonate (0.307 g, 0.943 mmol) were mixed in 1,4-dioxane (3 mL)/water (1 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 12 g cartridge; ethyl acetate/hexane=0 to 30%), and concentrated to obtain a title compound (0.016 g, 10.1%) in a white solid form.

$^1$H NMR (400 MHz, $CDCl_3$) δ 9.17 (d, J=1.6 Hz, 1H), 8.31 (dd, J=8.2, 2.2 Hz, 1H), 8.08 (d, J=2.4 Hz, 1H), 7.71-7.67 (m, 1H), 7.61 (dd, J=8.0, 1.3 Hz, 1H), 7.55-7.52 (m, 1H), 7.40 (d, J=8.2 Hz, 1H), 7.29-7.27 (m, 1H), 7.06-6.80 (m, 1H), 6.75 (d, J=8.5 Hz, 1H), 5.33 (s, 2H), 3.98 (s, 3H), 1.78 (s, 6H); LRMS (ES) m/z 506.2 ($M^+$+1).

Synthesis of Compound 95, 2-((5-(5-(difluoromethyl)-1,3,4-oxadiazole-2-yl)pyridine-2-yl)methyl)-8-(furan-3-yl)-4, 4-dimethylisoquinoline-1,3(2H, 4H)-dione

[Step 1] Synthesis of the Compound 95

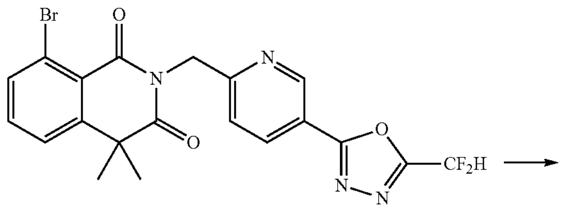

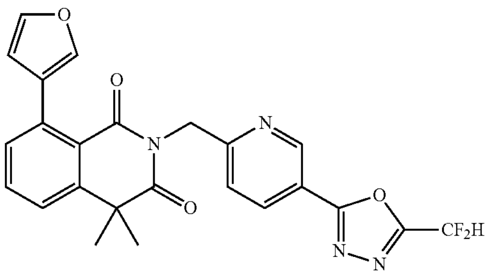

8-bromo-2-((5-(5-(difluoromethyl)-1,3,4-oxadiazole-2-yl)pyridine-2-yl)methyl)-4,4-dimethylisoquinoline-1,3(2H, 4H)-dione (0.150 g, 0.314 mmol), furan-3-ylboronic acid (0.042 g, 0.377 mmol), [1,1'-bis(di-tert-butylphosphino)ferrocene]palladium(II) dichloride (Pd(dtbpf)$Cl_2$, 0.010 g, 0.016 mmol) and cesium carbonate (0.307 g, 0.943 mmol) were mixed in 1,4-dioxane (3 mL)/water (1 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 30%), and concentrated to obtain a product, after which the resulting product was purified again via chromatography ($SiO_2$ plate, 20×20×1 mm; ethyl acetate/hexane aqueous solution=25%), and concentrated to obtain a title compound (0.046 g, 31.5%) in a light brown solid form.

$^1$H NMR (400 MHz, $CDCl_3$) δ 9.18 (d, J=1.5 Hz, 1H), 8.33 (dd, J=8.2, 2.2 Hz, 1H), 7.64 (t, J=7.7 Hz, 1H), 7.56 (dd, J=8.0, 1.3 Hz, 1H), 7.52~7.52 (m, 1H), 7.45~7.42 (m, 2H), 7.36 (dd, J=7.5, 1.3 Hz, 1H), 7.06~6.80 (m, 1H), 6.48~6.47 (m, 1H), 5.32 (s, 2H), 1.76 (s, 6H); LRMS (ES) m/z 465.0 ($M^+$+1).

Synthesis of Compound 96, 2-((5-(5-(difluoromethyl)-1,3,4-oxadiazole-2-yl)pyridine-2-yl)methyl)-8-(3,5-dimethylisooxazole-4-yl)-4,4-dimethylisoquinoline-1,3(2H,4H)-dione

[Step 1] Synthesis of the Compound 96

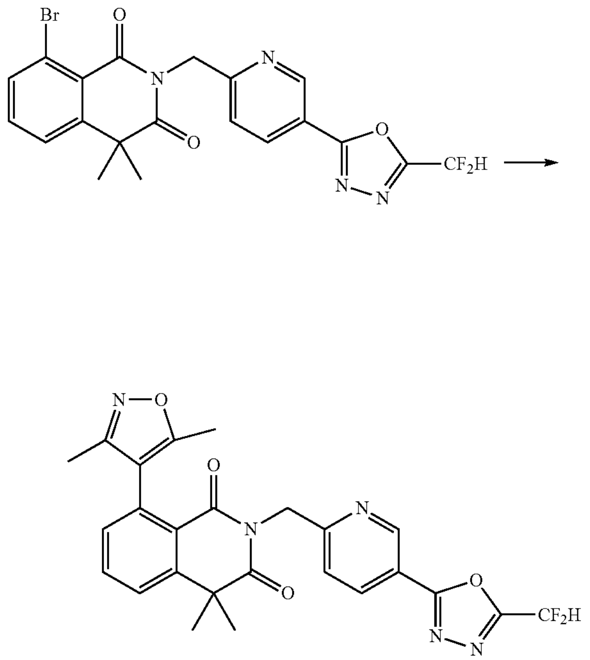

8-bromo-2-((5-(5-(difluoromethyl)-1,3,4-oxadiazole-2-yl)pyridine-2-yl)methyl)-4,4-dimethylisoquinoline-1,3(2H,4H)-dione (0.150 g, 0.314 mmol), (3,5-dimethylisooxazole-4-yl)boronic acid (0.053 g, 0.377 mmol), [1,1'-bis(di-tert-butylphosphino)ferrocene]palladium(II) dichloride (Pd(dtbpf)$Cl_2$, 0.010 g, 0.016 mmol) and cesium carbonate (0.307 g, 0.943 mmol) were mixed in 1,4-dioxane (3 mL)/water (1 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 30%), and concentrated to obtain a title compound (0.092 g, 59.3%) in a brown oil form.

$^1H$ NMR (400 MHz, $CDCl_3$) δ 9.13 (d, J=1.6 Hz, 1H), 8.32 (dd, J=8.2, 2.0 Hz, 1H), 7.71 (t, J=7.7 Hz, 1H), 7.64 (d, J=7.5 Hz, 1H), 7.43 (d, J=8.2 Hz, 1H), 7.20 (d, J=7.0 Hz, 1H), 7.06~6.80 (m, 1H), 5.34 (s, 2H), 2.24 (s, 3H), 1.99 (s, 3H), 1.77 (d, J=5.4 Hz, 6H); LRMS (ES) m/z 494.2 ($M^+$+1).

Synthesis of Compound 97, 7-bromo-3-((5-(5-(difluoromethyl)-1,3,4-oxadiazole-2-yl)pyridine-2-yl)methyl)-1-methylquinazoline-2,4(1H,3H)-dione

[Step 1] Synthesis of 2-amino-4-bromo-N-(tert-butyl)benzamide

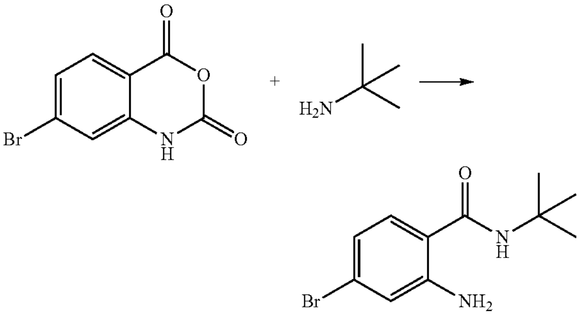

7-bromo-2H-benzo[d][1,3]oxazine-2,4(1H)-dione (10.000 g, 41.317 mmol), 2-methylpropane-2-amine (3.626 g, 49.581 mmol) and N,N-dimethylpyridine-4-amine (DMAP, 0.505 g, 4.132 mmol) were dissolved in N,N-dimethylformamide (30 mL) at room temperature, after which the resulting solution was stirred at the same temperature for 18 hours. Water (20 mL) was put into the reaction mixture and stirred, after which a precipitated solid was filtered, then washed with hexane, and then dried to obtain a title compound (7.700 g, 68.7%) in a white solid form.

[Step 2] Synthesis of methyl (5-bromo-2-(tert-butylcarbamoyl)phenyl)cabamate

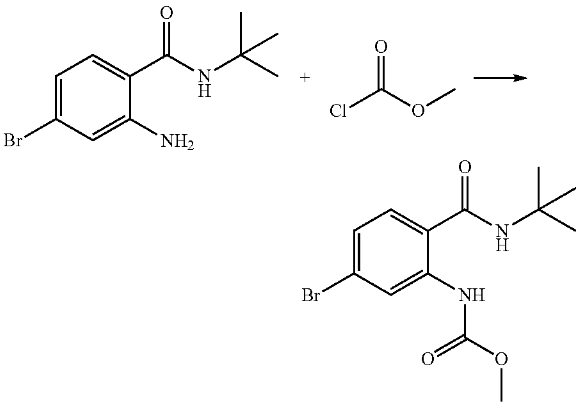

The 2-amino-4-bromo-N-(tert-butyl)benzamide (7.700 g, 28.397 mmol) prepared in the step 1, methyl carbonochloridate (2.683 g, 28.397 mmol) and N,N-diisopropylethylamine (7.419 mL, 42.595 mmol) were dissolved in dichloromethane (30 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure.

The resulting concentrate was purified via column chromatography ($SiO_2$, 40 g cartridge; ethyl acetate/hexane=0 to 30%), and concentrated to obtain a title compound (3.720 g, 39.8%) in a brown solid form.

[Step 3] Synthesis of 7-bromo-3-(tert-butyl)quinazoline-2,4(1H,3H)-dione

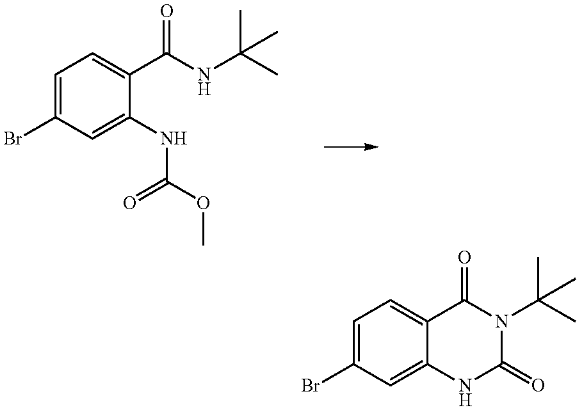

The methyl (5-bromo-2-(tert-butylcarbamoyl)phenyl)cabamate (3.720 g, 11.300 mmol) prepared in the step 2 and potassium hydroxide (6.340 g, 113.005 mmol) were dissolved in ethanol (30 mL) at 80° C., after which the resulting solution was stirred at the same temperature for 18 hours, and then a reaction was finished by lowering the temperature to room temperature. Solvent was removed from the reaction mixture under reduced pressure, after which water was poured into the resulting concentrate, and then an extraction was performed with ethyl acetate. An organic layer was washed with saturated sodium chloride aqueous solution, then dehydrated with anhydrous sodium sulfate, then filtered, and then concentrated under reduced pressure. An obtained product was used without an additional purification process (2.000 g, 59.6%, brown oil).

[Step 4] Synthesis of 7-bromo-3-(tert-butyl)-1-methylquinazoline-2,4(1H,3H)-dione

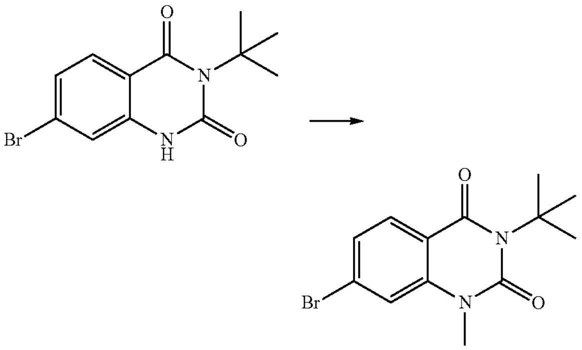

The 7-bromo-3-(tert-butyl)quinazoline-2,4(1H,3H)-dione (2.000 g, 6.731 mmol) prepared in the step 3 was dissolved in N,N-dimethylformamide (30 mL) at 0° C., after which iodomethane (0.629 mL, 10.096 mmol) was added into the resulting solution, and stirred at the same temperature for 30 minutes. Sodium hydride (60.00%, 0.404 g, 10.096 mmol) was added into the reaction mixture, and further stirred at room temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (2.000 g, 95.5%) in a white solid form.

[Step 5] Synthesis of 7-bromo-1-methylquinazoline-2,4(1H,3H)-dione

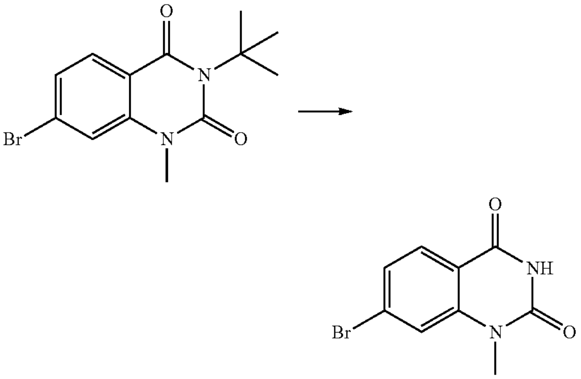

The 7-bromo-3-(tert-butyl)-1-methylquinazoline-2,4(1H,3H)-dione (2.000 g, 6.427 mmol) prepared in the step 4 and hydrochloric acid (6.00 M solution in $H_2O$, 16.068 mL, 96.407 mmol) were dissolved in 1,4-dioxane (20 mL) at 10° C., after which the resulting solution was stirred at the same temperature for 18 hours, and then a reaction was finished by lowering the temperature to room temperature. A precipitated solid was filtered, then washed with hexane, and then dried to obtain a title compound (1.500 g, 91.5%) in a brown solid form.

[Step 6] Synthesis of the Compound 97

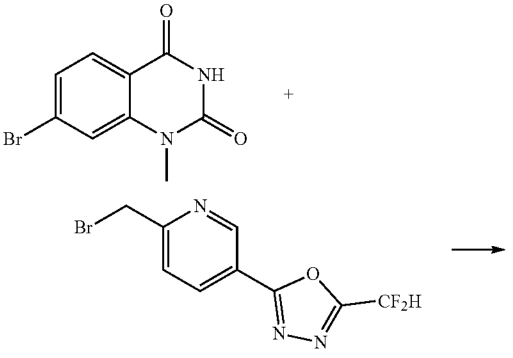

-continued

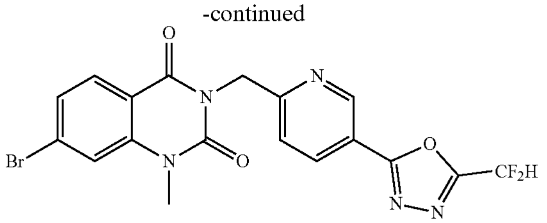

The 6-bromo-2-((5-(5-(difluoromethyl)-1,3,4-oxadiazole-2-yl)pyridine-2-yl)methyl)-4,4-dim ethylisoquinoline-1,3(2H,4H)-dione (0.100 g, 0.210 mmol) prepared in the step 5, pyridine-4-ylboronic acid (0.039 g, 0.314 mmol), [1,1'-bis(di-tert-butylphosphino)ferrocene]palladium(II) dichloride (Pd(dtbpf)$Cl_2$, 0.014 g, 0.021 mmol) and cesium carbonate (0.102 g, 0.314 mmol) were mixed in 1,4-dioxane (6 mL)/water (2 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (0.040 g, 40.2%) in a white foam solid form.

$^1$H NMR (400 MHz, $CDCl_3$) δ 9.22 (d, J=1.5 Hz, 1H), 8.36 (dd, J=8.2, 2.2 Hz, 1H), 8.12 (d, J=8.6 Hz, 1H), 7.51 (d, J=8.2 Hz, 1H), 7.45~7.42 (m, 2H), 7.06 (s, 0.25H), 6.93 (s, 0.5H), 6.80 (s, 0.25H), 5.51 (s, 2H), 3.63 (s, 3H).

Synthesis of Compound 98, 3-((5-(5-(difluoromethyl)-1,3,4-oxadiazole-2-yl)pyridine-2-yl)methyl)-7-(furan-2-yl)-1-methylquinazoline-2,4(1H,3H)-dione

[Step 1] Synthesis of the Compound 98

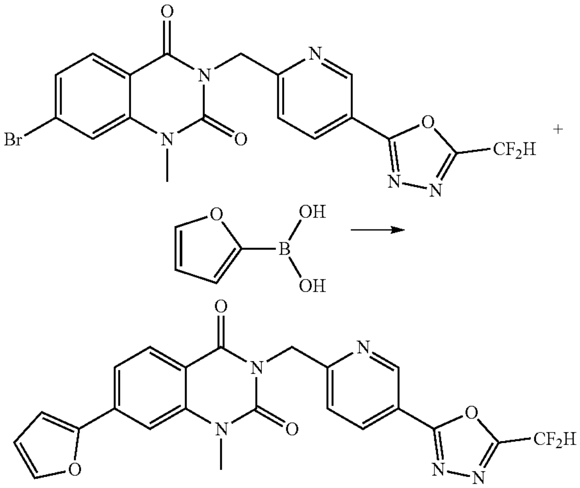

The 7-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol) prepared in the step 6 of the compound 97, furan-2-ylboronic acid (0.036 g, 0.323 mmol), [1,1'-bis(di-tert-butylphosphino)ferrocene]palladium(II) dichloride (Pd(dtbpf)$Cl_2$, 0.014 g, 0.022 mmol) and cesium carbonate (0.105 g, 0.323 mmol) were mixed in 1,4-dioxane (10 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.020 g, 20.6%) in a white solid form.

$^1$H NMR (400 MHz, $CDCl_3$) δ 9.24 (d, J=1.7 Hz, 1H), 8.36 (dd, J=8.2, 2.2 Hz, 1H), 8.25 (d, J=8.6 Hz, 1H), 7.60~7.50 (m, 4H), 7.06 (s, 0.25H), 6.94~6.92 (m, 1H), 6.93 (s, 0.5H), 6.80 (s, 0.25H), 6.59 (dd, J=3.3, 1.7 Hz, 1H), 5.54 (s, 2H), 3.72 (s, 3H); LRMS (ES) m/z 452.4 ($M^+$+1).

Synthesis of Compound 99, 3-((5-(5-(difluoromethyl)-1,3,4-oxadiazole-2-yl)pyridine-2-yl)methyl)-7-(2-fluorophenyl)-1-methylquinazoline-2,4(1H,3H)-dione

[Step 1] Synthesis of the Compound 99

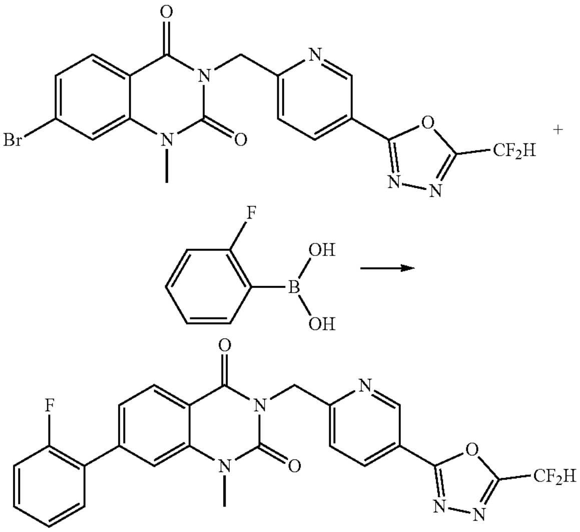

The 7-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol) prepared in the step 6 of the compound 97, (2-fluorophenyl)boronic acid (0.045 g, 0.323 mmol), [1,1'-bis(di-tert-butylphosphino)ferrocene]palladium(II) dichloride (Pd(dtbpf)$Cl_2$, 0.014 g, 0.022 mmol) and cesium carbonate (0.105 g, 0.323 mmol) were mixed in 1,4-dioxane (10 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.023 g, 22.3%) in a white solid form.

$^1$H NMR (400 MHz, $CDCl_3$) δ 9.24~9.23 (m, 1H), 8.37~8.32 (m, 2H), 7.54~7.42 (m, 5H), 7.32~7.21 (m, 2H), 7.07 (s, 0.25H), 6.94 (s, 0.5H), 6.81 (s, 0.25H), 5.56 (s, 2H), 3.69 (s, 3H); LRMS (ES) m/z 480.4 ($M^+$+1).

Synthesis of Compound 100, 3-((5-(5-(difluoromethyl)-1,3,4-oxadiazole-2-yl)pyridine-2-yl)methyl)-1-methyl-7-(pyridine-3-yl)quinazoline-2,4(1H,3H)-dione

[Step 1] Synthesis of the Compound 100

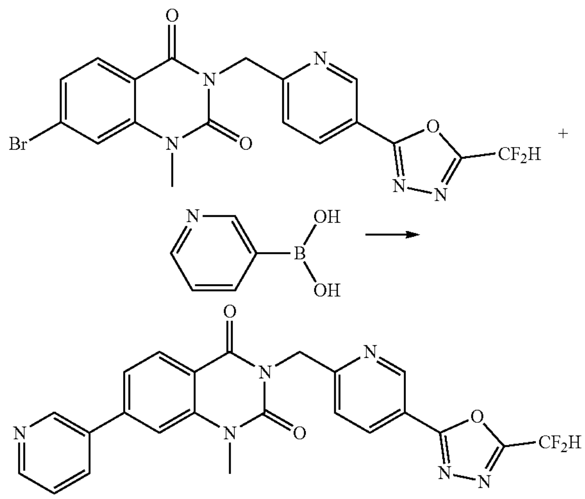

The 7-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol) prepared in the step 6 of the compound 97, pyridine-3-ylboronic acid (0.040 g, 0.323 mmol), [1,1'-bis(di-tert-butylphosphino)ferrocene] palladium(II) dichloride (Pd(dtbpf)$Cl_2$, 0.014 g, 0.022 mmol) and cesium carbonate (0.105 g, 0.323 mmol) were mixed in 1,4-dioxane (10 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.026 g, 26.1%) in a white solid form.

$^1$H NMR (400 MHz, $CDCl_3$) 9.22 (s, 1H), 8.93 (s, 1H), 8.73 (d, J=4.3 Hz, 1H), 8.38~8.35 (m, 2H), 7.98~7.96 (m, 1H), 7.62~7.42 (m, 4H), 7.07 (s, 1H), 6.94 (s, 1H), 6.81 (s, 1H), 5.56 (s, 2H), 3.73 (s, 3H); LRMS (ES) m/z 463.4 ($M^+$+1).

Synthesis of Compound 101, 3-((5-(5-(difluoromethyl)-1,3,4-oxadiazole-2-yl)pyridine-2-yl)methyl)-1-methyl-7-(pyridine-4-yl)quinazoline-2,4(1H,3H)-dione

[Step 1] Synthesis of the Compound 101

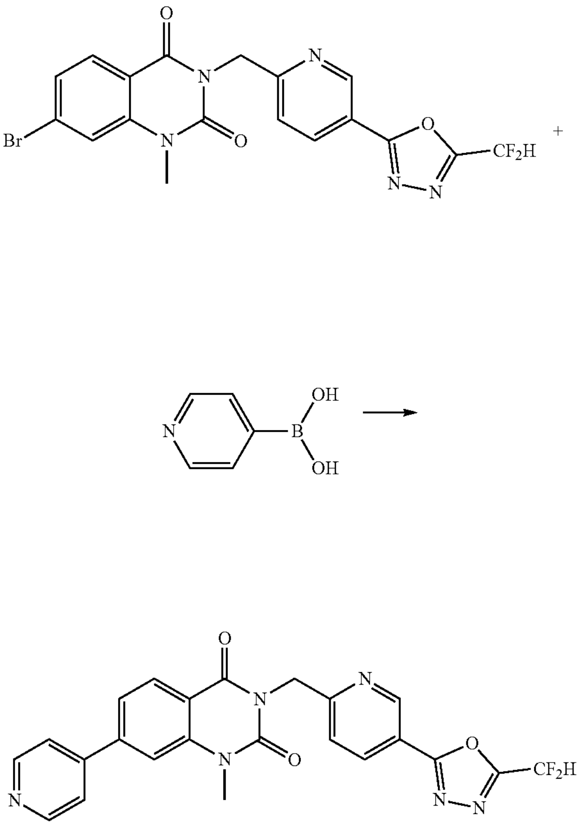

The 7-bromo-3-((5-(5-(difluoromethyl)-1,3,4-oxadiazole-2-yl)pyridine-2-yl)methyl)-1-methylquinazoline-2,4(1H,3H)-dione (0.100 g, 0.215 mmol) prepared in the step 6 of the compound 97, pyridine-4-ylboronic acid (0.040 g, 0.323 mmol), [1,1'-bis(di-tert-butylphosphino)ferrocene] palladium(II) dichloride (Pd(dtbpf)$Cl_2$, 0.014 g, 0.022 mmol) and cesium carbonate (0.105 g, 0.323 mmol) were mixed in 1,4-dioxane (10 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.030 g, 30.1%) in a white solid form.

$^1$H NMR (400 MHz, $CDCl_3$) δ 9.24~9.20 (m, 1H), 8.77 (dd, J=4.4, 1.6 Hz, 1H), 8.38~8.35 (m, 1H), 7.58~7.52 (m, 4H), 7.46 (d, J=1.4 Hz, 1H), 7.07 (s, 0.25H), 6.94 (s, 0.5H), 6.81 (s, 0.25H), 5.55 (s, 2H), 3.73 (s, 3H); LRMS (ES) m/z 463.4 ($M^+$+1).

Synthesis of Compound 102, 2-((5-(5-(difluoromethyl)-1,3,4-oxadiazole-2-yl)pyridine-2-yl)methyl)-6-(furan-3-yl)-4, 4-dimethylisoquinoline-1,3(2H, 4H)-dione

[Step 1] Synthesis of the Compound 102

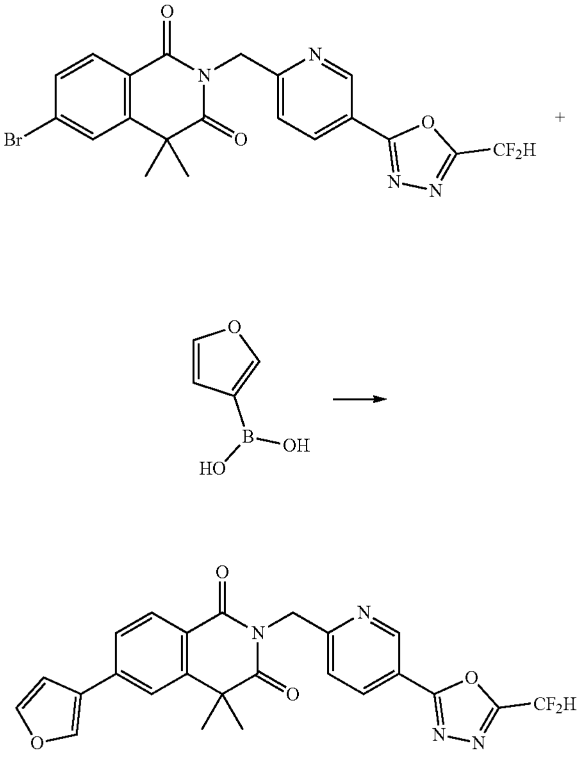

The 6-bromo-2-((5-(5-(difluoromethyl)-1,3,4-oxadiazole-2-yl)pyridine-2-yl)methyl)-4,4-dim ethylisoquinoline-1,3(2H,4H)-dione (0.100 g, 0.210 mmol) prepared in the step 6 of the compound 97, furan-3-ylboronic acid (0.035 g, 0.314 mmol), [1,1'-bis(di-tert-butylphosphino)ferrocene] palladium(II) dichloride (Pd(dtbpf)$Cl_2$, 0.014 g, 0.021 mmol) and cesium carbonate (0.102 g, 0.314 mmol) were mixed in 1,4-dioxane (30 mL)/water (10 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (0.034 g, 34.9%) in a white foam solid form.

$^1$H NMR (400 MHz, $CDCl_3$) δ 9.20 (dd, J=2.2, 0.8 Hz, 1H), 8.35 (dd, J=8.2, 2.2 Hz, 1H), 8.26 (dd, J=7.6, 1.2 Hz, 1H), 7.89 (dd, J=1.5, 0.9 Hz, 1H), 7.59~7.56 (m, 3H), 7.47 (dd, J=8.2, 0.8 Hz, 1H), 7.07 (s, 0.25H), 6.94 (s, 0.5H), 6.81 (s, 0.25H), 6.79 (dd, J=1.9, 0.9 Hz, 1H), 5.45 (s, 2H), 1.15 (s, 6H); LRMS (ES) m/z 465.4 ($M^+$+1).

Synthesis of Compound 103, 2-((5-(5-(difluoromethyl)-1,3,4-oxadiazole-2-yl)pyridine-2-yl)methyl)-6-(2-fluorophenyl)-4,4-dimethylisoquinoline-1,3(2H, 4H)-dione

[Step 1] Synthesis of the Compound 103

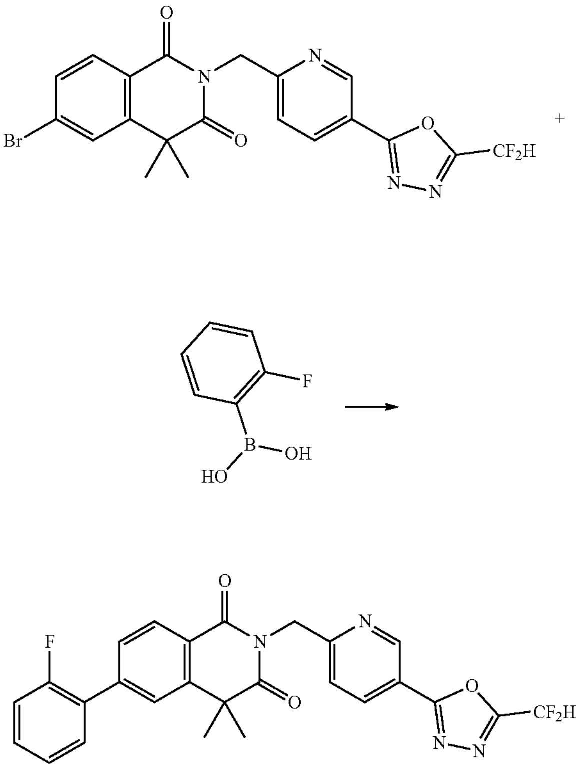

The 6-bromo-2-((5-(5-(difluoromethyl)-1,3,4-oxadiazole-2-yl)pyridine-2-yl)methyl)-4,4-dim ethylisoquinoline-1,3(2H,4H)-dione (0.100 g, 0.210 mmol) prepared in the step 6 of the compound 97, (2-fluorophenyl)boronic acid (0.044 g, 0.314 mmol), [1,1'-bis(di-tert-butylphosphino)ferrocene] palladium(II) dichloride (Pd(dtbpf)$Cl_2$, 0.014 g, 0.021 mmol) and cesium carbonate (0.102 g, 0.314 mmol) were mixed in 1,4-dioxane (30 mL)/water (10 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (0.035 g, 33.9%) in a white foam solid form.

$^1$H NMR (400 MHz, $CDCl_3$) δ 9.21 (dd, J=2.2, 0.6 Hz, 1H), 8.37~8.32 (m, 2H), 7.72~7.71 (m, 1H), 7.66~7.63 (m, 1H), 7.53~7.42 (m, 3H), 7.32~7.29 (m, 1H), 7.25~7.20 (m, 1H), 7.07 (s, 0.25H), 6.94 (s, 0.5H), 6.81 (s, 0.25H), 5.42 (s, 2H), 1.76 (s, 6H); LRMS (ES) m/z 493.4 ($M^+$+1).

Synthesis of Compound 104, 2-((5-(5-(difluoromethyl)-1,3,4-oxadiazole-2-yl)pyridine-2-yl)methyl)-4,4-dimethyl-6-(pyridine-3-yl)isoquinoline-1,3(2H,4H)-dione

[Step 1] Synthesis of the Compound 104

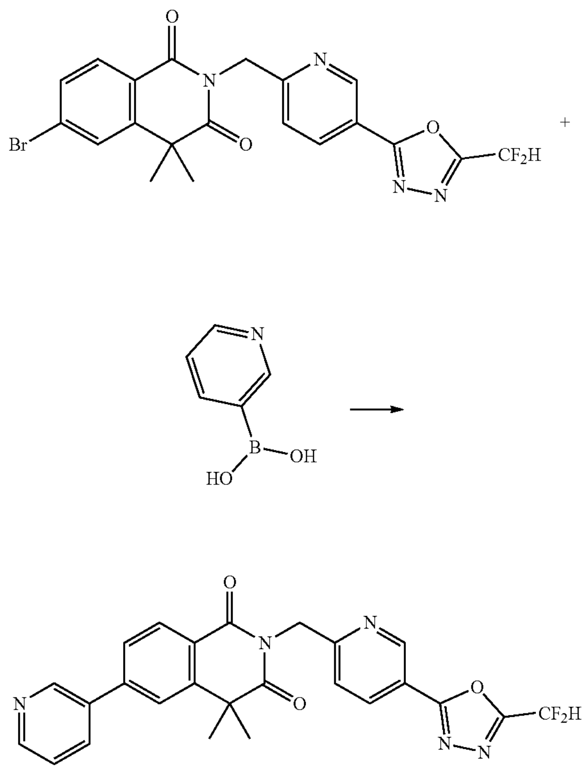

The 6-bromo-2-((5-(5-(difluoromethyl)-1,3,4-oxadiazole-2-yl)pyridine-2-yl)methyl)-4,4-dim ethylisoquinoline-1,3(2H,4H)-dione (0.100 g, 0.210 mmol) prepared in the step 6 of the compound 97, pyridine-3-ylboronic acid (0.039 g, 0.314 mmol), [1,1'-bis(di-tert-butylphosphino)ferrocene] palladium(II) dichloride ($Pd(dtbpf)Cl_2$, 0.014 g, 0.021 mmol) and cesium carbonate (0.102 g, 0.314 mmol) were mixed in 1,4-dioxane (30 mL)/water (10 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (0.010 g, 10.0%) in a colorless oil form.

$^1$H NMR (400 MHz, $CDCl_3$) δ 9.21 (d, J=1.6 Hz, 1H), 8.93 (dd, J=2.3, 0.7 Hz, 1H), 8.72 (dd, J=4.8, 1.6 Hz, 1H), 8.39~8.35 (m, 2H), 7.97~7.94 (m, 1H), 7.71~7.69 (m, 2H), 7.50~7.45 (m, 2H), 7.07 (s, 0.25H), 6.94 (s, 0.5H), 6.81 (s, 0.25H), 5.47 (s, 2H), 1.78 (s, 6H); LRMS (ES) m/z 476.3 ($M^+$+1).

Synthesis of Compound 105, 2-((5-(5-(difluoromethyl)-1,3,4-oxadiazole-2-yl)pyridine-2-yl)methyl)-4,4-dimethyl-6-(pyridine-4-yl)isoquinoline-1,3(2H,4H)-dione

[Step 1] Synthesis of the Compound 105

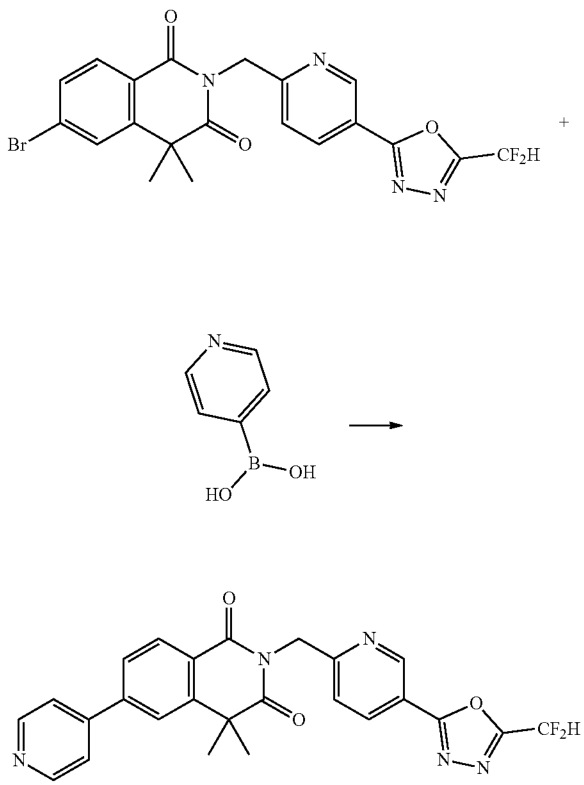

The 6-bromo-2-((5-(5-(difluoromethyl)-1,3,4-oxadiazole-2-yl)pyridine-2-yl)methyl)-4,4-dim ethylisoquinoline-1,3(2H,4H)-dione (0.100 g, 0.210 mmol) prepared in the step 6 of the compound 97, pyridine-4-ylboronic acid (0.039 g, 0.314 mmol), [1,1'-bis(di-tert-butylphosphino)ferrocene] palladium(II) dichloride ($Pd(dtbpf)Cl_2$, 0.014 g, 0.021 mmol) and cesium carbonate (0.102 g, 0.314 mmol) were mixed in 1,4-dioxane (6 mL)/water (2 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (0.040 g, 40.2%) in a white foam solid form.

$^1$H NMR (400 MHz, $CDCl_3$) δ 9.18 (dd, J=2.2, 0.7 Hz, 1H), 8.75 (d, J=6.0 Hz, 1H), 8.38~8.33 (m, 2H), 7.74~7.70 (m, 2H), 7.56~7.55 (m, 2H), 7.48 (dd, J=8.2, 0.6 Hz, 1H), 7.07 (s, 0.25H), 6.94 (s, 0.5H), 6.81 (s, 0.25H), 5.45 (s, 2H), 1.78 (s, 6H); LRMS (ES) m/z 476.4 ($M^+$+1).

Synthesis of Compound 106, 6'-bromo-2'-((5-(5-(difluoromethyl)-1,3,4-oxadiazole-2-yl)pyridine-2-yl)methyl)-1'H-spiro[cyclobutane-1,4'-isoquinoline]-1',3'(2'H)-dione

[Step 1] Synthesis of methyl 4-bromo-2-(1-(methoxycarbonyl)cyclobutyl)benzoate

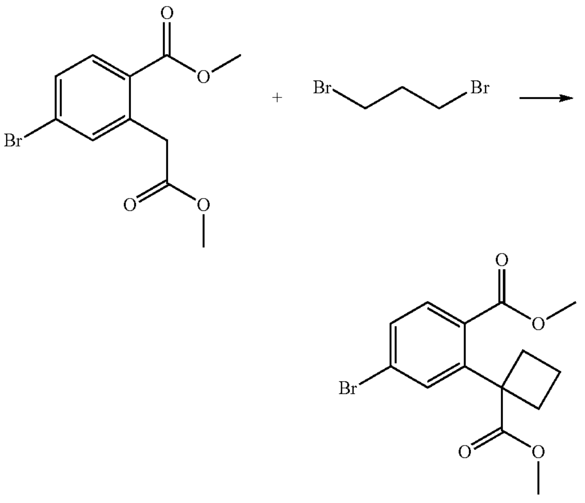

Methyl 4-bromo-2-(2-methoxy-2-oxoethyl)benzoate (2.500 g, 8.707 mmol) was dissolved in N,N-dimethylformamide (30 mL) at 0° C., after which sodium hydride (60.00%, 1.045 g, 26.122 mmol) was added into the resulting solution, and stirred at the same temperature for 30 minutes. 1,3-dibromopropane (1.758 g, 8.707 mmol) was added into the reaction mixture, and further stirred at room temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (1.100 g, 38.6%) in a white solid form.

[Step 2] Synthesis of 4-bromo-2-(1-carboxycyclobutyl)benzoic acid

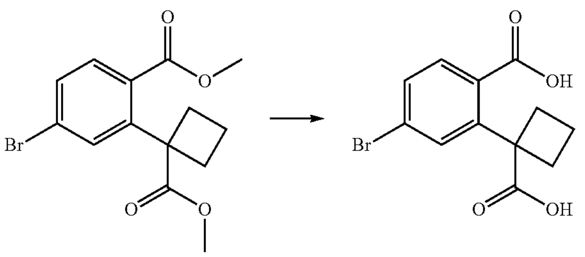 [SMILES: COC(=O)c1ccc(Br)cc1C1(C(=O)OC)CCC1 ; O=C(O)c1ccc(Br)cc1C1(C(=O)O)CCC1]

The methyl 4-bromo-2-(1-(methoxycarbonyl)cyclobutyl) benzoate (1.100 g, 3.362 mmol) prepared in the step 1 and potassium hydroxide (1.886 g, 33.622 mmol) were dissolved in methanol (10 mL)/water (10 mL) at 80° C., after which the resulting solution was stirred at the same temperature for 18 hours, and then a reaction was finished by lowering the temperature to room temperature. 1N-hydrochloric acid aqueous solution (20 mL) was put into the reaction mixture and stirred, after which a precipitated solid was filtered, then washed with hexane, and then dried to obtain a title compound (0.840 g, 83.5%) in a white solid form.

[Step 3] Synthesis of 6'-bromo-1'H-spiro[cyclobutane-1,4'-isoquinoline]-1',3'(2'H)-dione

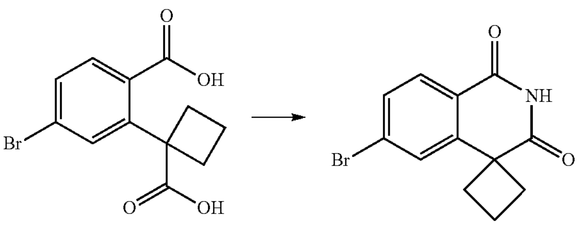 [SMILES: O=C(O)c1ccc(Br)cc1C1(C(=O)O)CCC1 ; O=C1NC(=O)C2(CCC2)c2cc(Br)ccc21]

The 4-bromo-2-(1-carboxycyclobutyl)benzoic acid (0.840 g, 2.808 mmol) prepared in the step 2 and urea (0.186 g, 3.089 mmol) were mixed in N,N-dimethylformamide (10 mL), then irradiated with microwave, then heated at 150° C. for 45 minutes, and then a reaction was finished by lowering the temperature to room temperature. A precipitated solid was filtered, then washed with hexane, and then dried to obtain a title compound (0.700 g, 89.0%) in a white solid form.

[Step 4] Synthesis of the Compound 106

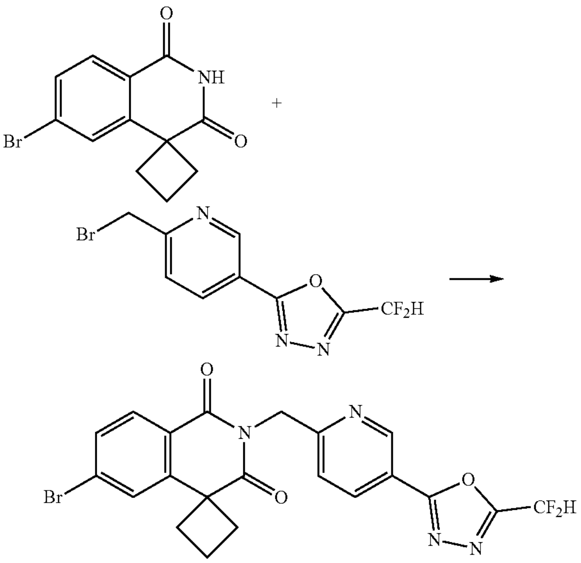

The 6'-bromo-1'H-spiro[cyclobutane-1,4'-isoquinoline]-1',3'(2'H)-dione (0.500 g, 1.785 mmol) prepared in the step 3, 2-(6-(bromomethyl)pyridine-3-yl)-5-(difluoromethyl)-1,3,4-oxadiazole (0.518 g, 1.785 mmol) and potassium carbonate (0.370 g, 2.677 mmol) were dissolved in N,N-dimethylformamide (10 mL) at 90° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.440 g, 50.4%) in a white foam solid form.

$^1$H NMR (400 MHz, $CDCl_3$) δ 9.19 (d, J=2.1 Hz, 1H), 8.36 (dd, J=8.2, 2.2 Hz, 1H), 8.09 (d, J=8.4 Hz, 1H), 8.00~7.98 (m, 1H), 7.62 (dd, J=8.4, 1.8 Hz, 1H), 7.48 (d, J=8.2 Hz, 1H), 7.06 (s, 0.25H), 6.93 (s, 0.5H), 6.80 (s, 0.25H), 5.45 (s, 2H), 3.06~2.99 (m, 2H), 2.55~2.45 (m, 2H), 2.44~2.29 (m, 2H).

Synthesis of Compound 107, 6'-bromo-2'-((5-(5-(difluoromethyl)-1,3,4-oxadiazole-2-yl)pyridine-2-yl)methyl)-1'H-spiro[cyclohexane-1,4'-isoquinoline]-1',3'(2'H)-dione

[Step 1] Synthesis of methyl 4-bromo-2-(1-(methoxycarbonyl)cyclohexyl)benzoate

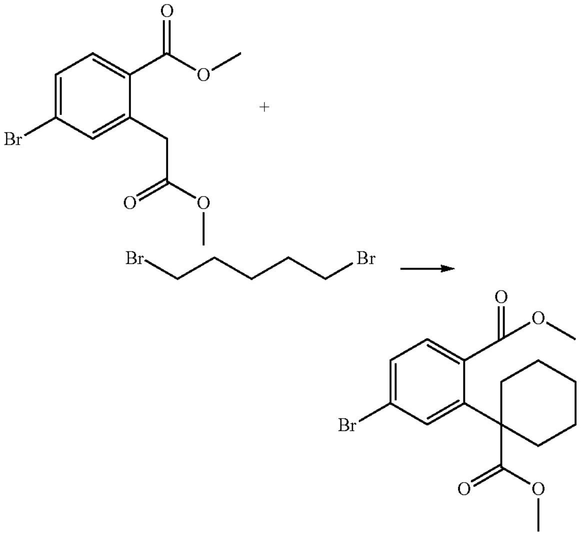

Methyl 4-bromo-2-(2-methoxy-2-oxoethyl)benzoate (2.500 g, 8.707 mmol) was dissolved in N,N-dimethylformamide (30 mL) at 0° C., after which sodium hydride (60.00%, 1.045 g, 26.122 mmol) was added into the resulting solution, and stirred at the same temperature for 30 minutes. 1,5-dibromopentane (2.002 g, 8.707 mmol) was added into the reaction mixture, and further stirred at room temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 30%), and concentrated to obtain a title compound (1.000 g, 32.3%) in a colorless oil form.

[Step 2] Synthesis of 4-bromo-2-(1-carboxycyclohexyl)benzoic acid

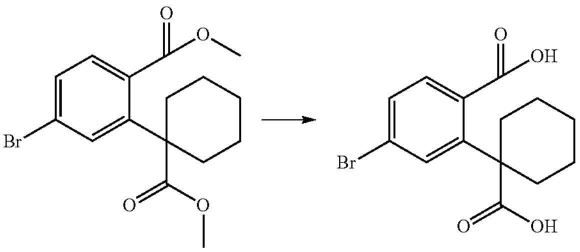 [SMILES: COC(=O)c1ccc(Br)cc1C1(C(=O)OC)CCCCC1 ; O=C(O)c1ccc(Br)cc1C1(C(=O)O)CCCCC1]

The methyl 4-bromo-2-(1-(methoxycarbonyl)cyclohexyl) benzoate (1.000 g, 2.815 mmol) prepared in the step 1 and potassium hydroxide (1.579 g, 28.151 mmol) were dissolved in methanol (10 mL)/water (10 mL) at 80° C., after which the resulting solution was stirred at the same temperature for 18 hours, and then a reaction was finished by lowering the temperature to room temperature. 1N-hydrochloric acid aqueous solution (20 mL) was put into the reaction mixture and stirred, after which a precipitated solid was filtered, then washed with hexane, and then dried to obtain a title compound (0.894 g, 97.1%) in a white solid form.

[Step 3] Synthesis of 6'-bromo-1'H-spiro[cyclohexane-1,4'-isoquinoline]-1',3'(2'H)-dione

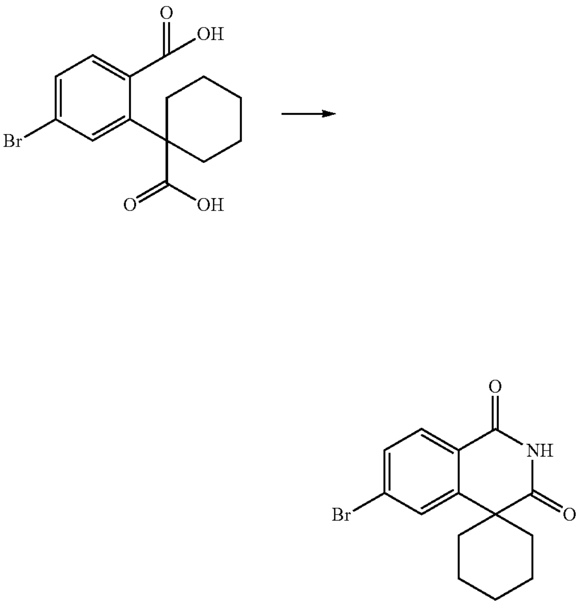

The 4-bromo-2-(1-carboxycyclohexyl)benzoic acid (0.890 g, 2.720 mmol) prepared in the step 2 and urea (0.180 g, 2.992 mmol) were mixed in N,N-dimethylformamide (10 mL), then irradiated with microwave, then heated at 150° C. for 45 minutes, and then a reaction was finished by lowering the temperature to room temperature. A precipitated solid was filtered, then washed with hexane, and then dried to obtain a title compound (0.347 g, 41.4%) in a white solid form.

[Step 4] Synthesis of the Compound 107

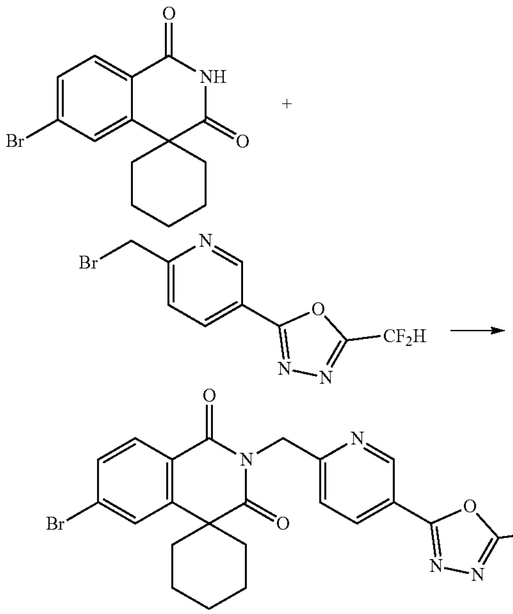

The 6'-bromo-1'H-spiro[cyclohexane-1,4'-isoquinoline]-1',3'(2'H)-dione (0.370 g, 1.201 mmol) prepared in the step 3, 2-(6-(bromomethyl)pyridine-3-yl)-5-(difluoromethyl)-1,3,4-oxadiazole (0.348 g, 1.201 mmol) and potassium carbonate (0.249 g, 1.801 mmol) were dissolved in N,N-dimethylformamide (10 mL) at 90° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.200 g, 32.2%) in a yellow solid form.

$^1H$ NMR (400 MHz, $CDCl_3$) δ 9.18~9.17 (m, 1H), 8.35 (dd, J=8.2, 2.2 Hz, 1H), 8.09 (d, J=8.4 Hz, 1H), 7.77 (d, J=1.8 Hz, 1H), 7.59 (dd, J=8.4, 1.8 Hz, 1H), 7.47 (dd, J=8.2, 0.5 Hz, 1H), 7.07 (s, 0.25H), 6.94 (s, 0.5H), 6.81 (s, 0.25H), 5.37 (s, 2H), 2.17~2.14 (m, 2H), 2.07~1.80 (m, 6H), 1.79~1.66 (m, 2H).

Synthesis of Compound 108, 2-((5-(5-(difluoromethyl)-1,3,4-oxadiazole-2-yl)pyridine-2-yl)methyl)-7-(3-fluorophenyl)-4,4-dimethylisoquinoline-1,3(2H,4H)-dione

[Step 1] Synthesis of the Compound 108

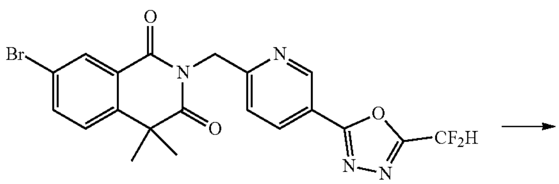

-continued

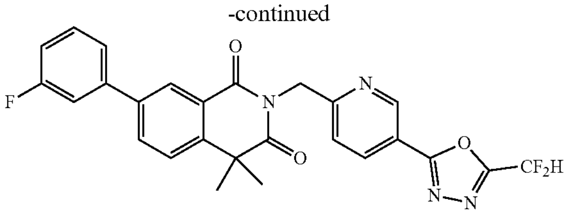

7-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), (3-fluorophenyl)boronic acid (0.035 g, 0.251 mmol), [1,1'-bis(di-tert-butylphosphino)ferrocene]palladium(II) dichloride (Pd(dtbpf)$Cl_2$, 0.007 g, 0.010 mmol) and cesium carbonate (0.205 g, 0.629 mmol) were mixed in 1,4-dioxane (1.5 mL)/water (0.5 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 40%), and concentrated to obtain a title compound (0.066 g, 64.0%) in a light brown solid form.

$^1H$ NMR (400 MHz, $CDCl_3$) δ 9.19 (d, J=1.3 Hz, 1H), 8.47 (d, J=1.8 Hz, 1H), 8.35 (dd, J=8.2, 2.1 Hz, 1H), 7.89 (dd, J=8.2, 2.0 Hz, 1H), 7.62 (d, J=8.2 Hz, 1H), 7.50~7.43 (m, 3H), 7.34 (d, J=10.1 Hz, 1H), 7.11~6.81 (m, 2H), 5.47 (s, 2H), 1.75 (s, 6H); LRMS (ES) m/z 493.3 ($M^+$+1).

Synthesis of Compound 109, 2-((5-(5-(difluoromethyl)-1,3,4-oxadiazole-2-yl)pyridine-2-yl)methyl)-7-(2-fluorophenyl)-4,4-dimethylisoquinoline-1,3(2H,4H)-dione

[Step 1] Synthesis of the Compound 109

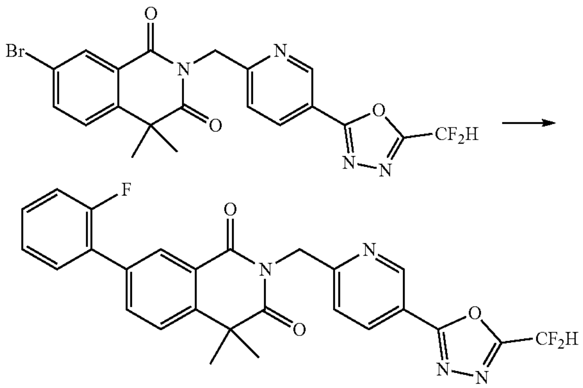

7-bromo-2-((5-(5-(difluoromethyl)-1,3,4-oxadiazole-2-yl)pyridine-2-yl)methyl)-4,4-dimethylisoquinoline-1,3(2H,4H)-dione (0.100 g, 0.210 mmol), (2-fluorophenyl)boronic acid (0.035 g, 0.251 mmol), [1,1'-bis(di-tert-butylphosphino)ferrocene]palladium(II) dichloride (Pd(dtbpf)$Cl_2$, 0.007 g, 0.010 mmol) and cesium carbonate (0.205 g, 0.629 mmol) were mixed in 1,4-dioxane (1.5 mL)/water (0.5 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 40%), and concentrated to obtain a title compound (0.057 g, 55.2%) in a light brown solid form.

$^1H$ NMR (400 MHz, $CDCl_3$) δ 9.19 (d, J=1.8 Hz, 1H), 8.43 (s, 1H), 8.35~8.33 (m, 1H), 7.91~7.88 (m, 1H), 7.61 (d, J=8.2 Hz, 1H), 7.52~7.46 (m, 2H), 7.38~7.35 (m, 1H), 7.28~7.16 (m, 2H), 7.07~6.81 (m, 1H), 5.46 (s, 2H), 1.75 (s, 6H); LRMS (ES) m/z 493.3 ($M^+$+1).

Synthesis of Compound 110, 2-((5-(5-(difluoromethyl)-1,3,4-oxadiazole-2-yl)pyridine-2-yl)methyl)-4,4-dimethyl-7-(pyridine-4-yl)isoquinoline-1,3(2H, 4H)-dione

[Step 1] Synthesis of the Compound 110

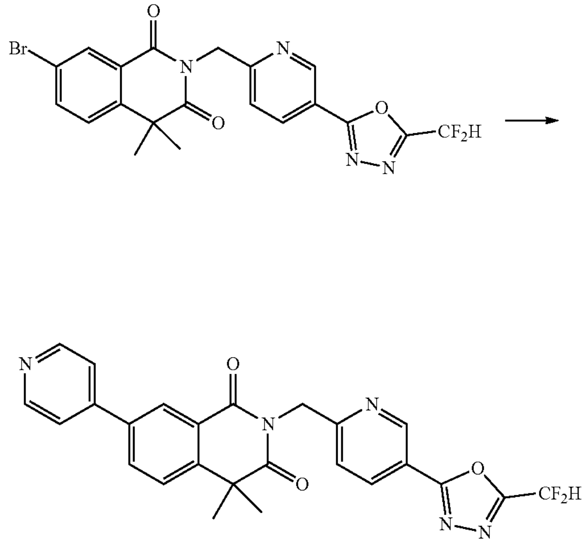

7-bromo-2-((5-(5-(difluoromethyl)-1,3,4-oxadiazole-2-yl)pyridine-2-yl)methyl)-4,4-dimethylisoquinoline-1,3(2H, 4H)-dione (0.100 g, 0.210 mmol), pyridine-4-ylboronic acid (0.031 g, 0.251 mmol), [1,1'-bis(di-tert-butylphosphino)ferrocene]palladium(II) dichloride (Pd(dtbpf)$Cl_2$, 0.007 g, 0.010 mmol) and cesium carbonate (0.205 g, 0.629 mmol) were mixed in 1,4-dioxane (1.5 mL)/water (0.5 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=10 to 60%), and concentrated to obtain a title compound (0.047 g, 47.2%) in a white solid form.

$^1H$ NMR (400 MHz, $CDCl_3$) δ 9.18 (d, J=2.0 Hz, 1H), 8.72 (d, J=4.6 Hz, 2H), 8.55 (d, J=2.0 Hz, 1H), 8.35 (dd, J=8.2, 2.2 Hz, 1H), 7.96 (dd, J=8.2, 2.1 Hz, 1H), 7.67 (d, J=8.2 Hz, 1H), 7.59 (d, J=4.9 Hz, 2H), 7.49 (d, J=8.2 Hz, 1H), 7.06~6.80 (m, 1H), 5.47 (s, 2H), 1.75 (s, 6H); LRMS (ES) m/z 476.2 ($M^+$+1).

Synthesis of Compound 111, 2-((5-(5-(difluoromethyl)-1,3,4-oxadiazole-2-yl)pyridine-2-yl)methyl)-4,4-dimethyl-7-(pyridine-3-yl)isoquinoline-1,3(2H, 4H)-dione

[Step 1] Synthesis of the Compound 111

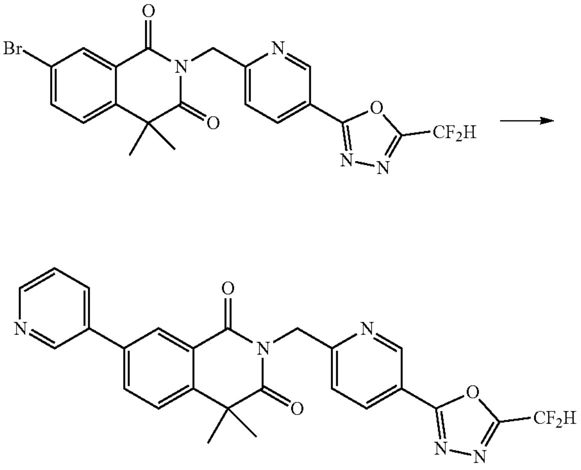

7-bromo-2-((5-(5-(difluoromethyl)-1,3,4-oxadiazole-2-yl)pyridine-2-yl)methyl)-4,4-dimethylisoquinoline-1,3(2H, 4H)-dione (0.100 g, 0.210 mmol), pyridine-3-ylboronic acid (0.031 g, 0.251 mmol), [1,1'-bis(di-tert-butylphosphino)ferrocene]palladium(II) dichloride (Pd(dtbpf)$Cl_2$, 0.007 g, 0.010 mmol) and cesium carbonate (0.205 g, 0.629 mmol) were mixed in 1,4-dioxane (1.5 mL)/water (0.5 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=10 to 60%), and concentrated to obtain a title compound (0.042 g, 42.2%) in a white solid form.

$^1H$ NMR (400 MHz, $CDCl_3$) δ 9.17 (d, J=2.0 Hz, 1H), 8.90 (d, J=1.3 Hz, 1H), 8.64 (d, J=4.1 Hz, 1H), 8.47 (d, J=2.0 Hz, 1H), 8.34 (dd, J=8.2, 2.2 Hz, 1H), 7.96~7.89 (m, 2H), 7.65 (d, J=8.2 Hz, 1H), 7.48 (d, J=8.2 Hz, 1H), 7.43~7.39 (m, 1H), 7.06~6.80 (m, 1H), 5.45 (s, 2H), 1.74 (s, 6H); LRMS (ES) m/z 476.4 ($M^+$+1).

Synthesis of Compound 112, 2-((5-(5-(difluoromethyl)-1,3,4-oxadiazole-2-yl)pyridine-2-yl)methyl)-7-(furan-3-yl)-4, 4-dimethylisoquinoline-1,3(2H, 4H)-dione

[Step 1] Synthesis of the Compound 112

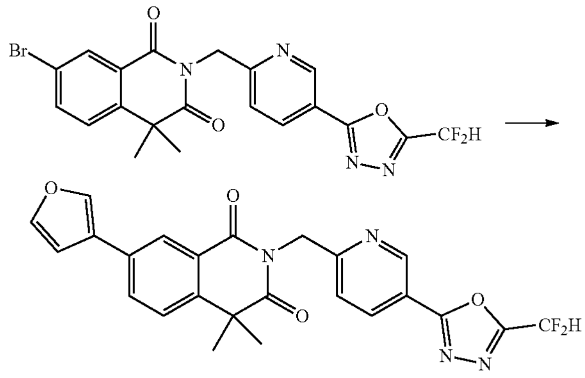

7-bromo-2-((5-(5-(difluoromethyl)-1,3,4-oxadiazole-2-yl)pyridine-2-yl)methyl)-4,4-dimethylisoquinoline-1,3(2H, 4H)-dione (0.100 g, 0.210 mmol), furan-2-ylboronic acid (0.028 g, 0.251 mmol), [1,1'-bis(di-tert-butylphosphino)ferrocene]palladium(II) dichloride (Pd(dtbpf)$Cl_2$, 0.007 g, 0.010 mmol) and cesium carbonate (0.205 g, 0.629 mmol) were mixed in 1,4-dioxane (1.5 mL)/water (0.5 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 40%), and concentrated to obtain a title compound (0.050 g, 51.4%) in a brown solid form.

$^1H$ NMR (400 MHz, $CDCl_3$) δ 9.19 (d, J=1.8 Hz, 1H), 8.37~8.34 (m, 2H), 7.84 (s, 1H), 7.80 (dd, J=8.2, 2.0 Hz, 1H), 7.55~7.52 (m, 2H), 7.47 (d, J=8.2 Hz, 1H), 7.06~6.78 (m, 2H), 5.46 (s, 2H), 1.72 (s, 6H); LRMS (ES) m/z 465.2 ($M^+$+1).

Synthesis of Compound 113, 2-((5-(5-(difluoromethyl)-1,3,4-oxadiazole-2-yl)pyridine-2-yl)methyl)-7-(furan-2-yl)-4, 4-dimethylisoquinoline-1,3(2H, 4H)-dione

[Step 1] Synthesis of the Compound 113

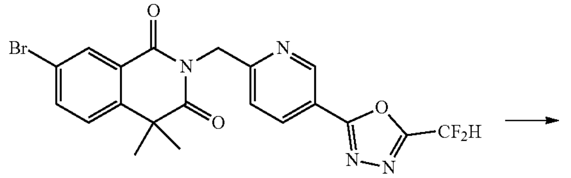

-continued

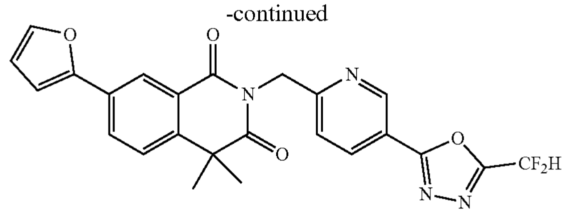

7-bromo-2-((5-(5-(difluoromethyl)-1,3,4-oxadiazole-2-yl)pyridine-2-yl)methyl)-4,4-dimethylisoquinoline-1,3(2H, 4H)-dione (0.100 g, 0.210 mmol), furan-3-ylboronic acid (0.028 g, 0.251 mmol), [1,1'-bis(di-tert-butylphosphino)ferrocene]palladium(II) dichloride (Pd(dtbpf)$Cl_2$, 0.007 g, 0.010 mmol) and cesium carbonate (0.205 g, 0.629 mmol) were mixed in 1,4-dioxane (1.5 mL)/water (0.5 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 40%), and concentrated to obtain a title compound (0.050 g, 51.4%) in a light brown solid form.

$^1H$ NMR (400 MHz, $CDCl_3$) δ 9.20 (d, J=1.7 Hz, 1H), 8.52 (d, J=1.9 Hz, 1H), 8.35 (dd, J=8.2, 2.2 Hz, 1H), 7.98 (dd, J=8.3, 2.0 Hz, 1H), 7.56~7.46 (m, 2H), 7.47 (d, J=8.2 Hz, 1H), 7.06~6.78 (m, 2H), 6.53~6.52 (m, 1H), 5.46 (s, 2H), 1.72 (s, 6H); LRMS (ES) m/z 465.3 ($M^+$+1).

Synthesis of Compound 114, 2-((5-(5-(difluoromethyl)-1,3,4-oxadiazole-2-yl)pyridine-2-yl)methyl)-4,4-dimethyl-7-(5-methylfuran-2-yl)isoquinoline-1,3(2H,4H)-dione

[Step 1] Synthesis of the Compound 114

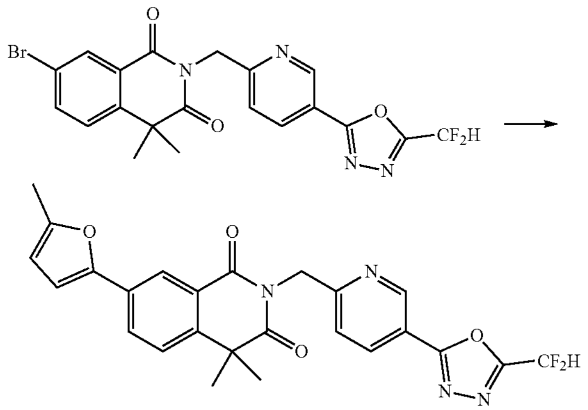

7-bromo-2-((5-(5-(difluoromethyl)-1,3,4-oxadiazole-2-yl)pyridine-2-yl)methyl)-4,4-dimethylisoquinoline-1,3(2H, 4H)-dione (0.100 g, 0.210 mmol), 4,4,5,5-tetramethyl-2-(5-methylfuran-2-yl)-1,3,2-dioxaborolane (0.052 g, 0.251 mmol), [1,1'-bis(di-tert-butylphosphino)ferrocene]palladium(II) dichloride (Pd(dtbpf)$Cl_2$, 0.007 g, 0.010 mmol) and cesium carbonate (0.205 g, 0.629 mmol) were mixed in 1,4-dioxane (1.5 mL)/water (0.5 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 40%), and concentrated to obtain a title compound (0.053 g, 52.9%) in a light brown solid form.

$^1H$ NMR (400 MHz, $CDCl_3$) δ 9.19 (d, J=1.7 Hz, 1H), 8.46 (d, J=1.9 Hz, 1H), 8.35 (dd, J=8.2, 2.1 Hz, 1H), 7.92 (dd, J=8.3, 2.0 Hz, 1H), 7.51 (d, J=8.3 Hz, 1H), 7.47 (d, J=8.2 Hz, 1H), 7.06~6.80 (m, 1H), 6.67 (d, J=3.2 Hz, 1H), 6.10~6.09 (m, 1H), 5.46 (s, 2H), 2.39 (s, 3H), 1.71 (s, 6H); LRMS (ES) m/z 479.2 ($M^+$+1).

Synthesis of Compound 115, 2-((5-(5-(difluoromethyl)-1,3,4-oxadiazole-2-yl)pyridine-2-yl)methyl)-7-(1H-indole-4-yl)-4,4-dimethylisoquinoline-1,3(2H, 4H)-dione

[Step 1] Synthesis of the Compound 115

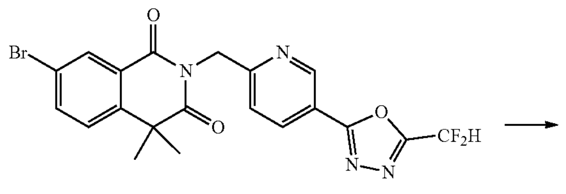

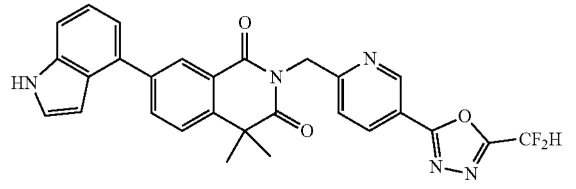

7-bromo-2-((5-(5-(difluoromethyl)-1,3,4-oxadiazole-2-yl)pyridine-2-yl)methyl)-4,4-dimethylisoquinoline-1,3(2H, 4H)-dione (0.100 g, 0.210 mmol), (1H-indole-4-yl)boronic acid (0.040 g, 0.251 mmol), [1,1'-bis(di-tert-butylphosphino)ferrocene]palladium(II) dichloride (Pd(dtbpf)$Cl_2$, 0.007 g, 0.010 mmol) and cesium carbonate (0.205 g, 0.629 mmol) were mixed in 1,4-dioxane (1.5 mL)/water (0.5 mL) at room temperature, after which the resulting mixture was irradiated with microwave, then heated at 100° C. for 20 minutes, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 50%), and concentrated to obtain a title compound (0.045 g, 41.8%) in a white solid form.

$^1H$ NMR (400 MHz, $CDCl_3$) δ 9.22 (d, J=1.7 Hz, 1H), 8.62 (d, J=1.9 Hz, 1H), 8.49 (brs, 1H), 8.34 (dd, J=8.2, 2.1 Hz, 1H), 8.05 (dd, J=8.2, 2.0 Hz, 1H), 7.65 (d, J=8.2 Hz, 1H), 7.48~7.44 (m, 2H), 7.32~7.24 (m, 3H), 7.06~6.80 (m, 1H), 6.75~6.74 (m, 1H), 5.49 (s, 2H), 1.79 (s, 6H); LRMS (ES) m/z 514.3 ($M^+$+1).

Synthesis of Compound 116, tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-7-yl)piperazine-1-carboxylate

[Step 1] Synthesis of tert-butyl 4-(4-(1-methoxy-2-methyl-1-oxopropane-2-yl)-3-(methoxycarbonyl)phenyl)piperazine-1-carboxylate

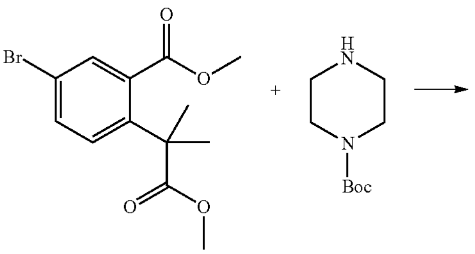

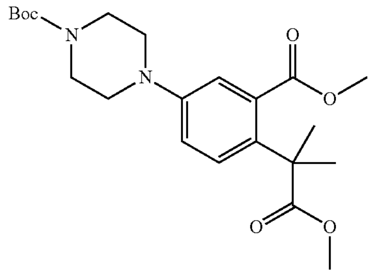

Methyl 5-bromo-2-(1-methoxy-2-methyl-1-oxopropane-2-yl)benzoate (4.990 g, 15.833 mmol), tert-butyl piperazine-1-carboxylate (3.834 g, 20.583 mmol), bis(tri-tert-butylphosphine)palladium (o, 0.809 g, 1.583 mmol) and cesium carbonate (12.897 g, 39.583 mmol) were dissolved in toluene (20 mL) at 100° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 80 g cartridge; ethyl acetate/dichloromethane=0 to 30%), and concentrated to obtain a title compound (2.020 g, 30.3%) in a yellow solid form.

[Step 2] Synthesis of 5-(4-(tert-butoxycarbonyl) piperazine-1-yl)-2-(2-carboxypropane-2-yl)benzoic acid

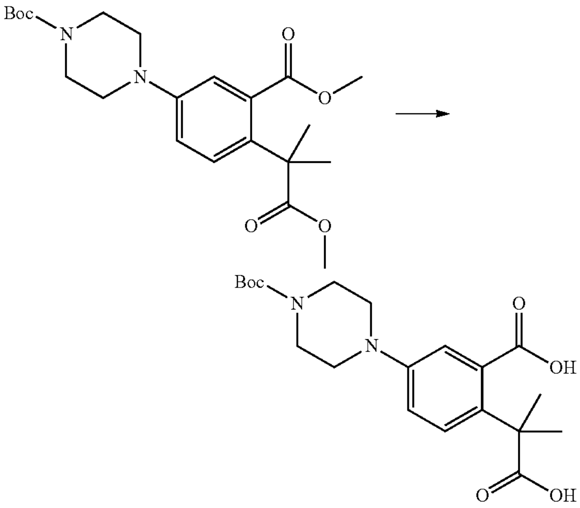

The tert-butyl 4-(4-(1-methoxy-2-methyl-1-oxopropane-2-yl)-3-(methoxycarbonyl)phenyl)piperazine-1-carboxylate (2.000 g, 4.756 mmol) prepared in the step 1 and potassium hydroxide (2.668 g, 47.561 mmol) were dissolved in methanol (30 mL)/water (30 mL) at 80° C., after which the resulting solution was stirred at the same temperature, and then a reaction was finished by lowering the temperature to room temperature. Solvent was removed from the reaction mixture under reduced pressure, after which 1N-hydrochloric acid aqueous solution was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. An obtained product was used without an additional purification process (1.500 g, 80.4%, white solid).

[Step 3] Synthesis of tert-butyl 4-(4,4-dimethyl-1,3-dioxo-1,2,3,4-tetrahydroisoquinoline-7-yl)piperazine-1-carboxylate

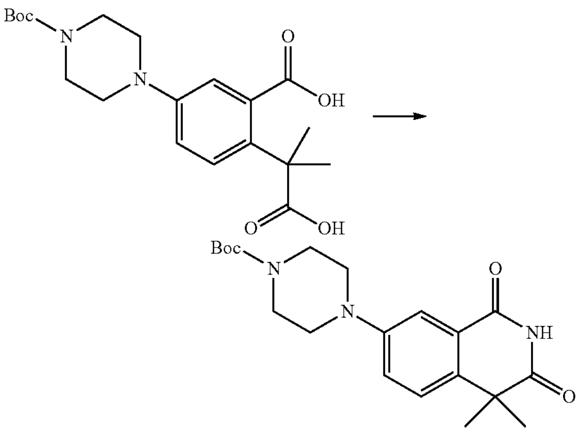

The 5-(4-(tert-butoxycarbonyl)piperazine-1-yl)-2-(2-carboxypropane-2-yl)benzoic acid (1.500 g, 3.822 mmol) prepared in the step 2 and urea (0.253 g, 4.204 mmol) were dissolved in N,N-dimethylformamide (20 mL), after which the resulting solution was stirred at 150° C. for 18 hours, then further stirred at the same temperature for 18 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 30%), and concentrated to obtain a title compound (0.530 g, 37.1%) in a yellow solid form.

[Step 4] Synthesis of the Compound 116

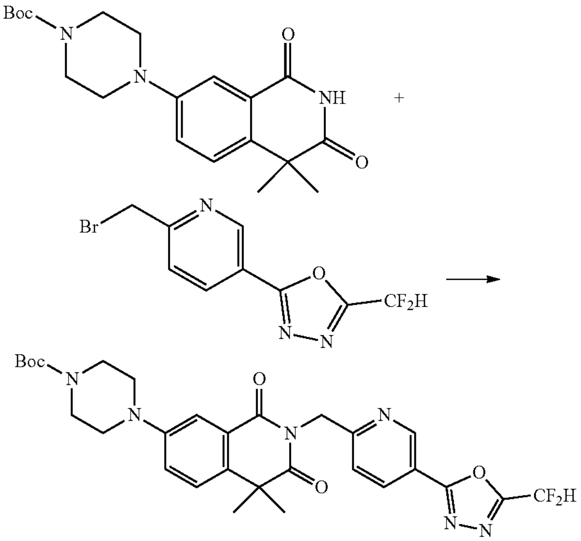

The tert-butyl 4-(4,4-dimethyl-1,3-dioxo-1,2,3,4-tetrahydroisoquinoline-7-yl)piperazine-1-carboxylate (0.420 g, 1.125 mmol) prepared in the step 3, 2-(6-(bromomethyl) pyridine-3-yl)-5-(difluoromethyl)-1,3,4-oxadiazole (0.359 g, 1.237 mmol) and potassium carbonate (0.311 g, 2.249 mmol) were dissolved in N,N-dimethylformamide (10 mL) at 90° C., after which the resulting solution was stirred at the same temperature for 18 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.400 g, 61.0%) in a yellow foam solid form.

$^1H$ NMR (400 MHz, $CDCl_3$) δ 9.20 (dd, J=2.2, 0.8 Hz, 1H), 8.34 (dd, J=8.2, 2.2 Hz, 1H), 7.73 (d, J=2.8 Hz, 1H), 7.45~7.40 (m, 2H), 7.28~7.27 (m, 1H), 7.07 (s, 0.25H), 6.93 (s, 0.5H), 6.80 (s, 0.25H), 5.45 (s, 2H), 3.62~3.59 (m, 4H), 3.24~3.22 (m, 4H), 1.66 (s, 6H), 1.50 (s, 9H).

Synthesis of Compound 117, 2'-((5-(5-(difluoromethyl)-1,3,4-oxadiazole-2-yl)pyridine-2-yl)methyl)-6'-(4-ethylpiperazine-1-yl)-1'H-spiro[cyclobutane-1,4'-isoquinoline]-1',3'(2'H)-dione

[Step 1] Synthesis of the Compound 117

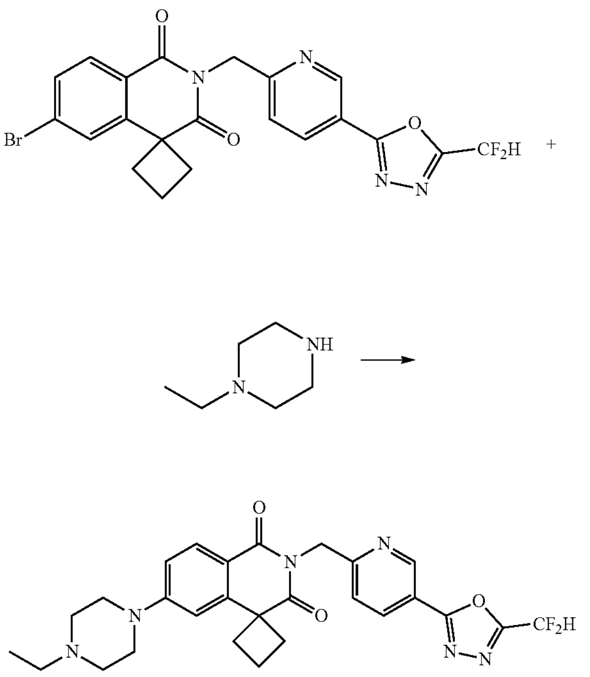

The 6'-bromo-2'-((5-(5-(difluoromethyl)-1,3,4-oxadiazole-2-yl)pyridine-2-yl)methyl)-1'H-spiro[cyclobutane-1,4'-isoquinoline]-1',3'(2'H)-dione (0.138 g, 0.282 mmol) prepared in the step 4 of the compound 106, 1-ethylpiperazine (0.064 g, 0.564 mmol), acetic acid palladium (II, 0.006 g, 0.028 mmol), ruphos (0.013 g, 0.028 mmol) and potassium carbonate (0.230 g, 0.705 mmol) were dissolved in toluene (10 mL) at 100° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.020 g, 13.6%) in a white foam solid form.

$^1H$ NMR (400 MHz, $CDCl_3$) δ 9.21 (d, J=1.8 Hz, 1H), 8.32 (dd, J=8.2, 2.3 Hz, 1H), 8.08 (d, J=8.9 Hz, 1H), 7.42 (d, J=8.2 Hz, 1H), 7.19 (d, J=2.3 Hz, 1H), 7.06 (s, 0.25H), 6.95 (dd, J=9.7, 3.0 Hz, 1H), 6.93 (s, 0.5H), 6.80 (s, 0.25H), 5.42 (s, 2H), 3.51~3.48 (m, 4H), 3.03~2.96 (m, 2H), 2.68~2.63 (m, 4H), 2.55~2.21 (m, 6H), 1.17~1.13 (m, 3H); LRMS (ES) m/z 523.3 ($M^+$+1).

Synthesis of Compound 118, 2-((5-(5-(difluoromethyl)-1,3,4-oxadiazole-2-yl)pyridine-2-yl)methyl)-4,4-dimethyl-7-(4-methylpiperazine-1-yl)isoquinoline-1,3(2H,4H)-dione

[Step 1] Synthesis of 2-((5-(5-(difluoromethyl)-1,3,4-oxadiazole-2-yl)pyridine-2-yl)methyl)-4,4-dimethyl-7-(piperazine-1-yl)isoquinoline-1,3(2H,4H)-dione 2,2,2-trifluoroacetate

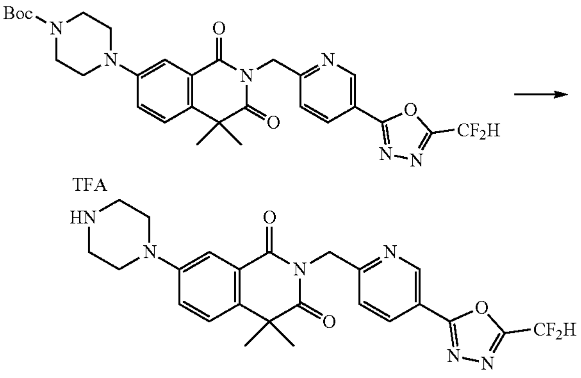

Tert-butyl 4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-7-yl)piperazine-1-carboxylate (0.400 g, 0.687 mmol) and trifluoroacetic acid (0.526 mL, 6.866 mmol) were dissolved in dichloromethane (10 mL) at room temperature, after which the resulting solution was stirred at the same temperature for 18 hours. Solvent was removed from the reaction mixture under reduced pressure, after which an obtained product was used without an additional purification process (0.400 g, 97.7%, yellow oil).

[Step 2] Synthesis of the Compound 118

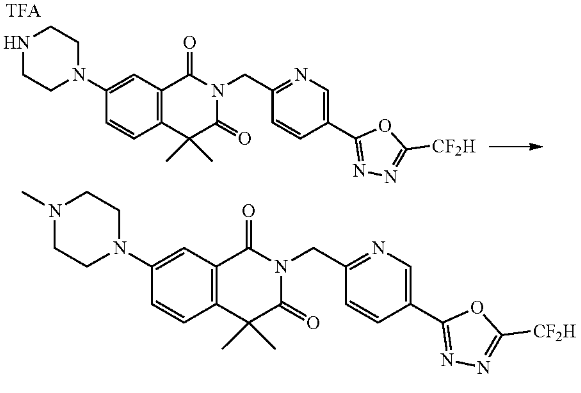

The 2-((5-(5-(difluoromethyl)-1,3,4-oxadiazole-2-yl)pyridine-2-yl)methyl)-4,4-dimethyl-7-(piperazine-1-yl)isoquinoline-1,3(2H,4H)-dione 2,2,2-trifluoroacetate (0.200 g, 0.335 mmol) prepared in the step 1, formaldehyde (0.020 g, 0.671 mmol), sodium triacetoxyborohydride (0.142 g, 0.671 mmol) and N,N-diisopropylethylamine (0.058 mL, 0.335 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.110 g, 66.1%) in a white foam solid form.

$^1$H NMR (400 MHz, $CDCl_3$) δ 9.18 (d, J=2.1 Hz, 1H), 8.32 (dd, J=8.2, 2.2 Hz, 1H), 7.71 (d, J=2.8 Hz, 1H), 7.43~7.37 (m, 2H), 7.25 (dd, J=8.7, 2.8 Hz, 1H), 7.06 (s, 0.25H), 6.93 (s, 0.5H), 6.80 (s, 0.25H), 5.42 (s, 2H), 3.30 (t, J=5.0 Hz, 4H), 2.61 (t, J=5.0 Hz, 4H), 2.36 (s, 3H), 1.64 (s, 6H); LRMS (ES) m/z 497.4 ($M^+$+1).

Synthesis of Compound 119, 2-((5-(5-(difluoromethyl)-1,3,4-oxadiazole-2-yl)pyridine-2-yl)methyl)-7-(4-isopropylpiperazine-1-yl)-4,4-dimethylisoquinoline-1,3(2H,4H)-dione

[Step 1] Synthesis of the Compound 119

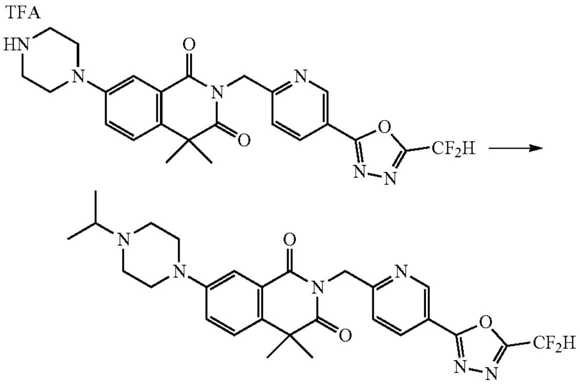

2-((5-(5-(difluoromethyl)-1,3,4-oxadiazole-2-yl)pyridine-2-yl)methyl)-4,4-dimethyl-7-(piperazine-1-yl)isoquinoline-1,3(2H,4H)-dione 2,2,2-trifluoroacetate (0.200 g, 0.335 mmol), acetone (0.039 g, 0.671 mmol), sodium triacetoxyborohydride (0.142 g, 0.671 mmol) and N,N-diisopropylethylamine (0.058 mL, 0.335 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.130 g, 73.9%) in a white foam solid form.

$^1$H NMR (400 MHz, $CDCl_3$) δ 9.20~9.19 (m, 1H), 8.33 (dd, J=8.2, 2.3 Hz, 1H), 7.72 (d, J=2.8 Hz, 1H), 7.44~7.38 (m, 2H), 7.26 (dd, J=8.7, 2.8 Hz, 1H), 7.06 (s, 0.25H), 6.93 (s, 0.5H), 6.80 (s, 0.25H), 5.42 (s, 2H), 3.32 (t, J=5.0 Hz, 4H), 2.81~2.78 (m, 1H), 2.75 (t, J=5.0 Hz, 4H), 1.65 (s, 6H), 1.13 (d, J=6.5 Hz, 6H); LRMS (ES) m/z 525.4 ($M^+$+1).

Synthesis of Compound 120, tert-butyl 4-(3-((5-(5-(difluoromethyl)-1,3,4-oxadiazole-2-yl)pyridine-2-yl)methyl)-1-methyl-2,4-dioxo-1,2,3,4-tetrahydroquinazoline-7-yl)-3,6-dihydropyridine-1(2H)-carboxylate

[Step 1] Synthesis of the Compound 120

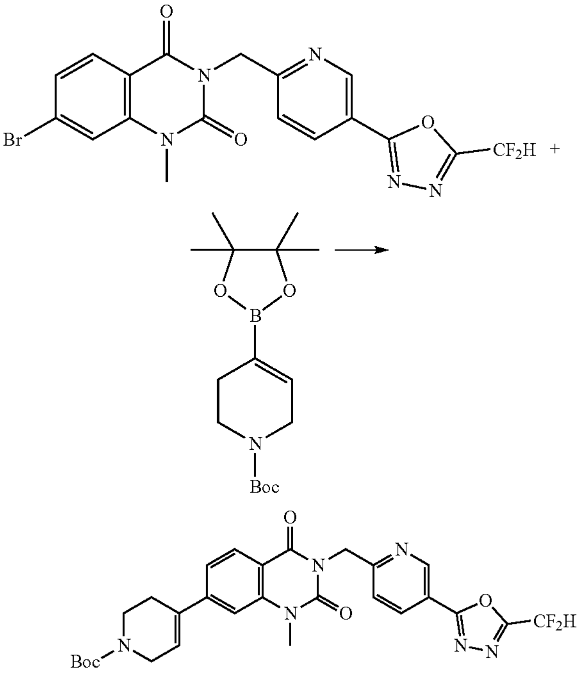

7-bromo-3-((5-(5-(difluoromethyl)-1,3,4-oxadiazole-2-yl)pyridine-2-yl)methyl)-1-methylquinazoline-2,4(1H,3H)-dione (0.729 g, 1.570 mmol), tert-butyl 4-(4,4,5,5-tetramethyl-1,3,2-dioxaborolane-2-yl)-3,6-dihydropyridine-1(2H)-carboxylat e (0.728 g, 2.356 mmol), [1,1'-bis(di-tert-butylphosphino)ferrocene]palladium(II) dichloride (Pd $(dtbpf)Cl_2$, 0.102 g, 0.157 mmol) and cesium carbonate (0.767 g, 2.356 mmol) were mixed in 1,4-dioxane (9 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 80%), and concentrated to obtain a title compound (0.700 g, 78.7%) in a colorless oil form.

$^1$H NMR (400 MHz, $CDCl_3$) δ 9.24~9.20 (m, 1H), 8.35 (dd, J=8.2, 2.2 Hz, 1H), 8.21 (d, J=8.3 Hz, 1H), 7.50 (dd, J=8.2, 0.8 Hz, 1H), 7.35~7.31 (m, 1H), 7.24 (d, J=2.2 Hz, 1H), 7.06 (s, 0.25H), 6.93 (s, 0.5H), 6.80 (s, 0.25H), 6.25~6.20 (m, 1H), 5.53 (s, 2H), 4.16~4.11 (m, 2H), 3.70~3.65 (m, 2H), 2.62~2.58 (m, 2H), 1.63 (s, 3H), 1.52 (s, 9H).

Synthesis of Compound 121, 2-((5-(5-(difluoromethyl)-1,3,4-oxadiazole-2-yl)pyridine-2-yl)methyl)-7-(3,6-dihydro-2H-thiopyran-4-yl)-4,4-dimethylisoquinoline-1,3(2H,4H)-dione

[Step 1] Synthesis of the Compound 121

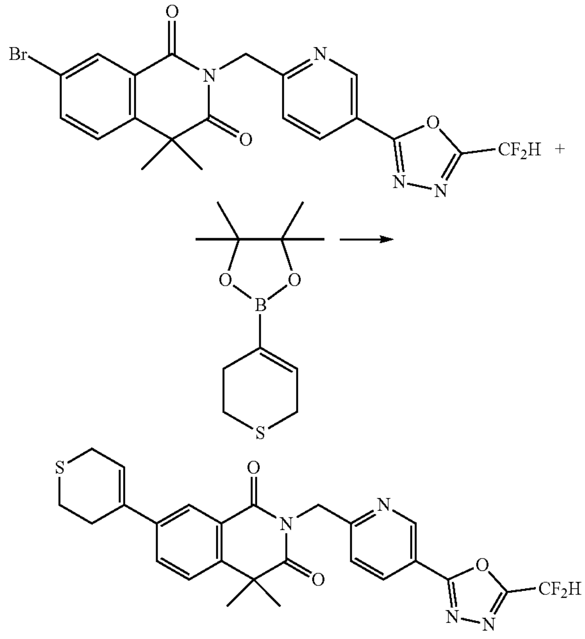

7-bromo-2-((5-(5-(difluoromethyl)-1,3,4-oxadiazole-2-yl)pyridine-2-yl)methyl)-4,4-dimethylisoquinoline-1,3(2H,4H)-dione (1.000 g, 2.095 mmol), 2-(3,6-dihydro-2H-thiopyran-4-yl)-4,4,5,5-tetramethyl-1,3,2-dioxaborolane (0.711 g, 3.143 mmol), [1,1'-bis(di-tert-butylphosphino)ferrocene] palladium(II) dichloride ($Pd(dtbpf)Cl_2$, 0.137 g, 0.210 mmol) and cesium carbonate (1.024 g, 3.143 mmol) were mixed in 1,4-dioxane (9 mL)/water (3 mL), after which the resulting mixture was irradiated with microwave, then heated at 100° C. for 20 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 70%), and concentrated to obtain a title compound (0.840 g, 80.7%) in a colorless oil form.

$^1H$ NMR (400 MHz, $CDCl_3$) δ 9.20 (d, J=1.4 Hz, 1H), 8.34~8.33 (m, 1H), 8.22 (d, J=2.1 Hz, 1H), 7.70~7.63 (m, 1H), 7.50~7.47 (m, 2H), 7.03 (s, 0.25H), 6.93 (s, 0.5H), 6.80 (s, 0.25H), 6.40~6.35 (m, 1H), 5.44 (s, 2H), 3.38~3.37 (m, 2H), 2.92~2.90 (m, 2H), 2.80~2.75 (m, 2H), 1.70 (s, 6H); LRMS (ES) m/z 497.0 ($M^+$+1).

Synthesis of Compound 122, 3-((5-(5-(difluoromethyl)-1,3,4-oxadiazole-2-yl)pyridine-2-yl)methyl)-1-methyl-7-(1,2,3,6-tetrahydropyridine-4-yl)quinazoline-2,4(1H,3H)-dione

[Step 1] Synthesis of the Compound 122

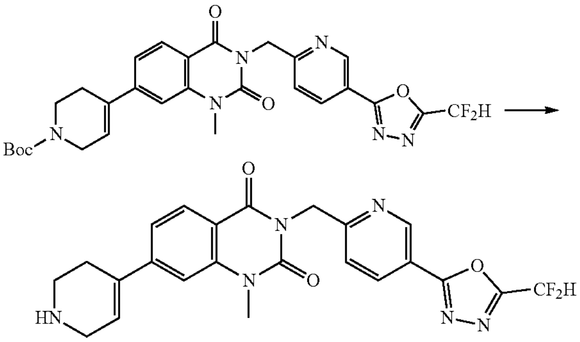

Tert-butyl 4-(3-((5-(5-(difluoromethyl)-1,3,4-oxadiazole-2-yl)pyridine-2-yl)methyl)-1-methyl-2,4-dioxo-1,2,3,4-tetrahydroquinazoline-7-yl)-3,6-dihydropyridine-1(2H)-carboxylate (0.720 g, 1.271 mmol) and trifluoroacetic acid (0.973 mL, 12.708 mmol) were dissolved in dichloromethane (10 mL) at room temperature, after which the resulting solution was stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. An obtained product was used without an additional purification process (0.700 g, 94.9%, white solid).

LRMS (ES) m/z 467.3 ($M^+$+1).

Synthesis of Compound 123, 2-((5-(5-(difluoromethyl)-1,3,4-oxadiazole-2-yl)pyridine-2-yl)methyl)-4,4-dimethyl-7-(1-oxydo-3,6-dihydro-2H-thiopyran-4-yl)isoquinoline-1,3(2H,4H)-dione

[Step 1] Synthesis of the Compound 123

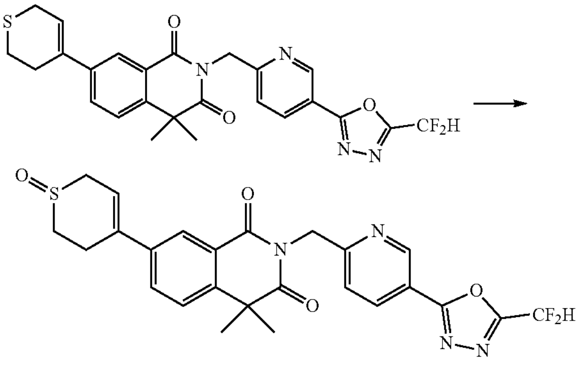

2-((5-(5-(difluoromethyl)-1,3,4-oxadiazole-2-yl)pyridine-2-yl)methyl)-7-(3,6-dihydro-2H-thiopyran-4-yl)-4,4-dimethylisoquinoline-1,3(2H,4H)-dione (0.730 g, 1.470 mmol) and 3-chloroperbenzoic acid (77.00%, 0.329 g, 1.470 mmol) were dissolved in dichloromethane (10 mL) at 0° C., after which the resulting solution was stirred at the same temperature for 1 hour. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 70%), and concentrated to obtain a title compound (0.300 g, 39.8%) in a white solid form.

$^1$H NMR (400 MHz, $CDCl_3$) δ 9.20 (dd, J=2.1, 0.7 Hz, 1H), 8.36 (dd, J=8.2, 2.2 Hz, 1H), 8.27 (d, J=2.0 Hz, 1H), 7.71 (dd, J=8.3, 2.2 Hz, 1H), 7.53 (d, J=8.3 Hz, 1H), 7.48 (dd, J=8.2, 0.7 Hz, 1H), 7.06 (s, 0.25H), 6.93 (s, 0.5H), 6.80 (s, 0.25H), 6.07~6.05 (m, 1H), 5.45 (s, 2H), 3.63~3.54 (m, 2H), 3.30~3.20 (m, 2H), 3.00~2.97 (m, 1H), 2.85~2.80 (m, 1H), 1.71 (s, 6H); LRMS (ES) m/z 513.3 ($M^+$+1).

Synthesis of Compound 124, 3-((5-(5-(difluoromethyl)-1,3,4-oxadiazole-2-yl)pyridine-2-yl)methyl)-7-(1-isopropyl-1,2,3,6-tetrahydropyridine-4-yl)-1-methylquinazoline-2,4(1H,3H)-dione

[Step 1] Synthesis of the Compound 124

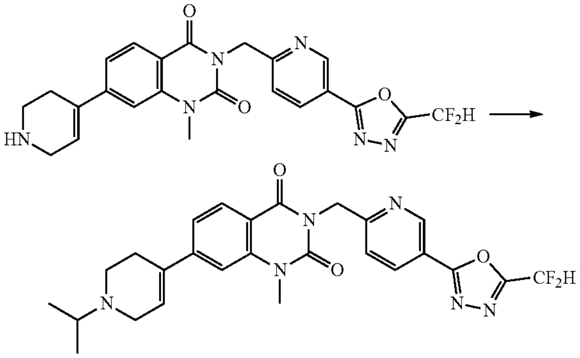

3-((5-(5-(difluoromethyl)-1,3,4-oxadiazole-2-yl)pyridine-2-yl)methyl)-1-methyl-7-(1,2,3,6-tetrahydropyridine-4-yl)quinazoline-2,4(1H,3H)-dione 2,2,2-trifluoroacetate (0.450 g, 0.775 mmol), acetone (0.090 g, 1.550 mmol), sodium triacetoxyborohydride (0.329 g, 1.550 mmol) and N,N-diisopropylethylamine (0.135 mL, 0.775 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.200 g, 50.7%) in a white foam solid form.

$^1$H NMR (400 MHz, $CDCl_3$) δ 9.21 (dd, J=2.2, 0.8 Hz, 1H), 8.33 (dd, J=8.2, 2.2 Hz, 1H), 8.18 (d, J=8.3 Hz, 1H), 7.49 (dd, J=8.3, 0.8 Hz, 1H), 7.32 (dd, J=8.3, 1.5 Hz, 1H), 7.25 (d, J=38.7 Hz, 1H), 7.06 (s, 0.25H), 6.93 (s, 0.5H), 6.80 (s, 0.25H), 6.28~6.27 (m, 1H), 5.51 (s, 2H), 3.65 (s, 3H), 3.48~3.46 (m, 2H), 3.12~3.09 (m, 1H), 2.98~2.95 (m, 2H), 2.74~2.72 (m, 2H), 1.22 (d, J=6.6 Hz, 6H); LRMS (ES) m/z 509.4 ($M^+$+1).

Synthesis of Compound 125, N-(4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-7-yl)-1-oxydo-3,6-dihydro-2H-1λ$^6$-thiopyran-1-ylidene)-2,2,2-trifluoroacetamide

[Step 1] Synthesis of the Compound 125

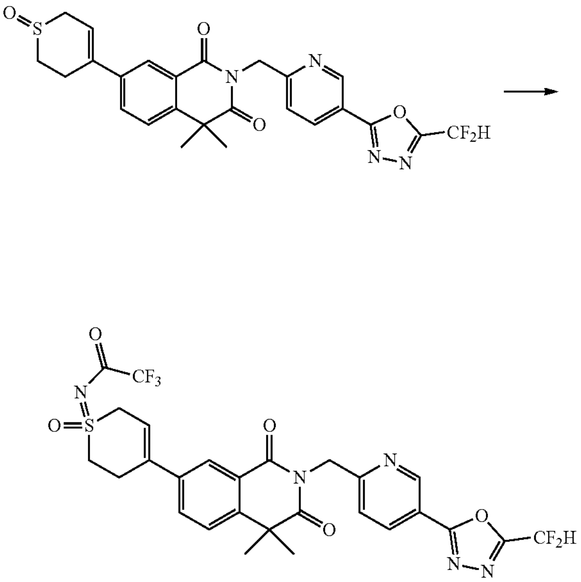

2-((5-(5-(difluoromethyl)-1,3,4-oxadiazole-2-yl)pyridine-2-yl)methyl)-4,4-dimethyl-7-(1-oxydo-3,6-dihydro-2H-thiopyran-4-yl)isoquinoline-1,3(2H,4H)-dione (0.157 g, 0.306 mmol), 2,2,2-trifluoroacetamide (0.069 g, 0.613 mmol), iodobenzene diacetate (0.148 g, 0.459 mmol), magnesium oxide (0.049 g, 1.225 mmol) and rhodium (II) acetate dimer (0.014 g, 0.031 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.100 g, 52.4%) in a violet oil form.

$^1$H NMR (400 MHz, $CDCl_3$) δ 9.20 (s, 1H), 8.38 (dd, J=8.2, 2.2 Hz, 1H), 8.26 (d, J=2.1 Hz, 1H), 7.68 (dd, J=8.3, 2.2 Hz, 1H), 7.57 (d, J=8.2 Hz, 1H), 7.49 (dd, J=8.3, 0.7 Hz, 1H), 7.07 (s, 0.25H), 6.94 (s, 0.5H), 6.81 (s, 0.25H), 6.05~6.03 (m, 2H), 5.46 (s, 2H), 4.58~4.56 (m, 1H), 4.22~4.19 (m, 1H), 3.84~3.82 (m, 1H), 3.68~3.64 (m, 1H), 3.28~3.26 (m, 2H), 1.76 (s, 6H); LRMS (ES) m/z 624.3 ($M^+$+1).

Synthesis of Compound 126, 2-((5-(5-(difluoromethyl)-1,3,4-oxadiazole-2-yl)pyridine-2-yl)methyl)-7-(1-imino-1-oxydo-1,2,3,6-tetrahydro-1λ$^6$-thiopyran-4-yl)-4,4-dimethylisoquinoline-1,3(2H,4H)-dione

[Step 1] Synthesis of the Compound 126

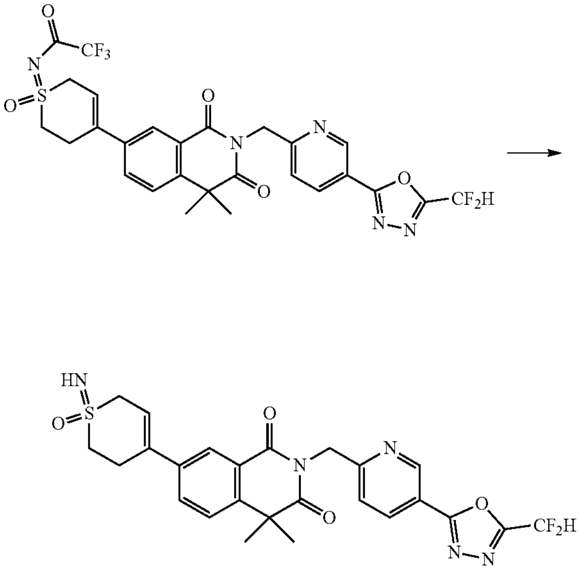

N-(4-(2-((5-(5-(difluoromethyl)-1,3,4-oxadiazole-2-yl)pyridine-2-yl)methyl)-4,4-dimethyl-1,3-dioxo-1,2,3,4-tetrahydroisoquinoline-7-yl)-1-oxydo-3,6-dihydro-2H-1λ$^6$-thiopyran-1-ylidene)-2,2,2-trifluoroacetamide (0.100 g, 0.160 mmol) and potassium carbonate (0.066 g, 0.481 mmol) were dissolved in methanol (5 mL) at room temperature, after which the resulting solution was stirred at the same temperature for 3 hours. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.010 g, 11.8%) in a white solid form.

$^1$H NMR (400 MHz, $CDCl_3$) δ 9.33~9.31 (m, 1H), 8.49~8.45 (m, 1H), 8.31~8.22 (m, 1H), 7.74~7.69 (m, 1H), 7.56~7.42 (m, 2H), 7.17 (s, 1H), 7.07 (s, 1H), 6.92 (s, 1H), 6.08~6.07 (m, 1H), 5.56 (s, 2H), 4.30~4.25 (m, 1H), 4.05~4.01 (m, 1H), 3.94 (s, 1H), 3.71~3.67 (m, 1H), 3.50~3.47 (m, 1H), 3.26~3.22 (m, 2H), 1.68 (s, 6H); LRMS (ES) m/z 528.22 ($M^+$+1).

Synthesis of Compound 127, 7-(1-acetylpiperidine-4-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 127

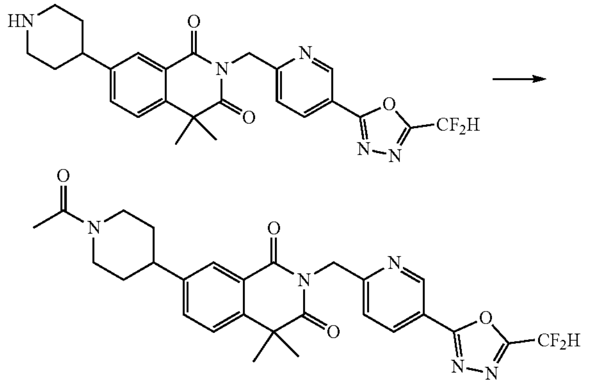

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione (0.100 g, 0.208 mmol) and triethylamine (0.058 mL, 0.415 mmol) were dissolved in dichloromethane (4 mL) at 0° C., after which acetic anhydride (0.029 mL, 0.312 mmol) was added into the resulting solution and stirred at room temperature for 18 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=40 to 90%), and concentrated to obtain a title compound (0.042 g, 38.6%) in a white solid form.

$^1$H NMR (400 MHz, $CDCl_3$) δ 9.19 (d, J=1.6 Hz, 1H), 8.35 (dd, J=8.2, 2.2 Hz, 1H), 8.10 (d, J=1.8 Hz, 1H), 7.54~7.45 (m, 3H), 7.06~6.81 (m, 1H), 5.44 (s, 2H), 4.83 (d, J=11.4 Hz, 1H), 3.98 (d, J=11.7 Hz, 1H), 3.21 (td, J=13.0, 2.2 Hz, 1H), 2.90~2.84 (m, 1H), 2.70~2.63 (m, 1H), 2.16 (s, 3H), 1.95 (t, J=14.7 Hz, 2H), 1.73~1.66 (m, 8H); LRMS (ES) m/z 524.4 ($M^+$+1).

Synthesis of Compound 128, 2-((5-(5-(difluoromethyl)-1,3,4-oxadiazole-2-yl)pyridine-2-yl)methyl)-4,4-dimethyl-7-(1-(methylsulfonyl)piperidine-4-yl) isoquinoline-1,3(2H,4H)-dione

[Step 1] Synthesis of the Compound 128

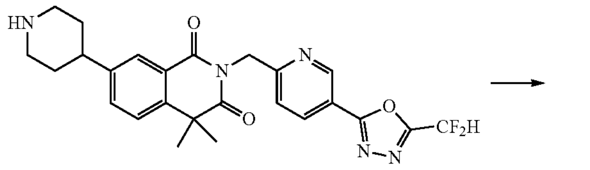

-continued

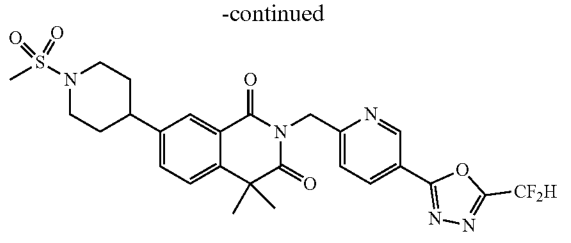

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione (0.100 g, 0.208 mmol) and triethylamine (0.058 mL, 0.415 mmol) were dissolved in dichloromethane (4 mL) at 0° C., after which methanesulfonyl chloride (0.024 mL, 0.312 mmol) was added into the resulting solution and stirred at room temperature for 18 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=30 to 70%), and concentrated to obtain a title compound (0.036 g, 31.0%) in a white solid form.

$^1H$ NMR (400 MHz, $CDCl_3$) δ 9.19 (d, J=1.6 Hz, 1H), 8.35 (dd, J=8.2, 2.2 Hz, 1H), 8.11 (d, J=1.9 Hz, 1H), 7.56~7.46 (m, 3H), 7.06~6.81 (m, 1H), 5.45 (s, 2H), 3.99 (d, J=11.9 Hz, 2H), 2.85~2.72 (m, 6H), 2.03~2.00 (m, 2H), 1.95~1.88 (m, 2H), 1.70 (s, 6H); LRMS (ES) m/z 560.4 ($M^+$+1).

Synthesis of Compound 129, 2-((5-(5-(difluoromethyl)-1,3,4-oxadiazole-2-yl)pyridine-2-yl)methyl)-7-(4-ethylpiperazine-1-yl)-4,4-dimethylisoquinoline-1,3(2H,4H)-dione

[Step 1] Synthesis of the Compound 129

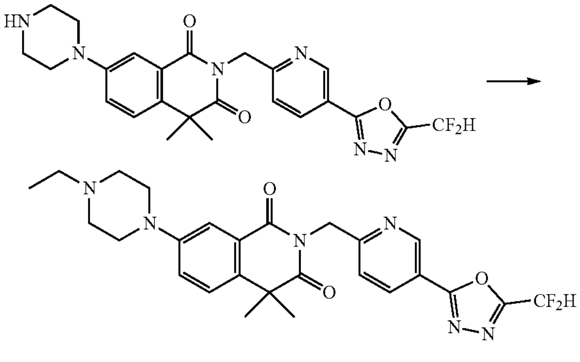

2-((5-(5-(difluoromethyl)-1,3,4-oxadiazole-2-yl)pyridine-2-yl)methyl)-4,4-dimethyl-7-(piperazine-1-yl)isoquinoline-1,3(2H,4H)-dione (0.116 g, 0.240 mmol), acetaldehyde (0.021 g, 0.481 mmol) and sodium triacetoxyborohydride (0.102 g, 0.481 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.060 g, 48.9%) in a white foam solid form.

$^1H$ NMR (400 MHz, $CDCl_3$) δ 9.18 (dd, J=2.2, 0.8 Hz, 1H), 8.33 (dd, J=8.2, 2.2 Hz, 1H), 7.71 (d, J=2.8 Hz, 1H), 7.43~7.37 (m, 2H), 7.25 (dd, J=8.7, 2.8 Hz, 1H), 7.06 (s, 0.25H), 6.93 (s, 0.5H), 6.80 (s, 0.25H), 5.42 (s, 2H), 3.33 (t, J=5.1 Hz, 4H), 2.70 (t, J=5.1 Hz, 4H), 2.56~2.54 (m, 2H), 1.16 (t, J=7.2 Hz, 3H); LRMS (ES) m/z 511.3 ($M^+$+1).

Synthesis of Compound 130, 2-((5-(5-(difluoromethyl)-1,3,4-oxadiazole-2-yl) pyridine-2-yl) methyl)-4,4-dimethyl-7-(4-propylpiperazine-1-yl) isoquinoline-1,3(2H,4H)-dione

[Step 1] Synthesis of the Compound 130

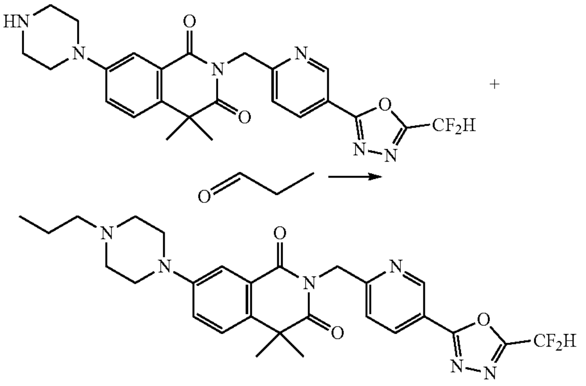

2-((5-(5-(difluoromethyl)-1,3,4-oxadiazole-2-yl) pyridine-2-yl) methyl)-4,4-dimethyl-7-(piperazine-1-yl) isoquinoline-1,3(2H,4H)-dione (0.100 g, 0.207 mmol), propionaldehyde (0.024 g, 0.415 mmol) and sodium triacetoxyborohydride (0.088 g, 0.415 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.050 g, 46.0%) in a white foam solid form.

$^1H$ NMR (400 MHz, $CDCl_3$) δ 9.19 (dd, J=2.2, 0.6 Hz, 1H), 8.33 (dd, J=8.2, 2.2 Hz, 1H), 7.71 (d, J=2.8 Hz, 1H), 7.44~7.38 (m, 2H), 7.25 (dd, J=8.7, 2.8 Hz, 1H), 7.06 (s, 0.25H), 6.93 (s, 0.5H), 6.80 (s, 0.25H), 3.32 (t, J=5.1 Hz, 4H), 2.68 (t, J=5.0 Hz, 4H), 2.40~2.40 (m, 2H), 1.66 (s, 6H), 1.65~1.57 (m, 2H), 0.94 (t, J=7.4 Hz, 3H); LRMS (ES) m/z 525.5 ($M^+$+1).

Synthesis of Compound 131, 2-((5-(5-(difluoromethyl)-1,3,4-oxadiazole-2-yl)pyridine-2-yl)methyl)-7-(4-isobutylpiperazine-1-yl)-4,4-dimethylisoquinoline-1,3(2H,4H)-dione

[Step 1] Synthesis of the Compound 131

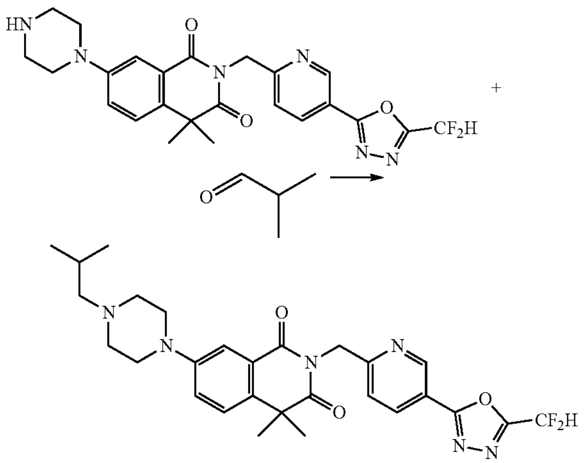

2-((5-(5-(difluoromethyl)-1,3,4-oxadiazole-2-yl)pyridine-2-yl)methyl)-4,4-dimethyl-7-(piperazine-1-yl)isoquinoline-1,3(2H,4H)-dione (0.100 g, 0.207 mmol), isobutyraldehyde (0.030 g, 0.415 mmol) and sodium triacetoxyborohydride (0.088 g, 0.415 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.060 g, 53.7%) in a white foam solid form.

$^1H$ NMR (400 MHz, $CDCl_3$) δ 9.19 (dd, J=2.2, 0.8 Hz, 1H), 8.33 (dd, J=8.2, 2.2 Hz, 1H), 7.71 (d, J=2.8 Hz, 1H), 7.43~7.37 (m, 2H), 7.25 (dd, J=8.8, 2.8 Hz, 1H), 7.06 (s, 0.25H), 6.93 (s, 0.5H), 6.80 (s, 0.25H), 5.42 (s, 2H), 3.28 (t, J=5.0 Hz, 4H), 2.58 (t, J=5.0 Hz, 4H), 2.17~2.15 (m, 2H), 1.90~1.85 (m, 1H), 1.66 (s, 6H), 0.94~0.91 (m, 6H); LRMS (ES) m/z 539.5 ($M^+$+1).

Synthesis of Compound 132, 2-((5-(5-(difluoromethyl)-1,3,4-oxadiazole-2-yl)pyridine-2-yl)methyl)-7-(4-isopentylpiperazine-1-yl)-4,4-dimethylisoquinoline-1,3(2H,4H)-dione

[Step 1] Synthesis of the Compound 132

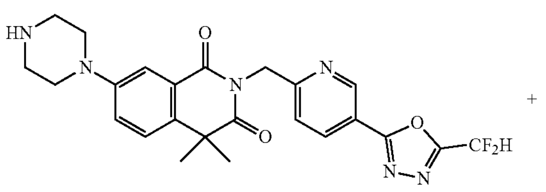

-continued

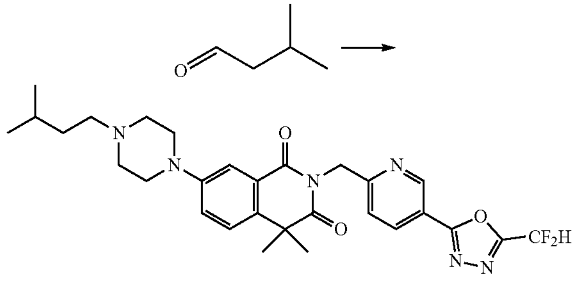

2-((5-(5-(difluoromethyl)-1,3,4-oxadiazole-2-yl)pyridine-2-yl)methyl)-4,4-dimethyl-7-(piperazine-1-yl)isoquinoline-1,3(2H,4H)-dione (0.100 g, 0.207 mmol), 3-methylbutanal (0.036 g, 0.415 mmol) and sodium triacetoxyborohydride (0.088 g, 0.415 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.060 g, 52.4%) in a white foam solid form.

$^1H$ NMR (400 MHz, $CDCl_3$) δ 9.18 (d, J=2.2 Hz, 1H), 8.32 (dd, J=8.2, 2.3 Hz, 1H), 7.70 (d, J=2.8 Hz, 1H), 7.43~7.37 (m, 2H), 7.24 (dd, J=8.7, 2.8 Hz, 1H), 7.06 (s, 0.25H), 6.93 (s, 0.5H), 6.80 (s, 0.25H), 5.41 (s, 2H), 3.33 (t, J=5.0 Hz, 4H), 2.73 (t, J=5.0 Hz, 4H), 2.51~2.47 (m, 2H), 1.66 (s, 6H), 1.48~1.46 (m, 2H), 0.94~0 0.91 (m, 6H); LRMS (ES) m/z 553.4 ($M^+$+1).

Synthesis of Compound 133, 2-((5-(5-(difluoromethyl)-1,3,4-oxadiazole-2-yl)pyridine-2-yl)methyl)-4,4-dimethyl-7-(4-(2,2,2-trifluoroethyl)piperazine-1-yl)isoquinoline-1,3(2H,4H)-dione

[Step 1] Synthesis of the Compound 133

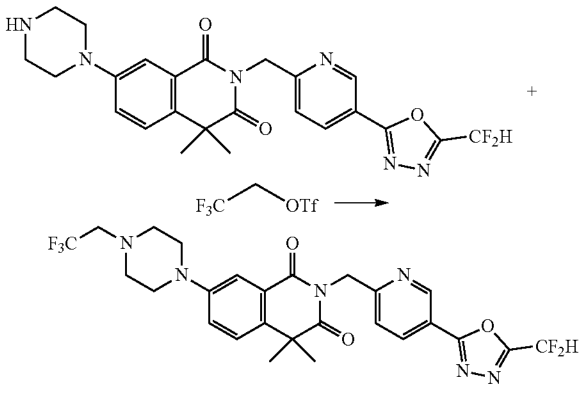

2-((5-(5-(difluoromethyl)-1,3,4-oxadiazole-2-yl)pyridine-2-yl)methyl)-4,4-dimethyl-7-(piperazine-1-yl)isoquinoline-1,3(2H,4H)-dione (0.130 g, 0.269 mmol), 2,2,2-trifluoroethyl trifluoromethanesulfonate (0.081 g, 0.350 mmol)

and potassium carbonate (0.074 g, 0.539 mmol) were dissolved in acetonitrile (10 mL) at room temperature, after which the resulting solution was stirred at the same temperature for 18 hours. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.100 g, 65.7%) in a white foam solid form.

$^1$H NMR (400 MHz, $CDCl_3$) δ 9.20 (dd, J=2.2, 0.8 Hz, 1H), 8.35 (dd, J=8.2, 2.2 Hz, 1H), 7.73 (d, J=2.8 Hz, 1H), 7.45~7.40 (m, 2H), 7.27~7.25 (m, 1H), 7.06 (s, 1H), 6.93 (s, 1H), 6.80 (s, 1H), 5.43 (s, 2H), 3.32 (t, J=5.0 Hz, 4H), 3.07 (dd, J=19.1, 9.5 Hz, 2H), 2.88 (t, J=5.0 Hz, 4H), 1.67 (s, 6H); LRMS (ES) m/z 565.5 ($M^+$+1).

Synthesis of Compound 134, 2-((5-(5-(difluoromethyl)-1,3,4-oxadiazole-2-yl)pyridine-2-yl)methyl)-7-(1-(2-hydroxyacetyl)piperidine-4-yl)-4,4-dimethylisoquinoline-1,3(2H,4H)-dione

[Step 1] Synthesis of the Compound 134

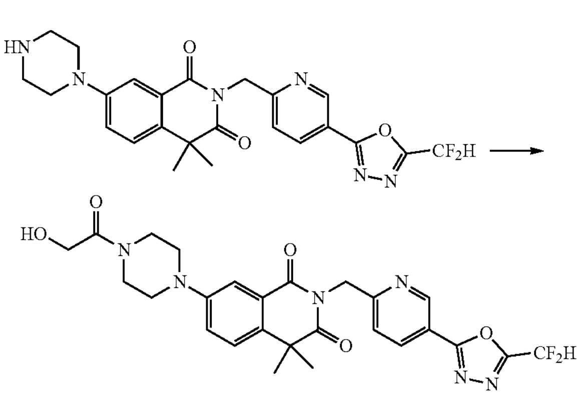

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione (0.100 g, 0.208 mmol), 2-hydroxyacetic acid (0.032 g, 0.415 mmol), 1-[bis(dimethylamino)methylene]-1H-1,2,3-triazolo[4,5-b]pyridinium 3-oxide hexafluorophosphate (HATU, 0.158 g, 0.415 mmol) and N,N-diisopropylethylamine (0.181 mL, 1.038 mmol) were dissolved in N,N-dimethylformamide (4 mL) at room temperature, after which the resulting solution was stirred at the same temperature for 18 hours. Solvent was removed from the reaction mixture under reduced pressure, after which the resulting concentrate was purified via column chromatography ($SiO_2$, 4 g cartridge; ethyl acetate/hexane=30 to 80%), and concentrated to obtain a product, after which the resulting product was purified again via chromatography ($SiO_2$ plate, 20×20×1 mm; ethyl acetate=100%), and concentrated to obtain a title compound (0.036 g, 32.1%) in a white solid form.

$^1$H NMR (400 MHz, $CDCl_3$) δ 9.19 (d, J=1.6 Hz, 1H), 8.35 (dd, J=8.2, 2.2 Hz, 1H), 8.10 (d, J=1.8 Hz, 1H), 7.54~7.46 (m, 3H), 7.06~6.81 (m, 1H), 5.44 (s, 2H), 4.80 (d, J=11.4 Hz, 1H), 4.24~4.15 (m, 2H), 3.76~3.64 (m, 2H), 3.16 (td, J=13.1, 2.3 Hz, 1H), 2.94~2.80 (m, 2H), 1.99 (d, J=12.8 Hz, 2H), 1.77~1.66 (m, 8H); LRMS (ES) m/z 540.5 ($M^+$+1).

Synthesis of Compound 135, 2-((5-(5-(difluoromethyl)-1,3,4-oxadiazole-2-yl)pyridine-2-yl)methyl)-4,4-dimethyl-7-(1-(2,2,2-trifluoroethyl)piperidine-4-yl)isoquinoline-1,3(2H,4H)-dione

[Step 1] Synthesis of the Compound 135

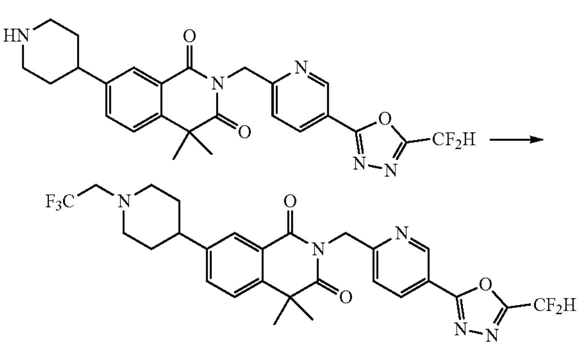

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione (0.100 g, 0.208 mmol), 2,2,2-trifluoroethyl trifluoromethanesulfonate (0.072 g, 0.312 mmol) and N,N-diisopropylethylamine (0.109 mL, 0.623 mmol) were dissolved in dichloromethane (4 mL) at room temperature, after which the resulting solution was stirred at the same temperature for 18 hours. Saturated sodium chloride aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=10 to 50%), and concentrated to obtain a title compound (0.032 g, 27.3%) in a colorless oil form.

$^1$H NMR (400 MHz, $CDCl_3$) δ 9.19 (d, J=1.8 Hz, 1H), 8.34 (dd, J=8.2, 2.2 Hz, 1H), 8.12 (d, J=1.9 Hz, 1H), 7.56 (dd, J=8.2, 2.0 Hz, 1H), 7.48~7.44 (m, 2H), 7.06~6.80 (m, 1H), 5.44 (s, 2H), 3.12 (d, J=11.6 Hz, 2H), 3.05 (q, J=9.7 Hz, 2H), 2.62~2.61 (m, 1H), 2.56~2.49 (m, 2H), 1.90~1.85 (m, 4H), 1.69 (s, 6H); LRMS (ES) m/z 564.5 ($M^+$+1).

Synthesis of Compound 136, 6-(4-acetylpiperazine-1-yl)-2-((5-(5-(difluoromethyl)-1,3,4-oxadiazole-2-yl)pyridine-2-yl)methyl)-4,4-diethylisoquinoline-1,3(2H,4H)-dione

[Step 1] Synthesis of methyl 4-bromo-2-(3-(methoxycarbonyl)pentane-3-yl)benzoate

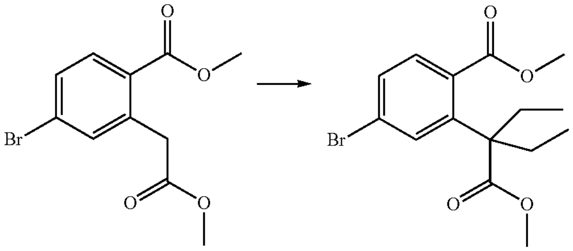 [SMILES: COC(=O)Cc1cc(Br)ccc1C(=O)OC ; CCC(CC)(C(=O)OC)c1cc(Br)ccc1C(=O)OC]

Methyl 4-bromo-2-(2-methoxy-2-oxoethyl)benzoate (3.000 g, 10.449 mmol) and sodium hydride (60.00%, 1.672 g, 41.796 mmol) were dissolved in N,N-dimethylformamide (150 mL) at 0° C., after which iodoethane (3.360 mL, 41.796 mmol) was added into the resulting solution, and stirred at room temperature for 18 hours. Saturated sodium hydrogen carbonate aqueous solution was poured into the reaction mixture, and an extraction was performed with ethyl acetate. An organic layer was washed with saturated sodium chloride aqueous solution, then dehydrated with anhydrous magnesium sulfate, then filtered, and then concentrated under reduced pressure. The resulting concentrate was purified via column chromatography ($SiO_2$, 40 g cartridge; ethyl acetate/hexane=0 to 10%), and concentrated to obtain a title compound (2.800 g, 78.1%) in a white solid form.

[Step 2] Synthesis of 4-bromo-2-(3-carboxypentane-3-yl)benzoic acid

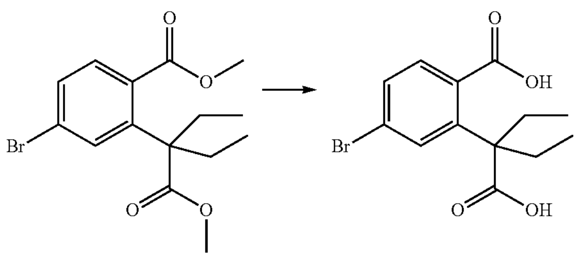 [SMILES: CCC(CC)(C(=O)OC)c1cc(Br)ccc1C(=O)OC ; CCC(CC)(C(=O)O)c1cc(Br)ccc1C(=O)O]

The methyl 4-bromo-2-(3-(methoxycarbonyl)pentane-3-yl)benzoate (2.800 g, 8.158 mmol) prepared in the step 1 and potassium hydroxide (4.577 g, 81.580 mmol) were dissolved in methanol (25 mL)/water (50 mL) at room temperature, after which the resulting solution was stirred at 100° C. for 18 hours, and then a reaction was finished by lowering the temperature to room temperature. 1N-hydrochloric acid aqueous solution was poured into the resulting reaction mixture, and an extraction was performed with dichloromethane. An organic layer was washed with saturated sodium chloride aqueous solution, then dehydrated with anhydrous magnesium sulfate, then filtered, and then concentrated under reduced pressure. An obtained product was used without an additional purification process (2.550 g, 99.2%, white solid).

[Step 3] Synthesis of 6-bromo-4,4-diethylisoquinoline-1,3(2H,4H)-dione

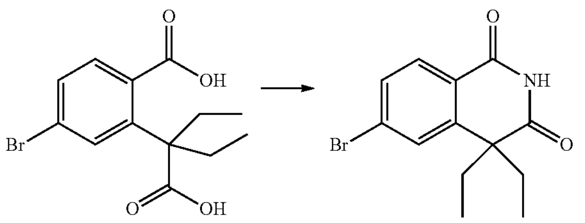 [SMILES: CCC(CC)(C(=O)O)c1cc(Br)ccc1C(=O)O ; CCC1(CC)C(=O)NC(=O)c2ccc(Br)cc21]

The 4-bromo-2-(3-carboxypentane-3-yl)benzoic acid (2.550 g, 8.091 mmol) prepared in the step 2 and urea (0.486 g, 8.091 mmol) were dissolved in N,N-dimethylformamide (150 mL) at room temperature, after which the resulting solution was stirred at 150° C. for 18 hours, and then a reaction was finished by lowering the temperature to room temperature. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 10%), and concentrated to obtain a title compound (0.301 g, 12.6%) in a white solid form.

[Step 4] Synthesis of N-((5-(5-(difluoromethyl)-1,3,4-oxadiazole-2-yl)pyridine-2-yl)methyl)-N-(3,4-difluorophenyl)-4-methylpiperazine-1-carboxamide

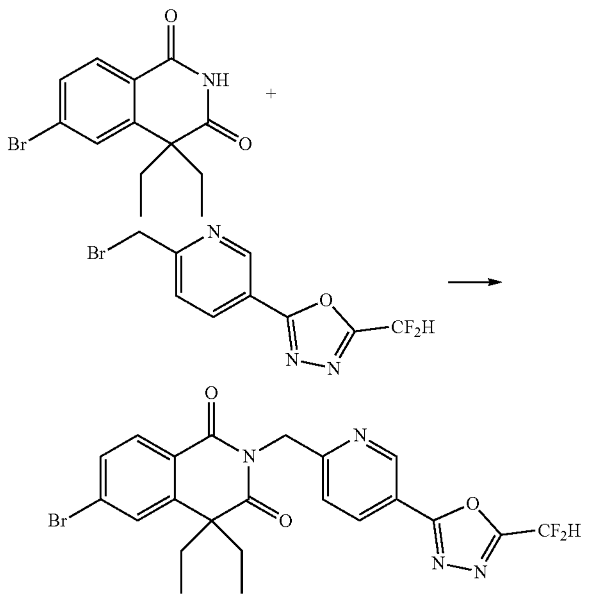

The 6-bromo-4,4-diethylisoquinoline-1,3(2H,4H)-dione (0.300 g, 1.013 mmol) prepared in the step 3, 2-(6-(bromomethyl)pyridine-3-yl)-5-(difluoromethyl)-1,3,4-oxadiazole (0.353 g, 1.216 mmol), potassium carbonate (0.420 g, 3.039 mmol) and potassium iodide (0.017 g, 0.101 mmol) were dissolved in N,N-dimethylformamide (5 mL) at room temperature, after which the resulting solution was stirred at 100° C. for 18 hours, and then a reaction was finished by lowering the temperature to room temperature. Solvent was removed from the reaction mixture under reduced pressure, after which water was poured into the resulting concentrate, and an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 12 g cartridge; ethyl acetate/hexane=0 to 20%), and concentrated to obtain a title compound (0.419 g, 81.9%) in a light yellow solid form.

[Step 5] Synthesis of the Compound 136

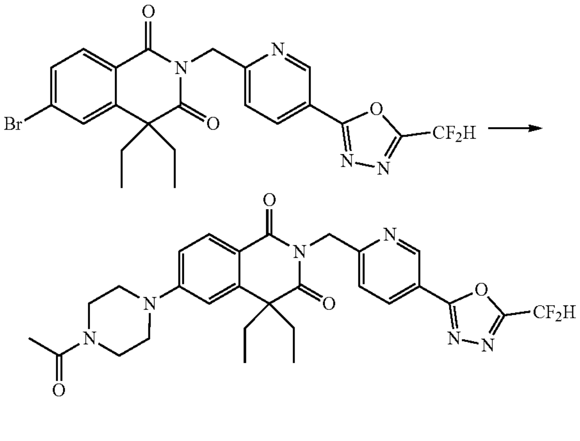

The N-((5-(5-(difluoromethyl)-1,3,4-oxadiazole-2-yl) pyridine-2-yl)methyl)-N-(3,4-difluorophenyl)-4-methylpiperazine-1-carboxamide (0.100 g, 0.198 mmol) prepared in the step 4, 1-acetyl piperazine (0.028 mL, 0.237 mmol), tris(dibenzylideneacetone)dipalladium ($Pd_2(dba)_3$, 0.018 g, 0.020 mmol), 4,5-bis(diphenylphosphino)-9,9-dimethylxanthene (Xantphos, 0.011 g, 0.020 mmol) and cesium carbonate (0.129 g, 0.396 mmol) were dissolved in 1,4-dioxane (4 mL) at room temperature, after which the resulting solution was stirred at 100° C. for 18 hours, and then a reaction was finished by lowering the temperature to room temperature. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=60 to 100%), and concentrated to obtain a title compound (0.034 g, 31.1%) in a yellow oil form.

$^1H$ NMR (400 MHz, $CDCl_3$) δ 9.19 (d, J=1.6 Hz, 1H), 8.34 (dd, J=8.2, 2.2 Hz, 1H), 8.17 (d, J=8.9 Hz, 1H), 7.48 (d, J=8.2 Hz, 1H), 7.06~6.80 (m, 2H), 6.73 (d, J=2.4 Hz, 1H), 5.44 (s, 2H), 3.84 (t, J=5.3 Hz, 2H), 3.71 (t, J=5.2 Hz, 2H), 3.46 (t, J=5.2 Hz, 2H), 3.41 (t, J=5.3 Hz, 2H), 2.38~2.32 (m, 2H), 2.18 (s, 3H), 1.92~1.87 (m, 2H), 0.64 (t, J=7.4 Hz, 6H); LRMS (ES) m/z 553.5 ($M^+$+1).

Synthesis of Compound 137, 2-((5-(5-(difluoromethyl)-1,3,4-oxadiazole-2-yl)pyridine-2-yl)methyl)-4,4-dimethyl-6-(4-(2,2,3,3-tetrafluoropropyl)piperazine-1-yl)isoquinoline-1,3(2H,4H)-dione

[Step 1] Synthesis of the Compound 137

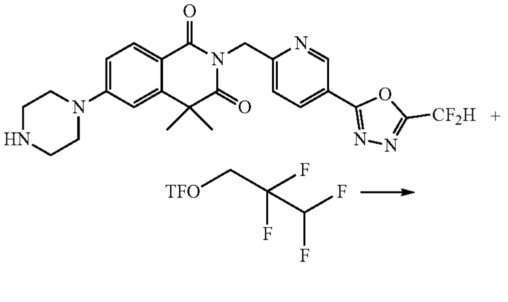

-continued

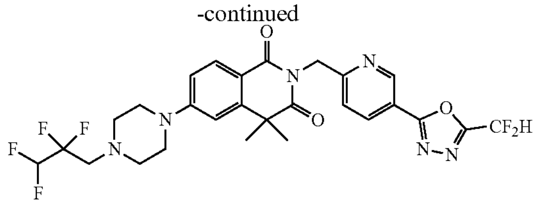

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione (0.100 g, 0.207 mmol), 2,2,3,3-tetrafluoropropyl trifluoromethanesulfonate (0.071 g, 0.269 mmol) and potassium carbonate (0.057 g, 0.415 mmol) were dissolved in acetonitrile (10 mL) at room temperature, after which the resulting solution was stirred at the same temperature for 18 hours. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.060 g, 48.5%) in a white solid form.

$^1H$ NMR (400 MHz, $CDCl_3$) δ 9.21 (dd, J=2.2, 0.7 Hz, 1H), 8.33 (dd, J=8.2, 2.2 Hz, 1H), 8.13 (d, J=8.9 Hz, 1H), 7.44~7.41 (m, 1H), 7.06 (s, 0.25H), 6.95~6.92 (m, 1H), 6.93 (s, 0.5H), 6.85 (d, J=2.4 Hz, 1H), 6.80 (s, 0.25H), 6.18 (t, J=4.7 Hz, 0.25H), 6.04 (t, J=4.9 Hz, 0.5H), 5.91 (t, J=4.9 Hz, 0.25H), 5.42 (s, 2H), 3.42 (t, J=5.1 Hz, 4H), 3.03 (t, J=14.1 Hz, 2H), 2.86 (t, J=5.0 Hz, 4H), 1.69 (s, 6H); LRMS (ES) m/z 597.5 ($M^+$+1).

Synthesis of Compound 138, 2-((5-(5-(difluoromethyl)-1,3,4-oxadiazole-2-yl)pyridine-2-yl)methyl)-6-(4-(2,2-difluoropropyl)piperazine-1-yl)-4,4-dimethylisoquinoline-1,3(2H,4H)-dione

[Step 1] Synthesis of the Compound 138

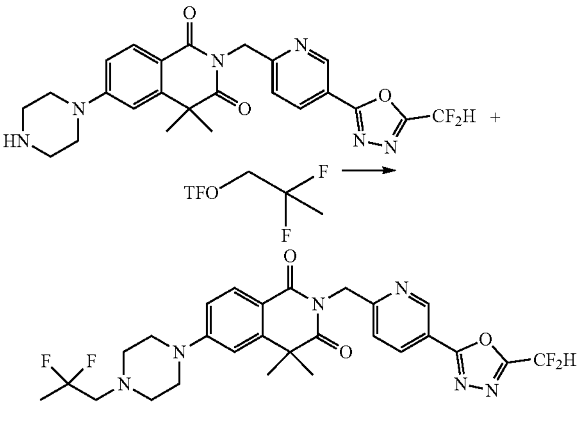

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione (0.100 g, 0.207 mmol), 2,2-difluoropropyl trifluoromethanesulfonate (0.057 g, 0.249 mmol) and potassium carbonate (0.057 g, 0.415 mmol) were dissolved in acetonitrile (10 mL) at room temperature, after which the resulting solution was stirred at the same temperature for 18 hours. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.050 g, 43.0%) in a white solid form.

$^1H$ NMR (400 MHz, $CDCl_3$) δ 9.20 (dd, J=2.2, 0.7 Hz, 1H), 8.33 (dd, J=8.2, 2.2 Hz, 1H), 8.11 (d, J=8.9 Hz, 1H), 7.42 (dd, J=8.2, 0.6 Hz, 1H), 7.06 (s, 0.25H), 6.94~6.91 (m, 1H), 6.93 (s, 0.5H), 6.84 (d, J=2.4 Hz, 1H), 6.80 (s, 0.25H), 5.41 (s, 2H), 3.42 (t, J=5.1 Hz, 4H), 2.81~2.74 (m, 6H), 1.75~1.65 (m, 9H).

Synthesis of Compound 139, 6-(4-(2,2-difluorobutyl)piperazine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 139

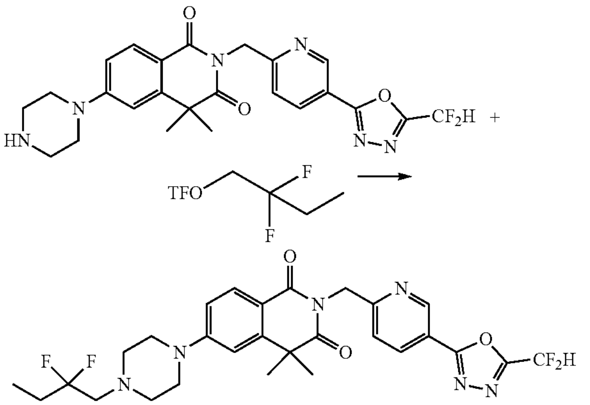

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione (0.100 g, 0.207 mmol), 2,2-difluorobutyl trifluoromethanesulfonate (0.065 g, 0.269 mmol) and potassium carbonate (0.057 g, 0.415 mmol) were dissolved in acetonitrile (10 mL) at room temperature, after which the resulting solution was stirred at the same temperature for 18 hours. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.050 g, 42.0%) in a white solid form.

$^1H$ NMR (400 MHz, $CDCl_3$) δ 9.20 (dd, J=2.2, 0.8 Hz, 1H), 8.33 (dd, J=8.2, 2.3 Hz, 1H), 8.11 (d, J=8.9 Hz, 1H), 7.42 (dd, J=8.2, 0.8 Hz, 1H), 7.06 (s, 0.25H), 6.93 (dd, J=8.9, 2.5 Hz, 1H), 6.93 (s, 0.5H), 6.84 (d, J=2.4 Hz, 1H), 6.80 (s, 0.25H), 5.41 (s, 2H), 3.42 (t, J=5.1 Hz, 4H), 2.81~2.74 (m, 6H), 2.05~1.99 (m, 2H), 1.68 (s, 6H), 1.06 (t, J=7.5 Hz, 3H).

Synthesis of Compound 140, 2-((5-(5-(difluoromethyl)-1,3,4-oxadiazole-2-yl)pyridine-2-yl)methyl)-6-(4-(2,2,3,3,4,4, 4-heptafluorobutyl)piperazine-1-yl)-4,4-dimethylisoquinoline-1,3(2H,4H)-dione

[Step 1] Synthesis of the Compound 140

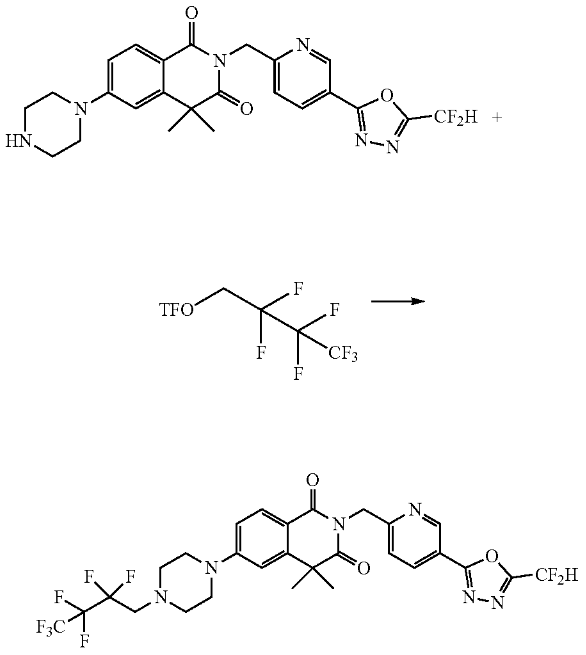

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione (0.100 g, 0.207 mmol), 2,2,3,3,4,4,4-heptafluorobutyl trifluoromethanesulfonate (0.089 g, 0.269 mmol) and potassium carbonate (0.057 g, 0.415 mmol) were dissolved in acetonitrile (10 mL) at room temperature, after which the resulting solution was stirred at the same temperature for 18 hours. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.040 g, 29.0%) in a white solid form.

$^1H$ NMR (400 MHz, $CDCl_3$) δ 9.21 (dd, J=2.2, 0.8 Hz, 1H), 8.33 (dd, J=8.2, 2.3 Hz, 1H), 8.12 (d, J=8.9 Hz, 1H), 7.42 (dd, J=8.3, 0.8 Hz, 1H), 7.06 (s, 0.25H), 6.94 (dd, J=8.5, 2.9 Hz, 1H), 6.93 (s, 0.5H), 6.85 (d, J=2.4 Hz, 1H), 6.80 (s, 0.25H), 5.42 (s, 2H), 3.43 (t, J=5.0 Hz, 4H), 3.14 (t, J=15.6 Hz, 2H), 2.88 (t, J=5.0 Hz, 4H), 1.68 (s, 6H); LRMS (ES) m/z 665.4 ($M^+$+1).

Synthesis of Compound 141, 2-((5-(5-(difluoromethyl)-1,3,4-oxadiazole-2-yl)pyridine-2-yl)methyl)-4,4-dimethyl-6-(4-(2,2,2-trifluoroethyl)piperazine-1-yl)isoquinoline-1,3(2H,4H)-dione

[Step 1] Synthesis of the Compound 141

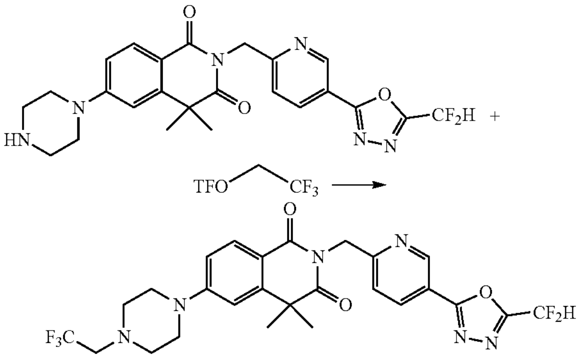

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione (0.100 g, 0.207 mmol), 2,2,2-trifluoroethyl trifluoromethanesulfonate (0.063 g, 0.269 mmol) and potassium carbonate (0.057 g, 0.415 mmol) were dissolved in acetonitrile (10 mL) at room temperature, after which the resulting solution was stirred at the same temperature for 18 hours. Solvent was removed from the reaction mixture under reduced pressure, after which water was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.070 g, 59.8%) in a white solid form.

$^1$H NMR (400 MHz, $CDCl_3$) δ 9.19 (dd, J=2.2, 0.8 Hz, 1H), 8.32 (dd, J=8.2, 2.2 Hz, 1H), 8.10 (d, J=8.9 Hz, 1H), 7.41 (dd, J=8.2, 0.7 Hz, 1H), 7.06 (s, 0.25H), 6.94~6.91 (m, 1H), 6.93 (s, 0.5H), 6.84 (d, J=2.4 Hz, 1H), 6.80 (s, 0.25H), 5.40 (s, 2H), 3.43 (t, J=5.0 Hz, 4H), 3.11~3.03 (m, 1H), 2.87 (t, J=5.0 Hz, 4H), 1.67 (s, 6H); LRMS (ES) m/z 564.52 ($M^+$+1).

Synthesis of Compound 142, 2-((5-(5-(difluoromethyl)-1,3,4-oxadiazole-2-yl)pyridine-2-yl)methyl)-4,4-diethyl-6-(4-ethylpiperazine-1-yl)isoquinoline-1,3(2H,4H)-dione

[Step 1] Synthesis of the Compound 142

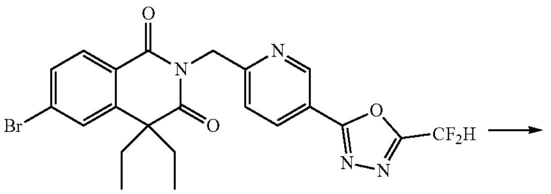

-continued

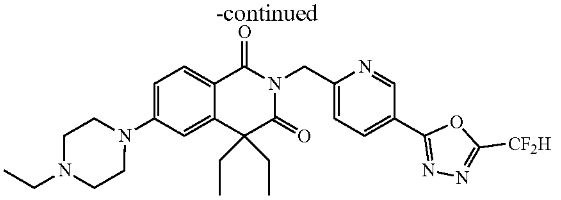

6-bromo-2-((5-(5-(difluoromethyl)-1,3,4-oxadiazole-2-yl)pyridine-2-yl)methyl)-4,4-diethylisoquinoline-1,3(2H,4H)-dione (0.100 g, 0.198 mmol), 1-ethylpiperazine (0.027 g, 0.237 mmol), tris(dibenzylideneacetone)dipalladium ($Pd_2(dba)_3$, 0.018 g, 0.020 mmol), 4,5-bis(diphenylphosphino)-9,9-dimethylxanthene (Xantphos, 0.011 g, 0.020 mmol) and cesium carbonate (0.129 g, 0.396 mmol) were dissolved in 1,4-dioxane (3 mL) at room temperature, after which the resulting solution was stirred at 100° C. for 18 hours, and then a reaction was finished by lowering the temperature to room temperature. Solvent was removed from the reaction mixture under reduced pressure, after which saturated sodium hydrogen carbonate aqueous solution was poured into the resulting concentrate, and an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; methanol/dichloromethane=0 to 5%), and concentrated to obtain a product, after which the resulting product was purified again via chromatography ($SiO_2$ plate, 20×20×1 mm; methanol/dichloromethane=5%), and concentrated to obtain a title compound (0.019 g, 17.8%) in a pink solid form.

$^1$H NMR (400 MHz, $CDCl_3$) δ 9.10 (d, J=1.6 Hz, 1H), 8.41 (dd, J=8.3, 2.1 Hz, 1H), 8.06 (d, J=9.0 Hz, 1H), 7.57 (d, J=8.3 Hz, 1H), 7.37~7.07 (m, 2H), 6.95 (d, J=2.0 Hz, 1H), 5.39 (s, 2H), 3.48 (t, J=4.9 Hz, 4H), 2.66 (t, J=4.8 Hz, 4H), 2.53 (q, J=7.2 Hz, 2H), 2.27~2.22 (m, 2H), 2.06~2.01 (m, 2H), 1.18 (t, J=7.2 Hz, 3H), 0.62 (t, J=7.3 Hz, 6H); LRMS (ES) m/z 539.5 ($M^+$+1).

Synthesis of Compound 143, 2-((5-(5-(difluoromethyl)-1,3,4-oxadiazole-2-yl) pyridine-2-yl) methyl)-4,4-dimethyl-7-(1-propylpiperidine-4-yl) isoquinoline-1,3 (2H,4H)-dione

[Step 1] Synthesis of the Compound 143

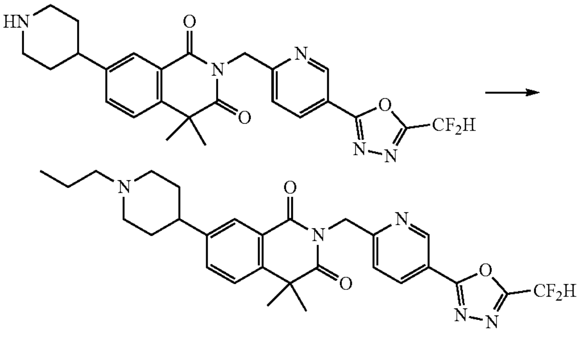

2-((5-(5-(difluoromethyl)-1,3,4-oxadiazole-2-yl) pyridine-2-yl) methyl)-4,4-dimethyl-7-(piperidine-4-yl) isoquinoline-1,3(2H,4H)-dione (0.100 g, 0.208 mmol) and propionaldehyde (0.018 g, 0.312 mmol) were dissolved in dichloromethane (4 mL) at room temperature, after which sodium triacetoxyborohydride (0.088 g, 0.415 mmol) was added into the resulting solution and stirred at the same temperature for 18 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; methanol/dichloromethane=0 to 5%), and concentrated to obtain a title compound (0.042 g, 38.6%) in a white solid form.

$^1$H NMR (400 MHz, $CDCl_3$) δ 9.18 (s, 1H), 8.33 (d, J=8.2 Hz, 1H), 8.12 (s, 1H), 7.57 (d, J=8.1 Hz, 1H), 7.45 (t, J=7.7 Hz, 2H), 7.06~6.80 (m, 1H), 5.43 (s, 2H), 3.12 (d, J=11.0 Hz, 2H), 2.65~2.61 (m, 1H), 2.38 (t, J=7.7 Hz, 2H), 2.14~2.05 (m, 2H), 1.88~1.87 (m, 4H), 1.68 (s, 6H), 1.63~1.55 (m, 2H), 0.93 (t, J=7.3 Hz, 3H); LRMS (ES) m/z 524.5 ($M^+$+1).

Synthesis of Compound 144, 2-((5-(5-(difluoromethyl)-1,3,4-oxadiazole-2-yl)pyridine-2-yl)methyl)-7-(1-isobutylpiperidine-4-yl)-4,4-dimethylisoquinoline-1,3(2H,4H)-dione

[Step 1] Synthesis of the Compound 144

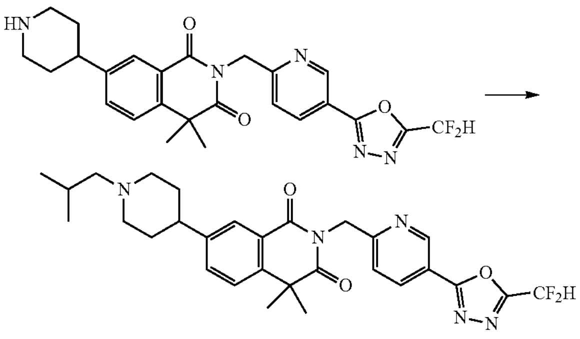

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione (0.100 g, 0.208 mmol) and isobutyraldehyde (0.022 g, 0.312 mmol) were dissolved in dichloromethane (4 mL) at room temperature, after which sodium triacetoxyborohydride (0.088 g, 0.415 mmol) was added into the resulting solution and stirred at the same temperature for 18 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; methanol/dichloromethane=0 to 5%), and concentrated to obtain a title compound (0.055 g, 49.3%) in a white solid form.

$^1$H NMR (400 MHz, $CDCl_3$) δ 9.19 (s, 1H), 8.34 (d, J=8.2 Hz, 1H), 8.13 (s, 1H), 7.56 (d, J=8.0 Hz, 1H), 7.46~7.44 (m, 2H), 7.06~6.80 (m, 1H), 5.43 (s, 2H), 3.01 (d, J=10.6 Hz, 2H), 2.61~2.57 (m, 1H), 2.13 (d, J=7.0 Hz, 2H), 2.05~1.99 (m, 2H), 1.83~1.79 (m, 5H), 1.69 (s, 6H), 0.93 (d, J=6.1 Hz, 6H); LRMS (ES) m/z 538.3 ($M^+$+1).

Synthesis of Compound 145, 7-(1-cyclobutylpiperidine-4-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 145

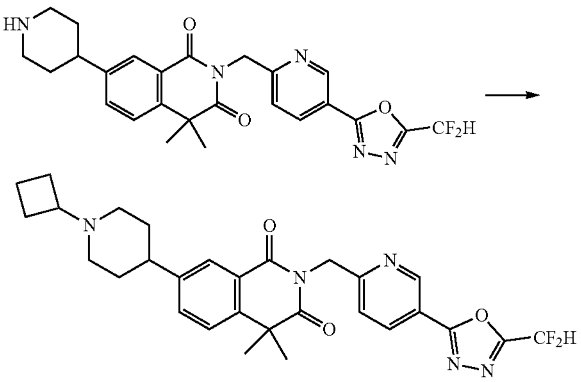

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione (0.100 g, 0.208 mmol) and cyclobutanone (0.016 g, 0.228 mmol) were dissolved in dichloromethane (4 mL) at room temperature, after which sodium triacetoxyborohydride (0.066 g, 0.312 mmol) was added into the resulting solution and stirred at the same temperature for 18 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; methanol/dichloromethane=0 to 5%), and concentrated to obtain a title compound (0.053 g, 47.6%) in a white solid form.

$^1$H NMR (400 MHz, $CDCl_3$) δ 9.17 (s, 1H), 8.32 (d, J=8.2 Hz, 1H), 8.12 (s, 1H), 7.56 (d, J=8.1 Hz, 1H), 7.44 (t, J=7.5 Hz, 2H), 7.05~6.79 (m, 1H), 5.42 (s, 2H), 3.04~3.03 (m, 2H), 2.77~2.73 (m, 1H), 2.60~2.59 (m, 1H), 2.07~2.05 (m, 2H), 1.95~1.69 (m, 10H), 1.67 (s, 6H); LRMS (ES) m/z 536.3 ($M^+$+1).

Synthesis of Compound 146, 2-((5-(5-(difluoromethyl)-1,3,4-oxadiazole-2-yl)pyridine-2-yl)methyl)-4,4-dimethyl-7-(1-(tetrahydrofuran-3-yl)piperidine-4-yl)isoquinoline-1,3(2H,4H)-dione

[Step 1] Synthesis of the Compound 146

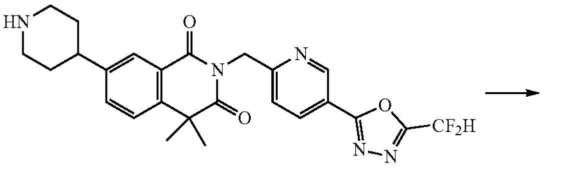

-continued

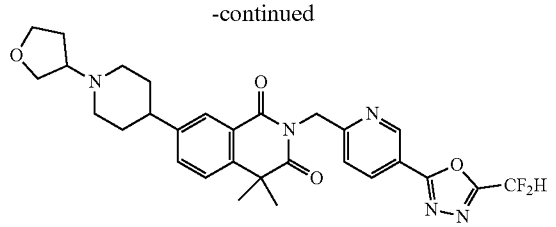

N-(4-(5-(difluoromethyl)-1,3,4-oxadiazole-2-yl)-2-fluorobenzyl)-3-fluoroaniline (0.500 g, 1.482 mmol) and dihydrofuran-3(2H)-one (0.191 g, 2.224 mmol) were dissolved in dichloromethane (4 mL) at room temperature, after which sodium triacetoxyborohydride (0.628 g, 2.965 mmol) was added into the resulting solution and stirred at the same temperature for 18 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; methanol/dichloromethane=0 to 5%), and concentrated to obtain a desired compound (0.062 g, 7.6%) in a white solid form.

$^1$H NMR (400 MHz, $CDCl_3$) δ 9.16 (d, J=2.0 Hz, 1H), 8.32 (dd, J=8.2, 2.2 Hz, 1H), 8.10 (d, J=1.8 Hz, 1H), 7.55 (dd, J=8.2, 1.9 Hz, 1H), 7.44 (t, J=8.7 Hz, 2H), 7.05~6.79 (m, 1H), 5.41 (s, 2H), 3.96~3.88 (m, 2H), 3.82~3.71 (m, 2H), 3.17 (d, J=11.3 Hz, 1H), 3.11~3.08 (m, 1H), 2.97 (d, J=12.2 Hz, 1H), 2.65~2.64 (m, 1H), 2.26~2.22 (m, 2H), 2.10~2.07 (m, 1H), 1.97~1.86 (m, 5H), 1.66 (s, 6H); LRMS (ES) m/z 552.5 ($M^+$+1).

Synthesis of Compound 147, 6-(4-butylpiperazine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 147

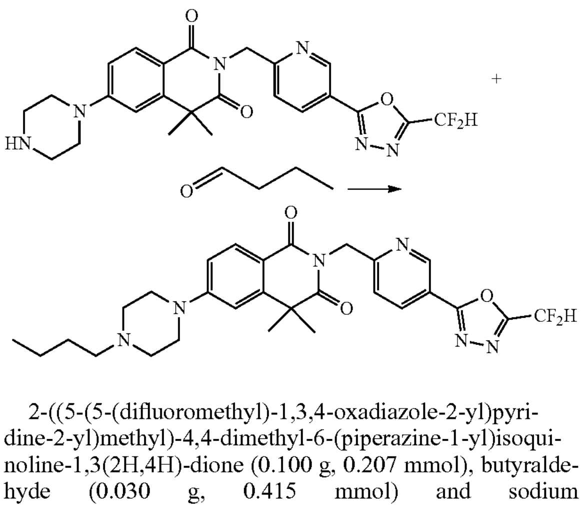

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione (0.100 g, 0.207 mmol), butyraldehyde (0.030 g, 0.415 mmol) and sodium triacetoxyborohydride (0.088 g, 0.415 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.060 g, 53.7%) in a white foam solid form.

$^1$H NMR (400 MHz, $CDCl_3$) δ 9.21 (dd, J=2.1, 0.6 Hz, 1H), 8.33 (dd, J=8.2, 2.2 Hz, 1H), 8.11 (d, J=8.9 Hz, 1H), 7.41 (dd, J=8.3, 0.5 Hz, 1H), 7.06 (s, 0.25H), 6.95~6.92 (m, 1H), 6.93 (s, 0.5H), 6.84 (d, J=2.4 Hz, 1H), 6.80 (s, 0.25H), 5.42 (s, 2H), 3.45~3.43 (m, 4H), 2.65~2.63 (m, 4H), 2.44 (t, J=7.5 Hz, 2H), 1.68 (s, 6H), 1.57~1.54 (m, 2H), 1.41~1.36 (m, 2H), 0.98~0 0.95 (m, 3H); LRMS (ES) m/z 539.5 ($M^+$+1).

[Step 1] Synthesis of the Compound 148

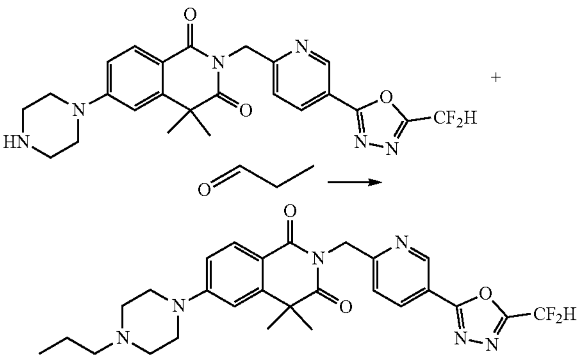

2-((5-(5-(difluoromethyl)-1,3,4-oxadiazole-2-yl) pyridine-2-yl) methyl)-4,4-dimethyl-6-(piperazine-1-yl) isoquinoline-1,3(2H,4H)-dione (0.100 g, 0.207 mmol), propionaldehyde (0.016 g, 0.269 mmol) and sodium triacetoxyborohydride (0.088 g, 0.415 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.050 g, 46.0%) in a white foam solid form.

$^1$H NMR (400 MHz, $CDCl_3$) δ 9.20 (dd, J=2.2, 0.6 Hz, 1H), 8.32 (dd, J=8.2, 2.2 Hz, 1H), 8.11 (d, J=9.1 Hz, 1H), 7.41 (dd, J=8.2, 0.6 Hz, 1H), 7.06 (s, 0.25H), 6.94~6.92 (m, 1H), 6.93 (s, 0.5H), 6.84 (d, J=2.4 Hz, 1H), 6.80 (s, 0.25H), 5.41 (s, 2H), 3.44 (t, J=5.0 Hz, 4H), 2.64 (t, J=4.8 Hz, 4H), 2.42~2.38 (m, 2H), 1.68 (s, 6H), 1.61~1.55 (m, 2H), 0.96 (t, J=7.4 Hz, 3H); LRMS (ES) m/z 525.5 ($M^+$+1).

Synthesis of Compound 149, 2-((5-(5-(difluoromethyl)-1,3,4-oxadiazole-2-yl)pyridine-2-yl)methyl)-6-(4-isobutylpiperazine-1-yl)-4,4-dimethylisoquinoline-1,3(2H,4H)-dione

[Step 1] Synthesis of the Compound 149

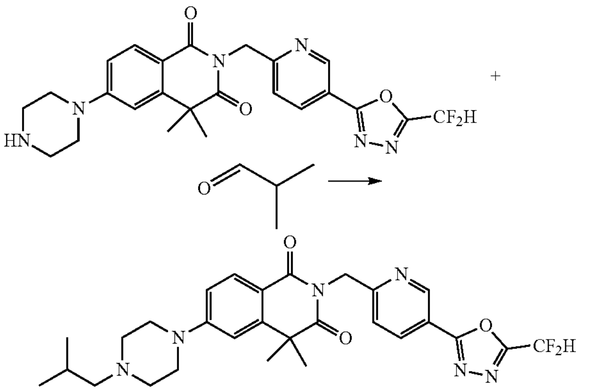

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione (0.100 g, 0.207 mmol), isobutyraldehyde (0.019 g, 0.269 mmol) and sodium triacetoxyborohydride (0.088 g, 0.415 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.050 g, 44.8%) in a white foam solid form.

$^1H$ NMR (400 MHz, $CDCl_3$) δ 9.21~9.20 (m, 1H), 8.33 (dd, J=8.2, 2.2 Hz, 1H), 8.11~8.09 (m, 1H), 7.41 (d, J=8.2 Hz, 1H), 7.06 (s, 0.25H), 6.94~6.92 (m, 1H), 6.93 (s, 0.5H), 6.84 (d, J=2.4 Hz, 1H), 6.80 (s, 0.25H), 5.43 (s, 2H), 3.43~3.40 (m, 4H), 2.60~2.55 (m, 4H), 2.18~2.16 (m, 2H), 1.86~1.81 (m, 1H), 1.68 (s, 6H), 0.98~0.96 (m, 6H); LRMS (ES) m/z 539.5 ($M^+$+1).

Synthesis of Compound 150, 6-(4-(4,4-difluorocyclohexyl)piperazine-1-yl)-2-((5-(5-(difluoromethyl)-1,3,4-oxadiazole-2-yl)pyridine-2-yl)methyl)-4,4-dimethylisoquinoline-1,3(2H,4H)-dione

[Step 1] Synthesis of the Compound 150

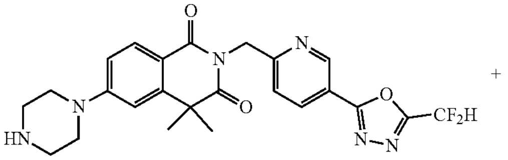

-continued

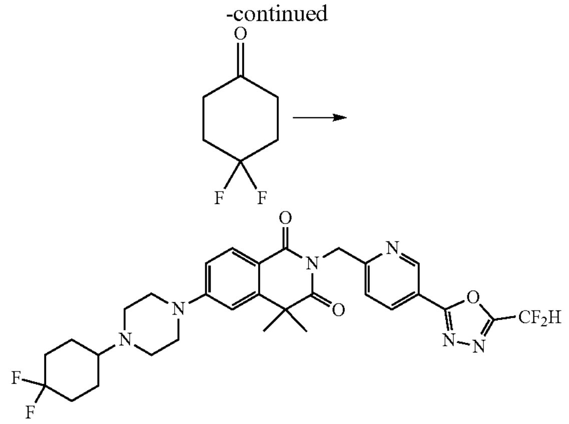

2-((5-(5-(difluoromethyl)-1,3,4-oxadiazole-2-yl)pyridine-2-yl)methyl)-4,4-dimethyl-6-(piperazine-1-yl)isoquinoline-1,3(2H,4H)-dione (0.100 g, 0.207 mmol), 4,4-difluorocyclohexane-1-one (0.036 g, 0.269 mmol) and sodium triacetoxyborohydride (0.088 g, 0.415 mmol) were dissolved in dichloromethane (10 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.090 g, 72.3%) in a white foam solid form.

$^1H$ NMR (400 MHz, $CDCl_3$) δ 9.21 (d, J=1.5 Hz, 1H), 8.33 (dd, J=8.2, 2.2 Hz, 1H), 8.12 (d, J=8.8 Hz, 1H), 7.42 (d, J=8.3 Hz, 1H), 7.06 (s, 0.25H), 6.94 (dd, J=8.8, 2.5 Hz, 1H), 6.93 (s, 0.5H), 6.85 (d, J=2.4 Hz, 1H), 6.80 (s, 0.25H), 5.42 (s, 2H), 3.44~3.40 (m, 4H), 2.77~2.73 (m, 4H), 2.55~2.45 (m, 1H), 2.00~1.40 (m, 8H), 1.69 (s, 6H); LRMS (ES) m/z 601.5 ($M^+$+1).

Synthesis of Compound 151, 2-((5-(5-(difluoromethyl)-1,3,4-oxadiazole-2-yl)pyridine-2-yl)methyl)-7-(1-(2-methoxyethyl)piperidine-4-yl)-4,4-dimethylisoquinoline-1,3(2H,4H)-dione

[Step 1] Synthesis of the Compound 151

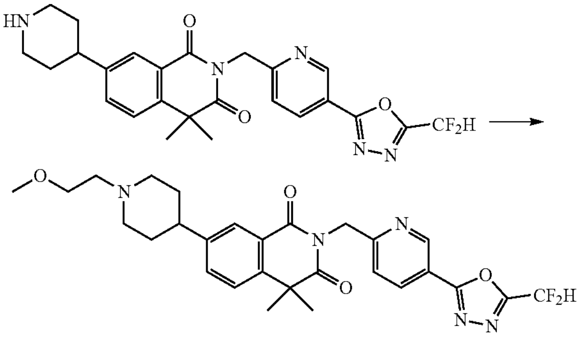

2-((5-(5-(difluoromethyl)-1,3,4-oxadiazole-2-yl)pyridine-2-yl)methyl)-4,4-dimethyl-7-(piperidine-4-yl)isoquinoline-1,3(2H,4H)-dione (0.100 g, 0.208 mmol), 1-chloro-2-methoxyethane (0.028 mL, 0.312 mmol) and potassium carbonate (0.057 g, 0.415 mmol) were dissolved in acetonitrile (4 mL) at room temperature, after which the resulting solution was stirred at 80° C. for 18 hours, and then a reaction was finished by lowering the temperature to room temperature. Solvent was removed from the reaction mixture under reduced pressure, after which water was poured into the resulting concentrate, and an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; methanol/dichloromethane=0 to 5%), and concentrated to obtain a product, after which the resulting product was purified again via chromatography ($SiO_2$ plate, 20×20×1 mm; methanol/dichloromethane aqueous solution=3%), and concentrated to obtain a title compound (0.010 g, 8.9%) in an orange solid form.

$^1H$ NMR (400 MHz, $CDCl_3$) δ 9.20 (d, J=2.1 Hz, 1H), 8.34 (dd, J=8.2, 2.2 Hz, 1H), 8.13 (d, J=2.0 Hz, 1H), 7.57 (dd, J=8.2, 1.9 Hz, 1H), 7.46 (t, J=8.0 Hz, 2H), 7.06~6.80 (m, 1H), 5.44 (s, 2H), 3.60 (t, J=5.6 Hz, 2H), 3.39 (s, 3H), 3.18 (d, J=11.4 Hz, 2H), 3.20~2.64 (m, 3H), 2.21 (t, J=10.6 Hz, 2H), 1.96~1.87 (m, 4H), 1.69 (s, 6H); LRMS (ES) m/z 506.2 ($M^+$+1).

Synthesis of Compound 152, 6-bromo-2-((5-(5-(difluoromethyl)-1,3,4-oxadiazole-2-yl)pyrimidine-2-yl)methyl)-4,4-dimethylisoquinoline-1,3(2H,4H)-dione

[Step 1] Synthesis of the Compound 152

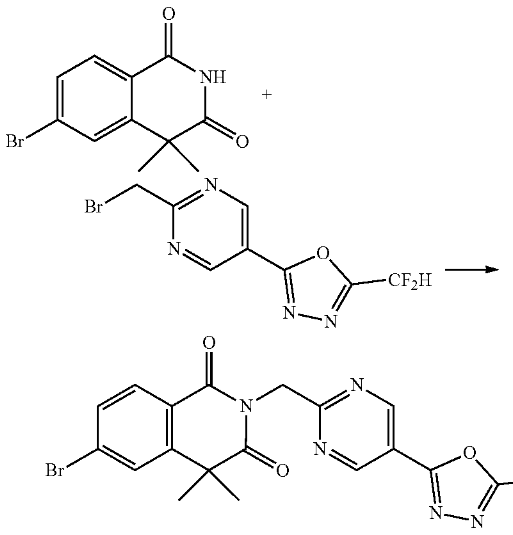

6-bromo-4,4-dimethylisoquinoline-1,3(2H,4H)-dione (1.700 g, 6.341 mmol), 2-(2-(bromomethyl)pyrimidine-5-yl)-5-(difluoromethyl)-1,3,4-oxadiazole (2.399 g, 8.243 mmol) and potassium carbonate (1.753 g, 12.681 mmol) were dissolved in N,N-dimethylformamide (20 mL) at 80° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 40 g cartridge; ethyl acetate/hexane=0 to 50%), and concentrated to obtain a title compound (1.900 g, 62.7%) in a yellow foam solid form.

$^1H$ NMR (400 MHz, $CDCl_3$) δ 9.31 (s, 2H), 8.13 (d, J=8.4 Hz, 1H), 7.70 (d, J=1.6 Hz, 1H), 7.63 (dd, J=8.4, 1.7 Hz, 1H), 7.08 (s, 0.25H), 6.95 (s, 0.5H), 6.82 (s, 0.25H), 5.55 (s, 2H), 1.73 (s, 6H).

Synthesis of Compound 153, 2-((5-(5-(difluoromethyl)-1,3,4-oxadiazole-2-yl)pyrimidine-2-yl)methyl)-4,4-dimethyl-6-(4-methylpiperazine-1-yl)isoquinoline-1,3(2H,4H)-dione

[Step 1] Synthesis of the Compound 153

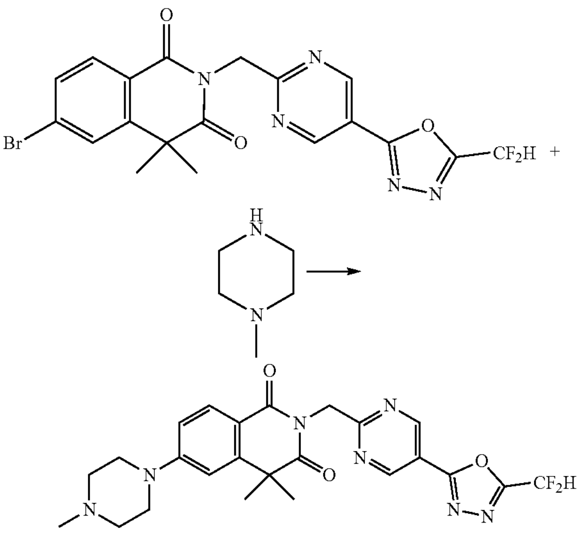

6-bromo-2-((5-(5-(difluoromethyl)-1,3,4-oxadiazole-2-yl)pyrimidine-2-yl)methy 1)-4,4-dimethylisoquinoline-1,3(2H,4H)-dione (0.100 g, 0.209 mmol), 1-methylpiperazine (0.047 mL, 0.418 mmol), tris(dibenzylideneacetone)dipalladium ($Pd_2(dba)_3$, 0.019 g, 0.021 mmol), 4,5-bis(diphenylphosphino)-9,9-dimethylxanthene (Xantphos, 0.012 g, 0.021 mmol) and cesium carbonate (0.204 g, 0.627 mmol) were dissolved in toluene (5 mL) at 80° C., after which the resulting solution was stirred at the same temperature for 18 hours, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.010 g, 9.4%) in a brown oil form.

$^1H$ NMR (400 MHz, $CDCl_3$) δ 9.30 (s, 2H), 8.13~8.10 (m, 1H), 7.08 (s, 0.25H), 6.96~6.93 (m, 1H), 6.94 (s, 0.5H), 6.87 (d, J=2.4 Hz, 1H), 6.82 (s, 0.25H), 5.55 (s, 2H), 3.48~3.45 (m, 4H), 2.68~2.64 (m, 4H), 2.43 (s, 3H), 1.71 (s, 6H); LRMS (ES) m/z 498.5 ($M^{+}$+1).

Synthesis of Compound 154, tert-butyl 4-(2-((5-(5-(difluoromethyl)-1,3,4-oxadiazole-2-yl)pyrimidine-2-yl)methyl)-4,4-dimethyl-1,3-dioxo-1,2,3,4-tetrahydroisoquinoline-6-yl)-3,6-dihydropyridine-1(2H)-carboxylate

[Step 1] Synthesis of the Compound 154

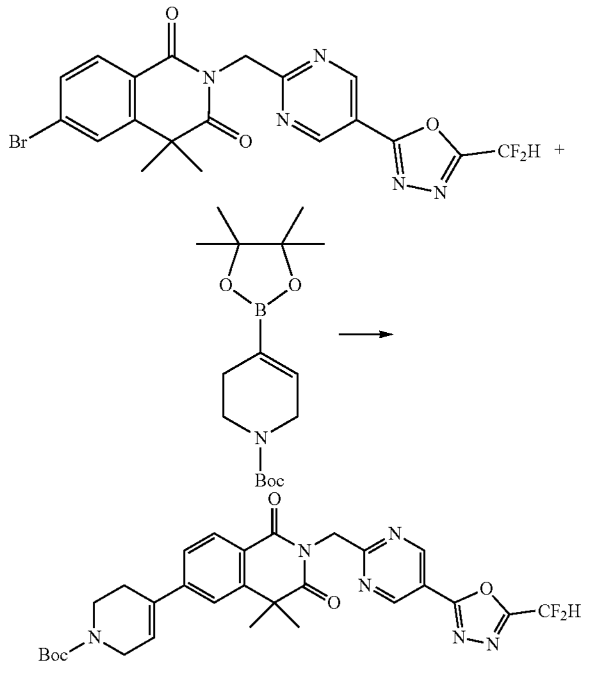

6-bromo-2-((5-(5-(difluoromethyl)-1,3,4-oxadiazole-2-yl)pyrimidine-2-yl)methy 1)-4,4-dimethylisoquinoline-1,3 (2H,4H)-dione (0.800 g, 1.673 mmol), tert-butyl 4-(4,4,5,5-tetramethyl-1,3,2-dioxaborolane-2-yl)-3,6-dihydropyridine-1(2H)-carboxylat e (0.672 g, 2.175 mmol), [1,1'-bis(di-tert-butylphosphino)ferrocene]palladium(II) dichloride (Pd (dtbpf)$Cl_2$, 0.109 g, 0.167 mmol) and cesium carbonate (0.818 g, 2.509 mmol) were mixed in 1,4-dioxane (9 mL)/water (3 mL), after which the resulting mixture was irradiated with microwave, then heated at 100° C. for 25 minutes, and then a reaction was finished by lowering the temperature to room temperature. Water was poured into the reaction mixture, and an extraction was performed with ethyl acetate. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; ethyl acetate/hexane=0 to 50%), and concentrated to obtain a title compound (0.381 g, 39.2%) in a yellow oil form.

$^{1}$H NMR (400 MHz, $CDCl_3$) δ 9.30 (s, 2H), 8.22 (d, J=2.5 Hz, 1H), 7.49~7.43 (m, 2H), 7.08 (s, 0.25H), 6.95 (s, 0.5H), 6.82 (s, 0.25H), 6.22 (s, 1H), 5.55 (s, 2H), 4.15~4.09 (m, 2H), 3.70~3.66 (m, 2H), 2.59 (s, 2H), 1.72 (s, 6H), 1.50 (s, 9H).

Synthesis of Compound 155, 2-((5-(5-(difluoromethyl)-1,3,4-oxadiazole-2-yl)pyrimidine-2-yl) methyl)-6-(1-ethyl-1,2, 3,6-tetrahydropyridine-4-yl)-4,4-dimethylisoquinoline-1,3(2H,4H)-dione

[Step 1] Synthesis of 2-((5-(5-(difluoromethyl)-1,3,4-oxadiazole-2-yl)pyrimidine-2-yl)methyl)-4,4-dimethyl-6-(1,2,3,6-tetrahydropyridine-4-yl)isoquinoline-1,3(2H,4H)-dione

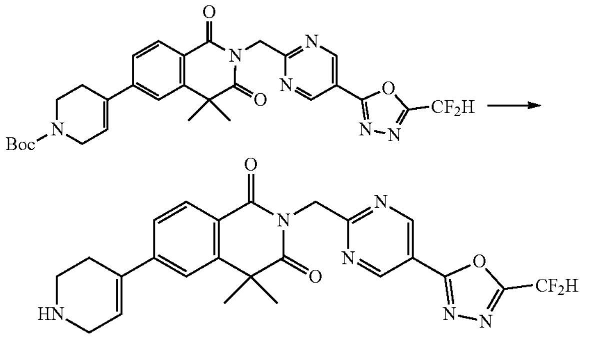

Tert-butyl 4-(2-((5-(5-(difluoromethyl)-1,3,4-oxadiazole-2-yl)pyrimidine-2-yl)methyl)-4,4-dimeth yl-1,3-dioxo-1,2,3,4-tetrahydroisoquinoline-6-yl)-3,6-dihydropyridine-1 (2H)-carboxylat e (0.381 g, 0.656 mmol) and trifluoroacetic acid (0.503 mL, 6.562 mmol) were dissolved in dichloromethane (10 mL) at room temperature, after which the resulting solution was stirred at the same temperature for 5 hours. Solvent was removed from the reaction mixture under reduced pressure, after which saturated sodium hydrogen carbonate aqueous solution was poured into the resulting concentrate, and then an extraction was performed with dichloromethane. An organic layer was washed with saturated sodium chloride aqueous solution, then dehydrated with anhydrous sodium sulfate, then filtered, and then concentrated under reduced pressure. An obtained product was used without an additional purification process (0.241 g, 76.4%, yellow oil).

[Step 2] Synthesis of the Compound 155

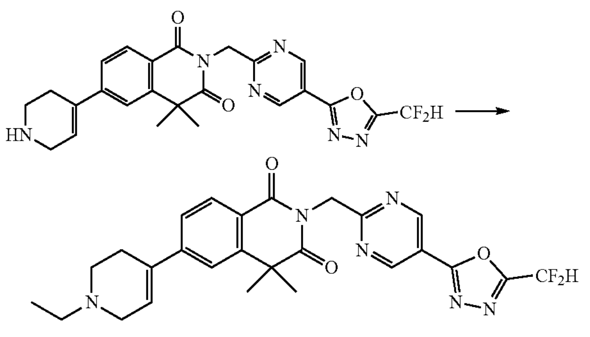

The 2-((5-(5-(difluoromethyl)-1,3,4-oxadiazole-2-yl)pyrimidine-2-yl)methyl)-4,4-dimethyl-6-(1,2,3,6-tetrahydropyridine-4-yl)isoquinoline-1,3(2H,4H)-dione (0.241 g, 0.502 mmol) prepared in the step 1, acetaldehyde (0.056 mL, 1.003 mmol) and sodium triacetoxyborohydride (0.213 g, 1.003 mmol) were dissolved in dichloromethane (20 mL) at room temperature, after which the resulting solution was stirred at the same temperature for 18 hours. Water was poured into the reaction mixture, and an extraction was performed with dichloromethane. An organic layer was washed with saturated sodium chloride aqueous solution, then dehydrated with anhydrous sodium sulfate, then filtered, and then concentrated under reduced pressure. The resulting concentrate was purified via column chromatography ($SiO_2$, 12 g cartridge; methanol/dichloromethane=0 to 10%), and concentrated to obtain a title compound (0.150 g, 58.8%) in a white foam solid form.

$^1H$ NMR (400 MHz, $CDCl_3$) δ 9.30 (s, 2H), 8.20 (d, J=8.2 Hz, 1H), 7.50~7.47 (m, 2H), 7.08 (s, 0.25H), 6.95 (s, 0.5H), 6.82 (s, 0.25H), 6.25 (s, 1H), 5.56 (s, 2H), 3.40~3.39 (m, 2H), 2.95~2.92 (m, 2H), 2.77~2.72 (m, 4H), 1.72 (s, 6H), 1.25 (t, J=7.2 Hz, 3H).

Synthesis of Compound 156, 2-((5-(5-(difluoromethyl)-1,3,4-oxadiazole-2-yl)pyrimidine-2-yl)methyl)-6-(1-ethylpiperidine-4-yl)-4,4-dimethylisoquinoline-1,3(2H,4H)-dione

[Step 1] Synthesis of the Compound 156

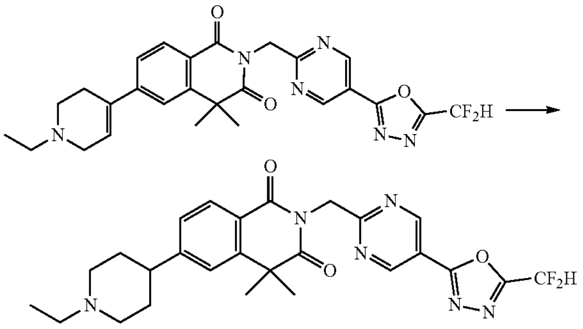

2-((5-(5-(difluoromethyl)-1,3,4-oxadiazole-2-yl)pyrimidine-2-yl)methyl)-6-(1-ethyl-1,2,3,6-tetrahydropyridine-4-yl)-4,4-dimethylisoquinoline-1,3(2H,4H)-dione (0.125 g, 0.246 mmol) were dissolved in methanol (10 mL) at room temperature, after which 10%-Pd/C (10 mg) was slowly added thereinto, and stirred for 18 hours in the presence of a hydrogen balloon attached thereto at the same temperature. The reaction mixture was filtered via a celite pad to remove a solid therefrom, after which solvent was removed from the resulting filtrate without the solid under reduced pressure. Then, the resulting concentrate was purified via column chromatography ($SiO_2$, 12 g cartridge; methanol/dichloromethane=0 to 10%), and concentrated to obtain a title compound (0.100 g, 79.7%) in a white foam solid form.

$^1H$ NMR (400 MHz, $CDCl_3$) δ 9.30 (s, 2H), 8.19 (d, J=8.1 Hz, 1H), 7.42 (d, J=1.4 Hz, 1H), 7.36 (dd, J=8.2, 1.5 Hz, 1H), 7.08 (s, 0.25H), 6.95 (s, 0.5H), 6.82 (s, 0.25H), 5.55 (s, 2H), 3.40~3.37 (m, 2H), 2.78~2.72 (m, 3H), 2.39~2.33 (m, 2H), 2.18~2.15 (m, 2H), 1.99~1.95 (m, 2H), 1.71 (s, 6H), 1.30~1.26 (m, 3H); LRMS (ES) m/z 511.4 ($M^+$+1).

Protocol for Measuring and Analyzing the Activity of the Inventive Compound

<Example 1> Identification of HDAC Enzyme Activity Inhibition (In Vitro)

A selective HDAC6 inhibitor is important for selectivity of HDAC1 inhibition, which is a cause of side effects, and thus HDAC1/6 enzyme selectivity and cell selectivity (HDAC1: histone acetylation/HDAC6: tubulin acetylation) were identified.

1. Experimental Method

HDAC enzyme inhibitory capacity of a test material was measured by using HDAC1 Fluorimetric Drug Discovery Assay Kit (Enzolifesciences: BML-AK511) and HDAC6 human recombinant (Calbiochem: 382180). For a HDAC1 assay, samples were treated at a concentration of 100, 1000 and 10000 nM. For a HDAC6 assay, samples were treated at a concentration of 0.1, 1, 10, 100 and 1000 nM. After the above sample treatment, a reaction was continued at 37° C. for 60 minutes, then treated with a developer, and then subjected to reaction at 37° C. for 30 minutes, after which fluorescence intensity (Ex 390, Em 460) was measured by using FlexStatin3 (Molecular device).

2. Experimental Results

The results thereof are shown in a following table 2.

TABLE 2

Test results of HDAC enzyme activity inhibition

| Compound | HDAC6 $IC_{50}$ (uM) | HDAC1 $IC_{50}$ (uM) |
|---|---|---|
| 1 | 0.057 | >10 |
| 2 | 0.561 | >10 |
| 3 | 0.318 | >10 |
| 4 | 0.032 | >10 |
| 5 | 0.513 | >10 |
| 6 | 0.647 | >10 |
| 7 | 0.145 | >10 |
| 8 | 0.030 | >10 |
| 9 | 0.126 | >10 |
| 10 | 0.455 | >10 |
| 11 | 1.021 | >10 |
| 12 | 0.083 | >10 |
| 13 | 0.225 | >10 |
| 14 | 0.053 | >10 |
| 15 | 0.196 | >10 |
| 16 | 0.257 | >10 |
| 17 | 0.165 | >10 |
| 18 | 0.132 | >10 |
| 19 | 0.249 | >10 |
| 20 | 0.159 | >10 |
| 21 | 0.273 | >10 |
| 22 | 0.210 | >10 |
| 23 | 0.065 | >10 |
| 24 | 0.021 | >10 |
| 25 | 0.158 | >10 |
| 26 | 0.022 | >10 |
| 27 | 0.043 | >10 |
| 28 | 0.024 | >10 |
| 29 | 0.018 | >10 |
| 30 | 0.046 | >10 |
| 31 | 0.029 | >10 |
| 32 | 0.025 | >10 |
| 33 | 0.034 | >10 |
| 34 | 0.027 | >10 |
| 35 | 0.026 | >10 |
| 36 | 0.024 | >10 |
| 37 | 0.015 | >10 |
| 38 | 0.024 | >10 |
| 39 | 0.018 | >10 |
| 40 | 0.022 | >10 |
| 41 | 0.134 | >10 |
| 42 | 0.035 | >10 |
| 43 | 0.038 | >10 |
| 44 | 0.019 | >10 |
| 45 | 0.156 | >10 |
| 46 | 0.121 | >10 |
| 47 | 0.049 | >10 |
| 48 | 0.342 | >10 |
| 49 | 0.041 | >10 |
| 50 | 0.052 | >10 |
| 51 | 0.038 | >10 |
| 52 | 0.040 | >10 |

TABLE 2-continued

| Test results of HDAC enzyme activity inhibition | | |
|---|---|---|
| Compound | HDAC6 $IC_{50}$ (uM) | HDAC1 $IC_{50}$ (uM) |
| 53 | 0.427 | >10 |
| 54 | 0.042 | >10 |
| 55 | 0.020 | >10 |
| 56 | 0.046 | >10 |
| 57 | 0.032 | >10 |
| 58 | 0.014 | >10 |
| 59 | 0.056 | >10 |
| 60 | 0.022 | >10 |
| 61 | 0.035 | >10 |
| 62 | 0.061 | >10 |
| 63 | 0.033 | >10 |
| 64 | 0.025 | >10 |
| 65 | 0.133 | >10 |
| 66 | 0.216 | >10 |
| 67 | 0.062 | >10 |
| 68 | 0.020 | >10 |
| 69 | 0.019 | >10 |
| 70 | 0.059 | >10 |
| 71 | 0.150 | >10 |
| 72 | 0.310 | >10 |
| 73 | 0.098 | >10 |
| 74 | 0.049 | >10 |
| 75 | 0.368 | >10 |
| 76 | 0.079 | >10 |
| 77 | 0.141 | >10 |
| 78 | 0.040 | >10 |
| 79 | 0.113 | >10 |
| 80 | 0.017 | >10 |
| 81 | 0.011 | >10 |
| 82 | 0.092 | >10 |
| 83 | 0.098 | >10 |
| 84 | 0.079 | >10 |
| 85 | 0.050 | >10 |
| 86 | 0.040 | >10 |
| 87 | 0.023 | >10 |
| 88 | 0.021 | >10 |
| 89 | 0.054 | >10 |
| 90 | 0.041 | >10 |
| 91 | 0.033 | >10 |
| 92 | 0.035 | >10 |
| 93 | 0.143 | >10 |
| 94 | 0.116 | >10 |
| 95 | 0.059 | >10 |
| 96 | 0.088 | >10 |
| 97 | 0.061 | >10 |
| 98 | 0.047 | >10 |
| 99 | 0.149 | >10 |
| 100 | 0.037 | >10 |
| 101 | 0.033 | >10 |
| 102 | 0.030 | >10 |
| 103 | 0.059 | >10 |
| 104 | 0.020 | >10 |
| 105 | 0.010 | >10 |
| 106 | 0.048 | >10 |
| 107 | 0.148 | >10 |
| 108 | 0.211 | >10 |
| 109 | 0.107 | >10 |
| 110 | 0.015 | >10 |
| 111 | 0.017 | >10 |
| 112 | 0.050 | >10 |
| 113 | 0.043 | >10 |
| 114 | 0.077 | >10 |
| 115 | 0.059 | >10 |
| 116 | 0.200 | >10 |
| 117 | 0.022 | >10 |
| 118 | 0.022 | >10 |
| 119 | 0.021 | >10 |
| 120 | 0.081 | >10 |
| 121 | 0.036 | >10 |
| 122 | 0.023 | >10 |
| 123 | 0.017 | >10 |
| 124 | 0.038 | >10 |
| 125 | 0.043 | >10 |
| 126 | 0.032 | >10 |
| 127 | 0.017 | >10 |
| 128 | 0.070 | >10 |
| 129 | 0.026 | >10 |
| 130 | 0.030 | >10 |
| 131 | 0.062 | >10 |
| 132 | 0.069 | >10 |
| 133 | 0.076 | >10 |
| 134 | 0.012 | >10 |
| 135 | 0.100 | >10 |
| 136 | 0.055 | >10 |
| 137 | 0.089 | >10 |
| 138 | 0.096 | >10 |
| 139 | 0.683 | >10 |
| 140 | 0.535 | >10 |
| 141 | 0.052 | >10 |
| 142 | 0.081 | >10 |
| 143 | 0.021 | >10 |
| 144 | 0.034 | >10 |
| 145 | 0.037 | >10 |
| 146 | 0.058 | >10 |
| 147 | 0.069 | >10 |
| 148 | 0.032 | >10 |
| 149 | 0.095 | >10 |
| 150 | 0.051 | >10 |
| 151 | 0.033 | >10 |
| 152 | 0.125 | >10 |
| 153 | 0.118 | >10 |
| 154 | 0.414 | >10 |
| 155 | 0.185 | >10 |
| 156 | 0.056 | >10 |

As described in the above table 2, from the results of testing the HDAC1 and HDAC6 activity inhibition, it could be understood that 1,3,4-oxadiazole homophthalimide derivative compounds of the present invention, stereoisomers thereof or pharmaceutically acceptable salts thereof show not only an excellent HDAC6 inhibitory activity, but also an excellent selective inhibitory activity of HDAC6 to HDAC1.

The invention claimed is:

1. A compound represented by a following chemical formula I, stereoisomers thereof or pharmaceutically acceptable salts thereof:

(Chemical Formula I)

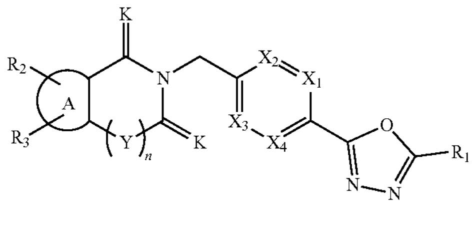

wherein, $X_1$ to $X_4$ are each independently $CR_0$ or N, wherein at least two of $X_1$ to $X_4$ are $CR_0$, in which each $R_0$ is independently hydrogen, halogen, straight or branched —$C_{1-7}$ alkyl, or straight or branched —O—$C_{1-7}$ alkyl, $R_1$ is straight or branched —$C_{1-5}$ haloalkyl, $R_2$ and $R_3$ are each independently H, halogen,

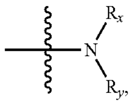

3- to 7-membered heterocycloalkyl comprising one to three heteroatoms selected from group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

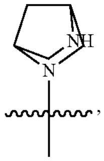

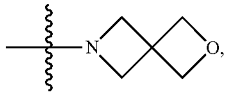

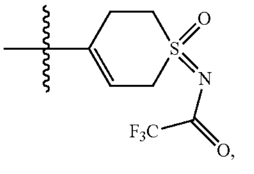

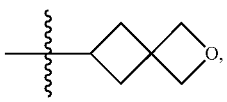 [SMILES: *C1CC2(COC2)C1]

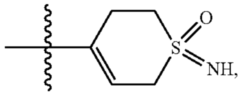

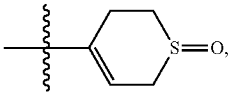

—$C_{1-7}$ alkyl, 3- to 7-membered cycloalkyl, 3- to 7-membered cycloalkenyl, cyclopenta-1,3-diene, phenyl, indolyl,

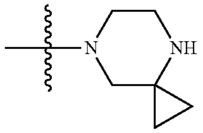 [SMILES: *N1CCNC2(CC2)C1]

or

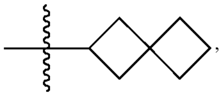

wherein at least one hydrogen of said 3- to 7-membered heterocycloalkyl comprising one to three heteroatoms selected from the group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

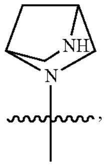

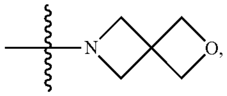

-continued

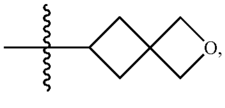

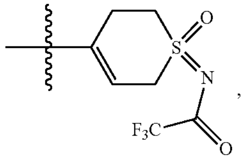

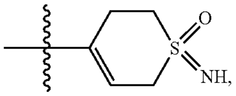

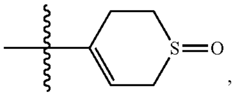

—$C_{1-7}$ alkyl, 3- to 7-membered cycloalkyl, 3- to 7-membered cycloalkenyl, cyclopenta-1,3-diene, phenyl, indolyl,

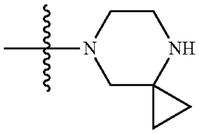

or

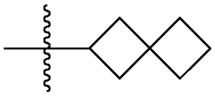

can be substituted with $R_4$, $R_4$ is halogen, —$C_{1-7}$ alkyl, —$C_{1-7}$ haloalkyl, —O—$C_{1-7}$ alkyl, —C(═O)—$C_{1-7}$ alkyl, —C(═O)—$C_{1-7}$ alkyl-OH, —C(═O)—O—$C_{1-7}$ alkyl, —S(═O)$_2$—$C_{1-7}$ alkyl, 3- to 7-membered cycloalkyl, 3- to 7-membered halocycloalkyl, 3- to 7-membered heterocycloalkyl comprising one to three heteroatoms selected from the group comprising N, O or S, 5- or 6-membered heteroaryl comprising one to three heteroatoms selected from the group comprising N, O or S,

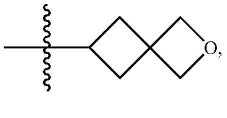

—$C_{1-7}$ alkyl-C(═O)—$R_5$, —$C_{1-7}$ alkyl-C(═O)—O—$R_6$, —$C_{1-7}$ alkyl-$R_7$, —$C_{1-7}$ alkyl-O—$R_8$, —$NR_9R_{10}$, —C(═O)—$NR_{11}R_{12}$ or —$C_{1-7}$ alkyl-$NR_{13}R_{14}$, in which $R_5$ is —$C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, cyclopenta-1,3-diene or phenyl, $R_6$ is —$C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, cyclopenta-1,3-diene or phenyl, $R_7$ is 3- to 7-membered heterocycloalkyl comprising one to three heteroatoms selected from the group comprising N, O or S, 3- to 7-membered cycloalkyl, 5- or 6-membered heteroaryl comprising one to three heteroatoms selected from the group comprising N, O or S, cyclopenta-1,3-diene or phenyl, $R_8$ is —$C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, cyclopenta-1,3-diene or phenyl, $R_9$ and $R_{10}$ are each independently H or —$C_{1-7}$ alkyl, $R_{11}$ and $R_{12}$ are each independently H or —$C_{1-7}$ alkyl, and $R_{13}$ and $R_{14}$ are each independently H or —$C_{1-7}$ alkyl, $R_x$ and $R_y$ are each independently —$C_{1-7}$ alkyl, —$C_{1-7}$ alkyl-$NR_{15}R_{16}$, H, —$C_{1-7}$ alkyl-O-$C_{1-7}$ alkyl, —C(═O)—$C_{1-7}$ alkyl, heteroaryl comprising one to three heteroatoms selected from the group comprising N, O or S, —C(═O)-heterocycloalkyl wherein the heterocycloalkyl is a 3-to 7-membered heterocycloalkyl comprising one to three heteroatoms selected from the group comprising N, O or S, —C(═O) cycloalkyl wherein the cycloalkyl is a 3- to 7-membered cycloalkyl, —$C_{1-7}$ alkyl-O-heterocycloalkyl wherein the heterocycloalkyl is a 3- to 7-membered heterocycloalkyl comprising one to three heteroatoms selected from the group comprising N, O or S or —$C_{1-7}$ alkyl-cycloalkyl wherein the cycloalkyl is a 3- to 7-membered cycloalkyl wherein at least one hydrogen of —$C_{1-7}$ alkyl, —$C_{1-7}$ alkyl-O—$C_{1-7}$ alkyl, —C(═O)—$C_{1-7}$ alkyl, —C(═O)-heteroaryl wherein the heteroaryl is a 5- or 6-membered heteroaryl comprising one to three heteroatoms selected from the group comprising N, O or S, —C(═O)-heterocycloalkyl wherein the heterocycloalkyl is a 3- to 7-membered heterocycloalkyl comprising one to three heteroatoms selected from the group comprising N, O or S, —C(═O) cycloalkyl wherein the cycloalkyl is a 3- to 7-membered cycloalkyl, —$C_{1-7}$ alkyl-O-heterocycloalkyl wherein the heterocycloalkyl is a 3- to 7-membered heterocycloalkyl comprising one to three heteroatoms selected from the group comprising N, O or S or —$C_{1-7}$ alkyl-cycloalkyl wherein the cycloalkyl is a 3- to 7-membered cycloalkyl can be substituted with —$C_{1-7}$ alkyl, halogen, —O—$C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, —S(═O)$_2$—$C_{1-7}$ alkyl, —$CF_3$,

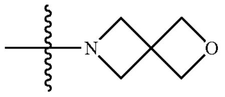
or
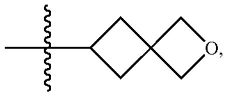

and $R_{15}$ and $R_{16}$ are each independently H or —$C_{1-7}$ alkyl),

K is O or S,

Y is $CR_aR_b$ or $NR_c$, $R_a$ and $R_b$ are each independently hydrogen, —$C_{1-7}$ alkyl, 3- to 7-membered cycloalkyl, —$C_{1-7}$ alkyl-O—$C_{1-7}$ alkyl, —$C_{1-7}$ alkyl-$NR_{17}R_{18}$, 3- to 7-membered heterocycloalkyl comprising one to three heteroatoms selected from the group comprising N, O or S, —$C_{1-7}$ alkyl-C(═O)—$C_{1-7}$ alkyl or —$C_{1-7}$ alkyl-C(═O)—O—$C_{1-7}$ alkyl, or $R_a$ and $R_b$ are linked to each other to form 3- to 7-membered cycloalkyl, wherein at least one hydrogen of —$C_{1-7}$ alkyl, 3- to 7-membered cycloalkyl, —$C_{1-7}$ alkyl-O—$C_{1-7}$ alkyl, —$C_{1-7}$ alkyl-$NR_{17}R_{18}$, 3- to 7-membered heterocycloalkyl comprising one to three heteroatoms selected from the group comprising N, O or S, —$C_{1-7}$ alkyl-C (═O)—$C_{1-7}$ alkyl or —$C_{1-7}$ alkyl-C(═O)—O—$C_{1-7}$ alkyl may be substituted with —$C_{1-7}$ alkyl, halogen, —O—$C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, —S(═O)$_2$—$C_{1-7}$ alkyl, —$CF_3$,

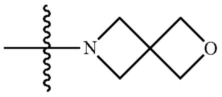
or
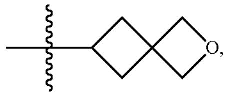

and $R_{17}$ and $R_{18}$ are each independently H or —$C_{1-7}$ alkyl, $R_c$ is hydrogen, —$C_{1-7}$ alkyl, —$C_{1-7}$ alkyl-heterocycloalkyl wherein the heterocycloalkyl is a 3- to 7-membered heterocycloalkyl comprising one to three heteroatoms selected from the group comprising N, O or S, —$C_{1-7}$ alkyl-phenyl, —$C_{1-7}$ alkyl-heteroaryl wherein the heteroaryl is a 5- or 6-membered heteroaryl comprising one to three heteroatoms selected from the group comprising N, O or S, —$C_{1-7}$ alkyl-O—$C_{1-7}$ alkyl, —$C_{1-7}$ alkyl-$NR_{19}R_{20}$, —$C_{1-7}$ alkyl-cycloalkyl wherein the cycloalkyl is a 3- to 7-membered cycloalkyl, a 3- to 7-membered heterocycloalkyl comprising one to three heteroatoms selected from the group comprising N, O or S, a 3- to 7-membered cycloalkyl, a 5- or 6-membered heteroaryl comprising one to three heteroatoms selected from the group comprising N, O or S, cyclopenta-1,3-diene, phenyl, —C(═O)—, —C(═O)-heterocycloalkyl wherein the heterocycloalkyl is a 3- to 7-membered heterocycloalkyl comprising one to three heteroatoms selected from the group comprising N, O or S, —C(═O) cycloalkyl wherein the cycloalkyl is a 3- to 7-membered cycloalkyl, —C(═O)-heteroaryl wherein the heteroaryl is a 5- or 6-membered heteroaryl comprising one to three heteroatoms selected from the group comprising N, O or S, —C(═O)-phenyl, —C(═O)—$C_{1-7}$ alkyl, —C(═O)—$C_{1-7}$ alkyl-O—$C_{1-7}$ alkyl or —C(═O)—$C_{1-7}$ alkyl-$NR_{19}R_{20}$, wherein at least one hydrogen of —$C_{1-7}$ alkyl, —$C_{1-7}$ alkyl-heterocycloalkyl wherein the heterocycloalkyl is a 3- to 7-membered heterocycloalkyl comprising one to three heteroatoms selected from the group comprising N, O or S, —$C_{1-7}$ alkyl-phenyl, —$C_{1-7}$ alkyl-heteroaryl wherein the heteroaryl is a 5- or 6-membered heteroaryl comprising one to three heteroatoms selected from the group comprising N, O or S, —$C_{1-7}$ alkyl-O—$C_{1-7}$ alkyl, —$C_{1-7}$ alkyl-$NR_{19}R_{20}$, —$C_{1-7}$ alkyl-cycloalkyl wherein the cycloalkyl is a 3- to 7-membered cycloalkyl, a 3- to 7-membered heterocycloalkyl comprising one to three heteroatoms selected from the group comprising N, O or S, a 3- to 7-membered cycloalkyl, a 5- or 6-membered heteroaryl comprising one to three heteroatoms selected from the group comprising N, O or S, cyclopenta-1,3-diene, phenyl, —C(═O)—, —C(═O)-heterocycloalkyl wherein the heterocycloalkyl is a 3- to 7-membered heterocycloalkyl comprising one to three heteroatoms selected from the group comprising N, O or S, —C(═O) cycloalkyl wherein the cycloalkyl is a 3- to 7-membered cycloalkyl, —C(═O)-heteroaryl wherein the heteroaryl is a 5- or 6-membered heteroaryl comprising one to three heteroatoms selected from the group comprising N, O or S, —C(═O)-phenyl, —C(═O)—$C_{1-7}$ alkyl, —C(═O)—$C_{1-7}$ alkyl-O—$C_{1-7}$ alkyl or —C(═O)—$C_{1-7}$ alkyl-$NR_{19}R_{20}$, can be substituted with —$C_{1-7}$ alkyl, halogen, —O—$C_{1-7}$ alkyl, a 3- to 7-membered heterocycloalkyl comprising one to three heteroatoms selected from the group comprising N, O or S, —C(=O)—O—$C_{1-7}$ alkyl, a 5- or 6-membered heteroaryl comprising one to three heteroatoms selected from the group comprising N, O or S, heteroaryl-$C_{1-5}$ haloalkyl wherein the heteroaryl is a 5- or 6-membered heteroaryl comprising one to three heteroatoms selected from the group comprising N, O or S, 3- to 7-membered cycloalkyl, —S(=O)$_2$—$C_{1-7}$alkyl, —$CF_3$,

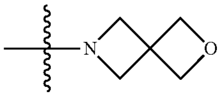 or 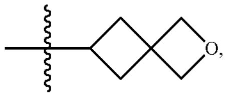

and $R_{19}$ and $R_{20}$ are each independently H or —$C_{1-7}$ alkyl,

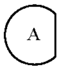

is phenylene or 5- or 6-membered heteroarylene comprising one to three heteroatoms selected from the group comprising N, O or S, halogen is F, Cl, Br or I, and n is 1.

2. The compound represented by the chemical formula I, stereoisomers thereof or pharmaceutically acceptable salts thereof according to claim 1, wherein $X_1$ to $X_4$ are each independently $CR_0$ or N, wherein at least two of $X_1$ to $X_4$ are $CR_0$, in which $R_0$ is hydrogen, halogen or —O—$C_{1-7}$ alkyl, $R_1$ is —$C_{1-5}$ haloalkyl, $R_2$ and $R_3$ are each independently H, halogen,

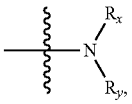

3- to 7-membered heterocycloalkyl comprising one to three heteroatoms selected from group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

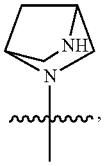, 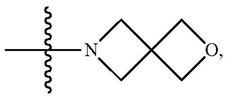

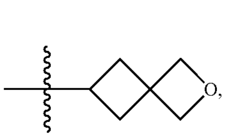 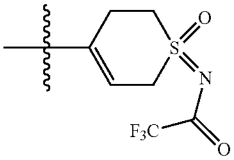,

-continued

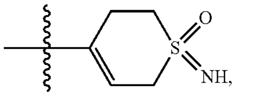 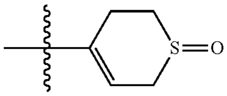, phenyl, indolyl,

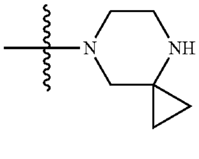

or —$C_{1-7}$ alkyl, (in which at least one hydrogen of said 3- to 7-membered heterocycloalkyl comprising one to three heteroatoms selected from the group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

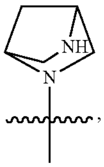, 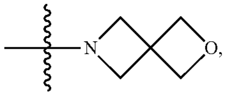

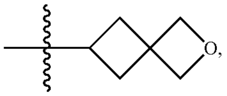 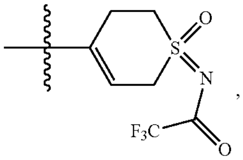,

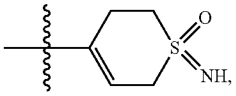 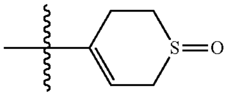, phenyl, indolyl,

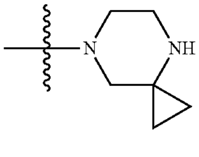 [SMILES: *N1CCNC2(CC2)C1]

or —$C_{1-7}$ alkyl can be substituted with $R_4$, $R_4$ is halogen, —$C_{1-7}$ alkyl, —$C_{1-7}$ haloalkyl, —O—$C_{1-7}$ alkyl, —C(=O)—$C_{1-7}$ alkyl, —C(=O)—$C_{1-7}$ alkyl-OH, —C(=O)—O—$C_{1-7}$ alkyl, —S(=O)$_2$—$C_{1-7}$ alkyl, 3- to 7-membered cycloalkyl, 3- to 7-membered halocycloalkyl, 3- to 7-membered heterocycloalkyl comprising one to three heteroatoms selected from the group comprising N, O or S, 5- or 6-membered heteroaryl comprising one to three heteroatoms selected from the group comprising N, O or S,

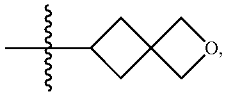 [SMILES: *C1CC2(COC2)C1], $-C_{1-7}$ alkyl-C(=O)—$R_5$, $-C_{1-7}$ alkyl-C(=O)—O—$R_6$, $-C_{1-7}$ alkyl-$R_7$, $-C_{1-7}$ alkyl-O—$R_8$, $-NR_9R_{10}$, —C(=O)—$NR_{11}R_{12}$ or $-C_{1-7}$ alkyl-$NR_{13}R_{14}$, in which $R_5$ is $-C_{1-7}$ alkyl or 3- to 7-membered heterocycloalkyl comprising one to three heteroatoms selected from the group comprising N, O or S, $R_6$ is $-C_{1-7}$ alkyl, $R_7$ is 3- to 7-membered heterocycloalkyl comprising one to three heteroatoms selected from the group comprising N, O or S or 3- to 7-membered cycloalkyl, $R_8$ is $-C_{1-7}$ alkyl, $R_9$ and $R_{10}$ are each independently H or $-C_{1-7}$ alkyl, $R_{11}$ and $R_{12}$ are each independently H or $-C_{1-7}$ alkyl, and $R_{13}$ and $R_{14}$ are each independently H or $-C_{1-7}$ alkyl), $R_x$ and $R_y$ are each independently $-C_{1-7}$ alkyl, $-C_{1-7}$ alkyl-$NR_{15}R_{16}$, H, $-C_{1-7}$ alkyl-O—$C_{1-7}$ alkyl, —C(=O)—$C_{1-7}$ alkyl, —C(=O)-heteroaryl wherein the heteroaryl is a 5- or 6-membered heteroaryl comprising one to three heteroatoms selected from the group comprising N, O or S, —C(=O)-heterocycloalkyl wherein the heterocycloalkyl is a 3-to 7-membered heterocycloalkyl comprising one to three heteroatoms selected from the group comprising N, O or S) or —C(=O) cycloalkyl wherein the cycloalkyl is a 3- to 7-membered cycloalkyl wherein at least one hydrogen of $-C_{1-7}$ alkyl, $-C_{1-7}$ alkyl-O—$C_{1-7}$ alkyl, —C(=O)—$C_{1-7}$ alkyl, —C(=O)-heteroaryl wherein the heteroaryl is a 5- or 6-membered heteroaryl comprising one to three heteroatoms selected from the group comprising N, O or S, —C(=O)-heterocycloalkyl wherein the heterocycloalkyl is a 3- to 7-membered heterocycloalkyl comprising one to three heteroatoms selected from the group comprising N, O or S or —C(=O)-cycloalkyl wherein the cycloalkyl is a 3- to 7-membered cycloalkyl can be substituted with-$C_{1-7}$ alkyl, halogen, —O—$C_{1-7}$ alkyl, 3- to 7-membered heterocycloalkyl comprising one to three heteroatoms selected from the group comprising N, O or S, a 5- or 6-membered heteroaryl comprising one to three heteroatoms selected from the group comprising N, O or S, a 3- to 7-membered cycloalkyl, $-S(=O)_2-C_{1-7}$ alkyl, $-CF_3$,

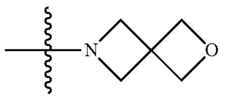 or 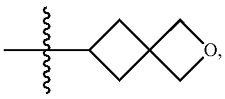, and $R_{15}$ and $R_{16}$ are each independently H or $-C_{1-7}$ alkyl, K is O or S, Y is $CR_aR_b$ or $NR_c$, $R_a$ and $R_b$ are each independently hydrogen, $-C_{1-7}$ alkyl, 3- to 7-membered cycloalkyl, $-C_{1-7}$ alkyl-O—$C_{1-7}$ alkyl, $-C_{1-7}$ alkyl-$NR_{17}R_{18}$, or $R_a$ and $R_b$ are linked to each other to form 3- to 7-membered cycloalkyl, wherein at least one hydrogen of $-C_{1-7}$ alkyl, 3- to 7-membered cycloalkyl, $-C_{1-7}$ alkyl-O—$C_{1-7}$ alkyl or $-C_{1-7}$ alkyl-$NR_{17}R_{18}$ can be substituted with $-C_{1-7}$ alkyl, halogen, —O—$C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, $-S(=O)_2-C_{1-7}$ alkyl, $-CF_3$,

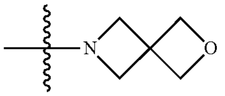 or 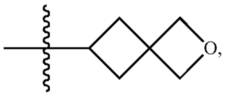, and $R_{17}$ and $R_{18}$ are each independently H or $-C_{1-7}$ alkyl, $R_c$ is hydrogen, $-C_{1-7}$ alkyl, $-C_{1-7}$ alkyl-heterocycloalkyl wherein the heterocycloalkyl is a 3- to 7-membered heterocycloalkyl comprising one to three heteroatoms selected from the group comprising N, O or S, $-C_{1-7}$ alkyl-phenyl, $-C_{1-7}$ alkyl-heteroaryl wherein the heteroaryl is a 5- or 6-membered heteroaryl comprising one to three heteroatoms selected from the group comprising N, O or S, $-C_{1-7}$ alkyl-O—$C_{1-7}$ alkyl, $-C_{1-7}$ alkyl-$NR_{19}R_{20}$, $-C_{1-7}$ alkyl-cycloalkyl wherein the cycloalkyl is a 3- to 7-membered cycloalkyl, a 3- to 7-membered heterocycloalkyl comprising one to three heteroatoms selected from the group comprising N, O or S, a 3- to 7-membered cycloalkyl, a 5- or 6-membered heteroaryl comprising one to three heteroatoms selected from the group comprising N, O or S, cyclopenta-1,3-diene, phenyl, —C(=O)—, —C(=O)-heterocycloalkyl wherein the heterocycloalkyl is a 3- to 7-membered heterocycloalkyl comprising one to three heteroatoms selected from the group comprising N, O or S, —C(=O) cycloalkyl wherein the cycloalkyl is a 3- to 7-membered cycloalkyl, —C(=O)-heteroaryl wherein the heteroaryl is a 5- or 6-membered heteroaryl comprising one to three heteroatoms selected from the group comprising N, O or S, —C(=O)-phenyl, —C(=O)—$C_{1-7}$ alkyl, —C(=O)—$C_{1-7}$ alkyl-O—$C_{1-7}$ alkyl or —C(=O)—$C_{1-7}$ alkyl-$NR_{19}R_{20}$, wherein at least one hydrogen of $-C_{1-7}$ alkyl, $-C_{1-7}$ alkyl-heterocycloalkyl wherein the heterocycloalkyl is a 3- to 7-membered heterocycloalkyl comprising one to three heteroatoms selected from the group comprising N, O or S, $-C_{1-7}$ alkyl-phenyl, $-C_{1-7}$ alkyl-heteroaryl wherein the heteroaryl is a 5- or 6-membered heteroaryl comprising one to three heteroatoms selected from the group comprising N, O or S, $-C_{1-7}$ alkyl-O—$C_{1-7}$ alkyl, $-C_{1-7}$ alkyl-$NR_{19}R_{20}$, $-C_{1-7}$ alkyl-cycloalkyl wherein the cycloalkyl is a 3- to 7-membered cycloalkyl, a 3- to 7-membered heterocycloalkyl comprising one to three heteroatoms selected from the group comprising N, O or S, a 3- to 7-membered cycloalkyl, a 5- or 6-membered heteroaryl comprising one to three heteroatoms selected from the group comprising N, O or S, cyclopenta-1,3-diene, phenyl, —C(=O)—, —C(=O)-heterocycloalkyl wherein the heterocycloalkyl is a 3- to 7-membered heterocycloalkyl comprising one to three heteroatoms selected from the group comprising N, O or S, —C(=O) cycloalkyl wherein the cycloalkyl is a 3- to 7-membered cycloalkyl, —C(=O)-heteroaryl wherein the heteroaryl is a 5- or 6-membered heteroaryl comprising one to three heteroatoms selected from the group comprising N, O or S, —C(=O)-phenyl, —C(=O)—$C_{1-7}$ alkyl, —C(=O)—$C_{1-7}$ alkyl-O—$C_{1-7}$ alkyl or —C(=O)—$C_{1-7}$ alkyl-$NR_{19}R_{20}$, can be substituted with $—C_{1-7}$ alkyl, halogen, $—O—C_{1-7}$ alkyl, a 3- to 7-membered heterocycloalkyl comprising one to three heteroatoms selected from the group comprising N, O or S, $—C(=O)—O—C_{1-7}$ alkyl, a 5- or 6-membered heteroaryl comprising one to three heteroatoms selected from the group comprising N, O or S, heteroaryl-$C_{1-5}$ haloalkyl wherein the heteroaryl is a 5- or 6-membered heteroaryl comprising one to three heteroatoms selected from the group comprising N, O or S, 3- to 7-membered cycloalkyl, $—S(=O)_2—C_{1-7}$alkyl, $—CF_3$,

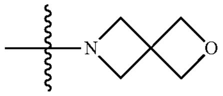 or 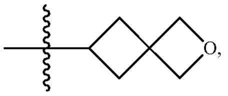

and $R_{19}$ and $R_{20}$ are each independently H or $—C_{1-7}$ alkyl,

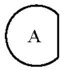

is phenylene or 5- or 6-membered heteroarylene comprising one to three heteroatoms selected from the group comprising N, O or S, halogen is F, Cl, Br or I, and n is 1.

3. The compound represented by the chemical formula I, stereoisomers thereof or pharmaceutically acceptable salts thereof according to claim 1, wherein $X_1$ to $X_4$ are each independently $CR_0$ or N, wherein at least two of $X_1$ to $X_4$ are $CR_0$, $R_0$ is hydrogen or halogen, $R_1$ is $—C_{1-5}$ haloalkyl, $R_2$ and $R_3$ are each independently H, halogen,

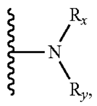

3- to 7-membered heterocycloalkyl comprising one to three heteroatoms selected from group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

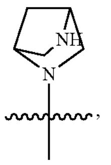 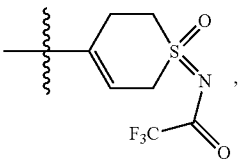 ,

-continued

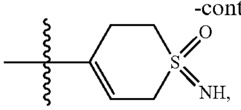 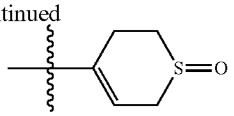 , phenyl, indolyl,

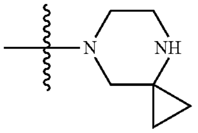 or 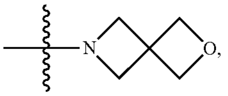

(in which at least one hydrogen of said 3- to 7-membered heterocycloalkyl comprising one to three heteroatoms selected from the group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

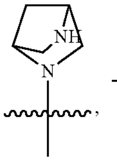 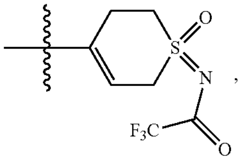 ,

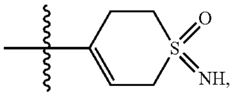 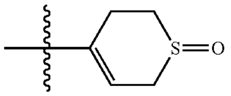 , phenyl, indolyl,

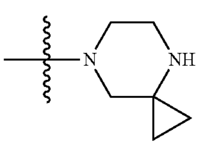 or 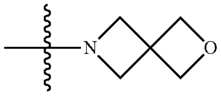

can be substituted with $R_4$, $R_4$ is halogen, $—C_{1-7}$ alkyl, $—C_{1-7}$ haloalkyl, $—O—C_{1-7}$ alkyl, $—C(=O)—C_{1-7}$ alkyl, $—C(=O)—C_{1-7}$ alkyl-OH, $—C(=O)—O—C_{1-7}$ alkyl, $—S(=O)_2—C_{1-7}$ alkyl, 3- to 7-membered cycloalkyl, 3- to 7-membered halocycloalkyl, 3- to 7-membered heterocycloalkyl comprising one to three heteroatoms selected from the group comprising N, O or S, 5- or 6-membered heteroaryl comprising one to three heteroatoms selected from the group comprising N, O or S,

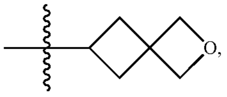

$—C_{1-7}$ alkyl-$C(=O)—R_5$, $—C_{1-7}$ alkyl-$R_7$, $—C_{1-7}$ alkyl-$O—R_8$, $—NR_9R_{10}$ or $—C(=O)—NR_{11}R_{12}$, in which $R_5$ is 3- to 7-membered heterocycloalkyl comprising one to three heteroatoms selected from the group comprising N, O or S, $R_7$ is 3- to 7-membered heterocycloalkyl comprising one to three heteroatoms selected from the group comprising N, O or S or 3- to 7-membered cycloalkyl, $R_a$ is —$C_{1-7}$ alkyl, $R_9$ and $R_{10}$ are each independently —$C_{1-7}$ alkyl, and $R_{11}$ and $R_{12}$ are each independently H or —$C_{1-7}$ alkyl), $R_x$ and $R_y$ are each independently —$C_{1-7}$ alkyl or —$C_{1-7}$ alkyl-$NR_{15}R_{16}$, (in which $R_{15}$ and $R_{16}$ are each independently —$C_{1-7}$ alkyl), K is O, Y is $CR_aR_b$ or $NR_c$, $R_c$ is hydrogen, —$C_{1-7}$ alkyl, —$C_{1-7}$ alkyl-heterocycloalkyl wherein the heterocycloalkyl is a 3- to 7-membered heterocycloalkyl comprising one to three heteroatoms selected from the group comprising N, O or S, —$C_{1-7}$ alkyl-phenyl, —$C_{1-7}$ alkyl-heteroaryl wherein the heteroaryl is a 5- or 6-membered heteroaryl comprising one to three heteroatoms selected from the group comprising N, O or S, —$C_{1-7}$ alkyl-O—$C_{1-7}$ alkyl or —$C_{1-7}$ alkyl-$NR_{19}R_{20}$, wherein at least one hydrogen of —$C_{1-7}$ alkyl, —$C_{1-7}$ alkyl-heterocycloalkyl (in this case, heterocycloalkyl is a 3- to 7-membered heterocycloalkyl comprising one to three heteroatoms selected from the group comprising N, O or S, —$C_{1-7}$ alkyl-phenyl, —$C_{1-7}$ alkyl-heteroaryl wherein the heteroaryl is a 5- or 6-membered heteroaryl comprising one to three heteroatoms selected from the group comprising N, O or S, —$C_{1-7}$ alkyl-O—$C_{1-7}$ alkyl, or —$C_{1-7}$ alkyl-$NR_{19}R_{20}$ can be substituted with —$C_{1-7}$ alkyl, —O—$C_{1-7}$ alkyl, 3- to 7-membered heterocycloalkyl comprising one to three heteroatoms selected from the group comprising N, O or S, heteroaryl-$C_{1-5}$ haloalkyl wherein the heteroaryl is a 5- or 6-membered heteroaryl comprising one to three heteroatoms selected from the group comprising N, O or S or —C(═O)—O—$C_{1-7}$ alkyl, and $R_{19}$ and $R_{20}$ are each independently —$C_{1-7}$ alkyl,

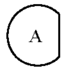

is phenylene, halogen is F or Br, and n is 1.

4. The compound represented by the chemical formula I, stereoisomers thereof or pharmaceutically acceptable salts thereof according to claim 1, wherein $X_1$ to $X_4$ are each independently $CR_0$ or N, wherein at least two of $X_1$ to $X_4$ are $CR_0$, $R_0$ is hydrogen or F, $R_1$ is $CF_2H$, $R_2$ and $R_3$ are each independently H, F, Br,

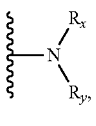

3- to 7-membered heterocycloalkyl comprising one to three heteroatoms selected from group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

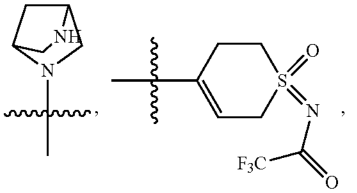

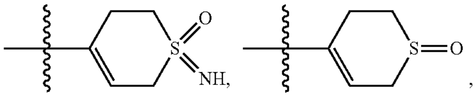

phenyl, indolyl,

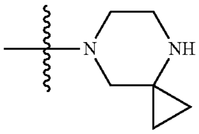 or 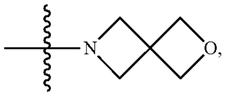 [SMILES: *C1CC2(COC2)C1]

wherein at least one hydrogen of said 3- to 7-membered heterocycloalkyl comprising one to three heteroatoms selected from the group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

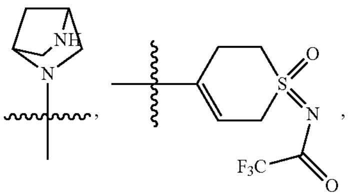

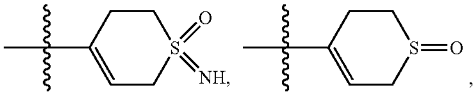

phenyl, indoyl,

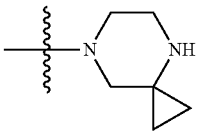 or 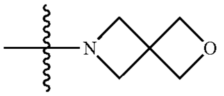

can be substituted with $R_4$, $R_4$ is F, —$C_{1-7}$ alkyl, —$C_{1-7}$ haloalkyl, —O—$C_{1-7}$ alkyl, —C(═O)—$C_{1-7}$ alkyl, —C(═O)—$C_{1-7}$ alkylOH, —C(═O)—O—$C_{1-7}$ alkyl, —S(═O)$_2$—$C_{1-7}$ alkyl, 3- to 7-membered cycloalkyl, 3- to 7-membered halocycloalkyl, 3- to 7-membered heterocycloalkyl comprising one to three heteroatoms selected from the group comprising N, O or S, 5- or 6-membered heteroaryl comprising one to three heteroatoms selected from the group comprising N, O or S,

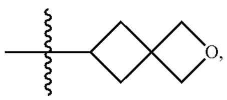 [SMILES: *C1CC2(COC2)C1]

—$C_{1-7}$ alkyl-C(=O)—$R_5$, —$C_{1-7}$ alkyl-$R_7$, —$C_{1-7}$ alkyl-O—$R_8$, —$NR_9R_{10}$ or —C(=O)—$NR_{11}R_{12}$, in which $R_5$ is 3- to 7-membered heterocycloalkyl comprising one to three heteroatoms selected from the group comprising N, O or S, $R_7$ is 3- to 7-membered heterocycloalkyl comprising one to three heteroatoms selected from the group comprising N, O or S or 3-to 7-membered cycloalkyl, $R_8$ is —$C_{1-7}$ alkyl, $R_9$ and $R_{10}$ are each independently —$C_{1-7}$ alkyl, and $R_{11}$ and $_{12}$ are each independently H or —$C_{1-7}$ alkyl), $R_x$ and $R_y$ are each independently —$C_{1-7}$ alkyl or —$C_{1-7}$ alkyl-$NR_{15}R_{16}$, wherein $R_{15}$ and $R_{16}$ are each independently —$C_{1-7}$ alkyl, K is O, Y is $CR_aR_b$ or $NR_c$, $R_a$ and $R_b$ are each independently hydrogen or —$C_{1-7}$ alkyl, or $R_a$ and $R_b$ are linked to each other to form 3- to 7-membered cycloalkyl, $R_c$ is hydrogen, —$C_{1-7}$ alkyl, —$C_{1-7}$ alkyl-heterocycloalkyl wherein the heterocycloalkyl is a 3- to 7-membered heterocycloalkyl comprising one to three heteroatoms selected from the group comprising N, O or S, —$C_{1-7}$ alkyl-phenyl, —$C_{1-7}$ alkyl-heteroaryl wherein the heteroaryl is a 5- or 6-membered heteroaryl comprising one to three heteroatoms selected from the group comprising N, O or S, —$C_{1-7}$ alkyl-O—$C_{1-7}$ alkyl or —$C_1$-7 alkyl-$NR_{19}R_{20}$, wherein at least one hydrogen of —$C_{1-7}$ alkyl, —$C_{1-7}$ alkyl-heterocycloalkyl (in this case, heterocycloalkyl is 3- to 7-membered heterocycloalkyl comprising one to three heteroatoms selected from the group comprising N, O or S, —$C_{1-7}$ alkyl-phenyl, —$C_{1-7}$ alkyl-heteroaryl wherein the heteroaryl is a 5- or 6-membered heteroaryl comprising one to three heteroatoms selected from the group comprising N, O or S, —$C_{1-7}$ alkyl-O—$C_{1-7}$ alkyl or —$C_{1-7}$ alkyl-$NR_{19}R_{20}$ can be substituted with-$C_{1-7}$ alkyl, —O—$C_{1-7}$ alkyl, 3- to 7-membered heterocycloalkyl comprising one to three heteroatoms selected from the group comprising N, O or S, heteroaryl-$C_{1-5}$ haloalkyl wherein the heteroaryl is 5- or 6-membered heteroaryl comprising one to three heteroatoms selected from the group comprising N, O or S or —C(=O)—O—$C_{1-7}$ alkyl, and $R_{19}$ and $R_{20}$ are each independently —$C_{1-7}$ alkyl,

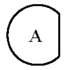

is phenylene, halogen is F or Br, and n is 1.

5. A compound represented by a following chemical formula II, stereoisomers thereof or pharmaceutically acceptable salts thereof:

(Chemical Formula II)

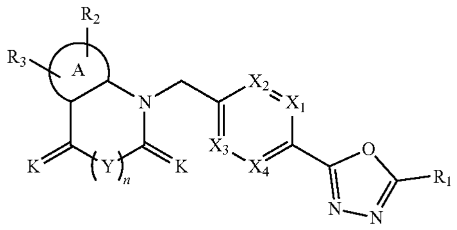

wherein, $X_1$ to $X_4$ are each independently $CR_0$ or N, wherein at least two of $X_1$ to $X_4$ are $CR_0$, in which each $R_0$ is independently hydrogen, halogen, straight or branched —$C_{1-7}$ alkyl, or straight or branched —O—$C_{1-7}$ alkyl, $R_1$ is straight or branched —$C_{1-5}$ haloalkyl, $R_2$ and $R_3$ are each independently H, halogen,

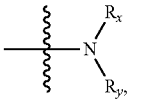

3- to 7-membered heterocycloalkyl comprising one to three heteroatoms selected from group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

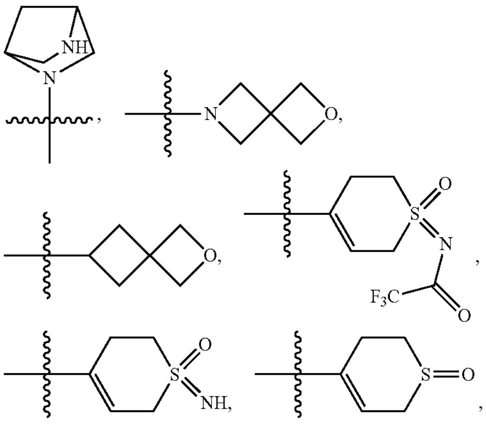

—$C_{1-7}$ alkyl, 3- to 7-membered cycloalkyl, 3- to 7-membered cycloalkenyl, cyclopenta-1,3-diene, phenyl, indolyl,

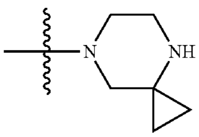 or 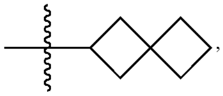

(in which at least one hydrogen of said 3- to 7-membered heterocycloalkyl comprising one to three heteroatoms selected from the group comprising N, O or S, 3- to 7-membered heterocycloalkenyl comprising one to three heteroatoms selected from the group comprising N, O or S, 5- or 6-membered heteroaryl comprising one to three heteroatoms selected from the group comprising N, O or S,

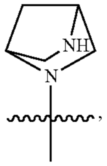, 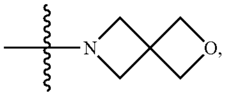

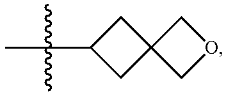 [SMILES: *C1CC2(COC2)C1] 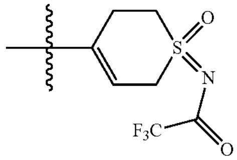,

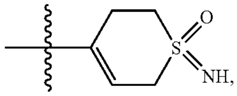 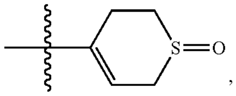, $-C_{1-7}$ alkyl, 3- to 7-membered cycloalkyl, 3- to 7-membered cycloalkenyl, cyclopenta-1,3-diene, phenyl, indolyl,

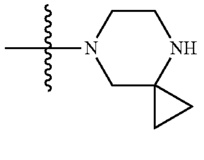 or 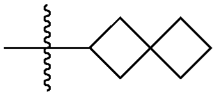

can be substituted with $R_4$, $R_4$ is halogen, $-C_{1-7}$ alkyl, $-C_{1-7}$ haloalkyl, $-O-C_{1-7}$ alkyl, $-C(=O)-C_{1-7}$ alkyl, $-C(=O)-C_{1-7}$ alkyl-OH, $-C(=O)-O-C_{1-7}$ alkyl, $-S(=O)_2-C_{1-7}$ alkyl, 3- to 7-membered cycloalkyl, 3- to 7-membered halocycloalkyl, 3- to 7-membered heterocycloalkyl comprising one to three heteroatoms selected from the group comprising N, O or S, 5- or 6-membered heteroaryl comprising one to three heteroatoms selected from the group comprising N, O or S,

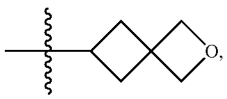

$-C_{1-7}$ alkyl-$C(=O)-R_5$, $-C_{1-7}$ alkyl-$C(=O)-O-R_6$, $-C_{1-7}$ alkyl-$R_7$, $-C_{1-7}$ alkyl-$O-R_8$, $-NR_9R_{10}$, $-C(=O)-NR_{11}R_{12}$ or $-C_{1-7}$ alkyl-$NR_{13}R_{14}$, in which $R_5$ is $-C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, cyclopenta-1,3-diene or phenyl, $R_6$ is $-C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, cyclopenta-1,3-diene or phenyl, $R_7$ is 3- to 7-membered heterocycloalkyl comprising one to three heteroatoms selected from the group comprising N, O or S, 3- to 7-membered cycloalkyl, 5- or 6-membered heteroaryl comprising one to three heteroatoms selected from the group comprising N, O or S, cyclopenta-1,3-diene or phenyl, $R_8$ is $-C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, cyclopenta-1,3-diene or phenyl, $R_9$ and $R_{10}$ are each independently H or $-C_{1-7}$ alkyl, $R_{11}$ and $R_{12}$ are each independently H or $-C_{1-7}$ alkyl, and $R_{13}$ and $R_{14}$ are each independently H or $-C_{1-7}$ alkyl, $R_x$ and $R_y$ are each independently $-C_{1-7}$ alkyl, $-C_{1-7}$ alkyl-$NR_{15}R_{16}$, H, $-C_{1-7}$ alkyl-$O-C_{1-7}$ alkyl, $-C(=O)-C_{1-7}$ alkyl, $-C(=O)$-heteroaryl wherein the heteroaryl is a 5- or 6-membered heteroaryl comprising one to three heteroatoms selected from the group comprising N, O or S, $-C(=O)$-heterocycloalkyl wherein the heterocycloalkyl is a 3-to 7-membered heterocycloalkyl comprising one to three heteroatoms selected from the group comprising N, O or S, $-C(=O)$ cycloalkyl wherein the cycloalkyl is a 3- to 7-membered cycloalkyl, $-C_{1-7}$ alkyl-O-heterocycloalkyl wherein the heterocycloalkyl is a 3- to 7-membered heterocycloalkyl comprising one to three heteroatoms selected from the group comprising N, O or S or $-C_{1-7}$ alkyl-cycloalkyl wherein the cycloalkyl is a 3- to 7-membered cycloalkyl in which wherein at least one hydrogen of $-C_{1-7}$ alkyl, $-C_{1-7}$ alkyl-$O-C_{1-7}$ alkyl, $-C(=O)-C_{1-7}$ alkyl, $-C(=O)$-heteroaryl wherein the heteroaryl is a 5- or 6-membered heteroaryl comprising one to three heteroatoms selected from the group comprising N, O or S, $-C(=O)$-heterocycloalkyl wherein the heterocycloalkyl is a 3- to 7-membered heterocycloalkyl comprising one to three heteroatoms selected from the group comprising N, O or S, $-C(=O)$ cycloalkyl wherein the cycloalkyl is a 3- to 7-membered cycloalkyl, $-C_{1-7}$ alkyl-O-heterocycloalkyl wherein the heterocycloalkyl is a 3- to 7-membered heterocycloalkyl comprising one to three heteroatoms selected from the group comprising N, O or S or $-C_{1-7}$ alkyl-cycloalkyl wherein the cycloalkyl is a 3-to 7-membered cycloalkyl can be substituted with $-C_{1-7}$ alkyl, halogen, $-O-C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, $-S(=O)_2-C_{1-7}$ alkyl, $-CF_3$,

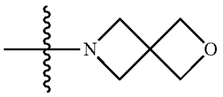 or 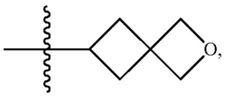

and $R_{15}$ and $R_{16}$ are each independently H or $-C_{1-7}$ alkyl),

K is O or S,

Y is $CR_aR_b$ or $NR_c$, $R_a$ and $R_b$ are each independently hydrogen, —$C_{1-7}$ alkyl, 3- to 7-membered cycloalkyl, —$C_{1-7}$ alkyl-O—$C_{1-7}$ alkyl, —$C_{1-7}$ alkyl-$NR_{17}R_{18}$, 3- to 7-membered heterocycloalkyl comprising one to three heteroatoms selected from the group comprising N, O or S, —$C_{1-7}$ alkyl-C(=O)—$C_{1-7}$ alkyl or —$C_{1-7}$ alkyl-C(=O)—O—$C_{1-7}$ alkyl, or $R_a$ and $R_b$ are linked to each other to form 3- to 7-membered cycloalkyl, wherein at least one hydrogen of —$C_{1-7}$ alkyl 3- to 7-membered cycloalkyl, —$C_{1-7}$ alkyl-O—$C_{1-7}$ alkyl, —$C_{1-7}$ alkyl-$NR_{17}R_{18}$, 3- to 7-membered heterocycloalkyl comprising one to three heteroatoms selected from the group comprising N, O or S, —$C_{1-7}$ alkyl-C(=O)—$C_{1-7}$ alkyl or —$C_{1-7}$ alkyl-C(=O)—O—$C_{1-7}$ alkyl may be substituted with-$C_{1-7}$ alkyl, halogen, —O—$C_{1-7}$ alkyl, 3- to 7-membered heterocycloalkyl comprising one to three heteroatoms selected from the group comprising N, O or S, 5- or 6-membered heteroaryl comprising one to three heteroatoms selected from the group comprising N, O or S, 3- to 7-membered cycloalkyl, —$S(=O)_2$—$C_{1-7}$ alkyl, —$CF_3$,

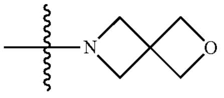
or
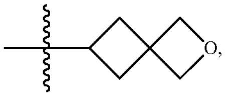

and $R_{17}$ and $R_{18}$ are each independently H or —$C_{1-7}$ alkyl, $R_c$ is hydrogen, —$C_{1-7}$ alkyl, —$C_{1-7}$ alkyl-heterocycloalkyl wherein the heterocycloalkyl is a 3- to 7-membered heterocycloalkyl comprising one to three heteroatoms selected from the group comprising N, O or S, —$C_{1-7}$ alkyl-phenyl, —$C_{1-7}$ alkyl-heteroaryl wherein the heteroaryl is a 5- or 6-membered heteroaryl comprising one to three heteroatoms selected from the group comprising N, O or S, —$C_{1-7}$ alkyl-O—$C_{1-7}$ alkyl, —$C_{1-7}$ alkyl-$NR_{19}R_{20}$, —$C_{1-7}$ alkyl-cycloalkyl wherein the cycloalkyl is a 3- to 7-membered cycloalkyl, a 3- to 7-membered heterocycloalkyl comprising one to three heteroatoms selected from the group comprising N, O or S, a 3- to 7-membered cycloalkyl, a 5- or 6-membered heteroaryl comprising one to three heteroatoms selected from the group comprising N, O or S, cyclopenta-1,3-diene, phenyl, —C(=O)—, —C(=O)-heterocycloalkyl wherein the heterocycloalkyl is a 3- to 7-membered heterocycloalkyl comprising one to three heteroatoms selected from the group comprising N, O or S, —C(=O) cycloalkyl wherein the cycloalkyl is a 3- to 7-membered cycloalkyl, —C(=O)-heteroaryl wherein the heteroaryl is a 5- or 6-membered heteroaryl comprising one to three heteroatoms selected from the group comprising N, O or S, —C(=O)-phenyl, —C(=O)—$C_{1-7}$ alkyl, —C(=O)—$C_{1-7}$ alkyl-O—$C_{1-7}$ alkyl or —C(=O)—$C_{1-7}$ alkyl-$NR_{19}R_{20}$, wherein at least one hydrogen of —$C_{1-7}$ alkyl, —$C_{1-7}$ alkyl-heterocycloalkyl wherein the heterocycloalkyl is a 3- to 7-membered heterocycloalkyl comprising one to three heteroatoms selected from the group comprising N, O or S, —$C_{1-7}$ alkyl-phenyl, —$C_{1-7}$ alkyl-heteroaryl wherein the heteroaryl is a 5- or 6-membered heteroaryl comprising one to three heteroatoms selected from the group comprising N, O or S, —$C_{1-7}$ alkyl-O—$C_{1-7}$ alkyl, —$C_{1-7}$ alkyl-$NR_{19}R_{20}$, —$C_{1-7}$ alkyl-cycloalkyl wherein the cycloalkyl is a 3- to 7-membered cycloalkyl, a 3- to 7-membered heterocycloalkyl comprising one to three heteroatoms selected from the group comprising N, O or S, a 3- to 7-membered cycloalkyl, a 5- or 6-membered heteroaryl comprising one to three heteroatoms selected from the group comprising N, O or S, cyclopenta-1,3-diene, phenyl, —C(=O)—, —C(=O)-heterocycloalkyl wherein the heterocycloalkyl is a 3- to 7-membered heterocycloalkyl comprising one to three heteroatoms selected from the group comprising N, O or S, —C(=O) cycloalkyl wherein the cycloalkyl is a 3- to 7-membered cycloalkyl, —C(=O)-heteroaryl wherein the heteroaryl is a 5- or 6-membered heteroaryl comprising one to three heteroatoms selected from the group comprising N, O or S, —C(=O)-phenyl, —C(=O)—$C_{1-7}$ alkyl, —C(=O)—$C_{1-7}$ alkyl-O—$C_{1-7}$ alkyl or —C(=O)—$C_{1-7}$ alkyl-$NR_{19}R_{20}$, can be substituted with —$C_{1-7}$ alkyl, halogen, —O—$C_{1-7}$ alkyl, a 3- to 7-membered heterocycloalkyl comprising one to three heteroatoms selected from the group comprising N, O or S, —C(=O)—O—$C_{1-7}$ alkyl, a 5- or 6-membered heteroaryl comprising one to three heteroatoms selected from the group comprising N, O or S, heteroaryl-$C_{1-5}$ haloalkyl wherein the heteroaryl is a 5- or 6-membered heteroaryl comprising one to three heteroatoms selected from the group comprising N, O or S, 3- to 7-membered cycloalkyl, —$S(=O)_2$—$C_{1-7}$alkyl, —$CF_3$,

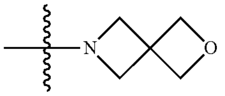
or
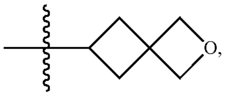

and $R_{19}$ and $R_{20}$ are each independently H or —$C_{1-7}$ alkyl,

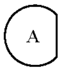

is phenylene or 5- or 6-membered heteroarylene comprising one to three heteroatoms selected from the group comprising N, O or S, halogen is F, Cl, Br or I, and n is 1.

6. A compound described in a following table, stereoisomers thereof or pharmaceutically acceptable salts thereof:

| Compound | Structure |
|---|---|
| 1 | 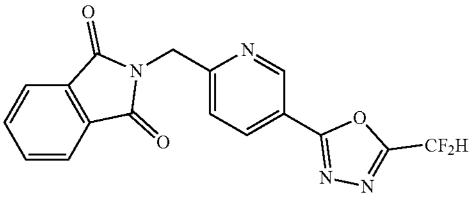 [SMILES: O=C1c2ccccc2C(=O)N1Cc1ccc(-c2nnc(C(F)F)o2)cn1] |
| 2 | 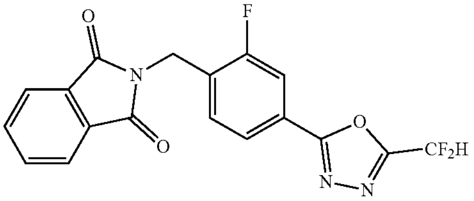 [SMILES: O=C1c2ccccc2C(=O)N1Cc1ccc(-c2nnc(C(F)F)o2)cc1F] |
| 3 | 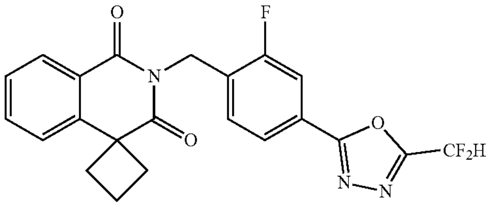 |
| 4 | 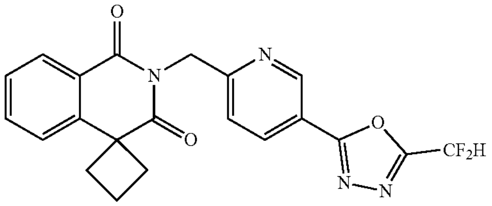 [SMILES: O=C1c2ccccc2C2(CCC2)C(=O)N1Cc1ccc(-c2nnc(C(F)F)o2)cn1] |
| 5 | 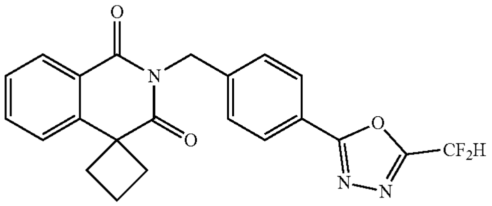 [SMILES: O=C1c2ccccc2C2(CCC2)C(=O)N1Cc1ccc(-c2nnc(C(F)F)o2)cc1] |
| 6 | 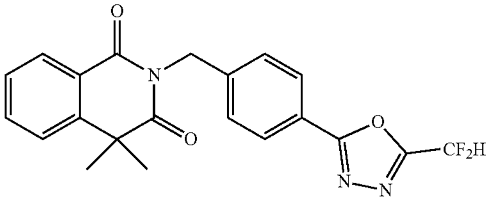 [SMILES: CC1(C)C(=O)N(Cc2ccc(-c3nnc(C(F)F)o3)cc2)C(=O)c2ccccc21] |
| 7 | 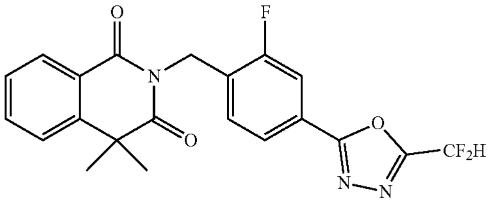 [SMILES: CC1(C)C(=O)N(Cc2ccc(-c3nnc(C(F)F)o3)cc2F)C(=O)c2ccccc21] |

-continued
| Compound | Structure |
| --- | --- |
| 8 | 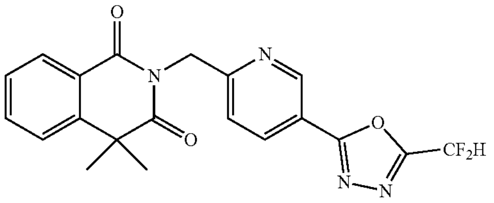 [SMILES: CC1(C)C(=O)N(Cc2ccc(-c3nnc(C(F)F)o3)cn2)C(=O)c2ccccc21] |
| 9 | 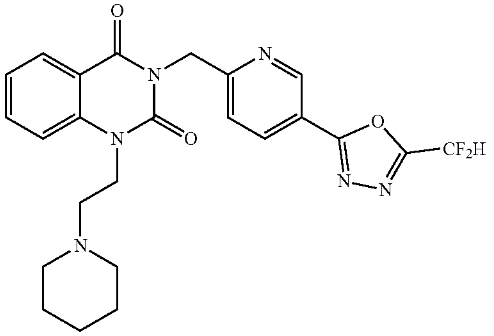 [SMILES: O=c1c2ccccc2n(CCN2CCCCC2)c(=O)n1Cc1ccc(-c2nnc(C(F)F)o2)cn1] |
| 10 | 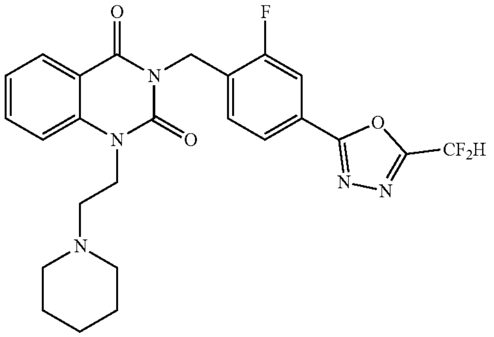 [SMILES: O=c1c2ccccc2n(CCN2CCCCC2)c(=O)n1Cc1ccc(-c2nnc(C(F)F)o2)cc1F] |
| 11 | 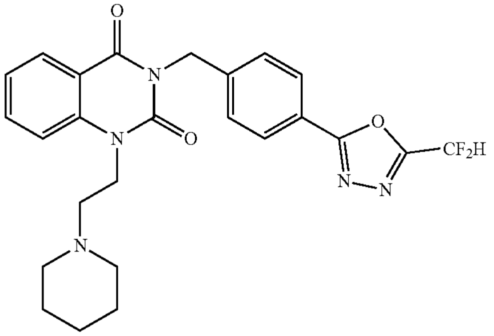 [SMILES: O=c1c2ccccc2n(CCN2CCCCC2)c(=O)n1Cc1ccc(-c2nnc(C(F)F)o2)cc1] |
| 12 | 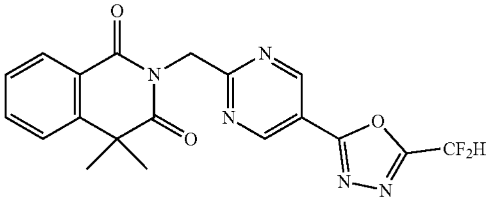 [SMILES: CC1(C)C(=O)N(Cc2ncc(-c3nnc(C(F)F)o3)cn2)C(=O)c2ccccc21] |

-continued
| Compound | Structure |
|---|---|
| 13 | 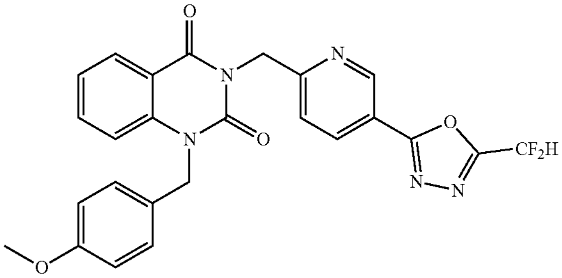 [SMILES: COc1ccc(Cn2c(=O)n(Cc3ccc(-c4nnc(C(F)F)o4)cn3)c(=O)c3ccccc32)cc1] |
| 14 | 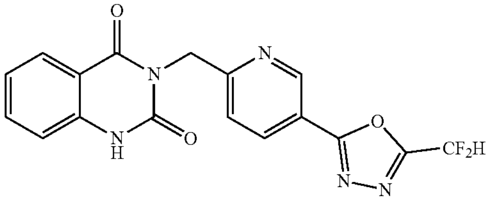 [SMILES: O=c1[nH]c2ccccc2c(=O)n1Cc1ccc(-c2nnc(C(F)F)o2)cn1] |
| 15 | 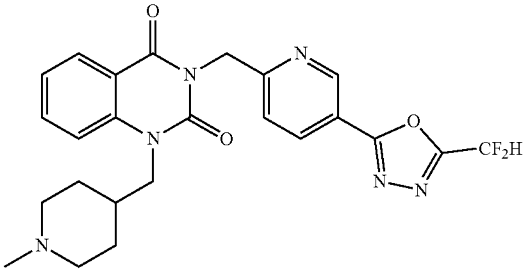 [SMILES: CN1CCC(Cn2c(=O)n(Cc3ccc(-c4nnc(C(F)F)o4)cn3)c(=O)c3ccccc32)CC1] |
| 16 | 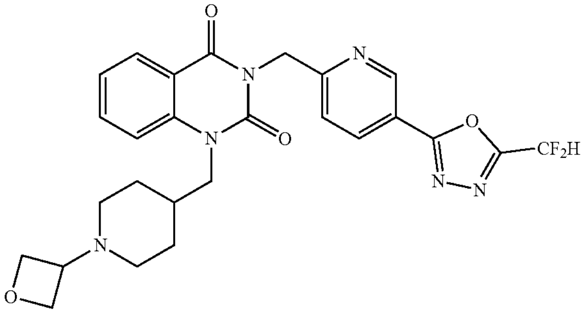 [SMILES: O=c1c2ccccc2n(CC2CCN(C3COC3)CC2)c(=O)n1Cc1ccc(-c2nnc(C(F)F)o2)cn1] |
| 17 | 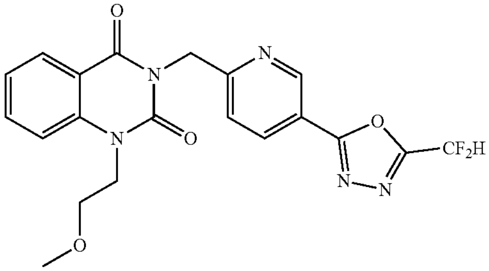 [SMILES: COCCn1c(=O)n(Cc2ccc(-c3nnc(C(F)F)o3)cn2)c(=O)c2ccccc21] |
| 18 | 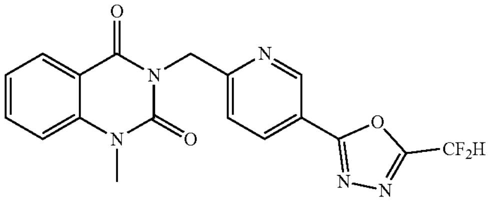 [SMILES: Cn1c(=O)n(Cc2ccc(-c3nnc(C(F)F)o3)cn2)c(=O)c2ccccc21] |

-continued
| Compound | Structure |
| --- | --- |
| 19 | 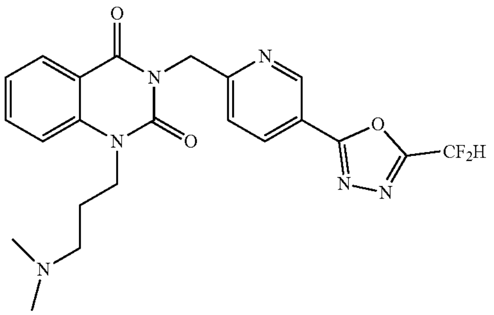 [SMILES: CN(C)CCCn1c(=O)n(Cc2ccc(-c3nnc(C(F)F)o3)cn2)c(=O)c2ccccc21] |
| 20 | 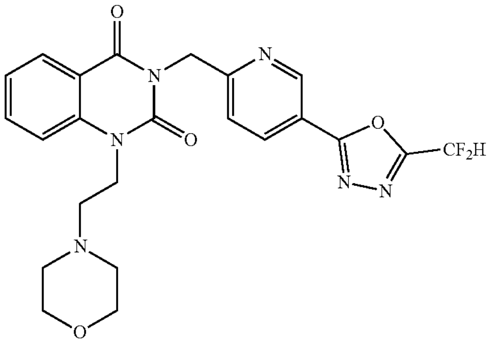 [SMILES: O=c1c2ccccc2n(CCN2CCOCC2)c(=O)n1Cc1ccc(-c2nnc(C(F)F)o2)cn1] |
| 21 | 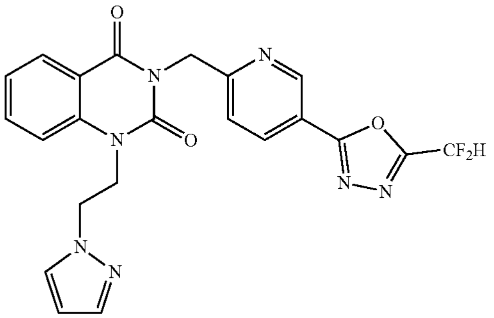 [SMILES: O=c1c2ccccc2n(CCn2cccn2)c(=O)n1Cc1ccc(-c2nnc(C(F)F)o2)cn1] |
| 22 | 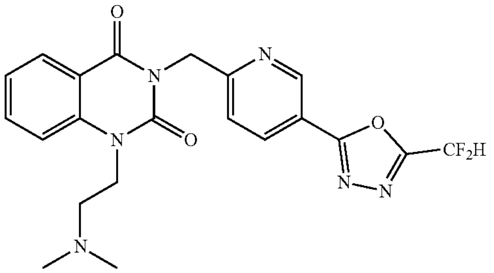 [SMILES: CN(C)CCn1c(=O)n(Cc2ccc(-c3nnc(C(F)F)o3)cn2)c(=O)c2ccccc21] |
| 23 | 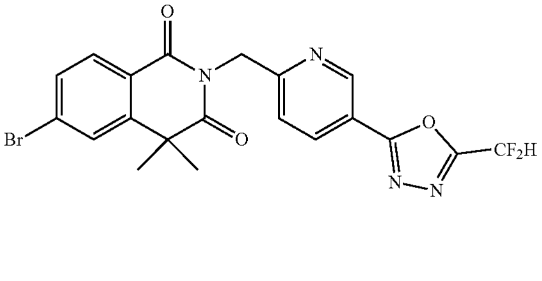 [SMILES: CC1(C)C(=O)N(Cc2ccc(-c3nnc(C(F)F)o3)cn2)C(=O)c2ccc(Br)cc21] |

-continued
| Compound | Structure |
|---|---|
| 24 | 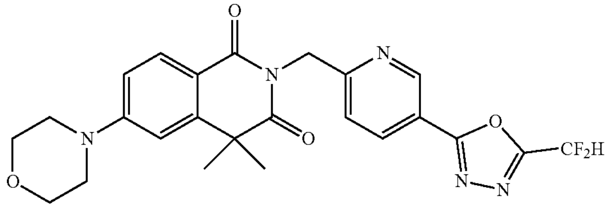 [SMILES: CC1(C)C(=O)N(Cc2ccc(-c3nnc(C(F)F)o3)cn2)C(=O)c2ccc(N3CCOCC3)cc21] |
| 25 | 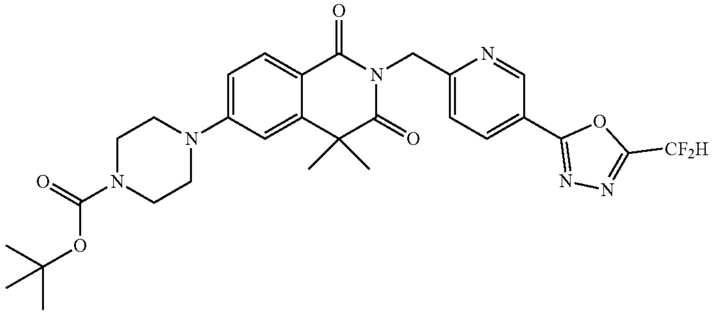 [SMILES: CC(C)(C)OC(=O)N1CCN(c2ccc3c(c2)C(C)(C)C(=O)N(Cc2ccc(-c4nnc(C(F)F)o4)cn2)C3=O)CC1] |
| 26 | 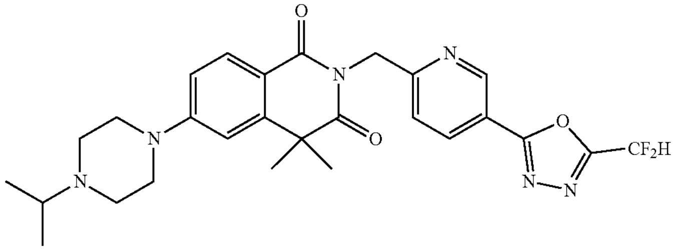 [SMILES: CC(C)N1CCN(c2ccc3c(c2)C(C)(C)C(=O)N(Cc2ccc(-c4nnc(C(F)F)o4)cn2)C3=O)CC1] |
| 27 | 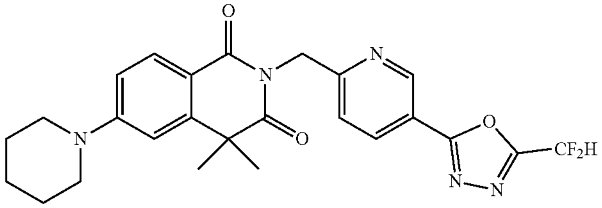 [SMILES: CC1(C)C(=O)N(Cc2ccc(-c3nnc(C(F)F)o3)cn2)C(=O)c2ccc(N3CCCCC3)cc21] |
| 28 | 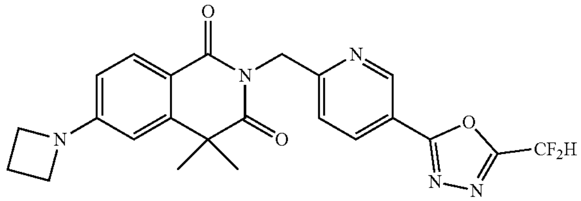 [SMILES: CC1(C)C(=O)N(Cc2ccc(-c3nnc(C(F)F)o3)cn2)C(=O)c2ccc(N3CCC3)cc21] |
| 29 | 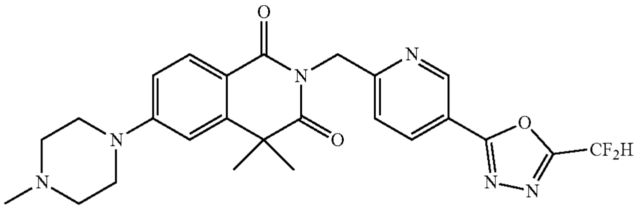 [SMILES: CN1CCN(c2ccc3c(c2)C(C)(C)C(=O)N(Cc2ccc(-c4nnc(C(F)F)o4)cn2)C3=O)CC1] |

-continued
| Compound | Structure |
|---|---|
| 30 | 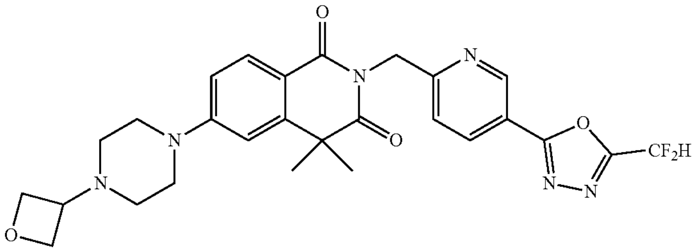 [SMILES: CC1(C)C(=O)N(Cc2ccc(-c3nnc(C(F)F)o3)cn2)C(=O)c2ccc(N3CCN(C4COC4)CC3)cc21] |
| 31 | 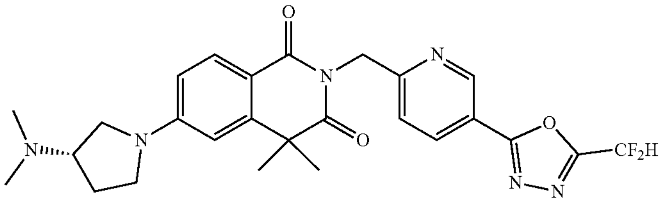 [SMILES: CN(C)[C@H]1CCN(c2ccc3c(c2)C(C)(C)C(=O)N(Cc2ccc(-c4nnc(C(F)F)o4)cn2)C3=O)C1] |
| 32 | 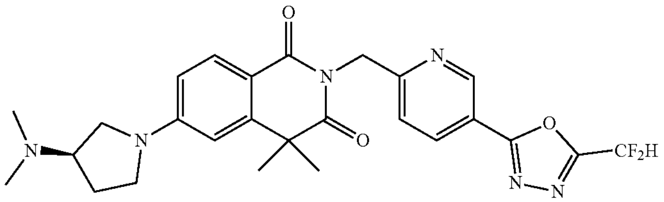 [SMILES: CN(C)[C@@H]1CCN(c2ccc3c(c2)C(C)(C)C(=O)N(Cc2ccc(-c4nnc(C(F)F)o4)cn2)C3=O)C1] |
| 33 | 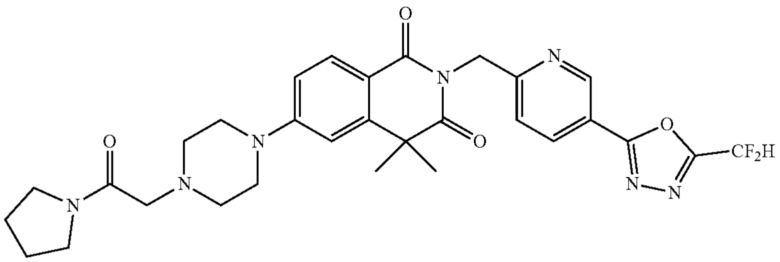 [SMILES: CC1(C)C(=O)N(Cc2ccc(-c3nnc(C(F)F)o3)cn2)C(=O)c2ccc(N3CCN(CC(=O)N4CCCC4)CC3)cc21] |
| 34 | 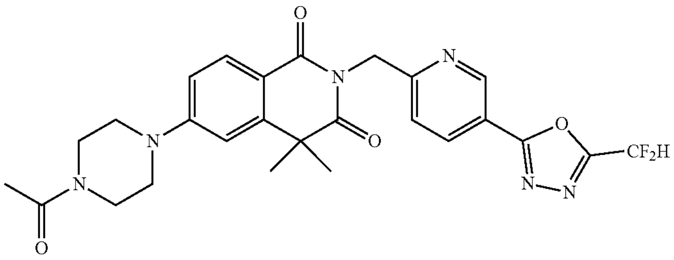 [SMILES: CC(=O)N1CCN(c2ccc3c(c2)C(C)(C)C(=O)N(Cc2ccc(-c4nnc(C(F)F)o4)cn2)C3=O)CC1] |
| 35 | 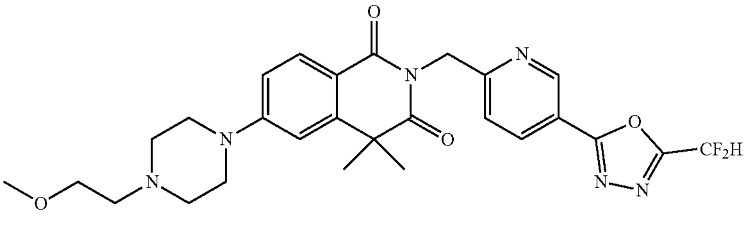 [SMILES: COCCN1CCN(c2ccc3c(c2)C(C)(C)C(=O)N(Cc2ccc(-c4nnc(C(F)F)o4)cn2)C3=O)CC1] |

-continued
| Compound | Structure |
| --- | --- |
| 36 | 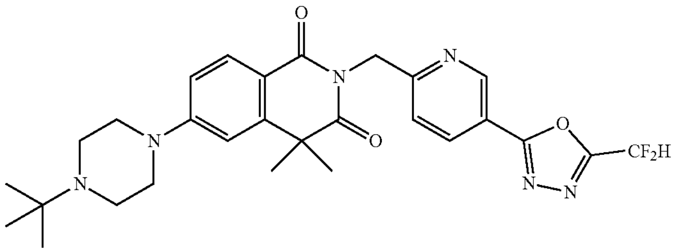 [SMILES: CC1(C)C(=O)N(Cc2ccc(-c3nnc(C(F)F)o3)cn2)C(=O)c2ccc(N3CCN(C(C)(C)C)CC3)cc21] |
| 37 | 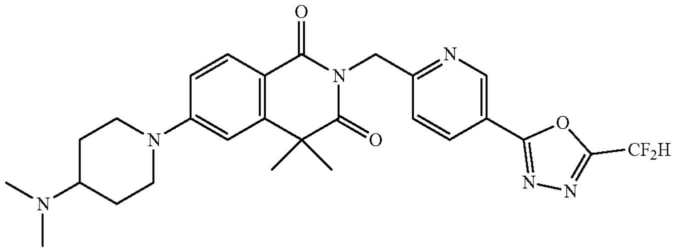 [SMILES: CN(C)C1CCN(c2ccc3c(c2)C(C)(C)C(=O)N(Cc2ccc(-c4nnc(C(F)F)o4)cn2)C3=O)CC1] |
| 38 | 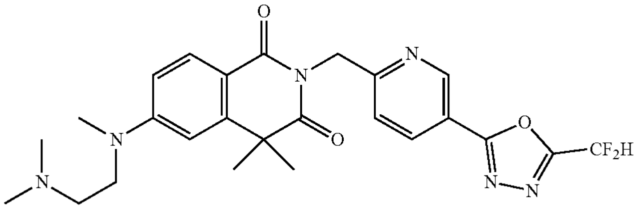 [SMILES: CN(C)CCN(C)c1ccc2c(c1)C(C)(C)C(=O)N(Cc1ccc(-c3nnc(C(F)F)o3)cn1)C2=O] |
| 39 | 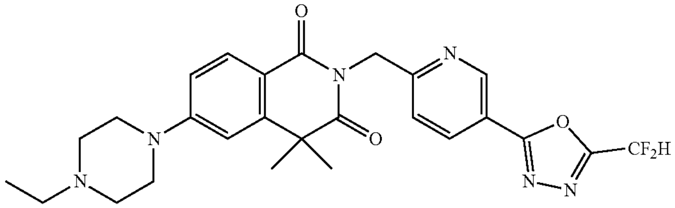 [SMILES: CCN1CCN(c2ccc3c(c2)C(C)(C)C(=O)N(Cc2ccc(-c4nnc(C(F)F)o4)cn2)C3=O)CC1] |
| 40 | 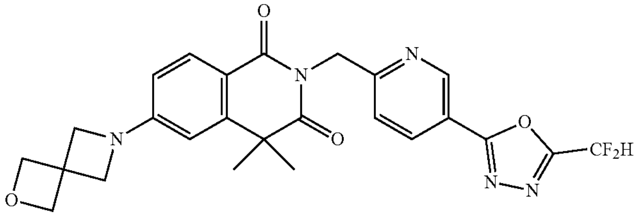 [SMILES: CC1(C)C(=O)N(Cc2ccc(-c3nnc(C(F)F)o3)cn2)C(=O)c2ccc(N3CC4(COC4)C3)cc21] |
| 41 | 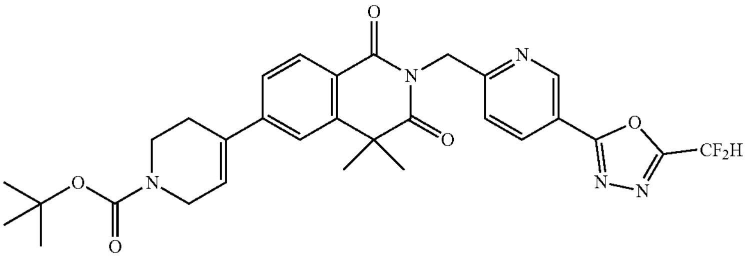 [SMILES: CC(C)(C)OC(=O)N1CC=C(c2ccc3c(c2)C(C)(C)C(=O)N(Cc2ccc(-c4nnc(C(F)F)o4)cn2)C3=O)CC1] |

-continued
| Compound | Structure |
|---|---|
| 42 | 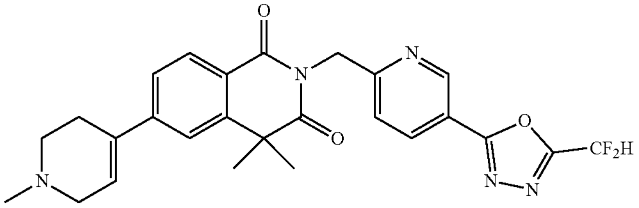 [SMILES: CN1CC=C(c2ccc3c(c2)C(C)(C)C(=O)N(Cc2ccc(-c4nnc(C(F)F)o4)cn2)C3=O)CC1] |
| 43 | 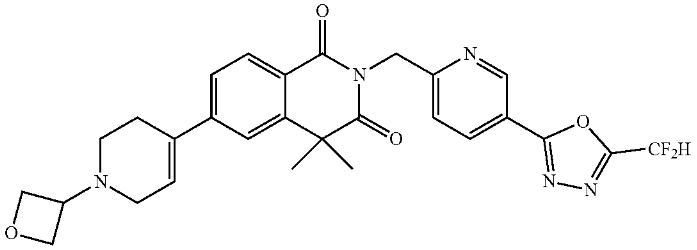 [SMILES: CC1(C)C(=O)N(Cc2ccc(-c3nnc(C(F)F)o3)cn2)C(=O)c2ccc(C3=CCN(C4COC4)CC3)cc21] |
| 44 | 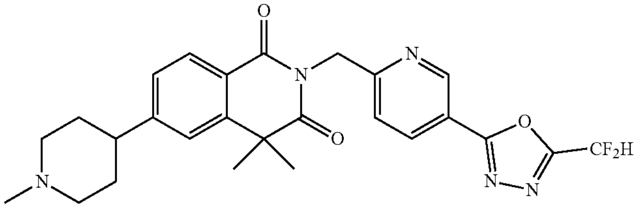 |
| 45 | 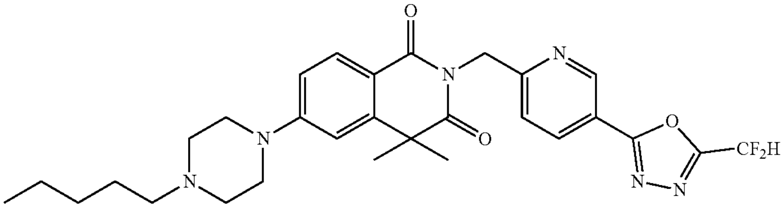 [SMILES: CCCCCN1CCN(c2ccc3c(c2)C(C)(C)C(=O)N(Cc2ccc(-c4nnc(C(F)F)o4)cn2)C3=O)CC1] |
| 46 | 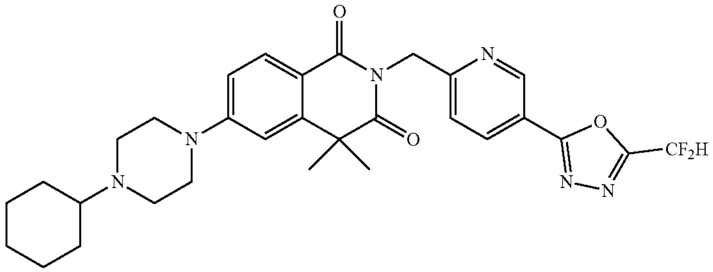 [SMILES: CC1(C)C(=O)N(Cc2ccc(-c3nnc(C(F)F)o3)cn2)C(=O)c2ccc(N3CCN(C4CCCCC4)CC3)cc21] |
| 47 | 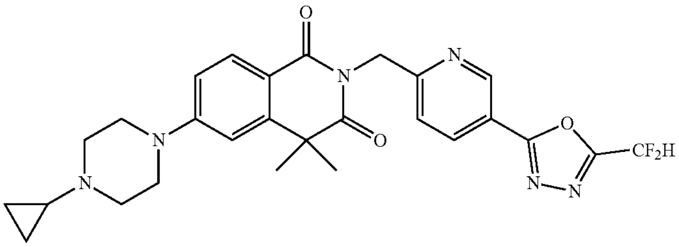 [SMILES: CC1(C)C(=O)N(Cc2ccc(-c3nnc(C(F)F)o3)cn2)C(=O)c2ccc(N3CCN(C4CC4)CC3)cc21] |

-continued
| Compound | Structure |
|---|---|
| 48 | 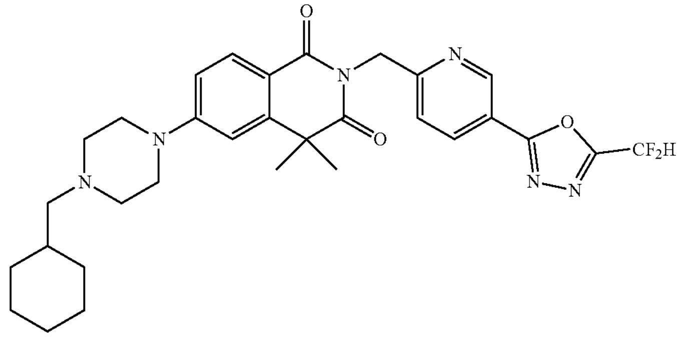 [SMILES: CC1(C)C(=O)N(Cc2ccc(-c3nnc(C(F)F)o3)cn2)C(=O)c2ccc(N3CCN(CC4CCCCC4)CC3)cc21] |
| 49 | 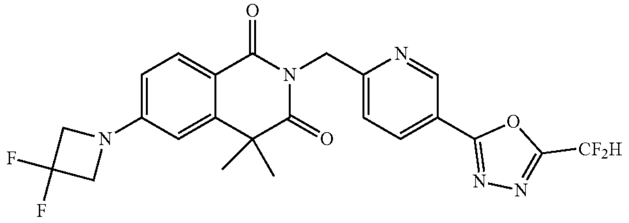 [SMILES: CC1(C)C(=O)N(Cc2ccc(-c3nnc(C(F)F)o3)cn2)C(=O)c2ccc(N3CC(F)(F)C3)cc21] |
| 50 | 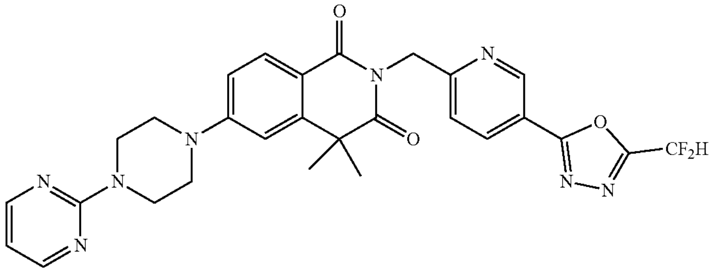 [SMILES: CC1(C)C(=O)N(Cc2ccc(-c3nnc(C(F)F)o3)cn2)C(=O)c2ccc(N3CCN(c4ncccn4)CC3)cc21] |
| 51 | 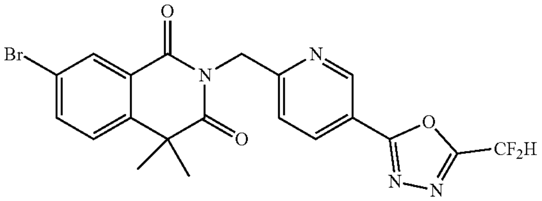 [SMILES: CC1(C)C(=O)N(Cc2ccc(-c3nnc(C(F)F)o3)cn2)C(=O)c2cc(Br)ccc21] |
| 52 | 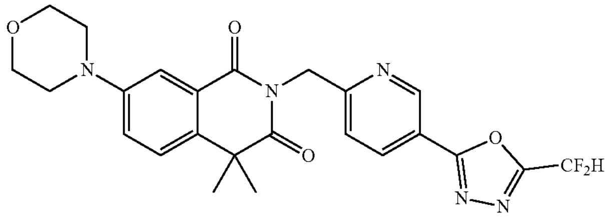 |
| 53 | 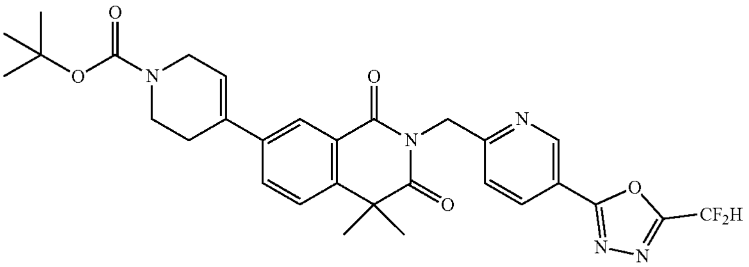 [SMILES: CC(C)(C)OC(=O)N1CC=C(c2ccc3c(c2)C(=O)N(Cc2ccc(-c4nnc(C(F)F)o4)cn2)C(=O)C3(C)C)CC1] |

-continued
| Compound | Structure |
|---|---|
| 54 | 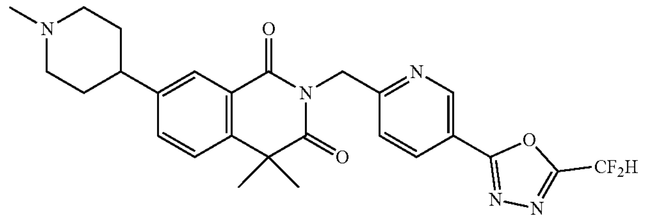 [SMILES: CN1CCC(c2ccc3c(c2)C(=O)N(Cc2ccc(-c4nnc(C(F)F)o4)cn2)C(=O)C3(C)C)CC1] |
| 55 | 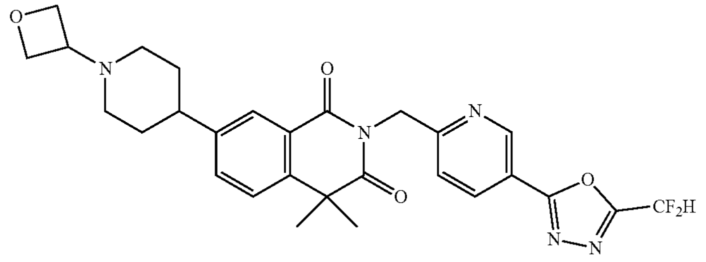 [SMILES: CC1(C)C(=O)N(Cc2ccc(-c3nnc(C(F)F)o3)cn2)C(=O)c2cc(C3CCN(C4COC4)CC3)ccc21] |
| 56 | 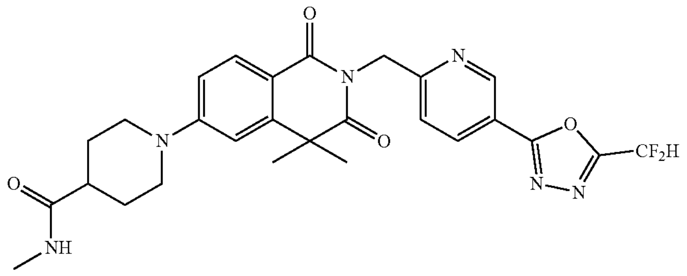 [SMILES: CNC(=O)C1CCN(c2ccc3c(c2)C(C)(C)C(=O)N(Cc2ccc(-c4nnc(C(F)F)o4)cn2)C3=O)CC1] |
| 57 | 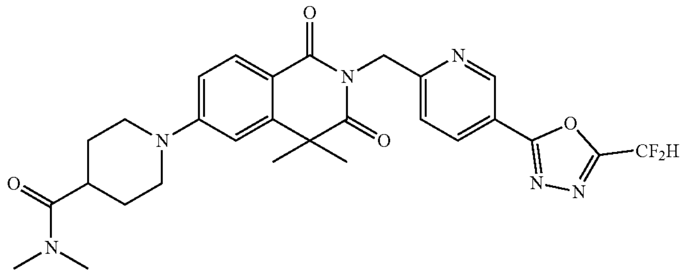 [SMILES: CN(C)C(=O)C1CCN(c2ccc3c(c2)C(C)(C)C(=O)N(Cc2ccc(-c4nnc(C(F)F)o4)cn2)C3=O)CC1] |
| 58 | 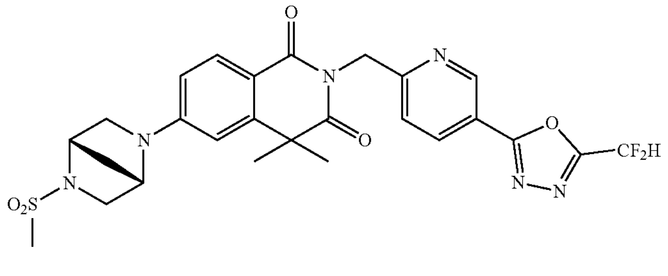 [SMILES: CC1(C)C(=O)N(Cc2ccc(-c3nnc(C(F)F)o3)cn2)C(=O)c2ccc(N3C[C@@H]4C[C@H]3CN4S(C)(=O)=O)cc21] |
| 59 | 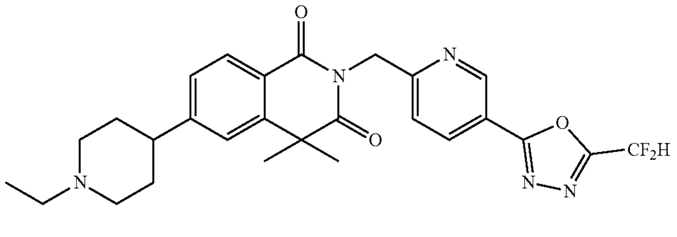 [SMILES: CCN1CCC(c2ccc3c(c2)C(C)(C)C(=O)N(Cc2ccc(-c4nnc(C(F)F)o4)cn2)C3=O)CC1] |

-continued
| Compound | Structure |
|---|---|
| 60 | 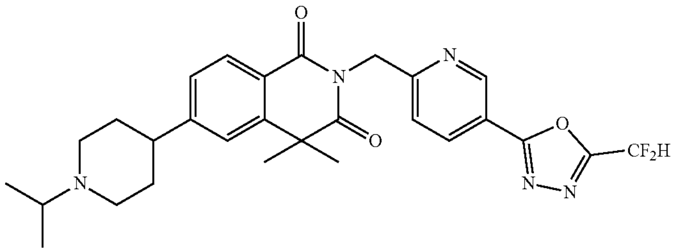 [SMILES: CC(C)N1CCC(c2ccc3c(c2)C(C)(C)C(=O)N(Cc2ccc(-c4nnc(C(F)F)o4)cn2)C3=O)CC1] |
| 61 | 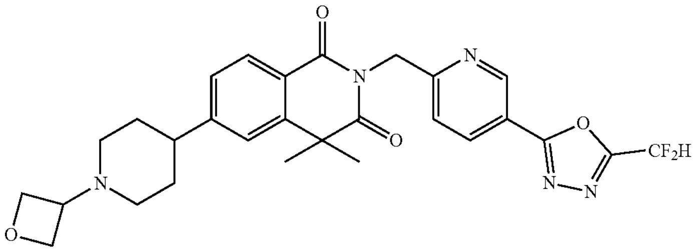 [SMILES: CC1(C)C(=O)N(Cc2ccc(-c3nnc(C(F)F)o3)cn2)C(=O)c2ccc(C3CCN(C4COC4)CC3)cc21] |
| 62 | 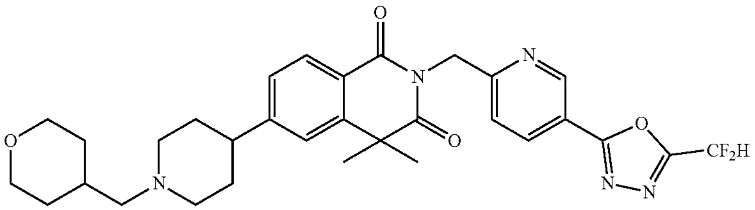 [SMILES: CC1(C)C(=O)N(Cc2ccc(-c3nnc(C(F)F)o3)cn2)C(=O)c2ccc(C3CCN(CC4CCOCC4)CC3)cc21] |
| 63 | 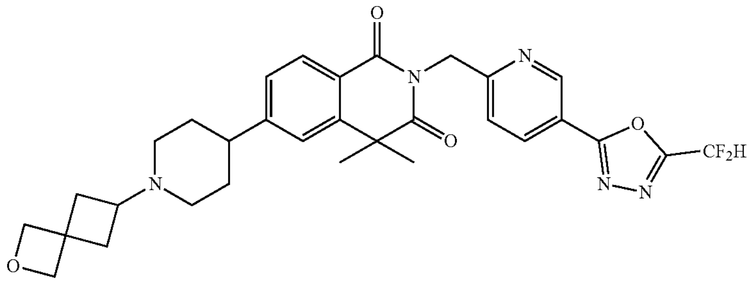 [SMILES: CC1(C)C(=O)N(Cc2ccc(-c3nnc(C(F)F)o3)cn2)C(=O)c2ccc(C3CCN(C4CC5(COC5)C4)CC3)cc21] |
| 64 | 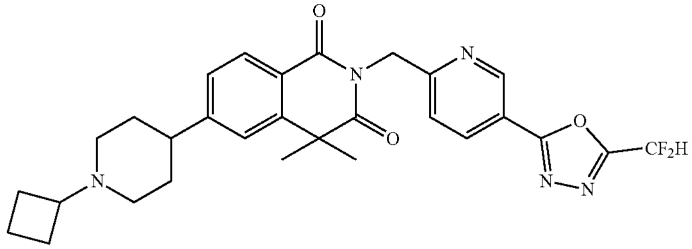 [SMILES: CC1(C)C(=O)N(Cc2ccc(-c3nnc(C(F)F)o3)cn2)C(=O)c2ccc(C3CCN(C4CCC4)CC3)cc21] |
| 65 | 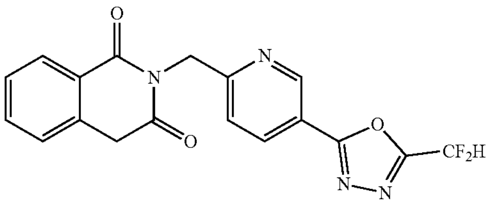 [SMILES: O=C1Cc2ccccc2C(=O)N1Cc1ccc(-c2nnc(C(F)F)o2)cn1] |

-continued
| Compound | Structure |
|---|---|
| 66 | 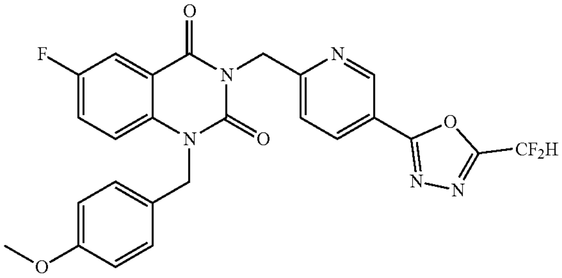 [SMILES: COc1ccc(Cn2c(=O)n(Cc3ccc(-c4nnc(C(F)F)o4)cn3)c(=O)c3cc(F)ccc32)cc1] |
| 67 | 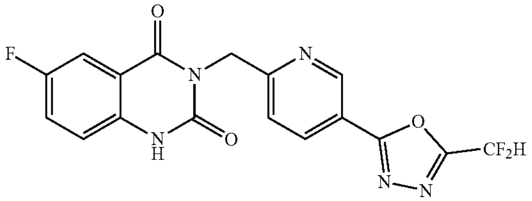 [SMILES: O=c1[nH]c2ccc(F)cc2c(=O)n1Cc1ccc(-c2nnc(C(F)F)o2)cn1] |
| 68 | 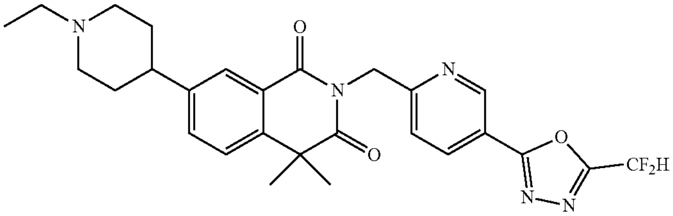 [SMILES: CCN1CCC(c2ccc3c(c2)C(=O)N(Cc2ccc(-c4nnc(C(F)F)o4)cn2)C(=O)C3(C)C)CC1] |
| 69 | 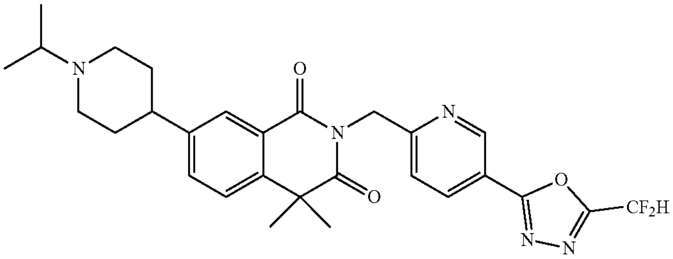 [SMILES: CC(C)N1CCC(c2ccc3c(c2)C(=O)N(Cc2ccc(-c4nnc(C(F)F)o4)cn2)C(=O)C3(C)C)CC1] |
| 70 | 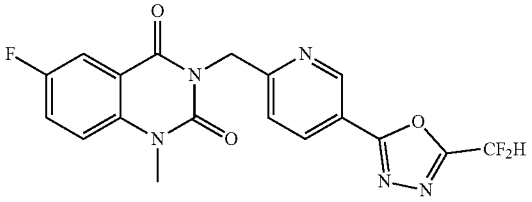 [SMILES: Cn1c(=O)n(Cc2ccc(-c3nnc(C(F)F)o3)cn2)c(=O)c2cc(F)ccc21] |
| 71 | 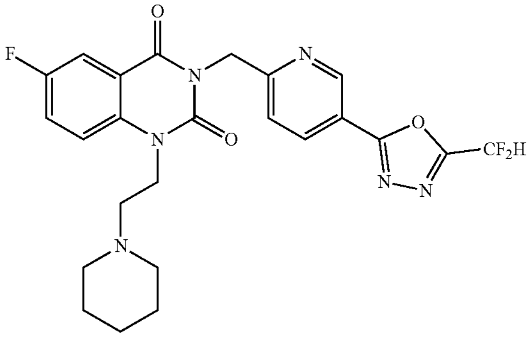 [SMILES: O=c1c2cc(F)ccc2n(CCN2CCCCC2)c(=O)n1Cc1ccc(-c2nnc(C(F)F)o2)cn1] |

-continued
| Compound | Structure |
|---|---|
| 72 | 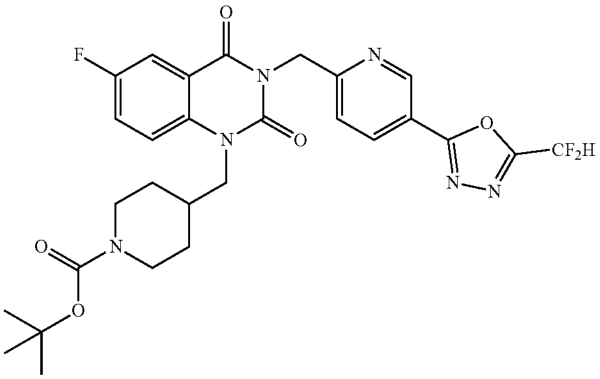 [SMILES: CC(C)(C)OC(=O)N1CCC(Cn2c(=O)n(Cc3ccc(-c4nnc(C(F)F)o4)cn3)c(=O)c3cc(F)ccc32)CC1] |
| 73 | 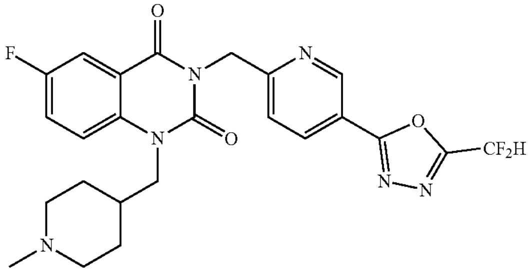 [SMILES: CN1CCC(Cn2c(=O)n(Cc3ccc(-c4nnc(C(F)F)o4)cn3)c(=O)c3cc(F)ccc32)CC1] |
| 74 | 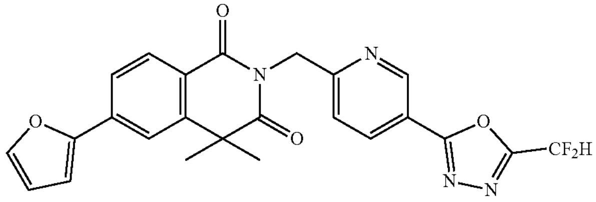 [SMILES: CC1(C)C(=O)N(Cc2ccc(-c3nnc(C(F)F)o3)cn2)C(=O)c2ccc(-c3ccco3)cc21] |
| 75 | 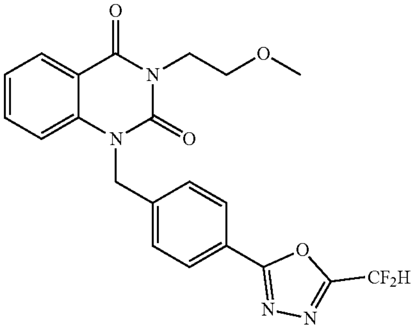 |
| 76 | 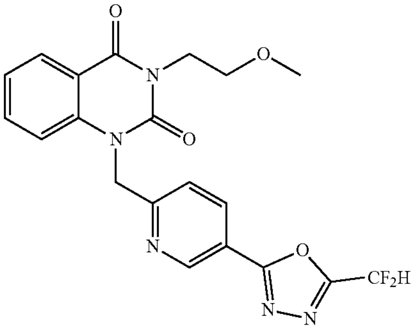 [SMILES: COCCn1c(=O)c2ccccc2n(Cc2ccc(-c3nnc(C(F)F)o3)cn2)c1=O] |

-continued
| Compound | Structure |
|---|---|
| 77 | 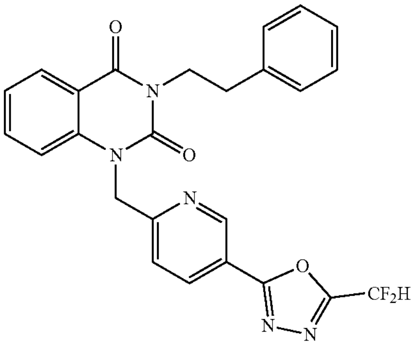 [SMILES: O=c1c2ccccc2n(Cc2ccc(-c3nnc(C(F)F)o3)cn2)c(=O)n1CCc1ccccc1] |
| 78 | 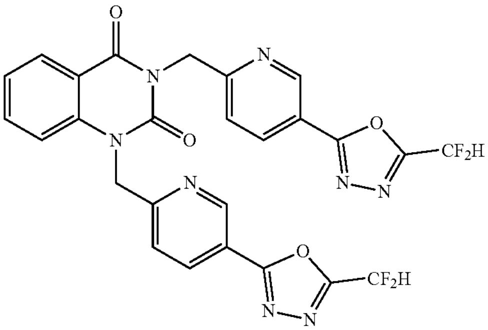 [SMILES: O=c1c2ccccc2n(Cc2ccc(-c3nnc(C(F)F)o3)cn2)c(=O)n1Cc1ccc(-c2nnc(C(F)F)o2)cn1] |
| 79 | 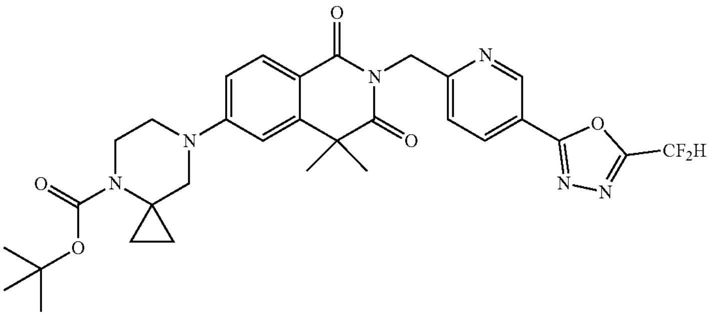 [SMILES: CC(C)(C)OC(=O)N1CCN(c2ccc3c(c2)C(C)(C)C(=O)N(Cc2ccc(-c4nnc(C(F)F)o4)cn2)C3=O)CC12CC2] |
| 80 | 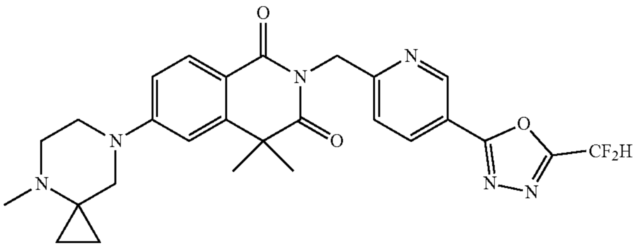 [SMILES: CN1CCN(c2ccc3c(c2)C(C)(C)C(=O)N(Cc2ccc(-c4nnc(C(F)F)o4)cn2)C3=O)CC12CC2] |
| 81 | 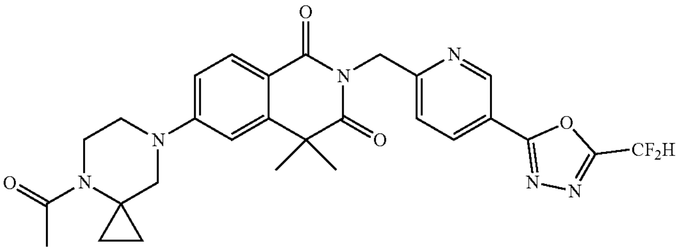 [SMILES: CC(=O)N1CCN(c2ccc3c(c2)C(C)(C)C(=O)N(Cc2ccc(-c4nnc(C(F)F)o4)cn2)C3=O)CC12CC2] |

-continued
| Compound | Structure |
|---|---|
| 82 | 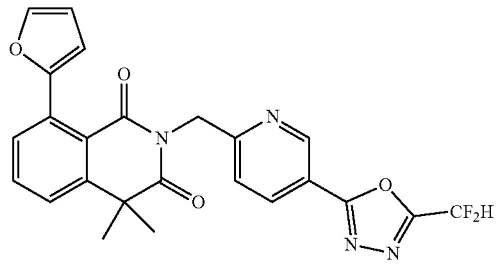 [SMILES: CC1(C)C(=O)N(Cc2ccc(-c3nnc(C(F)F)o3)cn2)C(=O)c2c(-c3ccco3)cccc21] |
| 83 | 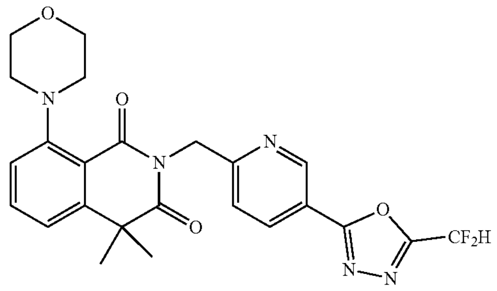 [SMILES: CC1(C)C(=O)N(Cc2ccc(-c3nnc(C(F)F)o3)cn2)C(=O)c2c(N3CCOCC3)cccc21] |
| 84 | 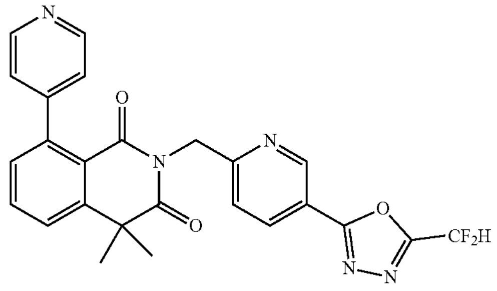 [SMILES: CC1(C)C(=O)N(Cc2ccc(-c3nnc(C(F)F)o3)cn2)C(=O)c2c(-c3ccncc3)cccc21] |
| 85 | 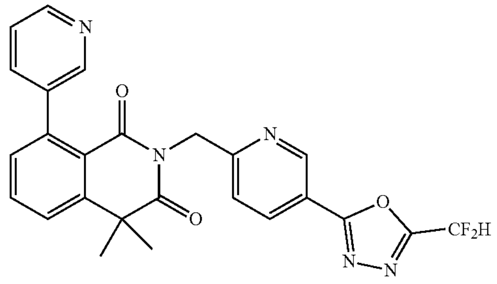 [SMILES: CC1(C)C(=O)N(Cc2ccc(-c3nnc(C(F)F)o3)cn2)C(=O)c2c(-c3cccnc3)cccc21] |
| 86 | 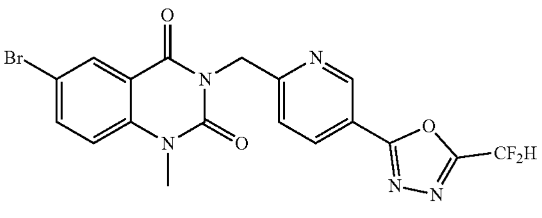 [SMILES: Cn1c(=O)n(Cc2ccc(-c3nnc(C(F)F)o3)cn2)c(=O)c2cc(Br)ccc21] |
| 87 | 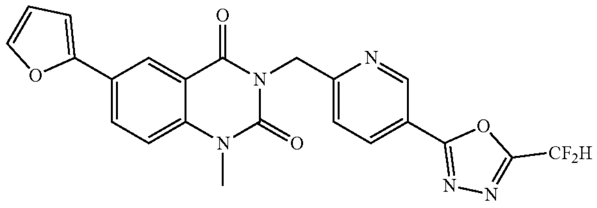 [SMILES: Cn1c(=O)n(Cc2ccc(-c3nnc(C(F)F)o3)cn2)c(=O)c2cc(-c3ccco3)ccc21] |

-continued
| Compound | Structure |
|---|---|
| 88 | 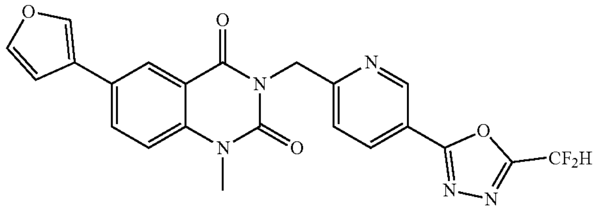 [SMILES: Cn1c(=O)n(Cc2ccc(-c3nnc(C(F)F)o3)cn2)c(=O)c2cc(-c3ccoc3)ccc21] |
| 89 | 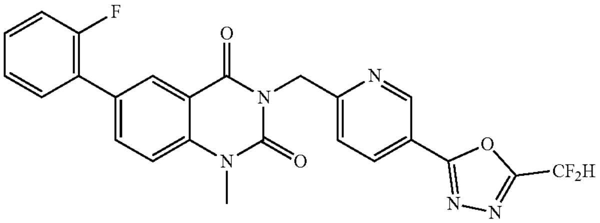 [SMILES: Cn1c(=O)n(Cc2ccc(-c3nnc(C(F)F)o3)cn2)c(=O)c2cc(-c3ccccc3F)ccc21] |
| 90 | 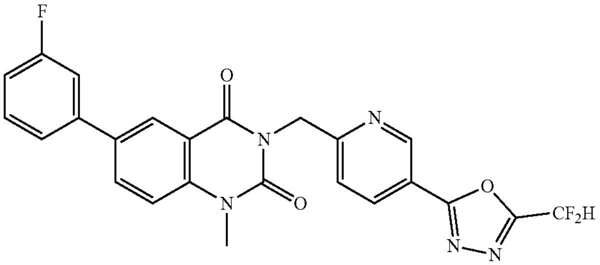 [SMILES: Cn1c(=O)n(Cc2ccc(-c3nnc(C(F)F)o3)cn2)c(=O)c2cc(-c3cccc(F)c3)ccc21] |
| 91 | 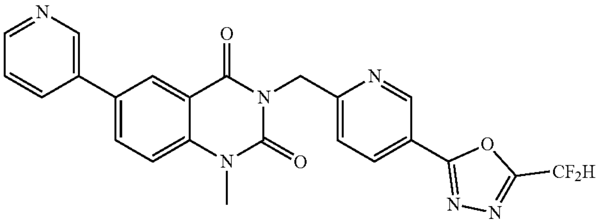 [SMILES: Cn1c(=O)n(Cc2ccc(-c3nnc(C(F)F)o3)cn2)c(=O)c2cc(-c3cccnc3)ccc21] |
| 92 | 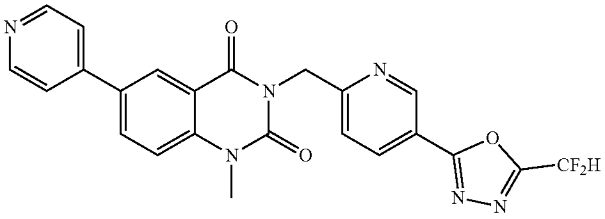 [SMILES: Cn1c(=O)n(Cc2ccc(-c3nnc(C(F)F)o3)cn2)c(=O)c2cc(-c3ccncc3)ccc21] |
| 93 | 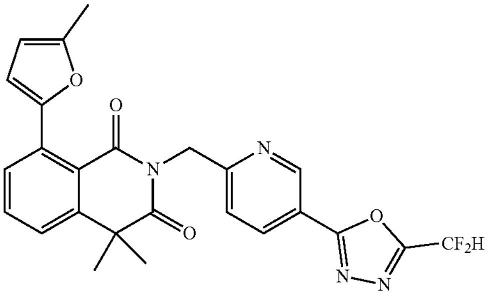 [SMILES: Cc1ccc(-c2cccc3c2C(=O)N(Cc2ccc(-c4nnc(C(F)F)o4)cn2)C(=O)C3(C)C)o1] |

-continued
| Compound | Structure |
|---|---|
| 94 | 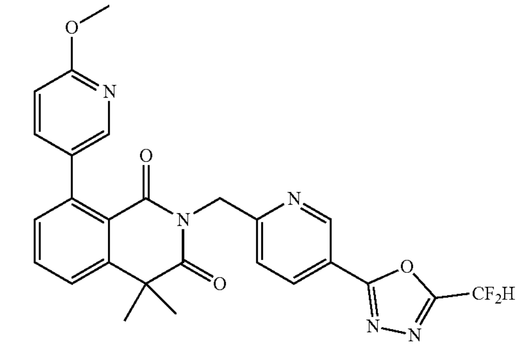 [SMILES: COc1ccc(-c2cccc3c2C(=O)N(Cc2ccc(-c4nnc(C(F)F)o4)cn2)C(=O)C3(C)C)cn1] |
| 95 | 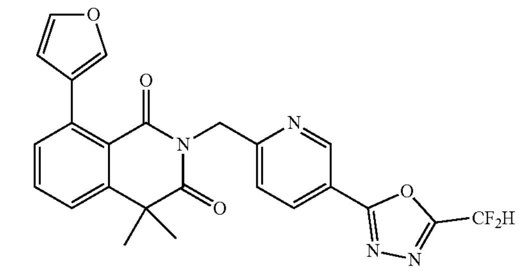 [SMILES: CC1(C)C(=O)N(Cc2ccc(-c3nnc(C(F)F)o3)cn2)C(=O)c2c(-c3ccoc3)cccc21] |
| 96 | 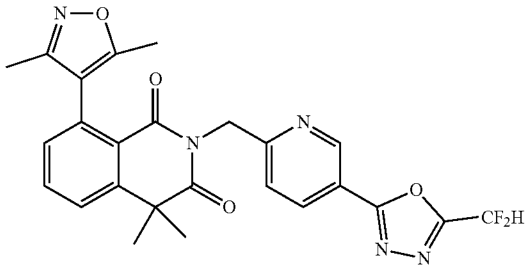 [SMILES: Cc1noc(C)c1-c1cccc2c1C(=O)N(Cc1ccc(-c3nnc(C(F)F)o3)cn1)C(=O)C2(C)C] |
| 97 | 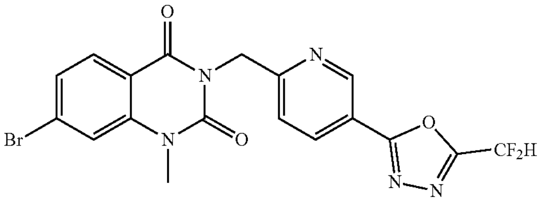 [SMILES: Cn1c(=O)n(Cc2ccc(-c3nnc(C(F)F)o3)cn2)c(=O)c2ccc(Br)cc21] |
| 98 | 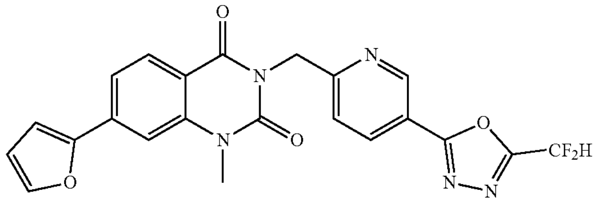 [SMILES: Cn1c(=O)n(Cc2ccc(-c3nnc(C(F)F)o3)cn2)c(=O)c2ccc(-c3ccco3)cc21] |
| 99 | 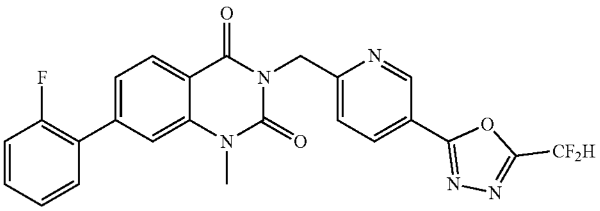 [SMILES: Cn1c(=O)n(Cc2ccc(-c3nnc(C(F)F)o3)cn2)c(=O)c2ccc(-c3ccccc3F)cc21] |

-continued
| Compound | Structure |
|---|---|
| 100 | 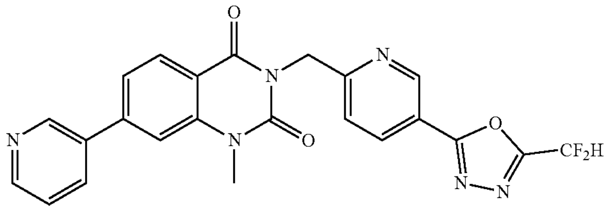 [SMILES: Cn1c(=O)n(Cc2ccc(-c3nnc(C(F)F)o3)cn2)c(=O)c2ccc(-c3cccnc3)cc21] |
| 101 | 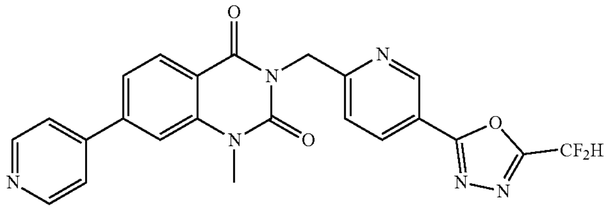 [SMILES: Cn1c(=O)n(Cc2ccc(-c3nnc(C(F)F)o3)cn2)c(=O)c2ccc(-c3ccncc3)cc21] |
| 102 | 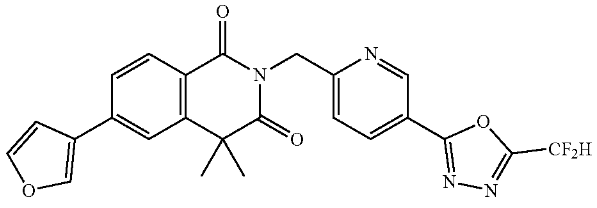 [SMILES: CC1(C)C(=O)N(Cc2ccc(-c3nnc(C(F)F)o3)cn2)C(=O)c2ccc(-c3ccoc3)cc21] |
| 103 | 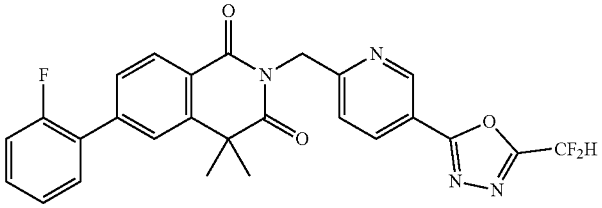 [SMILES: CC1(C)C(=O)N(Cc2ccc(-c3nnc(C(F)F)o3)cn2)C(=O)c2ccc(-c3ccccc3F)cc21] |
| 104 | 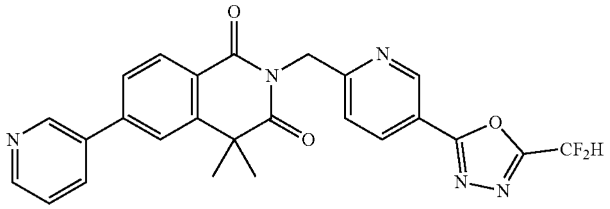 [SMILES: CC1(C)C(=O)N(Cc2ccc(-c3nnc(C(F)F)o3)cn2)C(=O)c2ccc(-c3cccnc3)cc21] |
| 105 | 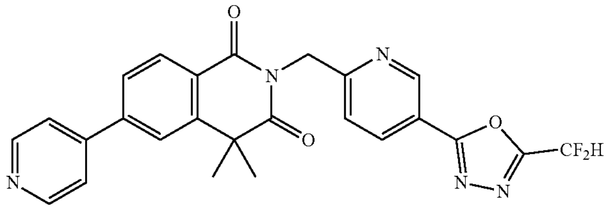 [SMILES: CC1(C)C(=O)N(Cc2ccc(-c3nnc(C(F)F)o3)cn2)C(=O)c2ccc(-c3ccncc3)cc21] |
| 106 | 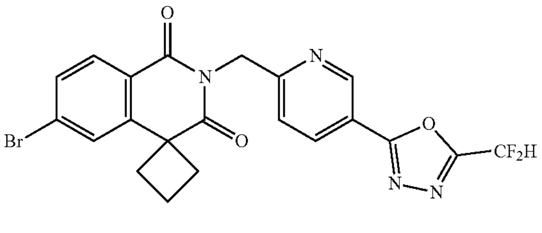 [SMILES: O=C1c2ccc(Br)cc2C2(CCC2)C(=O)N1Cc1ccc(-c2nnc(C(F)F)o2)cn1] |

-continued
| Compound | Structure |
|---|---|
| 107 | 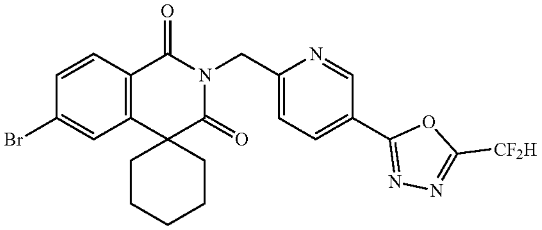 [SMILES: O=C1c2ccc(Br)cc2C2(CCCCC2)C(=O)N1Cc1ccc(-c2nnc(C(F)F)o2)cn1] |
| 108 | 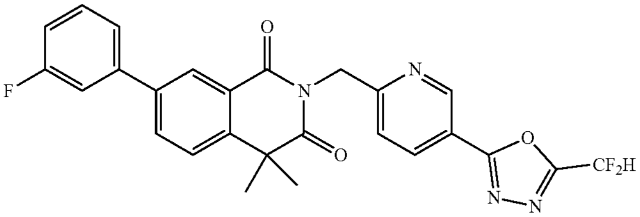 [SMILES: CC1(C)C(=O)N(Cc2ccc(-c3nnc(C(F)F)o3)cn2)C(=O)c2cc(-c3cccc(F)c3)ccc21] |
| 109 | 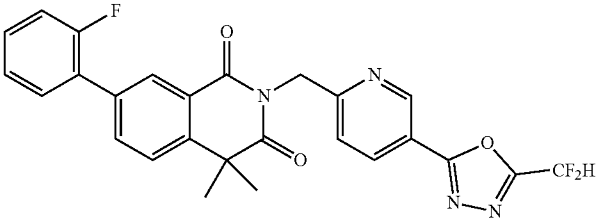 [SMILES: CC1(C)C(=O)N(Cc2ccc(-c3nnc(C(F)F)o3)cn2)C(=O)c2cc(-c3ccccc3F)ccc21] |
| 110 | 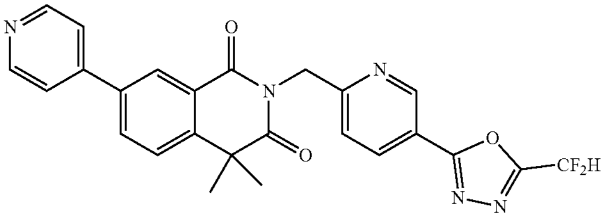 [SMILES: CC1(C)C(=O)N(Cc2ccc(-c3nnc(C(F)F)o3)cn2)C(=O)c2cc(-c3ccncc3)ccc21] |
| 111 | 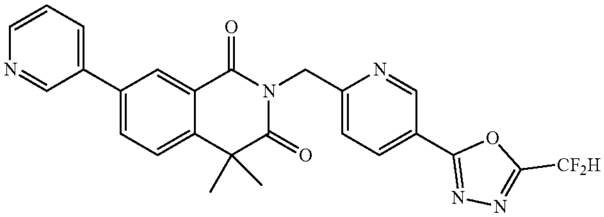 [SMILES: CC1(C)C(=O)N(Cc2ccc(-c3nnc(C(F)F)o3)cn2)C(=O)c2cc(-c3cccnc3)ccc21] |
| 112 | 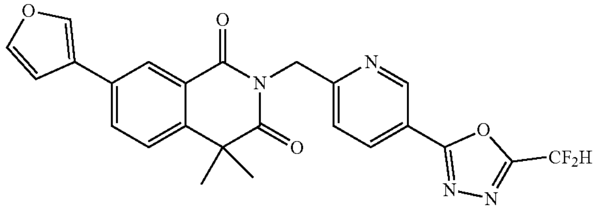 [SMILES: CC1(C)C(=O)N(Cc2ccc(-c3nnc(C(F)F)o3)cn2)C(=O)c2cc(-c3ccoc3)ccc21] |
| 113 | 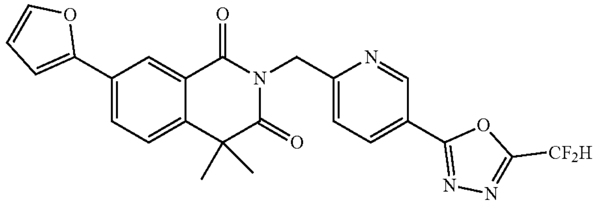 [SMILES: CC1(C)C(=O)N(Cc2ccc(-c3nnc(C(F)F)o3)cn2)C(=O)c2cc(-c3ccco3)ccc21] |

-continued
| Compound | Structure |
|---|---|
| 114 | 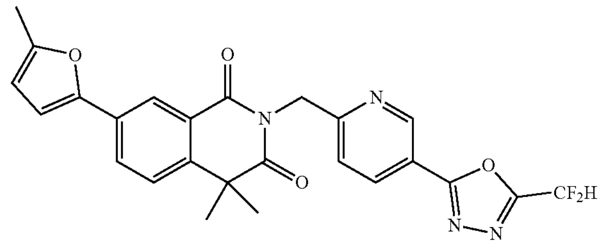 [SMILES: Cc1ccc(-c2ccc3c(c2)C(=O)N(Cc2ccc(-c4nnc(C(F)F)o4)cn2)C(=O)C3(C)C)o1] |
| 115 | 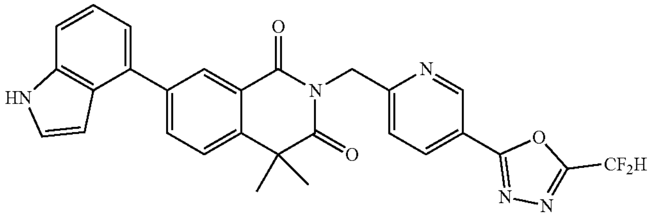 [SMILES: CC1(C)C(=O)N(Cc2ccc(-c3nnc(C(F)F)o3)cn2)C(=O)c2cc(-c3cccc4[nH]ccc34)ccc21] |
| 116 | 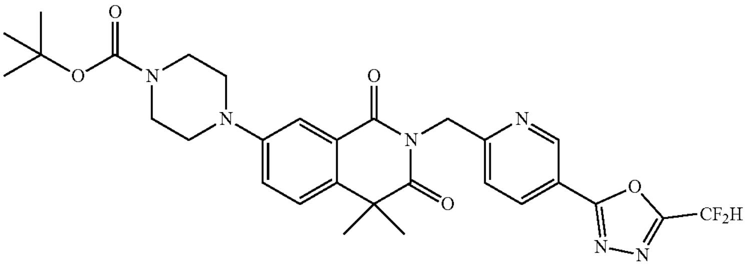 [SMILES: CC(C)(C)OC(=O)N1CCN(c2ccc3c(c2)C(=O)N(Cc2ccc(-c4nnc(C(F)F)o4)cn2)C(=O)C3(C)C)CC1] |
| 117 | 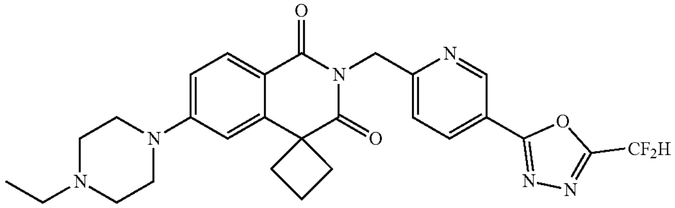 [SMILES: CCN1CCN(c2ccc3c(c2)C2(CCC2)C(=O)N(Cc2ccc(-c4nnc(C(F)F)o4)cn2)C3=O)CC1] |
| 118 | 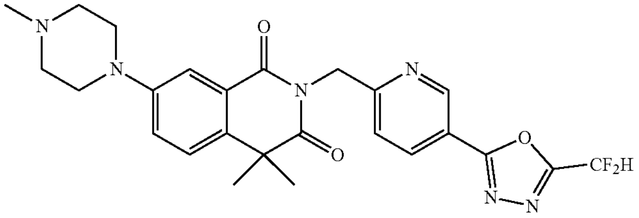 [SMILES: CN1CCN(c2ccc3c(c2)C(=O)N(Cc2ccc(-c4nnc(C(F)F)o4)cn2)C(=O)C3(C)C)CC1] |
| 119 | 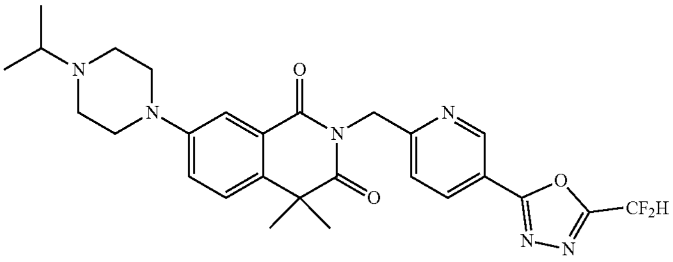 [SMILES: CC(C)N1CCN(c2ccc3c(c2)C(=O)N(Cc2ccc(-c4nnc(C(F)F)o4)cn2)C(=O)C3(C)C)CC1] |

-continued
| Compound | Structure |
|---|---|
| 120 | 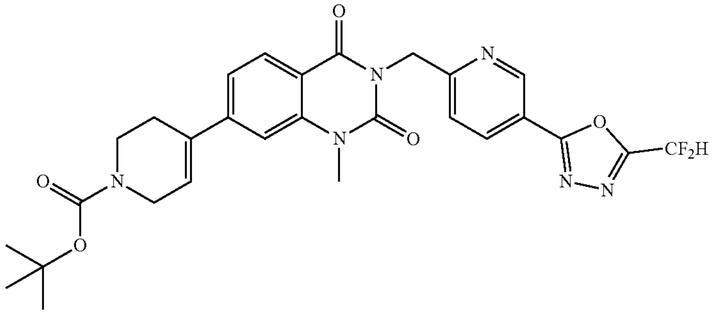 [SMILES: Cn1c(=O)n(Cc2ccc(-c3nnc(C(F)F)o3)cn2)c(=O)c2ccc(C3=CCN(C(=O)OC(C)(C)C)CC3)cc21] |
| 121 | 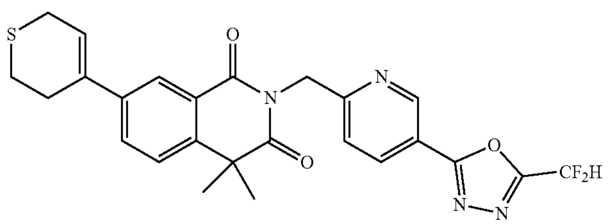 [SMILES: CC1(C)C(=O)N(Cc2ccc(-c3nnc(C(F)F)o3)cn2)C(=O)c2cc(C3=CCSCC3)ccc21] |
| 122 | 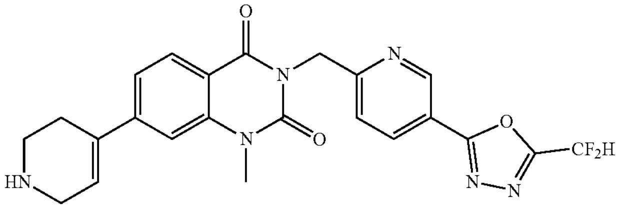 [SMILES: Cn1c(=O)n(Cc2ccc(-c3nnc(C(F)F)o3)cn2)c(=O)c2ccc(C3=CCNCC3)cc21] |
| 123 | 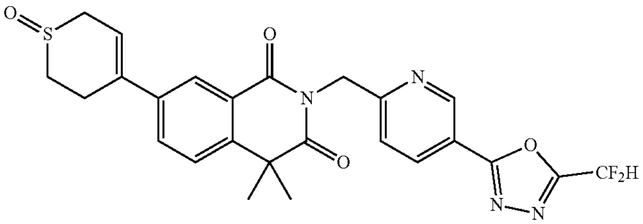 [SMILES: CC1(C)C(=O)N(Cc2ccc(-c3nnc(C(F)F)o3)cn2)C(=O)c2cc(C3=CCS(=O)CC3)ccc21] |
| 124 | 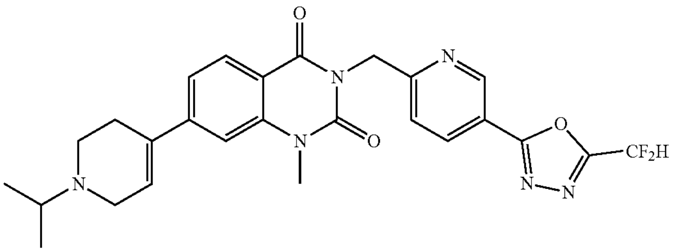 [SMILES: CC(C)N1CC=C(c2ccc3c(=O)n(Cc4ccc(-c5nnc(C(F)F)o5)cn4)c(=O)n(C)c3c2)CC1] |
| 125 | 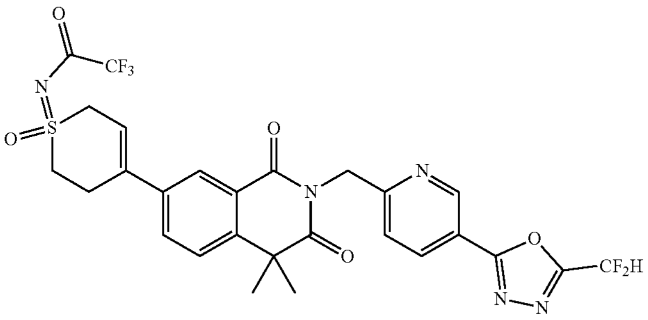 [SMILES: CC1(C)C(=O)N(Cc2ccc(-c3nnc(C(F)F)o3)cn2)C(=O)c2cc(C3=CCS(=O)(=NC(=O)C(F)(F)F)CC3)ccc21] |

-continued
| Compound | Structure |
|---|---|
| 126 | 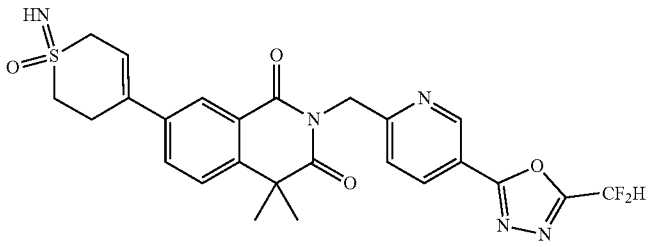 [SMILES: CC1(C)C(=O)N(Cc2ccc(-c3nnc(C(F)F)o3)cn2)C(=O)c2cc(C3=CCS(=N)(=O)CC3)ccc21] |
| 127 | 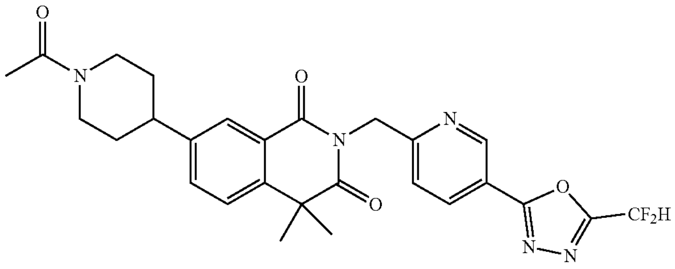 [SMILES: CC(=O)N1CCC(c2ccc3c(c2)C(=O)N(Cc2ccc(-c4nnc(C(F)F)o4)cn2)C(=O)C3(C)C)CC1] |
| 128 | 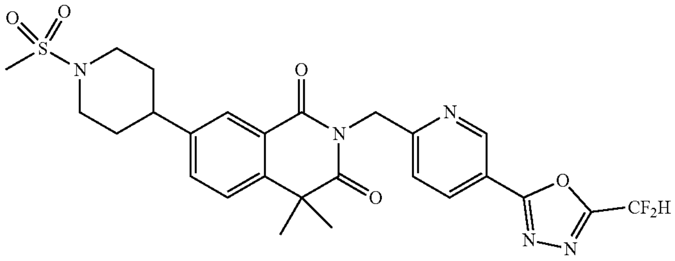 [SMILES: CC1(C)C(=O)N(Cc2ccc(-c3nnc(C(F)F)o3)cn2)C(=O)c2cc(C3CCN(S(C)(=O)=O)CC3)ccc21] |
| 129 | 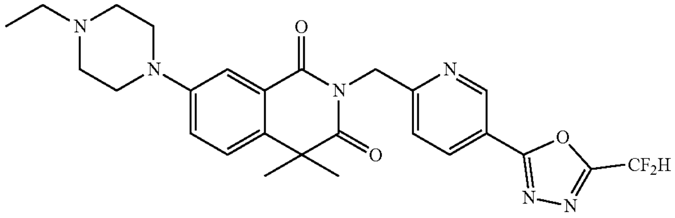 [SMILES: CCN1CCN(c2ccc3c(c2)C(=O)N(Cc2ccc(-c4nnc(C(F)F)o4)cn2)C(=O)C3(C)C)CC1] |
| 130 | 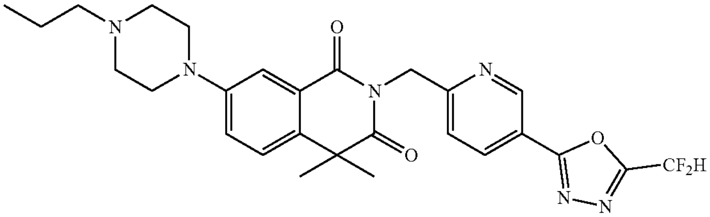 [SMILES: CCCN1CCN(c2ccc3c(c2)C(=O)N(Cc2ccc(-c4nnc(C(F)F)o4)cn2)C(=O)C3(C)C)CC1] |
| 131 | 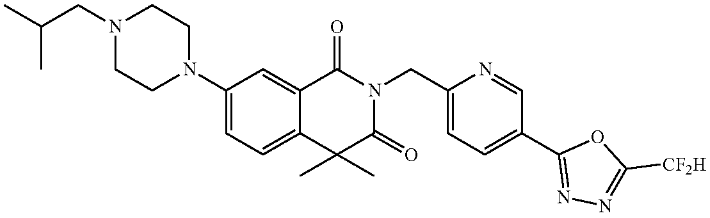 [SMILES: CC(C)CN1CCN(c2ccc3c(c2)C(=O)N(Cc2ccc(-c4nnc(C(F)F)o4)cn2)C(=O)C3(C)C)CC1] |

-continued
| Compound | Structure |
| --- | --- |
| 132 | 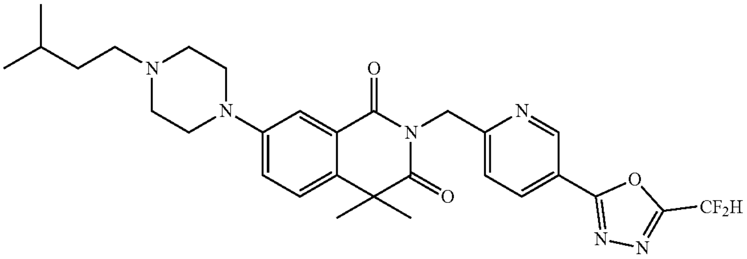 [SMILES: CC(C)CCN1CCN(c2ccc3c(c2)C(=O)N(Cc2ccc(-c4nnc(C(F)F)o4)cn2)C(=O)C3(C)C)CC1] |
| 133 | 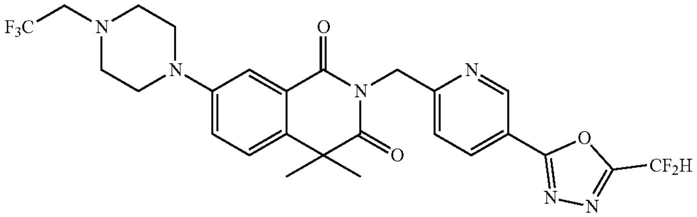 [SMILES: CC1(C)C(=O)N(Cc2ccc(-c3nnc(C(F)F)o3)cn2)C(=O)c2cc(N3CCN(CC(F)(F)F)CC3)ccc21] |
| 134 | 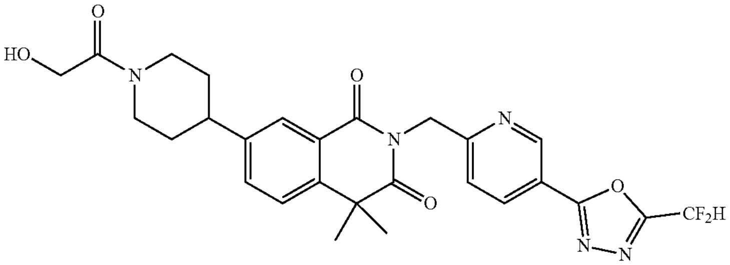 [SMILES: CC1(C)C(=O)N(Cc2ccc(-c3nnc(C(F)F)o3)cn2)C(=O)c2cc(C3CCN(C(=O)CO)CC3)ccc21] |
| 135 | 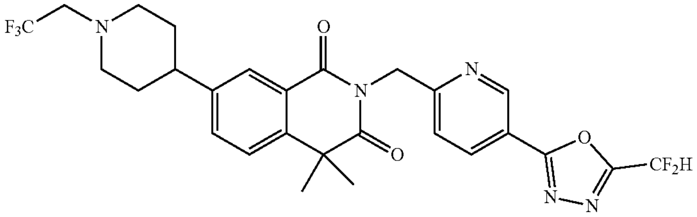 [SMILES: CC1(C)C(=O)N(Cc2ccc(-c3nnc(C(F)F)o3)cn2)C(=O)c2cc(C3CCN(CC(F)(F)F)CC3)ccc21] |
| 136 | 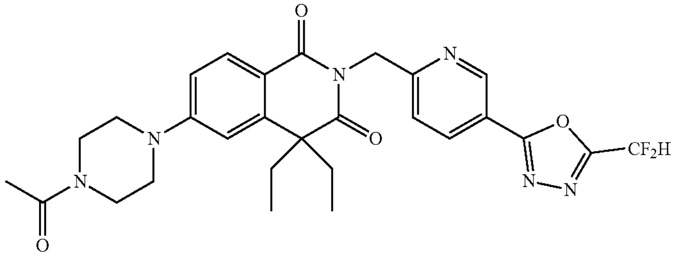 [SMILES: CCC1(CC)C(=O)N(Cc2ccc(-c3nnc(C(F)F)o3)cn2)C(=O)c2ccc(N3CCN(C(C)=O)CC3)cc21] |
| 137 | 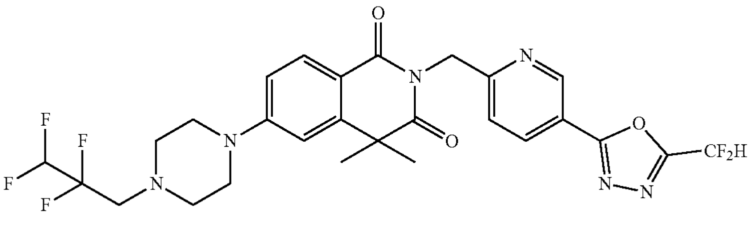 [SMILES: CC1(C)C(=O)N(Cc2ccc(-c3nnc(C(F)F)o3)cn2)C(=O)c2ccc(N3CCN(CC(F)(F)C(F)F)CC3)cc21] |

-continued
| Compound | Structure |
|---|---|
| 138 | 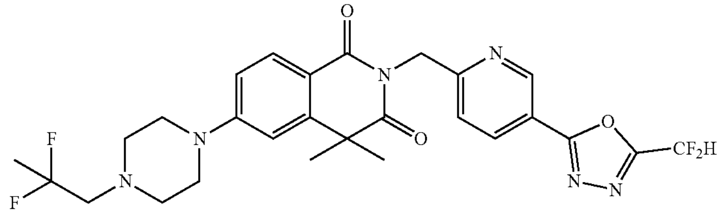 [SMILES: CC(F)(F)CN1CCN(c2ccc3c(c2)C(C)(C)C(=O)N(Cc2ccc(-c4nnc(C(F)F)o4)cn2)C3=O)CC1] |
| 139 | 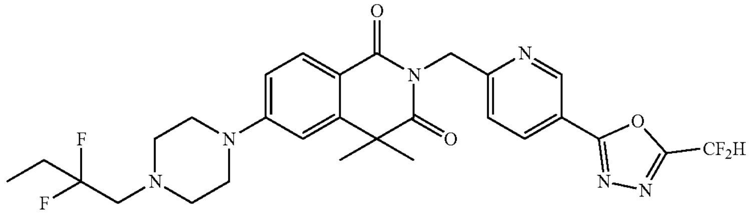 [SMILES: CCC(F)(F)CN1CCN(c2ccc3c(c2)C(C)(C)C(=O)N(Cc2ccc(-c4nnc(C(F)F)o4)cn2)C3=O)CC1] |
| 140 | 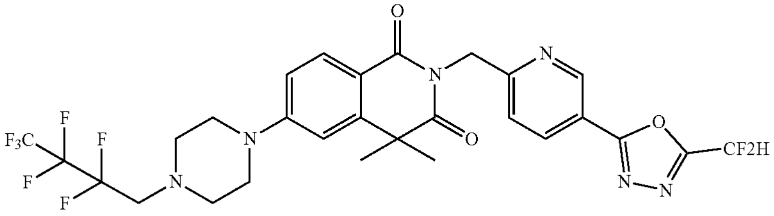 [SMILES: CC1(C)C(=O)N(Cc2ccc(-c3nnc(C(F)F)o3)cn2)C(=O)c2ccc(N3CCN(CC(F)(F)C(F)(F)C(F)(F)F)CC3)cc21] |
| 141 | 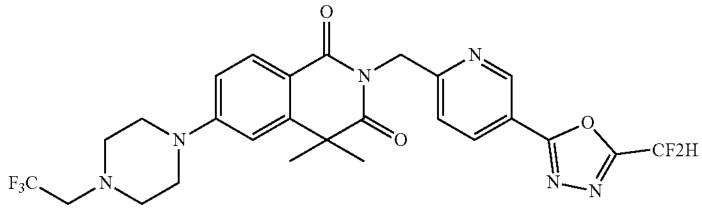 [SMILES: CC1(C)C(=O)N(Cc2ccc(-c3nnc(C(F)F)o3)cn2)C(=O)c2ccc(N3CCN(CC(F)(F)F)CC3)cc21] |
| 142 | 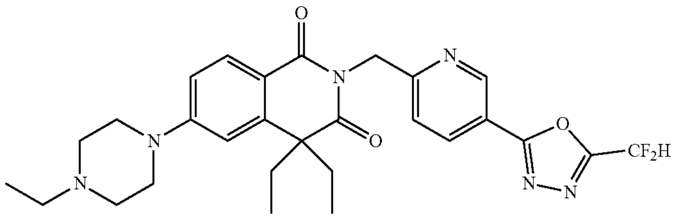 [SMILES: CCN1CCN(c2ccc3c(c2)C(CC)(CC)C(=O)N(Cc2ccc(-c4nnc(C(F)F)o4)cn2)C3=O)CC1] |
| 143 | 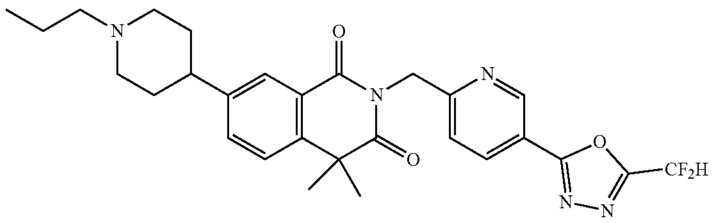 [SMILES: CCCN1CCC(c2ccc3c(c2)C(=O)N(Cc2ccc(-c4nnc(C(F)F)o4)cn2)C(=O)C3(C)C)CC1] |
| 144 | 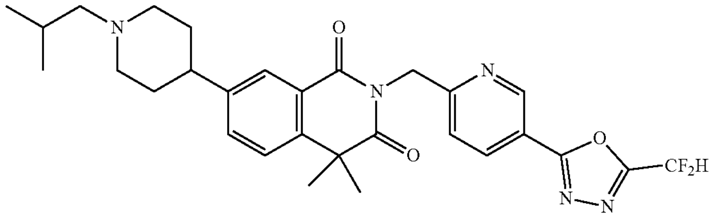 [SMILES: CC(C)CN1CCC(c2ccc3c(c2)C(=O)N(Cc2ccc(-c4nnc(C(F)F)o4)cn2)C(=O)C3(C)C)CC1] |

-continued
| Compound | Structure |
|---|---|
| 145 | 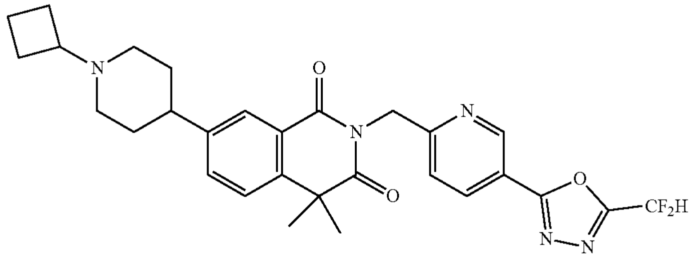 [SMILES: CC1(C)C(=O)N(Cc2ccc(-c3nnc(C(F)F)o3)cn2)C(=O)c2cc(C3CCN(C4CCC4)CC3)ccc21] |
| 146 | 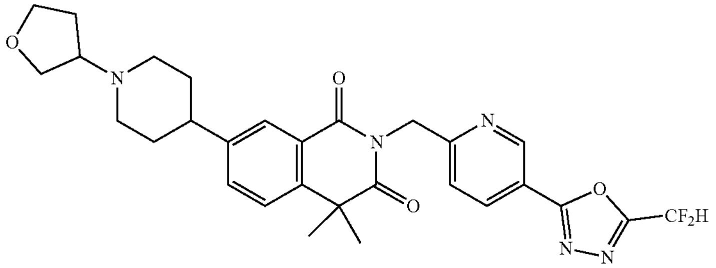 [SMILES: CC1(C)C(=O)N(Cc2ccc(-c3nnc(C(F)F)o3)cn2)C(=O)c2cc(C3CCN(C4CCOC4)CC3)ccc21] |
| 147 | 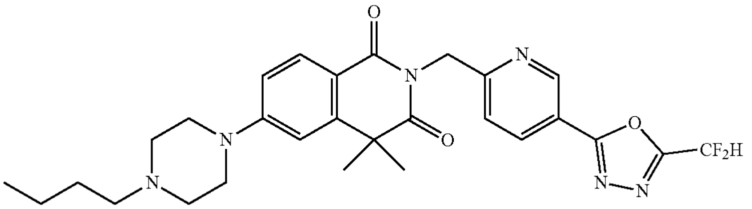 [SMILES: CCCCN1CCN(c2ccc3c(c2)C(C)(C)C(=O)N(Cc2ccc(-c4nnc(C(F)F)o4)cn2)C3=O)CC1] |
| 148 | 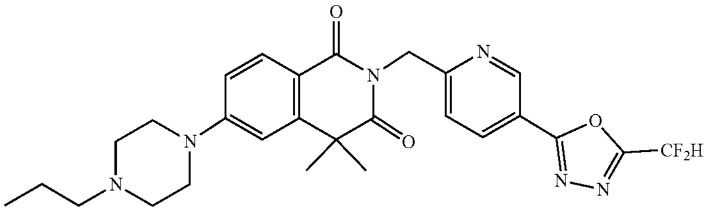 [SMILES: CCCN1CCN(c2ccc3c(c2)C(C)(C)C(=O)N(Cc2ccc(-c4nnc(C(F)F)o4)cn2)C3=O)CC1] |
| 149 | 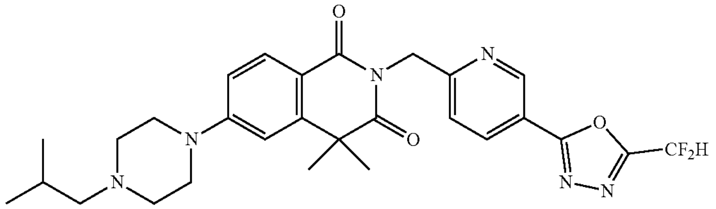 [SMILES: CC(C)CN1CCN(c2ccc3c(c2)C(C)(C)C(=O)N(Cc2ccc(-c4nnc(C(F)F)o4)cn2)C3=O)CC1] |
| 150 | 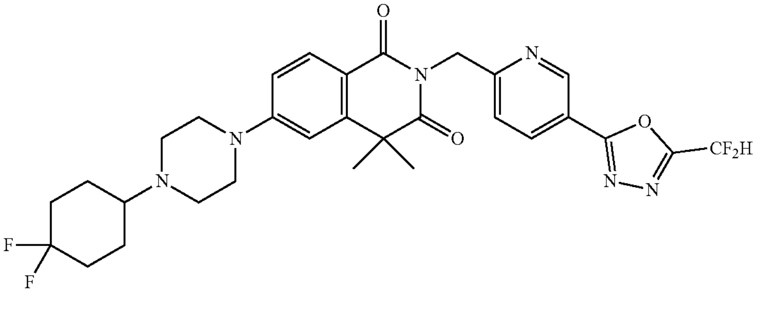 [SMILES: CC1(C)C(=O)N(Cc2ccc(-c3nnc(C(F)F)o3)cn2)C(=O)c2ccc(N3CCN(C4CCC(F)(F)CC4)CC3)cc21] |

-continued

| Compound | Structure |
| --- | --- |
| 151 | 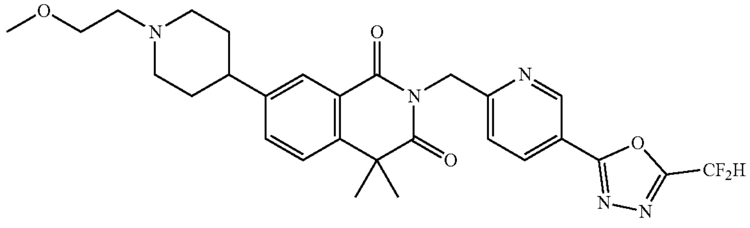 [SMILES: COCCN1CCC(c2ccc3c(c2)C(=O)N(Cc2ccc(-c4nnc(C(F)F)o4)cn2)C(=O)C3(C)C)CC1] |
| 152 | 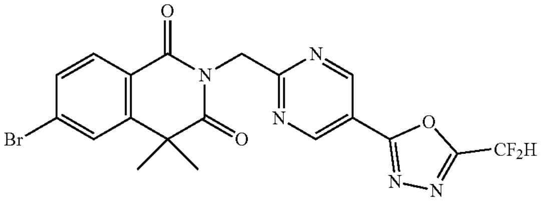 [SMILES: CC1(C)C(=O)N(Cc2ncc(-c3nnc(C(F)F)o3)cn2)C(=O)c2ccc(Br)cc21] |
| 153 | 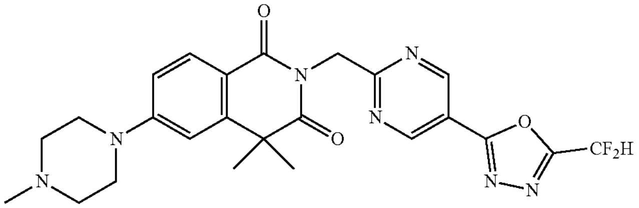 [SMILES: CN1CCN(c2ccc3c(c2)C(C)(C)C(=O)N(Cc2ncc(-c4nnc(C(F)F)o4)cn2)C3=O)CC1] |
| 154 | 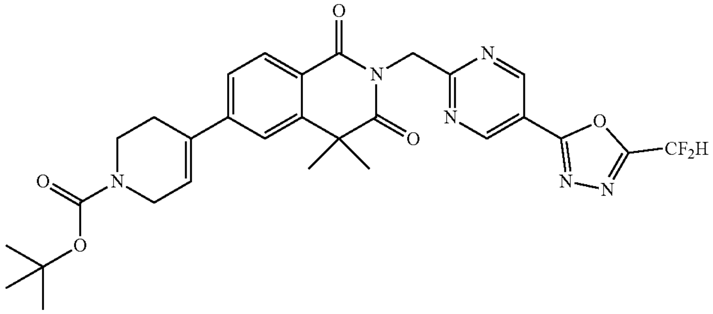 [SMILES: CC(C)(C)OC(=O)N1CC=C(c2ccc3c(c2)C(C)(C)C(=O)N(Cc2ncc(-c4nnc(C(F)F)o4)cn2)C3=O)CC1] |
| 155 | 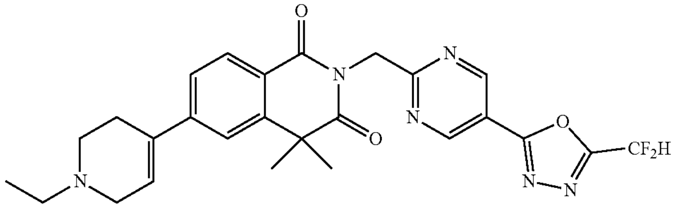 [SMILES: CCN1CC=C(c2ccc3c(c2)C(C)(C)C(=O)N(Cc2ncc(-c4nnc(C(F)F)o4)cn2)C3=O)CC1] |
| 156 | 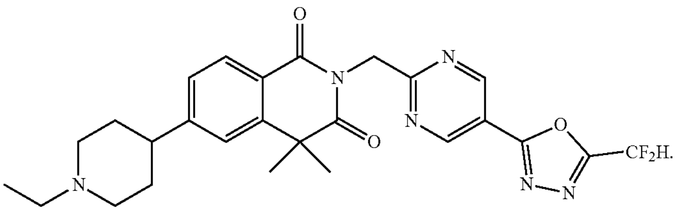 [SMILES: CCN1CCC(c2ccc3c(c2)C(C)(C)C(=O)N(Cc2ncc(-c4nnc(C(F)F)o4)cn2)C3=O)CC1] |

7. A pharmaceutical composition comprising the compound according to claim 1, stereoisomers thereof or pharmaceutically acceptable salts thereof as an effective component.

8. A method for treating histone deacetylase 6 activity-related diseases, comprising administering a therapeutically effective amount of the compound according to claim 1, stereoisomers thereof or pharmaceutically acceptable salts thereof.

9. A method according to claim 8, wherein histone deacetylase 6 activity-related diseases are at least one selected from the group consisting of infectious diseases;

neoplasm; endocrinopathy; nutritional and metabolic diseases; mental and behavioral disorders; neurological diseases; eye and ocular adnexal diseases; circulatory diseases; respiratory diseases; digestive diseases; skin and subcutaneous tissue diseases; musculoskeletal system and connective tissue diseases; and teratosis or deformities, and chromosomal aberration.

* * * * *